US008992908B2

(12) United States Patent
Smith et al.

(10) Patent No.: US 8,992,908 B2
(45) Date of Patent: Mar. 31, 2015

(54) ANTI-IL-6 ANTIBODIES FOR THE TREATMENT OF ORAL MUCOSITIS

(75) Inventors: Jeffrey T.L. Smith, Bellevue, WA (US); Leon F. Garcia-Martinez, Woodinville, WA (US); Andrew L. Feldhaus, Lynnwood, WA (US)

(73) Assignee: Alderbio Holdings LLC, Las Vegas, NV (US)

( * ) Notice: Subject to any disclaimer, the term of this patent is extended or adjusted under 35 U.S.C. 154(b) by 0 days.

(21) Appl. No.: 13/304,173

(22) Filed: Nov. 23, 2011

(65) Prior Publication Data

US 2012/0189629 A1 Jul. 26, 2012

Related U.S. Application Data

(60) Provisional application No. 61/416,332, filed on Nov. 23, 2010, provisional application No. 61/416,343, filed on Nov. 23, 2010, provisional application No. 61/416,351, filed on Nov. 23, 2010, provisional application No. 61/416,363, filed on Nov. 23, 2010, provisional application No. 61/489,857, filed on May 25, 2011, provisional application No. 61/511,797, filed on Jul. 26, 2011.

(51) Int. Cl.

| | |
|---|---|
| ***A61K 39/395*** | (2006.01) |
| ***A61K 31/7105*** | (2006.01) |
| ***A61K 38/20*** | (2006.01) |
| ***G01N 33/574*** | (2006.01) |
| ***A61K 31/713*** | (2006.01) |
| ***A61K 31/454*** | (2006.01) |
| *A61K 38/16* | (2006.01) |
| *C07K 16/24* | (2006.01) |
| *A61K 39/00* | (2006.01) |

(52) U.S. Cl.

CPC ...... *G01N 33/57407* (2013.01); *A61K 31/7105* (2013.01); *C07K 2317/92* (2013.01); *A61K 38/204* (2013.01); *C07K 2317/24* (2013.01); *C07K 2317/34* (2013.01); *G01N 33/57484* (2013.01); *A61K 2039/505* (2013.01); *A61K 2039/545* (2013.01); *C07K 2317/76* (2013.01); *C07K 2317/94* (2013.01); *A61K 31/713* (2013.01); *G01N 2800/52* (2013.01); *A61K 31/454* (2013.01); *C07K 16/248* (2013.01)

USPC .................. 424/130.1; 424/133.1; 424/135.1; 424/142.1; 424/145.1; 424/158.1; 530/387.1; 530/387.2; 530/387.3; 530/388.15; 530/388.23; 530/389.2; 514/16.6

(58) Field of Classification Search

None

See application file for complete search history.

(56) References Cited

U.S. PATENT DOCUMENTS

| | | | |
|---|---|---|---|
| 5,468,607 | A | 11/1995 | Revel et al. |
| 5,468,608 | A | 11/1995 | Revel et al. |
| 5,468,609 | A | 11/1995 | Revel et al. |
| 5,541,312 | A | 7/1996 | Revel et al. |
| 5,545,623 | A | 8/1996 | Matsumori |
| 5,554,513 | A | 9/1996 | Revel et al. |
| 5,556,947 | A | 9/1996 | Bock et al. |
| 5,559,012 | A | 9/1996 | Brailly et al. |
| 5,618,700 | A | 4/1997 | Novick et al. |
| 5,621,077 | A | 4/1997 | Novick et al. |
| 5,627,052 | A | 5/1997 | Schrader |
| 5,646,005 | A | 7/1997 | Kudsk |
| 5,670,373 | A | 9/1997 | Kishimoto |
| 5,707,624 | A | 1/1998 | Nickoloff et al. |
| 5,795,965 | A | 8/1998 | Tsuchiya et al. |
| 5,817,790 | A | 10/1998 | Tsuchiya et al. |
| 5,854,398 | A | 12/1998 | Chang et al. |
| 5,856,135 | A | 1/1999 | Tsuchiya et al. |
| 5,859,205 | A | 1/1999 | Adair et al. |
| 5,866,689 | A | 2/1999 | Kishimoto et al. |
| 5,882,872 | A | 3/1999 | Kudsk |
| 5,888,510 | A | 3/1999 | Kishimoto et al. |
| 5,888,511 | A | 3/1999 | Skurkovich et al. |
| 6,074,636 | A | 6/2000 | Nichols |
| 6,083,501 | A | 7/2000 | Miyata et al. |
| 6,086,874 | A | 7/2000 | Yoshida et al. |
| 6,121,423 | A | 9/2000 | Tsuchiya et al. |
| 6,231,536 | B1 | 5/2001 | Lentz |
| 6,235,281 | B1 | 5/2001 | Stenzel et al. |
| 6,261,560 | B1 | 7/2001 | Tsujinaka et al. |
| 6,306,393 | B1 | 10/2001 | Goldenberg |
| 6,342,587 | B1 | 1/2002 | Barbas, III et al. |

(Continued)

FOREIGN PATENT DOCUMENTS

| | | |
|---|---|---|
| EP | 0 488 470 | 6/1992 |
| JP | 2003-066047 | 3/2003 |
| JP | 2005-535341 A | 11/2005 |
| JP | 2007-528691 | 10/2007 |
| JP | 2008-538931 | 11/2008 |

(Continued)

OTHER PUBLICATIONS

Ding et al., Expert Opinion Investigation Drugs, Oct. 2009, vol. 18, No. 10, pp. 457-466.*

(Continued)

*Primary Examiner* — Bridget E Bunner
*Assistant Examiner* — Fozia Hamud
(74) *Attorney, Agent, or Firm* — LeClairRyan, a professional corporation; Robin L. Teskin

(57) ABSTRACT

The present invention is directed to therapeutic methods using IL-6 antagonists such as anti-IL-6 antibodies and fragments thereof having binding specificity for IL-6 to prevent or treat mucositis (e.g., oral mucositis) including persons on a treatment regimen with a drug or chemotherapy and/or radiation for cancer (e.g., head and neck cancer) that is associated with increased risk of mucositis, including oral mucositis.

35 Claims, 25 Drawing Sheets

(56) References Cited

U.S. PATENT DOCUMENTS

| | | | |
|---|---|---|---|
| 6,395,498 | B1 | 5/2002 | Tartaglia et al. |
| 6,399,054 | B1 | 6/2002 | Casorati et al. |
| 6,407,218 | B1 | 6/2002 | Tamarkin et al. |
| 6,419,944 | B2 | 7/2002 | Tobinick |
| 6,528,051 | B2 | 3/2003 | Tamarkin et al. |
| 6,551,592 | B2 | 4/2003 | Lindhofer et al. |
| 6,709,660 | B1 | 3/2004 | Scarlato et al. |
| 6,723,319 | B1 | 4/2004 | Ito et al. |
| 6,897,206 | B2 | 5/2005 | Sackeyfio et al. |
| 6,936,698 | B2 | 8/2005 | Taylor |
| 6,939,547 | B2 | 9/2005 | Aoki et al. |
| 6,984,383 | B1 | 1/2006 | Co et al. |
| 6,989,244 | B1 | 1/2006 | Tsuchiya et al. |
| 6,994,853 | B1 | 2/2006 | Lindhofer et al. |
| 7,018,632 | B2 | 3/2006 | Lindhofer et al. |
| 7,108,981 | B2 | 9/2006 | Aoki et al. |
| 7,169,573 | B2 | 1/2007 | Kurosawa et al. |
| 7,179,893 | B2 | 2/2007 | Le et al. |
| 7,235,365 | B2 | 6/2007 | Aoki et al. |
| 7,261,894 | B2 | 8/2007 | Sims et al. |
| 7,282,567 | B2 | 10/2007 | Goldenberg et al. |
| 7,285,269 | B2 | 10/2007 | Babcook et al. |
| 7,291,721 | B2 | 11/2007 | Giles-Komar et al. |
| 7,320,792 | B2 | 1/2008 | Ito et al. |
| 7,345,217 | B2 | 3/2008 | Zhang et al. |
| 7,374,756 | B2 | 5/2008 | Aoki et al. |
| 7,431,927 | B2 | 10/2008 | Couto et al. |
| 7,462,697 | B2 | 12/2008 | Couto et al. |
| 7,468,184 | B2 | 12/2008 | Sato et al. |
| 7,479,543 | B2 | 1/2009 | Tsuchiya et al. |
| 7,482,436 | B2 | 1/2009 | Sugimura et al. |
| 7,504,106 | B2 | 3/2009 | Skurkovich et al. |
| 7,504,256 | B1 | 3/2009 | Ogawa et al. |
| 7,534,427 | B2 | 5/2009 | Goldenberg et al. |
| 7,560,112 | B2 | 7/2009 | Chen et al. |
| 7,582,298 | B2 | 9/2009 | Stevens et al. |
| 7,611,857 | B2 | 11/2009 | Medlock et al. |
| 7,612,182 | B2 | 11/2009 | Giles-Komar et al. |
| 7,622,555 | B2 | 11/2009 | Davids et al. |
| 7,662,378 | B2 | 2/2010 | Goldenberg et al. |
| 7,695,716 | B2 | 4/2010 | Drachman et al. |
| 7,727,528 | B2 | 6/2010 | Adcock |
| 7,790,463 | B2 | 9/2010 | Mor et al. |
| 7,833,755 | B2 | 11/2010 | Chen et al. |
| 7,833,786 | B2 | 11/2010 | Giles-Komar et al. |
| 7,863,419 | B2 | 1/2011 | Taylor et al. |
| 7,906,117 | B2 | 3/2011 | Smith et al. |
| 7,915,388 | B2 | 3/2011 | Wu et al. |
| 7,935,340 | B2 | 5/2011 | Garcia-Martinez et al. |
| 7,955,597 | B2 | 6/2011 | Giles-Komar et al. |
| 7,993,641 | B2 | 8/2011 | Waldmann et al. |
| 8,062,864 | B2 | 11/2011 | Garcia-Martinez et al. |
| 8,062,866 | B2 | 11/2011 | Frey et al. |
| 8,067,003 | B2 | 11/2011 | Chen et al. |
| 8,080,528 | B2 | 12/2011 | Kenley et al. |
| 8,178,101 | B2 | 5/2012 | Garcia-Martinez et al. |
| 8,188,231 | B2 | 5/2012 | Lazar et al. |
| 8,226,611 | B2 | 7/2012 | Chen et al. |
| 8,252,286 | B2 | 8/2012 | Smith |
| RE43,672 | E | 9/2012 | Chen et al. |
| 8,268,582 | B2 | 9/2012 | Cregg et al. |
| 8,277,804 | B2 | 10/2012 | Smith |
| 8,323,649 | B2 | 12/2012 | Garcia-Martinez et al. |
| 8,337,847 | B2 | 12/2012 | Smith et al. |
| 8,623,362 | B2 | 1/2014 | Chen et al. |
| 2001/0001663 | A1 | 5/2001 | Kishimoto et al. |
| 2003/0180806 | A1 | 9/2003 | Kamei et al. |
| 2003/0219839 | A1 | 11/2003 | Bowdish et al. |
| 2003/0229030 | A1 | 12/2003 | Theoharides |
| 2004/0001831 | A1 | 1/2004 | Rottman et al. |
| 2004/0014658 | A1 | 1/2004 | Bogin et al. |
| 2004/0028681 | A1 | 2/2004 | Ito et al. |
| 2004/0071706 | A1 | 4/2004 | Ito et al. |
| 2004/0086979 | A1 | 5/2004 | Zhang et al. |
| 2004/0115197 | A1 | 6/2004 | Yoshizaki et al. |
| 2004/0185040 | A1 | 9/2004 | Garcia-Martinez et al. |
| 2005/0033031 | A1 | 2/2005 | Couto |
| 2005/0043517 | A1 | 2/2005 | Giles-Komar et al. |
| 2005/0118652 | A1 | 6/2005 | Lee et al. |
| 2005/0130230 | A1 | 6/2005 | Davalos et al. |
| 2005/0142635 | A1 | 6/2005 | Tsuchiya et al. |
| 2006/0018904 | A1 | 1/2006 | Chung et al. |
| 2006/0039857 | A1 | 2/2006 | Adcock |
| 2006/0039927 | A1 | 2/2006 | Aoki et al. |
| 2006/0040363 | A1 | 2/2006 | Kucherlapati et al. |
| 2006/0051348 | A1 | 3/2006 | Gorlach |
| 2006/0078532 | A1 | 4/2006 | Omoigui |
| 2006/0078533 | A1 | 4/2006 | Omoigui |
| 2006/0121042 | A1 | 6/2006 | Dall'Acqua et al. |
| 2006/0134113 | A1 | 6/2006 | Mihara |
| 2006/0159675 | A1 | 7/2006 | Jiao et al. |
| 2006/0165696 | A1 | 7/2006 | Okano et al. |
| 2006/0171943 | A1 | 8/2006 | Comeau et al. |
| 2006/0210563 | A1 | 9/2006 | Lopez De Silanes et al. |
| 2006/0240012 | A1 | 10/2006 | Sugimura et al. |
| 2006/0251653 | A1 | 11/2006 | Okuda et al. |
| 2006/0257407 | A1 | 11/2006 | Chen et al. |
| 2006/0275294 | A1 | 12/2006 | Omoigui |
| 2006/0281130 | A1 | 12/2006 | Bock et al. |
| 2006/0292147 | A1 | 12/2006 | Yoshizaki et al. |
| 2007/0005261 | A1 | 1/2007 | Serena et al. |
| 2007/0015197 | A1 | 1/2007 | Aoki et al. |
| 2007/0036785 | A1 | 2/2007 | Kishimoto et al. |
| 2007/0036788 | A1 | 2/2007 | Sheriff et al. |
| 2007/0048306 | A1 | 3/2007 | Giles-Komar et al. |
| 2007/0098714 | A1 | 5/2007 | Nishimoto et al. |
| 2007/0134242 | A1 | 6/2007 | Nishimoto et al. |
| 2007/0243162 | A1 | 10/2007 | Aoki et al. |
| 2007/0243189 | A1 | 10/2007 | Yoshizaki et al. |
| 2007/0280941 | A1 | 12/2007 | Chung et al. |
| 2007/0280945 | A1 | 12/2007 | Stevens et al. |
| 2008/0033027 | A1 | 2/2008 | Bascomb et al. |
| 2008/0075726 | A1 | 3/2008 | Smith et al. |
| 2008/0081041 | A1 | 4/2008 | Nemeth |
| 2008/0124325 | A1 | 5/2008 | Ito et al. |
| 2008/0166348 | A1 | 7/2008 | Kupper et al. |
| 2008/0260687 | A1 | 10/2008 | Aoki et al. |
| 2009/0022719 | A1 | 1/2009 | Mihara et al. |
| 2009/0028784 | A1 | 1/2009 | Garcia-Martinez et al. |
| 2009/0035281 | A1 | 2/2009 | Savino et al. |
| 2009/0104187 | A1 | 4/2009 | Kovacevich et al. |
| 2009/0181029 | A1 | 7/2009 | Okuda et al. |
| 2009/0238825 | A1 | 9/2009 | Kovacevich et al. |
| 2009/0291077 | A1 | 11/2009 | Smith et al. |
| 2009/0291082 | A1 | 11/2009 | Smith |
| 2009/0291089 | A1 | 11/2009 | Smith |
| 2009/0297436 | A1 | 12/2009 | Garcia-Martinez et al. |
| 2009/0297513 | A1 | 12/2009 | Garcia-Martinez et al. |
| 2009/0311718 | A1 | 12/2009 | Fukushima et al. |
| 2010/0129357 | A1 | 5/2010 | Garcia-Martinez et al. |
| 2010/0143294 | A1 | 6/2010 | Smith |
| 2010/0150829 | A1 | 6/2010 | Garcia-Martinez et al. |
| 2010/0158859 | A1 | 6/2010 | Smith et al. |
| 2010/0290993 | A1 | 11/2010 | Garcia-Martinez et al. |
| 2011/0104146 | A1 | 5/2011 | Faraday |
| 2011/0217303 | A1 | 9/2011 | Smith et al. |
| 2011/0218329 | A1 | 9/2011 | Giles-Komar et al. |
| 2011/0250201 | A1 | 10/2011 | Smith |
| 2011/0293622 | A1 | 12/2011 | Garcia-Martinez et al. |
| 2012/0014955 | A1 | 1/2012 | Smith |
| 2012/0096569 | A1 | 4/2012 | Giles-Komar et al. |
| 2012/0121594 | A1 | 5/2012 | Smith |
| 2012/0128626 | A1 | 5/2012 | Smith |
| 2012/0142900 | A1 | 6/2012 | Garcia-Martinez et al. |
| 2012/0189629 | A1 | 7/2012 | Smith |
| 2012/0288504 | A1 | 11/2012 | Smith |
| 2012/0294852 | A1 | 11/2012 | Smith |
| 2013/0017575 | A1 | 1/2013 | Garcia-Martinez et al. |
| 2013/0028860 | A1 | 1/2013 | Smith et al. |
| 2013/0034554 | A1 | 2/2013 | Garcia-Martinez et al. |
| 2013/0058949 | A1 | 3/2013 | Smith |
| 2013/0101598 | A1 | 4/2013 | Smith |
| 2013/0183264 | A1 | 7/2013 | Smith |
| 2013/0183293 | A1 | 7/2013 | Smith et al. |

(56) References Cited

U.S. PATENT DOCUMENTS

| | | | |
|---|---|---|---|
| 2013/0224201 | A1 | 8/2013 | Smith |
| 2013/0323238 | A1 | 12/2013 | Smith |
| 2014/0099311 | A1 | 4/2014 | Chen et al. |

FOREIGN PATENT DOCUMENTS

| | | | |
|---|---|---|---|
| WO | WO 91/02078 | | 2/1991 |
| WO | WO 91/09967 | | 7/1991 |
| WO | 03/010541 | | 2/2003 |
| WO | WO 03/045318 | | 6/2003 |
| WO | 2004/016740 | | 2/2004 |
| WO | WO 2004/039826 | | 5/2004 |
| WO | 2004/048552 | A2 | 6/2004 |
| WO | 2004078938 | A2 | 9/2004 |
| WO | WO 2004/106377 | | 12/2004 |
| WO | WO 2006/119115 | | 11/2006 |
| WO | 2007/076927 | | 7/2007 |
| WO | WO 2007/104529 | | 9/2007 |
| WO | 2008/019061 | | 2/2008 |
| WO | 2008/045140 | | 4/2008 |
| WO | 2008/065378 | | 5/2008 |
| WO | 2008/144763 | A2 | 11/2008 |
| WO | WO 2008/144757 | | 11/2008 |
| WO | 2010/065078 | | 6/2010 |
| WO | 2010/065078 | | 10/2010 |

OTHER PUBLICATIONS

Rossi et al, Bone Marrow Transplant, 2005, vol. 36, No. 9, pp. 771-779.*

Hudson et al., Nature Medicine, Jan. 2003, vol. 9, No. 1, pp. 129-134.*

Phillips, A., J Pharm Pharmacology, 2001, vol. 53, pp. 1169-1174.*

Vidal et al. European Journal of Cancer, 2005; 41: 2812-2818.*

Pirollo et al. Cancer Res, 2008;. 68(5): 1247-1250.*

Domingo-Domenech, et al. (2006) *Clin. Cancer Res.* 12(18): 5578-5586.

Rossi, et al. (2005) *Bone Marrow Transplantation* 36(9): 771-779.

Lederman et al. 1991, Mol Immunol, vol. 28, pp. 1171-1181.

Li et al. Proc Natl Acad Sci USA, 1980, vol. 77, pp. 3211-3214.

Paul, Fundamental Immunology, 3rd Edition, 1993, pp. 292-295.

Casset et al (Biochemical and Biophysical Research Communications,2003, vol. 307, apges198-205.

Nishimoto et al. "Improvement in Castleman's disease by humanized anti-interleukin-6 receptor antibody therapy"; Blood, Jan. 1, 2000, vol. 95, No. 1, pp. 56-61.

Lab Tests Online, D-Dimer: The Test, Oct. 20, 2008 [Retrieved form the Internet Jun. 17, 2010; <URL:http://web.archive.org/web/20071020065024/http://www.laptestsonli- ne.org/understanding/analytes/d.sub.--dimer/test.html>]; pp. 1-2.

Blay et al. "Role of Interleukin-6 in the Paraneoplastic Inflammatory Syndrome Associate with Renal-Cell Carcinoma" In J. Cancer 72, 1997, pp. 424-430.

Cata et al. "The effects of thalidomide and minocycline on taxol-induced hyperalgesia in rats" Brain Res 2008, Sep. 10, 2008, pp. 1-18.

Ridker et al. "Rosuvastatin to Prevent Vascular Events in Men and Women with Elevated C-Reactive Protein" The New England Journal of Medicine, Nov. 20, 2008, vol. 359, No. 21, pp. 2195-2207.

Nishimoto et al. "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease" Blood, Nov. 15, 2008, vol. 112, No. 10, pp. 3959-3964.

Lab Tests Online, Hypercoagulable Disorders, Mar. 1, 2008 [Retrieved from the internet Jun. 17, 2010: ,URL: http://web.archive.org/web/20080301224129/http://www.labtestsonline.org/u-nderstaning/conditions/hypercoagulable.sub.--disorders-6.html>.

Adam et al, "D-dimer antigen: current concepts and future prospects", Blood, 2009, 112; pp. 2878-2887.

Wells et al., Evaluation of D-dimer in the Diagnosis of Suspected Deep-Vein Thrombosis: The New England Journal of Medicine, Sep. 25, 2003, pp. 1227-1235.

Montero-Julian et al., Pharmacokinetic study of anti-interleukin-6 (IL-6) therapy with monoclonal antibodies; enhancement of IL-6 clearance by cocktails of anti-IL-6 antibodied, Blood 85(4): 917-924 (1995).

Van Zaanen et al., Chimaeric anti-interleukin 6 monoclonal antibodies in the treatment of advanced multiple myeloma a phase I dose-escalataing study. Bristish Journal of Haematology. 102: 783-790 (1998).

Matsuyama et al., Anti-interleukin-6 receptor antibody (Tocilizumab) treatment of multicentric Castleman's disease. International Medicine. 46(11): 771-774 (2007).

Fonesca et al., Interleukin-6 as a key player in systemic inflammation and joint destruction. Autoimmunity Reviews, 8: 533-542 (Jun. 2009).

Fayad et al., Interleukin-6 and interleukin-10 levels in chronic lymphocytic leukemia; correlation with phenotypic characteristics and outcome. Blood, 97: 256-263 (2001).

Bellone et al., High serum levels of interleukin-6 in endometrial carcinoma are associated with uterine serous papillary histology, a highly aggressive and chemotherapy-resistant variant of endometrial cancer. Gynecologic Oncology, 98: 92-98 (2005).

Taylor et al., Effect of anti-IL-6 and anti-10 monoclonal antibodies on the suppression of the normal T lymphocyte mitogenic response by steady state sickle cell disease sera. Immunological Investigation, 30(3): 209-219 (2001).

U.S. Appl. No. 13/849,597, filed Mar. 25, 2013.

Arnaud et al., "Statins Reduce Interleukin-6-Induced C-Reactive Protein in Human Hepatocytes: New Evidence for Direct Antiinflammatory Effects of Statins," Arteriosclerosis, Thrombosis, and Vascular Biology, 2005; 25: 1231-1236.

Beck et al., "Alleviation of Systemic Manifestations of Castleman's Disease by Monoclonal Anti-Interleukin-6 Antibody," New Engl. J. Med., Mar. 1994; 330(9):602-605.

Beheiri et al., "Role of elevated .alpha.sub.2.sub.-macroglobulin revisited: results of a case-control study in children with symptomatic thromboembolism," J Thromb Haemost. 2007, 5:1179-84.

Buccheri et al., "Plasma Levels of D-Dimer in Lung Carcinoma," Cancer, 2003; 97:3044-52.

Carrier et al., Thromb Res, 2008; 123:177-83.

Carter et al., Current Protocols in Immunology (2004) John Wiley & Sons, Inc. pp. 9.4.1-9.4.23.

Chang et al., "Construction and expression of synthetic single-chain variable domain fragement antibody (SCFV-A33) in *Pichia pastoris*," Abs. Gen. Meet. Am. Soc. Microbiol.; 103(21), 2003.

Damschroder et al., Molecular Immunology 41(10):985-1000 Aug. 2004.

Derhasching et al., " Effect of interleukin-6 blockade on tissue factor-induced coagulation in human endotoxemia," Critical Care Medicine, 2004; 32(5):1136-1140.

De Wildt, et al., "Isolation and Characterization of Single Anti-U1A-Specific B Cells from Autoimmune Patients," Annals of the NY Acad Sci, Apr. 5, 1997; 815:440-442.

Dohmen et al., "Production of recombinant Ig molecules from antigen-selected single B cells and restricted usage of Ig-gene segments by anti-D antibodies," J Immunol Meth, Mar. 1, 2005; 298(1-2):9-20.

"Fanconi anemia", www.nhlbi.nih.gov/health/health-topics/topics/fanconi/prevention.html; downloaded Nov. 20, 2013; 1 page.

Filep and Kebir, Future Cardiol. 2008, 4:495-504.

Haddad et al., "Chemotherapy-induced thrombosis," Thromb. Res. 2006;118(5):555-568. Epub Jan. 4, 2006.

Hamzaoui, K. et al., "Interleukin-6 in peripheral blood and inflammatory sites in Behcet's disease," Mediators of Inflammation 1992. 1(4):281-285.

"Hemolytic anemia", www.nhlbi.nih.govihealth/health-topics/topics/ha/prevention.html; downloaded Nov. 21, 2013; 1 page.

Immunobiology, The Immune System in Health and Disease, Third Edition, Janeway and Travers, Ed., 1997.

Ito et al., "HMG-CoA reductase inhibitors reduce interleukin-6 synthesis in human vascular smooth muscle cells," Cardiovascular Drugs Ther. Mar. 2003; 16(2):121-126.

(56) References Cited

OTHER PUBLICATIONS

Johnson et al., Circulation, 2004, 109:726-32.
Kodituwakku et al., "Isolation of antigen-specific B cells," Immunology and Cell Biology (2003); 81:163-170.
Kosuge et al., Circ J., 2007, 71:186-90.
Kruip et al., Arch Intern Med, 2002; 162:1631-5.
Levi, B J Haematol, 2004; 124:567-76.
Maini et al., Arthritis & Rheumatism, Sep. 2006; 54(9):2817-2829.
Meager et al., Hybridoma 6(3): 305-311, Jun. 1987.
Menapace and Khorana, Curr Opin Hematol, 2010; 17:450-6.
O'Brien et al., Methods in Molecular Biology, vol. 207: Recombinant Antibodies for Cancer Therapy: Methods and Protocols, Humana Press, pp. 81-100 (2003).
Ogasawara et al., Atherosclerosis, 2004, 174:349-56.
Okuda et al., "Successful use of a humanized anti-interleukin-6 receptor antibody, tocilizumab, to treat amyloid A amyloidosis complicating juvenile idiopathic arthritis," Arthritis & Rheumatism, 54(9):2997-3000 (2006).
Padlan, Mol. Immunology 31(3): 169-217 Feb. 1994.
Palareti et al., N Engl J Med, 2006; 355:1780-9.
"Pernicious anemica", www.nhlbi.nih.gov/health/health-topics/topics/prnanmia/prevention.html; downloaded Nov. 21, 2013; 2 pages.
Popkov, M. et al., "Rabbit Immune Repertories as Sources for Therapeutic Monoclonal Antibodies: The Impact of Kappa Allotype-correlated Variation in Cysteine Content on Antibody Libraries Selected by Phage Display," J. Mol. Biol., Jan. 10, 2003; 325(2):325-335.
Portolano et al., Journal of Immunology 150(3): 880-887 Feb. 1993.
Righini et al., Thromb Haemost, 2006; 95:715-9.
Rudikoff et al. Proc Natl Acad Sci USA 1982 vol. 79 p. 1979-1983.
Salgado, R. et al., "Circulating interleukin-6 predicts survival in patients with metastatic breast cancer," Intl. J. Cancer, Feb. 20 2003; 103(5):642-646.
Schutgens et al., J Lab Clin Med, 2004; 144:100-7.
"Sickle cell anemia," Harvard Medical School Faculty: Sickle cell anemia, Sep. 2009; downloaded from www.intelihealth.com/IH/ihtPrint/WSIHWO00/9339/9453.html?hide=t&k=basePrint; 4 pages.
Simmons et al., "Expression of full-length immunoglobulins in *Escherichia coli*: rapid and efficient production of aglycosylated antibodies," J. Immunol. Meth., Elsevier Science Publishers B.V., Amsterdam NL; 263(1-2):133-147, 2002.
Simonsson, et al., "Single, Antigen-Specific B Cells Used to Generate Fab Fragments Using CD40-Mediated Amplification or Direct PCR Cloning," Biotechniques, May 1, 1995; 18(5):862, 864-869.
Song et al., Atherosclerosis, 2009, 202:596-604.
Steenbakkers et al., "Efficient Generation of Monoclonal Antibodies from Preselected Antigen-Specific B Cells," Molecular Biology Reports, 1994; 19:125-134.
Trikha, Clinical Cancer Research, 2003; 9:4653-4665.
Vajdos et al., Journal of Molecular Biology 320(2): 415-428 Jul. 2002.
Van Belle et al., JAMA, 2006; 295:172-9.
Van der Poll et al., Journal of Experimental Medicine, 1994, 79:1253-1259.
Weitkamp et al., "Generation of recombinant human monoclonal antibodies to rotavirus from single antigen-specific B cells selected with fluorescent virus-like particles," Journal of Immunological Methods, Apr. 1, 2003; 275(1-2):223-237.
Wells, Biochemistry 29:8509-8517 (1990).
Wells et al., Ann Intern Med. 2001; 135:98-107.
Wijdenes, et al., Molecular Immunology, Nov. 1991; 28(11): 1183-1192.
Burks et al. PNAS; 1997, vol. 94, pp. 412-417.
Colman; Research in Immunol., 1994, vol. 145, pp. 33-36.
Kobayashi et al. Protein Engineering; 1999; vol. 12, pp. 879-844.
Groopman JE, et al., "Chemotherapy-induced anemia in adults: incidence and treatment," J Natl Cancer Inst. Oct. 6, 1999; 91(19)1616-34.
Alder Biopharmaceuticals. Phase 2a Study of ALD518 for Treatment of Non Small Cell Lung Cancer (NSCLC) Symptoms. MPR, Jun. 7, 2010. Web. May 7, 2014. <http://www.empr.com/phase-2a-study-of-ald518-for-treatment-of-non-small-cell-lung-cancer-nsclc-symptoms/article/171887/>.
Armstrong, "Brisol-Myers Rheumatoid Arthritis Drug Works in Mid-Stage Trial," Bloomberg. Oct. 26, 2013. Web. May 8, 2014.
Bataille et al., "Biologic effects of anti-interleukin-6 murine monoclonal antibody in advanced multiple myeloma," Blood, American Society of Hematology, 1995, 86(2):685-691.
Bristol-Myers Squibb. Promising Phase IIb Data on Clazakizumab In Patients With Moderate-To-Severe Rheumatoid Artritis To Be Presented At The 2013 Annual Meeting Of The American College of Rheumatology. Oct. 28, 2013. Web.
Bristol-Myers Squibb. Partnering News, R&D News. Bristol-Myers Squibb and Alder Biopharmaceuticals Enter Global Agreement on Rheumatoid Arthritis Biologic. MPR, Nov. 10, 2010. Web. May 7, 2014. <http://news.bms.com/press-release/rd-news/bristol-myers-squibb-and-alder-biopharmaceuticals-enter-global-agreement-rheum>.
Cregg et al., "Recent Advances in the Expression of Foreign Genes in Pichia pastoris," Biotechnology. Aug. 1993, vol. 11, pp. 905-910.
Emille et al., "Administration of an Anti-Interleukin-6 Monoclonal Antibody to Patients with Acquired Imunodeficiency Syndrome and Lymphoma: Effect on Lymphoma Growth and on B Clinical Systems,"Blood, 1994. 84(8):2472-2479.
Fujimoto-Ouchi et al., "Capecitabine improves cancer cachexia and normalizes IL-6 and PTHrP levels in mouse cancer cachexia models," Cancer Chemotherapy and Pharmacology, 2006. 59(6):807-815.
Heremans et al., "Protective effectof anti-interleukin (IL)-6 antibody against endotoxin, associated with paradoxically increased IL-6 levels," Immunology, 1992. 22(9):2395-2401.
Hinton, et al., "An engineered human IgG1 antibody with longer serum half-life," The Journal of Immunology, the American Association of Immunologists, 2006. 176(1):346-356.
King et al., Radiology, 2008; 247:854-61.
Klein et al., "Murine anti-interleukin-6 monoclonal antibody therapy for a patient with plasma cell leukemia," Blood, 1991. 78(5):1198-1204.
Mease et al., "ALD518 (BMS945429), A High Affinity Monoclonal Antibody Directed Against Interleukin-6, Reduces Disease Activity and Achieves Remission in Patients with Rheumatoid Arthritis and Inadequate Response to Methotrexate," [abstract]. Arthritis Rheum 2010; 62 Suppl 10:2168.
Strassmann et al., "Evidence for the involvement of interleukin 6 in experimental cancer cachexia," Journal of Clinical Investigation, 1992. 89(5):1681-1684.
Strassmann et al., "Inhibition of Experimental Cancer Cachexia by Anti-Cytokine and Anti-Cytokine-Receptor Therapy," Cytokines and Molecular Therapy, 1995. 1(2):107-113.
Tamura, et al., "Involvement of human interleukin 6 in experimental cachexia induced by a human uterine cervical carcinoma xenograft," Clinical Cancer Research, 1995. 1(1):1353-1358.
Zaki et al., "2003 ASCO Annual Meeting—Developmental Therapeutics—Clinical Pharmacology and Immunotherapy," Proc. Am. Soc. Clin. Oncol. 2003. 22:697.
Zhuang et al., "Diagnosis of factors causing senile deep venous thrombosis and therapy advance thereof," Geriatrics & Health Care, vol. 11, No. 2., pp. 127-129, 2005.
English language translation of Zhuang et al. first and last paragraph, 2005.
Kedar et al., "Thalomide Reduces Serum C-Reactive Protein and Interleukin-6 and Induces Response to IL-2 in a Fraction of Metastatic Renal Cell Cancer Patients Who Failed IL-2 Based Therapy", Int. J. Cancer (2004); 110:260-265.

* cited by examiner

FIG. 1

```
      FR1                                 CDR1         FR2                   CDR2          FR3
      1                              23   24       34  35                49  50      56    57                                 88
RbtVL AYDMTQTPASVEVAVGGTVTINC QASETIYSWLS WYQQKPGQPPKLLIY QASDLAS GVPSRFSGSGAGTEYTLTISGVQCDDAATYYC
L12A  DIQMTQSPSTLSASVGDRVTITC RASQSISSWLA WYQQKPGKAPKLLIY KASSLES GVPSRFSGSGSGTEFTLTISSLQPDDFATYYC (SEQ ID NO: 734)
V1    DIQMTQSPSTLSASVGDRVTITC RASQSISSWLA WYQQKPGKAPKLLIY DASSLES GVPSRFSGSGSGTEFTLTISSLQPDDFATYYC (SEQ ID NO: 735)
Vx02  DIQMTQSPSSLSASVGDRVTITC RASQSISSYLN WYQQKPGKAPKLLIY AASSLQS GVPSRFSGSGSGTDFTLTISSLQPEDFATYYC (SEQ ID NO: 736)

VLh   DIQMTQSPSTLSASVGDRVTITC QASETIYSWLS WYQQKPGKAPKLLIY QASDLAS GVPSRFSGSGSGTEFTLTISSLQPDDFATYYC

      CDR3          FR4
      89        100 101       111
RbtVL QQGYSGSNVDNV FGGGTEVVVKR (SEQ ID NO: 733)
                   FGGGTKVEIKR

VLh   QQGYSGSNVDNV FGGGTKVEIKR (SEQ ID NO: 737)


        FR1                             CDR1    FR2               CDR2              F3
        1                            30 31   35 36            49  50             66 67                              98
RbtVH   QEQLKESGGRLVTPGTPLTLTCTASGFSLN DHAMG WVRQAPGKGLEYIG FINS-GGSARYASWAEG RFTISRTST--TVDLKMTSLTTEDTATYFCVR
3-64-04 QVQLVESGGGLVQPGGSLRLSCSASGFTFS SYAMH WVRQAPGKGLEYVS AISSNGGSTYYADSVKG RFTISRDNSKNTLYLQMNSLRAEDTAVYYCAR (SEQ ID NO: 739)
3-66-04 EVQLVESGGGLVQPGGSLRLSCAASGFTVS SNYMS WVRQAPGKGLEWVS VIYS-GGSTYYADSVKG RFTISRDNSKNTLYLQMNSLRAEDTAVYYCAR (SEQ ID NO: 740)
3-53-02 EVQLVETGGGLIQPGGSLRLSCAASGFTVS SNYMS WVRQAPGKGLEWVS VIYS-GGSTYYADSVKG RFTISRDNSKNTLYLQMNSLRAEDTAVYYCAR (SEQ ID NO: 741)

VHh     QVQLVESGGGLVQPGGSLRLSCSASGFSLN DHAMG WVRQAPGKGLEYVG FINS-GGSARYASSAEG RFTISRDNSKNTLYLQMNSLRAEDTAVYYCAR

        CDR3         FR4
        99       110 111      121
RbtVH   GGAVWSIHSFDP WGPGTLVTVSS (SEQ ID NO: 738)
                     WGQGTLVTVSS

VHh     GGAVWSIHSFDP WGQGTLVTVSS (SEQ ID NO: 742)
```

FIGURE 2 – PREFERRED ANTI-IL-6 ANTIBODY HUMANIZATION

| | FR1 | CDR1 | FR2 | CDR2 | FR3 |
|---|---|---|---|---|---|
| SEQ ID NO: 647 | AYDMTQTPASVSAAVGGTVTIKC | QASQSINNELS | WYQQKPGQRPKLLIY | RASTLAS | GVSSRFKGSGSGTEFTLTISDLECADAATYYC |
| SEQ ID NO: 648 | AIQMTQSPSSLSASVGDRVTITC | RASQGIRNDLG | WYQQKPGKAPKLLIY | AASSLQS | GVPSRFSGSGSGTDFTLTISSLQPEDFATYYC |
| SEQ ID NO: 649 | DIQMTQSPSSLSASVGDRVTITC | RASQGISNYLA | WYQQKPGKVPKLLIY | AASTLQS | GVPSRFSGSGSGTDFTLTISSLQPEDVATYYC |
| SEQ ID NO: 650 | DIQMTQSPSTLSASVGDRVTITC | RSQSISSWLA | WYQQKPGKAPKLLIY | KASSLES | GVPSRFSGSGSGTEFTLTISSLQPDDFATYYC |
| SEQ ID NO: 651 | AIQMTQSPSSLSASVGDRVTITC | QASQSINNELS | WYQQKPGKAPKLLIY | RASTLAS | GVPSRFSGSGSGTDFTLTISSLQPEDFATYYC |
| SEQ ID NO: 651 | AIQMTQPSSLSASVGDRVTITC | QASQSINNELS | WYQQKPGKAPKLLIY | RASTLAS | GVPSRFSGSGSGTDFTLTISSLQPEDFATYYC |

| | CDR3 | FR4 |
|---|---|---|
| SEQ ID NO: 647 | QQGYSLRNIDNA | FGGGTEVVVKR |
| SEQ ID NO: 648 | | |
| SEQ ID NO: 649 | | FGGGTKVEIKR |
| SEQ ID NO: 650 | | |
| SEQ ID NO: 651 | QQGYSLRNIDNA | FGGGTKVEIKR |
| SEQ ID NO: 651 | QQGYSLRNIDNA | FGGGTKVEIKR |

| | FR1 | CDR1 | FR2 | CDR2 | FR3 |
|---|---|---|---|---|---|
| SEQ ID NO: 652 | -QSLEESGGRLVTPGTPLTLTCTASGFSLS | NYYVT | WVRQAPGKGLEWIG | IIYG-SDETAYATWAIG | RFTISKTST--TVDLKMTSLTAADTATYFCAR |
| SEQ ID NO: 653 | EVQLVESGGGLVQPGGSLRLSCAASGFTVS | SNYMS | WVRQAPGKGLEWVS | VIYS-GGSTYYADSVKG | RFTISRDNSKNTLYLQMNSLRAEDTAVYYCAR |
| SEQ ID NO: 654 | EVQLVESGGGLIQPGGSLRLSCAASGFTVS | SNYMS | WVRQAPGKGLEWVS | VIYS-GGSTYYADSVKG | RFTISRDNSKNTLYLQMNSLRAEDTAVYYCAR |
| SEQ ID NO: 655 | EVQLLESGGGLVQPGGSLRLSCAASGFTFS | SYAMS | WVRQAPGKGLEWVS | VIYSGGSSTYYADSVKG | RFTISRDNSKNTLYLQMNSLRAEDTAVYYCAK |
| SEQ ID NO:656 | EVQLVESGGGLVQPGGSLRLSCAASGFSLS | NYYVT | WVRQAPGKGLEWVG | IIYG-SDETAYATWAIG | RFTISRDNSKNTLYLQMNSLRAEDTAVYYCAR |
| SEQ ID NO: 657 | EVQLVESGGGLVQPGGSLRLSCAASGFSLS | NYYVT | WVRQAPGKGLEWVG | IIYG-SDETAYATSAIG | RFTISRDNSKNTLYLQMNSLRAEDTAVYYCAR |

| | CDR3 | FR4 |
|---|---|---|
| SEQ ID NO: 652 | DDSSDWDAKFNL | WGQGTLVTVSS |
| SEQ ID NO: 653 | | |
| SEQ ID NO: 654 | | WGQGTLVTVSS |
| SEQ ID NO: 655 | | |
| SEQ ID NO: 656 | DDSSDWDAKFNL | WGQGTLVTVSS |
| SEQ ID NO: 657 | DDSSDWDAKFNL | WGQGTLVTVSS |

FIGURE 3 – PREFERRED ANTI-IL-6 ANTIBODY HUMANIZATION

| | FR1 | CDR1 | FR2 | CDR2 | FR3 |
|---|---|---|---|---|---|
| SEQ ID NO: 647 | AYDMTQTPASVSAAVGGTVTIKC | QASQSINNELS | WYQQKPGQRPKLLIY | RASTLAS | GVSSRFKGSGSGTEFTLTISDLECADAATYYC |
| SEQ ID NO: 648 | AIQMTQSPSSLSASVGDRVTITC | RASQGIRNDLG | WYQQKPGKAPKLLIY | AASSLQS | GVPSRFSGSGSGTDFTLTISSLQPEDFATYYC |
| SEQ ID NO: 649 | DIQMTQSPSSLSASVGDRVTITC | RASQGISNYLA | WYQQKPGKVPKLLIY | AASTLQS | GVPSRFSGSGSGTDFTLTISSLQPEDVATYYC |
| SEQ ID NO: 650 | DIQMTQSPSTLSASVGDRVTITC | RASQSISSWLA | WYQQKPGKAPKLLIY | KASSLES | GVPSRFSGSGSGTEFTLTISSLQPDDFATYYC |
| SEQ ID NO: 709 | AIQMTQSPSSLSASVGDRVTITC | QASQSINNELS | WYQQKPGKAPKLLIY | RASTLAS | GVPSRFSGSGSGTDFTLTISSLQPDDFATYYC |
| SEQ ID NO: 709 | AIQMTQSPSSLSASVGDRVTITC | QASQSINNELS | WYQQKPGKAPKLLIY | RASTLAS | GVPSRFSGSGSGTDFTLTISSLQPDDFATYYC |

| | CDR3 | FR4 |
|---|---|---|
| SEQ ID NO: 647 | QQGYSLRNIDNA | FGGGTEVVVKR |
| SEQ ID NO: 648 | | |
| SEQ ID NO: 649 | | FGGGTKVEIKR |
| SEQ ID NO: 650 | | |
| SEQ ID NO: 709 | QQGYSLRNIDNA | FGGGTKVEIKR |
| SEQ ID NO: 709 | QQGYSLRNIDNA | FGGGTKVEIKR |

| | FR1 | CDR1 | FR2 | CDR2 | FR3 |
|---|---|---|---|---|---|
| SEQ ID NO: 652 | -QSLEESGGRLVTPGTPLTLTCTASGFSLS | NYYVT | WVRQAPGKGLEWIG | IIYG-SDETAYATWAIG | RFTISKTST--TVDLKMTSLTAADTATYFCAR |
| SEQ ID NO: 653 | EVQLVESGGGLVQPGGSLRLSCAASGFTVS | SNYMS | WVRQAPGKGLEWVS | VIYS-GGSTYYADSVKG | RFTISRDNSKNTLYLQMNSLRAEDTAVYYCAR |
| SEQ ID NO: 654 | EVQLVESGGGLIQPGGSLRLSCAASGFTVS | SNYMS | WVRQAPGKGLEWVS | VIYS-GGSTYYADSVKG | RFTISRDNSKNTLYLQMNSLRAEDTAVYYCAR |
| SEQ ID NO: 655 | EVQLLESGGGLVQPGGSLRLSCAASGFTFS | SYAMS | WVRQAPGKGLEWVS | VIYSGGSSTYYADSVKG | RFTISRDNSKNTLYLQMNSLRAEDTAVYYCAK |
| SEQ ID NO: 656 | EVQLVESGGGLVQPGGSLRLSCAASGFSLS | NYYVT | WVRQAPGKGLEWVG | IIYG-SDETAYATWAIG | RFTISRDNSKNTLYLQMNSLRAEDTAVYYCAR |
| SEQ ID NO: 657 | EVQLVESGGGLVQPGGSLRLSCAASGFSLS | NYYVT | WVRQAPGKGLEWVG | IIYG-SDETAYATSAIG | RFTISRDNSKNTLYLQMNSLRAEDTAVYYCAR |

| | CDR3 | FR4 |
|---|---|---|
| SEQ ID NO: 652 | DDSSDWDAKFNL | WGQGTLVTVSS |
| SEQ ID NO: 653 | | |
| SEQ ID NO: 654 | | WGQGTLVTVSS |
| SEQ ID NO: 655 | | |
| SEQ ID NO: 656 | DDSSDWDAKFNL | WGQGTLVTVSS |
| SEQ ID NO: 657 | DDSSDWDAKFNL | WGQGTLVTVSS |

FIGURE 4A – Alignment of Ab1 light chains

| | | FR1 | CDR1 | FR2 |
|---|---|---|---|---|
| SEQ ID NO:2 | MDTRAPTQLLGLLLLWLPGARC | AYDMTQTPASVSAAVGGTVTIKC | QASQSINNELS | WYZZKPGQRPKLLIY |
| SEQ ID NO:20 | | IQMTQSPSSLSASVGDRVTITC | QASQSINNELS | WYQQKPGKAPKLLIY |
| SEQ ID NO:647 | | AYDMTQTPASVSAAVGGTVTIKC | QASQSINNELS | WYQQKPGQRPKLLIY |
| SEQ ID NO:651 | | AIQMTQSPSSLSASVGDRVTITC | QASQSINNELS | WYQQKPGKAPKLLIY |
| SEQ ID NO:660 | MDTRAPTQLLGLLLLWLPGARC | AYDMTQTPASVSAAVGGTVTIKC | QASQSINNELS | WYQQKPGQRPKLLIY |
| SEQ ID NO:666 | | IQMTQSPSSLSASVGDRVTITC | QASQSINNELS | WYQQKPGKAPKLLIY |
| SEQ ID NO:699 | | AIQMTQSPSSLSASVGDRVTITC | QASQSINNELS | WYQQKPGKAPKLLIY |
| SEQ ID NO:702 | | AIQMTQSPSSLSASVGDRVTITC | QASQSINNELS | WYQQKPGKAPKLLIY |
| SEQ ID NO:706 | MKWVTFISLLFLFSSAYS | AIQMTQSPSSLSASVGDRVTITC | QASQSINNELS | WYQQKPGKAPKLLIY |
| SEQ ID NO:709 | | AIQMTQSPSSLSASVGDRVTITC | QASQSINNELS | WYQQKPGKAPKLLIY |

| | CDR2 | FRE | CDR3 |
|---|---|---|---|
| SEQ ID NO:2 | RASTLAS | GVSSRFKGSGSGTEFTLTISDLECADAATYYC | QQGYSLRNIDNA |
| SEQ ID NO:20 | RASTLAS | GVPSRFSGSGSGTDFTLTISSLQPDDFATYYC | QQGYSLRNIDNA |
| SEQ ID NO:647 | RASTLAS | GVSSRFKGSGSGTEFTLTISDLECADAATYYC | QQGYSLRNIDNA |
| SEQ ID NO:651 | RASTLAS | GVPSRFSGSGSGTDFTLTISSLQPEDFATYYC | QQGYSLRNIDNA |
| SEQ ID NO:660 | RASTLAS | GVSSRFKGSGSGTEFTLTISDLECADAATYYC | QQGYSLRNIDNA |
| SEQ ID NO:666 | RASTLAS | GVPSRFSGSGSGTDFTLTISSLQPDDFATYYC | QQGYSLRNIDNA |
| SEQ ID NO:699 | RASTLAS | GVPSRFSGSGSGTDFTLTISSLQPDDFATYYC | QQGYSLRNIDNA |
| SEQ ID NO:702 | RASTLAS | GVPSRFSGSGSGTDFTLTISSLQPDDFATYYC | QQGYSLRNIDNA |
| SEQ ID NO:706 | RASTLAS | GVPSRFSGSGSGTDFTLTISSLQPDDFATYYC | QQGYSLRNIDNA |
| SEQ ID NO:709 | RASTLAS | GVPSRFSGSGSGTDFTLTISSLQPDDFATYYC | QQGYSLRNIDNA |

FIGURE 4B – Alignment of Ab1 light chains (continued)

```
                   FR4              kappa constant light chain
SEQ ID NO:2   FGGGTEVVVKR T VAAPSVFIFPPSDEQLKSGTASVVCLLNN
SEQ ID NO:20
SEQ ID NO:647 FGGGTEVVVKR
SEQ ID NO:651 FGGGTKVEIKR
SEQ ID NO:660
SEQ ID NO:666 FGGGTKVEIKR T VAAPSVFIFPPSDEQLKSGTASVVCLLNNFYPREAKVQWKVDNALQSGN
SEQ ID NO:699 FGGGTKVEIKR T
SEQ ID NO:702 FGGGTKVEIKR T VAAPSVFIFPPSDEQLKSGTASVVCLLNNFYPREAKVQWKVDNALQSGN
SEQ ID NO:706 FGGGTKVEIKR T VAAPSVFIFPPSDEQLKSGTASVVCLLNNFYPREAKVQWKVDNALQSGN
SEQ ID NO:709 FGGGTKVEIKR

                kappa constant light chain (continued)

SEQ ID NO:2
SEQ ID NO:20
SEQ ID NO:647
SEQ ID NO:651
SEQ ID NO:660
SEQ ID NO:666 SQESVTEQDSKDSTYSLSSTLTLSKADYEKHKVYACEVTHQGLSSPVTKSFNRGEC
SEQ ID NO:699
SEQ ID NO:702 SQESVTEQDSKDSTYSLSSTLTLSKADYEKHKVYACEVTHQGLSSPVTKSFNRGEC
SEQ ID NO:706 SQESVTEQDSKDSTYSLSSTLTLSKADYEKHKVYACEVTHQGLSSPVTKSFNRGEC
SEQ ID NO:709
```

FIGURE 5A – Alignment of Ab1 heavy chains

| | | FR1 | CDR1 | FR2 |
|---|---|---|---|---|
| SEQ ID NO:3 | METGLRWLLLVAVLKGVQC | -QSLEESGGRLVTPGTPLTLTCTASGFSLS | NYYVT | WVRQAPGKGLEWIG |
| SEQ ID NO:18 | | EVQLVESGGGLVQPGGSLRLSCAASGFSLS | NYYVT | WVRQAPGKGLEWVG |
| SEQ ID NO:19 | | EVQLVESGGGLVQPGGSLRLSCAASGFSLS | NYYVT | WVRQAPGKGLEWVG |
| SEQ ID NO:652 | | -QSLEESGGRLVTPGTPLTLTCTASGFSLS | NYYVT | WVRQAPGKGLEWIG |
| SEQ ID NO:656 | | EVQLVESGGGLVQPGGSLRLSCAASGFSLS | NYYVT | WVRQAPGKGLEWVG |
| SEQ ID NO:657 | | EVQLVESGGGLVQPGGSLRLSCAASGFSLS | NYYVT | WVRQAPGKGLEWVG |
| SEQ ID NO:658 | METGLRWLLLVAVLKGVQC | -QSLEESGGRLVTPGTPLTLTCTASGFSLS | NYYVT | WVRQAPGKGLEWIG |
| SEQ ID NO:661 | METGLRWLLLVAVLKGVQC | -QSLEESGGRLVTPGTPLTLTCTASGFSLS | NYYVT | WVRQAPGKGLEWIG |
| SEQ ID NO:664 | | EVQLVESGGGLVQPGGSLRLSCAASGFSLS | NYYVT | WVRQAPGKGLEWVG |
| SEQ ID NO:665 | | EVQLVESGGGLVQPGGSLRLSCAASGFSLS | NYYVT | WVRQAPGKGLEWVG |
| SEQ ID NO:704 | | EVQLVESGGGLVQPGGSLRLSCAASGFSLS | NYYVT | WVRQAPGKGLEWVG |
| SEQ ID NO:708 | MKWVTFISLLFLFSSAYS | EVQLVESGGGLVQPGGSLRLSCAASGFSLS | NYYVT | WVRQAPGKGLEWVG |

| | CDR2 | FR3 | CDR3 | FR4 |
|---|---|---|---|---|
| SEQ ID NO:3 | IIYG-SDETAYATWAIG | RFTISKTST--TVDLKMTSLTAADTATYFCAR | DDSSDWDAKFNL | WGQGTLVTVSS |
| SEQ ID NO:18 | IIYG-SDETAYATWAIG | RFTISRDNSKNTLYLQMNSLRAEDTAVYYCAR | DDSSDWDAKFNL | |
| SEQ ID NO:19 | IIYG-SDETAYAT**S**AIG | RFTISRDNSKNTLYLQMNSLRAEDTAVYYCAR | DDSSDWDAKFNL | |
| SEQ ID NO:652 | IIYG-SDETAYAT**W**AIG | RFTISKTST--TVDLKMTSLTAADTATYFCAR | DDSSDWDAKFNL | WGQGTLVTVSS |
| SEQ ID NO:656 | IIYG-SDETAYATWAIG | RFTISRDNSKNTLYLQMNSLRAEDTAVYYCAR | DDSSDWDAKFNL | WGQGTLVTVSS |
| SEQ ID NO:657 | IIYG-SDETAYAT**S**AIG | RFTISRDNSKNTLYLQMNSLRAEDTAVYYCAR | DDSSDWDAKFNL | WGQGTLVTVSS |
| SEQ ID NO:658 | IIYG-SDETAYAT**S**AIG | RFTISKTST--TVDLKMTSLTAADTATYFCAR | DDSSDWDAKFNL | WGQGTLVTVSS |
| SEQ ID NO:661 | IIYG-SDETAYAT**W**AIG | RFTISKTST--TVDLKMTSLTAADTATYFCAR | DDSSDWDAKFNL | |
| SEQ ID NO:664 | IIYG-SDETAYATWAIG | RFTISRDNSKNTLYLQMNSLRAEDTAVYYCAR | DDSSDWDAKFNL | WGQGTLVTVSS |
| SEQ ID NO:665 | IIYG-SDETAYAT**S**AIG | RFTISRDNSKNTLYLQMNSLRAEDTAVYYCAR | DDSSDWDAKFNL | WGQGTLVTVSS |
| SEQ ID NO:704 | IIYG-SDETAYAT**S**AIG | RFTISRDNSKNTLYLQMNSLRAEDTAVYYCAR | DDSSDWDAKFNL | WGQGTLVTVSS |
| SEQ ID NO:708 | IIYG-SDETAYAT**S**AIG | RFTISRDNSKNTLYLQMNSLRAEDTAVYYCAR | DDSSDWDAKFNL | WGQGTLVTVSS |

FIGURE 5B – Alignment of Ab1 heavy chains, continued

```
                gamma-1 constant heavy chain polypeptide
SEQ ID NO:3     ASTKGPSVFPLAPSSKSTSGGTAALGCLVK
SEQ ID NO:658   ASTKGPSVFPLAPSSKSTSGGTAALGCLVK

SEQ ID NO:664   ASTKGPSVFPLAPSSKSTSGGTAALGCLVKDYFPEPVTVSWNSGALTSGVHTFPAVLQSSGLYSLSSVVTVPSSS
SEQ ID NO:665   ASTKGPSVFPLAPSSKSTSGGTAALGCLVKDYFPEPVTVSWNSGALTSGVHTFPAVLQSSGLYSLSSVVTVPSSS
SEQ ID NO:704   ASTKGPSVFPLAPSSKSTSGGTAALGCLVKDYFPEPVTVSWNSGALTSGVHTFPAVLQSSGLYSLSSVVTVPSSS
SEQ ID NO:708   ASTKGPSVFPLAPSSKSTSGGTAALGCLVKDYFPEPVTVSWNSGALTSGVHTFPAVLQSSGLYSLSSVVTVPSSS

                gamma-1 constant heavy chain polypeptide, continued
SEQ ID NO:664   LGTQTYICNVNHKPSNTKVDKRVEPKSCDKTHTCPPCPAPELLGGPSVFLFPPKPKDTLMISRTPEVTCVVVDVS
SEQ ID NO:665   LGTQTYICNVNHKPSNTKVDKRVEPKSCDKTHTCPPCPAPELLGGPSVFLFPPKPKDTLMISRTPEVTCVVVDVS
SEQ ID NO:704   LGTQTYICNVNHKPSNTKVDKRVEPKSCDKTHTCPPCPAPELLGGPSVFLFPPKPKDTLMISRTPEVTCVVVDVS
SEQ ID NO:708   LGTQTYICNVNHKPSNTKVDKRVEPKSCDKTHTCPPCPAPELLGGPSVFLFPPKPKDTLMISRTPEVTCVVVDVS

                gamma-1 constant heavy chain polypeptide, continued
SEQ ID NO:664   HEDPEVKFNWYVDGVEVHNAKTKPREEQYASTYRVVSVLTVLHQDWLNGKEYKCKVSNKALPAPIEKTISKAKGQ
SEQ ID NO:665   HEDPEVKFNWYVDGVEVHNAKTKPREEQYASTYRVVSVLTVLHQDWLNGKEYKCKVSNKALPAPIEKTISKAKGQ
SEQ ID NO:704   HEDPEVKFNWYVDGVEVHNAKTKPREEQYASTYRVVSVLTVLHQDWLNGKEYKCKVSNKALPAPIEKTISKAKGQ
SEQ ID NO:708   HEDPEVKFNWYVDGVEVHNAKTKPREEQYASTYRVVSVLTVLHQDWLNGKEYKCKVSNKALPAPIEKTISKAKGQ

                gamma-1 constant heavy chain polypeptide, continued
SEQ ID NO:664   PREPQVYTLPPSRDELTKNQVSLTCLVKGFYPSDIAVEWESNGOPENNYKTTPPVLDSDGSFFLYSKLTVDKSRW
SEQ ID NO:665   PREPQVYTLPPSRDELTKNQVSLTCLVKGFYPSDIAVEWESNGQPENNYKTTPPVLDSDGSFFLYSKLTVDKSRW
SEQ ID NO:704   PREPQVYTLPPSREEMTKNQVSLTCLVKGFYPSDIAVEWESNGQPENNYKTTPPVLDSDGSFFLYSKLTVDKSRW
SEQ ID NO:708   PREPQVYTLPPSREEMTKNQVSLTCLVKGFYPSDIAVEWESNGQPENNYKTTPPVLDSDGSFFLYSKLTVDKSRW

                gamma-1 constant heavy chain polypeptide, continued
SEQ ID NO:664   QQGNVFSCSVMHEALHNHYTQKSLSLSPGK
SEQ ID NO:665   QQGNVFSCSVMHEALHNHYTQKSLSLSPGK
SEQ ID NO:704   QQGNVFSCSVMHEALHNHYTQKSLSLSPGK
SEQ ID NO:708   QQGNVFSCSVMHEALHNHYTQKSLSLSPGK
```

*p<0.05 versus placebo using Wilcoxon Rank Sum Test. SC=subcutaneous; IV=intravenous

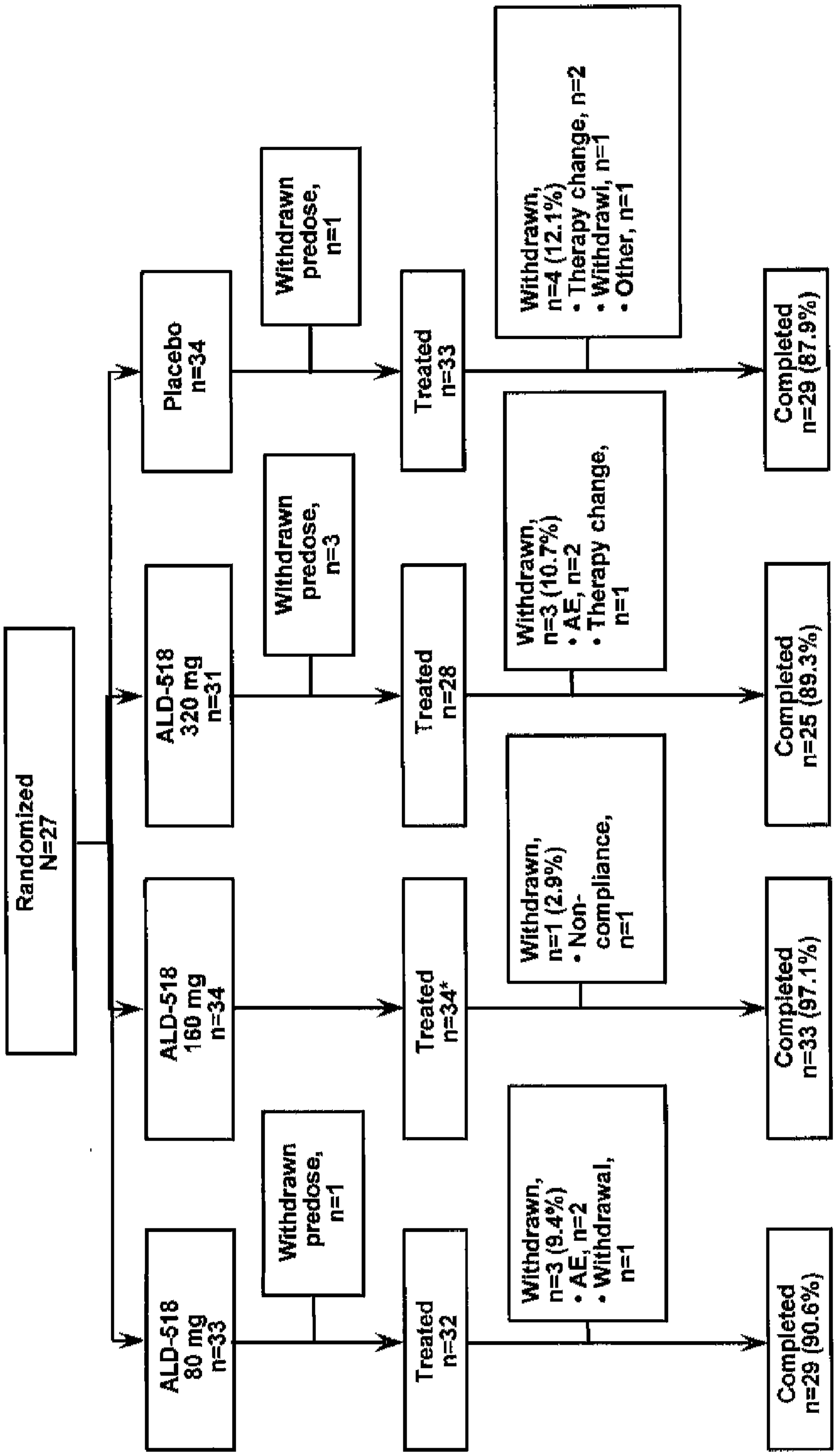
FIG. 26 Patient Disposition

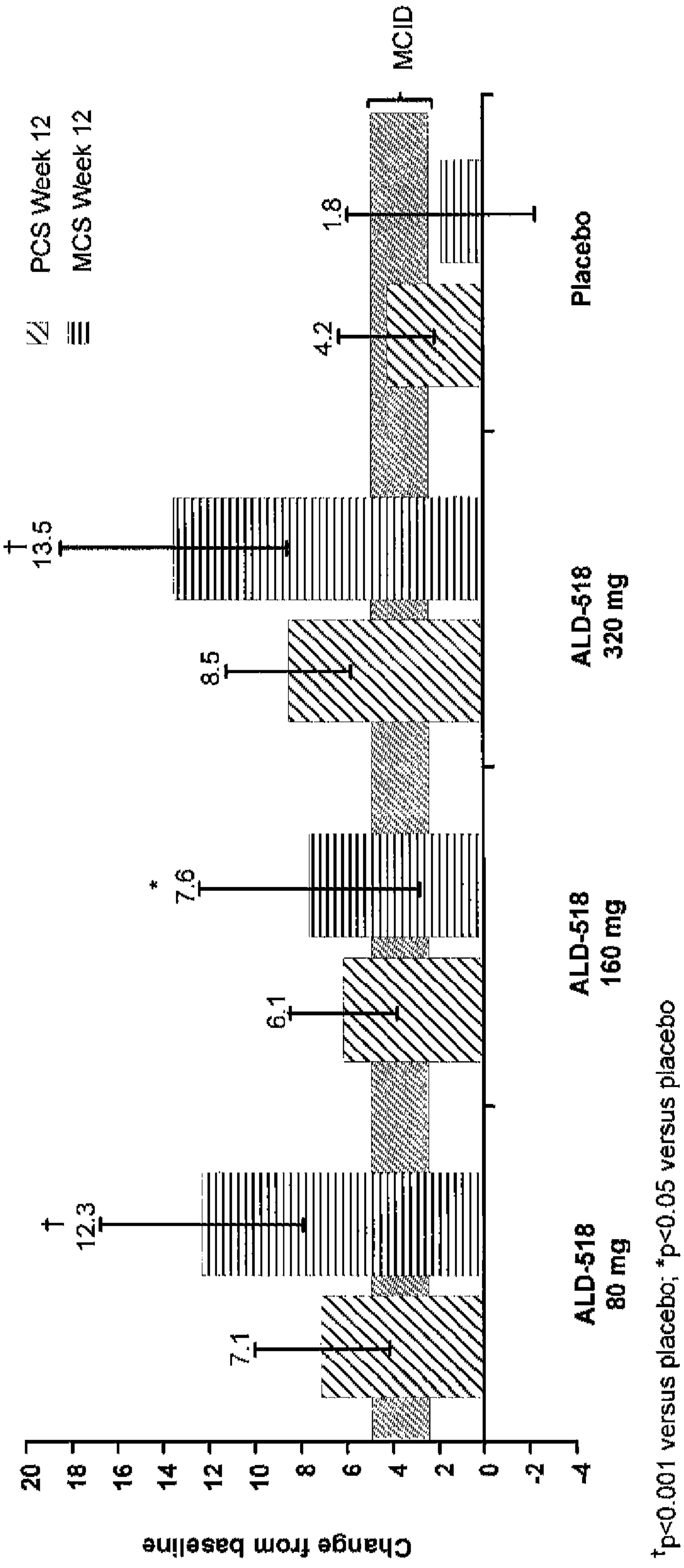
†p<0.001 versus placebo; *p<0.05 versus placebo
FIG 27 Mean Changes in SF-36 Composite Scores at Week 12

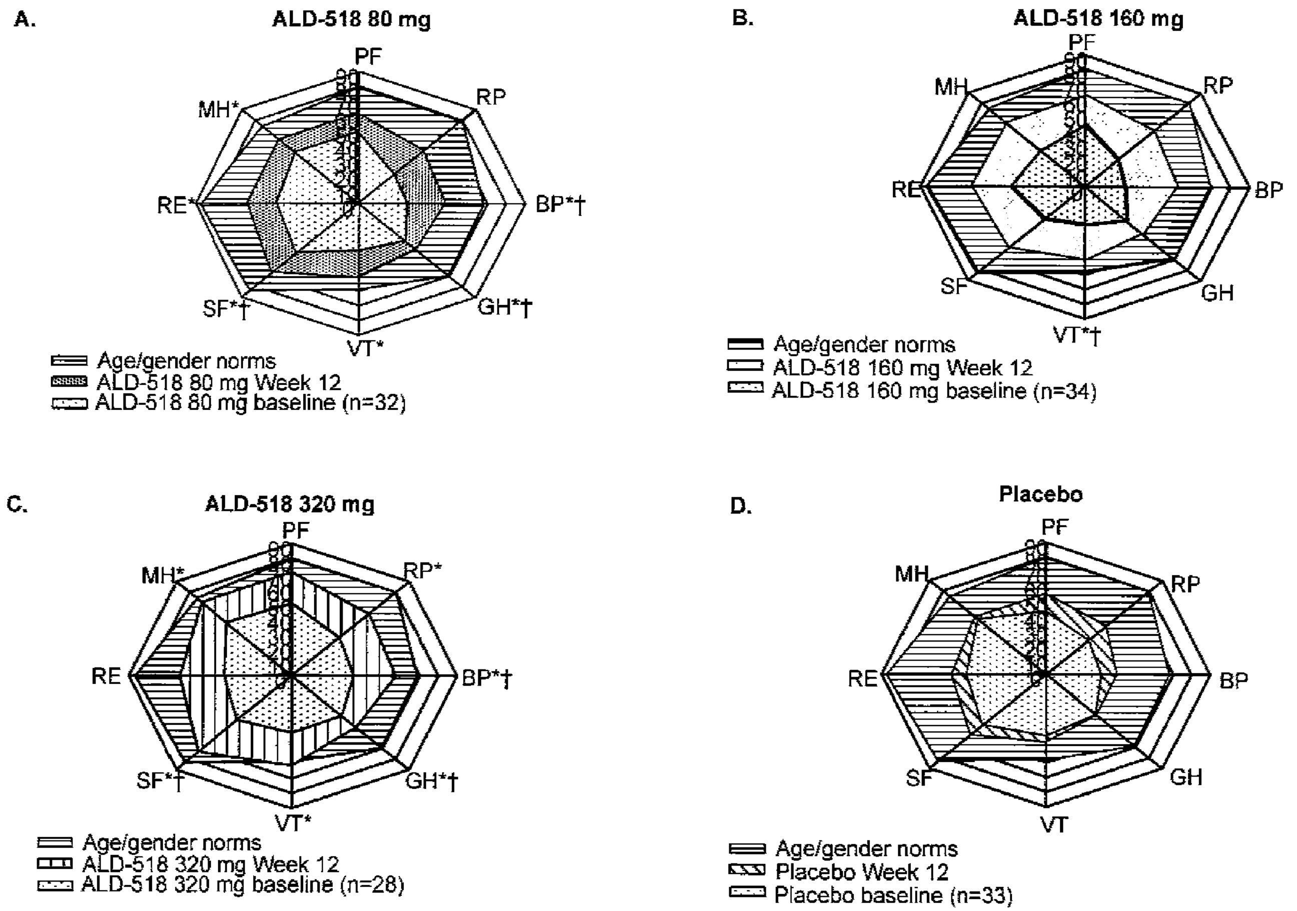
*$p<0.05$ for ALD-518 dose versus placebo at Week 12; †$p<0.05$ for ALD-518 dose versus placebo at Week 12 and maintained to Week 16;
FIG 28 Changes from Baseline to Week 12 in SF-36 Domain Scores Compared with Age/Gender Matched Norms

FIG 29 Changes from Baseline to Weeks 12 and 16 in SF-36 Domain Scores Compared with Age/Gender Matched Norms
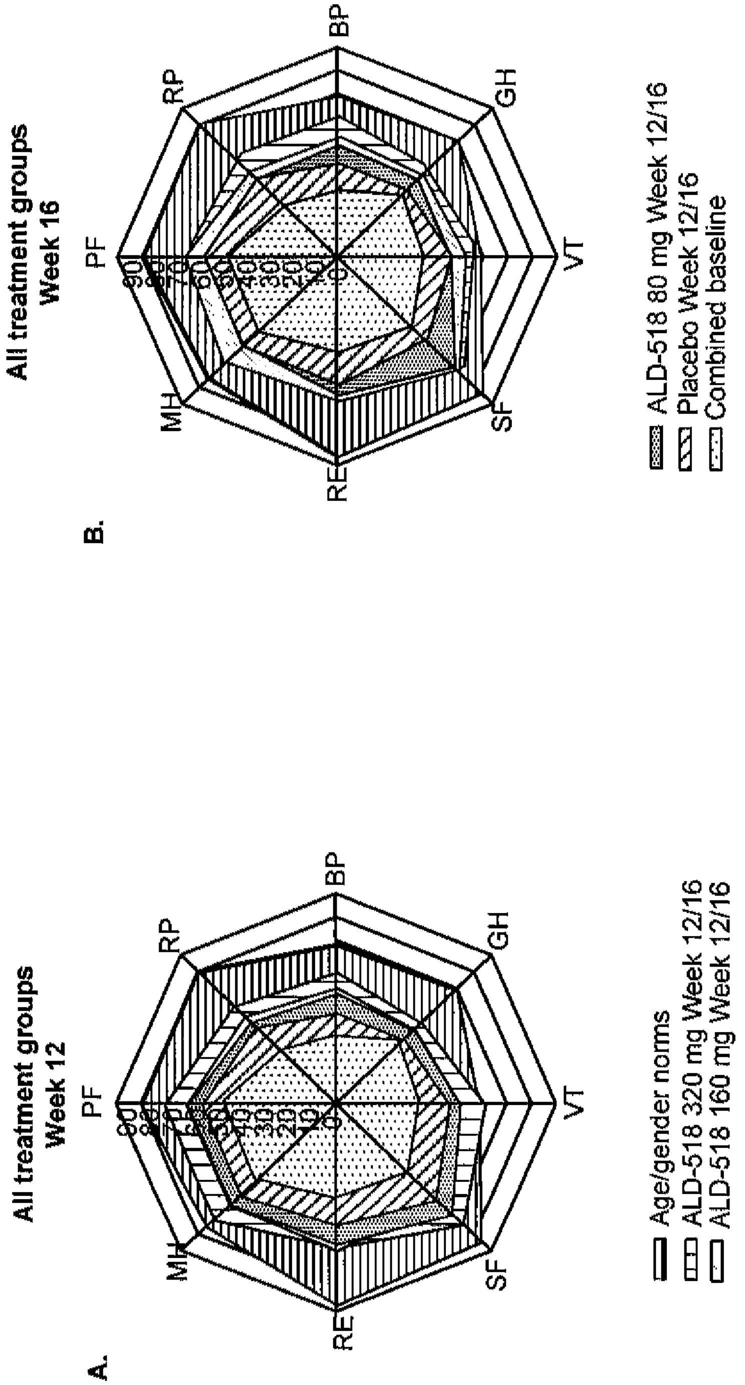

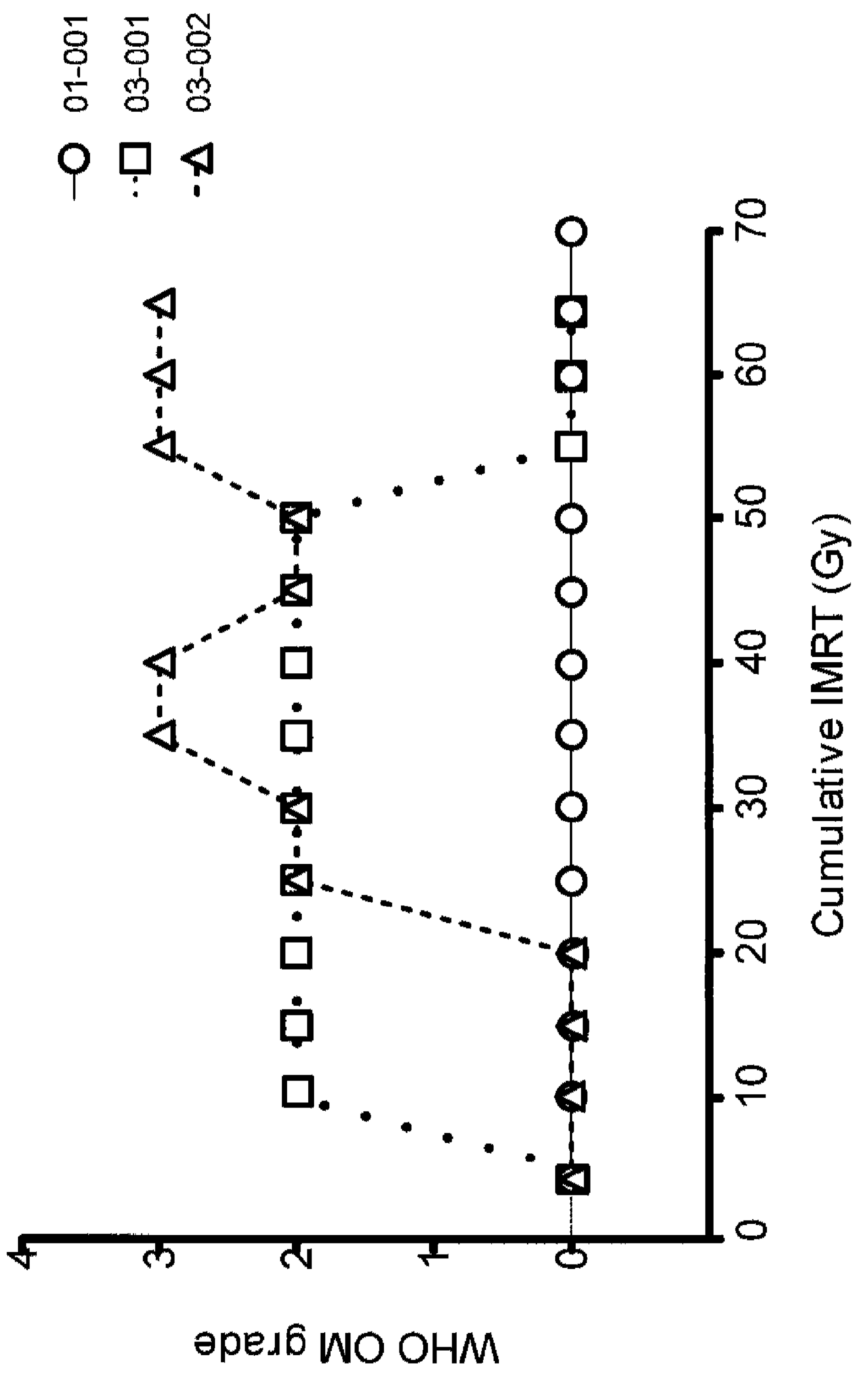
FIG 30 WHO oral mucositis grade versus cumulative IMRT (Gy): ALD518 160 mg intravenous at week 0 and week 4

ANTI-IL-6 ANTIBODIES FOR THE TREATMENT OF ORAL MUCOSITIS

CROSS-REFERENCE TO RELATED APPLICATIONS

This patent application claims priority to U.S. Provisional Patent Application No. 61/416,332, filed Nov. 23, 2010; U.S. Provisional Patent Application No. 61/416,343, filed Nov. 23, 2010; U.S. Provisional Patent Application No. 61/416,351, filed Nov. 23, 2010; U.S. Provisional Patent Application No. 61/416,363, filed Nov. 23, 2010; U.S. Provisional Patent Application No. 61/511,797, filed Jul. 26, 2011; and U.S. Provisional Patent Application No. 61/489,857, filed May 25, 2011, the disclosures of each of which are herein incorporated by reference in their entirety.

FIELD OF THE INVENTION

IL-6 antagonists, including anti-IL-6 antibodies and antibody fragments thereof, may be used to reduce C-reactive protein ("CRP levels") and inflammation and in methods and compositions for the treatment and prevention of mucositis, including oral, alimentary, and gastrointestinal tract mucositis.

BACKGROUND OF THE INVENTION

Interleukin-6 (IL-6)

Interleukin-6 ("IL-6") is a multifunctional cytokine involved in numerous biological processes such as the regulation of the acute inflammatory response, the modulation of specific immune responses including B- and T-cell differentiation, bone metabolism, thrombopoiesis, epidermal proliferation, menses, neuronal cell differentiation, neuroprotection, aging, cancer, and the inflammatory reaction occurring in Alzheimer's disease. See Papassotiropoulos, et al. (2001) *Neurobiology of Aging* 22: 863-871.

IL-6 is a member of a family of cytokines that promote cellular responses through a receptor complex consisting of at least one subunit of the signal-transducing glycoprotein gp130 and the IL-6 receptor ("IL-6R") (also known as gp80). The IL-6R may also be present in a soluble form ("sIL-6R"). IL-6 binds to IL-6R, which then dimerizes the signal-transducing receptor gp130. See Jones (2005) *Immunology* 175: 3463-3468.

IL-6 is a pleiotropic pro-inflammatory cytokine, which regulates the acute phase response and the transition from the innate to the adaptive immune response. IL-6 increases hepatic synthesis of proteins that are involved in the 'acute phase response' leading to symptoms such as fever, chills, and fatigue. It stimulates B cell differentiation and secretion of antibodies and prevents apoptosis of activated B cells. IL-6 activates and induces proliferation of T cells and in the presence of IL-2, induces differentiation of mature and immature CD8 T cells into cytotoxic T cells. IL-6 is also involved in the differentiation of Th17 cells and IL-17 production and inhibits regulatory T cells (Treg) differentiation. IL-6 also activates osteoclasts, synoviocytes, neutrophils, and other hematopoietic cells. Park, et al. (2007) *Bulletin of the NYU Hospital for Joint Diseases* 65 (suppl 1): S4-10; Guerne, et al. (1989) *J Clin Invest.* 83(2): 585-92; Houssiau, et al. (1988) *Arthritis Rheum.* 31(6): 784-8; Nishimotor, et al. (2006) *Nat Clin Pract Rheumatol.* 2(11): 619-26; Kishimoto (1989) *Blood* 74(1): 1-10; and Van Snick (1990) *Annu Rev Immunol.* 8: 253-78.

In humans, the gene encoding IL-6 is organized in five exons and four introns, and maps to the short arm of chromosome 7 at 7p21. Translation of IL-6 RNA and post-translational processing result in the formation of a 21 to 28 kDa protein with 184 amino acids in its mature form. See Papassotiropoulos, et al. (2001) *Neurobiology of Aging* 22:863-871.

The function of IL-6 is not restricted to the immune response as it acts in hematopoiesis, thrombopoiesis, osteoclast formation, elicitation of hepatic acute phase response resulting in the elevation of C-reactive protein (CRP) and serum amyloid A (SAA) protein. It is known to be a growth factor for epidermal keratinocytes, renal mesangial cells, myeloma and plasmacytoma cells. Grossman, et al. (1989) *Prot Natl Acad Sci.* 86(16): 6367-6371; Horii, et al. (1989) *J Immunol.* 143(12): 3949-3955; and Kawano, et al. (1988) *Nature* 332: 83-85. IL-6 is produced by a wide range of cell types including monocytes/macrophages, fibroblasts, epidermal keratinocytes, vascular endothelial cells, renal messangial cells, glial cells, condrocytes, T and B-cells and some tumor cells. Akira, et al. (1990) *FASEB J.* 4(11): 2860-2867. Except for tumor cells that constitutively produce IL-6, normal cells do not express IL-6 unless appropriately stimulated.

Elevated IL-6 levels have been observed in many types of cancer, including breast cancer, leukemia, ovarian cancer, prostate cancer, pancreatic cancer, lymphoma, lung cancer, renal cell carcinoma, colorectal cancer, and multiple myeloma. See, e.g., Chopra, et al. (2004) *MJAF* 160:45-49; Songur, et al. (2004) *Tumori* 90:196-200; Slay, et al. (1992) *Cancer Research* 52: 3317-3322; Nikiteas, et al. (2005) *World J. Gasterenterol.* 11:1639-1643; reviewed in Heikkila, et al. (2008) *Eur J Cancer* 44:937-945. Clinical studies (reviewed in Trikha, et al. (2003) *Clinical Cancer Research* 9: 4653-4665) have shown some improvement in patient outcomes due to administration of various anti-IL-6 antibodies, particularly in those cancers in which IL-6 plays a direct role promoting cancer cell proliferation or survival.

As noted above, IL-6 stimulates the hepatic acute phase response, resulting in increased production of CRP and elevated serum CRP levels. For this reason, C-reactive protein (CRP) has been reported to comprise a surrogate marker of IL-6 activity. Thus, elevated IL-6 activity can be detected through measurement of serum CRP. Conversely, effective suppression of IL-6 activity, e.g., through administration of a neutralizing anti-IL-6 antibody, can be detected by the resulting decrease in serum CRP levels.

IL-6 is believed to play a role in the development of a multitude of diseases and disorders, including but not limited to fatigue, cachexia, autoimmune diseases, diseases of the skeletal system, cancer, heart disease, obesity, diabetes, asthma, Alzheimer's disease and multiple sclerosis. See, e.g., WO 2011/066374, WO 2011/066371, WO 2011/066378, and WO 2011/066369.

A recent clinical trial demonstrated that administration of rosuvastatin to apparently healthy individuals having elevated CRP (greater than 2.0 mg/l) reduced their CRP levels by 37% and greatly decreased the incidence of myocardial infarction, stroke, arterial revascularization, hospitalization for unstable angina, or death from cardiovascular causes. Ridker et al., N Engl J Med. 2008 Nov. 9 [ Epub ahead of print].

In addition to its direct role in pathogenesis of some cancers and other diseases, chronically elevated IL-6 levels appear to adversely affect patient well-being and quality of life. For example, elevated IL-6 levels have been reported to be associated with cachexia and fever, and reduced serum albumin. Gauldie, et al. (1987) *PNAS* 84: 7251-7253; Heinric, et al. (1990) *Biochem J.* 265(3): 621-636; Zamir, et al. (1993) *Metabolism* 42: 204-208; Zamir, et al. (1992) *Arch Surg* 127:

170-174. Inhibition of IL-6 by a neutralizing antibody has been reported to ameliorate fever and cachexia in cancer patients, though improvement in these patients' serum albumin level has not been reported. Emilie, et al. (1994) *Blood* 84: 2472-2479; Blay, et (1992) *Cancer Research* 52: 3317-3322; Bataille, et al. (1995) *Blood* 86: 685-691.

Mucositis

Mucositis is the painful inflammation and ulceration of the mucous membranes lining the digestive tract, usually as an adverse effect of chemotherapy and radiotherapy treatment for cancer. Ridge, et al. "Head and Neck Tumors" in Pazdur R, Wagman L D, Camphausen K A, Hoskins W J (Eds) Cancer Management: A Multidisciplinary Approach. [11 Ed.] (2008). Mucositis can occur anywhere along the gastrointestinal (GI) tract. Oral mucositis is marked by inflammation and ulceration in the mouth and is a common and often debilitating complication of cancer treatment. Sonis (2004) *J Supportive Oncology* 2(Suppl 3): 3-8.

Oral and gastrointestinal mucositis is a toxicity of many forms of radiotherapy and chemotherapy. It has a significant impact on health, quality of life and economic outcomes that are associated with treatment. It also indirectly affects the success of antineoplastic therapy by limiting the ability of patients to tolerate optimal tumoricidal treatment. The complex pathogenesis of mucositis has only recently been appreciated and reflects the dynamic interactions of all of the cells and tissue types that comprise the epithelium and submucosa. The identification of the molecular events that lead to treatment-induced mucosal injury has provided targets for mechanistically based interventions to prevent and treat mucositis.

Historically, mucositis was thought to arise solely as a consequence of epithelial injury. It was hypothesized that radiation or chemotherapy nonspecifically targeted the rapidly proliferating cells of the basal epithelium, causing the loss of the ability of the tissue to renew itself. The atrophy, thinning and ulceration of the mucosal epithelium that is associated with mucositis was thought to be a consequence of these events. Furthermore, it was believed that the process was facilitated by trauma and oral microorganisms.

Radiation-induced mucositis was typically recognized as an 'outside-in' process, in which DNA strand breaks occurred in oral basal-epithelial cells. Chemotherapy-induced mucositis has mainly been attributed to basal-cell damage that results when drugs permeate to these cells from the submucosal blood supply. A role for saliva-borne chemotherapeutic agents in the induction of mucositis has been also been proposed, but not proven. Chemotherapy-induced mucositis can be further compounded by concomitant myelosuppression.

Radiation- or chemotherapy-induced mucositis is initiated by direct injury to basal epithelial cells and cells in the underlying tissue. DNA-strand breaks can result in cell death or injury. Non-DNA injury is initiated through a variety of mechanisms, some of which are mediated by the generation of reactive oxygen species. Radiation and chemotherapy are effective activators of several injury-producing pathways in endothelia, fibroblasts and epithelia. In these cells, the activation of transcription factors such as nuclear factor-κB (NF-κB) and NRF2 leads to the upregulation of genes that modulate the damage response. Immune cells (macrophages) produce pro-inflammatory cytokines, such as tumour-necrosis factor-α (TNF-α) and interleukin 6, which causes further tissue injury. These signaling molecules also participate in a positive-feedback loop that amplifies the original effects of radiation and chemotherapy. For example, TNF-α activates NF-κB and sphingomyelinase activity in the mucosa, leading to more cell death. In addition, direct and indirect damage to epithelial stem cells results in a loss of renewal capacity. As a result, the epithelium begins to thin and patients start to experience the early symptoms of mucositis.

Mucositis is observed during chemotherapeutic or radiation treatment of many different cancers including head and neck cancer, multiple myeloma, colorectal cancers, Because of the problems caused by mucositis which may preclude further radiation or chemotherapy and also impede nutrition because of the discomfort caused by mucositis during swallowing and digestion The most common symptoms of mucositis include redness, dryness, or swelling of the mouth, burning or discomfort when eating or drinking, open sores in the mouth and throat, abdominal cramps, and tenderness or rectal redness or ulcers. Essentially mucositis involves the inflammation of the lining of the mouth and digestive tract, and frequently occurs in cancer patients after chemotherapy and radiation therapy. The cheek, gums, soft plate, oropharynx, top and sides of tongue, and floor of the mouth may be affected, as well as the esophagus and rectal areas. Along with redness and swelling, patients typically experience a strong, burning pain.

Oral and gastrointestinal (GI) mucositis can affect up to 100% of patients undergoing high-dose chemotherapy and hematopoietic stem cell transplantation (HSCT), 80% of patients with malignancies of the head and neck receiving radiotherapy, and a wide range of patients receiving chemotherapy. Alimentary tract mucositis increases mortality and morbidity and contributes to rising health care costs. Rubenstein, et al. (2004) *Cancer* 100(9 Suppl): 2026-46.

For most cancer treatment, about 5-15% of patients get mucositis. However, with 5-fluorouracil (5-FU), up to 40% get mucositis, and 10-15% get grade 3-4 oral mucositis. Irinotecan is associated with severe GI mucositis in over 20% of patients. 75-85% of bone marrow transplantation recipients experience mucositis, of which oral mucositis is the most common and most debilitating, especially when melphalan is used. In grade 3 oral mucositis, the patient is unable to eat solid food, and in grade 4, the patient is unable to consume liquids as well. Rubenstein, et al., (2004) *Cancer* 100(9 Suppl): 2026-46.

Radiotherapy to the head and neck or to the pelvis or abdomen is associated with Grade 3 and Grade 4 oral or GI mucositis, respectively, often exceeding 50% of patients. Among patients undergoing head and neck radiotherapy, pain and decreased oral function may persist long after the conclusion of therapy. Fractionated radiation dosage increases the risk of mucositis to >70% of patients in most trials. Oral mucositis is particularly profound and prolonged among HSCT recipients who receive total-body irradiation. Rubenstein, et al., (2004) *Cancer* 100(9 Suppl): 2026-46.

Although there are factors that increase the likelihood and severity of mucositis, there is no reliable manner to predict who will be affected. Not only is mucositis more common in elderly patients, the degree of breakdown is often more debilitating. The severity of mucositis tends to be increased if a patient exercises poor oral hygiene or has a compromised nutritional status. A preexisting infection or irritation to the mucous membrane may also result in a more severe case of mucositis.

The types of drug used to treat cancer and the schedule by which they are given may influence the risk of developing mucositis. Doxorubicin and methotrexate, for example, frequently cause mucositis. The chemotherapy agent fluorouracil does not usually severely affect the mucous membranes when administered in small doses over continuous intravenous (IV) infusion. When the schedule is adjusted so that a higher dose is given over a shorter period of time (typically over five days), fluorouracil can cause very severe, painful, dose-limiting cases of mucositis. Patients undergoing treatment with high-dose chemotherapy and bone marrow rescue often develop mucositis.

In addition, mucositis also tends to develop in radiation therapy administered to the oral cavity, or in dosages that exceed 180 cGy per day over a five-day period. Combination therapy, either multiple chemotherapy agents or chemotherapy and radiation therapy to the oral cavity, can increase the incidence of mucositis.

Currently there is no real cure for mucositis, treatment is aimed at prevention and management of symptoms. Mucositis typically resolves a few weeks after treatment as the cells regenerate, and treatment cessation is only occasionally required. In some cases, drug therapy will be altered so that a less toxic agent is given.

Patients at risk for mucositis should be meticulous about their oral hygiene, brushing frequently with a soft toothbrush and flossing carefully with unwaxed dental floss. If bleeding of the gums develops, patients should replace their toothbrushes with soft toothettes or gauze. Dentures should also be cleaned regularly. Patients should be well-hydrated, drinking fluids frequently and rinsing the mouth several times a day. Mouthwashes that contain alcohol or hydrogen peroxide should be avoided as they may dry out the mouth and increase pain. Lips should also be kept moist. Physical irritation to the mouth should be avoided. If time permits, dental problems, such as cavities or ill-fitting dentures, should be resolved with a dentist prior to beginning cancer treatment. Patients are generally more comfortable eating mild, medium-temperature foods. Spicy, acidic, very hot or very cold foods can irritate the mucosa. Tobacco and alcohol should also be avoided.

Hospital personnel and the patients themselves should inspect the mouth frequently to look for signs and symptoms of mucositis. Evidence of mucositis (inflammation, white or yellow shiny mucous membranes developing into red, raw, painful membranes) may be present as early as four days after chemotherapy administration. Sodium bicarbonate mouth rinses are sometimes used to decrease the amount of oral flora and promote comfort, though there is no scientific evidence that this is beneficial. Typically, patients will rinse every few hours with a solution containing ½ teaspoon (tsp) salt and ½ tsp baking soda in one cup of water.

Pain relief is often required in patients with mucositis. In some cases, rinsing with a mixture of maalox, xylocalne, and diphenhydramine hydrochloride relieves pain. However, because of xylocalne's numbing effects, taste sensation may be altered. Worse, it may reduce the body's natural gag reflex, possibly causing problems with swallowing. Coating agents such as kaopectate and aluminum hydroxide gel may also help relieve symptoms. Rinsing with benzydamine has also shown promise, not only in managing pain, but also in preventing the development of mucositis. More severe pain may require liquid Tylenol with codeine, or even intravenous opioid drugs. Patients with severe pain may not be able to eat, and may also require nutritional supplements through an I.V. (intravenous line).

A treatment called cryotherapy has shown promise in patients being treated with fluorouracil administered in the aforementioned five-day, high-dose schedule. Patients continuously swish ice chips in their mouth during the thirty-minute infusion of the drug, causing the blood vessels to constrict, thereby reducing the drug's ability to affect the oral mucosa.

Chamomile and allopurinol mouthwashes have been tried in the past to manage mucositis, but studies have found them to be ineffective. Biologic response modifiers are being evaluated to determine their possible role in managing mucositis. Recent studies using topical antimicrobial lozenges have shown promise as well, but more research is needed. Patients with multiple myeloma receiving chemotherapy (dexamethasone and melphelan) and autologous stem cell transplantation (ASCT) who were in addition administered an anti-IL-6 antibody (BE8) had reduced CRP levels and a significant reduction in fever as well as reduced onset and severity of mucositis. Rossi, et al. (2005) *Bone Marrow Transplantation* 36: 771-779. Particularly, the mucositis in the treated patients was a lower grade of toxicity requiring no morphine infusion as compared to patients not receiving the anti-IL-6 antibody. Also, gastrointestinal mucositis symptoms such as diarrhea were reduced and quality of life was improved as evidenced by better oral intake of nutrition and daily activity.

Therefore, there is a strong need in the art for improved methods of treating and preventing mucositis, both oral and gastrointestinal mucositis, as this condition compromises the efficacy of chemotherapy or radiation cancer treatments as well as adversely affecting the quality of life of cancer patients because of the extreme pain and discomfort caused by this condition. The invention described herein provides compositions comprising anti-IL-6 antibodies and antibody fragments thereof, and methods of use which may be used to treat IL-6 related conditions.

SUMMARY OF THE INVENTION

The present invention provides compositions comprising IL-6 antagonists and methods of use thereof for treating mucositis. In one embodiment, the mucositis may be oral, gastrointestinal, or alimentary mucositis. In another embodiment, the mucositis may be associated with cancer, chemotherapy, radiotherapy, or the combination of chemotherapy and radiotherapy. In one embodiment of the invention, the IL-6 antagonist may target IL-6, IL-6 receptor alpha, gp130, p38 MAP kinase, JAK1, JAK2, JAK3, STAT3, SYK, or any combination thereof. In one embodiment of the invention, the IL-6 antagonist may be an antibody, an antibody fragment, a peptide, a glycoalkoid, an antisense nucleic acid, a ribozyme, a retinoid, an avemir, a small molecule, or any combination thereof. In one embodiment of the invention, the IL-6 antagonist may be an anti-IL-6R, anti-gp130, anti-p38 MAP kinase, anti-JAK1, anti-JAK2, anti-JAK3, anti-STAT3, or anti-SYK antibody or antibody fragment. In one embodiment of the invention, the IL-6 antagonist may be a small molecule comprising thalidomide, lenalidomide, or any combination thereof. In one embodiment of the invention, the IL-6 antagonist may be is an anti-IL-6 antibody or antibody fragment.

The present invention provides compositions comprising humanized monoclonal antibodies that selectively bind IL-6 and methods of treating mucositis. In one embodiment, anti-IL-6 antibodies (e.g., ALD518 antibodies, also known as Ab1) may be used in methods for the treatment of mucositis. In this embodiment of the invention anti-IL-6 antibody or antibody fragment may be administered prophylactically to patients at significant risk of developing mucositis. The invention also provides for humanized monoclonal anti-IL-6 antibodies may be used in the treatment of mucositis. The present invention further includes the prevention or treatment of inflammatory conditions by administration of anti-IL-6 antibodies according to the invention.

In one embodiment, the invention provides for a method of treating or preventing mucositis comprising administration of a composition comprising an effective amount of an IL-6 antagonist. In another embodiment, a method of treating or preventing oral mucositis may comprise administration of a composition comprising an effective amount of an IL-6 antagonist. In another embodiment, a method of treating or preventing alimentary tract mucositis may comprise administration of a composition comprising an effective amount of an IL-6 antagonist. In another embodiment, a method of treating or preventing gastrointestinal tract mucositis may comprise administration of a composition comprising an effective amount of an IL-6 antagonist.

In one embodiment, the method of treating or preventing mucositis associated with chemotherapy may comprise administration of a composition comprising an effective amount of an IL-6 antagonist. In another embodiment, a method of treating or preventing oral mucositis associated with chemotherapy may comprise administration of a composition comprising an effective amount of an IL-6 antagonist. In another embodiment, a method of treating or preventing alimentary tract mucositis associated with chemotherapy may comprise administration of a composition comprising an effective amount of an IL-6 antagonist. In another embodiment, a method of treating or preventing gastrointestinal tract mucositis associated with chemotherapy may comprise administration of a composition comprising an effective amount of an IL-6 antagonist.

In one embodiment, the method of treating or preventing mucositis associated with radiotherapy may comprise administration of a composition comprising an effective amount of an IL-6 antagonist. In another embodiment, a method of treating or preventing oral mucositis associated with radiotherapy may comprise administration of a composition comprising an effective amount of an IL-6 antagonist. In another embodiment, a method of treating or preventing alimentary tract mucositis associated with radiotherapy may comprise administration of a composition comprising an effective amount of an IL-6 antagonist. In another embodiment, a method of treating or preventing gastrointestinal tract mucositis associated with radiotherapy may comprise administration of a composition comprising an effective amount of an IL-6 antagonist.

In one embodiment, the method of treating or preventing mucositis associated with cancer may comprise administration of a composition comprising an effective amount of an IL-6 antagonist. In another embodiment, a method of treating or preventing oral mucositis associated with cancer may comprise administration of a composition comprising an effective amount of an IL-6 antagonist. In another embodiment, a method of treating or preventing alimentary tract mucositis associated with cancer may comprise administration of a composition comprising an effective amount of an IL-6 antagonist. In another embodiment, a method of treating or preventing gastrointestinal tract mucositis associated with cancer may comprise administration of a composition comprising an effective amount of an IL-6 antagonist.

In one embodiment, the method of treating or preventing mucositis associated with hematopoietic stem cell transplant (HSCT) may comprise administration of a composition comprising an effective amount of an IL-6 antagonist. In another embodiment, a method of treating or preventing oral mucositis associated with hematopoietic stem cell transplant (HSCT) may comprise administration of a composition comprising an effective amount of an IL-6 antagonist. In another embodiment, a method of treating or preventing alimentary tract mucositis associated with hematopoietic stem cell transplant (HSCT) may comprise administration of a composition comprising an effective amount of an IL-6 antagonist. In another embodiment, a method of treating or preventing gastrointestinal tract mucositis associated with hematopoietic stem cell transplant (HSCT) may comprise administration of a composition comprising an effective amount of an IL-6 antagonist.

In one embodiment, the method of treating or preventing diarrhea may comprise administration of a composition comprising an effective amount of an IL-6 antagonist. In another embodiment, a method of treating or preventing diarrhea associated with chemotherapy may comprise administration of a composition comprising an effective amount of an IL-6 antagonist, another embodiment, a method of treating or preventing diarrhea associated with radiotherapy may comprise administration of a composition comprising an effective amount of an IL-6 antagonist. In another embodiment, a method of treating or preventing diarrhea associated with hematopoietic stem cell transplant (HSCT) may comprise administration of a composition comprising an effective amount of an IL-6 antagonist.

In one embodiment, the method of treating or preventing emesis may comprise administration of a composition comprising an effective amount of an IL-6 antagonist. In another embodiment, a method of treating or preventing emesis associated with chemotherapy may comprise administration of a composition comprising an effective amount of an IL-6 antagonist. In another embodiment, a method of treating or preventing emesis associated with radiotherapy may comprise administration of a composition comprising an effective amount of an IL-6 antagonist. In another embodiment, a method of treating or preventing emesis associated with hematopoietic stem cell transplant (HSCT) may comprise administration of a composition comprising an effective amount of an IL-6 antagonist.

In one embodiment, the invention provides for the use of an IL-6 antagonist in the manufacture of a medicament for the treatment or prevention of mucositis. In further embodiment, the invention provides for the use of an IL-6 antagonist in the manufacture of a medicament for the treatment or prevention of oral mucositis. In further embodiment, the invention provides for the use of an IL-6 antagonist in the manufacture of a medicament for the treatment or prevention of alimentary tract mucositis. In further embodiment, the invention provides for the use of an IL-6 antagonist in the manufacture of a medicament for the treatment or prevention of gastrointestinal tract mucositis.

In one embodiment, the invention provides for the use of an IL-6 antagonist in the manufacture of a medicament for the treatment or prevention of mucositis associated with chemotherapy. In further embodiment, the invention provides for the use of an IL-6 antagonist in the manufacture of a medicament for the treatment or prevention of oral mucositis associated with chemotherapy. In further embodiment, the invention provides for the use of an IL-6 antagonist in the manufacture of a medicament for the treatment or prevention of alimentary tract mucositis associated with chemotherapy. In further embodiment, the invention provides for the use of an IL-6 antagonist in the manufacture of a medicament for the treatment or prevention of gastrointestinal tract mucositis associated with chemotherapy In one embodiment, the invention provides for the use of an IL-6 antagonist in the manufacture of a medicament for the treatment or prevention of mucositis associated with radiotherapy. In further embodiment, the invention provides for the use of an IL-6 antagonist in the manufacture of a medicament for the treatment or prevention of oral mucositis associated with radiotherapy. In further embodiment, the invention provides for the use of an IL-6 antagonist in the manufacture of a medicament for the treatment or prevention of alimentary tract mucositis associated with radiotherapy. In further embodiment, the invention provides for the use of an IL-6 antagonist in the manufacture of a medicament for the treatment or prevention of gastrointestinal tract mucositis associated with radiotherapy.

In one embodiment, the invention provides for the use of an IL-6 antagonist in the manufacture of a medicament for the treatment or prevention of mucositis associated with cancer. In further embodiment, the invention provides for the use of an IL-6 antagonist in the manufacture of a medicament for the treatment or prevention of oral mucositis associated with cancer. In further embodiment, the invention provides for the use of an IL-6 antagonist in the manufacture of a medicament for the treatment or prevention of alimentary tract mucositis associated with cancer. In further embodiment, the invention provides for the use of an IL-6 antagonist in the manufacture of a medicament for the treatment or prevention of gastrointestinal tract mucositis associated with cancer.

In one embodiment, the invention provides for the use of an IL-6 antagonist in the manufacture of a medicament for the treatment or prevention of mucositis associated with hematopoietic stem cell transplant (HSCT). In further embodiment, the invention provides for the use of an IL-6 antagonist in the manufacture of a medicament for the treatment or prevention of oral mucositis hematopoietic stem cell transplant (HSCT). In further embodiment, the invention provides for the use of an IL-6 antagonist in the manufacture of a medicament for the treatment or prevention of alimentary tract mucositis hematopoietic stem cell transplant (HSCT). In further embodiment, the invention provides for the use of an IL-6 antagonist in the manufacture of a medicament for the treatment or prevention of gastrointestinal tract mucositis hematopoietic stem cell transplant (HSCT).

In one embodiment, the invention provides for the use of an IL-6 antagonist in the manufacture of a medicament for the treatment or prevention of diarrhea. In further embodiment, the invention provides for the use of an IL-6 antagonist in the manufacture of a medicament for the treatment or prevention of diarrhea associated with chemotherapy. In further embodiment, the invention provides for the use of an IL-6 antagonist in the manufacture of a medicament for the treatment or prevention of diarrhea associated with radiotherapy. In further embodiment, the invention provides for the use of an IL-6 antagonist in the manufacture of a medicament for the treatment or prevention of diarrhea associated with hematopoietic stem cell transplant (HSCT).

In one embodiment, the invention provides for the use of an IL-6 antagonist in the manufacture of a medicament for the treatment or prevention of emesis. In further embodiment, the invention provides for the use of an IL-6 antagonist in the manufacture of a medicament for the treatment or prevention of emesis associated with chemotherapy. In further embodiment, the invention provides for the use of an IL-6 antagonist in the manufacture of a medicament for the treatment or prevention of emesis associated with radiotherapy. In further embodiment, the invention provides for the use of an IL-6 antagonist in the manufacture of a medicament for the treatment or prevention of emesis associated with hematopoietic stem cell transplant (HSCT).

The invention provides a method of treating or preventing mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides for a pharmaceutical composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of mucositis. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of mucositis. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of mucositis. In a further embodiment, said composition may be formulated for subcutaneous administration.

The invention provides a method of treating or preventing mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating oral mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing oral mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of oral mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of oral mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of oral mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of oral mucositis. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of oral mucositis. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of oral mucositis. In a further embodiment, said composition may be formulated for subcutaneous administration.

The invention provides a method of treating or preventing gastrointestinal tract mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating gastrointestinal tract mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing gastrointestinal tract mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of gastrointestinal tract mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of gastrointestinal tract mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of gastrointestinal tract mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of gastrointestinal tract mucositis. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of gastrointestinal tract mucositis. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of gastrointestinal tract mucositis. In a further embodiment, said composition may be formulated for subcutaneous administration.

The invention provides a method of treating or preventing alimentary tract mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating alimentary tract mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing alimentary tract mucositis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of alimentary tract mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of alimentary tract mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of alimentary tract mucositis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of alimentary tract mucositis. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of alimentary tract mucositis. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of alimentary tract mucositis. In a further embodiment, said composition may be formulated for subcutaneous administration.

The invention provides a method of treating or preventing mucositis associated with chemotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating mucositis associated with chemotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing mucositis associated with chemotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of mucositis associated with chemotherapy comprising an effective amount of an Ab1, Ab2, Ab3, Ab4, Ab5, Ab6, Ab7, Ab8, Ab9, Ab10, Ab11, Ab2, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of mucositis associated with chemotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of mucositis associated with chemotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of mucositis associated with chemotherapy. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of mucositis associated with chemotherapy. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of mucositis associated with chemotherapy. In a further embodiment, said composition may be formulated for subcutaneous administration.

The invention provides a method of treating or preventing mucositis associated with radiotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating mucositis associated with radiotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing mucositis associated with radiotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of mucositis associated with radiotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of mucositis associated with radiotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of mucositis associated with radiotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of mucositis associated with radiotherapy. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of mucositis associated with radiotherapy. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of mucositis associated with radiotherapy. In a further embodiment, said composition may be formulated for subcutaneous administration.

The invention provides a method of treating or preventing mucositis associated with hematopoietic stem cell transplant (HSCT) comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating mucositis associated with hematopoietic stem cell transplant (HSCT) comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing mucositis associated with hematopoietic stem cell transplant (HSCT) comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of mucositis associated with hematopoietic stem cell transplant (HSCT) comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of mucositis associated with hematopoietic stem cell transplant (HSCT) comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of mucositis associated with hematopoietic stem cell transplant (HSCT) comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of mucositis associated with hematopoietic stem cell transplant (HSCT). In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of mucositis associated with hematopoietic stem cell transplant (HSCT). In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of mucositis associated with hematopoietic stem cell transplant (HSCT). In a further embodiment, said composition may be formulated for subcutaneous administration.

The invention provides a method of treating or preventing diarrhea comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating diarrhea comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing diarrhea comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of diarrhea comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of diarrhea comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of diarrhea comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of diarrhea. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of diarrhea. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to 1'-6, for the manufacture of a medicament for the prevention of diarrhea.

In a further embodiment, said composition may be formulated for subcutaneous administration.

The invention provides a method of treating or preventing diarrhea associated with chemotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating diarrhea associated with chemotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing diarrhea associated with chemotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of diarrhea associated with chemotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of diarrhea associated with chemotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of diarrhea associated with chemotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of diarrhea associated with chemotherapy. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of diarrhea associated with chemotherapy. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of diarrhea associated with chemotherapy. In a further embodiment, said composition may be formulated for subcutaneous administration.

The invention provides a method of treating or preventing diarrhea associated with radiotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating diarrhea associated with radiotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing diarrhea associated with radiotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of diarrhea associated with radiotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of diarrhea associated with radiotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of diarrhea associated with radiotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of diarrhea associated with radiotherapy. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of diarrhea associated with radiotherapy. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of diarrhea associated with radiotherapy. In a further embodiment, said composition may be formulated for subcutaneous administration.

The invention provides a method of treating or preventing diarrhea associated with hematopoietic stem cell transplant (HSCT). comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating diarrhea associated with hematopoietic stem cell transplant (HSCT). comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing diarrhea associated with hematopoietic stem cell transplant (HSCT). comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of diarrhea associated with hematopoietic stem cell transplant (HSCT). comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of diarrhea associated with hematopoietic stem cell transplant (HSCT). comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of diarrhea associated with hematopoietic stem cell transplant (HSCT). comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of diarrhea associated with hematopoietic stem cell transplant (HSCT). In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of diarrhea associated with hematopoietic stem cell transplant (HSCT). In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of diarrhea associated with hematopoietic stem cell transplant (HSCT). In a further embodiment, said composition may be formulated for subcutaneous administration.

The invention provides a method of treating or preventing emesis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating emesis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing emesis comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of emesis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of emesis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of emesis comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of emesis. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of emesis. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of emesis. In a further embodiment, said composition may be formulated for subcutaneous administration.

The invention provides a method of treating or preventing emesis associated with chemotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating emesis associated with chemotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing emesis associated with chemotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of emesis associated with chemotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of emesis associated with chemotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of emesis associated with chemotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of emesis associated with chemotherapy. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of emesis associated with chemotherapy. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of emesis associated with chemotherapy. In a further embodiment, said composition may be formulated for subcutaneous administration.

The invention provides a method of treating or preventing emesis associated with radiotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating emesis associated with radiotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing emesis associated with radiotherapy comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of emesis associated with radiotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of emesis associated with radiotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of emesis associated with radiotherapy comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of emesis associated with radiotherapy. In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of emesis associated with radiotherapy. In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of emesis associated with radiotherapy. In a further embodiment, said composition may be formulated for subcutaneous administration.

The invention provides a method of treating or preventing emesis associated with hematopoietic stem cell transplant (HSCT). comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a method of treating emesis associated with hematopoietic stem cell transplant (HSCT). comprising administration of a composition comprising an, effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a method of preventing emesis associated with hematopoietic stem cell transplant (HSCT). comprising administration of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides a composition for the treatment or prevention of emesis associated with hematopoietic stem cell transplant (HSCT). comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention also provides a composition for the treatment of emesis associated with hematopoietic stem cell transplant (HSCT). comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention further provides a composition for the prevention of emesis associated with hematopoietic stem cell transplant (HSCT). comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment or prevention of emesis associated with hematopoietic stem cell transplant (HSCT). In a further embodiment, said composition may be formulated for subcutaneous administration.

The invention also provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the treatment of emesis associated with hematopoietic stem cell transplant (HSCT). In a further embodiment, said composition may be formulated for subcutaneous administration.

The invention provides for the use of a composition comprising an effective amount of an Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, or Ab36 antibody, or an antibody fragment thereof, to a subject in need thereof, wherein the antibody, or antibody fragment thereof, specifically binds to IL-6, for the manufacture of a medicament for the prevention of emesis associated with hematopoietic stem cell transplant (HSCT). In a further embodiment, said composition may be formulated for subcutaneous administration.

In one embodiment, the antibody may comprise at least one light chain selected from the group consisting of an amino acid sequence with at least about 90% sequence identity to an amino acid sequence of SEQ ID NO: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 648, 649, 650, 651, 655, 660, 666, 667, 671, 675, 679, 683, 687, 693, 699, 702, 706, or 709. In a further embodiment, the antibody may comprise at least one light chain selected from the group consisting of an amino acid sequence of SEQ ID NO: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 648, 649, 650, 651, 655, 660, 666, 667, 671, 675, 679, 683, 687, 693, 699, 702, 706, or 709. In another embodiment, the antibody may comprise at least one light chain selected from the group consisting of nucleic acid sequences with at least 90% sequence identity to a nucleic acid sequence of SEQ ID NO: 10, 29, 45, 61, 77, 93, 109, 130, 146, 162, 178, 194, 210, 226, 242, 258, 274, 290, 306, 322, 338, 354, 370, 386, 402, 418, 434, 450, 466, 482, 498, 514, 530, 546, 562, 578, 662, 669, 673, 677, 681, 685, 689, 698, 701, 705, 720, 721, 722, or 723, wherein said nucleic acid sequence encodes said light chain. In further embodiment, the antibody may comprise at least one light chain selected from the group consisting of nucleic acid sequences of SEQ ID NO: 10, 29, 45, 61, 77, 93, 109, 130, 146, 162, 178, 194, 210, 226, 242, 258, 274, 290, 306, 322, 338, 354, 370, 386, 402, 418, 434, 450, 466, 482, 498, 514, 530, 546, 562, 578, 662, 669, 673, 677, 681, 685, 689, 698, 701, 705, 720, 721, 722, or 723, wherein said nucleic acid sequence encodes said light chain.

In one embodiment, the antibody may comprise at least one heavy chain selected from the group consisting of an amino acid sequence with at least about 90% sequence identity to an amino acid sequence of SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 653, 654, 655, 656, 657, 658, 661, 664, 665, 668, 672, 676, 680, 684, 688, 691, 692, 704, or 708. In further embodiment, the antibody may comprise at least one heavy chain selected from the group consisting of an amino acid sequence of SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 653, 654, 655, 656, 657, 658, 661, 664, 665, 668, 672, 676, 680, 684, 688, 691, 692, 704, or 708. In another embodiment, the antibody may comprise at least one heavy chain selected from the group consisting of nucleic acid sequences with at least 90% sequence identity to a nucleic acid sequence of SEQ ID NO: 11, 30, 46, 62, 78, 94, 110, 131, 147, 163, 179, 195, 211, 227, 243, 259, 275, 291, 307, 323, 339, 355, 371, 387, 403, 419, 435, 451, 467, 483, 499, 515, 531, 547, 563, 579, 663, 670, 674, 678, 682, 686, 690, 700, 703, 707, 724, or 725, wherein said nucleic acid sequence encodes said heavy chain. In further embodiment, the antibody may comprise at least one heavy chain selected from the group consisting of SEQ ID NO: 11, 30, 46, 62, 78, 94, 110, 131, 147, 163, 179, 195, 211, 227, 243, 259, 275, 291, 307, 323, 339, 355, 371, 387, 403, 419, 435, 451, 467, 483, 499, 515, 531, 547, 563, 579, 663, 670, 674, 678, 682, 686, 690, 700, 703, 707, 724, or 725, wherein said nucleic acid sequence encodes said heavy chain.

In one embodiment, the antibody may comprise at least one CDR sequence selected from the group consisting of an amino acid sequence with at least about 90% sequence identity to an amino acid sequence of SEQ ID NO: 4, 7, 23, 26, 39, 42, 55, 58, 71, 74, 87, 90, 103, 106, 124, 127, 140, 143, 156, 159, 172, 175, 188, 191, 204, 207, 220, 223, 236, 239, 252, 255, 268, 271, 284, 287, 300, 303, 316, 319, 332, 335, 348, 351, 364, 367, 380, 383, 396, 399, 412, 415, 428, 431, 444, 447, 460, 463, 476, 479, 492, 495, 508, 511, 524, 527, 540, 543, 556, 559, 572, 575, 710, 711, 712, 716, 5, 8, 24, 27, 40, 43, 56, 59, 72, 75, 88, 91, 104, 107, 120, 121, 125, 128, 141, 144, 157, 160, 173, 176, 189, 192, 205, 208, 221, 224, 237, 240, 253, 256, 269, 272, 285, 288, 301, 304, 317, 320, 333, 336, 349, 352, 365, 368, 381, 384, 397, 400, 413, 416, 429, 432, 445, 448, 461, 464, 477, 480, 493, 496, 509, 512, 525, 528, 541, 544, 557, 560, 573, 576, 659, 713, 714, 715, 717, 718, 6, 9, 25, 28, 41, 44, 57, 60, 73, 76, 89, 92, 105, 108, 126, 129, 142, 145, 158, 161, 174, 177, 190, 193, 206, 209, 222, 225, 238, 241, 254, 257, 270, 273, 286, 289, 302, 305, 318, 321, 334, 337, 350, 353, 366, 369, 382, 385, 398, 401, 414, 417, 430, 433, 446, 449, 462, 465, 478, 481, 494, 497, 510, 513, 526, 529, 542, 545, 558, 561, 574, or 577. In another embodiment, the antibody may comprise at least one CDR sequence selected from the group consisting of an amino acid sequence of SEQ ID NO: 4, 7, 23, 26, 39, 42, 55, 58, 71, 74, 87, 90, 103, 106, 124, 127, 140, 143, 156, 159, 172, 175, 188, 191, 204, 207, 220, 223, 236, 239, 252, 255, 268, 271, 284, 287, 300, 303, 316, 319, 332, 335, 348, 351, 364, 367, 380, 383, 396, 399, 412, 415, 428, 431, 444, 447, 460, 463, 476, 479, 492, 495, 508, 511, 524, 527, 540, 543, 556, 559, 572, 575, 710, 711, 712, 716, 5, 8, 24, 27, 40, 43, 56, 59, 72, 75, 88, 91, 104, 107, 120, 121, 125, 128, 141, 144, 157, 160, 173, 176, 189, 192, 205, 208, 221, 224, 237, 240, 253, 256, 269, 272, 285, 288, 301, 304, 317, 320, 333, 336, 349, 352, 365, 368, 381, 384, 397, 400, 413, 416, 429, 432, 445, 448, 461, 464, 477, 480, 493, 496, 509, 512, 525, 528, 541, 544, 557, 560, 573, 576, 659, 713, 714, 715, 717, 718, 6, 9, 25, 28, 41, 44, 57, 60, 73, 76, 89, 92, 105, 108, 126, 129, 142, 145, 158, 161, 174, 177, 190, 193, 206, 209, 222, 225, 238, 241, 254, 257, 270, 273, 286, 289, 302, 305, 318, 321, 334, 337, 350, 353, 366, 369, 382, 385, 398, 401, 414, 417, 430, 433, 446, 449, 462, 465, 478, 481, 494, 497, 510, 513, 526, 529, 542, 545, 558, 561, 574, or 577.

In one embodiment, the antibody may comprise at least one CDR selected from the group consisting of nucleic acid sequences with at least about 90% sequence identity to a nucleic acid sequence of SEQ ID NO: 12, 15, 31, 34, 47, 50, 63, 66, 79, 82, 95, 98, 111, 114, 132, 135, 148, 151, 164, 167, 180, 183, 196, 199, 212, 215, 228, 231, 244, 247, 260, 263, 276, 279, 292, 295, 308, 311, 324, 327, 340, 343, 356, 359, 372, 375, 388, 391, 404, 407, 420, 423, 436, 439, 452, 455, 468, 471, 484, 487, 500, 503, 516, 519, 532, 535, 548, 551, 564, 567, 580, 583, 694, 13, 16, 32, 35, 48, 51, 64, 67, 80, 83, 96, 99, 112, 115, 133, 136, 149, 152, 165, 168, 181, 184, 197, 200, 213, 216, 229, 232, 245, 248, 261, 264, 277, 280, 293, 296, 309, 312, 325, 328, 341, 344, 357, 360, 373, 376, 389, 392, 405, 408, 421, 424, 437, 440, 453, 456, 469, 472, 485, 488, 501, 504, 517, 520, 533, 536, 549, 552, 565, 568, 581, 584, 696, 14, 17, 33, 36, 49, 52, 65, 68, 81, 84, 97, 100, 113, 116, 134, 137, 150, 153, 166, 169, 182, 185, 198, 201, 214, 217, 230, 233, 246, 249, 262, 265, 278, 281, 294, 297, 310, 313, 326, 329, 342, 345, 358, 361, 374, 377, 390, 393, 406, 409, 422, 425, 438, 441, 454, 457, 470, 473, 486, 489, 502, 505, 518, 521, 534, 537, 550, 553, 566, 569, 582, 585, 695, or 697, wherein said nucleic acid sequence encodes said CDR sequence. In a further embodiment, the antibody may comprise at least one CDR selected from the group consisting of nucleic acid sequences of SEQ ID NO: 12, 15, 31, 34, 47, 50, 63, 66, 79, 82, 95, 98, 111, 114, 132, 135, 148, 151, 164, 167, 180, 183, 196, 199, 212, 215, 228, 231, 244, 247, 260, 263, 276, 279, 292, 295, 308, 311, 324, 327, 340, 343, 356, 359, 372, 375, 388, 391, 404, 407, 420, 423, 436, 439, 452, 455, 468, 471, 484, 487, 500, 503, 516, 519, 532, 535, 548, 551, 564, 567, 580, 583, 694, 13, 16, 32, 35, 48, 51, 64, 67, 80, 83, 96, 99, 112, 115, 133, 136, 149, 152, 165, 168, 181, 184, 197, 200, 213, 216, 229, 232, 245, 248, 261, 264, 277, 280, 293, 296, 309, 312, 325, 328, 341, 344, 357, 360, 373, 376, 389, 392, 405, 408, 421, 424, 437, 440, 453, 456, 469, 472, 485, 488, 501, 504, 517, 520, 533, 536, 549, 552, 565, 568, 581, 584, 696, 14, 17, 33, 36, 49, 52, 65, 68, 81, 84, 97, 100, 113, 116, 134, 137, 150, 153, 166, 169, 182, 185, 198, 201, 214, 217, 230, 233, 246, 249, 262, 265, 278, 281, 294, 297, 310, 313, 326, 329, 342, 345, 358, 361, 374, 377, 390, 393, 406, 409, 422, 425, 438, 441, 454, 457, 470, 473, 486, 489, 502, 505, 518, 521, 534, 537, 550, 553, 566, 569, 582, 585, 695, or 697, wherein said nucleic acid sequence encodes said CDR sequence.

In another embodiment, the antibody or antibody fragment thereof may comprise at least one light chain CDR polypeptide selected from the group consisting of an amino acid sequence with at least about 90% sequence identity to an amino acid sequence of SEQ ID NO: 4, 23, 39, 55, 71, 74, 87, 103, 124, 140, 156, 172, 188, 204, 220, 236, 252, 268, 284, 300, 316, 332, 348, 364, 380, 396, 412, 428, 444, 460, 476, 492, 508, 524, 540, 556, 572, 710, 711, 712, 5, 24, 40, 56, 72, 88, 104, 125, 141, 157, 173, 189, 205, 221, 237, 253, 269, 285, 301, 317, 333, 349, 365, 381, 397, 413, 429, 445, 461, 477, 493, 509, 525, 541, 557, 573, 713, 714, 715, 718, 25, 41, 57, 73, 89, 105, 126, 142, 158, 174, 190, 206, 222, 238, 254, 270, 286, 302, 318, 334, 350, 366, 382, 398, 414, 430, 446, 462, 478, 494, 510, 526, 542, 558, or 574. In another embodiment, the antibody or antibody fragment thereof may comprise at least one light chain CDR1 polypeptide selected from the group consisting of an amino acid sequence with at least about 90% sequence identity to an amino acid sequence of SEQ ID NO: 4, 23, 39, 55, 71, 74, 87, 103, 124, 140, 156, 172, 188, 204, 220, 236, 252, 268, 284, 300, 316, 332, 348, 364, 380, 396, 412, 428, 444, 460, 476, 492, 508, 524, 540, 556, 572, 710, 711, or 712. In another embodiment, the antibody or antibody fragment thereof may comprise at least one light chain CDR2 polypeptide selected from the group consisting of an amino acid sequence with at least about 90% sequence identity to an amino acid sequence of SEQ ID NO: 5, 24, 40, 56, 72, 88, 104, 125, 141, 157, 173, 189, 205, 221, 237, 253, 269, 285, 301, 317, 333, 349, 365, 381, 397, 413, 429, 445, 461.7 477, 493, 509, 525, 541, 557, 573, 713, 714, 715, or 718. In another embodiment, the antibody or antibody fragment thereof may comprise at least one light chain CDR3 polypeptide selected from the group consisting of an amino acid sequence with at least about 90% sequence identity to an amino acid sequence of SEQ ID NO: 6, 25, 41, 57, 73, 89, 105, 126, 142, 158, 174, 190, 206, 222, 238, 254, 270, 286, 302, 318, 334, 350, 366, 382, 398, 414, 430, 446, 462, 478, 494, 510, 526, 542, 558, or 574. In another embodiment, the antibody or antibody fragment thereof may comprise at least two light chain CDR polypeptides. In another embodiment, the antibody or antibody fragment thereof may comprise three light chain CDR polypeptides.

In another embodiment, the antibody or antibody fragment thereof may comprise at least one heavy chain CDR polypeptide selected from the group consisting of an amino acid sequence with at least about 90% sequence identity to an amino acid sequence of SEQ ID NO: 7, 26, 42, 58, 74, 90, 106, 127, 143, 159, 175, 191, 207, 223, 239, 255, 271, 287, 303, 319, 335, 351, 367, 383, 399, 415, 431, 447, 463, 479, 495, 511, 527, 543, 559, 575, 716, 8, 27, 43, 59, 75, 91, 107, 120, 121, 128, 144, 160, 176, 192, 208, 224, 240, 256, 272, 288, 304, 320, 336, 352, 368, 384, 400, 416, 432, 448, 464, 480, 496, 512, 528, 544, 560, 576, 659, 717, 718, 9, 28, 44, 60, 76, 92, 108, 129, 145, 161, 177, 193, 209, 225, 241, 257, 273, 289, 305, 321, 337, 353, 369, 385, 401, 417, 433, 449, 465, 481, 497, 513, 529, 545, 561, or 577. In a further embodiment, the antibody or antibody fragment thereof may comprise at least one heavy chain CDR1 polypeptide selected from the group consisting of an amino acid sequence with at least about 90% sequence identity to an amino acid sequence of SEQ ID NO: 7, 26, 42, 58, 74, 90, 106, 127, 143, 159, 175, 191, 207, 223, 239, 255, 271, 287, 303, 319, 335, 351, 367, 383, 399, 415, 431, 447, 463, 479, 495, 511, 527, 543, 559, 575, or 716. In a further embodiment, the antibody or antibody fragment thereof may comprise at least one heavy chain CDR2 polypeptide selected from the group consisting of an amino acid sequence with at least about 90% sequence identity to an amino acid sequence of SEQ ID NO: 8, 27, 43, 59, 75, 91, 107, 120, 121, 128, 144, 160, 176, 192, 208, 224, 240, 256, 272, 288, 304, 320, 336, 352, 368, 384, 400, 416, 432, 448, 464, 480, 496, 512, 528, 544, 560, 576, 659, 717, or 718. In a further embodiment, the antibody or antibody fragment thereof may comprise at least one heavy chain CDR3 polypeptide selected from the group consisting of an amino acid sequence with at least about 90% sequence identity to an amino acid sequence of SEQ ID NO: 9, 28, 44, 60, 76, 92, 108, 129, 145, 161, 177, 193, 209, 225, 241, 257, 273, 289, 305, 321, 337, 353, 369, 385, 401, 417, 433, 449, 465, 481, 497, 513, 529, 545, 561, or 577. In a further embodiment, the antibody or antibody fragment thereof may comprise at least two heavy chain CDR polypeptides. In a further embodiment, the antibody or antibody fragment thereof may comprise three heavy chain CDR polypeptides.

In one embodiment, the light chain of said antibody may be selected from the amino acid sequences of light chains listed in TABLE 4. In one embodiment, the light chain of said antibody may be selected from the amino acid sequences of heavy chains listed in TABLE 4. In one embodiment, at least one CDR of said antibody may be selected from the amino acid sequences of CDRs listed in TABLE 4. In another embodiment, the light chain may have at least 90% sequence identity to an amino acid sequence listed in TABLE 4. In another embodiment, the light chain may have at least 95% sequence identity to an amino acid sequence listed in TABLE 4. In another embodiment, the light chain may comprise an amino acid sequence listed in TABLE 4. In further embodiment, the heavy chain may have at least 90% sequence identity to an amino acid sequence listed in TABLE 4. In further embodiment, the heavy chain may have at least 95% sequence identity to an amino acid sequence listed in TABLE 4. In further embodiment, the heavy chain may comprise an amino acid sequence listed in TABLE 4. In a still further embodiment, the CDR sequence of the antibody may have at least 90% sequence identity to an amino acid sequence listed in TABLE 4. In a still further embodiment, the CDR sequence of the antibody may have at least 95% sequence identity to an amino acid sequence listed in TABLE 4. In a still further embodiment, the CDR sequence of the antibody may comprise an amino acid sequence listed in TABLE 4.

In one embodiment, the antibody or antibody fragment thereof, comprises at least one of the CDRs contained in the $V_H$ polypeptide sequences comprising: SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 656, 657, 658, 661, 664, 665, 668, 672, 676, 680, 684, 688, 691, 692, 704, or 708 and/or at least one of the CDRs contained in the $V_L$ polypeptide sequence consisting of: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 651, 660, 666, 667, 671, 675, 679, 683, 687, 693, 699, 702, 706, or 709.

In one embodiment, the antibody may be an Ab1 antibody. In one embodiment, the antibody may comprise a light chain comprising the amino acid sequence of SEQ ID NO: 2, 20, 647, 648, 649, 650, 651, 660, 666, 699, 702, 706, or 709. In one embodiment, the antibody may comprise a humanized light chain comprising the amino acid sequence of SEQ ID NO: 648, 649, and 650. In one embodiment, the antibody may comprise at least one light chain CDR comprising the amino acid sequence selected from the group consisting of SEQ ID NO: 4, 5, 6, 710, 711, 712, 713, 714, and 715. In one embodiment, the antibody may comprise at least one humanized light chain CDR comprising the amino acid sequence selected from the group consisting of SEQ ID NO: 710, 711, 712, 713, 714, and 715. In another embodiment, the antibody may comprise a heavy chain comprising the amino acid sequence of SEQ ID NO: 3, 18, 19, 652, 653, 654, 655, 656, 657, 658, 661, 664, 665, 704, 708. In another embodiment, the antibody may comprise a humanized heavy chain comprising the amino acid sequence of SEQ ID NO: 653, 654, and 655. In another embodiment, the antibody may comprise at least one heavy chain CDR comprising the amino acid sequence selected from the group consisting of SEQ ID NO: 7, 9, 74, 716, 8, 120, 659, 717, and 718. In another embodiment, the antibody may comprise at least one humanized heavy chain CDR comprising the amino acid sequence selected from the group consisting of SEQ ID NO: 74, 716, 717, and 718. In a further embodiment, the Ab1 antibody may comprise a light chain comprising the amino acid sequence of SEQ ID NO: 709 and a heavy chain comprising the amino acid sequence of SEQ ID NO: 657. In a further embodiment, the Ab1 antibody may comprise a light chain comprising the amino acid sequence of SEQ ID NO: 20 and a heavy chain comprising the amino acid sequence of SEQ ID NO: 19.

In one embodiment, the antibody or antibody fragment thereof may be administered to the subject in the form of at least one nucleic acids that encode the antibody. In one embodiment, the light chain of said antibody or antibody fragment thereof may be encoded by at least one of the following nucleic acid sequences of SEQ ID NOs: 10, 29, 45, 61, 77, 93, 109, 130, 146, 162, 178, 194, 210, 226, 242, 258, 274, 290, 306, 322, 338, 354, 370, 386, 402, 418, 434, 450, 466, 482, 498, 514, 530, 546, 562, 578, 662, 669, 673, 677, 681, 685, 689, 698, 701, 705, 720, 721, 722, or 723. In another embodiment, the heavy chain of said antibody or antibody fragment thereof may be encoded by at least one of the following nucleic acid sequences of SEQ ID NOs: 11, 30, 46, 62, 78, 94, 110, 131, 147, 163, 179, 195, 211, 227, 243, 259, 275, 291, 307, 323, 339, 355, 371, 387, 403, 419, 435, 451, 467, 483, 499, 515, 531, 547, 563, 579, 663, 670, 674, 678, 682, 686, 690, 700, 703, 707, 724, or 725. In another embodiment, at least one of the CDRs of said antibody or antibody fragment thereof may be encoded by at least one of the following nucleic acid sequences of SEQ ID NOs: 12, 15, 31, 34, 47, 50, 63, 66, 79, 82, 95, 98, 111, 114, 132, 135, 148, 151, 164, 167, 180, 183, 196, 199, 212, 215, 228, 231, 244, 247, 260, 263, 276, 279, 292, 295, 308, 311, 324, 327, 340, 343, 356, 359, 372, 375, 388, 391, 404, 407, 420, 423, 436, 439, 452, 455, 468, 471, 484, 487, 500, 503, 516, 519, 532, 535, 548, 551, 564, 567, 580, 583, 694, 13, 16, 32, 35, 48, 51, 64, 67, 80, 83, 96, 99, 112, 115, 133, 136, 149, 152, 165, 168, 181, 184, 197, 200, 213, 216, 229, 232, 245, 248, 261, 264, 277, 280, 293, 296, 309, 312, 325, 328, 341, 344, 357, 360, 373, 376, 389, 392, 405, 408, 421, 424, 437, 440, 453, 456, 469, 472, 485, 488, 501, 504, 517, 520, 533, 536, 549, 552, 565, 568, 581, 584, 696, 14, 17, 33, 36, 49, 52, 65, 68, 81, 84, 97, 100, 113, 116, 134, 137, 150, 153, 166, 169, 182, 185, 198, 201, 214, 217, 230, 233, 246, 249, 262, 265, 278, 281, 294, 297, 310, 313, 326, 329, 342, 345, 358, 361, 374, 377, 390, 393, 406, 409, 422, 425, 438, 441, 454, 457, 470, 473, 486, 489, 502, 505, 518, 521, 534, 537, 550, 553, 566, 569, 582, 585, 695, or 697. In another embodiment, at least one nucleic acids may comprise the heavy and light chain polynucleotide sequences of SEQ ID NO: 723 and SEQ ID NO: 700; SEQ ID NO: 701 and SEQ ID NO: 703; SEQ ID NO: 705 and SEQ ID NO: 707; SEQ ID NO: 720 and SEQ ID NO: 724; and SEQ ID NO: 10 and SEQ ID NO: 11.

In one embodiment, the antibody or antibody fragment thereof may be asialated. In one embodiment, the antibody or antibody fragment thereof may be humanized. In one embodiment, the antibody or antibody fragment thereof may have a half-life of at least about 30 days. In one embodiment, the antibody or antibody fragment thereof may comprise the humanized variable light sequence of amino acid sequence of SEQ ID NO: 709. In one embodiment, the antibody or antibody fragment thereof may comprise humanized variable heavy sequence of amino acid sequence of SEQ ID NO: 657. In another embodiment, the antibody or antibody fragment thereof may comprise at least one light chain CDRs as set forth in the amino acid sequence of SEQ ID NOs: 4, 5, or 6. In another embodiment, the antibody or antibody fragment thereof may comprise at least one heavy chain CDRs as set forth in the amino acid sequence of SEQ ID NOs: 7, 120, or 9. In further embodiment, the antibody or antibody fragment thereof may be an asialated, humanized anti-IL-6 monoclonal antibody with a half-life of ~30 days comprising the humanized variable light and heavy sequences as set forth in SEQ ID NO: 20 and 19. In further embodiment, the antibody or antibody fragment thereof may be an asialated, humanized anti-IL-6 monoclonal antibody with a half-life of ~30 days comprising the humanized variable light and heavy sequences as set forth in SEQ ID NO: 709 and 657.

In a preferred embodiment this is effected by the administration of the antibodies described herein, comprising the sequences of the $V_H$, $V_L$ and CDR polypeptides described in Table 4, or humanized or chimeric or single chain versions thereof containing at least one of the CDRs of the exemplified anti-IL-6 antibody sequences and the polynucleotides encoding them. Preferably these antibodies will be aglycosylated. In more specific embodiments of the invention these antibodies will block gp130 activation and/or possess binding affinities (Kds) less than 50 picomolar and/or $K_{off}$ values less than or equal to $10^{-4}$ $S^{-1}$.

The invention also contemplates methods of making said humanized anti-IL-6 or anti-IL-6/IL-6R complex antibodies and binding fragments and variants thereof. In one embodiment, binding fragments include, but are not limited to, Fab, Fab', $F(ab')_2$, Fv and scFv fragments.

In one embodiment, the anti-IL-6 antibodies block the effects of IL-6. In another embodiment, the anti-IL-6 antibody is a humanized monoclonal antibody that binds to free human IL-6 and soluble IL-6R/IL-6 complex with an affinity of at least about 4 pM. In another embodiment, the anti-IL-6 antibody, has a serum half-life about at least 30 days. In another embodiment, the anti-IL-6 antibody is based on a consensus human IgG1 kappa framework that had asparagines modified to alanine to eliminate N-glycosylation sites.

In another embodiment, the antibodies and humanized versions may be derived from rabbit immune cells (B lymphocytes) and may be selected based on their homology (sequence identity) to human germ line sequences. These antibodies may require minimal or no sequence modifications, thereby facilitating retention of functional properties after humanization. In exemplary embodiments, the humanized antibodies may comprise human frameworks which are highly homologous (possess high level of sequence identity) to that of a parent (e.g. rabbit) antibody.

In an embodiment of the invention, the anti-IL-6 antibody or antibody fragment or variant thereof may specifically bind to the same linear or conformational epitopes on an intact IL-6 polypeptide or fragment thereof which may include at least fragments selected from those encompassing amino acid residues 37-51, amino acid residues 70-84, amino acid residues 169-183, amino acid residues 31-45 and/or amino acid residues 58-72.

In a preferred exemplary embodiment, the anti-IL-6 antibody will comprise at least one of the CDRs in listed in Table 4. In a more preferred embodiment the anti-IL-6 antibody will comprise the variable heavy and light chain sequences in SEQ ID NO: 657 and SEQ ID NO: 709, or variants thereof.

In a preferred embodiment the humanized anti-IL-6 antibody will comprise the variable heavy and variable light chain sequences respectively set forth in SEQ ID NO: 657 and SEQ ID NO: 709, and preferably further comprising the heavy chain and light chain constant regions respectively set forth in SEQ ID NO: 588 and SEQ ID NO: 586, and variants thereof comprising at least one amino acid substitutions or deletions that do not substantially affect IL-6 binding and/or desired effector function. This embodiment also contemplates polynucleotides comprising, or alternatively consisting of, at least one of the nucleic acids encoding the variable heavy chain (SEQ ID NO: 700) and variable light chain (SEQ ID NO: 723) sequences and the constant region heavy chain (SEQ ID NO: 589) and constant region light chain (SEQ ID NO: 587) sequences. This embodiment further contemplates nucleic acids encoding variants comprising at least one amino acid substitutions or deletions to the variable heavy and variable light chain sequences respectively set forth in SEQ ID NO: 657 and SEQ ID NO: 709 and the heavy chain and light chain constant regions respectively set forth in SEQ ID NO: 588 and SEQ ID NO: 586, that do not substantially affect IL-6 binding and/or desired effector function.

In an embodiment of the invention, the anti-IL-6 antibody or antibody fragment or variant thereof may be aglycosylated or substantially aglycosylated, e.g., as a result of one or more modifications in the Fc region of the antibody.

In an embodiment of the invention, the anti-IL-6 antibody or antibody fragment or variant thereof may contain an Fc region that has been modified to alter effector function, half-life, proteolysis, and/or glycosylation. Preferably the Fc region is modified to eliminate glycosylation.

In an embodiment of the invention, the anti-IL-6 antibody or antibody fragment or variant thereof may be a human, humanized, single chain or chimeric antibody.

In an embodiment of the invention, the anti-IL-6 antibody or antibody fragment or variant thereof may be a humanized antibody derived from a rabbit (parent) anti-IL-6 antibody.

In an embodiment of the invention, the framework regions (FRs) in the variable light region and the variable heavy regions of said anti-IL-6 antibody or antibody fragment or variant thereof respectively may be human FRs which are unmodified or which have been modified by the substitution of at most 2 or 3 human FR residues in the variable light or heavy chain region with the corresponding FR residues of the parent rabbit antibody, and the human FRs may have been derived from human variable heavy and light chain antibody sequences which have been selected from a library of human germline antibody sequences based on their high level of homology to the corresponding rabbit variable heavy or light chain regions relative to other human germline antibody sequences contained in the library. As disclosed in detail infra in a preferred embodiment the antibody will comprise human FRs which are selected based on their high level of homology (degree of sequence identity) to that of the parent antibody that is humanized.

In one embodiment of the invention, the anti-IL-6 antibody or antibody fragment or variant thereof may comprise a heavy chain polypeptide sequence comprising: SEQ ID NO: 3, 18, 19, 652, 656, 657, 658, 661, 664, 665, 704, or 708; and may further comprise a VL polypeptide sequence comprising: SEQ ID NO: 2, 20, 647, 651, 660, 666, 699, 702, 706, or 709 or a variant thereof wherein at least one of the framework residues (FR residues) in said VH or VL polypeptide may have been substituted with another amino acid residue resulting in an anti-IL-6 antibody or antibody fragment or variant thereof that specifically binds human IL-6, or may comprise a polypeptide wherein the CDRs therein are incorporated into a human framework homologous to said sequence. Preferably the variable heavy and light sequences comprise those in SEQ ID NO: 657 and 709.

In an embodiment of the invention, at least one of said FR residues may be substituted with an amino acid present at the corresponding site in a parent rabbit anti-IL-6 antibody from which the complementarity determining regions (CDRs) contained in said VH or VL polypeptides have been derived or by a conservative amino acid substitution.

In an embodiment of the invention, said anti-IL-6 antibody, or antibody fragment or variant thereof, may be humanized. In an embodiment of the invention, said anti-IL-6 antibody, or antibody fragment or variant thereof, may be chimeric.

In an embodiment of the invention, said anti-IL-6 antibody, or antibody fragment or variant thereof, further may comprise a human Fc, e.g., an Fc region comprised of the variable heavy and light chain constant regions set forth in SEQ ID NO: 704 and 702.

In an embodiment of the invention, said human Fc may be derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19.

In an embodiment of the invention, the anti-IL-6 antibody or antibody fragment or variant thereof may comprise a polypeptide having at least about 90% sequence homology to at least one of the polypeptide sequences of SEQ ID NO: 3, 18, 19, 652, 656, 657, 658, 661, 664, 665, 704, 708, 2, 20, 647, 651, 660, 666, 699, 702, 706, and 709.

In an embodiment of the invention, the anti-IL-6 antibody or antibody fragment or variant thereof may have an elimination half-life of at least about 30 days.

In one embodiment, the antibody, or antibody fragment thereof, may inhibit with at least one activity associated with IL-6. In another embodiment, the at least one activity associated with IL-6 may be an in vitro activity comprising stimulation of proliferation of T1165 cells; binding of IL-6 to IL-6R; activation (dimerization) of the gp130 signal-transducing glycoprotein; formation of IL-6/IL-6R/gp130 multimers; stimulation of haptoglobin production by HepG2 cells modified to express human IL-6 receptor; or any combination thereof. In one embodiment, prior to administration of the antibody, or antibody fragment thereof, the subject may have exhibited or may be at risk for developing at least one of the following symptoms: elevated serum C-reactive protein ("CRP"); elevated erythrocyte sedimentation rate; or a combination thereof.

In one embodiment, the antibody or antibody fragment thereof may comprise a Fab, Fab', $F(ab')_2$, Fv, scFv, IgNAR, SMIP, camelbody, or nanobody. In one embodiment, the antibody or antibody fragment thereof may have an in vivo half-life of at least about 30 days in a healthy human subject. In one embodiment, the antibody or antibody fragment thereof may have a binding affinity (Kd) for IL-6 of less than about 50 picomolar, or a rate of dissociation ($K_{off}$) from IL-6 of less than or equal to $10^{-4}$ $S^{-1}$. In one embodiment, the antibody or antibody fragment thereof may specifically binds to the same linear or conformational epitope(s) and/or competes for binding to the same linear or conformational epitope(s) on an intact human IL-6 polypeptide or fragment thereof as an anti-IL-6 antibody comprising the polypeptides of SEQ ID NO: 702 and SEQ ID NO: 704 or the polypeptides of SEQ ID NO: 2 and SEQ ID NO: 3. In one embodiment, the binding to the same linear or conformational epitope(s) and/or competition for binding to the same linear or conformational epitope(s) on an intact human IL-6 polypeptide or fragment thereof is ascertained by epitopic mapping using overlapping linear peptide fragments which span the full length of the native human IL-6 polypeptide and includes at least one residues comprised in IL-6 fragments selected from those respectively encompassing amino acid residues 37-51, amino acid residues 70-84, amino acid residues 169-183, amino acid residues 31-45 and/or amino acid residues 58-72 of SEQ ID NO: 1.

In one embodiment, the antibody or antibody fragment thereof, may be aglycosylated. In one embodiment, the antibody, or antibody fragment thereof, may contain an Fc region that has been modified to alter effector function, half-life, proteolysis, and/or glycosylation. In one embodiment, the antibody, or antibody fragment thereof, may be a human, humanized, single chain, or chimeric antibody. In one embodiment, the antibody, or antibody fragment thereof, may comprise a Fab, Fab', $F(ab')_2$, Fv, or scFv. In one embodiment, the antibody, or antibody fragment thereof, may further comprise a human $F_o$. In another embodiment, the $F_c$ may be derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18, or IgG19.

In one embodiment, the composition may comprise at least about 25, 80, 100, 160, 200, or 320 mg. In one embodiment, the effective amount may be between about 0.1 and 100 mg/kg of body weight of the subject. In one embodiment, the subject may be administered at least 1, 2, 3, 4, or 5 doses. In one embodiment, composition may be administered every 4 weeks. In one embodiment, the subject may be administered 25 mg every 4 weeks. In one embodiment, the subject may be administered 80 mg every 4 weeks. In one embodiment, the subject may be administered 100 mg every 4 weeks. In one embodiment, the subject may be administered 160 mg every 4 weeks. In one embodiment, the subject may be administered 200 mg every 4 weeks. In one embodiment, the subject may be administered 320 mg every 4 weeks. In another embodiment, the composition may be administered every 4 weeks for at least 16 weeks. In another embodiment, the composition may be administered every 4 weeks for at least 24 weeks.

In this embodiment, anti-IL-6 antibodies, or antibody fragments thereof may be administered at effective doses to less inflammation, pain, and loss of mobility experienced from mucositis, e.g., dosages ranging from about 25-500 mg, more preferably at least about 25, 80, 100, 120, 160, 200, 240, or 320 mg dosages.

In one embodiment, the antibody may comprise a light chain polypeptide that comprises at least one Ab1 light chain CDR polypeptide comprising a light chain CDR1 having at least 72.7% sequence identity to SEQ ID NO: 4; a light chain CDR2 having at least 85.7% sequence identity to SEQ ID NO: 5; a light chain CDR3 having at least about 90% sequence identity to SEQ ID NO: 6; a light chain CDR1 having at least 90.9% sequence identity to SEQ ID NO: 4; a light chain CDR2 having at least 100% sequence identity to SEQ ID NO: 5; or a light chain CDR3 having at least 66.6% sequence identity to SEQ ID NO: 6; and wherein the heavy chain polypeptide comprises at least one Ab1 heavy chain CDR polypeptide comprising a heavy chain CDR1 having at least 80% sequence identity to SEQ ID NO: 7; a heavy chain CDR2 having at least about 90% sequence identity to SEQ ID NO: 120; a heavy chain CDR3 having at least 33.3% sequence identity to SEQ ID NO: 9; a heavy chain CDR1 having at least 100% sequence identity to SEQ ID NO: 7; a heavy chain CDR2 having at least 56.2% sequence identity to SEQ ID NO: 120; or a heavy chain CDR3 having at least 50% sequence identity to SEQ ID NO: 9.

In a further embodiment, the antibody or antibody fragment may comprise a light chain polypeptide comprises at least one Ab1 light chain CDR polypeptide comprising a tight chain CDR1 having at least 81.8% sequence identity to SEQ ID NO: 4; a light chain CDR2 having at least 71.4% sequence identity to SEQ ID NO: 5; or a light chain CDR3 having at least 83.3% sequence identity to SEQ ID NO: 6; and wherein the heavy chain polypeptide comprises at least one Ab1 heavy chain CDR polypeptide comprising a heavy chain CDR1 having at least 60% sequence identity to SEQ ID NO: 7; a heavy chain CDR2 having at least 87.5% sequence identity to SEQ ID NO: 120; or a heavy chain CDR3 having at least 83.3% sequence identity to SEQ ID NO: 9. In a further embodiment, the antibody or antibody fragment may comprise antibody or antibody fragment comprises at least two of said light chain CDR polypeptides and at least two of said heavy chain CDR polypeptides.

In a further embodiment, the antibody or antibody fragment may comprise two or more Ab1 light chain CDR polypeptides comprising a light chain CDR1 having at least 72.7% sequence identity to SEQ ID NO: 4; a light chain CDR2 having at least 85.7% sequence identity to SEQ ID NO: 5; or a light chain CDR3 having at least about 90% sequence identity to SEQ ID NO: 6; and two or more Ab1 heavy chain CDR polypeptide comprising a heavy chain CDR1 having at least 80% sequence identity (identical to at least 4 out of 5 residues) to SEQ ID NO: 7; a heavy chain CDR2 having at least about 90% sequence identity to SEQ ID NO: 120; or a heavy chain CDR3 having at least 33.3% sequence identity to SEQ ID NO: 9; wherein the Ab1 antibody or antibody fragment specifically binds to IL-6 and antagonizes at least one activity associated with IL-6.

In a further embodiment, the antibody or antibody fragment may comprise two or more Ab1 light chain CDR polypeptides comprising a light chain CDR1 having at least 90.9% sequence identity to SEQ ID NO: 4; a light chain CDR2 having at least 100% sequence identity to SEQ ID NO: 5; or a light chain CDR3 having at least 66.6% sequence identity to SEQ ID NO: 6; and two or more Ab1 heavy chain CDR polypeptide comprising a heavy chain CDR1 having at least 100% sequence identity to SEQ ID NO: 7; a heavy chain CDR2 having at least 56.2% sequence identity to SEQ ID NO: 120; or a heavy chain CDR3 having at least 50% sequence identity to SEQ ID NO: 9; wherein the Ab1 antibody or antibody fragment specifically binds to IL-6 and antagonizes at least one activity associated with IL-6.

In a further embodiment, the Ab1 antibody or antibody fragment comprises said light chain CDR1, said light chain CDR3, said heavy chain CDR2, and said heavy chain CDR3.

In one embodiment, the antibody or antibody fragment may comprise antibody or antibody fragment thereof is administered to the subject in the form of at least one nucleic acids that encode the antibody or antibody fragment thereof.

In one embodiment, the antibody or antibody fragment may comprise a light chain of encoded by at least one of the following nucleic acid sequences of SEQ ID NOs: 10, 29, 45, 61, 77, 93, 109, 130, 146, 162, 178, 194, 210, 226, 242, 258, 274, 290, 306, 322, 338, 354, 370, 386, 402, 418, 434, 450, 466, 482, 498, 514, 530, 546, 562, 578, 662, 669, 673, 677, 681, 685, 689, 698, 701, 705, 720, 721, 722, or 723.

In one embodiment, the antibody or antibody fragment may comprise a heavy chain of said antibody or antibody fragment thereof is encoded by at least one of the following nucleic acid sequences of SEQ ID NOs: 11, 30, 46, 62, 78, 94, 110, 131, 147, 163, 179, 195, 211, 227, 243, 259, 275, 291, 307, 323, 339, 355, 371, 387, 403, 419, 435, 451, 467, 483, 499, 515, 531, 547, 563, 579, 663, 670, 674, 678, 682, 686, 690, 700, 703, 707, 724, or 725.

In one embodiment, the antibody or antibody fragment may comprise at least one of the CDRs of said antibody or antibody fragment thereof is encoded by at least one of the following nucleic acid sequences of SEQ ID NOs: 12, 15, 31, 34, 47, 50, 63, 66, 79, 82, 95, 98, 111, 114, 132, 135, 148, 151, 164, 167, 180, 183, 196, 199, 212, 215, 228, 231, 244, 247, 260, 263, 276, 279, 292, 295, 308, 311, 324, 327, 340, 343, 356, 359, 372, 375, 388, 391, 404, 407, 420, 423, 436, 439, 452, 455, 468, 471, 484, 487, 500, 503, 516, 519, 532, 535, 548, 551, 564, 567, 580, 583, 694, 13, 16, 32, 35, 48, 51, 64, 67, 80, 83, 96, 99, 112, 115, 133, 136, 149, 152, 165, 168, 181, 184, 197, 200, 213, 216, 229, 232, 245, 248, 261, 264, 277, 280, 293, 296, 309, 312, 325, 328, 341, 344, 357, 360, 373, 376, 389, 392, 405, 408, 421, 424, 437, 440, 453, 456, 469, 472, 485, 488, 501, 504, 517, 520, 533, 536, 549, 552, 565, 568, 581, 584, 696, 14, 17, 33, 36, 49, 52, 65, 68, 81, 84, 97, 100, 113, 116, 134, 137, 150, 153, 166, 169, 182, 185, 198, 201, 214, 217, 230, 233, 246, 249, 262, 265, 278, 281, 294, 297, 310, 313, 326, 329, 342, 345, 358, 361, 374, 377, 390, 393, 406, 409, 422, 425, 438, 441, 454, 457, 470, 473, 486, 489, 502, 505, 518, 521, 534, 537, 550, 553, 566, 569, 582, 585, 695, or 697.

In one embodiment, the antibody or antibody fragment may comprise at least one of the nucleic acids comprise the heavy and light chain polynucleotide sequences of SEQ ID NO: 723 and SEQ ID NO: 700; SEQ ID NO: 701 and SEQ ID NO: 703; SEQ ID NO: 705 and SEQ ID NO: 707; SEQ ID NO: 720 and SEQ ID NO: 724; and SEQ ID NO: 10 and SEQ ID NO: 11.

In one embodiment, the antibody or antibody fragment may comprise a humanized variable light sequence of amino acid sequence of SEQ ID NO: 709.

In one embodiment, the antibody or antibody fragment may comprise a humanized variable heavy sequence of amino acid sequence of SEQ ID NO: 657.

In one embodiment, the antibody or antibody fragment may comprise at least one light chain CDRs as set forth in the amino acid sequence of SEQ ID NOs: 4, 5, or 6.

In one embodiment, the antibody or antibody fragment may comprise at least one heavy chain CDRs as set forth in the amino acid sequence of SEQ ID NOs: 7, 120, or 9.

In one embodiment, the antibody or antibody fragment may be an asialated, humanized anti-IL-6 monoclonal antibody with a half-life of ~30 days comprising the humanized variable light and heavy sequences as set forth in SEQ ID NO: 20 and 19 or SEQ ID NO: 709 or 657.

In one embodiment, the antibody or antibody fragment may be expressed from a recombinant cell. In another embodiment, the cell may be a mammalian, yeast, bacterial, and insect cell. In another embodiment, the cell may be a yeast cell. In another embodiment, the cell may be a diploidal yeast cell. In another embodiment, the yeast cell may be a *Pichia* yeast. In one embodiment, the antibody may be asialated. In one embodiment, the antibody may be humanized.

In one embodiment, the antibody or antibody fragment thereof may comprise a Fab, Fab', $F(ab')_2$, Fv, scFv, IgNAR, SMIP, camelbody, or nanobody.

In one embodiment, the antibody or antibody fragment thereof may have an in vivo half-life of at least about 30 days.

In one embodiment, the antibody or antibody fragment thereof may have a binding affinity (Kd) for IL-6 of less than about 50 picomolar, or a rate of dissociation ($K_{off}$) from IL-6 of less than or equal to $10^{-4}$ $S^{-1}$.

In one embodiment, the antibody or antibody fragment thereof may specifically binds to the same linear or conformational epitope(s) and/or competes for binding to the same linear or conformational epitope(s) on an intact human IL-6 polypeptide or fragment thereof as an anti-IL-6 antibody comprising the polypeptides of SEQ ID NO: 702 and SEQ ID NO: 704 or the polypeptides of SEQ ID NO: 2 and SEQ ID NO: 3.

In one embodiment, the antibody or antibody fragment thereof may have binding to the same linear or conformational epitope(s) and/or competition for binding to the same linear or conformational epitope(s) on an intact human IL-6 polypeptide or fragment thereof is ascertained by epitopic mapping using overlapping linear peptide fragments which span the full length of the native human IL-6 polypeptide and includes at least one residues comprised in IL-6 fragments selected from those respectively encompassing amino acid residues 37-51, amino acid residues 70-84, amino acid residues 169-183, amino acid residues 31-45 and/or amino acid residues 58-72 of SEQ ID NO: 1.

In one embodiment, the antibody or antibody fragment thereof may be aglycosylated. In one embodiment, the antibody or antibody fragment thereof may comprise an Fc region that has been modified to alter effector function, half-life, proteolysis, and/or glycosylation. In one embodiment, the antibody or antibody fragment thereof may be a human, humanized, single chain, or chimeric antibody. In one embodiment, the antibody or antibody fragment thereof may further comprise a human $F_c$. The method or use of claim 126, wherein said human Fc is derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18, or IgG19.

In one embodiment, the chemotherapy may comprise administration of a chemotherapy agent selected from the group consisting of Alemtuzumab (Campath®), Asparaginase (Elspar®), Bleomycin (Blenoxane®), Busulfan (Myleran®, Busulfex®), Capecitabine (Xeloda®), Carboplatin (Paraplatin®), Cisplatin (PLATINOL®), Cyclophosphamide (Cytoxan®), Cytarabine (Cytosar-U®), Daunorubicin (Cerubidine®), Docetaxel (Taxotere®), Doxorubicin (Adriamycin®), Epirubicin (Ellence®), Etoposide (VePesid®), Fluorouracil (5-FU®), Gemcitabine (Gemzar®), Gemtuzumab ozogamicin (Mylotarg®), Hydroxyurea (Hydrea®), Idarubicin (Idamycin®), Interleukin 2 (Proleukin®), Irinotecan (Camptosar®), Lomustine (CeeNU®), Mechlorethamine (Mustargen®), Melphalan (Alkeran®), Methotrexate (Rheumatrex®), Mitomycin (Mutamycin®), Mitoxantrone (Novantrone®), Oxaliplatin (Eloxatin®), Paclitaxel (Taxol®), Pemetrexed (Alimta®), Pentostatin (Nipent®), Procarbazine (Matulane®), Thiotepa (Thioplex®), Topotecan (Hycamtin®), Trastuzumab (Herceptin®), Tretinoin (Vesanoid®), Vinblastine (Velban®), or Vincristine (Oncovin®).

In one embodiment, the patient may have elevated C-reactive protein ("CRP"). In one embodiment, the patient may have elevated IL-6 serum level. In one embodiment, the patient may have elevated IL-6 level in the joints.

In one embodiment, the IL-antagonist may inhibit at least one activity associated with IL-6. In another embodiment, the at least one activity associated with IL-6 is an in vitro activity comprising stimulation of proliferation of T1165 cells; binding of IL-6 to IL-6R; activation (dimerization) of the gp130 signal-transducing glycoprotein; formation of IL-6/IL-6R/gp130 multimers; stimulation of haptoglobin production by HepG2 cells modified to express human IL-6 receptor; or any combination thereof.

In another embodiment, prior to administration of the IL-6 antagonist, optionally an antibody or antibody fragment, the subject has exhibited or is at risk for developing at least one of the following symptoms: decreased serum albumin; elevated serum C-reactive protein ("CRP"); elevated erythrocyte sedimentation rate; fatigue; fever; anorexia (loss of appetite); weight loss; cachexia; weakness; decreased Glasgow Prognostic Score ("GPS"); elevated serum D-dimer; abnormal coagulation profile; and any combination thereof.

In another embodiment, the symptom may be a side-effect of another therapeutic agent administered to the subject prior to, concurrent with, or subsequent to administration of the antibody or antibody fragment. In another embodiment, the method may further comprise monitoring the subject to assess said symptom subsequent to administration of the antibody. In another embodiment, the symptom may be exhibited prior to administration of said IL-6 antagonist, optionally an anti-IL-6 antibody or antibody fragment. In another embodiment, the symptom may be improved or restored to a normal condition within about 1-5 weeks of administration of said IL-6 antagonist, optionally an anti-IL-6 antibody or antibody fragment. In another embodiment, the symptom may thereafter remains improved for an entire period intervening two consecutive administrations of said IL-6 antagonist, optionally an anti-IL-6 antibody or antibody fragment. In another embodiment, the patient treated may have at least one symptom of oral, alimentary, or gastrointestinal tract mucositis.

In another embodiment, the patient treated may have cancer or is being treated for cancer. In one embodiment, the cancer is selected from the group consisting of Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Müllerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sézary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenström's macroglobulinemia, Warthin's tumor, Wilms' tumor, and combination thereof. In one embodiment, the cancer is Colorectal Cancer, Non-Small Cell Lung Cancer, Cholangiocarcinoma, Mesothelioma, Castleman's disease, Renal Cell Carcinoma, or any combination thereof. In one embodiment, the patient may have a cancer selected from head and neck cancer, esophageal cancer, throat cancer, lung cancer, gastrointestinal cancers such as stomach cancer, colorectal cancer, pancreatic cancer, as well as hematological cancers such as multiple myeloma, leukemia, and lymphoma.

In one embodiment, the patient suffers from a disease or disorder selected from the group consisting of general fatigue, exercise-induced fatigue, cancer-related fatigue, inflammatory disease-related fatigue, chronic fatigue syndrome, cancer-related cachexia, cardiac-related cachexia, respiratory-related cachexia, renal-related cachexia, age-related cachexia, rheumatoid arthritis, systemic lupus erythematosis (SLE), systemic juvenile idiopathic arthritis, psoriasis, psoriatic arthropathy, ankylosing spondylitis, inflammatory bowel disease (IBD), polymyalgia rheumatica, giant cell arteritis, autoimmune vasculitis, graft versus host disease (GVHD), Sjogren's syndrome, adult onset Still's disease, rheumatoid arthritis, systemic juvenile idiopathic arthritis, osteoarthritis, osteoporosis, Paget's disease of bone, osteoarthritis, multiple myeloma, Hodgkin's lymphoma, non-Hodgkin's lymphoma, prostate cancer, leukemia, renal cell cancer, multicentric Castleman's disease, ovarian cancer, drug resistance in cancer chemotherapy, cancer chemotherapy toxicity, ischemic heart disease, atherosclerosis, obesity, diabetes, asthma, multiple sclerosis, Alzheimer's disease, cerebrovascular disease, fever, acute phase response, allergies, anemia, anemia of inflammation (anemia of chronic disease), hypertension, depression, depression associated with a chronic illness, thrombosis, thrombocytosis, acute heart failure, metabolic syndrome, miscarriage, obesity, chronic prostatitis, glomerulonephritis, pelvic inflammatory disease, reperfusion injury, transplant rejection, graft versus host disease (GVHD), avian influenza, smallpox, pandemic influenza, adult respiratory distress syndrome (ARDS), severe acute respiratory syndrome (SARS), sepsis, and systemic inflammatory response syndrome (SIRS).

In one embodiment, the patient has or is to receive autologous stem cell or bone marrow transplant.

In one embodiment, the IL-6 antagonist, optionally an anti-IL-6 antibody or antibody fragment, may be administered prior, concurrent or after chemotherapy or radiotherapy. In one embodiment, the chemotherapeutic is an EGFR inhibitor. In one embodiment, the EGFR inhibitor is selected from the group consisting of Cetuximab (Erbitux), Erlotinib (Tarceva), Gefitinib (Iressa), Lapatinib (Tykerb), Panitimumab (Vectibox), Sunitinib or Sutent (N-(2-diethylaminoethyl)-5-[(Z)-(5-fluoro-2-oxo-1H-indol-3-ylidene)methyl]-2,4-dimethyl-1H-pyrrole-3-carboxamide), Gefitinib or N-(3-chloro-4-fluoro-phenyl)-7-methoxy-6-(3-morpholin-4-ylpropoxy)quinazolin-4-amine, and Zalutumumab. In one embodiment, the patient may have a cancer that has exhibited resistance to said chemotherapeutic or radiation after at least one round of chemotherapy or radiation. In one embodiment, the chemotherapeutic or radiation reduces or prevents the treated cancer from invading or metastasizing to other sites in the body. In one embodiment, the chemotherapeutic or radiation results in increased apoptosis of the treated cancer cells.

In one embodiment, the treated cancer is selected from advanced and non-advanced cancers including metastasized cancers such as metastatic and non-metastatic lung cancer, breast cancer, head and neck cancer, (HNSCC), pharyngeal cancer, pancreatic cancer, colorectal cancer, anal cancer, glioblastoma multiforme, epithelial cancers, renal cell carcinomas, acute or chronic myelogenous leukemia and other leukemias.

In one embodiment, the results are used to facilitate design of an appropriate therapeutic regimen for mucositis or a disease associated with mucositis.

In one embodiment, the IL-6 antagonist, optionally an anti-IL-6 antibody or antibody fragment, is co-administered with another therapeutic agent selected from the group consisting of analgesics, antibiotics, anti-cachexia agents, anticoagulants, anti-cytokine agents, antiemetic agents, anti-fatigue agent, anti-fever agent, anti-inflammatory agents, antinausea agents, antipyretics, antiviral agents, anti-weakness agent, chemotherapy agents, cytokine antagonist, cytokines, cytotoxic agents, gene therapy agents, growth factors, IL-6 antagonists, immunosuppressive agents, local anesthetic, statins, other therapeutic agents, or any combination thereof.

In another embodiment, the analgesic is acetaminophen, amitriptyline, benzocaine, carbamazepine, codeine, dyclonine hydrochloride (HCl), dihydromorphine, fentanyl patch, Flupirtine, fluriprofen, gabapentin, hydrocodone APAP, hydromorphone, ibuprofen, ketoprofen, lidocaine, morphine, an opiate and derivatives thereof, oxycodone, pentazocine, pethidine, phenacetin, pregabalin, propoeylphene, propoyl APA, salicylamide, tramadol, tramadol APAP, Ulcerease® (0.6% Phenol), or voltaren.

In another embodiment, the local anesthetic is amethocaine, articaine, benzocaine, bupivacaine, mepivacaine, cocaine, cinchocaine, chloroprocaine, cyclomethycaine, dibucaine, dimethocaine, EMLA® (eutectic mixture of lidocaine and prilocalne), etidocaine, larocaine, levobupivacaine, lidocaine, lignocaine, procaine, piperocaine, prilocalne, proparacaine, propoxycaine, ropivacaine, saxitoxin, tetracaine, tetrodotoxin, or trimecaine.

In another embodiment, the anti-cachexia agent is *cannabis*, dronabinol (Marinol®), nabilone (Cesamet), cannabidiol, cannabichromene, tetrahydrocannabinol, Sativex, megestrol acetate, or any combination thereof.

In another embodiment, the anti-coagulant is abciximab (ReoPro®), acenocoumarol, antithrombin III, argatroban, aspirin, bivalirudin (Angiomax®), clopidogrel, dabigatran, dabigatran etexilate (Pradaxa®/Pradax®), desirudin (Revasc®/Iprivask®), dipyridamole, eptifibatide (Integrilin®), fondaparinux, heparin, hirudin, idraparinux, lepirudin (Refludan®), low molecular weight heparin, melagatran, phenindione, phenprocoumon, ticlopidine, tirofiban (Aggrastat®), warfarin, ximelagatran, ximelagatran (Exanta®/Exarta®), or any combination thereof.

In another embodiment, the anti-inflammatory agent is acetaminophen, azapropazone, diclofenac, diflunisal, etodolac, fenbufen, fenoprofen, flurbiprofen, ibuprofen, indomethacin, ketoprofen, ketorolac, mefenamic, meloxicam, nabumetone, naproxen, phenylbutazone, piroxicam, a salicylate, sulindac, tenoxicam, tiaprofenic acid, or tolfenamic acid. In still further embodiment, the salicylate is acetylsalicylic acid, amoxiprin, benorylate, choline magnesium salicylate, ethenzamide, faislamine, methyl salicylate, magnesium salicylate, salicyl salicylate, or salicylamide.

In another embodiment, the anti-nausea agent or anti-emetic agent is comprising 5-HT3 receptor antagonists, ajwain, alizapride, anticholinergics, antihistamines, aprepitant, benzodiazepines, cannabichromene, cannabidiol, cannabinoids, cannabis, casopitant, chlorpromazine, cyclizine, dexamethasone, dexamethasone, dimenhydrinate (Gravol®), diphenhydramine, dolasetron, domperidone, dopamine antagonists, doxylamine, dronabinol (Marinol®), droperidol, emetrol, ginger, granisetron, haloperidol, hydroxyzine, hyoscine, lorazepam, meclizine, metoclopramide, midazolam, muscimol, nabilone (Cesamet), nk1 receptor antagonists, ondansetron, palonosetron, peppermint, Phenergan, prochlorperazine, Promacot, promethazine, Pentazine, propofol, sativex, tetrahydrocannabinol, trimethobenzamide, tropisetron, nandrolone, stilbestrol, thalidomide, lenalidomide, ghrelin agonists, myostatin antagonists, anti-myostatin antibodies, selective androgen receptor modulators, selective estrogen receptor modulators, angiotensin All antagonists, beta two adenergic receptor agonists, beta three adenergic receptor agonists, or any combination thereof.

In another embodiment, the antiviral agent is selected from the group consisting of abacavir, aciclovir, acyclovir, adefovir, amantadine, amprenavir, an antiretroviral fixed dose combination, an antiretroviral synergistic enhancer, arbidol, atazanavir, atripla, brivudine, cidofovir, combivir, darunavir, delavirdine, didanosine, docosanol, edoxudine, efavirenz, emtricitabine, enfuvirtide, entecavir, entry inhibitors, famciclovir, fomivirsen, fosamprenavir, foscarnet, fosfonet, fusion inhibitor, ganciclovir, gardasil, ibacitabine, idoxuridine, imiquimod, immunovir, indinavir, inosine, integrase inhibitor, interferon, interferon type I, interferon type II, interferon type III, lamivudine, lopinavir, loviride, maraviroc, MK-0518, moroxydine, nelfinavir, nevirapine, nexavir, nucleoside analogues, oseltamivir, penciclovir, peramivir, pleconaril, podophyllotoxin, protease inhibitor, reverse transcriptase inhibitor, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, zidovudine, or any combination thereof.

In another embodiment, the cytotoxic agent, chemotherapeutic agent, or immunosuppressive agent is comprising 1-dehydrotestosterone, 1-methylnitrosourea, 5-fluorouracil, 6-mercaptopurine, 6-mercaptopurine, 6-thioguanine, Abatacept, abraxane, acitretin, aclarubicin, Actinium-225 ($^{225}Ac$), actinomycin, Adalimumab, adenosine deaminase inhibitors, Afelimomab, Aflibercept, Afutuzumab, Alefacept, alitretinoin, alkyl sulfonates, alkylating agents, altretamine, alvocidib, aminolevulinic acid/methyl aminolevulinate, aminopterin, aminopterin, amrubicin, amsacrine, amsacrine, anagrelide, Anakinra, anthracenediones, anthracyclines, anthracyclines, anthracyclines, anthramycin (AMC); antimytotic agents, antibiotics, anti-CD20 antibodies, antifolates, Anti-lymphocyte globulin, Antimetabolites, Anti-thymocyte globulin, arsenic trioxide, Aselizumab, asparaginase, asparagine depleters, Astatine-211 ($^{211}At$) Atlizumab, Atorolimumab, atrasentan, Avastin®, azacitidine, Azathioprine, azelastine, aziridines, Basiliximab, BAYX antibodies, Belatacept, Belimumab, belotecan, bendamustine, Bertilimumab, bexarotene, bisantrene, Bismuth-213 ($^{213}Bi$), Bismuth-212 ($^{212}Bi$), bleomycin, bleomycin, bleomycin, BLyS antibodies, bortezomib, busulfan, busulfan, Calcineurin inhibitors, calicheamicin, camptothecin, camptothecins, capecitabine, carboplatin (paraplatin), carboquone, caminomycin, carmofur, carmustine, carmustine (BSNU), CAT antibodies, CD11a antibodies, CD147/Basigin antibodies, CD154 antibodies, CD18 antibodies, CD20 antibodies, CD23 antibodies, CD3 antibodies, CD4 antibodies, CD40 antibodies, CD62L/L-selectin antibodies, CD80 antibodies, CDK inhibitors, Cedelizumab, celecoxib, Certolizumab pegol, chlorambucil, chlorambucils, Ciclosporin, cis-dichlorodiamine platinum (II) (DDP) cisplatin, cladribine, Clenoliximab, clofarabine, colchicin, Complement component 5 antibodies, Copper-67 ($^{67}Cu$), corticosteroids, CTLA-4 antibodies, CTLA-4 fusion proteins, Cyclophilin inhibitors, cyclophosphamides, cyclothosphamide, cytarabine, cytarabine, cytochalasin B, cytotoxic ribonucleases, dacarbazine, Daclizumab, dactinomycin, dactinomycin (actinomycin D), daunorubicin, daunorubicin, daunorubicin (formerly daunomycin), decitabine, Deforolimus, demecolcine, detorubicin, dibromomannitol, diethylcarbamazine, dihydrofolate reductase inhibitors, dihydroxy anthracin dione, diphtheria toxin, DNA polymerase inhibitors, docetaxel, Dorlimomab aritox, Dorlixizumab, doxorubicin (adriamycin), DXL625, Eculizumab, Efalizumab, efaproxiral, EGFR antagonists, elesclomol, elsamitrucin, Elsilimomab, emetine, endothelin receptor antagonists, epipodophyllotoxins, epirubicin, epothilones, Erbitux®, Erlizumab, estramustine, Etanercept, ethidium bromide, etoglucid, etoposide, etoposide phosphate, Everolimus, Faralimomab, farnesyltransferase inhibitors, FKBP inhibitors, floxuridine, fludarabine, fluorouracil, Fontolizumab, fotemustine, Galiximab, Gallium-67 ($^{67}Ga$), Gantenerumab, Gavilimomab, gemcitabine, glucocorticoids, Golimumab, Gomiliximab, gramicidin D, Gusperimus, Herceptin®, hydrazines, hydroxyurea, hypomethylating agents, idarubicin, Idarubicine, ifosfamide, IL-1 antagonists, IL-1 receptor antagonists, IL-12, IL-12 antibodies, IL-12R antagonists, IL-13 antibodies, IL-2, IL-2 inhibitors, IL-2 receptor/CD25 antibodies, IL-6 antibodies, imatinib mesylate, Immunoglobulin E antibodies, IMP dehydrogenase inhibitors, Infliximab, Inolimomab, Integrin antibodies, Interferon antibodies, interferons, Interleukin 5 antibodies, Interleukin-6 receptor antibodies, interleukins, Iodine-125 ($^{125}I$), Iodine-131 ($^{131}I$), Ipilimumab, irinotecan, ixabepilone, Keliximab, larotaxel, Lead-212 ($^{212}Pb$), Lebrilizumab, Leflunomide, Lenalidomide, Lerdelimumab, leucovorine, LFA-1 antibodies, lidocaine, lipoxygenase inhibitors, lomustine (CCNU), lonidamine, lucanthone, Lumiliximab, Lutetium-177 ($^{177}Lu$), Macrolides, mannosulfan, Maslimomab, masoprocol, mechlorethamine, melphalan, Mepolizumab, mercaptopurine, Metelimumab, Methotrexate, microtubule assembly inhibitors, microtubule stability enhancers, mithramycin, mitobronitol, mitoguazone, mitomycin, mitomycin C, mitotane, mitoxantrone, Morolimumab, mTOR inhibitors, Muromonab-CD3, mustines, Mycophenolic acid, mytotane (O,P'-(DDD)), Natalizumab, nedaplatin, Nerelimomab, nimustine, nitrogen mustards, nitrosoureas, nordihydroguaiaretic acid, oblimersen, ocrelizumab, Ocrelizumab, Odulimomab, ofatumumab, olaparib, Omalizumab, ortataxel, Otelixizumab, oxaliplatin, oxaliplatin, paclitaxel (taxol), Pascolizumab, PDGF antagonists, pegaspargase, pemetrexed, Pentostatin, Pertuzumab, Pexelizumab, phosphodiesterase inhibitors, Phosphorus-32 ($^{32}P$), Pimecrolimus Abetimus, pirarubicin, pixantrone, platins, plicamycin, poly ADP ribose polymerase inhibitors, porfimer sodium, porphyrin derivatives, prednimustine, procaine, procarbazine, procarbazine, propranolol, proteasome inhibitors, pseudomonas exotoxin, *Pseudomonas* toxin, purine synthesis inhibitors, puromycin, pyrimidine synthesis inhibitors, radionuclides, radiotherapy, raltitrexed, ranimustine, Reslizumab, retinoid X receptor agonists, retinoids, Rhenium-186 ($^{186}Re$), Rhenium-188 ($^{188}Re$), ribonucleotide reductase inhibitors, ricin, Rilonacept, Rituxan®, Rovelizumab, rubitecan, Ruplizumab, Samarium-153 ($^{153}Sm$), satraplatin, Scandium-47 ($^{47}Sc$), selective androgen receptor modulators, selective estrogen receptor modulators, seliciclib, semustine, sex hormone antagonists, siplizumab, sirolimus, steroid aromatase inhibitors, steroids, streptozocin, streptozotocin, Tacrolimus, talaporfin, Talizumab, taxanes, taxols, tegafur, Telimomab aritox, temoporfin, temozolomide, temsirolimus, Temsirolimus, Teneliximab, teniposide, Teplizumab, Teriflunomide, tesetaxel, testolactone, tetracaine, Thalidomide, thioepa chlorambucil, thiopurines thioguanine, ThioTEPA, thymidylate synthase inhibitors, tiazofurin, tipifarnib, T-lymphocyte antibodies, TNF antagonists, TNF antibodies, TNF fusion proteins, TNF receptor fusion proteins, TNF-alpha inhibitors, Tocilizumab, topoisomerase inhibitors, topotecan, Toralizumab, trabectedin, Tremelimumab, treosulfan, tretinoin, triazenes, triaziquone, triethylenemelamine, triplatin tetranitrate, trofosfamide, tumor antigen specific monoclonal antibodies, tyrosine kinase inhibitors, uramustine, Ustekinumab, valrubicin, Valrubicine, Vapaliximab, VEGF antagonists, Vepalimomab, verteporfin, vinblastine, vinca alkaloids, vincristine, vindesine, vinflunine, vinorelbine, Visilizumab, vorinostat, Yttrium-88 ($^{88}Y$), Yttrium-90 ($^{90}Y$), Zanolimumab, zileuton, Ziralimumab, Zolimomab aritox, zorubicin, Zotarolimus, or any combination thereof.

In another embodiment, the chemotherapy agent is selected from the group consisting of VEGF antagonists, EGFR antagonists, platins including cisplatin and carboplatin, taxols, irinotecan, 5-fluorouracil, gemcytabine, leucovorine, steroids, cyclophosphamide, melphalan, vinca alkaloids, vinblastine, vincristine, vindesine, vinorelbine, mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins, IL-12, IL-2, IL-12R antagonists, Toxin conjugated monoclonal antibodies, tumor antigen specific monoclonal antibodies, Erbitux®, Avastin®, Pertuzumab, anti-CD20 antibodies, Rituxan®, ocrelizumab, ofatumumab, DXL625, Herceptin®, or any combination thereof.

In another embodiment, the cytokine antagonist is an antagonist of tumor necrosis factor-alpha, interferon gamma, interleukin 1 alpha, interleukin 1 beta, interleukin 6, TNF-α, IL-1α, IL-1β, IL-2, IL-4, IL-6, IL-10, IL-12, IL-13, IL-18, IFN-α, IFN-γ, BAFF, CXCL13, IP-10, leukemia-inhibitory factor, or a combination thereof.

In another embodiment, the growth factor is VEGF, EPO, EGF, HRG, Hepatocyte Growth Factor (HGF), Hepcidin, or any combination thereof.

In another embodiment, the statin is comprising atorvastatin, cerivastatin, fluvastatin, lovastatin, mevastatin, pitavastatin, pravastatin, rosuvastatin, simvastatin, or any combination thereof.

In another embodiment, the other therapeutic agent is an antagonist of a factor comprising tumor necrosis factor-alpha, Interferon gamma, Interleukin 1 alpha, Interleukin 1 beta, Interleukin 6, proteolysis inducing factor, leukemia-inhibitory factor, tamoxifen, BCL-2 antagonists, estrogen, bisphosphonates, teriparatide, strontium ranelate, sodium alendronate (Fosamax), risedronate (Actonel), raloxifene, ibandronate (Boniva), Obatoclax, ABT-263, gossypol, gefitinib, epidermal growth factor receptor tyrosine kinase inhibitors, erlotinib, epidermal growth factor receptor inhibitors, psoralens, trioxysalen, methoxsalen, bergapten, retinoids, etretinate, acitretin, infliximab (Remicade®), adalimumab, infliximab, etanercept, Zenapax®, Cyclosporine, Methotrexate, granulocyte-colony stimulating factor, filgrastim, lenograstim, Neupogen, Neulasta, 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lornoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Sulfinpyrazone, Sulindac, Suprofen, Tenoxicam, Tiaprofenic acid, Tolfenamic acid, Tolmetin, and Valdecoxib. Antibiotics include Amikacin, Aminoglycosides, Amoxicillin, Ampicillin, Ansamycins, Arsphenamine, Azithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbimycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomycin, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithromycin, Tetracycline, Tetracyclines, Ticarcillin, Timidazole, Tobramycin, Trimethoprim, Trimethoprim-Sulfamethoxazole, Troleandomycin, Trovafloxacin, and Vancomycin. Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone, an agonist, antagonist, or modulator of a factor comprising TNF-alpha, IL-2, IL-4, IL-6, IL-10, IL-12, IL-13, IL-18, IFN-alpha, IFN-gamma, BAFF, CXCL13, IP-10, VEGF, EPO, EGF, HRG, Hepatocyte Growth Factor (HGF), Hepcidin, or any combination thereof.

In one embodiment, the IL-6 antagonist comprises anti-IL-6 antibodies or antibody fragments thereof, antisense nucleic acids, polypeptides, small molecules, or any combination thereof. In another embodiment, the antisense nucleic acid comprises at least approximately 10 nucleotides of a sequence encoding IL-6, IL-6 receptor alpha, gp130, p38 MAP kinase, JAK1, JAK2, JAK3, STAT3, or SYK. In another embodiment, the antisense nucleic acid comprises DNA, RNA, peptide nucleic acid, locked nucleic acid, morpholino (phosphorodiamidate morpholino oligo), glycerol nucleic acid, threose nucleic acid, or any combination thereof. In another embodiment, the IL-6 antagonist polypeptide comprises a fragment of a polypeptide having a sequence selected from the group consisting soluble IL-6, IL-6 receptor alpha, gp130, p38 MAP kinase, JAK1, JAK2, JAK3, STAT3, and SYK.

In one embodiment, the antibody or antibody fragment may be directly or indirectly coupled to a detectable label, half-life increasing moiety, cytotoxic agent, therapeutic agent, or an immunosuppressive agent. In another embodiment, the detectable label is comprising fluorescent dyes, bioluminescent materials, radioactive materials, chemiluminescent moieties, streptavidin, avidin, biotin, radioactive materials, enzymes, substrates, horseradish peroxidase, acetylcholinesterase, alkaline phosphatase, β-galactosidase, luciferase, rhodamine, fluorescein, fluorescein isothiocyanate, umbelliferone, dichlorotriazinylamine, phycoerythrin, dansyl chloride, luminol, luciferin, aequorin, Iodine 125 ($^{125}I$), Carbon 14 ($^{14}C$), Sulfur 35 ($^{35}S$), Tritium ($^{3}H$), Phosphorus 32 ($^{32}P$), or any combination thereof.

In one embodiment, the subject may receive concomitant chemotherapy. In another embodiment, the subject may receive receiving concomitant radiotherapy.

In another embodiment, the antibody may be the Ab1 antibody.

In another embodiment, the composition may be administered intravenously for at least about 1 hour. In another embodiment, the effective amount is or medicament comprises between about 0.1 and 20 mg/kg of body weight of recipient subject of said IL-6 antagonist. In another embodiment, the effective amount is or medicament comprises at least about 25, 80, 100, 160, 200, or 320 mg. In another embodiment, the effective amount is or medicament comprises between about 0.1 and 100 mg/kg of body weight of the subject.

In another embodiment, the subject may be administered at least 1, 2, 3, 4, or 5 doses. In another embodiment, the composition may be administered every 4 weeks. In another embodiment, the composition may be administered administered 160 mg every 4 weeks for a total of 2 doses. In another embodiment, the composition may be administered administered 160 mg every 4 weeks for a total of 2 doses. In another embodiment, the composition may be administered administered 320 mg every 4 weeks for a total of 2 doses.

In another embodiment, the oral and oropharyngeal mucositis may be induced by chemoradiation (CRT) regimens or HSCT used for the treatment of cancers of the head and neck.

In another embodiment, the method may further comprise assessment of the status of the oral mucositis or head and neck cancer.

In another embodiment, the assessment may comprise imaging modality selected from the group consisting of CAT, PET, and MRI exams.

In another embodiment, the subject may be administered 5-fluoracil (5-FU) or Irinotecan.

The invention also provides a method of identifying cancers that are potentially resistant to the effects of a chemotherapeutic or radiation by assaying for IL-6 using an antibody according to the invention in order to detect whether elevated IL-6 levels are present at the site of the treated cancer.

In another embodiment, a method for the reduction of oral mucositis in subjects with head and neck cancer receiving concomitant chemotherapy and radiotherapy comprises administering an effective amount of a humanized monoclonal antibody that selectively binds IL-6.

In another embodiment, a method for the treating oral mucositis in a subject with head and neck cancer receiving concomitant chemotherapy comprises administering an effective amount of a humanized monoclonal antibody that selectively binds IL-6, wherein said antibody is Ab1.

In another embodiment, a method for the treating alimentary tract mucositis in a subject with head and neck cancer receiving concomitant chemotherapy comprises administering an effective amount of a humanized monoclonal antibody that selectively binds IL-6, wherein said antibody is Ab1.

In another embodiment, a method for the treating gastrointestinal tract mucositis in a subject with head and neck cancer receiving concomitant chemotherapy comprises administering an effective amount of a humanized monoclonal antibody that selectively binds IL-6, wherein said antibody is Ab1.

In another embodiment, the invention provides for the use of an antibody according to the invention for preparing a diagnostic composition for identifying cancers that are potentially resistant to the effects of a chemotherapeutic or radiation by assaying for IL-6 in order to detect whether elevated IL-6 levels are present at the site of the treated cancer.

In another embodiment, the invention provides for the use of an antibody according to the invention for preparing a composition for the reduction of oral mucositis in subjects with head and neck cancer receiving concomitant chemotherapy and radiotherapy comprising administering an effective amount of a humanized monoclonal antibody that selectively binds IL-6.

In another embodiment, the invention provides for the use of an antibody according to the invention for preparing a composition for the treating oral mucositis in a subject with head and neck cancer receiving concomitant chemotherapy comprising administering an effective amount of a humanized monoclonal antibody that selectively binds IL-6, wherein said antibody is Ab1.

In another embodiment, the invention provides for the use of an antibody according to the invention for preparing a composition for the treating mucositis in a subject with head and neck cancer receiving concomitant chemotherapy comprising administering an effective amount of a humanized monoclonal antibody that selectively binds IL-6, wherein said antibody is Ab1.

In one embodiment, the composition may be administered subcutaneously. In another embodiment, the composition may be a pharmaceutical composition. In a further embodiment, the composition may be formulated for subcutanteous administration.

In one embodiment, the patient may have an elevated C-reactive protein ("CRP"). In one embodiment, the patient may have an elevated IL-6 serum level. In one embodiment, the patient may have an elevated IL-6 level in the joints. In one embodiment, the patient may have had an inadequate response to non-steroidal anti-inflammatory drugs (NSAIDs). In one embodiment, the patient may have had an inadequate response to non-biologic Disease Modifying Anti-Rheumatic Drugs (DMARDs).

In one embodiment, the antibody or antibody fragment may be directly or indirectly coupled to a detectable label, cytotoxic agent, therapeutic agent, or an immunosuppressive agent. In one embodiment, the detectable label may comprise a fluorescent dye, bioluminescent material, radioactive material, chemiluminescent moietie, streptavidin, avidin, biotin, radioactive material, enzyme, substrate, horseradish peroxidase, acetylcholinesterase, alkaline phosphatase, β-galactosidase, luciferase, rhodamine, fluorescein, fluorescein isothiocyanate, umbelliferone, dichlorotriazinylamine, phycoerythrin, dansyl chloride, luminol, luciferin, aequorin, Iodine 125 ($^{125}I$), Carbon 14 ($^{14}C$), Sulfur 35 ($^{35}S$), Tritium ($^{3}H$), Phosphorus 32 ($^{32}P$), or any combination thereof. In another embodiment, the IL-6 antagonist may be coupled to a half-life increasing moiety.

In one embodiment, the antibody or antibody fragment may be co-administered with another therapeutic agent selected from the group consisting of analgesics, antibiotics, anti-cachexia agents, anti-coagulants, anti-cytokine agents, antiemetic agents, anti-fatigue agent, anti-fever agent, anti-inflammatory agents, anti-nausea agents, antipyretics, antiviral agents, anti-weakness agent, chemotherapy agents, cytokine antagonist, cytokines, cytotoxic agents, gene therapy agents, growth factor, IL-6 antagonists, immunosuppressive agents, statins, or any combination thereof. In one embodiment, the cytokine antagonist may be an antagonist of a factor comprising tumor necrosis factor-alpha, interferon gamma, interleukin 1 alpha, interleukin 1 beta, interleukin 6, or any combination thereof. In one embodiment, the cytokine antagonist may be an antagonist of TNF-α, IL-1β, IL-2, IL-4, IL-6, IL-10, IL-12, IL-13, IL-18, IFN-α, IFN-γ, BAFF, CXCL13, IP-10, leukemia-inhibitory factor, or a combination thereof. In one embodiment, the growth factor may be VEGF, EPO, EGF, HRG, Hepatocyte Growth Factor (HGF), Hepcidin, or any combination thereof. In one embodiment, the IL-6 antagonist may comprise an anti-IL-6 antibodies or antibody fragments thereof, antisense nucleic acids, polypeptides, small molecules, or any combination thereof.

In another embodiment, the antisense nucleic acid may comprise at least approximately 10 nucleotides of a sequence encoding IL-6, IL-6 receptor alpha, gp130, p38 MAP kinase, JAK1, JAK2, JAK3, STAT3, or SYK. In another embodiment, the antisense nucleic acid may comprise DNA, RNA, peptide nucleic acid, locked nucleic acid, morpholino (phosphorodiamidate morpholino oligo), glycerol nucleic acid, threose nucleic acid, or any combination thereof. In another embodiment, the IL-6 antagonist polypeptide may comprise a fragment of a polypeptide having a sequence selected from the group consisting IL-6, IL-6 receptor alpha, gp130, p38 MAP kinase, JAK1, JAK2, JAK3, SYK, STAT3, or any combination thereof. In a further embodiment, the IL-6 antagonist may be an anti-IL-6R, anti-gp130, anti-p38 MAP kinase, anti-JAK1, anti-JAK2, anti-JAK3, anti-STAT3, or anti-SYK antibody or antibody fragment One embodiment encompasses specific humanized antibodies and fragments and variants thereof for treatment or prevention of mucositis capable of binding to IL-6 and/or the IL-6/IL-6R complex. These antibodies may bind soluble IL-6 or cell surface expressed IL-6. Also, these antibodies may inhibit the formation or the biological effects of at least one of IL-6, IL-6/IL-6R complexes, IL-6/IL-6R/gp130 complexes and/or multimers of IL-6/IL-6R/gp130. The present invention relates to novel therapies and therapeutic protocols using anti-IL-6 antibodies, preferably those described herein.

The invention also contemplates the administration of conjugates of anti-IL-6 antibodies and humanized, chimeric or single chain versions thereof and other binding fragments and variants thereof conjugated to at least one functional or detectable moieties.

In an embodiment of the invention, the anti-IL-6 antibody or antibody fragment or variant thereof may be directly or indirectly attached to a detectable label or therapeutic agent.

In one embodiment, the IL-6 antagonist may be an antisense nucleic acid. In another embodiment of the invention, the IL-6 antagonist may be an antisense nucleic acid, for example comprising at least approximately 10 nucleotides of a sequence encoding IL-6, IL-6 receptor alpha, gp130, p38 MAP kinase, JAK1, JAK2, JAK3, STAT3, or SYK. In a further embodiment of the invention, the antisense nucleic acid may comprise DNA, RNA, peptide nucleic acid, locked nucleic acid, morpholino (phosphorodiamidate morpholino oligo), glycerol nucleic acid, threose nucleic acid, or any combination thereof.

In one embodiment, the IL-6 antagonist may comprise Actemra® (Tocilizumab), Remicade®, Zenapax® (daclizumab), or any combination thereof.

In one embodiment, the IL-6 antagonist may comprise a polypeptide having a sequence comprising a fragment of IL-6, IL-6 receptor alpha, gp130, p38 MAP kinase, JAK1, JAK2, JAK3, SYK, or any combination thereof, such as a fragment or full-length polypeptide that is at least 40 amino acids in length. In another embodiment of the invention, the IL-6 antagonist may comprise a soluble IL-6, IL-6 receptor alpha, gp130, p38 MAP kinase, JAK1, JAK2, JAK3, SYK, STAT3, or any combination thereof.

In another aspect the invention provides pharmaceutical compositions and their use in novel combination therapies and comprising administration of an anti-IL-6 antibody, such as any one of Ab1-Ab36 antibodies described in Table 4 or a fragment or variant thereof, and at least one other therapeutic compound such as an anti-cytokine agent.

In an embodiment of the invention, the IL-6 antagonist may target IL-6, IL-6 receptor alpha, gp130, p38 MAP kinase, JAK1, JAK2, JAK3, SYK, or any combination thereof. In one embodiment, the IL-6 antagonist may comprise an antibody, an antibody fragment, a peptide, a glycoalkoid, an antisense nucleic acid, a ribozyme, a retinoid, an avemir, a small molecule, or any combination thereof. In one embodiment, the IL-6 antagonist may comprise an anti-IL-6R, anti-gp130, anti-p38 MAP kinase, anti-JAK1, anti-JAK2, anti-JAK3, or anti-SYK antibody, anti-STAT3, or antibody fragment. In an embodiment of the invention, the antagonist may comprise an anti-IL-6 antibody (e.g., any one of Ab1-Ab36 antibodies described in Table 4) or antibody fragment or variant thereof.

The present invention also pertains to methods of improving survivability or quality of life of a patient having or at risk of developing mucositis comprising administering to the patient an anti-IL-6 antibody (e.g., ALD518 antibody) or antibody fragment or variant thereof, whereby the patient's C-reactive protein ("CRP") level is lowered.

In one embodiment of the invention, the anti-IL-6 antibody or antibody fragment or variant thereof may be administered to the patient with a frequency at most once per period of approximately 4, 8, 12, 16, 20, or 24 weeks.

In an embodiment of the invention, the patient's quality of life may be improved.

This invention relates to novel anti-IL-6 antibodies, novel therapies and therapeutic protocols utilizing anti-IL-6 antibodies, and pharmaceutical formulations containing anti-IL-6 antibodies. In preferred embodiments, an anti-IL-6 antibody is any one of Ab1-Ab36 antibodies described in Table 4, which includes rabbit or humanized forms thereof, as well as heavy chains, light chains, fragments, variants, and CDRs thereof, or an antibody or antibody fragment that specifically binds to the same linear or conformational epitope(s) on an intact human IL-6 polypeptide fragment thereof as Ab1. The subject application pertains in particular to preferred formulations and therapeutic uses of an exemplary humanized antibody referred to herein as any one of Ab1-Ab36 antibodies described in Table 4 and variants thereof. In preferred embodiments, the anti-IL-6 antibody has an in vivo half-life of at least about 30 days, has an in vivo effect of lowering C-reactive protein, possesses a binding affinity (Kd) for IL-6 of less than about 50 picomolar, and/or has a rate of dissociation ($K_{off}$) from IL-6 of less than or equal to $10^{-4}$ $S^{-1}$.

In one aspect, this invention pertains to methods of improving survivability or quality of life of a patient in need thereof, comprising administering to a patient with or at risk of developing mucositis as a result of disease or a therapeutic regimen comprising the administration of an anti-IL-6 antibody, such as any one of Ab1-Ab36 antibodies described in Table 4 antibody or a fragment or variant thereof (e.g., Ab1).

Another embodiment relates to methods of improving survivability or quality of life of a patient diagnosed with mucositis, comprising administering to the patient an anti-IL-6 antibody or antibody fragment or variant thereof, whereby the patient's serum C-reactive protein ("CRP") level is stabilized and preferably reduced, and monitoring the patient to assess the reduction in the patient's serum CRP level. In an embodiment, the patient may have an elevated C-reactive protein (CRP) level prior to treatment. In an embodiment, the patient may have an elevated serum CRP level prior to treatment.

In an embodiment of the invention, the patient's serum CRP level may remain decreased for an entire period intervening two consecutive anti-IL-6 antibody administrations.

In one embodiment, the patient may have been diagnosed mucositis.

In one embodiment, the antibody, or antibody fragment thereof, may be expressed from a recombinant cell. In another embodiment, the cell may be selected from a mammalian, yeast, bacterial, and insect cell. In another embodiment, the cell may be a yeast cell. In another embodiment, the cell may be a diploidal yeast cell. In another embodiment, the yeast cell may be a *Pichia* yeast. In another embodiment, the anti-IL-6 antibody may be produced in a yeast based (*Pichia pastoris*) expression system using conventional fermentation processes and downstream purification. In one embodiment, the antibodies and antibody fragments described herein may be expressed in yeast cells. In one embodiment, the mating competent yeast may a member of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*. Other types of yeast potentially useful in the invention include *Yarrowia, Rhodosporidium, Candida, Hansenula, Filobasium, Filobasidellla, Sporidiobolus, Bullera, Leucosporidium*, and *Filobasidella*. In a preferred embodiment, the mating competent yeast may a member of the genus *Pichia*. In a further preferred embodiment, the mating competent yeast of the genus *Pichia* is one of the following species: *Pichia pastoris, Pichia methanolica*, and *Hansenula polymorpha* (*Pichia angusta*). In a particularly preferred embodiment, the mating competent yeast of the genus *Pichia* may the species *Pichia pastoris.*

In one embodiment, a composition for the reduction of oral mucositis in subjects with head and neck cancer receiving concomitant chemotherapy and radiotherapy may comprise an effective amount of a humanized monoclonal antibody that selectively binds IL-6.

In one embodiment, a composition for the treating oral mucositis in a subject with head and neck cancer receiving concomitant chemotherapy may comprise an effective amount of a humanized monoclonal antibody that selectively binds IL-6, wherein said antibody is Ab1.

In one embodiment, a composition comprising a humanized monoclonal antibody or fragment thereof that selectively binds IL-6 for treating oral mucositis induced by chemoradiation (CRT) regimens used for the treatment of cancers of the head and neck.

In one embodiment, a composition for treatment or prevention of oral mucositis may comprise a humanized monoclonal antibody that selectively binds IL-6 and saline solution.

In one embodiment, the oral mucositis may be induced by chemoradiation (CRT) regimens or HSCT regimens used for the treatment of cancers of the head and neck.

In one embodiment, a method of treating rheumatoid arthritis by subcutaneously administering a therapeutically effective dosage of an anti-IL-6 antibody or antibody fragment having the same epitopic specificity as Ab1 or an antibody that competes with Ab1 for binding to IL-6 to a patient in need thereof.

In one embodiment, the invention provides for the use of anti-IL-6 antibody or antibody fragment having the same epitopic specificity as Ab1 or an antibody that competes with Ab1 for binding to IL-6 for the preparation of a subcutaneously administrable composition for treating rheumatoid arthritis in a patient in need thereof.

In a further embodiment, a composition for treating rheumatoid arthritis may comprise a therapeutically effective dosage of an anti-IL-6 antibody or antibody fragment having the same epitopic specificity as Ab1 or an antibody that competes with Ab1 for binding to IL-6 to a patient in need thereof that is formulated for subcutaneous administration.

In one embodiment, the composition may comprise an anti-IL-6 antibody or antibody fragment contained in a composition that comprises, or alternatively consists of, said anti-IL-6 antibody or antibody fragment, about 5 mM Histidine base, about 5 mM Histidine HCl to make final pH 6, 250 mM sorbitol, and 0.015% (w/w) Polysorbate 80.

In one embodiment, the composition may comprise an anti-IL-6 antibody or antibody fragment contained in a composition that comprises, or alternatively consists of, said anti-IL-6 antibody or antibody fragment, about 5 mM Histidine base, about 5 mM Histidine HCl to make final pH 6, 250 to 280 mM sorbitol or sorbitol in combination with sucrose, and 0.015% (w/w) Polysorbate 80, said formulation having a nitrogen headspace in the shipping vials.

The invention also provides a composition for treating rheumatoid arthritis comprising a therapeutically effective dosage of an anti-IL-6 antibody or antibody fragment having the same epitopic specificity as Ab1 or an antibody that competes with Ab1 for binding to IL-6 to a patient in need thereof that is formulated for intravenous administration.

In one embodiment, the composition may comprise an anti-IL-6 antibody or antibody fragment contained in a composition comprising, or alternatively consisting of, anti-IL-6 antibody or antibody fragment, 25 mM Histidine base, Phosphoric acid q.s. to pH 6, and 250 mM sorbitol.

In one embodiment, the composition may comprise an anti-IL-6 antibody or antibody fragment contained in a composition comprising, or alternatively consisting of, said anti-IL-6 antibody or antibody fragment, 12.5 mM Histidine base, 12.5 mM Histidine HCl (or 25 mM Histidine base and Hydrochloric acid q.s. to pH 6), 250 mM sorbitol, and 0.015% (w/w) Polysorbate 80.

In one embodiment, the composition may comprise an anti-IL-6 antibody or antibody fragment contained in a composition comprising, or alternatively consisting of, said anti-IL-6 antibody or antibody fragment, about 5 mM Histidine base, about 5 mM Histidine HCl to make final pH 6, 250 mM sorbitol, and 0.015% (w/w) Polysorbate 80.

In one embodiment, the composition may comprise a concentration of an anti-IL-6 antibody or antibody fragment is at least about 10, 20, 30, 40, 50, 60, 70, 80, 90, 100 mg/mL or at least about 10-100 mg/mL.

In one embodiment, the composition may comprise at least about 50 or 100 mg of an anti-IL-6 antibody or antibody fragment.

In one embodiment, the composition may comprise at least about 80 mg, about 160 mg, or about 320 mg of an anti-IL-6 antibody or antibody fragment.

In one embodiment, the effective amount is between about 0.1 and 20 mg/kg of body weight of recipient subject.

In one embodiment, the effective amount is between about 0.1 and 100 mg/kg of body weight of the subject.

In one embodiment, the composition may comprise at least about 25, 80, 100, 160, 200, or 320 mg.

In one embodiment, the composition may be formulated for intravenous administration.

In one embodiment, the composition may comprise an excipient selected from the group consisting of histidine, sorbitol, and polysorbate 80.

In one embodiment, the composition may be administered every 4 weeks. In one embodiment, the composition may be administered 80 mg every 4 weeks for a total of 2 doses. In one embodiment, the composition may be administered 160 mg every 4 weeks for a total of 2 doses. In one embodiment, the composition may be administered 320 mg every 4 weeks for a total of 2 doses.

In one embodiment, the anti-IL-6 antibody may comprise a light chain polypeptide comprising a polypeptide having at least 75% identity, at least 80% identity, at least 85% identity, at least 90% identity, at least 95% identity, at least 96%, at least 97% identity, at least 98%, at least 99% identity, or 100% identity to SEQ ID NO: 709.

In one embodiment, the anti-IL-6 antibody may comprise a light chain polypeptide comprising a polypeptide encoded by a polynucleotide that has at least 75% identity, at least 80% identity, at least 85% identity, at least 90% identity, at least 95% identity, at least 96%, at least 97% identity, at least 98%, at least 99% identity, or 100% identity to SEQ ID NO: 723.

In one embodiment, the anti-IL-6 antibody may comprise a heavy chain polypeptide comprising a polypeptide having at least 75% identity, at least 80% identity, at least 85% identity, at least 90% identity, at least 95% identity, at least 96%, at least 97% identity, at least 98%, at least 99% identity, or 100% identity to SEQ ID NO: 657.

In one embodiment, the anti-IL-6 antibody may comprise a heavy chain polypeptide comprising a polypeptide encoded by a polynucleotide having at least 75% identity, at least 80% identity, at least 85% identity, at least 90% identity, at least 95% identity, at least 96%, at least 97% identity, at least 98%, at least 99% identity, or 100% identity to SEQ ID NO: 700.

In one embodiment, the anti-IL-6 antibody may comprise a light chain polypeptide comprising: a polypeptide having at least 75% identity to SEQ ID NO: 709, a polypeptide encoded by a polynucleotide that has at least 75% identity to the polynucleotide of SEQ ID NO: 723, a polypeptide encoded by a polynucleotide that hybridizes under medium stringency conditions to a polynucleotide having the sequence of the reverse complement of SEQ ID NO: 723, or a polypeptide encoded by a polynucleotide that hybridizes under high stringency conditions to a polynucleotide having the sequence of the reverse complement of SEQ ID NO: 723; and a heavy chain polypeptide comprising: a polypeptide having at least 75% identity to SEQ ID NO: 657, a polypeptide encoded by a polynucleotide that has at least 75% identity to the polynucleotide of SEQ ID NO: 700, a polypeptide encoded by a polynucleotide that hybridizes under medium stringency conditions to a polynucleotide having the sequence of the reverse complement of SEQ ID NO: 700, or a polypeptide encoded by a polynucleotide that hybridizes under high stringency conditions to a polynucleotide having the sequence of the reverse complement of SEQ ID NO: 700; wherein the Ab1 antibody or antibody fragment specifically binds to IL-6 and antagonizes one or more activity associated with IL-6.

In one embodiment, the anti-IL-6 antibody may comprise anti-IL-6 antibody comprises variable heavy and light chain sequences which are at least 90% identical to the variable heavy and light sequences contained in SEQ ID NO:19 and 20.

In one embodiment, the anti-IL-6 antibody may comprise anti-IL-6 antibody comprises variable heavy and light chain sequences which are at least 95% identical to the variable heavy and light sequences contained in SEQ ID NO:19 and 20.

In one embodiment, the anti-IL-6 antibody may comprise anti-IL-6 antibody comprises variable heavy and light chain sequences which are at least 98% identical to the variable heavy and light sequences contained in SEQ ID NO:19 and 20.

In one embodiment, the anti-IL-6 antibody may comprise anti-IL-6 antibody comprises the variable heavy and light sequences contained in SEQ ID NO:19 and 20.

In one embodiment, the anti-IL-6 antibody may comprise anti-IL-6 antibody further comprises the constant light chain sequence contained in SEQ ID NO: 586.

In one embodiment, the anti-IL-6 antibody may comprise the constant heavy chain sequence contained in SEQ ID NO: 588.

In one embodiment, the composition may further comprise methotrexate.

In one embodiment, the composition may further comprise at least one anti-inflammatory agent, analgesic agent, or disease-modifying antirheumatic drug (DMARD).

In one embodiment, the anti-inflammatory agent is selected from the group consisting of steroids, Cortisone, Glucocorticoids, prednisone, prednisolone, Hydrocortisone (Cortisol), Cortisone acetate, Methylprednisolone, Dexamethasone, Betamethasone, Triamcinolone, Beclometasone, and Fludrocortisone acetate, non-steroidal anti-inflammatory drug (NSAIDs), ibuprofen, naproxen, meloxicam, etodolac, nabumetone, sulindac, tolementin, choline magnesium salicylate, diclofenac, diflusinal, indomethicin, Ketoprofen, Oxaprozin, piroxicam, and nimesulide, Salicylates, Aspirin (acetylsalicylic acid), Diflunisal, Salsalate, p-amino phenol derivatives, Paracetamol, phenacetin, Propionic acid derivatives, Ibuprofen, Naproxen, Fenoprofen, Ketoprofen, Flurbiprofen, Oxaprozin, Loxoprofen, Acetic acid derivatives, Indomethacin, Sulindac, Etodolac, Ketorolac, Diclofenac, Nabumetone, Enolic acid (Oxicam) derivatives, Piroxicam, Meloxicam, Tenoxicam, Droxicam, Lornoxicam, Isoxicam, Fenamic acid derivatives (Fenamates), Mefenamic acid, Meclofenamic acid, Flufenamic acid, Tolfenamic acid, Selective COX-2 inhibitors (Coxibs), Celecoxib, Rofecoxib, Valdecoxib, Parecoxib, Lumiracoxib, Etoricoxib, Firocoxib, Sulphonanilides, Nimesulide, and Licofelone.

In one embodiment, the analgesic agent is selected from the group consisting of NSAIDs, COX-2 inhibitors, Celecoxib, Rofecoxib, Valdecoxib, Parecoxib, Lumiracoxib, Etoricoxib, Firocoxib, acetaminophen, opiates, Dextropropoxyphene, Codeine, Tramadol, Anileridine, Pethidine, Hydrocodone, Morphine, Oxycodone, Methadone, Diacetylmorphine, Hydromorphone, Oxymorphone, Levorphanol, Buprenorphine, Fentanyl, Sufentanyl, Etorphine, Carfentanil, dihydromorphine, dihydrocodeine, Thebaine, Papaverine, diproqualone, Flupirtine, Tricyclic antidepressants, and lidocaine.

In one embodiment, the DMARD may be selected from the group consisting of mycophenolate mofetil (CellCept), calcineurin inhibitors, cyclosporine, sirolimus, everolimus, oral retinoids, azathioprine, fumeric acid esters, D-penicillamine, cyclophosphamide, immunoadsorption column, Prosorba® column, a gold salt, auranofin, sodium aurothiomalate (Myocrisin), hydroxychloroquine, chloroquine, leflunomide, methotrexate (MTX), minocycline, sulfasalazine (SSZ), tumor necrosis factor alpha (TNFa) blockers, etanercept (Enbrel), infliximab (Remicade), adalimumab (Humira), certolizumab pegol (Cimzia), golimumab (Simponi)), Interleukin 1 (IL-1) blockers, e.g., anakinra (Kineret), monoclonal antibodies against B cells, rituximab (Rituxan)), T cell costimulation blockers, abatacept (Orencia), Interleukin 6 (IL-6) blockers, tocilizumab, RoActemra, and Actemra.

In one embodiment, the DMARD is not an antibody.

In one embodiment, the administration of a composition described herein to a patient in need thereof results in an improvement in at least one of the following: (i) improved DAS-28 scores, (ii) improved EULAR scores, (iii) improved LDAS scores (iv) improved ACR scores, (v) an increase in serum albumin, (vi) a decrease in CRP, (vii) improvement in one or more SF-36 domain scores, (viii) an improvement in SF-6D score, wherein said efficacy is measured relative to said patient's baseline prior to administration of said antibody or antibody fragment, relative untreated patients, relative to patients receiving a placebo or control formulation, or relative to age/gender norms.

In one embodiment, the administration of a composition described herein to a patient in need thereof results in a prolonged improvement in disease (observed at least 4, 6, 8, 10, 12, 14 or 16 weeks after antibody administration) as manifested by at least one of the following: (i) improved DAS-28 scores, (ii) improved EULAR scores, (iii) improved LDAS scores (iv) improved ACR scores, (v) an increase in serum albumin, (vi) a decrease in CRP, (vii) improvement in one or more SF-36 domain scores, (viii) an improvement in SF-6D score, wherein said efficacy is measured relative to said patient's baseline prior to administration of said antibody or antibody fragment, relative untreated patients, relative to patients receiving a placebo or control formulation, or relative to age/gender norms.

In a further embodiment, the improvement in SF-6D score is at least equal to the Minimum Important Difference (MID) relative to the patient's SF-6D prior to said administration.

In a further embodiment, the improvement in SF-6D score is at least twice the MID relative to the patient's SF-6D prior to said administration.

In a further embodiment, the improvement in SF-6D score is at least three times the MID relative to the patient's SF-6D prior to said administration.

In another embodiment, the improvement in SF-36 may comprise an improvement in the physical functioning domain score, said improvement being at least equal to the minimum clinically important difference (MCID), at least 2 times the MCID, at least 3 times the MCID, at least 4 times the MCID, at least 5 times the MCID, or at least 6 times the MCID for that domain score.

In another embodiment, the improvement in SF-36 may comprise an improvement in the role physical domain score, said improvement being at least equal to the MCID, at least 2 times the MCID, at least 3 times the MCID, at least 4 times the MCID, at least 5 times the MCID, or at least 6 times the MCID for that domain score.

In another embodiment, the improvement in SF-36 may comprise an improvement in the bodily pain domain score, said improvement being at least equal to the MCID, at least 2 times the MCID, at least 3 times the MCID, at least 4 times the MCID, at least 5 times the MCID, or at least 6 times the MCID for that domain score.

In another embodiment, the improvement in SF-36 may comprise an improvement in the general health domain score, said improvement being at least equal to the MCID, at least 2 times the MCID, at least 3 times the MCID, at least 4 times the MCID, at least 5 times the MCID, or at least 6 times the MCID for that domain score.

In another embodiment, the improvement in SF-36 may comprise an improvement in the role emotional domain score, said improvement being at least equal to the MCID, at least 2 times the MCID, at least 3 times the MCID, at least 4 times the MCID, at least 5 times the MCID, or at least 6 times the MCID for that domain score.

In another embodiment, the improvement in SF-36 may comprise an improvement in the vitality domain score, said improvement being at least equal to the MCID, at least 2 times the MCID, at least 3 times the MCID, at least 4 times the MCID, at least 5 times the MCID, or at least 6 times the MCID for that domain score.

In another embodiment, the improvement in SF-36 may comprise an improvement in the social functioning domain score, said improvement being at least equal to the MCID, at least 2 times the MCID, at least 3 times the MCID, at least 4 times the MCID, at least 5 times the MCID, or at least 6 times the MCID for that domain score.

In another embodiment, the improvement in SF-36 may comprise an improvement in the mental health domain score, said improvement being at least equal to the MCID, at least 2 times the MCID, at least 3 times the MCID, at least 4 times the MCID, at least 5 times the MCID, or at least 6 times the MCID for that domain score.

In one embodiment, method for treating rheumatoid arthritis may comprise administering a composition comprising at least about 10 mg/mL of an anti-IL-6 antibody having the epitopic specificity of Ab1 to a patient in need thereof.

The invention also provides for the use of an anti-IL-6 antibody having the epitopic specificity of Ab1 or any of the other anti-Il-6 antibodies disclosed herein for preparing a pharmaceutical composition for treating rheumatoid arthritis comprising at least about 10 mg/mL of an anti-IL-6 antibody having the epitopic specificity of Ab1 to a patient in need thereof.

The invention also provides for a composition for treating rheumatoid arthritis comprising at least about 10 mg/mL of an anti-IL-6 antibody to a patient in need thereof. In one embodiment, the composition may comprises at least about 20, 30, 40, 50, 60, 70, 80, or 100 mg/mL of an anti-IL-6 antibody. In one embodiment, the composition may comprise at least about 10-100 mg/mL of an anti-IL-6 antibody. In one embodiment, the composition may be formulated for subcutaneous administration and comprises at least about 100 mg/mL of an anti-IL-6 antibody. In one embodiment, the composition may be formulated for intravenous administration and comprises at least about 10, 20, 30, or 40 mg/mL, or 10-40 mg/mL of an anti-IL-6 antibody.

In one embodiment, a method of treating or preventing oral mucositis comprising administering a composition comprises 160 mg of an Ab1 antibody or antibody fragment thereof, wherein said patient does not develop oral mucositis more severe than a Grade 3 according to the WHO Oral Mucositis Scale. In another embodiment, the patient may be undergoing chemotherapy. In another embodiment, the patient may be undergoing radiotherapy. In another embodiment, the patient has head and neck cancer. In another embodiment, the patient may not develop oral mucosits more severe than Grade 2, 1, or 0.

BRIEF DESCRIPTION OF THE SEVERAL VIEWS OF THE DRAWINGS

FIG. 1 depicts alignments of variable light and variable heavy sequences between a rabbit antibody variable light and variable heavy sequences and homologous human sequences and the humanized sequences. Framework regions are identified FR1-FR4. Complementarity determining regions are identified as CDR1-CDR3. Amino acid residues are numbered as shown. The initial rabbit sequences are called RbtVL and RbtVH for the variable light and variable heavy sequences respectively. Three of the most similar human germline antibody sequences, spanning from Framework 1 through to the end of Framework 3, are aligned below the rabbit sequences. The human sequence that is considered the most similar to the rabbit sequence is shown first. In this example those most similar sequences are L12A for the light chain and 3-64-04 for the heavy chain. Human CDR3 sequences are not shown. The closest human Framework 4 sequence is aligned below the rabbit Framework 4 sequence. The vertical dashes indicate a residue where the rabbit residue is identical with at least one of the human residues at the same position. The bold residues indicate that the human residue at that position is identical to the rabbit residue at the same position. The final humanized sequences are called VLh and VHh for the variable light and variable heavy sequences respectively. The underlined residues indicate that the residue is the same as the rabbit residue at that position but different than the human residues at that position in the three aligned human sequences.

FIGS. 2 and 3 depicts alignments between a rabbit antibody light and variable heavy sequences and homologous human sequences and the humanized sequences. Framework regions are identified as FR1-FR4. Complementarity determining regions are identified as CDR1-CDR3.

FIGS. 4A-B and 5A-B depicts alignments between light and variable heavy sequences, respectively, of different forms of Ab1. Framework regions are identified as FR1-FR4. Complementarity determining regions are identified as CDR1-CDR3. Sequence differences within the CDR regions highlighted.

FIG. 26 depicts of patient disposition in a Phase II clinical trial for administration of ALD518 to patients with active rheumatoid arthritis (RA). An asterisk indicates that one patient did not receive treatment as randomized (the patient was randomized to receive 160 mg ALD518, but received 320 mg on Day 1 and 160 mg ALD518 at Week 8; AE=adverse event.

FIG. 27 graphically illustrates the mean changes in SF-36 composite scores at Week 12 in a Phase II clinical trial for administration of ALD518 to patients with active RA. Data are mean and error bars represent 95% confidence intervals (for each group, the left bar shows the PCS score and the right bar shows the MCS score). Mean changes in PCS and MCS scores at Week 12 exceeded the MCD in all ALD-518 treatment groups. Greater improvements in MCS score in favor of all ALD-518 treatment groups were demonstrated at Week 12 ($p<0.05$). MCS scores changes also exceeded the PCS scores in all ALD-518 treatment groups. SF-36=Short Form Health Survey-36; PCS=physical component score; MCS=mental component score; MCID=minimum clinically important difference.

FIG. 28A-D presents spydergrams summarizing the changes from baseline to week 12 in SF-36 domain scores compared with age/gender matched norms for a Phase II clinical trial for administration of ALD518 to patients with active RA. The spydergrams summarize age/gender norms, average baseline scores prior to treatment, and average scores after treatment in each of eight tested domains for patients receiving 80 mg (panel A), 160 mg (panel B), or 320 mg (panel C) ALD-518, or placebo (panel D). PF=physical function; RP=role physical; BP=bodily pain; GH=general health; VT=vitality; SF=social functioning; RE=role emotional; MH=mental health; SF-36=Short Form-36.

FIG. 29A-B presents spydergrams summarizing the changes from baseline to weeks 12 (A) and 16 (B) in SF-36 domain scores compared with age/gender matched norms for a Phase II clinical trial for administration of ALD518 to patients with active RA. The spydergrams summarize scores in eight tested domains for age/gender norms, combined average baseline scores prior to treatment, and average scores after treatment for each treatment group (ALD-518 dosages of 80 mg, 160 mg, or 320 mg), and the placebo group. Abbreviations are as in FIG. 28.

FIG. 30 depicts WHO oral mucositis grade versus cumulative IMRT (Gy): ALD518 160 mg intravenous at week 0 and week 4 for three patients.

DETAILED DESCRIPTION OF PREFERRED EMBODIMENTS

Definitions

Figure 6:
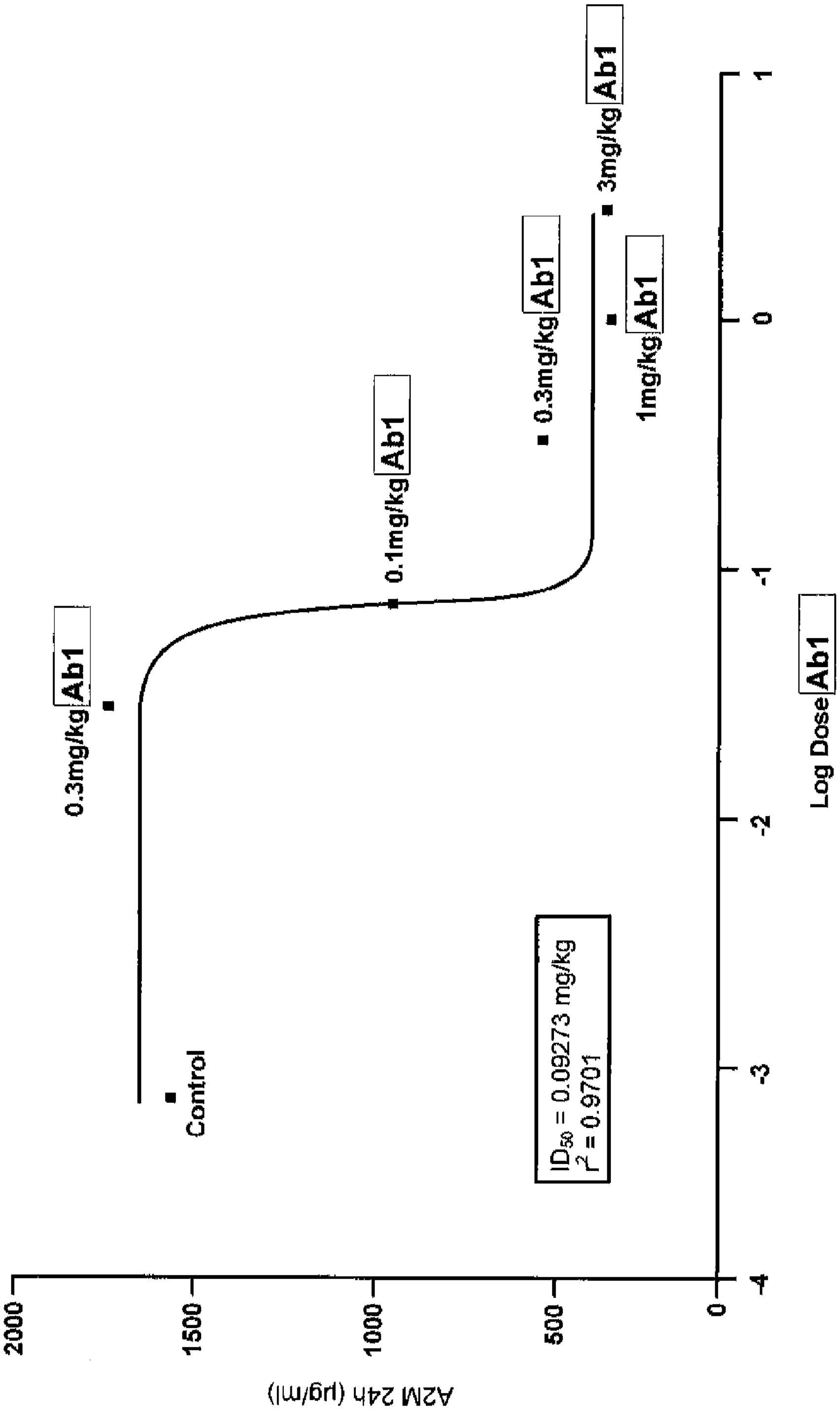
FIG. 6 provides the α-2-macroglobulin (A2M) dose response curve for antibody Ab1 administered intravenously at different doses one hour after a 100 μg/kg s.c. dose of human IL-6. See also WO 2011/066371.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Amplification as used herein, refers broadly to the amplification of polynucleotide sequences is the in vitro production of multiple copies of a particular nucleic acid sequence. The amplified sequence is usually in the form of DNA. A variety of techniques for carrying out such amplification are known in the art. See, e.g., Van Brunt (1990) *Bio/Technol.* 8(4): 291-294. Polymerase chain reaction or PCR is a prototype of nucleic acid amplification, and use of PCR herein should be considered exemplary of other suitable amplification techniques.

Antibody, as used herein, refers broadly to any polypeptide chain-containing molecular structure with a specific shape that fits to and recognizes an epitope, where at least one non-covalent binding interactions stabilize the complex between the molecular structure and the epitope. The archetypal antibody molecule is the immunoglobulin, and all types of immunoglobulins, IgG, IgM, IgA, IgE, IgD, from all sources, e.g., human, rodent, rabbit, cow, sheep, pig, dog, chicken, are considered to be "antibodies." Antibodies include but are not limited to chimeric antibodies, human antibodies and other non-human mammalian antibodies, humanized antibodies, single chain antibodies (scFvs), camelbodies, nanobodies, IgNAR (single-chain antibodies derived from sharks), small-modular immunopharmaceuticals (SMIPs), and antibody fragments (e.g., Fabs, Fab', $F(ab')_2$.) Numerous antibody coding sequences have been described; and others may be raised by methods well-known in the art. See Streltsov, et al. (2005) *Protein Sci.* 14(11): 2901-9; Greenberg, et al. (1995) *Nature* 374(6518): 168-173; Nuttall, et al. (2001) *Mol Immunol.* 38(4): 313-26; Hamers-Casterman, et al. (1993) *Nature* 363(6428): 446-8; Gill, et al. (2006) *Curr Opin Biotechnol.* 17(6): 653-8.

Antibody fragment, as used herein, refers broadly to a fragment of an antibody which recognizes an antigen (e.g., paratopes, antigen-binding fragment.) The antibody fragment may comprise a paratope that may be a small region (e.g., 15-22 amino acids) of the antibody's Fv region and may contain parts of the antibody's heavy and light chains. See Goldsby, et al. *Antigens* (Chapter 3) Immunology ($5^{th}$ Ed.) New York: W.H. Freeman and Company, pages 57-75.

C-Reactive Protein (CRP), as used herein, refers broadly to a 224 amino acid protein found in the blood that rise in response to inflammation [(e.g., GenBank Protein Accession No. NP_000558 (SEQ ID NO: 726)]. CRP also encompasses any pre-pro, pro- and mature forms of this CRP amino acid sequence, as well as mutants and variants including allelic variants of this sequence. CRP levels, e.g. in the serum, liver, or elsewhere in the body, can be readily measured using routine methods and commercially available reagents, e.g. ELISA, antibody test strip, immunoturbidimetry, rapid immunodiffusion, visual agglutination, Western blot, Northern blot As mentioned above CRP levels may in addition be measured in patients having or at risk of developing thrombosis according to the invention.

Coding sequence, as used herein refers broadly to an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence. A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

Complementarity determining region, hypervariable region, or CDR, as used herein refer broadly to at least one of the hyper-variable or complementarity determining regions (CDRs) found in the variable regions of light or heavy chains of an antibody (See Kabat, E. A. et al. (1987) Sequences of Proteins of Immunological Interest, National Institutes of Health, Bethesda, Md.). These expressions include the hypervariable regions as defined by Kabat et al. ("Sequences of Proteins of Immunological Interest," Kabat E., et al. (1983) US Dept. of Health and Human Services) or the hypervariable loops in 3-dimensional structures of antibodies. Chothia and Lesk (1987) *J. Mol. Biol.* 196: 901-917. The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri (2005) Methods 36:25-34). CDRs for exemplary anti-IL-6 antibodies are provided herein.

Disease or condition, as used herein, refers broadly to a disease or condition that a patient has been diagnosed with or is suspected of having, particularly a disease or condition associated with elevated IL-6. A disease or condition encompasses, without limitation thereto, mucositis, as well as idiopathic conditions characterized by symptoms that include elevated IL-6.

Effective amount, as used herein, refers broadly to an amount of an active ingredient that is effective to relieve or reduce to some extent at least one of the symptoms of the disease in need of treatment, or to retard initiation of clinical markers or symptoms of a disease in need of prevention, when the compound is administered. Thus, an effective amount refers to an amount of the active ingredient which exhibit effects such as (i) reversing the rate of progress of a disease; (ii) inhibiting to some extent further progress of the disease; and/or, (iii) relieving to some extent (or, preferably, eliminating) at least one symptoms associated with the disease. The effective amount may be empirically determined by experimenting with the compounds concerned in known in vivo and in vitro model systems for a disease in need of treatment. The context in which the phrase "effective amount" is used may indicate a particular desired effect. For example, "an amount of an anti-IL-6 antibody effective to prevent or treat a hypercoagulable state" and similar phrases refer to an amount of anti-IL-6 antibody that, when administered to a subject, will cause a measurable improvement in the subject's coagulation profile, or prevent, slow, delay, or arrest, a worsening of the coagulation profile for which the subject is at risk. Similarly, "an amount of an anti-IL-6 antibody effective to reduce serum CRP levels" and similar phrases refer to an amount of anti-IL-6 antibody that, when administered to a subject, will cause a measurable decrease in serum CRP levels, or prevent, slow, delay, or arrest, an increase in serum CRP levels for which the subject is at risk. Similarly, "an amount of an anti-IL-6 antibody effective to increase serum albumin levels" and similar phrases refer to an amount of anti-IL-6 antibody that, when administered to a subject, will cause a measurable increase in serum albumin levels, or prevent, slow, delay, or arrest, a decrease in serum albumin levels for which the subject is at risk. Similarly, "an amount of an anti-IL-6 antibody effective to reduce weakness" and similar phrases refer to an amount of anti-IL-6 antibody that, when administered to a subject, will cause a measurable decrease in weakness as determined by the hand grip strength test. Similarly, "an amount of an anti-IL-6 antibody effective to increase weight" and similar phrases refer to an amount of anti-IL-6 antibody that, when administered to a subject, will cause a measurable increase in a patient's weight. An effective amount will vary according to the weight, sex, age and medical history of the individual, as well as the severity of the patient's condition(s), the type of disease(s), mode of administration, and the like. An effective amount may be readily determined using routine experimentation, e.g., by titration (administration of increasing dosages until an effective dosage is found) and/or by reference to amounts that were effective for prior patients. Generally, the anti-IL-6 antibodies of the present invention will be administered in dosages ranging between about 0.1 mg/kg and about 20 mg/kg of the patient's body-weight.

Expression Vector, as used herein, refers broadly to a DNA vectors contain elements that facilitate manipulation for the expression of a foreign protein within the target host cell. Conveniently, manipulation of sequences and production of DNA for transformation is first performed in a bacterial host (e.g., *E. coli*) and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, Dawson, & Stearns (2000) *Methods in Yeast Genetics:*

*a Cold Spring Harbor Laboratory course manual.* Cold Spring Harbor Laboratory Press.

Folding, as used herein, refers broadly to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity.

Framework region or FR, as used herein refers broadly to at least one of the framework regions within the variable regions of the light and heavy chains of an antibody. See Kabat, et al. (1987) Sequences of Proteins of Immunological Interest, National Institutes of Health, Bethesda, Md. These expressions include those amino acid sequence regions interposed between the CDRs within the variable regions of the light and heavy chains of an antibody. As mentioned in the preferred embodiments, the FRs may comprise human FRs highly homologous to the parent antibody (e.g., rabbit antibody).

Glasgow Prognostic Score (GPS), as used herein, refers broadly to an inflammation-based prognostic score that awards one point for a serum albumin level less than <35 mg/L and one point for a CRP level above 10 mg/L. Thus, a GPS of 0 indicates normal albumin and CRP, a GPS of 1 indicates reduced albumin or elevated CRP, and a GPS of 2 indicates both reduced albumin and elevated CRP.

gp130 (also called Interleukin-6 receptor subunit beta), as used herein, refers broadly to a transmembrane protein that forms one subunit of type I cytokine receptors in the IL-6 receptor family [(e.g., 918 precursor amino acid sequence available as Swiss-Prot Protein Accession No. P40189 (SEQ ID NO: 728)]. gp130 also encompasses any pre-pro, pro- and mature forms of this amino acid sequence, such as the mature form encoded by amino acids 23 through 918 of the sequence shown, as well as mutants and variants including allelic variants of this sequence.

Heterologous region or domain of a DNA construct, as used herein, refers broadly to an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

Homology, as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison. The term "sequence identity" may be used interchangeably with "homology."

Host cell, as used herein, refers broadly to a cell that contains an expression vector and supports the replication or expression of the expression vector. Host cells may be prokaryotic cells such as *E. coli*, or eukaryotic cells such as yeast, insect (e.g., SF9), amphibian, or mammalian cells such as CHO, HeLa, HEK-293 (e.g., cultured cells, explants, and cells in vivo.)

Isolated, as used herein, refers broadly to material removed from its original environment in which it naturally occurs, and thus is altered by the hand of man from its natural environment. Isolated material may be, for example, exogenous nucleic acid included in a vector system, exogenous nucleic acid contained within a host cell, or any material which has been removed from its original environment and thus altered by the hand of man (e.g., "isolated antibody").

Improved, as used herein, refers broadly to any beneficial change resulting from a treatment. A beneficial change is any way in which a patient's condition is better than it would have been in the absence of the treatment. "Improved" includes prevention of an undesired condition, slowing the rate at which a condition worsens, delaying the development of an undesired condition, and restoration to an essentially normal condition. For example, improvement in mucositis encompasses any decrease in pain, swelling, joint stiffness, or inflammation, and/or an increase in joint mobility.

IL-6 antagonist, as used herein, refers broadly to any composition that prevents, inhibits, or lessens the effect(s) of IL-6 signaling. Generally, such antagonists may reduce the levels or activity of IL-6, IL-6 receptor alpha, gp130, or a molecule involved in IL-6 signal transduction, or may reduce the levels or activity complexes between the foregoing (e.g., reducing the activity of an IL-6/IL-6 receptor complex). Antagonists include antisense nucleic acids, including DNA, RNA, or a nucleic acid analogue such as a peptide nucleic acid, locked nucleic acid, morpholino (phosphorodiamidate morpholino oligo), glycerol nucleic acid, or threose nucleic acid. See Heasman (2002) *Dev Biol.* 243(2): 209-14; Hannon and Rossi (2004) *Nature* 431(7006):371-8; Paul, et al. (2002) *Nat Biotechnol.* 20(5):505-8; Zhang, et al. (2005) *J Am Chem Soc.* 127(12):4174-5; Wahlestedt, et al. (2000) *Proc Natl Acad Sci USA.* 97(10):5633-8; Hanvey, et al. (1992) *Science* 258 (5087):1481-5; Braasch, et al. (2002) *Biochemistry* 41(14): 4503-10; Schoning, et al. (2000) *Science* 290(5495): 1347-51. In addition IL-6 antagonists specifically include peptides that block IL-6 signaling such as those described in any of U.S. Pat. Nos. 5,210,075; 6,172,042; 6,599,875; 6,841,533; and 6,838,433. Also, IL-6 antagonists according to the invention may include p38 MAP kinase inhibitors such as those reported in U.S. Patent Application No. 2007/0010529 given this kinase's role in cytokine production and more particularly IL-6 production. Further, IL-6 antagonists according to the invention include the glycoalkaloid compounds reported in U.S. Patent Application Publication No. 2005/0090453 as well as other IL-6 antagonist compounds isolatable using the IL-6 antagonist screening assays reported therein. Other IL-6 antagonists include antibodies, such as anti-IL-6 antibodies, anti-IL-6 receptor alpha antibodies, anti-gp130 antibodies, and anti-p38 MAP kinase antibodies including (but not limited to) the anti-IL-6 antibodies disclosed herein, Actemra® (Tocilizumab), Remicade®, Zenapax® (daclizumab), or any combination thereof. Other IL-6 antagonists include portions or fragments of molecules involved in IL-6 signaling, such as IL-6, IL-6 receptor alpha, and gp130, which may be native, mutant, or variant sequence, and may optionally be coupled to other moieties (such as half-life-increasing moieties, e.g. an Fc domain). For example, an IL-6 antagonist may be a soluble IL-6 receptor or fragment, a soluble IL-6 receptor:Fc fusion protein, a small molecule inhibitor of IL-6, an anti-IL-6 receptor antibody or antibody fragment or variant thereof, antisense nucleic acid. Other IL-6 antagonists include avemirs, such as C326 (Silverman, et al. (2005) *Nat Biotechnol.* 23(12): 1556-61) and small molecules, such as synthetic retinoid AM80 (tamibarotene) (Takeda, et al. (2006) *Arterioscler Thromb Vasc Biol.* 26(5): 1177-83). Such IL-6 antagonists may be administered by any means known in the art, including contacting a subject with nucleic acids which encode or cause to be expressed any of the foregoing polypeptides or antisense sequences.

Interleukin-6 (IL-6), as used herein, refers broadly to interleukin-6 (IL-6) encompasses not only the following 212 amino acid sequence available as GenBank Protein Accession No. NP_000591 (e.g., SEQ ID NO: 1), but also any pre-pro, pro- and mature forms of this IL-6 amino acid sequence, as well as mutants and variants including allelic variants of this sequence.

Interleukin-6 receptor (IL-6R) (IL-6 receptor alpha (IL-6RA) [CD126], as used herein, refers broadly to 468 amino acid protein that binds IL-6, a potent pleiotropic cytokine that regulates cell growth and differentiation and also plays an important role in immune response (e.g., Swiss-Prot Protein Accession No. P08887 and SEQ ID NO: 727). IL-6R also includes any pre-pro, pro- and mature forms of this amino acid sequence, as well as mutants and variants including allelic variants of this sequence.

Mammal, as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, goats, gorillas, hamsters, horses, humans, lemurs, llamas, mice, non-human primates, pigs, rats, sheep, shrews, squirrels, and tapirs. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C.

Meiosis, as used herein, refers broadly to a process by which a diploid yeast cell undergoes reductive division to form four haploid spore products. Each spore may then germinate and form a haploid vegetatively growing cell line.

Nucleic acid or nucleic acid sequence, as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

Operatively linked, as used herein, refers broadly to when two DNA fragments are joined such that the amino acid sequences encoded by the two DNA fragments remain in-frame.

Paratope, as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. *Antigens* (*Chapter* 3) Immunology ($5^{th}$ Ed.) New York: W.H. Freeman and Company, pages 57-75.

Patient, as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient".

Polyploid yeast that stably expresses or expresses a desired secreted heterologous polypeptide for prolonged time, as used herein, refers broadly to a yeast culture that secretes said polypeptide for at least several days to a week, more preferably at least a month, still more preferably at least about 1-6 months, and even more preferably for more than a year at threshold expression levels, typically at least about 10-25 mg/liter and preferably substantially greater.

Polyploidal yeast culture that secretes desired amounts of recombinant polypeptide, as used herein, refers broadly to cultures that stably or for prolonged periods secrete at least about 10-25 mg/liter of heterologous polypeptide, more preferably at least about 50-500 mg/liter, and most preferably at least about 500-1000 mg/liter or more.

Prolonged reduction in serum CRP, and similar phrases, as used herein refer broadly to a measurable decrease in serum CRP level relative to the initial serum CRP level (i.e. the serum CRP level at a time before treatment begins) that is detectable within about a week from when a treatment begins (e.g. administration of an anti-IL-6 antibody) and remains below the initial serum CRP level for an prolonged duration, e.g. at least about 14 days, at least about 21 days, at least about 28 days, at least about 35 days, at least about 40 days, at least about 50 days, at least about 60 days, at least about 70 days, at least about 11 weeks, or at least about 12 weeks from when the treatment begins.

Promoter, as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

Prophylactically effective amount, as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

Prophylaxis, as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

Recombinant as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

Selectable Marker, as used herein, refers broadly to a selectable marker is a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two ts mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to ZEOMYCIN® (zeocin), neomycin, G418, LYS3, MET1, MET3a, ADE1, ADE3, and URA3.

Specifically (or selectively) binds to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeneous population of proteins and other biologics. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

Signs of disease, as used herein, refers broadly to any abnormality indicative of disease, discoverable on examination of the patient; an objective indication of disease, in contrast to a symptom, which is a subjective indication of disease.

Solid support, support, and substrate, as used herein, refers broadly to any material that provides a solid or semi-solid structure with which another material can be attached including but not limited to smooth supports (e.g., metal, glass, plastic, silicon, and ceramic surfaces) as well as textured and porous materials.

Subjects as used herein, refers broadly to anyone suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g., rats and mice), lagomorphs, primates, humans. Any mammalian subject in need of being treated according to the present invention is suitable. Human subjects of both genders and at any stage of development (i.e., neonate, infant, juvenile, adolescent, adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "patients."

Mating competent yeast species, as used herein refers broadly encompass any diploid or tetraploid yeast which can be grown in culture. Such species of yeast may exist in a haploid, diploid, or tetraploid form. The cells of a given ploidy may, under appropriate conditions, proliferate for indefinite number of generations in that form. Diploid cells can also sporulate to form haploid cells. Sequential mating can result in tetraploid strains through further mating or fusion of diploid strains. In the present invention the diploid or polyploidal yeast cells are preferably produced by mating or spheroplast fusion.

Haploid Yeast Cell, as used herein, refers broadly to a cell having a single copy of each gene of its normal genomic (chromosomal) complement.

Polyploid Yeast Cell, as used herein, refers broadly to a cell having more than one copy of its normal genomic (chromosomal) complement.

Diploid Yeast Cell, as used herein, refers broadly to a cell having two copies (alleles) of essentially every gene of its normal genomic complement, typically formed by the process of fusion (mating) of two haploid cells.

Tetraploid Yeast Cell, as used herein, refers broadly to a cell having four copies (alleles) of essentially every gene of its normal genomic complement, typically formed by the process of fusion (mating) of two haploid cells. Tetraploids may carry two, three, four, or more different expression cassettes. Such tetraploids might be obtained in *S. cerevisiae* by selective mating homozygotic heterothallic a/a and alpha/alpha diploids and in *Pichia* by sequential mating of haploids to obtain auxotrophic diploids. For example, a [met his] haploid can be mated with [ade his] haploid to obtain diploid [his]; and a [met arg] haploid can be mated with [ade arg] haploid to obtain diploid [arg]; then the diploid [his]×diploid [arg] to obtain a tetraploid prototroph. It will be understood by those of skill in the art that reference to the benefits and uses of diploid cells may also apply to tetraploid cells.

Yeast Mating, as used herein, refers broadly to a process by which two haploid yeast cells naturally fuse to form one diploid yeast cell.

Variable region or VR as used herein refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

Variants, as used herein refers broadly to single-chain antibodies, dimers, multimers, sequence variants, and domain substitution variants. Single-chain antibodies such as SMIPs, shark antibodies, nanobodies (e.g., Camelidiae antibodies). Sequence variants can be specified by percentage identity (similarity, sequence homology) e.g., 99%, 95%, 90%, 85%, 80%, 70%, 60%, or by numbers of permitted conservative or non-conservative substitutions. Domain substitution variants include replacement of a domain of one protein with a similar domain of a related protein. A similar domain may be identified by similarity of sequence, structure (actual or predicted), or function. For example, domain substitution variants include the substitution of at least one CDRs and/or framework regions.

The techniques and procedures are generally performed according to conventional methods well known in the art and as described in various general and more specific references that are cited and discussed throughout the present specification. See, e.g., Sambrook, et al. (2001) *Molec. Cloning: Lab. Manual [3rd Ed]* Cold Spring Harbor Laboratory Press. Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

Mucositis

Mucositis is a medical term that is used to refer to mouth sores, oral mucositis, or esophagitis. It can range in severity from a red, sore mouth and/or gums to open sores that can cause a patient to be unable to eat. The lining of the entire gastrointestinal tract (e.g., mouth, throat, stomach, and bowel) is made up of epithelial cells, which divide and replicate rapidly, and are killed by chemotherapy and radiation therapy. Thus the entire lining of the entire gastrointestinal tract from the mouth to the anus are susceptible to mucositis (e.g., alimentary tract mucositis). Mucositis can occur in areas of the alimentary tract; for example, gastrointestinal (GI) mucositis. Emesis (vomiting) and diarrhea are also common in mucositis, especially gastrointestinal mucositis. See Lalla, et al. (2008) *Dent Clin North Am.* 52(1): 61-viii.

Patients treated with radiation therapy for head and neck cancer typically receive an approximately 200 cGy daily dose of radiation, five days per week, for 5-7 continuous weeks. Almost all such patients will develop some degree of oral mucositis. In recent studies, severe oral mucositis occurred in 29-66% of all patients receiving radiation therapy for head and neck cancer. The incidence of oral mucositis was especially high in (A) patients with primary tumors in the oral cavity, oropharynx or nasopharynx, (B) those who also received concomitant chemotherapy, (C) those who received a total dose over 5000 cGy, and (D) those who were treated with altered fractionation radiation schedules (e.g., more than one radiation treatment per day). See Lalla, et al. (2008) *Dent Clin North Am.* 52(1): 61-viii.

Recent studies have indicated that the fundamental mechanisms involved in the pathogenesis of mucositis are much more complex than direct damage to epithelium alone. Mechanisms for radiation-induced and chemotherapy-induced mucositis are believed to be similar. The following five-stage model for the pathogenesis of mucositis:

1. Initiation of tissue injury: Radiation and/or chemotherapy induce cellular damage resulting in death of the basal epithelial cells. The generation of reactive oxygen species (free radicals) by radiation or chemotherapy is also believed to exert a role in the initiation of mucosal injury. These small highly reactive molecules are byproducts of oxygen metabolism and can cause significant cellular damage.
2. Upregulation of inflammation via generation of messenger signals: In addition to causing direct cell death, free radicals activate second messengers that transmit signals from receptors on the cellular surface to the inside of the cell. This leads to upregulation of pro-inflammatory cytokines, tissue injury and cell death.
3. Signaling and amplification: Upregulation of proinflammatory cytokines such as tumor necrosis factor-alpha (TNF-α), produced mainly by macrophages, causes injury to mucosal cells, and also activates molecular pathways that amplify mucosal injury.
4. Ulceration and inflammation: There is a significant inflammatory cell infiltrate associated with the mucosal ulcerations, based in part on metabolic byproducts of the colonizing oral microflora. Production of pro-inflammatory cytokines is also further upregulated due to this secondary infection.
5. Healing: This phase is characterized by epithelial proliferation as well as cellular and tissue differentiation, restoring the integrity of the epithelium.

The degree and extent of oral mucositis that develops in any particular patient and site appears to depend on factors such as age, gender, underlying systemic disease and race as well as tissue specific factors (e.g., epithelial types, local microbial environment and function). See Lalla, et al. (2008) *Dent Clin North Am.* 52(1): 61-viii.

The IL-6 antagonists described herein, include but are not limited to anti-IL-6 antibodies and antibody fragments, and may be used in methods and compositions for the treatment of mucositis (e.g., oral, esophageal, alimentary, gastrointestinal tract mucositis).

Oral Mucositis

Oral mucositis is a significant problem in patients undergoing chemotherapeutic management for solid tumors. In one study, it was reported that 303 of 599 patients (51%) receiving chemotherapy for solid tumors or lymphoma developed oral and/or GI mucositis. Oral mucositis developed in 22% of 1236 cycles of chemotherapy, GI mucositis in 7% of cycles and both oral and GI mucositis in 8% of cycles. An even higher percentage (approximately 75-80%) of patients who receive high-dose chemotherapy prior to hematopoietic cell transplantation develop clinically significant oral mucositis. See Lalla, et al. (2008) *Dent Clin North Am.* 52(1): 61-viii.

Oral mucositis leads to several problems, including pain, nutritional problems as a result of inability to eat, and increased risk of infection due to open sores in the mucosa. Oral mucositis has a significant effect on the patient's quality of life and can be dose-limiting (requiring a reduction in subsequent chemotherapy doses).

Signs and symptoms of mucositis include: red, shiny, or swollen mouth and gums; blood in the mouth; sores in the mouth or on the gums or tongue; soreness or pain in the mouth or throat; difficulty swallowing or talking; feeling of dryness, mild burning, or pain when eating food; soft, whitish patches or pus in the mouth or on the tongue; and Increased mucus or thicker saliva in the mouth.

Over forty percent of patients who receive chemotherapy will develop some degree of mucositis during the course of their treatment. Patients receiving radiation to the head, neck, or chest areas, and patients who undergo bone marrow or stem cell transplant, are even more likely to develop mucositis. Certain chemotherapy agents are more likely to cause this side effect (Table 1), as is total body irradiation which is often used for bone marrow transplants.

TABLE 1

| Select chemotherapy agents known to cause mucositis. | | |
|---|---|---|
| Alemtuzumab (Campath ®) | Bleomycin (Blenoxane ®) | Asparaginase (Elspar ®) |
| Cyclophosphamide (Cytoxan ®) | Cytarabine (Cytosar-U ®) | Busulfan (Myleran ®, Busulfex ®) |
| Docetaxel (Taxotere ®) | Doxorubicin (Adriamycin ®) | Capecitabine (Xeloda ®) |
| Fluorouracil (5-FU ®) | Gemcitabine (Gemzar ®) | Carboplatin (Paraplatin ®) |
| Gemtuzumab ozogamicin (Mylotarg ®) | Hydroxyurea (Hydrea ®) | Daunorubicin (Cerubidine ®) |
| Idarubicin (Idamycin ®) | Interleukin 2 (Proleukin ®) | Epirubicin (Ellence ®) |
| Lomustine (CeeNU ®) | Melphalan (Alkeran ®) | Etoposide (VePesid ®) |
| Mitomycin (Mutamycin ®) | Mitoxantrone (Novantrone ®) | Irinotecan (Camptosar ®) |
| Oxaliplatin (Eloxatin ®) | Paclitaxel (Taxol ®) | Methotrexate (Rheumatrex ®) |
| Pentostatin (Nipent ®) | Procarbazine (Matulane ®) | Mechlorethamine (Mustargen ®) |
| Topotecan (Hycamtin ®) | Trastuzumab (Herceptin ®) | Pemetrexed (Alimta ®) |
| Vinblastine (Velban ®) | Vincristine (Oncovin ®) | Thiotepa (Thioplex ®) |
| Tretinoin (Vesanoid ®) | Cisplatin (PLATINOL ®) | |

Poor oral or dental health, smoking, using chewing tobacco, drinking alcohol, dehydration, and diseases such as kidney disease, diabetes or HIV/AIDS can increase the likelihood of developing mucositis or worsen it.

Monitoring the development and resolution of mucositis can be difficult, given that the experience is different for every patient. The World Health Organization (WHO) oral toxicity scale is a commonly used grading systems developed to assist in evaluating the severity of mucositis:

TABLE 2

Oral Mucositis Severity Scale (adapted from WHO ORAL TOXICITY SCALE)

| Grade 0 | Grade 1 | Grade 2 | Grade 3 | Grade 4 |
|---|---|---|---|---|
| None | Soreness & erythema | Erythema, ulcers; Patient can swallow solid diet | Ulcers, extensive erythema; Patients cannot swallow solid diet | Mucositis to the extent that alimentation is not possible |

Numerous studies using many different medications and interventions have been tried to reduce the incidence and severity of oral mucositis. Unfortunately, only a few of these interventions have shown much success. Currently, good oral care regimen (Table 3) is the most effective in preventing or decreasing the severity of mucositis and help prevent the development of infection through open mouth sores. The mainstay of an oral care regimen is mouth rinses, and numerous studies have determined old salt water is an effective mouth rinse. The mouth rinse aides in removing debris and keeping the oral tissue moist and clean. Other important components include using mouth and lip moisturizers, using a soft-bristle toothbrush, maintaining adequate intake of fluids and protein, and avoiding irritating foods, alcohol and tobacco.

TABLE 3

| Example of oral care protocol<br>Oral Care Protocol Recommendations |
|---|
| Normal saline (1 tsp of table salt to 1 quart (32 oz.) of water) [e.g., salt and soda (one-half tsp of salt and 2 tbsp of sodium bicarbonate in 1 quart of warm water)] |
| Use a soft-bristle toothbrush after meals and at bedtime. If the brush causes pain, toothettes may be used |
| Use a non-abrasive toothpaste (or mix 1 tsp baking soda in 2 cups water). Avoid toothpastes with whiteners. |
| Keep lips moist with moisturizers. Avoid using Vaseline (the oil base can promote infection). |

TABLE 3-continued

| Example of oral care protocol<br>Oral Care Protocol Recommendations |
|---|
| Avoid products that irritate the mouth and gums: avoid commercial mouthwashes and those with alcohol |
| Limit use of dental floss, DO NOT use with platelets below 40,000 |
| Do not use lemon or glycerin swabs or toothbrushes without soft bristles |
| Increase your fluid intake. |
| Try to include foods high in protein in your diet. |
| Avoid hot, spicy or acidic foods, alcohol, hard or coarse foods (crusty bread, chips, crackers). |
| If you wear dentures: remove whenever possible to expose gums to air |
| Loose fitting dentures can irritate the mouth and gums and should not be worn |
| Do not wear dentures if mouth sores are severe |
| Do not smoke cigarettes, cigars or pipes. Do not use smokeless tobacco (chewing tobacco, snuff) |

Cryotherapy, which involves sucking on ice chips during chemotherapy administration, has shown some effect in alleviating mucositis caused by 5-FU (fluorouracil). Two agents, Gelclair® and Zilactin®, are mucosal protectants that work by coating the mucosa, forming a protective barrier for exposed nerve endings. These agents resulted in improved pain control, and ability to eat and speak. Amifostine (Ethyol®), a drug that protects against the damage to the mucosa caused by radiation (approved by the FDA for patients receiving radiation therapy for cancers of the head and neck).

Keratinocyte growth factor (KGF) stimulates the growth, repair, and survival of cells that protect the lining of the mouth and GI tract. Recombinant human KGF has been developed as the drug KEPIVANCE® (palifermin) and is currently used for treating oral mucositis in patients with hematologic malignancies receiving myelotoxic therapy requiring hematopoietic stem cell support (HSCT). Palifermin was found to decrease the length and severity of oral mucositis in these patients. "Coping with Cancer" by Vachani of the Abramson Cancer Center of the University of Pennsylvania (2009). The IL-6 antagonists, including anti-IL-6 antibodies and antibody fragments thereof, may be used in methods and compositions for the treatment of mucositis, including oral mucositis associated with chemotherapy and radiotherapy. Emesis and diarrhea may also be seen in patients suffering from oral mucositis. The IL-6 antagonists, including anti-IL-6 antibodies may be used in methods and compositions for the treatment of emesis and diarrhea associated with chemotherapy, radiotherapy, and oral mucositis.

Alimentary Tract Mucositis

Mucositis is a major acute clinical problem in oncology, caused by the cytotoxic effects of chemotherapy and radiotherapy. The condition may affect the mucosa of the entire alimentary tract (AT), causing mouth and throat pain, ulceration, abdominal pain, bloating, vomiting (emesis), and diarrhea. Mucositis is extremely common, occurring in approximately 40% of patients following standard doses of chemotherapy and in almost all patients undergoing high-dose chemotherapy with stem-cell transplantation or head-and-neck radiation. Bowen, et al. (2011) *Journal of Supportive Oncology* 9(5): 161-168.

Alimentary tract mucositis refers to the expression of mucosal injury across the continuum of oral and gastrointestinal mucosa, from the mouth to the anus. Incidence of WHO grade 3 or 4 oral mucositis can be as high as ~75% in patients undergoing hematopoietic stem-cell transplantation (HSCT), depending on the intensity of the conditioning regimen used and the use of methotrexate. For all tumor sites, chemotherapy with 5-fluorouracil (5-FU), capecitabine or tegafur leads to a high rate (e.g. 20-50%) of alimentary tract mucositis. Chemotherapy with methotrexate and other antimetabolites leads to a 20-60% rate of alimentary tract mucositis according to the drug's given dose per cycle. See Peterson, et al. (2009) *Annals of Oncology* 20(Supplement 4): iv174-iv177 and Logan, et al. (2008) *Cancer chemotherapy and Pharmacology* 62(1): 33-41. The IL-6 antagonists, including anti-IL-6 antibodies and antibody fragments thereof, may be used in methods and compositions for the treatment of alimentary tract mucositis, including alimentary tract mucositis associated with chemotherapy and radiotherapy. Emesis and diarrhea are also commonly seen in patients suffering from mucositis, especially alimentary tract mucositis. The IL-6 antagonists, including anti-IL-6 antibodies may be used in methods and compositions for the treatment of emesis and diarrhea associated with chemotherapy, radiotherapy, and alimentary tract mucositis.

Gastrointestinal Tract Mucositis

Gastrointestinal mucositis may result from chemotherapy and/or radiotherapy and refers to inflammatory lesions in the gastrointestinal tract. Vomiting (emesis), and diarrhea are common elements of gastrointestinal mucositis.

Basic bowel care including maintenance of adequate hydration is recommended for patients undergoing chemotherapy and radiotherapy to limit the effects of gastrointestinal mucositis. Current recommendations also include administration of 500 mg sulfasalazine orally twice daily to reduce the incidence and severity of radiation-induced enteropathy in patients receiving external beam radiotherapy to the pelvis. Amifostine is also suggested in a dose of at least 340 mg/m$^2$ to prevent radiation proctitis in those receiving standard-dose radiotherapy for rectal cancer. Additionally, octreotide at a dose of at least 100 μg s.c. twice daily when loperamide fails to control diarrhea induced by standard-dose or high-dose chemotherapy associated with HSCT as well as amifostine is suggested to reduce esophagitis induced by concomitant chemotherapy and radiotherapy in patients with non-small-cell lung cancer. See Peterson, et al. (2009) *Annals of Oncology* 20(Supplement 4): iv174-iv177. The IL-6 antagonists, including anti-IL-6 antibodies and antibody fragments thereof, may be used in methods and compositions for the treatment of gastrointestinal mucositis, including gastrointestinal mucositis associated with chemotherapy and radiotherapy.

Emesis and diarrhea are also commonly seen in patients suffering from mucositis, especially gastrointestinal tract mucositis. See Lalla, et al. (2008) *Dent Clin North Am.* 51(1): 61-viii. The IL-6 antagonists, including anti-IL-6 antibodies may be used in methods and compositions for the treatment of emesis and diarrhea associated with chemotherapy, radiotherapy, and gastrointestinal tract mucositis.

Treatment of Rheumatoid Arthritis

This invention also relates to the use of IL-6 antagonists including anti-IL-6 antibodies described herein, such as Ab1 or humanized forms thereof for treating or preventing rheumatoid arthritis. This application provides results of clinical studies showing safety, pharmacokinetics, and pharmacodynamics for subcutaneous and intravenous administration of an exemplary anti-IL-6 antibody, Ab1 (also known as ALD-518, exemplary sequences are provided in Table 4.) The clinical data demonstrates that an anti-IL-6 antibody decreases disease severity in rheumatoid arthritis patients which have been subcutaneously (SC) or intravenously (IV) administered ALD-518, including improvement in mental and physical components of disease.

The anti-IL-6 antibody (e.g., ALD518) was well tolerated when administered in a single subcutaneous (SC) dose; injection site reactions were generally mild. The bioavailability of SC ALD518 was ~60% of IV ALD518, and the half life was ~30 days. Rapid and significant reductions in CRP (C-reactive protein) were observed, which were sustained over 24 weeks of assessment. The half-life of ALD518 when administered subcutaneously (approximately 30 days) is similar to the half-life previously observed with IV administration. Additionally, subcutaneous ALD518 led to rapid and large reductions in serum CRP and the reductions in CRP observed during the first 12 weeks of the study were sustained over 24 weeks of assessment. These results are also similar to those observed with N administration. Together, these results suggest that anti-IL-6 antibodies, such as Ab1 (ALD518) may be used for the treatment of RA, as well as prevention or treatment of other IL-6 associated conditions. These therapeutic regimens may be combined with other RA therapeutics, including methotrexate or other RA drugs identified herein and generally known in the art, including analgesics, disease-modifying antirheumatic drugs (DMARDS), anti-inflammatories, and others.

The invention further provides specific dosage regimens and dosage formulations for treating rheumatoid arthritis by subcutaneous or intravenous administration of anti-IL-6 antibodies or antibody fragments according to the invention such as humanized Ab1 antibodies. For example, a subject may be administered 80, 160, or 320 mg of an anti-IL-6 antibody (e.g., Ab1).

The anti-IL-6 antibodies may be used to subcutaneously administer antibodies of the invention, including Ab1, for rheumatoid arthritis indications, the administration formulation comprises, or alternatively consists of, about 50 or 100 mg/mL of antibody, about 5 mM Histidine base, about 5 mM Histidine HCl to make final pH 6, 250 mM sorbitol, and 0.015% (w/w) Polysorbate 80. In another embodiment of the invention that may be used to subcutaneously administer antibodies of the invention, including Ab1, for rheumatoid arthritis indications, the administration formulation comprises, or alternatively consists of, about 20 or 100 mg/mL of antibody, about 5 mM Histidine base, about 5 mM Histidine HCl to make final pH 6, 250 to 280 mM sorbitol (or sorbitol in combination with sucrose), and 0.015% (w/w) Polysorbate 80, said formulation having a nitrogen headspace in the shipping vials.

Therapeutic regimens for the prevention or treatment of RA may be combined with other RA therapeutics, including analgesics, analgesics, DMARDS, anti-inflammatories, and others. For example, analgesics and anti-inflammatory drugs, including steroids, may provide relief of disease symptoms, while disease-modifying antirheumatic drugs (DMARDs), may inhibit or halt the underlying immune process and prevent further long-term damage. In exemplary embodiments, ALD518 (or another antibody of the present disclosure) may be administered to a patient at approximately the same time as another RA therapeutic (which may or may not be formulated together) or may be administered to a patient who is also undergoing another therapeutic regiment but not necessarily at the same time. A regimen may be considered to provide a combination of therapeutics as long as the patient concurrently experiences the effects of the combined therapeutics. Due to possible differences in dosing schedule, a combination may include administration of different therapeutics at different times, e.g., a patient may receive a drug such as methotrexate on a weekly schedule (e.g., at least 10 mg per week) and may receive ALD518 (or another anti-IL-6 antibody of the present disclosure) less frequently (such as about every eight weeks, every twelve weeks, every three months). Exemplary DMARDs that may administered in combination with ALD518 (or another antibody of the present disclosure) include, but are not limited to Mycophenolate mofetil (CellCept®), calcineurin inhibitors (e.g., cyclosporine, sirolimus, everolimus), oral retinoids, azathioprine, fumeric acid esters, D-penicillamine, cyclophosphamide, immunoadsorption columns (e.g., Prosorba® columns), gold salts (e.g., Auranofin, sodium aurothiomalate (Myocrisin)), hydroxychloroquine, chloroquine, leflunomide, methotrexate (MTX), minocycline, sulfasalazine (SSZ), tumor necrosis factor alpha (TNFα) blockers (e.g., etanercept (Enbrel), infliximab (Remicade), adalimumab (Humira), certolizumab pegol (Cimzia), golimumab (Simponi)), Interleukin 1 (IL-1) blockers (e.g., anakinra (Kineret)), monoclonal antibodies against B cells (e.g., rituximab (Rituxan)), T cell costimulation blockers (e.g., abatacept (Orencia)), Interleukin 6 (IL-6) blockers (e.g., tocilizumab (an anti-IL-6 receptor antibody), RoActemra, Actemra). Exemplary anti-inflammatory agents that may administered in combination with ALD518 (or another antibody of the present disclosure) include, but are not limited to, anti-inflammatory steroids such as Cortisone, Glucocorticoids, prednisone, prednisolone, Hydrocortisone (Cortisol), Cortisone acetate, Methylprednisolone, Dexamethasone, Betamethasone, Triamcinolone, Beclometasone, and Fludrocortisone acetate, and non-steroidal anti-inflammatory drug (NSAIDs) (which may also act as analgesics), such as ibuprofen, naproxen, meloxicam, etodolac, nabumetone, sulindac, tolementin, choline magnesium salicylate, diclofenac, diflusinal, indomethicin, Ketoprofen, Oxaprozin, piroxicam, and nimesulide, Salicylates, Aspirin (acetylsalicylic acid), Diflunisal, Salsalate, p-amino phenol derivatives, Paracetamol, phenacetin, Propionic acid derivatives, Ibuprofen, Naproxen, Fenoprofen, Ketoprofen, Flurbiprofen, Oxaprozin, Loxoprofen, Acetic acid derivatives, Indomethacin, Sulindac, Etodolac, Ketorolac, Diclofenac, Nabumetone, Enolic acid (Oxicam) derivatives, Piroxicam, Meloxicam, Tenoxicam, Droxicam, Lornoxicam, Isoxicam, Fenamic acid derivatives (Fenamates), Mefenamic acid, Meclofenamic acid, Flufenamic acid, Tolfenamic acid, Selective COX-2 inhibitors (Coxibs), Celecoxib, Rofecoxib, Valdecoxib, Parecoxib, Lumiracoxib, Etoricoxib, Firocoxib, Sulphonanilides, Nimesulide, and Licofelone. Exemplary analgesics include that may administered in combination with ALD518 (or another antibody of the present disclosure) include, but are not limited to, NSAIDs, COX-2 inhibitors (including Celecoxib, Rofecoxib, Valdecoxib, Parecoxib, Lumiracoxib, Etoricoxib, and Firocoxib), acetaminophen, opiates (e.g., Dextropropoxyphene, Codeine, Tramadol, Anileridine, Pethidine, Hydrocodone, Morphine [e.g., oral, intravenous (IV), or intramuscular (IM)], Oxycodone, Methadone, Diacetylmorphine, Hydromorphone, Oxymorphone, Levorphanol, Buprenorphine, Fentanyl, Sufentanyl, Etorphine, Carfentanil, dihydromorphine, dihydrocodeine, Thebaine, and Papaverine), diproqualone, Flupirtine, Tricyclic antidepressants, and lidocaine (topical).

Anti-IL-6 Antagonists

The IL-6 antagonist may comprise an antibody, an antibody fragment, a peptide, a glycoalkoid, an antisense nucleic acid, a ribozyme, a retinoid, an avemir, a small molecule, or any combination thereof. The IL-6 antagonist may be an agent that blocks signal transmission by IL-6, blocks IL-6 binding to its receptor, suppresses/interferes with IL-6 expression, and/or inhibits the biological activity of IL-6. The IL-6 antagonists may be attached directly or indirectly to immunoglobulin polypeptides or effector moieties such as therapeutic or detectable entities.

Examples of IL-6 antagonists include but are not limited to anti-IL-6 antibody, anti-IL-6R antibody, anti-gp130 antibody, IL-6 mutant, IL-6R antisense oligonucleotide, and partial peptides of IL-6 or IL-6R. An example of the IL-6 mutant used in the present invention is disclosed in Brakenhoff, et al. (1994) *J. Biol. Chem.* 269: 86-93 or Savino, et al. (1994) *EMBO J.* 13: 1357-1367. The IL-6 mutant polypeptide or fragment thereof does not possess the signal transmission effects of IL-6 but retains the binding activity with IL-6R, and is produced by introducing a mutation in the form of a substitution, deletion or insertion into the amino acid sequence of IL6. While there are no limitations on the animal species used, it is preferable to use an IL6 of human origin. Similarly, any IL-6 partial peptides or IL-6R partial peptides used in the present invention provided they prevent IL6 or IL6R (gp80) or gp130 from affecting signal transduction and thereby prevent IL-6 associated biological activity. For details regarding IL-6 partial peptides and IL-6R partial peptides, see, e.g., U.S. Pat. No. 5,210,075 and EP Patent No. 617126. Additionally, a mutated soluble IL-6 receptor may be used as an IL-6 antagonist. See Salvati, et al. (1995) *The Journal of Biological Chemistry* 270: 12242-12249.

IL-6 signaling is mediated by the Jak-Tyk family of cytoplasmic tyrosine kinases, including JAK1, JAK2, and JAK3 (reviewed in Murray (2007) *J Immunol.* 178(5): 2623-9). Inhibitors of JAK1, JAK2, or JAK3 may be used as IL-6 antagonists of IL-6. Sivash, et al. (2004) *British Journal of Cancer* 91: 1074-1080. An inhibitor of Syk may be used as an IL-6 antagonist. Ulanova, et al. (2005) *Am J Physiol Lung Cell Mol Physiol.* 288(3): L497-507. Thalidomide, and derivatives thereof, such as lenalidomide, may be useful antagonists of IL-6. Kedar, et al. (2004) *Int J Cancer.* 110(2): 260-5.

Further, oligonucleotides capable of IL6 or IL6R RNA silencing or antisense mechanisms can be used in the method of the present invention (JP5-300338 for details regarding IL-6R antisense oligonucleotide).

Additionally, the IL-6 antagonist may target IL-6, IL-6 receptor α, gp130, p38 MAP kinase, JAK1, JAK2, JAK3, SYK, or any combination thereof. For example, SANT-7 is an IL-6 receptor antagonist that interferes with the formation of IL-6/IL-6R/gp130 heteromers. See Hönemann, et al. (2001) *Int. J. Cancer* 93: 674-680.

The IL-6 antagonist may comprise an anti-IL-6 receptor (e.g., TOCILIZUMAB®, ACTEMRA®), anti-IL6 (e.g., SILTUXIMAB®), anti-gp130, anti-p38 MAP kinase, anti-JAK1, anti-JAK2, anti-JAK3, or anti-SYK antibody or antibody fragment. See Nishimoto, et al. (2005) *Blood* 106(8): 2627-32; van Rhee, et al. (2010) *Journal of Clinical Oncology* 28(23): 3701-3708; WO 2010/056948; U.S. Patent Application Publication No. 2010/0138945.

The IL-6 antagonist may comprise a small molecule including but not limited to thalidomide, lenalidomide, aryl hodrocarbon receptor agonists (e.g., 7,12-dimethylbenz[a] anthracene (DMBA) and 2,3,7,8-tetrachlorodibenzo-p-dioxin (TCDD)) or any combination thereof. See Jensen, et al. (2003) *Environmental Health: A Global Access Science Source* 2:16.

IL-6 antagonist may be an IL-6 antagonist peptide. See, e.g., U.S. Pat. No. 6,838,433. For example, a truncated IL-6 molecule may act as an IL-6 antagonist. See Alberti, et al. (2005) *J. Cancer Res* 65: 2-5.

The IL-6 antagonist may be an anti-IL-6 antibody. See also U.S. Patent Application Publication No. 2007/0292420. The IL-6 antagonist may comprise an anti-IL-6 antibody or antibody fragment as described in further detail herein. The invention includes antibodies having binding specificity to IL-6 and possessing a variable light chain sequence comprising the sequence set forth in the polypeptide sequence of SEQ ID NO: 2 or SEQ ID NO: 709 and humanized versions and variants thereof including those set forth in FIGS. 1-5, and those identified in Table 4.

Anti-IL-6 Antibodies and Antibody Fragments Thereof

Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the Fab region; the stem portion of the "Y" configuration is designated the Fc region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to γ, μ, α, δ, and ϵ (gamma, mu, alpha, delta, or epsilon) heavy chain constant regions). The constant region or class determines subsequent effector function of the antibody, including activation of complement (Kabat, E. A. (1976) Structural Concepts in Immunology and Immunochemistry [$2^{nd}$ Ed.] pages 413-436, Holt, Rinehart, Winston), and other cellular responses (Andrews, et al. (1980) *Clinical Immunobiology* pages 1-18, W. B. Sanders; Kohl, et al. (1983) *Immunology* 48: 187); while the variable region determines the antigen with which it will react. Light chains are classified as either κ (kappa) or λ (lambda). Each heavy chain class can be paired with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

For example, antibodies or antigen binding fragments or variants thereof may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of at least one cysteine residues that are not necessary for function. Variants can be designed so as to retain or have enhanced biological activity of a particular region of the protein (e.g., a functional domain, catalytic amino acid residues). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287. In a preferred embodiment, humanization may be effected as disclosed in detail infra. This scheme grafts CDRs onto human FRs highly homologous to the parent antibody that is being humanized.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention.

Exemplary Anti-IL-6 Antibodies

The invention also includes antibodies having binding specificity to IL-6 and possessing a variable heavy chain sequence comprising the sequence set forth in the polypeptide sequences of SEQ ID NO: 3 and SEQ ID NO: 657 and humanized versions and variants thereof including those set forth in FIGS. 1-5, and those identified in Table 4.

The invention further includes antibodies having binding specificity to IL-6 and possessing a variable heavy chain sequence which is a modified version of SEQ ID NO: 3 wherein the tryptophan residue in CDR2 is changed to a serine as set forth in the polypeptide sequence of SEQ ID NO: 658 and humanized versions and variants thereof including those set forth in FIGS. 1-5, and those identified in Table 4.

The invention further contemplates antibodies comprising at least one of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2, and/or at least one of the polypeptide sequences of SEQ ID NO: 7; SEQ ID NO: 8 or 120; and SEQ ID NO: 9 which correspond to the complementarity-determining regions (CDRs, or hypervariable regions) of the variable heavy chain sequence of SEQ ID NO: 3 or 19, or combinations of these polypeptide sequences. In another embodiment of the invention, the antibodies of the invention include combinations of the CDRs and the variable heavy and light chain sequences set forth herein.

In another embodiment, the invention contemplates other antibodies, such as for example chimeric antibodies, comprising at least one of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2, and/or at least one of the polypeptide sequences of SEQ ID NO: 7; SEQ ID NO: 8 or 120; and SEQ ID NO: 9 which correspond to the complementarity-determining regions (CDRs, or hypervariable regions) of the variable heavy chain sequence of SEQ ID NO: 3 or 19, or combinations of these polypeptide sequences. In another embodiment of the invention, the antibodies of the invention include combinations of the CDRs and humanized versions of the variable heavy and light chain sequences set forth above.

The invention also contemplates fragments of the antibody having binding specificity to IL-6. In one embodiment of the invention, antibody fragments of the invention comprise, or alternatively consist of, humanized versions of the polypeptide sequence of SEQ ID NO: 2, 20, 647, 651, 660, 666, 699, 702, 706, or 709. In another embodiment of the invention, antibody fragments of the invention comprise, or alternatively consist of, humanized versions of the polypeptide sequence of SEQ ID NO: 3, 18, 19, 652, 656, 657, 658, 661, 664, 665, 704, or 708.

In a further embodiment of the invention, fragments of the antibody having binding specificity to IL-6 comprise, or alternatively consist of, at least one of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2 or SEQ ID NO: 709.

In a further embodiment of the invention, fragments of the antibody having binding specificity to IL-6 comprise, or alternatively consist of, at least one of the polypeptide sequences of SEQ ID NO: 7; SEQ ID NO: 8 or SEQ ID NO: 120; and SEQ ID NO: 9 which correspond to the complementarity-determining regions (CDRs, or hypervariable regions) of the variable heavy chain sequence of SEQ ID NO: 3 and 657 or 19.

The invention also contemplates antibody fragments which include at least one of the antibody fragments described herein. In one embodiment of the invention, fragments of the antibodies having binding specificity to IL-6 comprise, or alternatively consist of, one, two, three or more, including all of the following antibody fragments: the variable light chain region of SEQ ID NO: 2; the variable heavy chain region of SEQ ID NO: 3; the complementarity-determining regions (SEQ ID NO: 4; SEQ ID NO: 5; and SEQ ID NO: 6) of the variable light chain region of SEQ ID NO: 2; and the complementarity-determining regions (SEQ ID NO: 7; SEQ ID NO: 8 or SEQ ID NO: 120; and SEQ ID NO: 9) of the variable heavy chain region of SEQ ID NO: 3 and 657 or 19.

The invention also contemplates variants wherein either of the heavy chain polypeptide sequences of SEQ ID NO: 18 or SEQ ID NO: 19 is substituted for the heavy chain polypeptide sequence of SEQ ID NO: 3 or 657; the light chain polypeptide sequence of SEQ ID NO: 20 is substituted for the light chain polypeptide sequence of SEQ ID NO: 2 or SEQ ID NO: 709; and the heavy chain CDR sequence of SEQ ID NO: 120 is substituted for the heavy chain CDR sequence of SEQ ID NO: 8.

In a preferred embodiment of the invention, the anti-IL-6 antibody is Ab1, comprising SEQ ID NO: 2 and SEQ ID NO: 3, or more particularly an antibody comprising SEQ ID NO: 657 and SEQ ID NO: 709 (which are respectively encoded by the nucleic acid sequences in SEQ ID NO: 700 and SEQ ID NO: 723) or one comprised of the alternative SEQ ID NOs set forth in the preceding paragraph, and having at least one of the biological activities set forth herein. In a preferred embodiment the anti-IL-6 antibody will comprise a humanized sequence as shown in FIGS. 1-5.

Sequences of anti-IL-6 antibodies of the present invention are shown in Table 4. Exemplary sequence variants other alternative forms of the heavy and light chains of Ab1 through Ab36 are shown. The antibodies of the present invention encompass additional sequence variants, including conservative substitutions, substitution of at least one CDR sequences and/or FR sequences.

Exemplary Ab1 embodiments include an antibody comprising a variant of the light chain and/or heavy chain. Exemplary variants of the light chain of Ab1 include the sequence of any of the Ab1 light chains shown (i.e., any of SEQ ID NO: 2, 20, 647, 651, 660, 666, 699, 702, 706, or 709) wherein the entire CDR1 sequence is replaced or wherein at least one residues in the CDR1 sequence is substituted by the residue in the corresponding position of any of the other light chain CDR1 sequences set forth (i.e., any of SEQ ID NO: 23, 39, 55, 71, 87, 103, 124, 140, 156, 172, 188, 204, 220, 236, 252, 268, 284, 300, 316, 332, 348, 364, 380, 396, 412, 428, 444, 460, 476, 492, 508, 524, 540, 556, or 572); and/or wherein the entire CDR2 sequence is replaced or wherein at least one residues in the CDR2 sequence is substituted by the residue in the corresponding position of any of the other light chain CDR2 sequences set forth (i.e., any of SEQ ID NO: 24, 40, 56, 72, 88, 104, 125, 141, 157, 173, 189, 205, 221, 237, 253, 269, 285, 301, 317, 333, 349, 365, 381, 397, 413, 429, 445, 461, 477, 493, 509, 525, 541, 557, or 573); and/or wherein the entire CDR3 sequence is replaced or wherein at least one residues in the CDR3 sequence is substituted by the residue in the corresponding position of any of the other light chain CDR3 sequences set forth (i.e., any of SEQ ID NO: 25, 41, 57, 73, 89, 105, 126, 142, 158, 174, 190, 206, 222, 238, 254, 270, 286, 302, 318, 334, 350, 366, 382, 398, 414, 430, 446, 462, 478, 494, 510, 526, 542, 558, or 574).

Exemplary variants of the heavy chain of Ab1 include the sequence of any of the Ab1 heavy chains shown (i.e., any of SEQ ID NO: 3, 18, 19, 652, 656, 657, 658, 661, 664, 665, 704, or 708) wherein the entire CDR1 sequence is replaced or wherein at least one residues in the CDR1 sequence is substituted by the residue in the corresponding position of any of the other heavy chain CDR1 sequences set forth (i.e., any of SEQ ID NO: 26, 42, 58, 74, 90, 106, 127, 143, 159, 175, 191, 207, 223, 239, 255, 271, 287, 303, 319, 335, 351, 367, 383, 399, 415, 431, 447, 463, 479, 495, 511, 527, 543, 559, or 575); and/or wherein the entire CDR2 sequence is replaced or wherein at least one residues in the CDR2 sequence is substituted by the residue in the corresponding position of an Ab1 heavy chain CDR2, such as those set forth in Table 4 (i.e., any of SEQ ID NO: 8, or 120) or any of the other heavy chain CDR2 sequences set forth (i.e., any of SEQ ID NO: 27, 43, 59, 75, 91, 107, 121, 128, 144, 160, 176, 192, 208, 224, 240, 256, 272, 288, 304, 320, 336, 352, 368, 384, 400, 416, 432, 448, 464, 480, 496, 512, 528, 544, 560, or 576); and/or wherein the entire CDR3 sequence is replaced or wherein at least one residues in the CDR3 sequence is substituted by the residue in the corresponding position of any of the other heavy chain CDR3 sequences set forth (i.e., any of SEQ ID NO: 28, 44, 60, 76, 92, 108, 129, 145, 161, 177, 193, 209, 225, 241, 257, 273, 289, 305, 321, 337, 353, 369, 385, 401, 417, 433, 449, 465, 481, 497, 513, 529, 545, 561, or 577).

In another embodiment, the invention contemplates other antibodies, such as for example chimeric or humanized antibodies, comprising at least one of the polypeptide sequences of SEQ ID NO: 4; SEQ ID NO: 5; and SEQ ID NO: 6 which correspond to the complementarity-determining regions (CDRs, or hypervariable regions) of the variable light chain sequence of SEQ ID NO: 2, and/or at least one of the polypeptide sequences of SEQ ID NO: 7 (CDR1); SEQ ID NO: 8 (CDR2); SEQ ID NO: 120 (CDR2); and SEQ ID NO: 9 (CDR3) which correspond to the complementarity-determining regions (CDRs, or hypervariable regions) of the variable heavy chain sequence of SEQ ID NO: 3 or SEQ ID NO: 19, or combinations of these polypeptide sequences. In another embodiment of the invention, the antibodies of the invention include combinations of the CDRs and the variable heavy and light chain sequences set forth above including those set forth in FIGS. 1-5, and those identified in Table 4.

In another embodiment the anti-IL-6 antibody of the invention is one comprising at least one of the following: a CDR1 light chain encoded by the sequence in SEQ ID NO: 12 or SEQ ID NO: 694; a light chain CDR2 encoded by the sequence in SEQ ID NO: 13; a light chain CDR3 encoded by the sequence in SEQ ID NO: 14 or SEQ ID NO: 695; a heavy chain CDR1 encoded by the sequence in SEQ ID NO: 15, a heavy chain CDR2 encoded by SEQ ID NO: 16 or SEQ ID NO: 696 and a heavy chain CDR3 encoded by SEQ ID NO: 17 or SEQ ID NO: 697. In addition the invention embraces such nucleic acid sequences and variants thereof.

In another embodiment the invention is directed to amino acid sequences corresponding to the CDRs of said anti-IL-6 antibody which are selected from SEQ ID NO: 4 (CDR1), SEQ ID NO: 5 (CDR2), SEQ ID NO: 6 (CDR3), SEQ ID NO: 7, SEQ ID NO: 120 and SEQ ID NO: 9.

In another embodiment the anti-IL-6 antibody of the invention comprises a light chain nucleic acid sequence of SEQ ID NO: 10, 662, 698, 701, 705, 720, 721, 722, or 723; and/or a heavy chain nucleic acid sequence of SEQ ID NO: 11, 663, 700, 703, 707, 724, or 725. In addition the invention is directed to the corresponding polypeptides encoded by any of the foregoing nucleic acid sequences and combinations thereof.

In a specific embodiment of the invention the anti-IL-6 antibodies or a portion thereof will be encoded by a nucleic acid sequence selected from those comprised in SEQ ID NO: 10, 12, 13, 14, 662, 694, 695, 698, 701, 705, 720, 721, 722, 723, 11, 15, 16, 17, 663, 696, 697, 700, 703, 707, 724, and 725. For example the CDR1 in the light chain may be encoded by SEQ ID NO: 12 or 694, the CDR2 in the light chain may be encoded by SEQ ID NO: 13, the CDR3 in the light chain may be encoded by SEQ ID NO: 14 or 695; the CDR1 in the heavy chain may be encoded by SEQ ID NO: 15, the CDR2 in the heavy chain may be encoded by SEQ ID NO: 16 or 696, the CDR3 in the heavy chain may be encoded by SEQ ID NO: 17 or 697. As discussed infra antibodies containing these CDRs may be constructed using appropriate human frameworks based on the humanization methods disclosed herein.

In another specific embodiment of the invention the variable light chain will be encoded by SEQ ID NO: 10, 662, 698, 701, 705, 720, 721, 722, or 723 and the variable heavy chain of the anti-IL-6 antibodies will be encoded by SEQ ID NO: 11, 663, 700, 703, 707, 724, or 725.

In a more specific embodiment variable light and heavy chains of the anti-IL-6 antibody respectively will be encoded by SEQ ID NO: 10 and 11, or SEQ ID NO: 698 and SEQ ID NO: 700, or SEQ ID NO: 701 and SEQ ID NO: 703 or SEQ ID NO: 705 and SEQ ID NO: 707.

In another specific embodiment the invention covers nucleic acid constructs containing any of the foregoing nucleic acid sequences and combinations thereof as well as recombinant cells containing these nucleic acid sequences and constructs containing wherein these nucleic acid sequences or constructs may be extrachromosomal or integrated into the host cell genome In another specific embodiment the invention covers polypeptides containing any of the CDRs or combinations thereof recited in SEQ ID NO: 4, SEQ ID NO: 5, SEQ ID NO: 6, SEQ ID NO: 7, SEQ ID NO: 8, SEQ ID NO: 120, SEQ ID NO: 9 or polypeptides comprising any of the variable light polypeptides comprised in SEQ ID NO: 2, 20, 647, 651, 660, 666, 699, 702, 706, or 709 and/or the variable heavy polypeptides comprised in SEQ ID NO: 3, 18, 19, 652, 656, 657, 658, 661, 664, 665, 704, or 708.

In another embodiment the anti-IL-6 antibody is one comprising at least one of the following: a variable light chain encoded by the sequence in SEQ ID NO: 10 or SEQ ID NO: 698 or SEQ ID NO: 701 or SEQ ID NO: 705 and a variable chain encoded by the sequence in SEQ ID NO: 11 or SEQ ID NO: 700 or SEQ ID NO: 703 or SEQ ID NO: 707.

In another embodiment the anti-IL-6 antibody is a variant of the foregoing sequences that includes at least one substitution in the framework and/or CDR sequences and which has at least one of the properties of Ab1 in vitro and/or upon in vivo administration.

These in vitro and in vivo properties are described in more detail in the examples below and include: competing with Ab1 for binding to IL-6 and/or peptides thereof; having a binding affinity (Kd) for IL-6 of less than about 50 picomolar, and/or a rate of dissociation ($K_{off}$) from IL-6 of less than or equal to $10^{-4}$ $S^{-1}$; having an in-vivo half-life of at least about 22 days in a healthy human subject; ability to prevent or treat hypoalbunemia; ability to prevent or treat elevated CRP; ability to prevent or treat abnormal coagulation; and/or ability to decrease the risk of thrombosis in an individual having a disease or condition associated with increased risk of thrombosis. Additional non-limiting examples of anti-IL-6 activity are set forth herein, for example, under the heading "Anti-IL-6 Activity."

In another embodiment the anti-IL-6 antibody includes at least one of the Ab1 light-chain and/or heavy chain CDR sequences (see Table 4) or variant(s) thereof which has at least one of the properties of Ab1 in vitro and/or upon in vivo administration (examples of such properties are discussed in the preceding paragraph). One of skill in the art would understand how to combine these CDR sequences to form an antigen-binding surface, e.g. by linkage to at least one scaffold which may comprise human or other mammalian framework sequences, or their functional orthologs derived from a SMIP (Small Modular ImmunoPharmaceutical), camelbody, nanobody, IgNAR, other immunoglobulin, or other engineered antibody. See, e.g., Robak & Robak (2011) *BioDrugs* 25(1): 13-25 and Wesolowski, et al. (2009) *Med Microbiol Immunol* 198: 157-174. For example, embodiments may specifically bind to human IL-6 and include one, two, three, four, five, six, or more of the following CDR sequences or variants thereof: a polypeptide having at least 72.7% sequence identity (i.e., 8 out of 11 amino acids) to the light chain CDR1 of SEQ ID NO: 4; a polypeptide having at least 81.8% (i.e., 9 out of 11 amino acids) identity to the light chain CDR1 of SEQ ID NO: 4; a polypeptide having at least 90.9% (i.e., 10 out of 11 amino acids) identity to the light chain CDR1 of SEQ ID NO: 4; a polypeptide having 100% (i.e., 11 out of 11 amino acids) identity to the light chain CDR1 of SEQ ID NO: 4; a polypeptide having at least 85.7% sequence identity (i.e., 6 out of 7 amino acids) to the light chain CDR2 of SEQ ID NO: 5; a polypeptide having 100% (i.e., 7 out of 7 amino acids) identity to the light chain CDR2 of SEQ ID NO: 5; a polypeptide having at least 50% sequence identity (i.e., 6 out of 12 amino acids) to the light chain CDR3 of SEQ ID NO: 6; a polypeptide having at least 58.3% sequence identity (i.e., 7 out of 12 amino acids) to the light chain CDR3 of SEQ ID NO: 6;

a polypeptide having at least 66.6% (i.e., 8 out of 12 amino acids) identity to the light chain CDR3 of SEQ ID NO: 6; a polypeptide having at least 75% (i.e., 9 out of 12 amino acids) identity to the light chain CDR3 of SEQ ID NO: 6; a polypeptide having at least 83.3% sequence identity (i.e., 10 out of 12 amino acids) to the light chain CDR3 of SEQ ID NO: 6; a polypeptide having at least 91.6% sequence identity (i.e., 11 out of 12 amino acids) to the light chain CDR3 of SEQ ID NO: 6; a polypeptide having 100% (i.e., 12 out of 12 amino acids) identity to the light chain CDR3 of SEQ ID NO: 6; a polypeptide having at least 80% sequence identity (i.e., 4 out of 5 amino acids) to the heavy chain CDR1 of SEQ ID NO: 7; a polypeptide having 100% (i.e., 5 out of 5 amino acids) identity to the heavy chain CDR1 of SEQ ID NO: 7; a polypeptide having at least 50% sequence identity (i.e., 8 out of 16 amino acids) to the heavy chain CDR2 of SEQ ID NO: 120; a polypeptide having at least 56.2% sequence identity (i.e., 9 out of 16 amino acids) to the heavy chain CDR2 of SEQ ID NO: 120; a polypeptide having at least 62.5% sequence identity (i.e., 10 out of 16 amino acids) to the heavy chain CDR2 of SEQ ID NO: 120; a polypeptide having at least 68.7% sequence identity (i.e., 11 out of 16 amino acids) to the heavy chain CDR2 of SEQ ID NO: 120; a polypeptide having at least 75% sequence identity (i.e., 12 out of 16 amino acids) to the heavy chain CDR2 of SEQ ID NO: 120;

a polypeptide having at least 81.2% sequence identity (i.e., 13 out of 16 amino acids) to the heavy chain CDR2 of SEQ ID NO: 120; a polypeptide having at least 87.5% sequence identity (i.e., 14 out of 16 amino acids) to the heavy chain CDR2 of SEQ ID NO: 120; a polypeptide having at least 93.7% sequence identity (i.e., 15 out of 16 amino acids) to the heavy chain CDR2 of SEQ ID NO: 120; a polypeptide having 100% (i.e., 16 out of 16 amino acids) identity to the heavy chain CDR2 of SEQ ID NO: 120; a polypeptide having at least 33.3% sequence identity (i.e., 4 out of 12 amino acids) to the heavy chain CDR3 of SEQ ID NO: 9; a polypeptide having at least 41.6% (i.e., 5 out of 12 amino acids) identity to the heavy chain CDR3 of SEQ ID NO: 9; a polypeptide having at least 50% sequence identity (i.e., 6 out of 12 amino acids) to the heavy chain CDR3 of SEQ ID NO: 9; a polypeptide having at least 58.3% sequence identity (i.e., 7 out of 12 amino acids) to the heavy chain CDR3 of SEQ ID NO: 9; a polypeptide having at least 66.6% sequence identity (i.e., 8 out of 12 amino acids) to the heavy chain CDR3 of SEQ ID NO: 9; a polypeptide having at least 75% sequence identity (i.e., 9 out of 12 amino acids) to the heavy chain CDR3 of SEQ ID NO: 9; a polypeptide having at least 83.3% sequence identity (i.e., 10 out of 12 amino acids) to the heavy chain CDR3 of SEQ ID NO: 9; a polypeptide having at least 91.6% sequence identity (i.e., 11 out of 12 amino acids) to the heavy chain CDR3 of SEQ ID NO: 9; a polypeptide having 100% (i.e., 12 out of 12 amino acids) identity to the heavy chain CDR3 of SEQ ID NO: 9; a polypeptide having at least 90.9% sequence identity (i.e., 10 out of 11 amino acids) to the light chain CDR1 of SEQ ID NO: 4; a polypeptide having 100% (i.e., 11 out of 11 amino acids) similarity to the light chain CDR1 of SEQ ID NO: 4; a polypeptide having at least 85.7% sequence identity (i.e., 6 out of 7 amino acids) to the light chain CDR2 of SEQ ID NO: 5; a polypeptide having 100% (i.e., 7 out of 7 amino acids) similarity to the light chain CDR2 of SEQ ID NO: 5; a polypeptide having at least 66.6% sequence identity (i.e., 8 out of 12 amino acids) to the light chain CDR3 of SEQ ID NO: 6; a polypeptide having at least 75% sequence identity (i.e., 9 out of 12 amino acids) to the light chain CDR3 of SEQ ID NO: 6; a polypeptide having at least 83.3% sequence identity (i.e., 10 out of 12 amino acids) to the light chain CDR3 of SEQ ID NO: 6; a polypeptide having at least 91.6% sequence identity (i.e., 11 out of 12 amino acids) to the light chain CDR3 of SEQ ID NO: 6; a polypeptide having 100% (i.e., 12 out of 12 amino acids) similarity to the light chain CDR3 of SEQ ID NO: 6; a polypeptide having at least 80% sequence identity (i.e., 4 out of 5 amino acids) to the heavy chain CDR1 of SEQ ID NO: 7; a polypeptide having 100% (i.e., 5 out of 5 amino acids) similarity to the heavy chain CDR1 of SEQ ID NO: 7; a polypeptide having at least 56.2% sequence identity (i.e., 9 out of 16 amino acids) to the heavy chain CDR2 of SEQ ID NO: 120; a polypeptide having at least 62.5% sequence identity (i.e., 10 out of 16 amino acids) to the heavy chain CDR2 of SEQ ID NO: 120; a polypeptide having at least 68.7% sequence identity (i.e., 11 out of 16 amino acids) to the heavy chain CDR2 of SEQ ID NO: 120; a polypeptide having at least 75% sequence identity (i.e., 12 out of 16 amino acids) to the heavy chain CDR2 of SEQ ID NO: 120; a polypeptide having at least 81.2% sequence identity (i.e., 13 out of 16 amino acids) to the heavy chain CDR2 of SEQ ID NO: 120; a polypeptide having at least 87.5% sequence identity (i.e., 14 out of 16 amino acids) to the heavy chain CDR2 of SEQ ID NO: 120; a polypeptide having at least 93.7% sequence identity (i.e., 15 out of 16 amino acids) to the heavy chain CDR2 of SEQ ID NO: 120; a polypeptide having 100% (i.e., 16 out of 16 amino acids) similarity to the heavy chain CDR2 of SEQ ID NO: 120; a polypeptide having at least 50% sequence similarity (i.e., 6 out of 12 amino acids) to the heavy chain CDR3 of SEQ ID NO: 9; a polypeptide having at least 58.3% sequence identity (i.e., 7 out of 12 amino acids) to the heavy chain CDR3 of SEQ ID NO: 9; a polypeptide having at least 66.6% sequence identity (i.e., 8 out of 12 amino acids) to the heavy chain CDR3 of SEQ ID NO: 9; a polypeptide having at least 75% sequence identity (i.e., 9 out of 12 amino acids) to the heavy chain CDR3 of SEQ ID NO: 9; a polypeptide having at least 83.3% sequence identity (i.e., 10 out of 12 amino acids) to the heavy chain CDR3 of SEQ ID NO: 9; a polypeptide having at least 91.6% sequence identity (i.e., 11 out of 12 amino acids) to the heavy chain CDR3 of SEQ ID NO: 9; or a polypeptide having 100% (i.e., 12 out of 12 amino acids) similarity to the heavy chain CDR3 of SEQ ID NO: 9.

Other exemplary embodiments include at least one polynucleotides encoding any of the foregoing, e.g., a polynucleotide encoding a polypeptide that specifically binds to human IL-6 and includes one, two, three, four, five, six, or more of the following CDRs or variants thereof:

a polynucleotide encoding a polypeptide having at least 72.7% sequence identity (i.e., 8 out of 11 amino acids) to the light chain CDR1 of SEQ ID NO: 4; a polynucleotide encoding a polypeptide having at least 81.8% sequence identity (i.e., 9 out of 11 amino acids) to the light chain CDR1 of SEQ ID NO: 4; a polynucleotide encoding a polypeptide having at least 90.9% sequence identity (i.e., 10 out of 11 amino acids) to the light chain CDR1 of SEQ ID NO: 4; a polynucleotide encoding a polypeptide having 100% sequence identity to the light chain CDR1 of SEQ ID NO: 4; a polynucleotide encoding a polypeptide having at least 85.7% sequence identity (i.e., 6 out of 7 amino acids) to the light chain CDR2 of SEQ ID NO: 5; a polynucleotide encoding a polypeptide having 100% sequence identity to the light chain CDR2 of SEQ ID NO: 5; a polynucleotide encoding a polypeptide having at least 50% sequence identity (i.e., 6 out of 12 amino acids) to the light chain CDR3 of SEQ ID NO: 6; a polynucleotide encoding a polypeptide having at least 58.3% sequence identity (i.e., 7 out of 12 amino acids) to the light chain CDR3 of SEQ ID NO: 6; a polynucleotide encoding a polypeptide having at least 66.6% sequence identity (i.e., 8 out of 12 amino acids) to the light chain CDR3 of SEQ ID NO: 6; a polynucleotide encoding a polypeptide having at least 75% sequence identity (i.e., 9 out of 12 amino acids) to the light chain CDR3 of SEQ ID NO: 6; a polynucleotide encoding a polypeptide having at least 83.3% sequence identity (i.e., 10 out of 12 amino acids) to the light chain CDR3 of SEQ ID NO: 6; a polynucleotide encoding a polypeptide having at least 91.6% sequence identity (i.e., 11 out of 12 amino acids) to the light chain CDR3 of SEQ ID NO: 6; a polynucleotide encoding a polypeptide having 100% identity to the light chain CDR3 of SEQ ID NO: 6; a polynucleotide encoding a polypeptide having at least 80% sequence identity (i.e., 4 out of 5 amino acids) to the heavy chain CDR1 of SEQ ID NO: 7; a polynucleotide encoding a polypeptide having 100% identity to the heavy chain CDR1 of SEQ ID NO: 7; a polynucleotide encoding a polypeptide having at least 50% sequence identity (i.e., 8 out of 16 amino acids) to the heavy chain CDR2 of SEQ ID NO: 120; a polynucleotide encoding a polypeptide having at least 56.2% sequence identity (i.e., 9 out of 16 amino acids) to the heavy chain CDR2 of SEQ ID NO: 120; a polynucleotide encoding a polypeptide having at least 62.5% sequence identity (i.e., 10 out of 16 amino acids) to the heavy chain CDR2 of SEQ ID NO: 120; a polynucleotide encoding a polypeptide having at least 68.7% sequence identity (i.e., 11 out of 16 amino acids) to the heavy chain CDR2 of SEQ ID NO: 120; a polynucleotide encoding a polypeptide having at least 75% sequence identity (i.e., 12 out of 16 amino acids) to the heavy chain CDR2 of SEQ ID NO: 120; a polynucleotide encoding a polypeptide having at least 81.2% sequence identity (i.e., 13 out of 16 amino acids) to the heavy chain CDR2 of SEQ ID NO: 120; a polynucleotide encoding a polypeptide having at least 87.5% sequence identity (i.e., 14 out of 16 amino acids) to the heavy chain CDR2 of SEQ ID NO: 120; a polynucleotide encoding a polypeptide having at least 93.7% sequence identity (i.e., 15 out of 16 amino acids) to the heavy chain CDR2 of SEQ ID NO: 120; a polynucleotide encoding a polypeptide having 100% identity to the heavy chain CDR2 of SEQ ID NO: 120; a polynucleotide encoding a polypeptide having at least 33.3% sequence identity (i.e., 4 out of 12 amino acids) to the heavy chain CDR3 of SEQ ID NO: 9; a polynucleotide encoding a polypeptide having at least 41.6% (i.e., 5 out of 12 amino acids) identity to the heavy chain CDR3 of SEQ ID NO: 9; a polynucleotide encoding a polypeptide having at least 50% sequence identity (i.e., 6 out of 12 amino acids) to the heavy chain CDR3 of SEQ ID NO: 9; a polynucleotide encoding a polypeptide having at least 58.3% sequence identity (i.e., 7 out of 12 amino acids) to the heavy chain CDR3 of SEQ ID NO: 9; a polynucleotide encoding a polypeptide having at least 66.6% sequence identity (i.e., 8 out of 12 amino acids) to the heavy chain CDR3 of SEQ ID NO: 9; a polynucleotide encoding a polypeptide having at least 75% sequence identity (i.e., 9 out of 12 amino acids) to the heavy chain CDR3 of SEQ ID NO: 9; a polynucleotide encoding a polypeptide having at least 83.3% sequence identity (i.e., 10 out of 12 amino acids) to the heavy chain CDR3 of SEQ ID NO: 9; a polynucleotide encoding a polypeptide having at least 91.6% sequence identity (i.e., 11 out of 12 amino acids) to the heavy chain CDR3 of SEQ ID NO: 9; a polynucleotide encoding a polypeptide having 100% (i.e., 12 out of 12 amino acids) identity to the heavy chain CDR3 of SEQ ID NO: 9; a polynucleotide encoding a polypeptide having at least 90.9% sequence identity (i.e., 10 out of 11 amino acids) to the light chain CDR1 of SEQ ID NO: 4; a polynucleotide encoding a polypeptide having 100% sequence similarity to the light chain CDR1 of SEQ ID NO: 4; a polynucleotide encoding a polypeptide having at least 85.7% sequence identity (i.e., 6 out of 7 amino acids) to the light chain CDR2 of SEQ ID NO: 5; a polynucleotide encoding a polypeptide having 100% sequence similarity to the light chain CDR2 of SEQ ID NO: 5; a polynucleotide encoding a polypeptide having at least 66.6% sequence identity (i.e., 8 out of 12 amino acids) to the light chain CDR3 of SEQ ID NO: 6; a polynucleotide encoding a polypeptide having at least 75% sequence identity (i.e., 9 out of 12 amino acids) to the light chain CDR3 of SEQ ID NO: 6; a polynucleotide encoding a polypeptide having at least 83.3% sequence identity (i.e., 10 out of 12 amino acids) to the light chain CDR3 of SEQ ID NO: 6; a polynucleotide encoding a polypeptide having at least 91.6% sequence identity (i.e., 11 out of 12 amino acids) to the light chain CDR3 of SEQ ID NO: 6; a polynucleotide encoding a polypeptide having 100% sequence similarity to the light chain CDR3 of SEQ ID NO: 6; a polynucleotide encoding a polypeptide having at least 80% sequence identity (i.e., 4 out of 5 amino acids) to the heavy chain CDR1 of SEQ ID NO: 7; a polynucleotide encoding a polypeptide having 100% sequence similarity to the heavy chain CDR1 of SEQ ID NO: 7; a polynucleotide encoding a polypeptide having at least 56.2% sequence identity (i.e., 9 out of 16 amino acids) to the heavy chain CDR2 of SEQ ID NO: 120; a polynucleotide encoding a polypeptide having at least 62.5% sequence identity (i.e., 10 out of 16 amino acids) to the heavy chain CDR2 of SEQ ID NO: 120; a polynucleotide encoding a polypeptide having at least 68.7% sequence identity (i.e., 11 out of 16 amino acids) to the heavy chain CDR2 of SEQ ID NO: 120; a polynucleotide encoding a polypeptide having at least 75% sequence identity (i.e., 12 out of 16 amino acids) to the heavy chain CDR2 of SEQ ID NO: 120; a polynucleotide encoding a polypeptide having at least 81.2% sequence identity (i.e., 13 out of 16 amino acids) to the heavy chain CDR2 of SEQ ID NO: 120; a polynucleotide encoding a polypeptide having at least 87.5% sequence identity (i.e., 14 out of 16 amino acids) to the heavy chain CDR2 of SEQ ID NO: 120; a polynucleotide encoding a polypeptide having at least 93.7% sequence identity (i.e., 15 out of 16 amino acids) to the heavy chain CDR2 of SEQ ID NO: 120;

a polynucleotide encoding a polypeptide having 100% sequence similarity (i.e., 16 out of 16 amino acids) to the heavy chain CDR2 of SEQ ID NO: 120; a polynucleotide encoding a polypeptide having at least 50% sequence similarity (i.e., 6 out of 12 amino acids) to the heavy chain CDR3 of SEQ ID NO: 9; a polynucleotide encoding a polypeptide having at least 58.3% sequence identity (i.e., 7 out of 12 amino acids) to the heavy chain CDR3 of SEQ ID NO: 9; a polynucleotide encoding a polypeptide having at least 66.6% sequence identity (i.e., 8 out of 12 amino acids) to the heavy chain CDR3 of SEQ ID NO: 9; a polynucleotide encoding a polypeptide having at least 75% sequence identity (i.e., 9 out of 12 amino acids) to the heavy chain CDR3 of SEQ ID NO: 9; a polynucleotide encoding a polypeptide having at least 83.3% sequence identity (i.e., 10 out of 12 amino acids) to the heavy chain CDR3 of SEQ ID NO: 9; a polynucleotide encoding a polypeptide having at least 91.6% sequence identity (i.e., 11 out of 12 amino acids) to the heavy chain CDR3 of SEQ ID NO: 9; a polynucleotide encoding a polypeptide having 100% sequence similarity (i.e., 12 out of 12 amino acids) to the heavy chain CDR3 of SEQ ID NO: 9.

TABLE 4

Sequences of exemplary anti-IL-6 antibodies.

| | Antibody chains | | CDR1 | | CDR2 | | CDR3 | |
|---|---|---|---|---|---|---|---|---|
| Antibody | PRT. | Nuc. | PRT. | Nuc. | PRT. | Nuc. | PRT. | Nuc. |
| Ab1 light chains * | 2 | 10 | 4 | 12 | 5 | 13 | 6 | 14 |
| | 20 | 720 | 4 | 12 | 5 | 13 | 6 | 14 |
| | 647 | 721 | 4 | 12 | 5 | 13 | 6 | 14 |
| | 651 | | 4 | 12 | 5 | 13 | 6 | 14 |
| | 660 | 662 | 4 | 12 | 5 | 13 | 6 | 14 |
| | 666 | 722 | 4 | 12 | 5 | 13 | 6 | 14 |
| | 699 | 698 | 4 | 694 | 5 | 13 | 6 | 695 |
| | 702 | 701 | 4 | 694 | 5 | 13 | 6 | 695 |
| | 706 | 705 | 4 | 694 | 5 | 13 | 6 | 695 |
| | 709 | 723 | 4 | 12 | 5 | 13 | 6 | 14 |
| Human light | 648 | | 710 | | 713 | | | |
| chains used in | 649 | | 711 | | 714 | | | |
| Ab1 humanization | 650 | | 712 | | 715 | | | |
| Ab1 heavy chains | 3 | 11 | 7 | 15 | 8 | 16 | 9 | 17 |
| | 18 | | 7 | 15 | 8 | 16 | 9 | 17 |
| | 19 | 724 | 7 | 15 | 120 | 696 | 9 | 17 |
| | 652 | 725 | 7 | 15 | 8 | 16 | 9 | 17 |
| | 656 | | 7 | 15 | 8 | 16 | 9 | 17 |
| | 657 | 700 | 7 | 15 | 659 | 696 | 9 | 697 |
| | 658 | | 7 | 15 | 120 | 696 | 9 | 17 |
| | 661 | 663 | 7 | 15 | 8 | 16 | 9 | 17 |
| | 664 | | 7 | 15 | 8 | 16 | 9 | 17 |
| | 665 | | 7 | 15 | 120 | 696 | 9 | 17 |
| | 704 | 703 | 7 | 15 | 120 | 696 | 9 | 697 |
| | 708 | 707 | 7 | 15 | 120 | 696 | 9 | 697 |
| Human heavy | 653 | | 716 | | 717 | | | |
| chains used in | 654 | | 716 | | 717 | | | |
| Ab1 humanization | 655 | | 74 | 82 | 718 | | | |
| Ab2 light chains | 21 | 29 | 23 | 31 | 24 | 32 | 25 | 33 |
| | 667 | 669 | 23 | 31 | 24 | 32 | 25 | 33 |
| Ab2 heavy chains | 22 | 30 | 26 | 34 | 27 | 35 | 28 | 36 |
| | 668 | 670 | 26 | 34 | 27 | 35 | 28 | 36 |
| Ab3 light chains | 37 | 45 | 39 | 47 | 40 | 48 | 41 | 49 |
| | 671 | 673 | 39 | 47 | 40 | 48 | 41 | 49 |
| Ab3 heavy chains | 38 | 46 | 42 | 50 | 43 | 51 | 44 | 52 |
| | 672 | 674 | 42 | 50 | 43 | 51 | 44 | 52 |
| Ab4 light chains | 53 | 61 | 55 | 63 | 56 | 64 | 57 | 65 |
| | 675 | 677 | 55 | 63 | 56 | 64 | 57 | 65 |
| Ab4 heavy chains | 54 | 62 | 58 | 66 | 59 | 67 | 60 | 68 |
| | 676 | 678 | 58 | 66 | 59 | 67 | 60 | 68 |
| Ab5 light chains | 69 | 77 | 71 | 79 | 72 | 80 | 73 | 81 |
| | 679 | 681 | 71 | 79 | 72 | 80 | 73 | 81 |
| Ab5 heavy chains | 70 | 78 | 74 | 82 | 75 | 83 | 76 | 84 |
| | 680 | 682 | 74 | 82 | 75 | 83 | 76 | 84 |
| Ab6 light chains | 85 | 93 | 87 | 95 | 88 | 96 | 89 | 97 |
| | 683 | 685 | 87 | 95 | 88 | 96 | 89 | 97 |
| Ab6 heavy chains | 86 | 94 | 90 | 98 | 91 | 99 | 92 | 100 |
| | 684 | 686 | 90 | 98 | 91 | 99 | 92 | 100 |
| Ab7 light chains | 101 | 109 | 103 | 111 | 104 | 112 | 105 | 113 |
| | 119 | | 103 | 111 | 104 | 112 | 105 | 113 |
| | 687 | 689 | 103 | 111 | 104 | 112 | 105 | 113 |
| | 693 | | 103 | 111 | 104 | 112 | 105 | 113 |

TABLE 4-continued

Sequences of exemplary anti-IL-6 antibodies.

| | Antibody chains | | CDR1 | | CDR2 | | CDR3 | |
|---|---|---|---|---|---|---|---|---|
| Antibody | PRT. | Nuc. | PRT. | Nuc. | PRT. | Nuc. | PRT. | Nuc. |
| Ab7 heavy chains | 102 | 110 | 106 | 114 | 107 | 115 | 108 | 116 |
| | 117 | | 106 | 114 | 107 | 115 | 108 | 116 |
| | 118 | | 106 | 114 | 121 | | 108 | 116 |
| | 688 | 690 | 106 | 114 | 107 | 115 | 108 | 116 |
| | 691 | | 106 | 114 | 107 | 115 | 108 | 116 |
| | 692 | | 106 | 114 | 121 | | 108 | 116 |
| Ab8 light chain | 122 | 130 | 124 | 132 | 125 | 133 | 126 | 134 |
| Ab8 heavy chain | 123 | 131 | 127 | 135 | 128 | 136 | 129 | 137 |
| Ab9 light chain | 138 | 146 | 140 | 148 | 141 | 149 | 142 | 150 |
| Ab9 heavy chain | 139 | 147 | 143 | 151 | 144 | 152 | 145 | 153 |
| Ab10 light chain | 154 | 162 | 156 | 164 | 157 | 165 | 158 | 166 |
| Ab10 heavy chain | 155 | 163 | 159 | 167 | 160 | 168 | 161 | 169 |
| Ab11 light chain | 170 | 178 | 172 | 180 | 173 | 181 | 174 | 182 |
| Ab11 heavy chain | 171 | 179 | 175 | 183 | 176 | 184 | 177 | 185 |
| Ab12 light chain | 186 | 194 | 188 | 196 | 189 | 197 | 190 | 198 |
| Ab12 heavy chain | 187 | 195 | 191 | 199 | 192 | 200 | 193 | 201 |
| Ab13 light chain | 202 | 210 | 204 | 212 | 205 | 213 | 206 | 214 |
| Ab13 heavy chain | 203 | 211 | 207 | 215 | 208 | 216 | 209 | 217 |
| Ab14 light chain | 218 | 226 | 220 | 228 | 221 | 229 | 222 | 230 |
| Ab14 heavy chain | 219 | 227 | 223 | 231 | 224 | 232 | 225 | 233 |
| Ab15 light chain | 234 | 242 | 236 | 244 | 237 | 245 | 238 | 246 |
| Ab15 heavy chain | 235 | 243 | 239 | 247 | 240 | 248 | 241 | 249 |
| Ab16 light chain | 250 | 258 | 252 | 260 | 253 | 261 | 254 | 262 |
| Ab16 heavy chain | 251 | 259 | 255 | 263 | 256 | 264 | 257 | 265 |
| Ab17 light chain | 266 | 274 | 268 | 276 | 269 | 277 | 270 | 278 |
| Ab17 heavy chain | 267 | 275 | 271 | 279 | 272 | 280 | 273 | 281 |
| Ab18 light chain | 282 | 290 | 284 | 292 | 285 | 293 | 286 | 294 |
| Ab18 heavy chain | 283 | 291 | 287 | 295 | 288 | 296 | 289 | 297 |
| Ab19 light chain | 298 | 306 | 300 | 308 | 301 | 309 | 302 | 310 |
| Ab19 heavy chain | 299 | 307 | 303 | 311 | 304 | 312 | 305 | 313 |
| Ab20 light chain | 314 | 322 | 316 | 324 | 317 | 325 | 318 | 326 |
| Ab20 heavy chain | 315 | 323 | 319 | 327 | 320 | 328 | 321 | 329 |
| Ab21 light chain | 330 | 338 | 332 | 340 | 333 | 341 | 334 | 342 |
| Ab21 heavy chain | 331 | 339 | 335 | 343 | 336 | 344 | 337 | 345 |
| Ab22 light chain | 346 | 354 | 348 | 356 | 349 | 357 | 350 | 358 |
| Ab22 heavy chain | 347 | 355 | 351 | 359 | 352 | 360 | 353 | 361 |
| Ab23 light chain | 362 | 370 | 364 | 372 | 365 | 373 | 366 | 374 |
| Ab23 heavy chain | 363 | 371 | 367 | 375 | 368 | 376 | 369 | 377 |
| Ab24 light chain | 378 | 386 | 380 | 388 | 381 | 389 | 382 | 390 |
| Ab24 heavy chain | 379 | 387 | 383 | 391 | 384 | 392 | 385 | 393 |
| Ab25 light chain | 394 | 402 | 396 | 404 | 397 | 405 | 398 | 406 |
| Ab25 heavy chain | 395 | 403 | 399 | 407 | 400 | 408 | 401 | 409 |
| Ab26 light chain | 410 | 418 | 412 | 420 | 413 | 421 | 414 | 422 |
| Ab26 heavy chain | 411 | 419 | 415 | 423 | 416 | 424 | 417 | 425 |
| Ab27 light chain | 426 | 434 | 428 | 436 | 429 | 437 | 430 | 438 |
| Ab27 heavy chain | 427 | 435 | 431 | 439 | 432 | 440 | 433 | 441 |
| Ab28 light chain | 442 | 450 | 444 | 452 | 445 | 453 | 446 | 454 |
| Ab28 heavy chain | 443 | 451 | 447 | 455 | 448 | 456 | 449 | 457 |
| Ab29 light chain | 458 | 466 | 460 | 468 | 461 | 469 | 462 | 470 |
| Ab29 heavy chain | 459 | 467 | 463 | 471 | 464 | 472 | 465 | 473 |
| Ab30 light chain | 474 | 482 | 476 | 484 | 477 | 485 | 478 | 486 |
| Ab30 heavy chain | 475 | 483 | 479 | 487 | 480 | 488 | 481 | 489 |
| Ab31 light chain | 490 | 498 | 492 | 500 | 493 | 501 | 494 | 502 |
| Ab31 heavy chain | 491 | 499 | 495 | 503 | 496 | 504 | 497 | 505 |
| Ab32 light chain | 506 | 514 | 508 | 516 | 509 | 517 | 510 | 518 |
| Ab32 heavy chain | 507 | 515 | 511 | 519 | 512 | 520 | 513 | 521 |
| Ab33 light chain | 522 | 530 | 524 | 532 | 525 | 533 | 526 | 534 |
| Ab33 heavy chain | 523 | 531 | 527 | 535 | 528 | 536 | 529 | 537 |
| Ab34 light chain | 538 | 546 | 540 | 548 | 541 | 549 | 542 | 550 |
| Ab34 heavy chain | 539 | 547 | 543 | 551 | 544 | 552 | 545 | 553 |
| Ab35 light chain | 554 | 562 | 556 | 564 | 557 | 565 | 558 | 566 |
| Ab35 heavy chain | 555 | 563 | 559 | 567 | 560 | 568 | 561 | 569 |
| Ab36 light chain | 570 | 578 | 572 | 580 | 573 | 581 | 574 | 582 |
| Ab36 heavy chain | 571 | 579 | 575 | 583 | 576 | 584 | 577 | 585 |

* Exemplary sequence variant forms of heavy and light chains are shown on separate lines.

(PRT.: Polypeptide sequence Nuc.: Exemplary coding sequence)

For reference, sequence identifiers other than those included in Table 4 are summarized in Table 5.

TABLE 5

Summary of sequence identifiers in this application.

| SEQ ID | Description |
|---|---|
| 1 | Human IL-6 |
| 586 | kappa constant light chain polypeptide sequence |
| 587 | kappa constant light chain polynucleotide sequence |
| 588 | gamma-1 constant heavy chain polypeptide sequence |
| 589 | gamma-1 constant heavy chain polynucleotide sequence |
| 590-646 | Human IL-6 peptides (Example 14) |
| 719 | gamma-1 constant heavy chain polypeptide sequence (differs from SEQ ID NO: 518 at two positions) |
| 726 | C-reactive protein polypeptide sequence |
| 727 | IL-6 receptor alpha |
| 728 | IL-6 receptor beta/gp130 |

Such antibody fragments or variants thereof may be present in at least one of the following non-limiting forms: Fab, Fab', F(ab')2, Fv and single chain Fv antibody forms. In a preferred embodiment, the anti-IL-6 antibodies described herein further comprises the kappa constant light chain sequence comprising the sequence set forth in the polypeptide sequence of SEQ ID NO: 586.

In another preferred embodiment, the anti-IL-6 antibodies described herein further comprises the gamma-1 constant heavy chain polypeptide sequence comprising one of the sequences set forth in the polypeptide sequence of SEQ ID NO: 588 and SEQ ID NO: 719.

Embodiments of antibodies described herein may include a leader sequence, such as a rabbit Ig leader, albumin prepeptide, a yeast mating factor pre pro secretion leader sequence (such as *P. pastoris* or *Saccharomyces cerevisiae* a or alpha factor), or human HAS leader. Exemplary leader sequences are shown offset from FR1 at the N-terminus of polypeptides shown in FIGS. 4A-B and 5A-B as follows: rabbit Ig leader sequences in SEQ ID NOs: 2 and 660 and SEQ ID NOs: 3 and 661; and an albumin prepeptide in SEQ ID NOs: 706 and 708, which facilitates secretion. Other leader sequences known in the art to confer desired properties, such as secretion, improved stability or half-life, may also be used, either alone or in combinations with one another, on the heavy and/or light chains, which may optionally be cleaved prior to administration to a subject. For example, a polypeptide may be expressed in a cell or cell-free expression system that also expresses or includes (or is modified to express or include) a protease, e.g., a membrane-bound signal peptidase, that cleaves a leader sequence.

In another embodiment, the invention contemplates an isolated anti-IL-6 antibody comprising a $V_H$ polypeptide sequence comprising: SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 656, 657, 658, 661, 664, 665, 668, 672, 676, 680, 684, 688, 691, 692, 704, or 708; and further comprising a $V_L$ polypeptide sequence comprising: SEQ ID NO: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 651, 660, 666, 667, 671, 675, 679, 683, 687, 693, 699, 702, 706, or 709 or a variant thereof wherein at least one of the framework residues (FR residues) or CDR residues in said $V_H$ or $V_L$ polypeptide has been substituted with another amino acid residue resulting in an anti-IL-6 antibody that specifically binds IL-6. The invention contemplates humanized and chimeric forms of these antibodies wherein preferably the FR will comprise human FRs highly homologous to the parent antibody. The chimeric antibodies may include an Fc derived from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions and in particular a variable heavy and light chain constant region as set forth in SEQ ID NO: 588 and SEQ ID NO: 586.

In one embodiment of the invention, the antibodies or $V_H$ or $V_L$ polypeptides originate or are selected from at least one rabbit B cell populations prior to initiation of the humanization process referenced herein.

In another embodiment of the invention, the anti-IL-6 antibodies and fragments and variants thereof have binding specificity for primate homologs of the human IL-6 protein. Non-limiting examples of primate homologs of the human IL-6 protein are IL-6 obtained from *Macaca fascicularis* (cynomolgus monkey) and the Rhesus monkey. In another embodiment of the invention, the anti-IL-6 antibodies and fragments and variants thereof inhibits the association of IL-6 with IL-6R, and/or the production of IL-6/IL-6R/gp130 complexes and/or the production of IL-6/IL-6R/gp130 multimers and/or antagonizes the biological effects of at least one of the foregoing.

Polyclonal Antibody

Polyclonal antibodies are heterogeneous populations of antibody molecules derived from the sera of animals immunized with an antigen. Polyclonal antibodies which selectively bind the IL-6 may be made by methods well-known in the art. See, e.g., Howard & Kaser (2007) Making and Using Antibodies: A Practical Handbook CRC Press.

Monoclonal Antibody

A monoclonal antibody contains a substantially homogeneous population of antibodies specific to antigens, which population contains substantially similar epitope binding sites. Monoclonal antibodies may be obtained by methods known to those skilled in the art. See, e.g. Kohler and Milstein (1975) Nature 256: 495-497; U.S. Pat. No. 4,376,110; Ausubel, et al. [Eds.] (2011) CURRENT PROTOCOLS IN MOLECULAR BIOLOGY, Greene Publishing Assoc. and Wiley Interscience, NY.; and Harlow & Lane (1998) USING ANTIBODIES: A LABORATORY MANUAL Cold Spring Harbor Laboratory; Colligan, et al. (2005) [Eds.] Current Protocols in Immunology Greene Publishing Assoc. and Wiley Interscience, NY. Such antibodies may be of any immunoglobulin class including IgG, IgM, IgE, IgA, GILD, and any subclass thereof. A hybridoma producing an antibody of the present invention may be cultivated in vitro, in situ, or in vivo.

Chimeric Antibody

Chimeric antibodies are molecules different portions of which are derived from different animal species, such as those having variable region derived from a murine antibody and a human immunoglobulin constant region, which are primarily used to reduce immunogenicity in application and to increase yields in production, for example, where murine monoclonal antibodies have higher yields from hybridomas but higher immunogenicity in humans, such that human murine chimeric monoclonal antibodies are used. Chimeric antibodies and methods for their production are known in the art. See Cabilly, et al. (1984) *Proc. Natl. Acad. Sci. USA* 81: 3273-3277; Morrison, et al. (1994) *Proc. Natl. Acad. Sci. USA* 81: 6851-6855, Boulianne, et al. (1984) *Nature* 312: 643-646; Neuberger, et al. (1985) *Nature* 314: 268-270; European Patent Application 173494 (1986); WO 86/01533 (1986); European Patent 184187 (1992); Sahagan, et al. (1986) *J*

*Immunol.* 137: 1066-1074; Liu, et al. (1987) *Proc. Natl. Acad. Sci. USA* 84: 3439-3443; Sun, et al. (1987) *Proc. Natl. Acad. Sci. USA* 84: 214-218; Better, et al. (1988) *Science* 240: 1041-1043; and Harlow & Lane (1998) USING ANTIBODIES: A LABORATORY MANUAL Cold Spring Harbor Laboratory; and U.S. Pat. No. 5,624,659.

Humanized Antibody

Humanized antibodies are engineered to contain even more human-like immunoglobulin domains, and incorporate only the complementarity-determining regions of the animal-derived antibody. This may be accomplished by examining the sequence of the hyper-variable loops of the variable regions of the monoclonal antibody, and fitting them to the structure of the human antibody chains. See, e.g., U.S. Pat. No. 6,187, 287. Likewise, other methods of producing humanized antibodies are now well known in the art. See, e.g., U.S. Pat. Nos. 5,225,539; 5,530,101; 5,585,089; 5,693,762; 6,054,297; 6,180,370; 6,407,213; 6,548,640; 6,632,927; and 6,639,055; Jones, et al. (1986) *Nature* 321: 522-525; Reichmann, et al. (1988) *Nature* 332: 323-327; Verhoeyen, et al. (1988) *Science* 239: 1534-36; and Zhiqiang An (2009) [Ed.] Therapeutic Monoclonal Antibodies: From Bench to Clinic John Wiley & Sons, Inc.

Antibody Fragments (Antigen-Binding Fragments)

In addition to entire immunoglobulins (or their recombinant counterparts), immunoglobulin fragments comprising the epitope binding site (e.g., Fab', F(ab')2, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. Antibody fragments of immunoglobulins include but are not limited to SMIPs (small molecule immunopharmaceuticals), camelbodies, nanobodies, and IgNAR. Further, antigen-binding fragments may comprise the epitope binding site and have the same antigen binding selectivity as the antibody.

An antigen-binding fragment (e.g., Fab fragment) may comprise at least one constant and one variable domain of each of the heavy and the light chain of the antibody from which it is derived. These domains shape the paratope—the antigen-binding site—at the amino terminal end of the monomer. The two variable domains bind the epitope on their specific antigens. Fc and Fab fragments may be generated using papain that cleaves the immunoglobulin monomer into two Fab fragments and an Fc fragment. Pepsin cleaves below hinge region, so a $F(ab')_2$ fragment and a pFc' fragment may be formed. Another enzyme, IdeS (Immunoglobulin degrading enzyme from *Streptococcus pyogenes*, trade name FabRICATOR®) cleaves IgG in a sequence specific manner at neutral pH. The $F(ab')_2$ fragment may be split into two Fab' fragments by mild reduction. Additionally, the variable regions of the heavy and light chains may be fused together to form a single-chain variable fragment (scFv), which is only half the size of the Fab fragment, but retains the original specificity of the parent antibody.

Anti-Idiotypic Antibody

An anti-idiotypic (anti-Id) antibody is an antibody which recognizes unique determinants generally associated with the antigen-binding site of an antibody. An Id antibody may be prepared by immunizing an animal of the same species and genetic type (e.g., mouse strain) as the source of the antibody with the antibody to which an anti-Id is being prepared. The immunized animal will recognize and respond to the idiotypic determinants of the immunizing antibody by producing an antibody to these idiotypic determinants (the anti-Id antibody). See e.g., U.S. Pat. No. 4,699,880. The anti-Id antibody may also be used as an "immunogen" to induce an immune response in yet another animal, producing a so-called anti-anti-Id antibody. The anti-anti-Id may be epitopically identical to the original antibody which induced the anti-Id. Thus, by using antibodies to the idiotypic determinants of an antibody it is possible to identify other clones expressing antibodies of identical specificity.

Engineered and Modified Antibodies

An antibody of the invention further may be prepared using an antibody having at least one of the VH and/or VL sequences derived from an antibody starting material to engineer a modified antibody, which modified antibody may have altered properties from the starting antibody. An antibody may be engineered by modifying at least one residues within one or both variable regions (i.e., VH and/or VL), for example within at least one CDR regions and/or within at least one framework regions. Additionally or alternatively, an antibody may be engineered by modifying residues within the constant region(s), for example to alter the effector function(s) of the antibody.

One type of variable region engineering that may be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. See, e.g., Riechmann, et al. (1998) *Nature* 332: 323-327; Jones, et al. (1986) *Nature* 321: 522-525; Queen, et al. (1989) *Proc. Natl. Acad. U.S.A.* 86: 10029-10033; U.S. Pat. Nos. 5,225,539; 5,530,101; 5,585,089; 5,693,762; and 6,180,370.

Suitable framework sequences may be obtained from public DNA databases or published references that include germline antibody gene sequences. For example, germline DNA sequences for human heavy and light chain variable region genes may be found in the "VBase" human germline sequence database (available on the Internet), as well as in Kabat, E. A., et al. (1991) Sequences of Proteins of Immunological Interest, Fifth Edition, U.S. Department of Health and Human Services, NIH Publication No. 91-3242; Tomlinson, et al. (1992) "The Repertoire of Human Germline VH Sequences Reveals about Fifty Groups of VH Segments with Different Hypervariable Loops" *J. Mol. Biol.* 227: 776-798; and Cox, et al. (1994) *Eur. J Immunol.* 24: 827-836.

Another type of variable region modification is to mutate amino acid residues within the VH and/or VL CDR 1, CDR2 and/or CDR3 regions to thereby improve at least one binding properties (e.g., affinity) of the antibody of interest. Site-directed mutagenesis or PCR-mediated mutagenesis may be performed to introduce the mutation(s) and the effect on antibody binding, or other functional property of interest, may be evaluated in appropriate in vitro or in vivo assays. Preferably conservative modifications (as discussed herein) may be introduced. The mutations may be amino acid substitutions, additions or deletions, but are preferably substitutions. Moreover, typically no more than one, two, three, four or five residues within a CDR region are altered.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" at least one framework residues to the corresponding germline sequence. More specifically, an antibody that has undergone somatic mutation may contain framework residues that differ from the germline sequence from which the antibody is derived. Such residues may be identified by comparing the antibody framework sequences to the germline sequences from which the antibody is derived.

In addition or alternative to modifications made within the framework or CDR regions, antibodies of the invention may be engineered to include modifications within the Fc region, typically to alter at least one functional properties of the antibody, such as serum half-life, complement fixation, Fc receptor binding, and/or antigen-dependent cellular cytotoxicity. Furthermore, an antibody of the invention may be chemically modified (e.g., at least one chemical moieties may be attached to the antibody) or be modified to alter its glycosylation, again to alter at least one functional properties of the antibody. Such embodiments are described further below. The numbering of residues in the Fc region is that of the EU index of Kabat.

The hinge region of CH1 may be modified such that the number of cysteine residues in the hinge region is altered, e.g., increased or decreased. See U.S. Pat. No. 5,677,425. The number of cysteine residues in the hinge region of CH1 may be altered to, for example, facilitate assembly of the light and heavy chains or to increase or decrease the stability of the antibody. The Fc hinge region of an antibody may be mutated to decrease the biological half life of the antibody. More specifically, at least one amino acid mutations may be introduced into the CH2-CH3 domain interface region of the Fc-hinge fragment such that the antibody has impaired Staphylococcyl protein A (SpA) binding relative to native Fc-hinge domain SpA binding. See, e.g., U.S. Pat. No. 6,165,745.

The antibody may be modified to increase its biological half life. Various approaches are possible. For example, at least one of the following mutations may be introduced: T252L, T254S, T256F. See U.S. Pat. No. 6,277,375. Alternatively, to increase the biological half life, the antibody may be altered within the CH1 or CL region to contain a salvage receptor binding epitope taken from two loops of a CH2 domain of an Fc region of an IgG. See U.S. Pat. Nos. 5,869,046 and 6,121,022.

The Fc region may be altered by replacing at least one amino acid residue with a different amino acid residue to alter the effector function(s) of the antibody. For example, at least one amino acids selected from amino acid residues 234, 235, 236, 237, 297, 318, 320 and 322 may be replaced with a different amino acid residue such that the antibody has an altered affinity for an effector ligand but retains the antigen-binding ability of the parent antibody. The effector ligand to which affinity may be altered may be, for example, an Fc receptor or the C1 component of complement. See U.S. Pat. Nos. 5,624,821 and 5,648,260.

The Fc region may be modified to increase the affinity of the antibody for an Fcy receptor by modifying at least one amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. See WO 00/42072. Moreover, the binding sites on human IgG1 for FcγRI, FcγRII, FcγRIII and FcRn have been mapped and variants with improved binding. See Shields, et al. (2001) *J. Biol. Chem.* 276: 6591-6604. Specific mutations at positions 256, 290, 298, 333, 334 and 339 are shown to improve binding to FcγRIII. Additionally, the following combination mutants are shown to improve FcγRIII binding: T256A/S298A, S298A/E333A, S298A/K224A and S298A/E333A/K334A.

The glycosylation of an antibody may be modified. For example, an aglycoslated antibody may be made (i.e., the antibody lacks glycosylation). Glycosylation may be altered to, for example, increase the affinity of the antibody for antigen. Such carbohydrate modifications may be accomplished by, for example, altering at least one sites of glycosylation within the antibody sequence. For example, at least one amino acid substitutions may be made that result in elimination of at least one variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody may be made that has an altered type of glycosylation, such as a hypofucosylated antibody having reduced amounts of fucosyl residues or an antibody having increased bisecting GlcNac structures. Such carbohydrate modifications may be accomplished by, for example, expressing the antibody in a host cell with altered glycosylation machinery. Cells with altered glycosylation machinery have been described in the art and may be used as host cells in which to express recombinant antibodies of the invention to thereby produce an antibody with altered glycosylation. See U.S. Patent Application Publication No. 2004/0110704 and Yamane-Ohnuki, et al. (2004) *Biotechnol Bioeng.* 87: 614-22; EP 1,176,195; WO 2003/035835; Shields, et al. (2002) *J. Biol. Chem.* 277: 26733-26740; WO 99/54342; Umana, et al. (1999) *Nat. Biotech.* 17: 176-180; and Tarentino, et al. (1975) *Biochem.* 14: 5516-23.

An antibody may be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which at least one PEG groups become attached to the antibody or antibody fragment. Preferably, the pegylation is carried out via an acylation reaction or an alkylation reaction with a reactive PEG molecule (or an analogous reactive water-soluble polymer).

The invention also provides variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of at least one amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. In another embodiment, the invention further contemplates the above-recited polypeptide homologs of the antibody fragments, variable regions and CDRs set forth herein further having anti-IL-6 activity. Non-limiting examples of anti-IL-6 activity are set forth herein, for example, under the heading "Anti-IL-6 Activity," infra.

Anti-IL-6 antibodies have also been disclosed in the following published and unpublished patent applications, which are co-owned by the assignee of the present application: WO 2008/144763; U.S. Patent Application Publication Nos. 2009/0028784, 2009/0297513, and 2009/0297436. Other anti-IL-6 antibodies have been disclosed in the following U.S. Pat. Nos. 7,482,436; 7,291,721; 6,121,423; U.S. Patent Application Publication Nos. 2008/0075726; 2007/0178098; 2007/0154481; 2006/0257407; and 2006/0188502.

Polypeptide Sequence Variants

For any anti-IL-6 antibodies sequence described herein, further characterization or optimization may be achieved by systematically either adding or removing amino acid residues to generate longer or shorter peptides, and testing those and sequences generated by walking a window of the longer or shorter size up or down the antigen from that point. Coupling this approach to generating new candidate targets with testing for effectiveness of antigenic molecules based on those sequences in an immunogenicity assay, as known in the art or as described herein, may lead to further manipulation of the antigen. Further still, such optimized sequences may be adjusted by, e.g., the addition, deletions, or other mutations as known in the art and/or discussed herein to further optimize the anti-IL-6 antibodies (e.g., increasing serum stability or circulating half-life, increasing thermal stability, enhancing delivery, enhance immunogenicity, increasing solubility, targeting to a particular in vivo location or cell type).

In another embodiment, the invention contemplates polypeptide sequences having at least about 90% sequence homology to any at least one of the polypeptide sequences of antibody fragments, variable regions and CDRs set forth herein. More preferably, the invention contemplates polypeptide sequences having at least about 95% sequence homology, even more preferably at least about 98% sequence homology, and still more preferably at least about 99% sequence homology to any at least one of the polypeptide sequences of antibody fragments, variable regions and CDRs set forth herein. Methods for determining homology between nucleic acid and amino acid sequences are well known to those of ordinary skill in the art.

The anti-IL-6 antibodies polypeptides described herein may comprise conservative substitution mutations, (i.e., the substitution of at least one amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid.

Anti-IL-6 antibodies polypeptide sequences may have at least about 60, 65, 70, 75, 80, 81, 82, 83, 84, 85, 86, 87, 88, 89, 90, 91, 92, 93, 94, 95, 96, 97, 98, 98.5, 99, 99.5, 99.8, 99.9, or 100% sequence homology to any at least one of the polypeptide sequences set forth herein. More preferably, the invention contemplates polypeptide sequences having at least about 95% sequence homology, even more preferably at least about 98% sequence homology, and still more preferably at least about 99% sequence homology to any at least one of the polypeptide sequences of Anti-IL-6 antibodies polypeptide sequences set forth herein. Methods for determining homology between amino acid sequences, as well as nucleic acid sequences, are well known to those of ordinary skill in the art. See, e.g., Nedelkov & Nelson (2006) *New and Emerging Proteomic Techniques* Humana Press. Thus, an anti-IL-6 antibodies polypeptide may have at least about 60, 65, 70, 75, 80, 81, 82, 83, 84, 85, 86, 87, 88, 89, 90, 91, 92, 93, 94, 95, 96, 97, 98, 98.5, 99, 99.5, 99.8, 99.9, or 100% sequence homology with a polypeptide sequence.

The term homology, or identity, is understood as meaning the number of agreeing amino acids (identity) with other proteins, expressed in percent. The identity is preferably determined by comparing a given sequence with other proteins with the aid of computer programs. If sequences which are compared with each other are different in length, the identity is to be determined in such a way that the number of amino acids which the short sequence shares with the longer sequence determines the percentage identity. The identity can be determined routinely by means of known computer programs which are publicly available such as, for example, Clustal W. Thompson, et al. (1994) *Nucleic Acids Research* 22: 4673-4680. ClustalW is publicly available from the European Molecular Biology Laboratory and may be downloaded from various internet pages, inter alia the IGBMC (Institut de Génétique et de Biologie Moléculaire et Cellulaire) and the EBI and all mirrored EBI internet pages (European Bioinformatics Institute). If the ClustalW computer program Version 1.8 is used to determine the identity between, for example, the reference protein of the present application and other proteins, the following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP. See also European Bioinformatics Institute (EBI) toolbox available on-line and Smith (2002) *Protein Sequencing Protocols [2nd* Ed.] Humana Press.

One possibility of finding similar sequences is to carry out sequence database researches. Here, at least one sequences may be entered as what is known as a query. This query sequence is then compared with sequences present in the selected databases using statistical computer programs. Such database queries (blast searches) are known to the skilled worker and may be carried out at different suppliers. If, for example, such a database query is carried out at the NCBI (National Center for Biotechnology Information), the standard settings for the respective comparison query should be used. For protein sequence comparisons (blastp), these settings are: Limit entrez=not activated; Filter=low complexity activated; Expect value=10; word size=3; Matrix=BLOSUM62; Gap costs: Existence=11, Extension=1. The result of such a query is, among other parameters, the degree of identity between the query sequence and the similar sequences found in the databases. Methods and materials for making fragments of Anti-IL-6 antibodies polypeptides are well known in the art. See, e.g., Maniatis, et al. (2001) Molecular Cloning: A Laboratory Manual [3rd Ed.] Cold Spring Harbor Laboratory Press.

Variant anti-IL-6 antibodies polypeptides may retain their antigenic specificity to bind IL-6. Fully specific variants may contain only conservative variations or variations in non-critical residues or in non-critical regions. Variants may also contain substitution of similar amino acids that result in no change or an insignificant change in their specificity. Alternatively, such substitutions may positively or negatively affect specificity to some degree. Non-specific variants typically contain at least one non-conservative amino acid substitutions, deletions, insertions, inversions, or truncation or a substitution, insertion, inversion, or deletion in a critical residue or critical region of an epitope. Molecular biology and biochemistry techniques for modifying anti-IL-6 antibodies polypeptides while preserving specificity are well known in the art. See, e.g., Ho, et al. (1989) *Gene* 77(1): 51-59; Landt, et al. (1990) *Gene* 96(1): 125-128; Hopp & Woods (1991) *Proc. Natl. Acad. Sci. USA* 78(6): 3824-3828; Kolaskar & Tongaonkar (1990) *FEBS Letters* 276(1-2): 172-174; and Welling, et al. (1985) *FEBS Letters* 188(2): 215-218.

Amino acids that are essential for function may be identified by methods known in the art, such as site-directed mutagenesis or alanine-scanning mutagenesis. Cunningham, et al. (1989) Sci. 244: 1081-85. The latter procedure introduces single alanine mutations at every residue in the molecule. The resulting mutant molecules are then tested for biological activity such as epitope binding. Sites that are critical for ligand-receptor binding may also be determined by structural analysis such as crystallography, nuclear magnetic resonance, or photoaffinity labeling. Smith, et al. (1992) *J. Mol. Biol.* 224: 899-904; de Vos, et al. (1992) *Sci.* 255: 306-12.

For example, one class of substitutions is conserved amino acid substitutions. Such substitutions are those that substitute a given amino acid in a Anti-IL-6 antibodies polypeptide with another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr. Guidance concerning which amino acid changes are likely to be phenotypically silent is found in, for example, Bowie, et al. (1990) *Sci.* 247: 1306-10. Hence, one of ordinary skill in the art appreciates that the inventors possess peptide variants without delineation of all the specific variants. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. See, e.g., Creighton (1992) Proteins: Structures and Molecular Properties [2$^{nd}$ Ed.] W.H. Freeman.

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, g-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See Creighton (1992) Proteins: Structure and Molecular Properties [2$^{nd}$ Ed.] and Lundblad (1995) Techniques in Protein Modification [1$^{st}$ Ed.] Many detailed reviews are available on this subject. See, e.g., Wold (1983) Posttranslational Covalent Modification of Proteins Acad. Press, NY; Seifter, et al. (1990) *Meth. Enzymol.* 182: 626-46; and Rattan, et al. (1992) *Ann. NY Acad. Sci.* 663: 48-62.

In another embodiment, the invention further contemplates the generation and use of anti-idiotypic antibodies that bind any of the foregoing sequences. In an exemplary embodiment, such an anti-idiotypic antibody could be administered to a subject who has received an anti-IL-6 antibody to modulate, reduce, or neutralize, the effect of the anti-IL-6 antibody. A further exemplary use of such anti-idiotypic antibodies is for detection of the anti-IL-6 antibodies of the present invention, for example to monitor the levels of the anti-IL-6 antibodies present in a subject's blood or other bodily fluids.

The present invention also contemplates anti-IL-6 antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein. As noted preferred anti-IL-6 antibodies or fragments or variants thereof may contain a variable heavy and/or light sequence as shown in FIG. 2-5, such as SEQ ID NO: 651, 657, 709 or variants thereof wherein at least one CDR or FR residues are modified without adversely affecting antibody binding to IL-6 or other desired functional activity.

Polynucleotides Encoding Anti-IL-6 Antibody Polypeptides

The invention is further directed to polynucleotides encoding polypeptides of the antibodies having binding specificity to IL-6. In one embodiment of the invention, polynucleotides of the invention comprise, or alternatively consist of, the following polynucleotide sequence encoding the variable light chain polypeptide sequence of SEQ ID NO: 2 which is encoded by the polynucleotide sequence of SEQ ID NO: 10 or the polynucleotide sequence of SEQ ID NO: 662, 698, 701, or 705.

In another embodiment of the invention, polynucleotides of the invention comprise, or alternatively consist of, the following polynucleotide sequence encoding the variable heavy chain polypeptide sequence of SEQ ID NO: 3 which is encoded by the polynucleotide sequence of SEQ ID NO: 11 or the polynucleotide sequence of SEQ ID NO: 663, 700, 703, or 707.

In a further embodiment of the invention, polynucleotides encoding fragments or variants of the antibody having binding specificity to IL-6 comprise, or alternatively consist of, at least one of the polynucleotide sequences of SEQ ID NO: 12 or 694; SEQ ID NO: 13; and SEQ ID NO: 14 or 695 which correspond to polynucleotides encoding the complementarity-determining regions (CDRs, or hypervariable regions) of the light chain variable sequence of SEQ ID NO: 2.

In a further embodiment of the invention, polynucleotides encoding fragments or variants of the antibody having binding specificity to IL-6 comprise, or alternatively consist of, at least one of the polynucleotide sequences of SEQ ID NO: 15; SEQ ID NO: 16 or 696; and SEQ ID NO: 17 or 697 which correspond to polynucleotides encoding the complementarity-determining regions (CDRs, or hypervariable regions) of the heavy chain variable sequence of SEQ ID NO: 3 or SEQ ID NO: 661 or SEQ ID NO: 657 or others depicted in FIG. 4 or 5.

The invention also contemplates polynucleotide sequences including at least one of the polynucleotide sequences encoding antibody fragments or variants described herein. In one embodiment of the invention, polynucleotides encoding fragments or variants of the antibody having binding specificity to IL-6 comprise, or alternatively consist of, one, two, three or more, including all of the following polynucleotides encoding antibody fragments: the polynucleotide SEQ ID NO: 10 encoding the light chain variable region of SEQ ID NO: 2; the polynucleotide SEQ ID NO: 11 encoding the heavy chain variable region of SEQ ID NO: 3; the polynucleotide SEQ ID NO: 720 encoding the light chain polypeptide of SEQ ID NO: 20; the polynucleotide SEQ ID NO: 721 encoding the light chain polypeptide of SEQ ID NO: 647; the polynucleotide SEQ ID NO: 662 encoding the light chain polypeptide of SEQ ID NO: 660; the polynucleotide SEQ ID NO: 722 encoding the light chain polypeptide of SEQ ID NO: 666; the polynucleotide SEQ ID NO: 698 encoding the light chain polypeptide of SEQ ID NO: 699; the polynucleotide SEQ ID NO: 701 encoding the light chain polypeptide of SEQ ID NO: 702; the polynucleotide SEQ ID NO: 705 encoding the light chain polypeptide of SEQ ID NO: 706; the polynucleotide SEQ ID NO: 723 encoding the light chain polypeptide of SEQ ID NO: 709; the polynucleotide SEQ ID NO: 724 encoding the heavy chain polypeptide of SEQ ID NO: 19; the polynucleotide SEQ ID NO: 725 encoding the heavy chain polypeptide of SEQ ID NO: 652; the polynucleotide SEQ ID NO: 700 encoding the heavy chain polypeptide of SEQ ID NO: 657; the polynucleotide SEQ ID NO: 663 encoding the heavy chain polypeptide of SEQ ID NO: 661; the polynucleotide SEQ ID NO: 703 encoding the heavy chain polypeptide of SEQ ID NO: 704; the polynucleotide SEQ ID NO: 707 encoding the heavy chain polypeptide of SEQ ID NO: 708; the polynucleotides of SEQ ID NO: 12, 13, 14, 694 and 695 encoding the complementarity-determining regions of the aforementioned light chain polypeptides; and the polynucleotides of SEQ ID NO: 15, 16, 17, 696 and 697 encoding the complementarity-determining regions of the aforementioned heavy chain polypeptides, and polynucleotides encoding the variable heavy and light chain sequences in SEQ ID NO: 657 and SEQ ID NO: 709 respectively, e.g., the nucleic acid sequences in SEQ ID NO: 700 and SEQ ID NO: 723 and fragments or variants thereof, e.g., based on codon degeneracy. These nucleic acid sequences encoding variable heavy and light chain sequences may be expressed alone or in combination and these sequences preferably are fused to suitable variable constant sequences, e.g., those in SEQ ID NO: 589 and SEQ ID NO: 587.

Exemplary nucleotide sequences encoding anti-IL-6 antibodies of the present invention are identified in Table 4. The polynucleotide sequences shown are to be understood to be illustrative, rather than limiting. One of skill in the art can readily determine the polynucleotide sequences that would encode a given polypeptide and can readily generate coding sequences suitable for expression in a given expression system, such as by adapting the polynucleotide sequences provided and/or by generating them de novo, and can readily produce codon-optimized expression sequences, for example as described in published U.S. Patent Application No. 2008/0120732 or using other methods known in the art.

In another embodiment of the invention, polynucleotides of the invention further comprise, the following polynucleotide sequence encoding the kappa constant light chain sequence of SEQ ID NO: 586 which is encoded by the polynucleotide sequence of SEQ ID NO: 587.

In another embodiment of the invention, polynucleotides of the invention further comprise, the following polynucleotide sequence encoding the gamma-1 constant heavy chain polypeptide sequence of SEQ ID NO: 588 which is encoded by the polynucleotide sequence of SEQ ID NO: 589.

In one embodiment, the invention is directed to an isolated polynucleotide comprising a polynucleotide encoding an anti-IL-6 $V_H$ antibody amino acid sequence selected from SEQ ID NO: 3, 18, 19, 652, 656, 657, 658, 661, 664, 665, 704, and 708 or encoding a variant thereof wherein at least one framework residue (FR residue) has been substituted with an amino acid present at the corresponding position in a rabbit anti-IL-6 antibody $V_H$ polypeptide or a conservative amino acid substitution. In addition, the invention specifically encompasses humanized anti-IL-6 antibodies or humanized antibody binding fragments or variants thereof and nucleic acid sequences encoding the foregoing comprising the humanized variable heavy chain and/or light chain polypeptides depicted in the sequences contained in FIG. 1-5, or those identified in Table 4, or variants thereof wherein at least one framework or CDR residues may be modified. Preferably, if any modifications are introduced they will not affect adversely the binding affinity of the resulting anti-IL-6 antibody or fragment or variant thereof.

In another embodiment, the invention is directed to an isolated polynucleotide comprising the polynucleotide sequence encoding an anti-IL-6 $V_L$ antibody amino acid sequence selected from SEQ ID NO: 2, 20, 647, 651, 660, 666, 699, 702, 706, and 709 or encoding a variant thereof wherein at least one framework residue (FR residue) has been substituted with an amino acid present at the corresponding position in a rabbit anti-IL-6 antibody $V_L$ polypeptide or a conservative amino acid substitution.

In yet another embodiment, the invention is directed to at least one heterologous polynucleotides comprising a sequence encoding the polypeptides set forth in SEQ ID NO: 2 and SEQ ID NO: 3; SEQ ID NO: 2 and SEQ ID NO: 18; SEQ ID NO: 2 and SEQ ID NO: 19; SEQ ID NO: 20 and SEQ ID NO: 3; SEQ ID NO: 20 and SEQ ID NO: 18; or SEQ ID NO: 20 and SEQ ID NO: 19.

In another embodiment, the invention is directed to an isolated polynucleotide that expresses a polypeptide containing at least one CDR polypeptide derived from an anti-IL-6 antibody wherein said expressed polypeptide alone specifically binds IL-6 or specifically binds IL-6 when expressed in association with another polynucleotide sequence that expresses a polypeptide containing at least one CDR polypeptide derived from an anti-IL-6 antibody wherein said at least one CDR is selected from those contained in the $V_L$ or $V_H$ polypeptides set forth in SEQ ID NO: 3, 18, 19, 652, 656, 657, 658, 661, 664, 665, 704, 708, 2, 20, 647, 651, 660, 666, 699, 702, 706, or 709.

Host cells and vectors comprising said polynucleotides are also contemplated.

In another specific embodiment the invention covers nucleic acid constructs containing any of the foregoing nucleic acid sequences and combinations thereof as well as recombinant cells containing these nucleic acid sequences and constructs containing wherein these nucleic acid sequences or constructs may be extrachromosomal or integrated into the host cell genome.

The invention further contemplates vectors comprising the polynucleotide sequences encoding the variable heavy and light chain polypeptide sequences, as well as the individual complementarity determining regions (CDRs, or hypervariable regions) set forth herein, as well as host cells comprising said sequences. In one embodiment of the invention, the host cell is a yeast cell. In another embodiment of the invention, the yeast host cell belongs to the genus *Pichia*.

In some instances, more than one exemplary polynucleotide encoding a given polypeptide sequence is provided, as summarized in Table 2.

TABLE 2

Multiple exemplary polynucleotides encoding particular polypeptides.

| Polypeptide SEQ ID NO | Exemplary coding SEQ ID NOs |
|---|---|
| 4 | 12, 111, 694 |
| 5 | 13, 112, 389, 501 |
| 6 | 14, 113, 695 |
| 9 | 17, 116, 697 |
| 39 | 47, 260 |
| 40 | 48, 261 |
| 60 | 68, 265 |
| 72 | 80, 325, 565, 581 |
| 89 | 97, 134, 166 |
| 103 | 12, 111, 694 |
| 104 | 13, 112, 389, 501 |
| 105 | 14, 113, 695 |
| 108 | 17, 116, 697 |
| 126 | 97, 134, 166 |
| 158 | 97, 134, 166 |
| 190 | 198, 214 |
| 191 | 199, 215 |
| 205 | 213, 469, 485 |
| 206 | 198, 214 |
| 207 | 199, 215 |
| 252 | 47, 260 |
| 253 | 48, 261 |
| 257 | 68, 265 |
| 317 | 80, 325, 565, 581 |
| 333 | 341, 533 |
| 381 | 13, 112, 389, 501 |
| 415 | 423, 439 |
| 431 | 423, 439 |
| 461 | 213, 469, 485 |
| 475 | 483, 499 |
| 476 | 484, 500 |
| 477 | 213, 469, 485 |
| 478 | 486, 502 |
| 479 | 487, 503 |
| 480 | 488, 504 |
| 481 | 489, 505 |
| 491 | 483, 499 |
| 492 | 484, 500 |
| 493 | 13, 112, 389, 501 |
| 494 | 486, 502 |
| 495 | 487, 503 |
| 496 | 488, 504 |
| 497 | 489, 505 |
| 525 | 341, 533 |
| 545 | 553, 585 |
| 554 | 562, 578 |
| 556 | 564, 580 |
| 557 | 80, 325, 565, 581 |
| 558 | 566, 582 |
| 570 | 562, 578 |
| 572 | 564, 580 |
| 573 | 80, 325, 565, 581 |
| 574 | 566, 582 |
| 577 | 553, 585 |

In some instances, multiple sequence identifiers refer to the same polypeptide or polynucleotide sequence, as summarized in Table 3. References to these sequence identifiers are understood to be interchangeable, except where context indicates otherwise.

TABLE 3

Repeated sequences. Each cell lists a group of repeated sequences included in the sequence listing.

| SEQ ID NOs of repeated sequences |
|---|
| 4, 103 |
| 5, 104, 381, 493 |
| 6, 105 |
| 9, 108 |
| 12, 111 |
| 13, 112 |
| 14, 113 |
| 17, 116 |
| 39, 252 |
| 40, 253 |
| 48, 261 |
| 60, 257 |
| 68, 265 |
| 72, 317, 557, 573 |
| 80, 325, 565, 581 |
| 89, 126, 158 |
| 97, 134, 166 |
| 120, 659 |
| 190, 206 |
| 191, 207 |
| 198, 214 |
| 199, 215 |
| 205, 461, 477 |
| 213, 469 |
| 333, 525 |
| 415, 431 |
| 423, 439 |
| 475, 491 |
| 476, 492 |
| 478, 494 |
| 479, 495 |
| 480, 496 |
| 481, 497 |
| 483, 499 |
| 484, 500 |
| 486, 502 |
| 487, 503 |
| 488, 504 |
| 489, 505 |
| 545, 577 |
| 554, 570 |
| 556, 572 |
| 558, 574 |
| 562, 578 |
| 564, 580 |
| 566, 582 |

Certain exemplary embodiments include polynucleotides that hybridize under moderately or highly stringent hybridization conditions to a polynucleotide having one of the exemplary coding sequences recited in Table 4, and also include polynucleotides that hybridize under moderately or highly stringent hybridization conditions to a polynucleotide encoding the same polypeptide as a polynucleotide having one of the exemplary coding sequences recited in Table 4, or polypeptide encoded by any of the foregoing polynucleotides.

The phrase "high stringency hybridization conditions" refers to conditions under which a probe will hybridize to its target subsequence, typically in a complex mixture of nucleic acid, but to no other sequences. High stringency conditions are sequence dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, high stringency conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). High stringency conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). High stringency conditions may also be achieved with the addition of destabilizing agents such as formamide. For selective or specific hybridization, a positive signal is at least two times background, optionally 10 times background hybridization. Exemplary high stringency hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under high stringency conditions are still substantially related if the polypeptides that they encode are substantially related. This occurs, for example, when a copy of a nucleic acid is created using the maximum codon degeneracy permitted by the genetic code. In such cases, the nucleic acids typically hybridize under moderate stringency hybridization conditions. Exemplary "moderate stringency hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

Expression vectors for use in the methods of the invention will further include yeast specific sequences, including a selectable auxotrophic or drug marker for identifying transformed yeast strains. A drug marker may further be used to amplify copy number of the vector in a yeast host cell.

The polypeptide coding sequence of interest is operably linked to transcriptional and translational regulatory sequences that provide for expression of the polypeptide in yeast cells. These vector components may include, but are not limited to, at least one of the following: an enhancer element, a promoter, and a transcription termination sequence. Sequences for the secretion of the polypeptide may also be included, e.g. a signal sequence. A yeast origin of replication is optional, as expression vectors are often integrated into the yeast genome.

In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The yeast promoter fragment may also serve as the site for homologous recombination and integration of the expression vector into the same site in the yeast genome; alternatively a selectable marker is used as the site for homologous recombination. *Pichia* transformation is described in Cregg, et al. (1985) *Mol. Cell. Biol.* 5:3376-3385.

Examples of suitable promoters from *Pichia* include the AOX1 and promoter (Cregg, et al. (1989) *Mol. Cell. Biol.* 9:1316-1323); ICL1 promoter (Menendez, et al. (2003) *Yeast* 20(13):1097-108); glyceraldehyde-3-phosphate dehydrogenase promoter (GAP) (Waterham, et al. (1997) *Gene* 186(1): 37-44); and FLD1 promoter (Shen, et al. (1998) *Gene* 216(1): 93-102). The GAP promoter is a strong constitutive promoter and the AOX and FLD 1 promoters are inducible.

Other yeast promoters include ADH1, alcohol dehydrogenase II, GAL4, PHO3, PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The *S. cerevisiae* alpha factor pre-pro signal has proven effective in the secretion of a variety of recombinant proteins from *P. pastoris*. Other yeast signal sequences include the alpha mating factor signal sequence, the invertase signal sequence, and signal sequences derived from other secreted yeast polypeptides. Additionally, these signal peptide sequences may be engineered to provide for enhanced secretion in diploid yeast expression systems. Other secretion signals of interest also include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. See Hashimoto, et al. (1998) *Protein Eng* 11(2): 75; and Kobayashi, et al. (1998) *Therapeutic Apheresis* 2(4): 257.

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing at least one of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin® (phleomycin)) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) *Ann. Rev. Biochem.* 58: 913-949; and are known to those of skill in the art. Such methods utilize intermolecular DNA recombination that is mediated by a mixture of lambda and *E. coli*-encoded recombination proteins. Recombination occurs between specific attachment (att) sites on the interacting DNA molecules. For a description of att sites See Weisberg and Landy (1983) *Site-Specific Recombination in Phage Lambda* Cold Spring Harbor, N.Y.:Cold Spring Harbor Press), pages 211-250. The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites.

The expression host may be further modified by the introduction of sequences encoding at least one enzymes that enhance folding and disulfide bond formation, i.e. foldases, chaperonins, Such sequences may be constitutively or inducibly expressed in the yeast host cell, using vectors, markers, are known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, each of the haploid parental strains expresses a distinct folding enzyme, e.g. one strain may express BIP, and the other strain may express PDI or combinations thereof.

Vectors are used to introduce a foreign substance, such as DNA, RNA or protein, into an organism or host cell. Typical vectors include recombinant viruses (for polynucleotides) and liposomes or other lipid aggregates (for polypeptides and/or polynucleotides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence. Exemplary expression vectors and techniques for their use are described in the following publications: Old, et al. (1989) *Principles of Gene Manipulation: An Introduction to Genetic Engineering*, Blackwell Scientific Publications [$4^{th}$ Ed.]; Sambrook, et al. (1989) *Molecular Cloning: A Laboratory Manual,* 2nd Edition, Cold Spring Harbor Laboratory Press; Sambrook, et al. (2001) *Molecular Cloning: A Laboratory Manual [*$3^{rd}$ Ed.] Cold Spring Harbor Laboratory Press; Gorman, "High Efficiency Gene Transfer into Mammalian Cells," in DNA Cloning, Volume II, Glover, D. M., Ed., IRL Press, Washington, D.C., pages 143-190.

For example, a liposomes or other lipid aggregate may comprise a lipid such as phosphatidylcholines (lecithins) (PC), phosphatidylethanolamines (PE), lysolecithins, lysophosphatidylethanolamines, phosphatidylserines (PS), phosphatidylglycerols (PG), phosphatidylinositol (PI), sphingomyelins, cardiolipin, phosphatidic acids (PA), fatty acids, gangliosides, glucolipids, glycolipids, mono-, di or triglycerides, ceramides, cerebrosides and combinations thereof; a cationic lipid (or other cationic amphiphile) such as 1,2-dioleyloxy-3-(trimethylamino) propane (DOTAP); N-cholesteryloxycarbaryl-3,7,12-triazapentadecane-1,15-diamine (CTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3 beta [N—(N',N'-dimethylaminoethane)carbamoly] cholesterol (DC-Choi); and dimethyldioctadecylammonium (DDAB); dioleoylphosphatidyl ethanolamine (DOPE), cholesterol-containing DOPC; and combinations thereof; and/or a hydrophilic polymer such as polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and combinations thereof. Other suitable cationic lipids are described in Miller (1998) *Angewandte Chemie International Edition* 37(13-14): 1768-1785 and Cooper, et al. (1998) *Chem. Eur. J.* 4(1): 137-151. Liposomes can be crosslinked, partially crosslinked, or free from crosslinking. Crosslinked liposomes can include crosslinked as well as non-crosslinked components. Suitable cationic liposomes or cytofectins are commercially available and can also be prepared as described in Sipkins, et al. (1998) *Nature Medicine* 4(5): 623-626 or as described in Miller, supra. Exemplary liposomes include a polymerizable zwitterionic or neutral lipid, a polymerizable integrin targeting lipid and a polymerizable cationic lipid suitable for binding a nucleic acid. Liposomes can optionally include peptides that provide increased efficiency, for example as described in U.S. Pat. No. 7,297,759. Additional exemplary liposomes and other lipid aggregates are described in U.S. Pat. No. 7,166, 298.

Methods of Producing Antibodies and Fragments Thereof.

The invention is also directed to the production of the antibodies described herein or fragments thereof. Recombinant polypeptides corresponding to the antibodies described herein or fragments thereof are secreted from polyploidal, preferably diploid or tetraploid strains of mating competent yeast. In an exemplary embodiment, the invention is directed to methods for producing these recombinant polypeptides in secreted form for prolonged periods using cultures comprising polyploid yeast, i.e., at least several days to a week, more preferably at least a month or several months, and even more preferably at least 6 months to a year or longer. These polyploid yeast cultures will express at least 10-25 mg/liter of the polypeptide, more preferably at least 50-250 mg/liter, still more preferably at least 500-1000 mg/liter, and most preferably a gram per liter or more of the recombinant polypeptide(s).

In one embodiment of the invention a pair of genetically marked yeast haploid cells are transformed with expression vectors comprising subunits of a desired heteromultimeric protein. One haploid cell comprises a first expression vector, and a second haploid cell comprises a second expression vector. In another embodiment diploid yeast cells will be transformed with at least one expression vectors that provide for the expression and secretion of at least one of the recombinant polypeptides. In still another embodiment a single haploid cell may be transformed with at least one vectors and used to produce a polyploidal yeast by fusion or mating strategies. In yet another embodiment a diploid yeast culture may be transformed with at least one vectors providing for the expression and secretion of a desired polypeptide or polypeptides. These vectors may comprise vectors e.g., linearized plasmids or other linear DNA products that integrate into the yeast cell's genome randomly, through homologous recombination, or using a recombinase such as Cre/Lox or Flp/Frt. Optionally, additional expression vectors may be introduced into the haploid or diploid cells; or the first or second expression vectors may comprise additional coding sequences; for the synthesis of heterotrimers; heterotetramers. The expression levels of the non-identical polypeptides may be individually calibrated, and adjusted through appropriate selection, vector copy number, promoter strength and/or induction and the like. The transformed haploid cells are genetically crossed or fused. The resulting diploid or tetraploid strains are utilized to produce and secrete fully assembled and biologically functional proteins, humanized antibodies described herein or fragments thereof.

The use of diploid or tetraploid cells for protein production provides for unexpected benefits. The cells can be grown for production purposes, i.e. scaled up, and for extended periods of time, in conditions that can be deleterious to the growth of haploid cells, which conditions may include high cell density; growth in minimal media; growth at low temperatures; stable growth in the absence of selective pressure; and which may provide for maintenance of heterologous gene sequence integrity and maintenance of high level expression over time. Without wishing to be bound thereby, the inventors theorize that these benefits may arise, at least in part, from the creation of diploid strains from two distinct parental haploid strains. Such haploid strains can comprise numerous minor autotrophic mutations, which mutations are complemented in the diploid or tetraploid, enabling growth and enhanced production under highly selective conditions.

Transformed mating competent haploid yeast cells provide a genetic method that enables subunit pairing of a desired protein. Haploid yeast strains are transformed with each of two expression vectors, a first vector to direct the synthesis of one polypeptide chain and a second vector to direct the synthesis of a second, non-identical polypeptide chain. The two haploid strains are mated to provide a diploid host where optimized target protein production can be obtained.

Optionally, additional non-identical coding sequence(s) are provided. Such sequences may be present on additional expression vectors or in the first or the second expression vectors. As is known in the art, multiple coding sequences may be independently expressed from individual promoters; or may be coordinately expressed through the inclusion of an "internal ribosome entry site" or "IRES", which is an element that promotes direct internal ribosome entry to the initiation codon, such as ATG, of a cistron (a protein encoding region), thereby leading to the cap-independent translation of the gene. IRES elements functional in yeast are described by Thompson, et al. (2001) *PNAS* 98: 12866-12868.

In one embodiment of the invention, antibody sequences are produced in combination with a secretory J chain, which provides for enhanced stability of IgA. See U.S. Pat. Nos. 5,959,177 and 5,202,422.

In a preferred embodiment the two haploid yeast strains are each auxotrophic, and require supplementation of media for growth of the haploid cells. The pair of auxotrophs are complementary, such that the diploid product will grow in the absence of the supplements required for the haploid cells. Many such genetic markers are known in yeast, including requirements for amino acids (e.g. met, lys, his, arg), nucleosides (e.g. ura3, ade1); and the like. Amino acid markers may be preferred for the methods of the invention. Alternatively diploid cells which contain the desired vectors can be selected by other means, e.g., by use of other markers, such as green fluorescent protein, antibiotic resistance genes, various dominant selectable markers, and the like.

Two transformed haploid cells may be genetically crossed and diploid strains arising from this mating event selected by their hybrid nutritional requirements and/or antibiotic resistance spectra. Alternatively, populations of the two transformed haploid strains are spheroplasted and fused, and diploid progeny regenerated and selected. By either method, diploid strains can be identified and selectively grown based on their ability to grow in different media than their parents. For example, the diploid cells may be grown in minimal medium that may include antibiotics. The diploid synthesis strategy has certain advantages. Diploid strains have the potential to produce enhanced levels of heterologous protein through broader complementation to underlying mutations, which may impact the production and/or secretion of recombinant protein. Furthermore, once stable strains have been obtained, any antibiotics used to select those strains do not necessarily need to be continuously present in the growth media.

As noted above, in some embodiments a haploid yeast may be transformed with a single or multiple vectors and mated or fused with a non-transformed cell to produce a diploid cell containing the vector or vectors. In other embodiments, a diploid yeast cell may be transformed with at least one vectors that provide for the expression and secretion of a desired heterologous polypeptide by the diploid yeast cell.

In one embodiment of the invention, two haploid strains are transformed with a library of polypeptides, e.g. a library of antibody heavy or light chains. Transformed haploid cells that synthesize the polypeptides are mated with the complementary haploid cells. The resulting diploid cells are screened for functional protein. The diploid cells provide a means of rapidly, conveniently and inexpensively bringing together a large number of combinations of polypeptides for functional testing. This technology is especially applicable for the generation of heterodimeric protein products, where optimized subunit synthesis levels are critical for functional protein expression and secretion.

In another embodiment of the invention, the expression level ratio of the two subunits is regulated in order to maximize product generation. Heterodimer subunit protein levels have been shown previously to impact the final product generation. Simmons (2002) *J Immunol Methods.* 263(1-2): 133-47. Regulation can be achieved prior to the mating step by selection for a marker present on the expression vector. By stably increasing the copy number of the vector, the expression level can be increased. In some cases, it may be desirable to increase the level of one chain relative to the other, so as to reach a balanced proportion between the subunits of the polypeptide. Antibiotic resistance markers are useful for this purpose, e.g. Zeocin® (phleomycin) resistance marker, G418 resistance and provide a means of enrichment for strains that contain multiple integrated copies of an expression vector in a strain by selecting for transformants that are resistant to higher levels of Zeocin® (phleomycin) or G418. The proper ratio (e.g. 1:1; 1:2) of the subunit genes may be important for efficient protein production. Even when the same promoter is used to transcribe both subunits, many other factors contribute to the final level of protein expressed and therefore, it can be useful to increase the number of copies of one encoded gene relative to the other. Alternatively, diploid strains that produce higher levels of a polypeptide, relative to single copy vector strains, are created by mating two haploid strains, both of which have multiple copies of the expression vectors.

Host cells are transformed with the above-described expression vectors, mated to form diploid strains, and cultured in conventional nutrient media modified as appropriate for inducing promoters, selecting transformants or amplifying the genes encoding the desired sequences. A number of minimal media suitable for the growth of yeast are known in the art. Any of these media may be supplemented as necessary with salts (such as sodium chloride, calcium, magnesium, and phosphate), buffers (such as phosphate, HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Secreted proteins are recovered from the culture medium. A protease inhibitor, such as phenyl methyl sulfonyl fluoride (PMSF) may be useful to inhibit proteolytic degradation during purification, and antibiotics may be included to prevent the growth of adventitious contaminants. The composition may be concentrated, filtered, dialyzed, using methods known in the art.

The diploid cells of the invention are grown for production purposes. Such production purposes desirably include growth in minimal media, which media lacks pre-formed amino acids and other complex biomolecules, e.g., media comprising ammonia as a nitrogen source, and glucose as an energy and carbon source, and salts as a source of phosphate, calcium and the like. Preferably such production media lacks selective agents such as antibiotics, amino acids, purines, pyrimidines The diploid cells can be grown to high cell density, for example at least about 50 g/L; more usually at least about 100 g/L; and may be at least about 300, about 400, about 500 g/L or more.

In one embodiment of the invention, the growth of the subject cells for production purposes is performed at low temperatures, which temperatures may be lowered during log phase, during stationary phase, or both. The term "low temperature" refers to temperatures of at least about 15° C., more usually at least about 17° C., and may be about 20° C., and is usually not more than about 25° C., more usually not more than about 22° C. In another embodiment of the invention, the low temperature is usually not more than about 28° C. Growth temperature can impact the production of full-length secreted proteins in production cultures, and decreasing the culture growth temperature can strongly enhance the intact product yield. The decreased temperature appears to assist intracellular trafficking through the folding and post-translational processing pathways used by the host to generate the target product, along with reduction of cellular protease degradation.

The methods of the invention provide for expression of secreted, active protein, preferably a mammalian protein. In one embodiment, secreted, "active antibodies", as used herein, refers to a correctly folded multimer of at least two properly paired chains, which accurately binds to its cognate antigen. Expression levels of active protein are usually at least about 10-50 mg/liter culture, more usually at least about 100 mg/liter, preferably at least about 500 mg/liter, and may be 1000 mg/liter or more.

The methods of the invention can provide for increased stability of the host and heterologous coding sequences during production. The stability is evidenced, for example, by maintenance of high levels of expression of time, where the starting level of expression is decreased by not more than about 20%, usually not more than 10%, and may be decreased by not more than about 5% over about 20 doublings, 50 doublings, 100 doublings, or more.

The strain stability also provides for maintenance of heterologous gene sequence integrity over time, where the sequence of the active coding sequence and requisite transcriptional regulatory elements are maintained in at least about 99% of the diploid cells, usually in at least about 99.9% of the diploid cells, and preferably in at least about 99.99% of the diploid cells over about 20 doublings, 50 doublings, 100 doublings, or more. Preferably, substantially all of the diploid cells maintain the sequence of the active coding sequence and requisite transcriptional regulatory elements.

Other methods of producing antibodies are well known to those of ordinary skill in the art. For example, methods of producing chimeric antibodies are now well known in the art. See, e.g., U.S. Pat. No. 4,816,567; Morrison, et al. (1984) *PNAS USA* 81: 8651-55; Neuberger, et al. (1985) *Nature* 314: 268-270; Boulianne, et al. (1984) *Nature* 312: 643-46.

Likewise, other methods of producing humanized antibodies are now well known in the art. See, e.g., U.S. Pat. Nos. 5,225,539; 5,530,101; 5,585,089; 5,693,762; 6,054,297; 6,180,370; 6,407,213; 6,548,640; 6,632,927; and 6,639,055; Jones, et al. (1986) *Nature* 321: 522-525; Reichmann, et al. (1988) *Nature* 332: 323-327; Verhoeyen, et al. (1988) *Science* 239: 1534-36.

Antibody polypeptides of the invention having IL-6 binding specificity may also be produced by constructing, using conventional techniques well known to those of ordinary skill in the art, an expression vector containing an operon and a DNA sequence encoding an antibody heavy chain in which the DNA sequence encoding the CDRs required for antibody specificity is derived from a non-human cell source, preferably a rabbit B-cell source, while the DNA sequence encoding the remaining parts of the antibody chain is derived from a human cell source.

A second expression vector is produced using the same conventional means well known to those of ordinary skill in the art, said expression vector containing an operon and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding an operon and a light chain-derived polypeptide and the second vector containing DNA encoding an operon and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA.

The host cells used to express the antibody polypeptides may be either a bacterial cell such as *E. coli*, or a eukaryotic cell. In a particularly preferred embodiment of the invention, a mammalian cell of a well-defined type for this purpose, such as a myeloma cell or a Chinese hamster ovary (CHO) cell line may be used.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an *E. coli*-derived bacterial strain, or a yeast cell line, may alternatively be used.

Similarly, once produced the antibody polypeptides may be purified according to standard procedures in the art, such as for example cross-flow filtration, ammonium sulphate precipitation, affinity column chromatography and the like.

The antibody polypeptides described herein may also be used for the design and synthesis of either peptide or non-peptide mimetics that would be useful for the same therapeutic applications as the antibody polypeptides of the invention. See, e.g., Saragobi et al. (1991) *Science* 253: 792-795.

B-Cell Screening and Isolation

The present invention provides methods of isolating a clonal population of antigen-specific B cells that may be used for isolating at least one antigen-specific cell. As described and exemplified infra, these methods contain a series of culture and selection steps that can be used separately, in combination, sequentially, repetitively, or periodically. Preferably, these methods are used for isolating at least one antigen-specific cell, which can be used to produce a monoclonal antibody, which is specific to a desired antigen, or a nucleic acid sequence corresponding to such an antibody.

The present invention provides a method comprising the steps of:

(a) preparing a cell population comprising at least one antigen-specific B cell;

(b) enriching the cell population, e.g., by chromatography, to form an enriched cell population comprising at least one antigen-specific B cell;

(c) isolating a single B cell from the enriched B cell population; and (d) determining whether the single B cell produces an antibody specific to the antigen.

The present invention provides an improvement to a method of isolating a single, antibody-producing B cell, the improvement comprising enriching a B cell population obtained from a host that has been immunized or naturally exposed to an antigen, wherein the enriching step precedes any selection steps, comprises at least one culturing step, and results in a clonal population of B cells that produces a single monoclonal antibody specific to said antigen.

Throughout this application, a "clonal population of B cells" refers to a population of B cells that only secrete a single antibody specific to a desired antigen. That is to say that these cells produce only one type of monoclonal antibody specific to the desired antigen.

In the present application, "enriching" a cell population cells means increasing the frequency of desired cells, typically antigen-specific cells, contained in a mixed cell population, e.g., a B cell-containing isolate derived from a host that is immunized against a desired antigen. Thus, an enriched cell population encompasses a cell population having a higher frequency of antigen-specific cells as a result of an enrichment step, but this population of cells may contain and produce different antibodies.

The general term "cell population" encompasses pre- and a post-enrichment cell populations, keeping in mind that when multiple enrichment steps are performed, a cell population can be both pre- and post-enrichment. For example, in one embodiment, the present invention provides a method:

(a) harvesting a cell population from an immunized host to obtain a harvested cell population;

(b) creating at least one single cell suspension from the harvested cell population;

(c) enriching at least one single cell suspension to form a first enriched cell population;

(d) enriching the first enriched cell population to form a second enriched cell population;

(e) enriching the second enriched cell population to form a third enriched cell population; and (f) selecting an antibody produced by an antigen-specific cell of the third enriched cell population.

Each cell population may be used directly in the next step, or it can be partially or wholly frozen for long- or short-term storage or for later steps. Also, cells from a cell population can be individually suspended to yield single cell suspensions. The single cell suspension can be enriched, such that a single cell suspension serves as the pre-enrichment cell population. Then, at least one antigen-specific single cell suspensions together form the enriched cell population; the antigen-specific single cell suspensions can be grouped together, e.g., re-plated for further analysis and/or antibody production.

In one embodiment, the present invention provides a method of enriching a cell population to yield an enriched cell population having an antigen-specific cell frequency that is about 50% to about 100%, or increments therein. Preferably, the enriched cell population has an antigen-specific cell frequency at least about 50%, 60%, 70%, 75%, 80%, 90%, 95%, 99%, or 100%.

In another embodiment, the present invention provides a method of enriching a cell population whereby the frequency of antigen-specific cells is increased by at least about 2-fold, 5-fold, 10-fold, 20-fold, 50-fold, 100-fold, or increments therein.

Throughout this application, the term "increment" is used to define a numerical value in varying degrees of precision, e.g., to the nearest 10, 1, 0.1, 0.01. The increment can be rounded to any measurable degree of precision, and the increment need not be rounded to the same degree of precision on both sides of a range. For example, the range 1 to 100 or increments therein includes ranges such as 20 to 80, 5 to 50, and 0.4 to 98. When a range is open-ended, e.g., a range of less than 100, increments therein means increments between 100 and the measurable limit. For example, less than 100 or increments therein means 0 to 100 or increments therein unless the feature, e.g., temperature, is not limited by 0.

Antigen-specificity can be measured with respect to any antigen. The antigen can be any substance to which an antibody can bind including, but not limited to, peptides, proteins or fragments thereof; carbohydrates; organic and inorganic molecules; receptors produced by animal cells, bacterial cells, and viruses; enzymes; agonists and antagonists of biological pathways; hormones; and cytokines. Exemplary antigens include, but are not limited to, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF) and Hepcidin. Preferred antigens include IL-6, IL-13, TNF-α, VEGF-α, Hepatocyte Growth Factor (HGF) and Hepcidin. In a method utilizing more than one enrichment step, the antigen used in each enrichment step can be the same as or different from one another. Multiple enrichment steps with the same antigen may yield a large and/or diverse population of antigen-specific cells; multiple enrichment steps with different antigens may yield an enriched cell population with cross-specificity to the different antigens.

Enriching a cell population can be performed by any cell-selection means known in the art for isolating antigen-specific cells. For example, a cell population can be enriched by chromatographic techniques, e.g., Miltenyi bead or magnetic bead technology. The beads can be directly or indirectly attached to the antigen of interest. In a preferred embodiment, the method of enriching a cell population includes at least one chromatographic enrichment step.

A cell population can also be enriched by performed by any antigen-specificity assay technique known in the art, e.g., an ELISA assay or a halo assay. ELISA assays include, but are not limited to, selective antigen immobilization (e.g., biotinylated antigen capture by streptavidin, avidin, or neutravidin coated plate), non-specific antigen plate coating, and through an antigen build-up strategy (e.g., selective antigen capture followed by binding partner addition to generate a heteromeric protein-antigen complex). The antigen can be directly or indirectly attached to a solid matrix or support, e.g., a column. A halo assay comprises contacting the cells with antigen-loaded beads and labeled anti-host antibody specific to the host used to harvest the B cells. The label can be, e.g., a fluorophore. In one embodiment, at least one assay enrichment step is performed on at least one single cell suspension. In another embodiment, the method of enriching a cell population includes at least one chromatographic enrichment step and at least one assay enrichment step.

Methods of "enriching" a cell population by size or density are known in the art. See, e.g., U.S. Pat. No. 5,627,052. These steps can be used in the present method in addition to enriching the cell population by antigen-specificity.

The cell populations of the present invention contain at least one cell capable of recognizing an antigen. Antigen-recognizing cells include, but are not limited to, B cells, plasma cells, and progeny thereof. In one embodiment, the present invention provides a clonal cell population containing a single type of antigen-specific B-cell, i.e., the cell population produces a single monoclonal antibody specific to a desired antigen.

In such embodiment, it is believed that the clonal antigen-specific population of B cells consists predominantly of antigen-specific, antibody-secreting cells, which are obtained by the novel culture and selection protocol provided herein. Accordingly, the present invention also provides methods for obtaining an enriched cell population containing at least one antigen-specific, antibody-secreting cell. In one embodiment, the present invention provides an enriched cell population containing about 50% to about 100%, or increments therein, at least about 60%, 70%, 80%, 90%, or 100% of antigen-specific, antibody-secreting cells.

In one embodiment, the present invention provides a method of isolating a single B cell by enriching a cell population obtained from a host before any selection steps, e.g., selecting a particular B cell from a cell population and/or selecting an antibody produced by a particular cell. The enrichment step can be performed as one, two, three, or more steps. In one embodiment, a single B cell is isolated from an enriched cell population before confirming whether the single B cell secretes an antibody with antigen-specificity and/or a desired property.

In one embodiment, a method of enriching a cell population is used in a method for antibody production and/or selection. Thus, the present invention provides a method comprising enriching a cell population before selecting an antibody. The method can include the steps of: preparing a cell population comprising at least one antigen-specific cell, enriching the cell population by isolating at least one antigen-specific cell to form an enriched cell population, and inducing antibody production from at least one antigen-specific cell. In a preferred embodiment, the enriched cell population contains more than one antigen-specific cell. In one embodiment, each antigen-specific cell of the enriched population is cultured under conditions that yield a clonal antigen-specific B cell population before isolating an antibody producing cell therefrom and/or producing an antibody using said B cell, or a nucleic acid sequence corresponding to such an antibody. In contrast to prior techniques where antibodies are produced from a cell population with a low frequency of antigen-specific cells, the present invention allows antibody selection from among a high frequency of antigen-specific cells. Because an enrichment step is used prior to antibody selection, the majority of the cells, preferably virtually all of the cells, used for antibody production are antigen-specific. By producing antibodies from a population of cells with an increased frequency of antigen specificity, the quantity and variety of antibodies are increased.

In the antibody selection methods of the present invention, an antibody is preferably selected after an enrichment step and a culture step that results in a clonal population of antigen-specific B cells. The methods can further comprise a step of sequencing a selected antibody or portions thereof from at least one isolated, antigen-specific cells. Any method known in the art for sequencing can be employed and can include sequencing the heavy chain, light chain, variable region(s), and/or complementarity determining region(s) (CDR).

In addition to the enrichment step, the method for antibody selection can also include at least one steps of screening a cell population for antigen recognition and/or antibody functionality. For example, the desired antibodies may have specific structural features, such as binding to a particular epitope or mimicry of a particular structure; antagonist or agonist activity; or neutralizing activity, e.g., inhibiting binding between the antigen and a ligand. In one embodiment, the antibody functionality screen is ligand-dependent. Screening for antibody functionality includes, but is not limited to, an in vitro protein-protein interaction assay that recreates the natural interaction of the antigen ligand with recombinant receptor protein; and a cell-based response that is ligand dependent and easily monitored (e.g., proliferation response).

In one embodiment, the method for antibody selection includes a step of screening the cell population for antibody functionality by measuring the inhibitory concentration (IC50). In one embodiment, at least one of the isolated, antigen-specific cells produces an antibody having an IC50 of less than about 100, 50, 30, 25, 10 μg/mL, or increments therein.

In addition to the enrichment step, the method for antibody selection can also include at least one steps of screening a cell population for antibody binding strength. Antibody binding strength can be measured by any method known in the art (e.g., Biacore®). In one embodiment, at least one of the isolated, antigen-specific cells produces an antibody having a high antigen affinity, e.g., a dissociation constant (Kd) of less than about $5\times10^{10}$ M-1, preferably about $1\times10^{-13}$ to $5\times10^{-20}$, $1\times10^{-12}$ to $1\times10^{-11}$, $1\times10^{-12}$ to $7.5\times10^{-11}$, $1\times10^{-11}$ to $2\times10^{-11}$, about $1.5\times10^{-11}$ or less, or increments therein. In this embodiment, the antibodies are said to be affinity mature. In a preferred embodiment, the affinity of the antibodies is comparable to or higher than the affinity of any one of Panorex® (edrecolomab), Rituxan® (rituximab), Herceptin® (traztuzumab), Mylotarg® (gentuzumab), Campath® (alemtuzumab), Zevalin® (ibritumomab), Erbitux® (cetuximab), Avastin® (bevicizumab), Raptiva® (efalizumab), Remicade® (infliximab), Humira® (adalimumab), or Xolair® (omalizumab). Preferably, the affinity of the antibodies is comparable to or higher than the affinity of Humira®. The affinity of an antibody can also be increased by known affinity maturation techniques. In one embodiment, at least one cell population is screened for at least one of, preferably both, antibody functionality and antibody binding strength.

In addition to the enrichment step, the method for antibody selection can also include at least one steps of screening a cell population for antibody sequence homology, especially human homology. In one embodiment, at least one of the isolated, antigen-specific cells produces an antibody that has a homology to a human antibody of at least about 50% to about 100%, or increments therein, or at least about 60%, 70%, 80%, 85%, 90%, or 95% homologous. The antibodies can be humanized to increase the homology to a human sequence by techniques known in the art such as CDR grafting or selectivity determining residue grafting (SDR).

In another embodiment, the present invention also provides the antibodies themselves according to any of the embodiments described above in terms of IC50, Kd, and/or homology.

Methods of Humanizing Antibodies

The invention also provides a method for humanizing antibody heavy and light chains. In this embodiment, the following method may be followed for the humanization of the heavy and light chains:

Light Chain

1. Identify the amino acid that is the first one following the signal peptide sequence. This is the start of Framework 1. The signal peptide starts at the first initiation methionine and is typically, but not necessarily 22 amino acids in length for rabbit light chain protein sequences. The start of the mature polypeptide can also be determined experimentally by N-terminal protein sequencing, or can be predicted using a prediction algorithm. This is also the start of Framework 1 as classically defined by those in the field.

Example

RbtVL Amino Acid Residue 1 in FIG. 1, Starting 'AYDM . . . ' (SEQ ID NO: 733)

2. Identify the end of Framework

3. This is typically 86-90 amino acids following the start of Framework 1 and is typically a cysteine residue preceded by two tyrosine residues. This is the end of the Framework 3 as classically defined by those in the field.

Example

RbtVL Amino Acid Residue 88 in FIG. 1, Ending as 'TYYC' (SEQ ID NO: 733)

3. Use the rabbit light chain sequence of the polypeptide starting from the beginning of Framework 1 to the end of Framework 3 as defined above and perform a sequence homology search for the most similar human antibody protein sequences. This will typically be a search against human germline sequences prior to antibody maturation in order to reduce the possibility of immunogenicity, however any human sequences can be used. Typically a program like BLAST can be used to search a database of sequences for the most homologous. Databases of human antibody sequences can be found from various sources such as NCBI (National Center for Biotechnology Information).

Example

RbtVL amino acid sequence from residues numbered 1 through 88 in FIG. 1 is BLASTed against a human antibody germline database. The top three unique returned sequences are shown in FIG. 1 as L12A (SEQ ID NO: 734), V1 (SEQ ID NO: 735), and Vx02 (SEQ ID NO: 736).

4. Generally the most homologous human germline variable light chain sequence is then used as the basis for humanization. However those skilled in the art may decide to use another sequence that wasn't the highest homology as determined by the homology algorithm, based on other factors including sequence gaps and framework similarities.

Example

In FIG. 1, L12A (SEQ ID NO: 734) was the most homologous human germline variable light chain sequence and is used as the basis for the humanization of RbtVL.

5. Determine the framework and CDR arrangement (FR1, FR2, FR3, CDR1 & CDR2) for the human homolog being used for the light chain humanization. This is using the traditional layout as described in the field. Align the rabbit variable light chain sequence with the human homolog, while maintaining the layout of the framework and CDR regions.

Example

In FIG. 1, the RbtVL sequence is aligned with the human homologous sequence L12A, and the framework and CDR domains are indicated.

6. Replace the human homologous light chain sequence CDR1 and CDR2 regions with the CDR1 and CDR2 sequences from the rabbit sequence. If there are differences in length between the rabbit and human CDR sequences then use the entire rabbit CDR sequences and their lengths. It is possible that the specificity, affinity and/or immunogenicity of the resulting humanized antibody may be unaltered if smaller or larger sequence exchanges are performed, or if specific residue(s) are altered, however the exchanges as described have been used successfully, but do not exclude the possibility that other changes may be permitted.

Example

In FIG. 1, the CDR1 and CDR2 amino acid residues of the human homologous variable light chain L12A are replaced with the CDR1 and CDR2 amino acid sequences from the RbtVL rabbit antibody light chain sequence. The human L12A frameworks 1, 2 and 3 are unaltered. The resulting humanized sequence is shown below as VLh from residues numbered 1 through 88. Note that the only residues that are different from the L12A human sequence are underlined, and are thus rabbit-derived amino acid residues. In this example only 8 of the 88 residues are different than the human sequence.

7. After framework 3 of the new hybrid sequence created in Step 6, attach the entire CDR3 of the rabbit light chain antibody sequence. The CDR3 sequence can be of various lengths, but is typically 9 to 15 amino acid residues in length. The CDR3 region and the beginning of the following framework 4 region are defined classically and identifiable by those skilled in the art. Typically the beginning of Framework 4, and thus after the end of CDR3 consists of the sequence 'FGGG . . . ' (SEQ ID NO: 743), however some variation may exist in these residues.

Example

In FIG. 1, the CDR3 of RbtVL (amino acid residues numbered 89-100) is added after the end of framework 3 in the humanized sequence indicated as VLh.

8. The rabbit light chain framework 4, which is typically the final 11 amino acid residues of the variable light chain and begins as indicated in Step 7 above and typically ends with the amino acid sequence ' . . . VVKR' (SEQ ID NO: 744) is replaced with the nearest human light chain framework 4 homolog, usually from germline sequence. Frequently this human light chain framework 4 is of the sequence 'FGGGTKVEIKR' (SEQ ID NO: 745). It is possible that other human light chain framework 4 sequences that are not the most homologous or otherwise different may be used without affecting the specificity, affinity and/or immunogenicity of the resulting humanized antibody. This human light chain framework 4 sequence is added to the end of the variable light chain humanized sequence immediately following the CDR3 sequence from Step 7 above. This is now the end of the variable light chain humanized amino acid sequence.

Example

In FIG. 1, Framework 4 (FR4) of the RbtVL rabbit light chain sequence is shown above a homologous human FR4 sequence. The human FR4 sequence is added to the humanized variable light chain sequence (VLh) right after the end of the CD3 region added in Step 7 above.

In addition, FIGS. 4 and 5 depict preferred humanized anti-IL-6 variable heavy and variable light chain sequences humanized from the variable heavy and light regions in Ab1 according to the invention. These humanized light and heavy chain regions are respectively contained in the polypeptides set forth in SEQ ID NO: 647, or 651 and in SEQ ID NO: 652, 656, 657 or 658. The CDR2 of the humanized variable heavy region in SEQ ID NO: 657 (containing a serine substitution in CDR2) is set forth in SEQ ID NO: 658. Alignments illustrating variants of the light and heavy chains are shown in FIGS. 2 and 3, respectively, with sequence differences within the CDR regions highlighted. Sequence identifiers of CDR sequences and of exemplary coding sequences are summarized in Table 4, above.

Heavy Chain

1. Identify the amino acid that is the first one following the signal peptide sequence. This is the start of Framework 1. The signal peptide starts at the first initiation methionine and is typically 19 amino acids in length for rabbit heavy chain protein sequences. Typically, but not necessarily always, the final 3 amino acid residues of a rabbit heavy chain signal peptide are ' . . . VQC', followed by the start of Framework 1. The start of the mature polypeptide can also be determined experimentally by N-terminal protein sequencing, or can be predicted using a prediction algorithm. This is also the start of Framework 1 as classically defined by those in the field.

Example

RbtVH Amino Acid Residue 1 in FIG. 1, Starting 'QEQL . . . ' (SEQ ID NO: 738)

2. Identify the end of Framework 3. This is typically 95-100 amino acids following the start of Framework 1 and typically has the final sequence of ' . . . CAR' (although the alanine can also be a valine). This is the end of the Framework 3 as classically defined by those in the field.

Example

RbtVH Amino Acid Residue 98 in FIG. 1, Ending as ' . . . FCVR' (SEQ ID NO: 738)

3. Use the rabbit heavy chain sequence of the polypeptide starting from the beginning of Framework 1 to the end of Framework 3 as defined above and perform a sequence homology search for the most similar human antibody protein sequences. This will typically be against a database of human germline sequences prior to antibody maturation in order to reduce the possibility of immunogenicity, however any human sequences can be used. Typically a program like BLAST can be used to search a database of sequences for the most homologous. Databases of human antibody sequences can be found from various sources such as NCBI (National Center for Biotechnology Information).

Example

RbtVH amino acid sequence from residues numbered 1 through 98 in FIG. 1 is BLASTed against a human antibody germline database. The top three unique returned sequences are shown in FIG. 1 as 3-64-04 (SEQ ID NO: 739), 3-66-04 (SEQ ID NO: 740), and 3-53-02 (SEQ ID NO: 741).

4. Generally the most homologous human germline variable heavy chain sequence is then used as the basis for humanization. However those skilled in the art may decide to use another sequence that wasn't the most homologous as determined by the homology algorithm, based on other factors including sequence gaps and framework similarities.

Example 3-64-04 in FIG. 1 was the most homologous human germline variable heavy chain sequence and is used as the basis for the humanization of RbtVH.

5. Determine the framework and CDR arrangement (FR1, FR2, FR3, CDR1 & CDR2) for the human homolog being used for the heavy chain humanization. This is using the traditional layout as described in the field. Align the rabbit variable heavy chain sequence with the human homolog, while maintaining the layout of the framework and CDR regions.

Example

In FIG. 1, the RbtVH sequence is aligned with the human homologous sequence 3-64-04, and the framework and CDR domains are indicated.

6. Replace the human homologous heavy chain sequence CDR1 and CDR2 regions with the CDR1 and CDR2 sequences from the rabbit sequence. If there are differences in length between the rabbit and human CDR sequences then use the entire rabbit CDR sequences and their lengths. In addition, it may be necessary to replace the final three amino acids of the human heavy chain Framework 1 region with the final three amino acids of the rabbit heavy chain Framework 1. Typically but not always, in rabbit heavy chain Framework 1 these three residues follow a Glycine residue preceded by a Serine residue. In addition, it may be necessary replace the final amino acid of the human heavy chain Framework 2 region with the final amino acid of the rabbit heavy chain Framework 2. Typically, but not necessarily always, this is a Glycine residue preceded by an Isoleucine residue in the rabbit heavy chain Framework 2. It is possible that the specificity, affinity and/or immunogenicity of the resulting humanized antibody may be unaltered if smaller or larger sequence exchanges are performed, or if specific residue(s) are altered, however the exchanges as described have been used successfully, but do not exclude the possibility that other changes may be permitted. For example, a tryptophan amino acid residue typically occurs four residues prior to the end of the rabbit heavy chain CDR2 region, whereas in human heavy chain CDR2 this residue is typically a Serine residue. Changing this rabbit tryptophan residue to a the human Serine residue at this position has been demonstrated to have minimal to no effect on the humanized antibody's specificity or affinity, and thus further minimizes the content of rabbit sequence-derived amino acid residues in the humanized sequence.

Example

In FIG. 1, The CDR1 and CDR2 amino acid residues of the human homologous variable heavy chain are replaced with the CDR1 and CDR2 amino acid sequences from the RbtVH rabbit antibody light chain sequence, except for the boxed residue, which is tryptophan in the rabbit sequence (position number 63) and Serine at the same position in the human sequence, and is kept as the human Serine residue. In addition to the CDR1 and CDR2 changes, the final three amino acids of Framework 1 (positions 28-30) as well as the final residue of Framework 2 (position 49) are retained as rabbit amino acid residues instead of human. The resulting humanized sequence is shown below as VHh from residues numbered 1 through 98. Note that the only residues that are different from the 3-64-04 human sequence are underlined, and are thus rabbit-derived amino acid residues. In this example only 15 of the 98 residues are different than the human sequence.

7. After framework 3 of the new hybrid sequence created in Step 6, attach the entire CDR3 of the rabbit heavy chain antibody sequence. The CDR3 sequence can be of various lengths, but is typically 5 to 19 amino acid residues in length. The CDR3 region and the beginning of the following framework 4 region are defined classically and are identifiable by those skilled in the art. Typically the beginning of framework 4, and thus after the end of CDR3 consists of the sequence WGXG . . . (where X is usually Q or P) (SEQ ID NO: 746), however some variation may exist in these residues.

Example

The CDR3 of RbtVH (amino acid residues numbered 99-110) is added after the end of framework 3 in the humanized sequence indicated as VHh.

8. The rabbit heavy chain framework 4, which is typically the final 11 amino acid residues of the variable heavy chain and begins as indicated in Step 7 above and typically ends with the amino acid sequence '. . . TVSS' (SEQ ID NO: 747) is replaced with the nearest human heavy chain framework 4 homolog, usually from germline sequence. Frequently this human heavy chain framework 4 is of the sequence 'WGQGTLVTVSS' (SEQ ID NO: 748). It is possible that other human heavy chain framework 4 sequences that are not the most homologous or otherwise different may be used without affecting the specificity, affinity and/or immunogenicity of the resulting humanized antibody. This human heavy chain framework 4 sequence is added to the end of the variable heavy chain humanized sequence immediately following the CDR3 sequence from Step 7 above. This is now the end of the variable heavy chain humanized amino acid sequence.

Example

In FIG. 1, framework 4 (FR4) of the RbtVH rabbit heavy chain sequence is shown above a homologous human heavy FR4 sequence. The human FR4 sequence is added to the humanized variable heavy chain sequence (VHh) right after the end of the CD3 region added in Step 7 above.

Additional Exemplary Embodiments of the Invention

In another embodiment, the invention contemplates at least one anti-IL-6 antibodies or antibody fragments or variants thereof which may specifically bind to the same linear or conformational epitope(s) and/or compete for binding to the same linear or conformational epitope(s) on an intact human IL-6 polypeptide or fragment thereof as an anti-IL-6 antibody comprising Ab1 and chimeric, humanized, single chain antibodies and fragments thereof (containing at least one CDRs of the afore-identified antibodies) that specifically bind IL-6, which preferably are aglycosylated. In a preferred embodiment, the anti-IL-6 antibody or fragment or variant thereof may specifically bind to the same linear or conformational epitope(s) and/or compete for binding to the same linear or conformational epitope(s) on an intact human IL-6 polypeptide or a fragment thereof as Ab1 and chimeric, humanized, single chain antibodies and fragments thereof (containing at least one CDRs of the afore-mentioned antibody) that specifically bind IL-6, which preferably are aglycosylated.

In another embodiment of the invention, the anti-IL-6 antibody which may specifically bind to the same linear or conformational epitopes on an intact IL-6 polypeptide or fragment thereof that is (are) specifically bound by Ab1 may bind to an IL-6 epitope(s) ascertained by epitopic mapping using overlapping linear peptide fragments which span the full length of the native human IL-6 polypeptide. In one embodiment of the invention, the IL-6 epitope comprises, or alternatively consists of, at least one residues comprised in IL-6 fragments selected from those respectively encompassing amino acid residues 37-51, amino acid residues 70-84, amino acid residues 169-183, amino acid residues 31-45 and/or amino acid residues 58-72.

The invention is also directed to an anti-IL-6 antibody that binds with the same IL-6 epitope and/or competes with an anti-IL-6 antibody for binding to IL-6 as an antibody or antibody fragment disclosed herein, including but not limited to an anti-IL-6 antibody selected from Ab1 and chimeric, humanized, single chain antibodies and fragments thereof (containing at least one CDRs of the afore-mentioned antibody) that specifically bind IL-6, which preferably are aglycosylated.

In another embodiment, the invention is also directed to an isolated anti-IL-6 antibody or antibody fragment or variant thereof comprising at least one of the CDRs contained in the $V_H$ polypeptide sequences comprising: SEQ ID NO: 3, 18, 19, 22, 38, 54, 70, 86, 102, 117, 118, 123, 139, 155, 171, 187, 203, 219, 235, 251, 267, 283, 299, 315, 331, 347, 363, 379, 395, 411, 427, 443, 459, 475, 491, 507, 523, 539, 555, 571, 652, 656, 657, 658, 661, 664, 665, 668, 672, 676, 680, 684, 688, 691, 692, 704, or 708 and/or at least one of the CDRs contained in the $V_L$ polypeptide sequence consisting of: 2, 20, 21, 37, 53, 69, 85, 101, 119, 122, 138, 154, 170, 186, 202, 218, 234, 250, 266, 282, 298, 314, 330, 346, 362, 378, 394, 410, 426, 442, 458, 474, 490, 506, 522, 538, 554, 570, 647, 651, 660, 666, 667, 671, 675, 679, 683, 687, 693, 699, 702, 706, or 709 and the VH and VL sequences depicted in the antibody alignments comprised in FIGS. 1-5 of this application.

In one embodiment of the invention, the anti-IL-6 antibody described herein may comprise at least 2 complementarity determining regions (CDRs) in each the variable light and the variable heavy regions which are identical to those contained in an anti-IL-6 antibody comprising Ab1 and chimeric, humanized, single chain antibodies and fragments thereof (containing at least one CDRs of the afore-mentioned antibody) that specifically bind IL-6, which preferably are aglycosylated.

In a preferred embodiment, the anti-IL-6 antibody described herein may comprise at least 2 complementarity determining regions (CDRs) in each the variable light and the variable heavy regions which are identical to those contained in Ab1. In another embodiment, all of the CDRs of the anti-IL-6 antibody discussed above are identical to the CDRs contained in an anti-IL-6 antibody comprising Ab1 and chimeric, humanized, single chain antibodies and fragments thereof (containing at least one CDRs of the afore-mentioned antibody) that specifically bind IL-6, which preferably are aglycosylated. In a preferred embodiment of the invention, all of the CDRs of the anti-IL-6 antibody discussed above are identical to the CDRs contained in Ab1, e.g., an antibody comprised of the VH and VL sequences comprised in SEQ ID NO: 657 and SEQ ID NO: 709 respectively.

The invention further contemplates that the one or more anti-IL-6 antibodies discussed above are aglycosylated or substantially non-glycosylated (e.g., may contain one or more, e.g., 1-5 mannose residues); that contain an Fc region that has been modified to alter effector function, half-life, proteolysis, and/or glycosylation; are human, humanized, single chain or chimeric; and are a humanized antibody derived from a rabbit (parent) anti-IL-6 antibody. Exemplary constant regions that provide for the production of aglycosylated antibodies in *Pichia* are comprised in SEQ ID NO: 588 and SEQ ID NO: 586 which respectively are encoded by the nucleic acid sequences in SEQ ID NO: 589 and SEQ ID NO: 587.

The invention further contemplates at least one anti-IL-6 antibodies wherein the framework regions (FRs) in the variable light region and the variable heavy regions of said antibody respectively are human FRs which are unmodified or which have been modified by the substitution of at most 2 or 3 human FR residues in the variable light or heavy chain region with the corresponding FR residues of the parent rabbit antibody, and wherein said human FRs have been derived from human variable heavy and light chain antibody sequences which have been selected from a library of human germline antibody sequences based on their high level of homology to the corresponding rabbit variable heavy or light chain regions relative to other human germline antibody sequences contained in the library.

In one embodiment of the invention, the anti-IL-6 antibody or fragment or variant thereof may specifically bind to IL-6 expressing human cells and/or to circulating soluble IL-6 molecules in vivo, including IL-6 expressed on or by human cells in a patient with a disease associated with cells that express IL-6.

The invention further contemplates anti-IL-6 antibodies or fragments or variants thereof directly or indirectly attached to a detectable label or therapeutic agent.

The invention also contemplates at least one nucleic acid sequences which result in the expression of an anti-IL-6 antibody or antibody fragment or variant thereof as set forth above, including those comprising, or alternatively consisting of, yeast or human preferred codons. The invention also contemplates vectors (including plasmids or recombinant viral vectors) comprising said nucleic acid sequence(s). The invention also contemplates host cells or recombinant host cells expressing at least one of the antibodies set forth above, including a mammalian, yeast, bacterial, and insect cells. In a preferred embodiment, the host cell is a yeast cell. In a further preferred embodiment, the yeast cell is a diploidal yeast cell. In a more preferred embodiment, the yeast cell is a *Pichia* yeast.

The invention also contemplates a method of treatment comprising administering to a patient with a disease or condition associated with mucositis a therapeutically effective amount of at least one anti-IL-6 antibody or antibody fragment or variant thereof. The diseases that may be treated are presented in the non-limiting list set forth above. In another embodiment the treatment further includes the administration of another therapeutic agent or regimen selected from chemotherapy, radiotherapy, cytokine administration or gene therapy agent. For example, TNF-α inhibitors including but not limited to glyococordicoids, triamcinolone, dexamethasone, prednisone, may also be administered sequentially or subsequently with at least one anti-IL-6 antibody or antibody fragment or variant thereof described herein. Further examples of drugs that may be included with the IL-6 antagonists include but are not limited to ARISTOCORT® (triamcinolone), BAYCADROM® (dexamethasone), DECADRON® (dexamethasone), DELTASONE® (prednisone), DEXAMETHASONE INTENSOL® (dexamethasone), ENBREL® (etancercept), HUMIRA® (adalimumab), REMICADE® (infliximab), RIDUARA® (aruaofin), and SIMPONI® (golimumab).

Exemplary Embodiments of Heavy and Light Chain Polypeptides and Polynucleotides

This section recites exemplary embodiments of heavy and light chain polypeptides, as well as exemplary polynucleotides encoding such polypeptides. These exemplary polynucleotides are suitable for expression in the disclosed *Pichia* expression system.

In certain embodiments, the present invention encompasses polynucleotides having at least about 70%, 75%, 80%, 85%, 90%, 91%, 92%, 93%, 94%, 95%, 96%, 97%, 98%, 99%, or 100% sequence identity (sequence homology) to the polynucleotides recited in this application or that encode polypeptides recited in this application, or that hybridize to said polynucleotides under conditions of low-stringency, moderate-stringency, or high-stringency conditions, preferably those that encode polypeptides (e.g. an immunoglobulin heavy and light chain, a single-chain antibody, an antibody fragment) that have at least one of the biological activities set forth herein, including without limitation thereto specific binding to an IL-6 polypeptide. In another aspect, the invention encompasses a composition comprising such a polynucleotide and/or a polypeptide encoded by such a polynucleotide. In yet another aspect, the invention encompasses a method of treatment of a disease or condition associated with IL-6 or that may be prevented, treated, or ameliorated with an IL-6 antagonist such as Ab1 (e.g. mucositis) comprising administration of a composition comprising such a polynucleotide and/or polypeptide.

In certain preferred embodiments, a heavy chain polypeptide will comprise at least one of the CDR sequences of the heavy and/or light chain polypeptides recited herein (including those contained in the heavy and light chain polypeptides recited herein) and at least one of the framework region polypeptides recited herein, including those depicted in FIGS. 1-5 or Table 4, and contained in the heavy and light chain polypeptide sequences recited herein. In certain preferred embodiments, a heavy chain polypeptide will comprise at least one Framework 4 region sequences as depicted in FIGS. 1-5 or Table 4, or as contained in a heavy or light chain polypeptide recited herein.

In certain preferred embodiments, a light chain polypeptide will comprise at least one of the CDR sequences of the heavy and/or light chain polypeptides recited herein (including those contained in the heavy and light chain polypeptides recited herein) and at least one of the Framework region polypeptides recited herein, including those depicted in FIGS. 1-5 or Table 4, and contained in the heavy and light chain polypeptide sequences recited herein. In certain preferred embodiments, a light chain polypeptide will comprise at least one Framework 4 region sequences as depicted in FIGS. 1-5 or Table 4, or as contained in a heavy or light chain polypeptide recited herein.

In any of the embodiments recited herein, certain of the sequences recited may be substituted for each other, unless the context indicates otherwise. The recitation that particular sequences may be substituted for one another, where such recitations are made, are understood to be illustrative rather than limiting, and it is also understood that such substitutions are encompassed even when no illustrative examples of substitutions are recited, For example, wherever at least one of the Ab1 light chain polypeptides is recited, e.g. any of SEQ ID NO: 2, 20, 647, 651, 660, 666, 699, 702, 706, or 709, another Ab1 light chain polypeptide may be substituted unless the context indicates otherwise. Similarly, wherever one of the Ab1 heavy chain polypeptides is recited, e.g. any of SEQ ID NO: 3, 18, 19, 652, 656, 657, 658, 661, 664, 665, 704, or 708, another Ab1 heavy chain polypeptide may be substituted unless the context indicates otherwise. Likewise, wherever one of the Ab1 light chain polynucleotides is recited, e.g. any of SEQ ID NO: 10, 662, 698, 701, or 705, another Ab1 light chain polynucleotide may be substituted unless the context indicates otherwise. Similarly, wherever one of the Ab1 heavy chain polynucleotides is recited, e.g. any of SEQ ID NO: 11, 663, 700, 703, or 707, another Ab1 heavy chain polynucleotide may be substituted unless the context indicates otherwise.

Additionally, recitation of any member of any of the following groups is understood to encompass substitution by any other member of the group, as follows: Ab2 Light chain polypeptides (SEQ ID NO: 21 and 667); Ab2 Light chain polynucleotides (SEQ ID NO: 29 and 669); Ab2 Heavy chain polypeptides (SEQ ID NO: 22 and 668); Ab2 Heavy chain polynucleotides (SEQ ID NO: 30 and 670); Ab3 Light chain polypeptides (SEQ ID NO: 37 and 671); Ab3 Light chain polynucleotides (SEQ ID NO: 45 and 673); Ab3 Heavy chain polypeptides (SEQ ID NO: 38 and 672); Ab3 Heavy chain polynucleotides (SEQ ID NO: 46 and 674); Ab4 Light chain polypeptides (SEQ ID NO: 53 and 675); Ab4 Light chain polynucleotides (SEQ ID NO: 61 and 677); Ab4 Heavy chain polypeptides (SEQ ID NO: 54 and 676); Ab4 Heavy chain polynucleotides (SEQ ID NO: 62 and 678); Ab5 Light chain polypeptides (SEQ ID NO: 69 and 679); Ab5 Light chain polynucleotides (SEQ ID NO: 77 and 681); Ab5 Heavy chain polypeptides (SEQ ID NO: 70 and 680); Ab5 Heavy chain polynucleotides (SEQ ID NO: 78 and 682); Ab6 Light chain polypeptides (SEQ ID NO: 85 and 683); Ab6 Light chain polynucleotides (SEQ ID NO: 93 and 685); Ab6 Heavy chain polypeptides (SEQ ID NO: 86 and 684); Ab6 Heavy chain polynucleotides (SEQ ID NO: 94 and 686); Ab7 Light chain polypeptides (SEQ ID NO: 101, 119, 687, 693); Ab7 Light chain polynucleotides (SEQ ID NO: 109 and 689); Ab7 Heavy chain polypeptides (SEQ ID NO: 102, 117, 118, 688, 691, and 692); Ab7 Heavy chain polynucleotides (SEQ ID NO: 110 and 690); Ab1 Light Chain CDR1 polynucleotides (SEQ ID NO: 12 and 694); Ab1 Light Chain CDR3 polynucleotides (SEQ ID NO: 14 and 695); Ab1 Heavy Chain CDR2 polynucleotides (SEQ ID NO: 16 and 696) and Ab1 Heavy Chain CDR3 polynucleotides (SEQ ID NO: 17 and 697). Exemplary Ab1-encoding polynucleotide sequences include but are not limited to SEQ ID NO: 662, 663, 698, 700, 701, 703, 705, 707, 720, 721, 722, 723, 724, and 725.

Anti-IL-6 Activity

As stated previously, IL-6 is a member of a family of cytokines that promote cellular responses through a receptor complex consisting of at least one subunit of the signal-transducing glycoprotein gp130 and the IL-6 receptor (IL-6R). The IL-6R may also be present in a soluble form (sIL-6R). IL-6 binds to IL-6R, which then dimerizes the signal-transducing receptor gp130.

It is believed that the anti-IL-6 antibodies of the invention, or IL-6 binding fragments or variants thereof, are useful by exhibiting anti-IL-6 activity. In one non-limiting embodiment of the invention, the anti-IL-6 antibodies of the invention, or IL-6 binding fragments or variants thereof, exhibit anti-IL-6 activity by binding to IL-6 which may be soluble IL-6 or cell surface expressed IL-6 and/or may prevent or inhibit the binding of IL-6 to IL-6R and/or activation (dimerization) of the gp 130 signal-transducing glycoprotein and the formation of IL-6/IL-6R/gp130 multimers and the biological effects of any of the foregoing. The subject anti-IL-6 antibodies may possess different antagonistic activities based on where (i.e., epitope) the particular antibody binds IL-6 and/or how it affects the formation of the foregoing IL-6 complexes and/or multimers and the biological effects thereof. Consequently, different anti-IL-6 antibodies according to the invention e.g., may be better suited for preventing or treating conditions involving the formation and accumulation of substantial soluble IL-6 such as rheumatoid arthritis whereas other antibodies may be favored in treatments wherein the prevention of IL-6/IL-6R/gp130 or IL-6/IL-6R/gp130 multimers is a desired therapeutic outcome. This can be determined in binding and other assays.

The anti-IL-6 activity of the anti-IL-6 antibody of the present invention, and fragments and variants thereof having binding specificity to IL-6, may also be described by their strength of binding or their affinity for IL-6. This also may affect their therapeutic properties. In one embodiment of the invention, the anti-IL-6 antibodies of the present invention, and fragments thereof having binding specificity to IL-6, bind to IL-6 with a dissociation constant ($K_D$) of less than or equal to $5\times10^{-7}$, $10^{-7}$, $5\times10^{-8}$, $10^{-8}$, $5\times10^{-9}$, $10^{-9}$, $5\times10^{-10}$, $10^{-10}$, $5\times10^{-11}$, $10^{-11}$, $5\times10^{-12}$, $10^{-12}$, $5\times10^{-13}$, $10^{-13}$, $5\times10^{-14}$, $10^{-14}$, $5\times10^{-15}$ or $10^{-15}$. Preferably, the anti-IL-6 antibodies and fragments and variants thereof bind IL-6 with a dissociation constant of less than or equal to $5\times10^{-10}$.

In another embodiment of the invention, the anti-IL-6 activity of the anti-IL-6 antibodies of the present invention, and fragments and variants thereof having binding specificity to IL-6, bind to IL-6 with an off-rate of less than or equal to $10^{-4}\ S^{-1}$, $5\times10^{-5}\ S^{-1}$, $10^{-5}\ S^{-1}$, $5\times10^{-6}\ S^{-1}$, $10^{-6}\ S^{-1}$, $5\times10^{-7}\ S^{-1}$, or $10^{-7}\ S^{-1}$. In one embodiment of the invention, the anti-IL-6 antibodies of the invention, and fragments and variants thereof having binding specificity to IL-6, bind to a linear or conformational IL-6 epitope.

In a further embodiment of the invention, the anti-IL-6 activity of the anti-IL-6 antibodies of the present invention, and fragments and variants thereof having binding specificity to IL-6, exhibit anti-IL-6 activity by ameliorating or reducing the symptoms of, or alternatively treating, or preventing, diseases and disorders associated with IL-6. Non-limiting examples of diseases and disorders associated with IL-6 are set forth infra. In another embodiment of the invention, the anti-IL-6 antibodies described herein, or IL-6 binding fragments and variants thereof, do not have binding specificity for IL-6R or the gp-130 signal-transducing glycoprotein.

Screening Assays

The invention also includes screening assays designed to assist in the identification of diseases and disorders associated with IL-6 in patients exhibiting symptoms of an IL-6 associated disease or disorder, especially mucositis.

In one embodiment of the invention, the anti-IL-6 antibodies of the invention, or IL-6 binding fragments or variants thereof, are used to detect the presence of IL-6 in a biological sample obtained from a patient exhibiting symptoms of a disease or disorder associated with IL-6. The presence of IL-6, or elevated levels thereof when compared to pre-disease levels of IL-6 in a comparable biological sample, may be beneficial in diagnosing a disease or disorder associated with IL-6.

Another embodiment of the invention provides a diagnostic or screening assay to assist in diagnosis of diseases or disorders associated with IL-6 in patients exhibiting symptoms of an IL-6 associated disease or disorder identified herein, comprising assaying the level of IL-6 expression in a biological sample from said patient using a post-translationally modified anti-IL-6 antibody or binding fragment or variant thereof. The anti-IL-6 antibody or binding fragment or variant thereof may be post-translationally modified to include a detectable moiety such as set forth previously in the disclosure.

The IL-6 level in the biological sample is determined using a modified anti-IL-6 antibody or binding fragment or variant thereof as set forth herein, and comparing the level of IL-6 in the biological sample against a standard level of IL-6 (e.g., the level in normal biological samples). The skilled clinician would understand that some variability may exist between normal biological samples, and would take that into consideration when evaluating results.

The above-recited assay may also be useful in monitoring a disease or disorder, where the level of IL-6 obtained in a biological sample from a patient believed to have an IL-6 associated disease or disorder is compared with the level of IL-6 in prior biological samples from the same patient, in order to ascertain whether the IL-6 level in said patient has changed with, for example, a treatment regimen. A skilled clinician would understand that a biological sample includes, but is not limited to, sera, plasma, urine, saliva, mucous, pleural fluid, synovial fluid and spinal fluid.

The IL-6 antagonists described herein, including the anti-IL-6 antibodies (e.g., Ab1 antibody) may be used in methods of studying mucositis. For example, the IL-6 antagonists described herein, including the anti-IL-6 antibodies (e.g., Ab1 antibody), may be compared to other therapeutic agents, both known and experimental, to test for effectiveness in treating mucositis. See Bowen, et al. (2011) *J Support Oncol.* 9(5): 161-8.

Fusion Proteins

Fusion proteins comprising IL-6 antagonists are also provided by the present invention. Fusions comprising the anti-IL-6 antibodies polypeptides are also within the scope of the present invention. For example, the fusion protein may be linked to a GST fusion protein in which the anti-IL-6 antibodies polypeptide sequences are fused to the C-terminus of the GST sequences. Such fusion proteins may facilitate the purification of the recombinant Anti-IL-6 antibodies polypeptides. Alternatively, anti-IL-6 antibodies polypeptides may be fused with a protein that binds B-cell follicles, thus initiating both a humoral immune response and activation of T cells. Berney, et al. (1999) *J. Exp. Med.* 190: 851-60. Alternatively, for example, the Anti-IL-6 antibodies polypeptides may be genetically coupled with and anti-dendritic cell antibody to deliver the antigen to the immune system and stimulate a cellular immune response. He, et al. (2004) *Clin. Cancer Res.* 10: 1920-27. A chimeric or fusion protein of the invention may be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene may be synthesized by conventional techniques including automated DNA synthesizers.

Fusion proteins may include C-terminal or N-terminal translocation sequences. Further, fusion proteins can comprise additional elements, e.g., for protein detection, purification, or other applications. Detection and purification facilitating domains including but not limited to metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAG extension/affinity purification system (Immunex Corp, Seattle Wash.)

A fusion protein may be prepared from a protein of the invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises CH2 and CH3 domains. Although any IgG subtype may optionally be used, the IgG1 subtype is preferred. The Fc chain may optionally be a known or "wild type" Fc chain, or alternatively may be mutated. See, e.g., U.S. Patent Application Publication No. 2006/0034852. The term "Fc chain" also optionally comprises any type of Fc fragment. Several of the specific amino acid residues that are involved in antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect. See McCafferty, et al. (2002) *Antibody Engineering: A Practical Approach* (Eds.) Oxford University Press.

The inclusion of a cleavable linker sequences such as Factor Xa (see, e.g., Ottavi, (1998) *Biochimie* 80: 289-93), subtilisin protease recognition motif (see, e.g., Polyak (1997) *Protein Eng.* 10: 615-19); enterokinase (Invitrogen, San Diego, Calif.), between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams (1995) Biochemistry 34: 1787-97), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the art. See, e.g., Kroll (1993) *DNA Cell. Biol.* 12: 441-53.

Conjugates

IL-6 antagonists may be conjugated to other moieties (e.g., conjugates). Further, the anti-IL-6 antibodies, antibodies that bind the Anti-IL-6 antibodies and fragments thereof, may be conjugated to other moieties. Such conjugates are often used in the preparation of vaccines. The anti-IL-6 antibodies polypeptide may be conjugated to a carbohydrate (e.g., mannose, fucose, glucose, GlcNAs, maltose), which is recognized by the mannose receptor present on dendritic cells and macrophages. The ensuing binding, aggregation, and receptor-mediated endocytosis and phagocytosis functions provide enhanced innate and adaptive immunity. See Mahnke, et al. (2000) *J. Cell Biol.* 151: 673-84; Dong, et al. (1999) *J. Immonol.* 163: 5427-34. Other moieties suitable for conjugation to elicit an immune response includes but not limited to Keyhole Limpit Hemocyannin (KLH), diphtheria toxoid, cholera toxoid, *Pseudomonas* exoprotein A, and microbial outer membrane proteins (OMPS).

Labels

As stated above, antibodies and fragments and variants thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

The anti-IL-6 antibodies and antibody fragments thereof described herein may be modified post-translationally to add effector moieties such as chemical linkers, detectable moieties such as for example fluorescent dyes, enzymes, substrates, bioluminescent materials, radioactive materials, chemiluminescent moieties, a cytotoxic agent, radioactive materials, or functional moieties.

A wide variety of entities, e.g., ligands, may be coupled to the oligonucleotides as known in the art. Ligands may include naturally occurring molecules, or recombinant or synthetic molecules. Exemplary ligands include, but are not limited to, avadin, biotin, peptides, peptidomimetics, polylysine (PLL), polyethylene glycol (PEG), mPEG, cationic groups, spermine, spermidine, polyamine, thyrotropin, melanotropin, lectin, glycoprotein, surfactant protein A, mucin, glycosylated polyaminoacids, transferrin, aptamer, immunoglobulins (e.g., antibodies), insulin, transferrin, albumin, sugar, lipophilic molecules (e.g., steroids, bile acids, cholesterol, cholic acid, and fatty acids), vitamin A, vitamin E, vitamin K, vitamin B, folic acid, B12, riboflavin, biotin, pyridoxal, vitamin cofactors, lipopolysaccharide, hormones and hormone receptors, lectins, carbohydrates, multivalent carbohydrates, radiolabeled markers, fluorescent dyes, and derivatives thereof. See, e.g., U.S. Pat. Nos. 6,153,737; 6,172,208; 6,300,319; 6,335,434; 6,335,437; 6,395,437; 6,444,806; 6,486,308; 6,525,031; 6,528,631; and 6,559,279.

Additionally, moieties may be added to the antigen or epitope to increase half-life in vivo (e.g., by lengthening the time to clearance from the blood stream. Such techniques include, for example, adding PEG moieties (also termed pegilation), and are well-known in the art. See U.S. Patent Application Publication No. 2003/0031671.

An anti-IL-6 antibody or antigen binding fragment thereof, described herein may be "attached" to a substrate when it is associated with the solid label through a non-random chemical or physical interaction. The attachment may be through a covalent bond. However, attachments need not be covalent or permanent. Materials may be attached to a label through a "spacer molecule" or "linker group." Such spacer molecules are molecules that have a first portion that attaches to the biological material and a second portion that attaches to the label. Thus, when attached to the label, the spacer molecule separates the label and the biological materials, but is attached to both. Methods of attaching biological material (e.g., label) to a label are well known in the art, and include but are not limited to chemical coupling.

Detectable Labels

The anti-IL-6 antibody or antibody fragments described herein may be modified post-translationally to add effector labels such as chemical linkers, detectable labels such as for example fluorescent dyes, enzymes, substrates, bioluminescent materials, radioactive materials, and chemiluminescent labels, or functional labels such as for example streptavidin, avidin, biotin, a cytotoxin, a cytotoxic agent, and radioactive materials. Further exemplary enzymes include, but are not limited to, horseradish peroxidase, acetylcholinesterase, alkaline phosphatase, β-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent labels include, but are not limited to, luminol. Further exemplary bioluminescent materials include, but are not limited to, luciferin and aequorin. Further exemplary radioactive materials include, but are not limited to, bismuth-213 ($^{213}$Bs), carbon-14 ($^{14}$C), carbon-11 ($^{11}$C), chlorine-18 ($^{18}$Cl), chromium-51 ($^{51}$Cr), cobalt-57 ($^{57}$Co), cobalt-60 ($^{60}$Co), copper-64 ($^{64}$Cu), copper-67 ($^{67}$Cu), dysprosium-165 ($^{165}$Dy), erbium-169 ($^{169}$Er), fluorine-18 ($^{18}$F), gallium-67 ($^{67}$Ga), gallium-68 ($^{68}$Ga), germanium-68 ($^{68}$Ge), holmium-166 ($^{166}$Ho), indium-111 ($^{111}$In), iodine-125 ($^{125}$I), iodine-123 ($^{124}$I), iodine-124 ($^{124}$I), iodine-131 ($^{131}$I), iridium-192 (192Ir) iron-59 ($^{59}$Fe), krypton-81 ($^{81}$Kr), lead-212 ($^{212}$Pr) lutetium-177 ($^{177}$Lu), molybdenum-99 ($^{99}$Mo), nitrogen-13 ($^{13}$N), oxygen-15 ($^{15}$O), palladium-103 ($^{103}$Pd), phosphorus-32 ($^{32}$P), potassium-42 ($^{42}$K), rhenium-186 ($^{186}$Re), rhenium-188 ($^{188}$Re), rubidium-81 ($^{81}$Rb), rubidium-82 ($^{82}$Rb), samarium-153 ($^{153}$Sm), selenium-75 ($^{75}$Se), sodium-24 ($^{24}$Na), strontium-82 ($^{82}$Sr), strontium-89 ($^{8}$9Sr), sulfur 35 ($^{35}$S), technetium-99m ($^{99}$Tc), thallium-201 ($^{201}$Tl), tritium ($^{3}$H), xenon-133 ($^{133}$Xe), ytterbium-169 ($^{169}$Yb), ytterbium-177 ($^{177}$Yb), and yttrium-90 ($^{90}$Y).

Cytotoxic Agents

The anti-IL-6 antibodies and antibody fragments described herein may be conjugated to cytotoxic agents including, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, caminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (TAXOL®), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Erbitux®, Avastin®, Pertuzumab, anti-CD20 antibodies, Rituxan®, ocrelizumab, ofatumumab, DXL625, Herceptin®, or any combination thereof. Toxic enzymes from plants and bacteria such as ricin, diphtheria toxin and *Pseudomonas* toxin may be conjugated to the humanized antibodies, or binding fragments thereof, to generate cell-type-specific-killing reagents. Youle, et al. (1980) *Proc. Nat'l Acad. Sci. USA* 77: 5483; Gilliland, et al. (1980) *Proc. Nat'l Acad. Sci. USA* 77: 4539; Krolick, et al. (1980) *Proc. Nat'l Acad. Sci. USA* 77: 5419. Other cytotoxic agents include cytotoxic ribonucleases. See U.S. Pat. No. 6,653,104.

The anti-IL-6 antibodies and antibody fragments described herein may be conjugated to a radionuclide that emits alpha or beta particles (e.g., radioimmunoconjuagtes). Such radioactive isotopes include but are not limited to beta-emitters such as phosphorus-32 ($^{32}$P), scandium-47 ($^{47}$Sc), copper-67 ($^{67}$Cu), gallium-67 ($^{67}$Ga), yttrium-88 ($^{88}$Y), yttrium-90 ($^{90}$Y), iodine-125 ($^{125}$I), iodine-131 ($^{131}$I), samarium-153 ($^{153}$Sm), lutetium-177 ($^{177}$Lu), rhenium-186 ($^{186}$Re), rhenium-188 ($^{188}$Re), and alpha-emitters such as astatine-211 ($^{211}$At), lead-212 ($^{212}$Pb), bismuth-212 ($^{212}$Bi), bismuth-213 ($^{213}$Bi) or actinium-225 ($^{225}$Ac).

Methods are known in the art for conjugating an anti-IL-6 antibody described herein to a label, such as those methods described by Hunter, et al. (1962) *Nature* 144: 945; David, et al. (1974) *Biochemistry* 13: 1014; Pain, et al. (1981) *J. Immunol. Meth.* 40: 219; and Nygren (1982) *Histochem and Cytochem* 30: 407.

Substrates

The anti-IL-6 antibodies and antibody fragments thereof described herein may be attached to a substrate. A number of substrates (e.g., solid supports) known in the art are suitable for use with the anti-IL-6 antibody described herein. The substrate may be modified to contain channels or other configurations. See Fung (2004) [Ed.] Protein Arrays: Methods and Protocols Humana Press and Kambhampati (2004) [Ed.] Protein Microarray Technology John Wiley & Sons.

Substrate materials include, but are not limited to acrylics, agarose, borosilicate glass, carbon (e.g., carbon nanofiber sheets or pellets), cellulose acetate, cellulose, ceramics, gels, glass (e.g., inorganic, controlled-pore, modified, soda-lime, or functionalized glass), latex, magnetic beads, membranes, metal, metalloids, nitrocellulose, NYLON®, optical fiber bundles, organic polymers, paper, plastics, polyacryloylmorpholide, poly(4-methylbutene), poly(ethylene terephthalate), poly(vinyl butyrate), polyacrylamide, polybutylene, polycarbonate, polyethylene, polyethyleneglycol terephthalate, polyformaldehyde, polymethacrylate, polymethylmethacrylate, polypropylene, polysaccharides, polystyrene, polyurethanes, polyvinylacetate, polyvinylchloride, polyvinylidene difluoride (PVDF), polyvinylpyrrolidinone, rayon, resins, rubbers, semiconductor materials, Sepharose®, silica, silicon, styrene copolymers, TEFLON®, and variety of other polymers.

Substrates need not be flat and can include any type of shape including spherical shapes (e.g., beads) or cylindrical shapes (e.g., fibers). Materials attached to solid supports may be attached to any portion of the solid support (e.g., may be attached to an interior portion of a porous solid support material).

The substrate body may be in the form of a bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial. The substrate may be a singular discrete body (e.g., a single tube, a single bead), any number of a plurality of substrate bodies (e.g., a rack of 10 tubes, several beads), or combinations thereof (e.g., a tray comprises a plurality of microtiter plates, a column filled with beads, a microtiter plate filed with beads).

An anti-IL-6 antibody or antibody fragment thereof may be "attached" to a substrate when it is associated with the solid substrate through a non-random chemical or physical interaction. The attachment may be through a covalent bond. However, attachments need not be covalent or permanent.

Materials may be attached to a substrate through a "spacer molecule" or "linker group." Such spacer molecules are molecules that have a first portion that attaches to the biological material and a second portion that attaches to the substrate. Thus, when attached to the substrate, the spacer molecule separates the substrate and the biological materials, but is attached to both. Methods of attaching biological material (e.g., label) to a substrate are well known in the art, and include but are not limited to chemical coupling.

Plates, such as microtiter plates, which support and contain the solid-phase for solid-phase synthetic reactions may be used. Microtiter plates may house beads that are used as the solid-phase. By "particle" or "microparticle" or "nanoparticle" or "bead" or "microbead" or "microsphere" herein is meant microparticulate matter having any of a variety of shapes or sizes. The shape may be generally spherical but need not be spherical, being, for example, cylindrical or polyhedral. As will be appreciated by those in the art, the particles may comprise a wide variety of materials depending on their use, including, but not limited to, cross-linked starch, dextrans, cellulose, proteins, organic polymers including styrene polymers such as polystyrene and methylstyrene as well as other styrene co-polymers, plastics, glass, ceramics, acrylic polymers, magnetically responsive materials, colloids, thoriasol, carbon graphite, titanium dioxide, nylon, latex, and TEFLON®. See e.g., "Microsphere Detection Guide" from Bangs Laboratories, Fishers, Ind.

The anti-IL-6 antibody or antibody fragment may be attached to on any of the forms of substrates described herein (e.g., bead, box, column, cylinder, disc, dish (e.g., glass dish, PETRI dish), fiber, film, filter, microtiter plate (e.g., 96-well microtiter plate), multi-bladed stick, net, pellet, plate, ring, rod, roll, sheet, slide, stick, tray, tube, or vial). In particular, particles or beads may be a component of a gelling material or may be separate components such as latex beads made of a variety of synthetic plastics (e.g., polystyrene). The label (e.g., streptavidin) may be bound to a substrate (e.g., bead).

Assessment of Inflammatory Markers

Known inflammatory markers (e.g., IL-6) may be measured to assess the risk for mucositis or the severity of mucositis. These markers may be measured from serum, synovial fluid, or skin biopsies using known methods in the art (e.g., immunoassays).

IL-6 Serum Levels

Serum IL-6 levels may be measured as a pharmacodynamic marker evaluate the effect of neutralization of IL-6 levels. Serum IL-6 levels may be measured using an immunoassay (e.g., ELISA assay). A decrease of serum IL-6 levels may be indicative of a lessening of inflammation.

Serum Inflammatory Biomarkers

Serum biomarkers may be measured to determine the expression of pro-inflammatory cytokines and other soluble biomarkers that may correlate with mucositis (e.g., oral, alimeniary, or gastrointestinal tract mucositis) disease activity including but not limited to acute phase reactants, serum pro-inflammatory cytokines (e.g., IL-1, TNF-α, IFN-γ, IL-12p40, IL-17), chemokines (e.g., RANTES, MIP-1α, MCP-1), matrix metalloproteinases (e.g., MMP-2, MMP-3, MMP-9) and other biomarkers associated with inflammation and autoimmune pathways that are known in the art. Soluble biomarkers of bone and cartilage metabolism (e.g., osteocalcin and other collagen degradation products) may also be assessed by an immunoassay (e.g., ELISA). A decrease in a serum inflammatory biomark may be indicative of a lessening of inflammation.

Immunohistochemistry of Skin Biopsies

Skin biopsies may be collected for biomarker analysis including whole genome array analysis and immunohistochemistry (IHC). Immunohistochemical analysis may include the measurement of epidermal thickness, frequency of resident and inflammatory cell populations (e.g., T cells, macrophages, keratinocytes) and other inflammatory markers related to the IL-6 pathway known in the art. Specifically, the following specific antigens may be assessed per standard IHC procedure using the formalin-fixed samples: CD3, CD68, keratin 16, FoxP3, IL-6R and MMP-3. A decrease in an inflammatory biomarker in a skin biopsy may be indicative of a lessening of inflammation.

Administration

In one embodiment of the invention, the anti-IL-6 antibodies described herein, or IL-6 binding fragments or variants thereof, as well as combinations of said antibody fragments or variants, are administered to a subject at a concentration of between about 0.1 and 20 mg/kg, such as about 0.4 mg/kg, about 0.8 mg/kg, about 1.6 mg/kg, or about 4 mg/kg, of body weight of recipient subject. For example, compositions comprising the IL-6 antagonists described herein may comprise at least about 0, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg. For example, compositions comprising the anti-IL-6 antibodies described herein may comprise at least about 0, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg.

For example, a composition for treating mucositis may comprise 80, 160, or 320 mg of an anti-IL-6 antibody (e.g., Ab1). A composition for treating oral mucositis may comprise 80, 160, or 320 mg of an anti-IL-6 antibody (e.g., Ab1). A composition for treating mucositis associated with chemotherapy may comprise 80, 160, or 320 mg of an anti-IL-6 antibody (e.g., Ab1). A composition for treating oral mucositis associated with chemotherapy may comprise 80, 160, or 320 mg of an anti-IL-6 antibody (e.g., Ab1). A composition for treating mucositis associated with radiotherapy may comprise 80, 160, or 320 mg of an anti-IL-6 antibody (e.g., Ab1). A composition for treating oral mucositis associated with radiotherapy may comprise 80, 160, or 320 mg of an anti-IL-6 antibody (e.g., Ab1). A composition for treating mucositis associated with cancer may comprise 80, 160, or 320 mg of an anti-IL-6 antibody (e.g., Ab1). A composition for treating oral mucositis associated with cancer may comprise 80, 160, or 320 mg of an anti-IL-6 antibody (e.g., Ab1). For example, compositions comprising the anti-IL-6 antibodies described herein may comprise at least about 0.5-10 mg/kg of the anti-IL-6 antibody. In a preferred embodiment of the invention, the anti-IL-6 antibodies described herein, or IL-6 binding fragments or variants thereof, as well as combinations of said antibody fragments or variants, are administered to a subject at a concentration of about 0.4 mg/kg of body weight of recipient subject. In a preferred embodiment of the invention, the anti-IL-6 antibodies described herein, or IL-6 binding fragments or variants thereof, as well as combinations of said antibody fragments or variants, are administered to a recipient subject with a frequency of once every twenty-six weeks or less, such as once every sixteen weeks or less, once every eight weeks or less, or once every four weeks, or less. In another preferred embodiment of the invention, the anti-IL-6 antibodies described herein, or IL-6 binding fragments or variants thereof, as well as combinations thereof, are administered to a recipient subject with a frequency at most once per period of approximately one week, such as at most once per period of approximately two weeks, such as at most once per period of approximately four weeks, such as at most once per period of approximately eight weeks, such as at most once per period of approximately twelve weeks, such as at most once per period of approximately sixteen weeks, such as at most once per period of approximately twenty-four weeks.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are intravenous injection or infusion. The administration can be local, where the composition is administered directly, close to, in the locality, near, at, about, or in the vicinity of, the site(s) of disease, e.g., local (joint) or systemic, wherein the composition is given to the patient and passes through the body widely, thereby reaching the site(s) of disease. Local administration (e.g., subcutaneous injection) may be accomplished by administration to the cell, tissue, organ, and/or organ system, which encompasses and/or is affected by the disease, and/or where the disease signs and/or symptoms are active or are likely to occur (e.g., swollen joint). Administration can be topical with a local effect, composition is applied directly where its action is desired (e.g., joint). Further, administration of a composition comprising an effective amount of an anti-IL-6 antibody selected from the group consisting of Ab1-Ab36 or an antibody fragment thereof, may be subcutaneous.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

In further embodiments, the present invention provides kits including at least one containers comprising pharmaceutical dosage units comprising an effective amount of at least one antibodies and fragments thereof of the present invention. Kits may include instructions, directions, labels, marketing information, warnings, or information pamphlets.

Dosages

The amount of anti-IL-6 antibodies in a therapeutic composition according to any embodiments of this invention may vary according to factors such as the disease state, age, gender, weight, patient history, risk factors, predisposition to disease, administration route, preexisting treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

For example, for the treatment of mucositis (e.g., oral, esophageal, alimentary, and gastrointestinal tract mucositis) a composition may comprise at least about 80, 160, or 320 mg IL-6 antagonists may be administered to a patient in need thereof. In another embodiment, for the treatment of oral mucositis a composition may comprise at least about 80, 160, or 320 mg IL-6 antagonists may be administered to a patient in need thereof. Further, for the treatment of mucositis a composition may comprise at least about 80, 160, or 320 mg anti-IL-6 antibody (e.g., Ab1) may be administered to a patient in need thereof. In another embodiment, for the treatment of oral mucositis a composition may comprise at least about 80, 160, or 320 mg anti-IL-6 antibody (e.g., Ab1) may be administered to a patient in need thereof. The dosage of IL-6 antagonist, may depend upon the mode of administration. For example, for subcutaneous administration of a composition may comprise an IL-6 antagonist, the composition may comprise at least about 1-500 mg/mL, 10-250 mg/mL, 10-100 mg/mL, or 40-100 mg/mL of an IL-antagonist. For example, a composition for subcutaneous administration may comprise at least about 10, 20, 30, 40, 50, 60, 70, 80, 90, or 100 mg/mL of an IL-6 antagonist. Thus, a composition for subcutaneous administration may comprise at least about at least about 1-500 mg/mL, 10-250 mg/mL, 10-100 mg/mL, or 40-100 mg/mL of an anti-IL-6 antibody (e.g., Ab1). or at least about 10, 20, 30, 40, 50, 60, 70, 80, 90, or 100 mg/mL of an anti-IL-6 antibody (e.g., Ab1). For intravenous administration of a composition may comprise an IL-6 antagonist, the composition may comprise at least about 1-500 mg/mL, 10-250 mg/mL, 10-100 mg/mL, or 40-100 mg/mL of an IL-antagonist. For example, a composition for intravenous administration may comprise at least about 10, 20, 30, 40, 50, 60, 70, 80, 90, or 100 mg/mL of an IL-6 antagonist. Thus, a composition for intravenous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). The mucositis may be associated with chemotherapy, radiotherapy, cancer, or hematopoietic stem cell transplants. For example, the oral mucositis may be associated with chemotherapy, radiotherapy, cancer, or hematopoietic stem cell transplants.

For example, a composition for the treatment of alimentary tract mucositis may comprise at least about 80, 160, or 320 mg IL-6 antagonists may be administered to a patient in need thereof. Further, a composition for the treatment of alimentary tract mucositis may comprise at least about 80, 160, or 320 mg anti-IL-6 antibody (e.g., Ab1) may be administered to a patient in need thereof. For example, a composition for the treatment of alimentary tract mucositis formulated for subcutaneous administration may comprise at least about 10, 20, 30, 40, 50, 60, 70, 80, 90, or 100 mg/mL of an IL-6 antagonist. Thus, a composition for the treatment of alimentary tract mucositis formulated for subcutaneous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). A composition for the treatment of alimentary tract mucositis formulated for intravenous administration may comprise at least about 10, 20, 30, 40, 50, 60, 70, 80, 90, or 100 mg/mL of an IL-6 antagonist. Thus, a composition for the treatment of alimentary tract mucositis formulated for intravenous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). The alimentary tract mucositis may be associated with chemotherapy, radiotherapy, cancer, or hematopoietic stem cell transplants.

For example, a composition for the treatment of gastrointestinal tract mucositis may comprise at least about 80, 160, or 320 mg IL-6 antagonists may be administered to a patient in need thereof. Further, a composition for the treatment of gastrointestinal tract mucositis may comprise at least about 80, 160, or 320 mg anti-IL-6 antibody (e.g., Ab1) may be administered to a patient in need thereof. For example, a composition for the treatment of gastrointestinal tract mucositis formulated for subcutaneous administration may comprise at least about 10, 20, 30, 40, 50, 60, 70, 80, 90, or 100 mg/mL of an IL-6 antagonist. Thus, a composition for the treatment of gastrointestinal tract mucositis formulated for subcutaneous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). A composition for the treatment of gastrointestinal tract mucositis formulated for intravenous administration may comprise at least about 10, 20, 30, 40, 50, 60, 70, 80, 90, or 100 mg/mL of an IL-6 antagonist. Thus, a composition for the treatment of gastrointestinal tract mucositis formulated for intravenous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). The gastrointestinal tract mucositis may be associated with chemotherapy, radiotherapy, cancer, or hematopoietic stem cell transplants.

Further, an intravenous formulation of an Ab1 anti-IL-6 antibody may comprise at least about 10 mg/mL or 40 mg/L for the treatment of rheumatoid arthritis and a subcutaneous formulation of an Ab1 anti-IL-6 antibody may comprise at least about 100 mg/mL for the treatment of rheumatoid arthritis. For example, a composition for the treatment of rheumatoid arthritis formulated for subcutaneous administration may comprise at least about 10, 20, 30, 40, 50, 60, 70, 80, 90, or 100 mg/mL of an IL-6 antagonist. Thus, a composition for the treatment of rheumatoid arthritis formulated for subcutaneous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). A composition for the treatment of rheumatoid arthritis formulated for intravenous administration may comprise at least about 10, 20, 30, 40, 50, 60, 70, 80, 90, or 100 mg/mL of an IL-6 antagonist. Thus, a composition for the treatment of rheumatoid arthritis formulated for intravenous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). The rheumatoid arthritis may be associated with chemotherapy, radiotherapy, cancer, or hematopoietic stem cell transplants.

For example, a composition for the treatment of emesis may comprise at least about 80, 160, or 320 mg IL-6 antagonists may be administered to a patient in need thereof. Further, a composition for the treatment of emesis may comprise at least about 80, 160, or 320 mg anti-IL-6 antibody (e.g., Ab1) may be administered to a patient in need thereof. For example, a composition for the treatment of emesis formulated for subcutaneous administration may comprise at least about 10, 20, 30, 40, 50, 60, 70, 80, 90, or 100 mg/mL of an IL-6 antagonist. Thus, a composition for the treatment of emesis formulated for subcutaneous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). A composition for the treatment of emesis formulated for intravenous administration may comprise at least about 10, 20, 30, 40, 50, 60, 70, 80, 90, or 100 mg/mL of an IL-6 antagonist. Thus, a composition for the treatment of emesis formulated for intravenous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). The emesis may be associated with chemotherapy, radiotherapy, cancer, or hematopoietic stem cell transplants.

For example, a composition for the treatment of diarrhea may comprise at least about 80, 160, or 320 mg IL-6 antagonists may be administered to a patient in need thereof. Further, a composition for the treatment of emesis may comprise at least about 80, 160, or 320 mg anti-IL-6 antibody (e.g., Ab1) may be administered to a patient in need thereof. For example, a composition for the treatment of diarrhea formulated for subcutaneous administration may comprise at least about 10, 20, 30, 40, 50, 60, 70, 80, 90, or 100 mg/mL of an IL-6 antagonist. Thus, a composition for the treatment of diarrhea formulated for subcutaneous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). A composition for the treatment of diarrhea formulated for intravenous administration may comprise at least about 10, 20, 30, 40, 50, 60, 70, 80, 90, or 100 mg/mL of an IL-6 antagonist. Thus, a composition for the treatment of diarrhea formulated for intravenous administration may comprise at least about at least about 1-500 mg/mL, 10-250 mg/mL, 10-100 mg/mL, or 40-100 mg/mL of an anti-IL-6 antibody (e.g., Ab1) or at least about 10, 20, 30, 40, 50, 60, 70, 80, 90, or 100 mg/mL of an anti-IL-6 antibody (e.g., Ab1). The diarrhea may be associated with chemotherapy, radiotherapy, cancer, or hematopoietic stem cell transplants.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of antibodies, or antibody fragments thereof, calculated to produce the desired therapeutic effect in association with the required pharmaceutical carrier. The specification for the dosage unit forms of the invention are dictated by and directly dependent on the unique characteristics of the antibodies, and fragments thereof, and the particular therapeutic effect to be achieved, and the limitations inherent in the art of compounding such an antibodies, and fragments thereof, for the treatment of sensitivity in individuals. In therapeutic use for treatment of conditions in mammals (e.g., humans) for which the antibodies and fragments thereof of the present invention or an appropriate pharmaceutical composition thereof are effective, the antibodies and fragments thereof of the present invention may be administered in an effective amount. The dosages as suitable for this invention may be a composition, a pharmaceutical composition or any other compositions described herein.

The dosage may be administered as a single dose, a double dose, a triple dose, a quadruple dose, and/or a quintuple dose. The dosages may be administered singularly, simultaneously, and sequentially. For example, two doses may be administered on the same day followed by subsequent two doses four weeks later.

The dosage form may be any form of release known to persons of ordinary skill in the art. The compositions of the present invention may be formulated to provide immediate release of the active ingredient or sustained or controlled release of the active ingredient. In a sustained release or controlled release preparation, release of the active ingredient may occur at a rate such that blood levels are maintained within a therapeutic range but below toxic levels over an extended period of time (e.g., 4 to 24 hours). The preferred dosage forms include immediate release, extended release, pulse release, variable release, controlled release, timed release, sustained release, delayed release, long acting, and combinations thereof, and are known in the art.

It will be appreciated that the pharmacological activity of the compositions may be monitored using standard pharmacological models that are known in the art. Furthermore, it will be appreciated that the compositions comprising an anti-IL-6 antibodies or antibody fragments thereof may be incorporated or encapsulated in a suitable polymer matrix or membrane for site-specific delivery, or may be functionalized with specific targeting agents capable of effecting site specific delivery. These techniques, as well as other drug delivery techniques are well known in the art. Determination of optimal dosages for a particular situation is within the capabilities of those skilled in the art. See, e.g., Grennaro (2005) [Ed.] *Remington: The Science and Practice of Pharmacy [*21st Ed.]

In another embodiment of the invention, the anti-IL-6 antibodies described herein, or IL-6 binding fragments or variants thereof, as well as combinations of said antibody fragments or variants, are administered to a subject in a pharmaceutical formulation.

A "pharmaceutical composition" refers to a chemical or biological composition suitable for administration to a mammal. Such compositions may be specifically formulated for administration via at least one of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration. Further, a pharmaceutical composition comprising an anti-IL-6 antibody described herein (e.g., ALD518) may be administered subcutaneously.

In one embodiment of the invention, the anti-IL-6 antibodies described herein, or IL-6 binding fragments or variants thereof, as well as combinations of said antibody fragments or variants, may be optionally administered in combination with at least one active agents. Such active agents include analgesic, antipyretic, anti-inflammatory, antibiotic, antiviral, and anti-cytokine agents. Active agents include agonists, antagonists, and modulators of TNF-alpha, IL-2, IL-4, IL-6, IL-10, IL-12, IL-13, IL-18, IFN-alpha, IFN-gamma, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors. Active agents also include 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lornoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Sulfinpyrazone, Sulindac, Suprofen, Tenoxicam, Tiaprofenic acid, Tolfenamic acid, Tolmetin, and Valdecoxib. Antibiotics include Amikacin, Aminoglycosides, Amoxicillin, Ampicillin, Ansamycins, Arsphenamine, Azithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbimycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomycin, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithromycin, Tetracycline, Tetracyclines, Ticarcillin, Timidazole, Tobramycin, Trimethoprim, Trimethoprim-Sulfamethoxazole, Troleandomycin, Trovafloxacin, and Vancomycin. Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone. Antiviral agents include but are not limited to abacavir, aciclovir, acyclovir, adefovir, amantadine, amprenavir, an antiretroviral fixed dose combination, an antiretroviral synergistic enhancer, arbidol, atazanavir, atripla, brivudine, cidofovir, combivir, darunavir, delavirdine, didanosine, docosanol, edoxudine, efavirenz, emtricitabine, enfuvirtide, entecavir, entry inhibitors, famciclovir, fomivirsen, fosamprenavir, foscarnet, fosfonet, fusion inhibitor, ganciclovir, gardasil, ibacitabine, idoxuridine, imiquimod, immunovir, indinavir, inosine, integrase inhibitor, interferon, interferon type I, interferon type II, interferon type III, lamivudine, lopinavir, loviride, maraviroc, MK-0518, moroxydine, nelfinavir, nevirapine, nexavir, nucleoside analogues, oseltamivir, penciclovir, peramivir, pleconaril, podophyllotoxin, protease inhibitor, reverse transcriptase inhibitor, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or at least one fragments or variants thereof. The excipient generally does not provide any pharmacological activity to the formulation, though it may provide chemical and/or biological stability, and release characteristics. Exemplary formulations can be found, for example, in Grennaro (2005) [Ed.] *Remington: The Science and Practice of Pharmacy [*$21^{st}$ Ed.]

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition may be formulated as a solution, microemulsion, liposome, or other ordered structure suitable to high drug concentration. The carrier may be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition.

The antibodies and fragments thereof, of the present invention thereof may be formulated into pharmaceutical compositions of various dosage forms. For example, the antibody may be ALD518, a humanized anti-interleukin-6 (anti-IL-6) monoclonal immunoglobulin 1 (IgG1) antibody manufactured in the yeast *Pichia pastoris*. ALD518 may be supplied as a pH 6.0 frozen injection in single-use vials (80 mg or 160 mg) for intravenous administration. Examplary non-active excipients include but are not limited to histidine (e.g., 25 mM) and sorbitol (e.g., 250 mM). For example, a 160 mg formulation may comprise as non-active excipients, 25 mM histidine, 250 mM sorbitol, and 0.015% polysorbate 80. To prepare the pharmaceutical compositions of the invention, at least one anti-IL-6 antibodies or binding fragments thereof, as the active ingredient may be intimately mixed with appropriate carriers and additives according to techniques well known to those skilled in the art of pharmaceutical formulations. See Grennaro (2005) [Ed.] *Remington: The Science and Practice of Pharmacy [*$21^{st}$ Ed.] For example, the antibodies described herein may be formulated in phosphate buffered saline pH 7.2 and supplied as a 5.0 mg/mL clear colorless liquid solution.

Similarly, compositions for liquid preparations include solutions, emulsions, dispersions, suspensions, syrups, and elixirs, with suitable carriers and additives including but not limited to water, alcohols, oils, glycols, preservatives, flavoring agents, coloring agents, and suspending agents. Typical preparations for parenteral administration comprise the active ingredient with a carrier such as sterile water or parenterally acceptable oil including but not limited to polyethylene glycol, polyvinyl pyrrolidone, lecithin, arachis oil or sesame oil, with other additives for aiding solubility or preservation may also be included. In the case of a solution, it may be lyophilized to a powder and then reconstituted immediately prior to use. For dispersions and suspensions, appropriate carriers and additives include aqueous gums, celluloses, silicates, or oils.

For each of the recited embodiments, the anti-IL-6 antibodies or binding fragments thereof, may be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

In many cases, it will be preferable to include isotonic agents, e.g., sugars, polyalcohols such as mannitol, sorbitol, or sodium chloride in the composition. Prolonged absorption of the injectable compositions may be brought about by including in the composition an agent which delays absorption, e.g., monostearate salts and gelatin. Moreover, the compounds described herein may be formulated in a time release formulation, e.g. in a composition that includes a slow release polymer. The anti-IL-6 antibodies may be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

In one embodiment of the invention that may be used to intravenously administer antibodies of the invention, including ALD518, for mucositis indications, the administration formulation comprises, or alternatively consists of, about 10.5 mg/mL of antibody, 25 mM Histidine base, Phosphoric acid q.s. to pH 6, and 250 mM sorbitol.

In another embodiment of the invention that may be used to intravenously administer antibodies of the invention, including ALD581, for mucositis indications, the administration formulation comprises, or alternatively consists of, about 10.5 mg/mL of antibody, 12.5 mM Histidine base, 12.5 mM Histidine HCl (or 25 mM Histidine base and Hydrochloric acid q.s. to pH 6), 250 mM sorbitol, and 0.015% (w/w) Polysorbate 80.

In one embodiment of the invention that may be used to subcutaneously administer antibodies of the invention, including ALD518, for mucositis indications, the administration formulation comprises, or alternatively consists of, about 50 or 100 mg/mL of antibody, about 5 mM Histidine base, about 5 mM Histidine HCl to make final pH 6, 250 mM sorbitol, and 0.015% (w/w) Polysorbate 80. In another embodiment of the invention that may be used to subcutaneously administer antibodies of the invention, including Ab1, for mucositis indications, the administration formulation comprises, or alternatively consists of, about 20 or 100 mg/mL of antibody, about 5 mM Histidine base, about 5 mM Histidine HCl to make final pH 6, 250 to 280 mM sorbitol (or sorbitol in combination with sucrose), and 0.015% (w/w) Polysorbate 80, said formulation having a nitrogen headspace in the shipping vials.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the alkaline polypeptide can be formulated in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

A person of skill in the art would be able to determine an effective dosage and frequency of administration through routine experimentation, for example guided by the disclosure herein and the teachings in Goodman, et al. (2011) Goodman & Gilman's The Pharmacological Basis of Therapeutics [$12^{th}$ Ed.]; Howland, et al. (2005) Lippincott's Illustrated Reviews: Pharmacology [$2^{nd}$ Ed.]; and Golan, (2008) Principles of Pharmacology: The Pathophysiologic Basis of Drug Therapy [$2^{nd}$ Ed.] See, also, Grennaro (2005) [Ed.] Remington: The Science and Practice of Pharmacy [$21^{st}$ Ed.]

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to methods for obtaining a clonal population of antigen-specific B cells were disclosed in U.S. Patent Application Publication No. 2007/0269868.

Certain teachings related to humanization of rabbit-derived monoclonal antibodies and preferred sequence modifications to maintain antigen binding affinity were disclosed in U.S. Patent Application Publication No. 2009/0104187.

Certain teachings related to producing antibodies or fragments thereof using mating competent yeast and corresponding methods were disclosed in U.S. Patent Application Publication No. 2006/0270045.

Certain teachings related to anti-IL-6 antibodies, methods of producing antibodies or fragments thereof using mating competent yeast and corresponding methods were disclosed in U.S. Patent Application Publication No. 2009/0104187.

Certain teachings related to anti-IL-6 antibodies and methods of using those antibodies or fragments thereof to address certain diseases and/or disorders were disclosed in U.S. Patent Application Publication No. 2010/0150829.

Certain anti-IL-6 antibody polynucleotides and polypeptides are disclosed in the sequence listing accompanying this patent application filing, and the disclosure of said sequence listing is herein incorporated by reference in its entirety.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations) but some experimental errors and deviations should be allowed for. Unless otherwise indicated, parts are parts by weight, molecular weight is average molecular weight, temperature is in degrees centigrade; and pressure is at or near atmospheric.

EXAMPLES

In the following examples, the term "Ab1" refers to an antibody comprising the light chain sequence of SEQ ID NO: 702 and the heavy chain sequence of SEQ ID NO: 704, except where the context indicates otherwise. The laboratory designation "Ab1" also encompasses an anti-IL-6 antibody also known as "ALD518" and "BMS-945429" comprising the light chain sequence of SEQ ID NO: 19 and the heavy chain sequence of SEQ ID NO: 20.

Example 1

Production of Enriched Antigen-Specific B Cell Antibody Culture

Panels of antibodies are derived by immunizing traditional antibody host animals to exploit the native immune response to a target antigen of interest. Typically, the host used for immunization is a rabbit or other host that produces antibodies using a similar maturation process and provides for a population of antigen-specific B cells producing antibodies of comparable diversity, e.g., epitopic diversity. The initial antigen immunization can be conducted using complete Freund's adjuvant (CFA), and the subsequent boosts effected with incomplete adjuvant. At about 50-60 days after immunization, preferably at day 55, antibody titers are tested, and the Antibody Selection (ABS) process is initiated if appropriate titers are established. The two key criteria for ABS initiation are potent antigen recognition and function-modifying activity in the polyclonal sera.

At the time positive antibody titers are established, animals are sacrificed and B cell sources isolated. These sources include: the spleen, lymph nodes, bone marrow, and peripheral blood mononuclear cells (PBMCs). Single cell suspensions are generated, and the cell suspensions are washed to make them compatible for low temperature long term storage. The cells are then typically frozen.

To initiate the antibody identification process, a small fraction of the frozen cell suspensions are thawed, washed, and placed in tissue culture media. These suspensions are then mixed with a biotinylated form of the antigen that was used to generate the animal immune response, and antigen-specific cells are recovered using the Miltenyi magnetic bead cell selection methodology. Specific enrichment is conducted using streptavidin beads. The enriched population is recovered and progressed in the next phase of specific B cell isolation.

Example 2

Production of Clonal, Antigen-Specific B Cell-Containing Culture

Enriched B cells produced according to Example 1 are then plated at varying cell densities per well in a 96 well microtiter plate. Generally, this is at 50, 100, 250, or 500 cells per well with 10 plates per group. The media is supplemented with 4% activated rabbit T cell conditioned media along with 50K frozen irradiated EL4B feeder cells. These cultures are left undisturbed for 5-7 days at which time supernatant-containing secreted antibody is collected and evaluated for target properties in a separate assay setting. The remaining supernatant is left intact, and the plate is frozen at −70° C. Under these conditions, the culture process typically results in wells containing a mixed cell population that comprises a clonal population of antigen-specific B cells, i.e., a single well will only contain a single monoclonal antibody specific to the desired antigen.

Example 3

Screening of Antibody Supernatants for Monoclonal Antibody of Desired Specificity and/or Functional Properties Antibody-containing supernatants derived from the well containing a clonal antigen-specific B cell population produced according to Example 2 are initially screened for antigen recognition using ELISA methods. This includes selective antigen immobilization (e.g., biotinylated antigen capture by streptavidin coated plate), non-specific antigen plate coating, or alternatively, through an antigen build-up strategy (e.g., selective antigen capture followed by binding partner addition to generate a heteromeric protein-antigen complex). Antigen-positive well supernatants are then optionally tested in a function-modifying assay that is strictly dependant on the ligand. One such example is an in vitro protein-protein interaction assay that recreates the natural interaction of the antigen ligand with recombinant receptor protein. Alternatively, a cell-based response that is ligand dependent and easily monitored (e.g., proliferation response) is utilized. Supernatant that displays significant antigen recognition and potency is deemed a positive well. Cells derived from the original positive well are then transitioned to the antibody recovery phase.

Example 4

Recovery of Single, Antibody-Producing B Cell of Desired Antigen Specificity Cells are isolated from a well that contains a clonal population of antigen-specific B cells (produced according to Example 2 or 3), which secrete a single antibody sequence. The isolated cells are then assayed to isolate a single, antibody-secreting cell. Dynal® (magnetic beads) streptavidin beads are coated with biotinylated target antigen under buffered medium to prepare antigen-containing microbeads compatible with cell viability. Next antigen-loaded beads, antibody-producing cells from the positive well, and a fluorescein isothiocyanate (FITC)-labeled anti-host H&L IgG antibody (as noted, the host can be any mammalian host, e.g., rabbit, mouse, rat) are incubated together at 37° C. This mixture is then re-pipetted in aliquots onto a glass slide such that each aliquot has on average a single, antibody-producing B-cell. The antigen-specific, antibody-secreting cells are then detected through fluorescence microscopy. Secreted antibody is locally concentrated onto the adjacent beads due to the bound antigen and provides localization information based on the strong fluorescent signal. Antibody-secreting cells are identified via FITC detection of antibody-antigen complexes formed adjacent to the secreting cell. The single cell found in the center of this complex is then recovered using a micromanipulator. The cell is snap-frozen in an eppendorf PCR tube for storage at −80° C. until antibody sequence recovery is initiated.

Example 5

Isolation of Antibody Sequences from Antigen-Specific B Cell

Antibody sequences are recovered using a combined RT-PCR based method from a single isolated B-cell produced according to Example 4 or an antigenic specific B cell isolated from the clonal B cell population obtained according to Example 2. Primers are designed to anneal in conserved and constant regions of the target immunoglobulin genes (heavy and light), such as rabbit immunoglobulin sequences, and a two-step nested PCR recovery step is used to obtain the antibody sequence. Amplicons from each well are analyzed for recovery and size integrity. The resulting fragments are then digested with AluI to fingerprint the sequence clonality. Identical sequences display a common fragmentation pattern in their electrophoretic analysis. Significantly, this common fragmentation pattern which proves cell clonality is generally observed even in the wells originally plated up to 1000 cells/well. The original heavy and light chain amplicon fragments are then restriction enzyme digested with HindIII and XhoI or HindIII and BsiWI to prepare the respective pieces of DNA for cloning. The resulting digestions are then ligated into an expression vector and transformed into bacteria for plasmid propagation and production. Colonies are selected for sequence characterization.

Example 6

Recombinant Production of Monoclonal Antibody of Desired Antigen Specificity and/or Functional Properties Correct full-length antibody sequences for each well containing a single monoclonal antibody is established and mini-prep DNA is prepared using Qiagen solid-phase methodology. This DNA is then used to transfect mammalian cells to produce recombinant full-length antibody. Crude antibody product is tested for antigen recognition and functional properties to confirm the original characteristics are found in the recombinant antibody protein. Where appropriate, large-scale transient mammalian transfections are completed, and antibody is purified through Protein A affinity chromatography. Kd is assessed using standard methods (e.g., Biacore®) as well as IC50 in a potency assay.

Example 7

Preparation of Antibodies that Bind Human IL-6

By using the antibody selection protocol described herein, one can generate an extensive panel of antibodies. The antibodies have high affinity towards IL-6 (single to double digit pM Kd) and demonstrate potent antagonism of IL-6 in multiple cell-based screening systems (T1165 and HepG2). Furthermore, the collection of antibodies displays distinct modes of antagonism toward IL-6-driven processes.

Immunization Strategy

Rabbits were immunized with huIL-6 (R&R). Immunization consisted of a first subcutaneous (sc) injection of 100 μg in complete Freund's adjuvant (CFA) (Sigma) followed by two boosts, two weeks apart, of 50 μg each in incomplete Freund's adjuvant (IFA) (Sigma). Animals were bled on day 55, and serum titers were determined by ELISA (antigen recognition) and by non-radioactive proliferation assay (Promega) using the T1165 cell line.

Antibody Selection Titer Assessment

Antigen recognition was determined by coating Immulon 4 plates (Thermo) with 1 μg/mL of huIL-6 (50 μL/well) in phosphate buffered saline (PBS, Hyclone) overnight at 4° C. On the day of the assay, plates were washed 3 times with PBS/Tween 20 (PBST tablets, Calbiochem). Plates were then blocked with 200 μL/well of 0.5% fish skin gelatin (FSG, Sigma) in PBS for 30 minutes at 37° C. Blocking solution was removed, and plates were blotted. Serum samples were made (bleeds and pre-bleeds) at a starting dilution of 1:100 (all dilutions were made in FSG 50 μL/well) followed by 1:10 dilutions across the plate (column 12 was left blank for background control). Plates were incubated for 30 minutes at 37° C. Plates were washed 3 times with PBS/Tween 20. Goat anti-rabbit Fc-HRP (Pierce) diluted 1:5000 was added to all wells (50 μL/well), and plates were incubated for 30 minutes at 37° C. Plates were washed as described above. 50 μL/well of TMB-Stable stop (Fitzgerald Industries) was added to plates, and color was allowed to develop, generally for 3 to 5 minutes. The development reaction was stopped with 50 μL/well 0.5 M HCl. Plates were read at 450 nm. Optical density (OD) versus dilution was plotted using Graph Pad Prizm software, and titers were determined.

Functional Titer Assessment

The functional activity of the samples was determined by a T1165 proliferation assay. T1165 cells were routinely maintained in modified RPMI medium (Hyclone) supplemented with HEPES, sodium pyruvate, sodium bicarbonate, L-glutamine, high glucose, penicillin/streptomycin, 10% heat inactivated fetal bovine serum (FBS) (all supplements from Hyclone), 2-mercaptoethanol (Sigma), and 10 ng/mL of huIL-6 (R&D). On the day of the assay, cell viability was determined by trypan blue (Invitrogen), and cells were seeded at a fixed density of 20,000 cells/well. Prior to seeding, cells were washed twice in the medium described above without human-IL-6 (by centrifuging at 13000 rpm for 5 minutes and discarding the supernatant). After the last wash, cells were resuspended in the same medium used for washing in a volume equivalent to 50 μL/well. Cells were set aside at room temperature.

In a round-bottom, 96-well plate (Costar), serum samples were added starting at 1:100, followed by a 1:10 dilution across the plate (columns 2 to 10) at 30 μL/well in replicates of 5 (rows B to F: dilution made in the medium described above with no huIL-6). Column 11 was medium only for IL-6 control. 30 μL/well of huIL-6 at 4× concentration of the final EC50 (concentration previously determined) were added to all wells (huIL-6 was diluted in the medium described above). Wells were incubated for 1 hour at 37° C. to allow antibody binding to occur. After 1 hour, 50 μL/well of antibody-antigen (Ab—Ag) complex were transferred to a flat-bottom, 96-well plate (Costar) following the plate map format laid out in the round-bottom plate. On Row G, 50 μL/well of medium were added to all wells (columns 2 to 11) for background control. 50 μL/well of the cell suspension set aside were added to all wells (columns 2 to 11, rows B to G). On Columns 1 and 12 and on rows A and H, 200 μL/well of medium was added to prevent evaporation of test wells and to minimize edge effect. Plates were incubated for 72 hours at 37° C. in 4% $CO_2$. At 72 hours, 20 μL/well of CellTiter96 (Promega) reagents was added to all test wells per manufacturer protocol, and plates were incubated for 2 hours at 37° C. At 2 hours, plates were gently mixed on an orbital shaker to disperse cells and to allow homogeneity in the test wells. Plates were read at 490 nm wavelength. Optical density (OD) versus dilution was plotted using Graph Pad Prizm software, and functional titer was determined. A positive assay control plate was conducted as described above using MAB2061 (R&D Systems) at a starting concentration of 1 μg/mL (final concentration) followed by 1:3 dilutions across the plate.

Tissue Harvesting

Once acceptable titers were established, the rabbit(s) were sacrificed. Spleen, lymph nodes, and whole blood were harvested and processed as follows:

Spleen and lymph nodes were processed into a single cell suspension by disassociating the tissue and pushing through sterile wire mesh at 70 μm (Fisher) with a plunger of a 20 cc syringe. Cells were collected in the modified RPMI medium described above without huIL-6, but with low glucose. Cells were washed twice by centrifugation. After the last wash, cell density was determined by trypan blue. Cells were centrifuged at 1500 rpm for 10 minutes; the supernatant was discarded. Cells were resuspended in the appropriate volume of 10% dimethyl sulfoxide (DMSO, Sigma) in FBS (Hyclone) and dispensed at 1 mL/vial. Vials were then stored at −70° C. for 24 h prior to being placed in a liquid nitrogen (LN2) tank for long-term storage.

Peripheral blood mononuclear cells (PBMCs) were isolated by mixing whole blood with equal parts of the low glucose medium described above without FBS. 35 mL of the whole blood mixture was carefully layered onto 8 mL of Lympholyte Rabbit (Cedarlane) into a 45 mL conical tube (Corning) and centrifuged 30 minutes at 2500 rpm at room temperature without brakes. After centrifugation, the PBMC layers were carefully removed using a glass Pasteur pipette (VWR), combined, and placed into a clean 50 mL vial. Cells were washed twice with the modified medium described above by centrifugation at 1500 rpm for 10 minutes at room temperature, and cell density was determined by trypan blue staining. After the last wash, cells were resuspended in an appropriate volume of 10% DMSO/FBS medium and frozen as described herein.

B Cell Culture

On the day of setting up B cell culture, PBMC, splenocyte, or lymph node vials were thawed for use. Vials were removed from LN2 tank and placed in a 37° C. water bath until thawed. Contents of vials were transferred into 15 mL conical centrifuge tube (Corning) and 10 mL of modified RPMI described above was slowly added to the tube. Cells were centrifuged for 5 minutes at 1.5K RPM, and the supernatant was discarded. Cells were resuspended in 10 mL of fresh media. Cell density and viability was determined by trypan blue. Cells were washed again and resuspended at 1E07 cells/80 μL medium. Biotinylated huIL-6 (B huIL-6) was added to the cell suspension at the final concentration of 3 μg/mL and incubated for 30 minutes at 4° C. Unbound B huIL-6 was removed with two 10 mL washes of phosphate-buffered (PBF):Ca/Mg free PBS (Hyclone), 2 mM ethylenediamine tetraacetic acid (EDTA), 0.5% bovine serum albumin (BSA) (Sigma-biotin free). After the second wash, cells were resuspended at 1E07 cells/80 μL PBF. 20 μL of MACS® streptavidin beads (Milteni)/10E7 cells were added to the cell suspension. Cells were incubated at 4° C. for 15 minutes. Cells were washed once with 2 mL of PBF/10E7 cells. After washing, the cells were resuspended at 1E08 cells/500 μL of PBF and set aside. A MACS® MS column (Milteni) was pre-rinsed with 500 mL of PBF on a magnetic stand (Milteni). Cell suspension was applied to the column through a pre-filter, and unbound fraction was collected. The column was washed with 1.5 mL of PBF buffer. The column was removed from the magnet stand and placed onto a clean, sterile 5 mL Polypropylene Falcon tube. 1 mL of PBF buffer was added to the top of the column, and positive selected cells were collected. The yield and viability of positive and negative cell fraction was determined by trypan blue staining. Positive selection yielded an average of 1% of the starting cell concentration.

A pilot cell screen was established to provide information on seeding levels for the culture. Three 10-plate groups (a total of 30 plates) were seeded at 50, 100, and 200 enriched B cells/well. In addition, each well contained 50K cells/well of irradiated EL-4.B5 cells (5,000 Rads) and an appropriate level of T cell supernatant (ranging from 1-5% depending on preparation) in high glucose modified RPMI medium at a final volume of 250 μL/well. Cultures were incubated for 5 to 7 days at 37° C. in 4% $CO_2$.

Identification of Selective Antibody Secreting B Cells

Cultures were tested for antigen recognition and functional activity between days 5 and 7.

Antigen Recognition Screening

The ELISA format used is as described above except 50 μL of supernatant from the B cell cultures (BCC) wells (all 30 plates) was used as the source of the antibody. The conditioned medium was transferred to antigen-coated plates. After positive wells were identified, the supernatant was removed and transferred to a 96-well master plate(s). The original culture plates were then frozen by removing all the supernatant except 40 μL/well and adding 60 μL/well of 16% DMSO in FBS. Plates were wrapped in paper towels to slow freezing and placed at −70° C.

Functional Activity Screening

Master plates were then screened for functional activity in the T1165 proliferation assay as described before, except row B was media only for background control, row C was media+IL-6 for positive proliferation control, and rows D-G and columns 2-11 were the wells from the BCC (50 μL/well, single points). 40 μL of IL-6 was added to all wells except the media row at 2.5 times the EC50 concentration determined for the assay. After 1 hour incubation, the Ab/Ag complex was transferred to a tissue culture (TC) treated, 96-well, flat-bottom plate. 20 μL of cell suspension in modified RPMI medium without huIL-6 (T1165 at 20,000 cells/well) was added to all wells (100 μL final volume per well). Background was subtracted, and observed OD values were transformed into % of inhibition.

B Cell Recovery

Plates containing wells of interest were removed from −70° C., and the cells from each well were recovered with 5-200 μL washes of medium/well. The washes were pooled in a 1.5 mL sterile centrifuge tube, and cells were pelleted for 2 minutes at 1500 rpm.

The tube was inverted, the spin repeated, and the supernatant carefully removed. Cells were resuspended in 100 μL/tube of medium. 100 μL biotinylated IL-6 coated streptavidin M280 dynabeads (Invitrogen) and 16 μL of goat anti-rabbit H&L IgG-FITC diluted 1:100 in medium was added to the cell suspension.

20 μL of cell/beads/FITC suspension was removed, and 5 μL droplets were prepared on a glass slide (Corning) previously treated with Sigmacote (Sigma), 35 to 40 droplets/slide. An impermeable barrier of paraffin oil (JT Baker) was added to submerge the droplets, and the slide was incubated for 90 minutes at 37° C., 4% $CO_2$ in the dark.

Specific B cells that produce antibody can be identified by the fluorescent ring around them due to antibody secretion, recognition of the bead-associated biotinylated antigen, and subsequent detection by the fluorescent-IgG detection reagent. Once a cell of interest was identified, the cell in the center of the fluorescent ring was recovered via a micromanipulator (Eppendorf). The single cell synthesizing and exporting the antibody was transferred into a 250 μL microcentrifuge tube and placed in dry ice. After recovering all cells of interest, these were transferred to −70° C. for long-term storage.

Example 8

Yeast Cell Expression

Antibody Genes:

Genes were cloned and constructed that directed the synthesis of a chimeric humanized rabbit monoclonal antibody.

Expression Vector:

The vector contains the following functional components: 1) a mutant ColE1 origin of replication, which facilitates the replication of the plasmid vector in cells of the bacterium *Escherichia coli;* 2) a bacterial Sh ble gene, which confers resistance to the antibiotic Zeocin® (phleomycin) and serves as the selectable marker for transformations of both *E. coli* and *P. pastoris;* 3) an expression cassette composed of the glyceraldehyde dehydrogenase gene (GAP gene) promoter, fused to sequences encoding the *Saccharomyces cerevisiae* alpha mating factor pre pro secretion leader sequence, followed by sequences encoding a *P. pastoris* transcriptional termination signal from the *P. pastoris* alcohol oxidase I gene (AOX1). The Zeocin® (phleomycin) resistance marker gene provides a means of enrichment for strains that contain multiple integrated copies of an expression vector in a strain by selecting for transformants that are resistant to higher levels of Zeocin® (phleomycin).

*Pichia pastoris* Strains:

*Pichia pastoris* strains met1, lys3, ura3 and ade1 may be used. Although any two complementing sets of auxotrophic strains could be used for the construction and maintenance of diploid strains, these two strains are especially suited for this method for two reasons. First, they grow more slowly than diploid strains that are the result of their mating or fusion. Thus, if a small number of haploid ade1 or ura3 cells remain present in a culture or arise through meiosis or other mechanism, the diploid strain should outgrow them in culture.

The second is that it is easy to monitor the sexual state of these strains since diploid Ade+ colonies arising from their mating are a normal white or cream color, whereas cells of any strains that are haploid ade1 mutants will form a colony with a distinct pink color. In addition, any strains that are haploid ura3 mutants are resistant to the drug 5-fluoro-orotic acid (FOA) and can be sensitively identified by plating samples of a culture on minimal medium+uracil plates with FOA. On these plates, only uracil-requiring ura3 mutant (presumably haploid) strains can grow and form colonies. Thus, with haploid parent strains marked with ade1 and ura3, one can readily monitor the sexual state of the resulting antibody-producing diploid strains (haploid versus diploid).

Methods

Construction of pGAPZ-alpha expression vectors for transcription of light and heavy chain antibody genes. The humanized light and heavy chain fragments were cloned into the pGAPZ expression vectors through a PCR directed process. The recovered humanized constructs were subjected to amplification under standard KOD polymerase (Novagen) kit conditions ((1) 94° C., 2 minutes; (2) 94° C., 30 seconds (3) 55° C., 30 seconds; (4) 72° C., 30 seconds-cycling through steps 2-4 for 35 times; (5) 72° C. 2 minutes) employing the following primers (1) light chain forward AGCGCTTATTCCGCTATCCAGATGACCCAGTC—the AfeI site is single underlined (SEQ ID NO: 729). The end of the HSA signal sequence is double underlined, followed by the sequence for the mature variable light chain (not underlined); the reverse CGTACGTTTGATTTCCACCTTG (SEQ ID NO: 730).

Variable light chain reverse primer. BsiWI site is underlined, followed by the reverse complement for the 3' end of the variable light chain. Upon restriction enzyme digest with AfeI and BsiWI this enable insertion in-frame with the pGAPZ vector using the human HAS leader sequence in frame with the human kapp light chain constant region for export. (2) A similar strategy is performed for the heavy chain. The forward primer employed is AGCGCTTATTCCGAGGTGCAGCTGGTGGAGTC (SEQ ID NO: 731). The AfeI site is single underlined. The end of the HSA signal sequence is double underlined, followed by the sequence for the mature variable heavy chain (not underlined). The reverse heavy chain primer is CTCGAGACGGTGACGAGGGT (SEQ ID NO: 732). The XhoI site is underlined, followed by the reverse complement for the 3' end of the variable heavy chain. This enables cloning of the heavy chain in-frame with IgG-γ1 CH1-CH2-CH3 region previous inserted within pGAPZ using a comparable directional cloning strategy.

Transformation of Expression Vectors into Haploid Ade1 Ura3, Met1 and Lys3 Host Strains of *P. pastoris.*

All methods used for transformation of haploid *P. pastoris* strains and genetic manipulation of the *P. pastoris* sexual cycle are as described in Higgins, D. R., and Cregg, J. M., Eds. 1998. *Pichia Protocols. Methods in Molecular Biology*. Humana Press, Totowa, N.J.

Prior to transformation, each expression vector is linearized within the GAP promoter sequences with AvrII to direct the integration of the vectors into the GAP promoter locus of the *P. pastoris* genome. Samples of each vector are then individually transformed into electrocompetent cultures of the ade1, ura3, met1 and lys3 strains by electroporation and successful transformants are selected on YPD Zeocin® (phleomycin) plates by their resistance to this antibiotic. Resulting colonies are selected, streaked for single colonies on YPD Zeocin® (phleomycin) plates and then examined for the presence of the antibody gene insert by a PCR assay on genomic DNA extracted from each strain for the proper antibody gene insert and/or by the ability of each strain to synthesize an antibody chain by a colony lift/immunoblot method. Wung, et al. (1996) *Biotechniques* 21: 808-812. Haploid ade1, met1 and lys3 strains expressing one of the three heavy chain constructs are collected for diploid constructions along with haploid ura3 strain expressing light chain gene. The haploid expressing heavy chain genes are mated with the appropriate light chain haploid ura3 to generate diploid secreting protein.

Mating of haploid strains synthesizing a single antibody chain and selection of diploid derivatives synthesizing tetrameric functional antibodies. To mate *P. pastoris* haploid strains, each ade1 (or met1 or lys3) heavy chain producing strain to be crossed is streaked across a rich YPD plate and the ura3 light chain producing strain is streaked across a second YPD plate (~10 streaks per plate). After one or two days incubation at 30° C., cells from one plate containing heavy chain strains and one plate containing ura3 light chain strains are transferred to a sterile velvet cloth on a replica-plating block in a cross hatched pattern so that each heavy chain strain contain a patch of cells mixed with each light chain strain. The cross-streaked replica plated cells are then transferred to a mating plate and incubated at 25° C. to stimulate the initiation of mating between strains. After two days, the cells on the mating plates are transferred again to a sterile velvet on a replica-plating block and then transferred to minimal medium plates. These plates are incubated at 30° C. for three days to allow for the selective growth of colonies of prototrophic diploid strains. Colonies that arose are picked and streaked onto a second minimal medium plate to single colony isolate and purify each diploid strain. The resulting diploid cell lines are then examined for antibody production.

Putative diploid strains are tested to demonstrate that they are diploid and contain both expression vectors for antibody production. For diploidy, samples of a strain are spread on mating plates to stimulate them to go through meiosis and form spores. Haploid spore products are collected and tested for phenotype. If a significant percentage of the resulting spore products are single or double auxotrophs it may be concluded that the original strain must have been diploid. Diploid strains are examined for the presence of both antibody genes by extracting genomic DNA from each and utilizing this DNA in PCR reactions specific for each gene.

Fusion of haploid strains synthesizing a single antibody chain and selection of diploid derivatives synthesizing tetrameric functional antibodies. As an alternative to the mating procedure described above, individual cultures of single-chain antibody producing haploid ade1 and ura3 strains are spheroplasted and their resulting spheroplasts fused using polyethylene glycol/$CaCl_2$. The fused haploid strains are then embedded in agar containing 1 M sorbitol and minimal medium to allow diploid strains to regenerate their cell wall and grow into visible colonies. Resulting colonies are picked from the agar, streaked onto a minimal medium plate, and the plates are incubated for two days at 30° C. to generate colonies from single cells of diploid cell lines. The resulting putative diploid cell lines are then examined for diploidy and antibody production as described above.

Purification and analysis of antibodies. A diploid strain for the production of full length antibody is derived through the mating of met1 light chain and lys3 heavy chain using the methods described above. Culture media from shake-flask or fermenter cultures of diploid *P. pastoris* expression strains are collected and examined for the presence of antibody protein via SDS-PAGE and immunoblotting using antibodies directed against heavy and light chains of human IgG, or specifically against the heavy chain of IgG.

To purify the yeast secreted antibodies, clarified media from antibody producing cultures are passed through a protein A column and after washing with 20 mM sodium phosphate, pH 7.0, binding buffer, protein A bound protein is eluted using 0.1 M glycine HCl buffer, pH 3.0. Fractions containing the most total protein are examined by Coomasie blue strained SDS-PAGE and immunoblotting for antibody protein. Antibody is characterized using the ELISA described above for IL-6 recognition.

Assay for Antibody Activity.

The recombinant yeast-derived humanized antibody is evaluated for functional activity through the IL-6 driven T1165 cell proliferation assay and IL-6 stimulated HepG2 haptoglobin assay described above.

Example 9

Acute Phase Response Neutralization by Intravenous Administration of Anti-IL-6 Antibody Ab1

Human IL-6 can provoke an acute phase response in rats, and one of the major acute phase proteins that is stimulated in the rat is alpha-2 macroglobulin (A2M). A study was designed to assess the dose of antibody Ab1 required to ablate the A2M response to a single subcutaneous injection of 100 μg of human IL-6 given one hour after different doses (0.03, 0.1, 0.3, 1, and 3 mg/kg) of antibody Ab1 administered intravenously (n=10 rats/dose level) or polyclonal human IgG1 as the control (n=10 rats). Plasma was recovered and the A2M was quantitated via a commercial sandwich ELISA kit (ICL Inc., Newberg Oreg.; cat. no.-E-25A2M). The endpoint was the difference in the plasma concentration of A2M at the 24 hour time point (post-Ab1).

The ID50 for antibody Ab1 was 0.1 mg/kg with complete suppression of the A2M response at the 0.3 mg/kg. See FIG. 6. This demonstrates that the IL-6 may be neutralized in vivo by anti-IL-6 antibodies described herein.

Example 10

RXF393 Cachexia Model Study 1

Introduction

The human renal cell cancer cell line, RXF393 produces profound weight loss when transplanted into athymic nude mice. Weight loss begins around day 15 after transplantation with 80% of all animals losing at least 30% of their total body weight by day 18-20 after transplantation. RXF393 secretes human IL-6 and the plasma concentration of human IL-6 in these animals is very high at around 10 ng/ml. Human IL-6 can bind murine soluble IL-6 receptor and activate IL-6 responses in the mouse. Human IL-6 is approximately 10 times less potent than murine IL-6 at activating IL-6 responses in the mouse. The objectives of this study were to determine the effect of antibody Ab1, on survival, body weight, serum amyloid A protein, hematology parameters, and tumor growth in athymic nude mice transplanted with the human renal cell cancer cell line, RXF393.

Methods

Eighty, 6 week old, male athymic nude mice were implanted with RXF393 tumor fragments (30-40 mg) subcutaneously in the right flank. Animals were then divided into eight groups of ten mice. Three groups were given either antibody Ab1 at 3 mg/kg, 10 mg/kg, or 30 mg/kg intravenously weekly on day 1, day 8, day 15 and day 22 after transplantation (progression groups). Another three groups were given either antibody Ab1 at 3 mg/kg, or 10 mg/kg, or 30 mg/kg intravenously weekly on day 8, day 15 and day 22 after transplantation (regression groups). Finally, one control group was given polyclonal human IgG 30 mg/kg and a second control group was given phosphate buffered saline intravenously weekly on day 1, day 8, day 15 and day 22 after transplantation.

Animals were euthanized at either day 28, when the tumor reached 4,000 $mm^3$ or if they became debilitated (>30% loss of body weight). Animals were weighed on days 1, 6 and then daily from days 9 to 28 after transplantation. Mean Percent Body Weight (MPBW) was used as the primary parameter to monitor weight loss during the study. It was calculated as follows: (Body Weight−Tumor Weight)/Baseline Body Weight×100. Tumor weight was measured on days 1, 6, 9, 12, 15, 18, 22, 25 and 28 after transplantation. Blood was taken under anesthesia from five mice in each group on days 5 and 13 and all ten mice in each group when euthanized (day 28 in most cases). Blood was analyzed for hematology and serum amyloid A protein (SAA) concentration. An additional group of 10 non-tumor bearing 6 week old, athymic nude male mice had blood samples taken for hematology and SAA concentration estimation to act as a baseline set of values.

Results—Survival

No animals were euthanized or died in any of the antibody Ab1 groups prior to the study termination date of day 28. In the two control groups, 15 animals (7/9 in the polyclonal human IgG group and 8/10 in the phosphate buffered saline group) were found dead or were euthanized because they were very debilitated (>30% loss of body weight). Median survival time in both control groups was 20 days.

Figure 7:
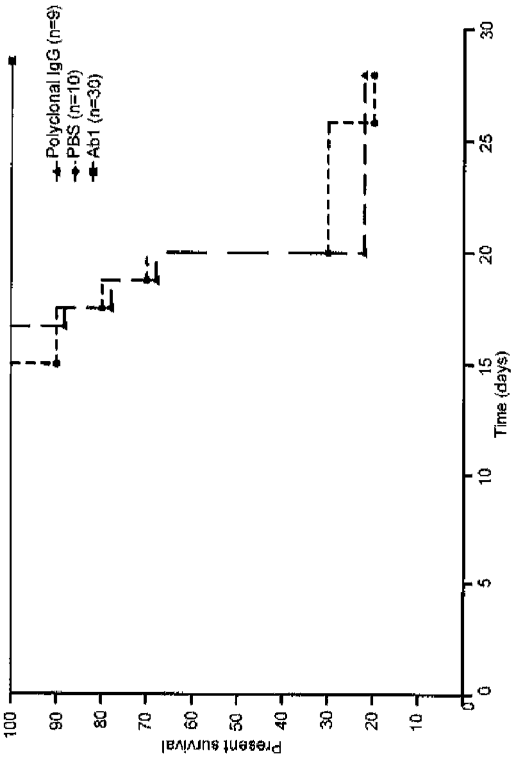
FIG. 7 provides survival data for the antibody Ab1 progression groups versus control groups. See also WO 2011/066371.

The survival curves for the two control groups and the antibody Ab1 progression (dosed from day 1 of the study) groups are presented in FIG. 7.

Figure 8:
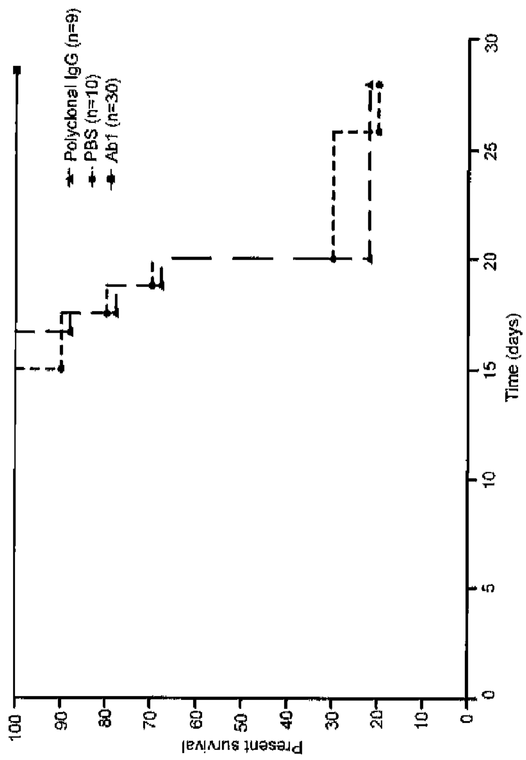
FIG. 8 provides additional survival data for the antibody Ab1 regression groups versus control groups. See also WO 2011/066371.

The survival curves for the two control groups and the antibody Ab1 regression (dosed from day 8 of the study) groups are presented in FIG. 8.

There was a statistically significant difference between the survival curves for the polyclonal human IgG (p=0.0038) and phosphate buffered saline (p=0.0003) control groups and the survival curve for the six antibody Ab1 groups. There was no statistically significant difference between the two control groups (p=0.97).

Results—Tumor Size

Tumor size in surviving mice was estimated by palpation. For the first 15 days of the study, none of the mice in any group were found dead or were euthanized, and so comparison of tumor sizes between groups on these days was free from sampling bias. No difference in tumor size was observed between the antibody Ab1 progression or regression groups and the control groups through day 15. Comparison of the tumor size between surviving mice in the control and treatment groups subsequent to the onset of mortality in the controls (on day 15) was not undertaken because tumor size the surviving control mice was presumed to be biased and accordingly the results of such comparison would not be meaningful.

As administration of antibody Ab1 promoted survival without any apparent reduction in tumor size, elevated serum IL-6 may contribute to mortality through mechanisms independent of tumor growth. These observations supports the hypothesis that antibody Ab1 can promote cancer patient survivability without directly affecting tumor growth, possibly by enhancing general patient well-being.

Results—Weight Loss

Compared to controls, mice dosed with Ab1 were protected from weight loss. On day 18, MPBW in control mice was 75%, corresponding to an average weight loss of 25%. In contrast, on the same day, MPBW in Ab-1 treatment groups was minimally changed (between 97% and 103%). There was a statistically significant difference between the MPBW curves for the controls (receiving polyclonal human IgG or PBS) and the 10 mg/kg dosage group ($p<0.0001$) or 3 mg/kg and 30 mg/kg dosage groups ($p<0.0005$). There was no statistically significant difference between the two control groups.

Control mice are emaciated compared to the normal appearance of the Ab1-treated mouse. These results suggest that Ab1 may be useful to prevent or treat cachexia caused by elevated IL-6 in humans.

Results—Plasma Serum Amyloid A

The mean (±SEM) plasma serum amyloid A concentration versus time for the two control groups and the antibody Ab1 progression (dosed from day 1 of the study) and regression (dosed from day 8 of the study) groups are presented in Table 6.

TABLE 6

Mean Plasma SAA - antibody Ab1, all groups versus control groups

| | Mean Plasma SAA ± SEM Day 5 (μg/ml) | Mean Plasma SAA ± SEM Day 13 (μg/ml) | Mean Plasma SAA ± SEM Terminal Bleed (μg/ml) |
|---|---|---|---|
| Polyclonal IgG 30 mg/kg iv weekly from day 1 | 675 ± 240 (n = 5) | 3198 ± 628 (n = 4) | 13371 ± 2413 (n = 4) |
| PBS iv weekly from day 1 | 355 ± 207 (n = 5) | 4844 ± 1126 (n = 5) | 15826 ± 802 (n = 3) |
| Ab1 30 mg/kg iv weekly from day 1 | 246 ± 100 (n = 5) | 2979 ± 170 (n = 5) | 841 ± 469 (n = 10) |
| Ab1 10 mg/kg iv weekly from day 1 | 3629 ± 624 (n = 5) | 3096 ± 690 (n = 5) | 996 ± 348 (n = 10) |
| Ab1 3 mg/kg iv weekly from day 1 | 106 ± 9 (n = 5) | 1623 ± 595 (n = 4) | 435 ± 70 (n = 9) |
| Ab1 30 mg/kg iv weekly from day 8 | 375 ± 177 (n = 5) | 1492 ± 418 (n = 4) | 498 ± 83 (n = 9) |
| Ab1 10 mg/kg iv weekly from day 8 | 487 ± 170 (n = 5) | 1403 ± 187 (n = 5) | 396 ± 58 (n = 10) |
| Ab1 3 mg/kg iv weekly from day 8 | 1255 ± 516 (n = 5) | 466 ± 157 (n = 5) | 685 ± 350 (n = 5) |

SAA is up-regulated via the stimulation of hIL-6 and this response is directly correlated with circulating levels of hIL-6 derived from the implanted tumor. The surrogate marker provides an indirect readout for active hIL-6. Thus in the two treatment groups described above there are significantly decreased levels of SAA due to the neutralization of tumor-derived hIL-6. This further supports the contention that antibody Ab1 displays in vivo efficacy.

Example 11

RXF393 Cachexia Model Study 2

Introduction

A second study was performed in the RXF-393 cachexia model where treatment with antibody Ab1 was started at a later stage (days 10 and 13 post-transplantation) and with a more prolonged treatment phase (out to 49 days post transplantation). The dosing interval with antibody Ab1 was shortened to 3 days from 7 and also daily food consumption was measured. There was also an attempt to standardize the tumor sizes at the time of initiating dosing with antibody Ab1.

Methods

Eighty, 6 week old, male athymic nude mice were implanted with RXF393 tumor fragments (30-40 mg) subcutaneously in the right flank. 20 mice were selected whose tumors had reached between 270-320 mg in size and divided into two groups. One group received antibody Ab1 at 10 mg/kg i.v. every three days and the other group received polyclonal human IgG10 mg/kg every 3 days from that time-point (day 10 after transplantation). Another 20 mice were selected when their tumor size had reached 400-527 mg in size and divided into two groups. One group received antibody Ab1 at 10 mg/kg i.v. every three days and the other group received polyclonal human IgG10 mg/kg every 3 days from that time-point (day 13 after transplantation). The remaining 40 mice took no further part in the study and were euthanized at either day 49, when the tumor reached 4,000 $mm^3$ or if they became very debilitated (>30% loss of body weight).

Animals were weighed every 3-4 days from day 1 to day 49 after transplantation. Mean Percent Body Weight (MPBW) was used as the primary parameter to monitor weight loss during the study. It was calculated as follows: ((Body Weight−Tumor Weight)/Baseline Body Weight)×100. Tumor weight was measured every 3-4 days from day 5 to day 49 after transplantation. Food consumption was measured (amount consumed in 24 hours by weight (g) by each treatment group) every day from day 10 for the 270-320 mg tumor groups and day 13 for the 400-527 mg tumor groups.

Results—Survival

Figure 9:
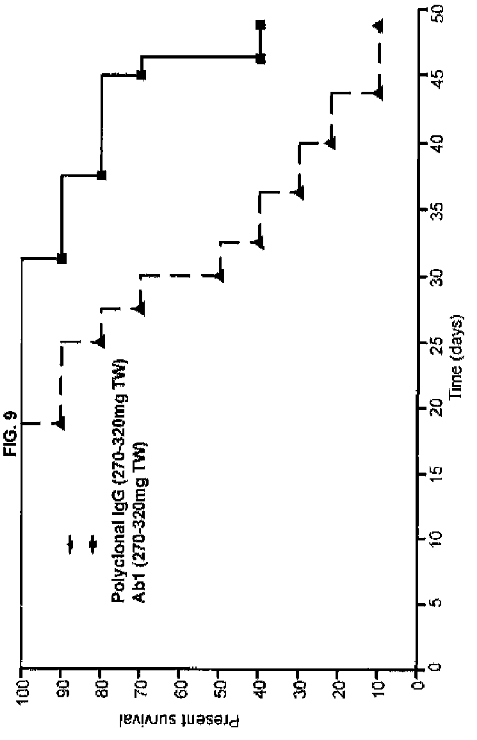
FIG. 9 provides survival data for polyclonal human IgG at 10 mg/kg i.v. every three days (270-320 mg tumor size) versus antibody Ab1 at 10 mg/kg i.v. every three days (270-320 mg tumor size). See also WO 2011/066371.

The survival curves for antibody Ab1 at 10 mg/kg i.v. every three days (270-320 mg tumor size) and for the polyclonal human IgG10 mg/kg i.v. every three days (270-320 mg tumor size) are presented in FIG. 9.

Median survival for the antibody Ab1 at 10 mg/kg i.v. every three days (270-320 mg tumor size) was 46 days and for the polyclonal human IgG at 10 mg/kg i.v. every three days (270-320 mg tumor size) was 32.5 days (p=0.0071).

Figure 10:
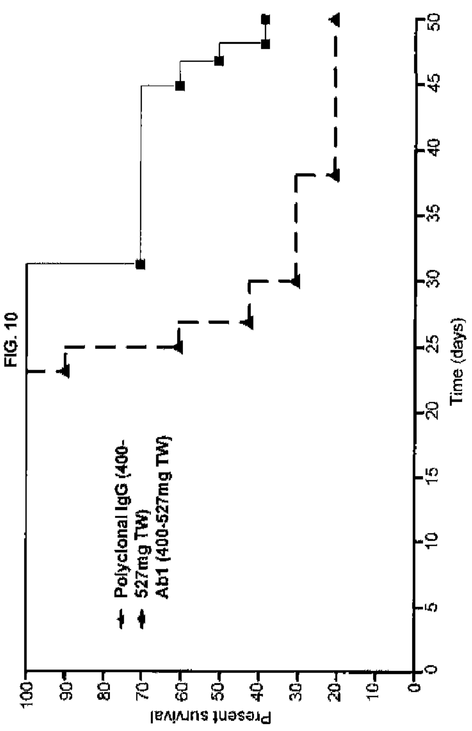
FIG. 10 provides survival data for polyclonal human IgG at 10 mg/kg i.v. every three days (400-527 mg tumor size) versus antibody Ab1 at 10 mg/kg i.v. every three days (400-527 mg tumor size). See also WO 2011/066371.

The survival curves for the antibody Ab1 at 10 mg/kg i.v. every three days (400-527 mg tumor size) and for the polyclonal human IgG at 10 mg/kg i.v. every three days (400-527 mg tumor size) are presented in FIG. 10. Median survival for the antibody Ab1 at 10 mg/kg i.v. every three days (400-527 mg tumor size) was 46.5 days and for the polyclonal human IgG at 10 mg/kg i.v. every three days (400-527 mg tumor size) was 27 days (p=0.0481).

Example 12

Multi-Dose Pharmacokinetic Evaluation of Antibody Ab1 in Non-Human Primates

Antibody Ab1 was dosed in a single bolus infusion to a single male and single female cynomologus monkey in phosphate buffered saline. Plasma samples were removed at fixed time intervals and the level of antibody Ab1 was quantitated through of the use of an antigen capture ELISA assay. Biotinylated IL-6 (50 μl of 3 μg/mL) was captured on Streptavidin coated 96 well microtiter plates. The plates were washed and blocked with 0.5% Fish skin gelatin. Appropriately diluted plasma samples were added and incubated for 1 hour at room temperature. The supernatants removed and an anti-hFc-HRP conjugated secondary antibody applied and left at room temperature.

The plates were then aspirated and TMB added to visualize the amount of antibody. The specific levels were then determined through the use of a standard curve. A second dose of antibody Ab1 was administered at day 35 to the same two cynomologus monkeys and the experiment replicated using an identical sampling plan.

This humanized full length aglycosylated antibody expressed and purified *Pichia pastoris* displays comparable characteristics to mammalian expressed protein. In addition, multiple doses of this product display reproducible half-lives inferring that this production platform does not generate products that display enhanced immunogenicity.

Example 13

Octet Mechanistic Characterization of Antibody Proteins

IL-6 signaling is dependent upon interactions between IL-6 and two receptors, IL-6R1 (CD126) and gp 130 (IL-6 signal transducer). To determine the antibody mechanism of action, mechanistic studies were performed using bio-layer interferometry with an Octet QK instrument (ForteBio; Menlo Park, Calif.). Studies were performed in two different configurations. In the first orientation, biotinylated IL-6 (R&D systems part number 206-IL-001MG/CF, biotinylated using Pierce EZ-link sulfo-NHS-LC-LC-biotin product number 21338 according to manufacturer's protocols) was initially bound to a streptavidin coated biosensor (ForteBio part number 18-5006). Binding is monitored as an increase in signal.

The IL-6 bound to the sensor was then incubated either with the antibody in question or diluent solution alone. The sensor was then incubated with soluble IL-6R1 (R&D systems product number 227-SR-025/CF) molecule. If the IL-6R1 molecule failed to bind, the antibody was deemed to block IL-6/IL-6R1 interactions. These complexes were incubated with gp130 (R&D systems 228-GP-010/CF) in the presence of IL-6R1 for stability purposes. If gp130 did not bind, it was concluded that the antibody blocked gp130 interactions with IL-6.

In the second orientation, the antibody was bound to a biosensor coated with an anti-human IgG1 Fc-specific reagent (ForteBio part number 18-5001). The IL-6 was bound to the immobilized antibody and the sensor was incubated with IL-6R1. If the IL-6R1 did not interact with the IL-6, then it was concluded that the IL-6 binding antibody blocked IL-6/IL-6R1 interactions. In those situations where antibody/IL-6/IL-6R1 was observed, the complex was incubated with gp 130 in the presence of IL-6R1. If gp 130 did not interact, then it was concluded that the antibody blocked IL-6/gp130 interactions. All studies were performed in a 200 μL final volume, at 30° C. and 1000 rpm. For these studies, all proteins were diluted using ForteBio's sample diluent buffer (part number 18-5028). Results are presented in TABLE 7.

TABLE 7

Anti-IL6 Antibodies binding to R1 or GP130

| Antibody | Blocks IL6 binding to R1 | Blocks IL6 Binding to GP130 |
|---|---|---|
| Ab1 | Yes | Yes |
| Ab2 | No | Partial |
| Ab3 | No | Yes |
| Ab4 | No | Yes |
| Ab6 | Yes | Yes |
| Ab7 | Yes | Yes |
| Ab8 | No | Yes |

Example 14

Peptide Mapping

In order to determine the epitope recognized by Ab1 on human IL-6, the antibody was employed in a western-blot based assay. The form of human IL-6 utilized in this example had a sequence of 183 amino acids in length. A 57-member library of overlapping 15 amino acid peptides encompassing this sequence was commercially synthesized and covalently bound to a PepSpots nitrocellulose membrane (JPT Peptide technologies, Berlin, Germany). The sequences of the overlapping 15 amino acid peptides is in SEQ ID NOs: 590-646. Blots were prepared and probed according to the manufacturer's recommendations.

Briefly, blots were pre-wet in methanol, rinsed in PBS, and blocked for over 2 hours in 10% non-fat milk in PBS/0.05% Tween (Blocking Solution). The Ab1 antibody was used at 1 mg/mL final dilution, and the HRP-conjugated Mouse Anti-Human-Kappa secondary antibody (Southern BioTech #9220-05) was used at a 1:5000 dilution. Antibody dilutions/incubations were performed in blocking solution. Blots were developed using Amersham ECL advance reagents (GE# RPN2135) and chemiluminescent signal documented using a CCD camera (AlphaInnotec). The sequence of the form of human IL-6 utilized to generate peptide library is set forth in SEQ ID NO: 1.

Example 15

Ab1 has High Affinity for IL-6

Surface plasmon resonance was used to measure association rate (Ka), dissociation rate (Kd) and dissociation constant (KD) for Ab1 to IL-6 from rat, mouse, dog, human, and cynomolgus monkey at 25° C. (TABLE 5). The dissociation constant for human IL-6 was 4 pM, indicating very high affinity. As expected, affinity generally decreased with phylogenetic distance from human. The dissociation constants of Ab1 for IL-6 of cynomolgus monkey, rat, and mouse were 31 pM, 1.4 nM, and 0.4 nM, respectively. Ab1 affinity for dog IL-6 below the limit of quantitation of the experiment.

The high affinity of Ab1 for mouse, rat, and cynomolgus monkey IL-6 suggest that Ab1 may be used to inhibit IL-6 of these species. This hypothesis was tested using a cell proliferation assay. In brief, each species's IL-6 was used to stimulate proliferation of T1165 cells, and the concentration at which Ab1 could inhibit 50% of proliferation (IC50) was measured. Inhibition was consistent with the measured dissociation constants (TABLE 6). These results demonstrate that Ab1 can inhibit the native IL-6 of these species, and suggest the use of these organisms for in vitro or in vivo modeling of IL-6 inhibition by Ab1. Further, other IL-6 antibodies described herein may have similar properties.

TABLE 8

Surface Plasmon Resonance: Averaged binding constants determined at 25° C. for Ab1 to IL-6.

| Species (IL-6) | $K_a$ ($M^{-1}s^{-1}$) | $K_d$ ($s^{-1}$) | $K_D$ |
|---|---|---|---|
| Rat | $1.6e^6$ | $2.2e^{-3}$ | 1.4 nM |
| Mouse | $1.1e^6$ | $4.0e^{-4}$ | 0.4 nM |
| Dog | Below LOQ[a] | Below LOQ[a] | Below LOQ[a] |
| Human | $1.6e^5$ | $5e^{-7}$ | 4 pM |
| Cynomolgus monkey | $9.6e^4$ | $3e^{-6}$ | 31 pM |

[a]Below Limit of Quantitation

TABLE 9

IC50 values for Ab1 against human, cynomolgus monkey, mouse, rat and dog IL-6 in the T1165 assay.

| IL-6 Species | IC50 (pM) |
|---|---|
| Human | 13 |
| Cynomolgus monkey | 12 |
| Mouse | 1840 |
| Rat | 2060 |
| Dog | No inhibition of cell proliferation |

Example 16

Multi-Dose Pharmacokinetic Evaluation of Antibody Ab1 in Healthy Human Volunteers Antibody Ab1 was dosed in a single bolus infusion in histidine and sorbitol to healthy human volunteers. Dosages of 1 mg, 3 mg, 10 mg, 30 mg or 100 mg were administered to each individual in dosage groups containing five to six individuals. Plasma samples were removed at fixed time intervals for up to twelve weeks. Human plasma was collected via venipuncture into a vacuum collection tube containing EDTA. Plasma was separated and used to assess the circulating levels of Ab1 using a monoclonal antibody specific for Ab1, as follows. A 96 well microtiter plate was coated overnight with the monoclonal antibody specific for Ab1 in 1×PBS overnight at 4° C. The remaining steps were conducted at room temperature. The wells were aspirated and subsequently blocked using 0.5% Fish Skin Gelatin (FSG) (Sigma) in 1×PBS for 60 minutes. Human plasma samples were then added and incubated for 60 minutes, then aspirated, then 50 μL of 1 μg/mL biotinylated IL-6 was then added to each well and incubated for 60 minutes. The wells were aspirated, and 50 μL streptavidin-HRP (Pharmingen), diluted 1:5,000 in 0.5% FSG/PBS, was added and incubated for 45 minutes. Development was conducted using standard methods employing TMB for detection. Levels were then determined via comparison to a standard curve prepared in a comparable format.

Average plasma concentration of Ab1 for each dosage group was examined. Mean AUC and Cmax increased linearly with dosage. For dosages of 30 mg and above, the average Ab1 half-life in each dosage group was between approximately 25 and 30 days. The pharmocokinetics is shown in Table 10.

TABLE 10

Summary of Ab1 Pharmacokinetics in Health Human Volunteers

| Dose of Ab1 | $T_{1/2}$ (days) | AUC (μg · h/mL) | $C_{max}$ (μg/mL) | $T_{max}$ |
|---|---|---|---|---|
| 1 mg | 10.3 | 35 | 0.1 | 8 |
| 3 mg | 11.6 | 229 | 0.7 | 4 |
| 10 mg | 22.4 | 1473 | 4.0 | 4 |
| 30 mg | 25.1 | 9076 | 19.7 | 4 |
| 100 mg | 30.3 | 26128 | 48.0 | 12 |
| 300 mg | 26.2 | 92891 | 188.0 | 12 |
| 640 mg | 30.2 | 175684 | 306.0 | 12 |

Example 17

Pharmacokinetics of Ab1 in Patients with Advanced Cancer

Antibody Ab1 was dosed in a single bolus infusion in phosphate buffered saline to five individuals with advanced cancer. Each individual received a dosage of 80 mg (n=2) or 160 mg (n=3) of Ab1. Plasma samples were drawn weekly, and the level of antibody Ab1 was quantitated as in Example 16. Average plasma concentration of Ab1 in these individuals as a function of time was examined. The average Ab1 half-life was approximately 31 days. The anti-IL-6 antibodies described herein may have similarly long half-lives.

Example 18

Ab1 has an Unexpectedly Long Half-Life

Overall, the average half-life of Ab1 was approximately 31 days in humans (for dosages of 10 mg and above), and approximately 15-21 days in cynomolgus monkey. The Ab1 half-life in humans and cynomolgus monkeys are unprecedented when compared with the half-lives of other anti-IL-6 antibodies (TABLE 11). As described above, Ab1 was derived from humanization of a rabbit antibody, and is produced from *Pichia pastoris* in an aglycosylated form. These characteristics results in an antibody with very low immunogenicity in humans. Moreover, the lack of glycosylation prevents Ab1 from interacting with the Fc receptor or complement. Without intent to be limited by theory, it is believed that the unexpectedly long half-life of Ab1 is at least partially attributable to the humanization and/or the lack of glycosylation. The particular sequence and/or structure of the antigen binding surfaces may also contribute to Ab1's half-life. See also WO 2011/066369.

TABLE 11

Elimination Half-life of Ab1

| Dose of AB1 | Cynomolgus Monkey (days) | Human (days) |
|---|---|---|
| Ab1 | 15-21 | ~31 |
| Acemra (Tocilizumab) | 7 | 6 |
| Remicade | 5 | 8-9.5 |
| Synagis | 8.6 | 20 |
| Erbitux | 3-7 | 5 |
| Zenapax | 7 | 20 |
| Avastin | 10 | 20 |
| Pertuzumab | 10 | 18-22 |

Example 19

Figure 11:
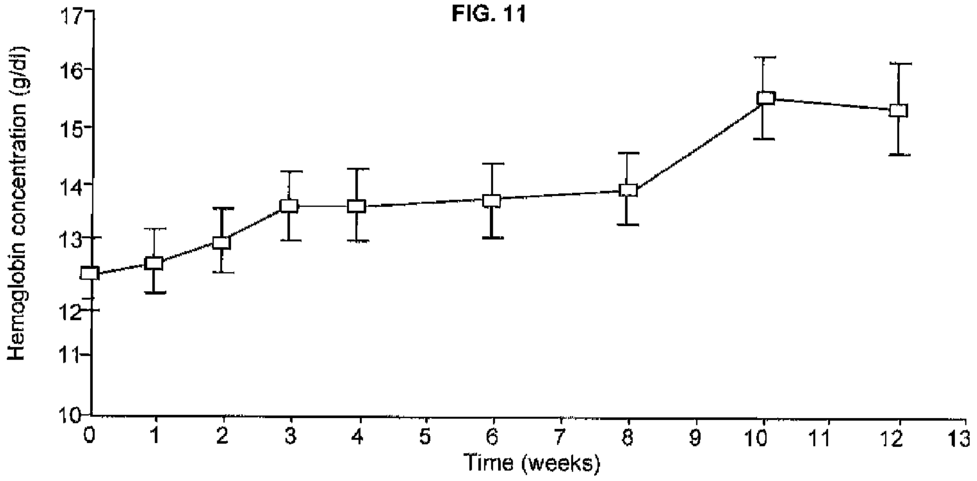
FIG. 11 shows increased hemoglobin concentration following administration of Ab1 to patients with advanced cancer. See also WO 2011/066371.
Figure 12:
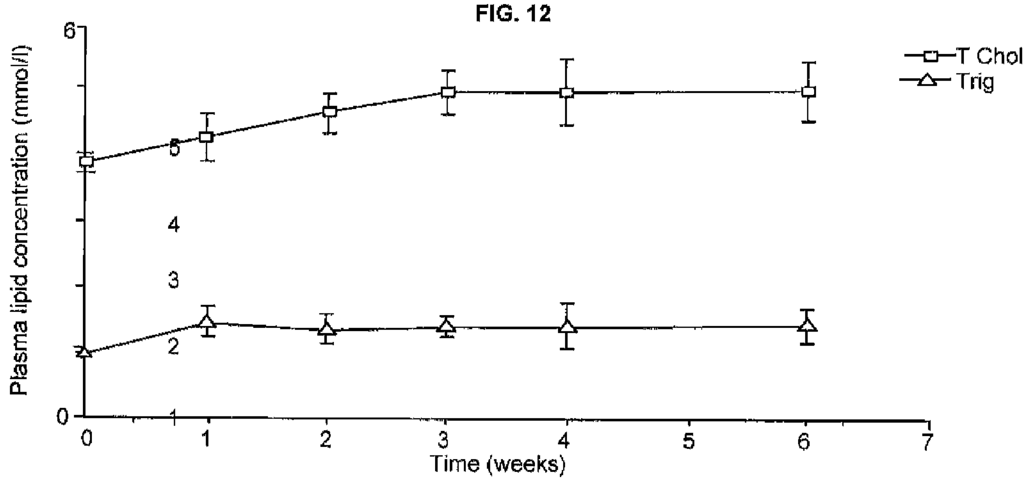
FIG. 12 depicts mean plasma lipid concentrations following administration of Ab1 to patients with advanced cancer. See also WO 2011/066371.
Figure 13:
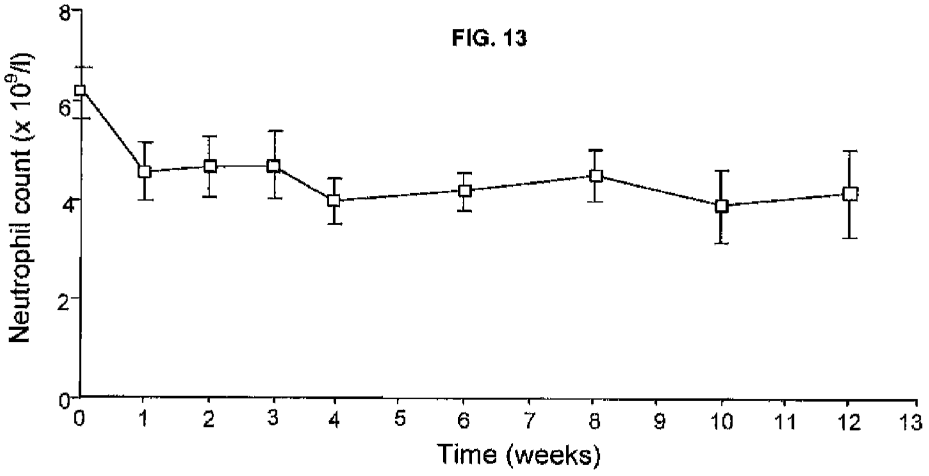
FIG. 13 depicts mean neutrophil counts following administration of Ab1 to patients with advanced cancer. See also WO 2011/066371.

Ab1 Effect on Hemoglobin Concentration, Plasma Lipid Concentration, and Neutrophil Counts in Patients with Advanced Cancer Antibody Ab1 was dosed in a single bolus infusion in phosphate buffered saline to eight individuals with advanced cancer (NSCLC, colorectal cancer, cholangiocarcinoma, or mesothelioma). Each individual received a dosage of 80 mg, 160 mg, or 320 mg of Ab1. Blood samples were removed just prior to infusion and at fixed time intervals for six weeks, and the hemoglobin concentration, plasma lipid concentration, and neutrophil counts were determined. Average hemoglobin concentration rose slightly (FIG. 11), as did total cholesterol and triglycerides (FIG. 12), while mean neutrophil counts fell slightly (FIG. 13).

These results further demonstrate some of the beneficial effects of administration of Ab1 to chronically ill individuals. Because IL-6 is the main cytokine responsible for the anemia of chronic disease (including cancer-related anemia), neutralization of IL-6 by Ab1 increases hemoglobin concentration in these individuals. Similarly, as IL-6 is centrally important in increasing neutrophil counts in inflammation, the observed slight reduction in neutrophil counts further confirms that Ab1 inhibits IL-6. Finally, IL-6 causes anorexia as well as cachexia in these patients; neutralization of IL-6 by Ab1 results in the return of appetite and reversal of cachexia. The increase in plasma lipid concentrations reflects the improved nutritional status of the patients. Taken together, these results further demonstrate that Ab1 effectively reverses these adverse consequences of IL-6 in these patients.

Example 20

Ab1 Suppresses Serum CRP in Healthy Volunteers and in Patients with Advanced Cancer Introduction Serum CRP concentrations have been identified as a strong prognostic indicator in patients with certain forms of cancer. For example, Hashimoto et al. performed univariate and multivariate analysis of preoperative serum CRP concentrations in patients with hepatocellular carcinoma in order to identify factors affecting survival and disease recurrence. Hashimoto, et al. (2005) *Cancer* 103(9): 1856-1864. Patients were classified into two groups, those with serum CRP levels >1.0 mg/dL ("the CRP positive group") and those with serum CRP levels <1.0 mg/dL ("the CRP negative group"). The authors identified "a significant correlation between preoperative serum CRP level and tumor size." Id. Furthermore, the authors found that "[t]he overall survival and recurrence-free survival rates in the CRP-positive group were significantly lower compared with the rates in the CRP-negative group." Id. The authors concluded that the preoperative CRP level of patients is an independent and significant predictive indicator or poor prognosis and early recurrence in patients with hepatocellular carcinoma.

Similar correlations have been identified by other investigators. For example, Karakiewicz et al. determined that serum CRP was an independent and informative predictor of renal cell carcinoma-specific mortality. Karakiewicz, et al. (2007) *Cancer.* 110(6):1241-1247. Accordingly, there remains a need in the art for methods and/or treatments that reduce serum C-Reactive Protein (CRP) concentrations in cancer patients, and particularly those with advanced cancers.

Methods

Healthy volunteers received a single 1-hour intravenous (IV) infusion of either 100 mg (5 patients), 30 mg (5 patients), 10 mg (6 patients), 3 mg (6 patients) or 1 mg (6 patients) of the Ab1 monoclonal antibody, while another 14 healthy volunteers received intravenous placebo. Comparatively, 2 patients with advanced forms of colorectal cancer received a single 1-hour intravenous (IV) infusion of 80 mg of the Ab1 monoclonal antibody. No further dosages of the Ab1 monoclonal antibody were administered to the test population.

Patients were evaluated prior to administration of the dosage, and thereafter on a weekly basis for at least 5 weeks post dose. At the time of each evaluation, patients were screened for serum CRP concentration.

Results—Healthy Volunteers

Figure 14A:
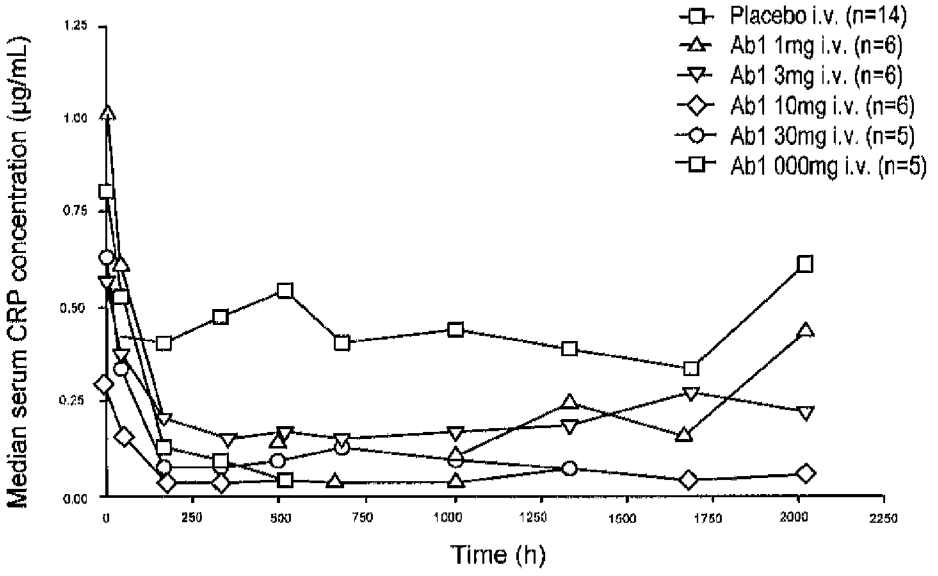
FIG. 14A demonstrates suppression of serum CRP levels in healthy individuals.

As noted above, serum CRP levels are a marker of inflammation; accordingly, baseline CRP levels are typically low in healthy individuals. The low baseline CRP levels can make a further reduction in CRP levels difficult to detect. Nonetheless, a substantial reduction in serum CRP concentrations was detectable in healthy volunteers receiving all concentrations of the Ab1 monoclonal antibody, compared to controls (FIG. 14A). The reduction in serum CRP levels was rapid, occurring within one week of antibody administration, and prolonged, continuing at least through the final measurement was taken (8 or 12 weeks from antibody administration).

Results—Cancer Patients

Figure 14B:
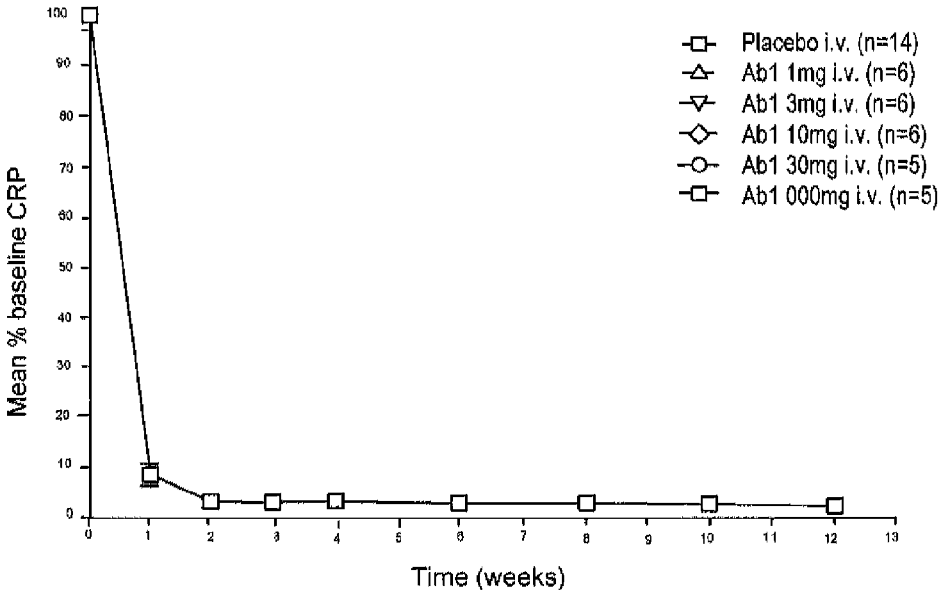
FIG. 14B demonstrates suppression of serum CRP levels in advanced cancer patients.

Five advanced cancer patients (colorectal cancer, cholangiocarcinoma, or NSCLC) having elevated serum CRP levels were dosed with 80 mg or 160 mg of Ab1. Serum CRP levels were greatly reduced in these patients (FIG. 14B). The reduction in serum CRP levels was rapid, with 90% of the decrease occurring within one week of Ab1 administration, and prolonged, continuing at least until the final measurement was taken (up to twelve weeks). In two representative individuals, the CRP levels were lowered to below the normal reference range (less than 5-6 mg/l) within one week. Thus, administration of Ab1 to patients can cause a rapid and sustained suppression of serum CRP levels.

Example 21

Ab1 Improved Muscular Strength, Improved Weight, and Reduced Fatigue in Patients with Advanced Cancer Introduction Weight loss and fatigue (and accompanying muscular weakness) are very common symptoms of patients with advanced forms of cancer, and these symptoms can worsen as the cancer continues to progress. Fatigue, weight loss and muscular weakness can have significant negative effects on the recovery of patients with advanced forms of cancer, for example by disrupting lifestyles and relationships and affecting the willingness or ability of patients to continue cancer treatments. Known methods of addressing fatigue, weight loss and muscular weakness include regular routines of fitness and exercise, methods of conserving the patient's energy, and treatments that address anemia-induced fatigue and muscular weakness. Nevertheless, there remains a need in the art for methods and/or treatments that improve fatigue, weight loss and muscular weakness in cancer patients.

Methods

Four patients with advanced forms of cancer [(colorectal cancer (2), NSCLC (1), cholangiocarcinoma (1)] received a single 1-hour intravenous (IV) infusion of either 80 mg or 160 mg of the Ab1 monoclonal antibody. No further dosages of the Ab1 monoclonal antibody were administered to the test population.

Patients were evaluated prior to administration of the dosage, and thereafter for at least 6 weeks post dose. At the time of each evaluation, patients were screened for the following: a.) any change in weight; b.) fatigue as measured using the Facit-F Fatigue Subscale questionnaire a medically recognized test for evaluating fatigue. See, e.g., Cella, et al. (2002) *Cancer* 94(2): 528-538; Cella, et al. (2002) *Journal of Pain & Symptom Management* 24(6): 547-561); and hand-grip strength (a medically recognized test for evaluating muscle strength, typically employing a handgrip dynamometer).

Results—Weight Change

The averaged data for both dosage concentrations (80 mg and 160 mg) of the Ab1 monoclonal antibody demonstrated an increase of about 2 kilograms of weight per patient over the period of 6 weeks.

Fatigue

The averaged data for both dosage concentrations (80 mg and 160 mg) of the Ab1 monoclonal antibody demonstrated an increase in the mean Facit-F FS subscale score of at least about 10 points in the patient population over the period of 6 weeks.

Hand-Grip Strength

The averaged data for both dosage concentrations (80 mg and 160 mg) of the Ab1 monoclonal antibody demonstrated an increase in the mean hand-grip strength of at least about 10 percent in the patient population over the period of 6 weeks. See, e.g., WO 2011/066371.

Example 22

Ab1 for Prevention of Thrombosis

Prior studies have shown that administration of an anti-IL-6 antibody can cause decreased platelet counts. Emilie, et al. (1994) *Blood* 84(8): 2472-9; Blay, et al. (1997) *Int J Cancer* 72(3): 424-30. These results have apparently been viewed as an indicator of potential danger, because further decreases in platelet counts could cause complications such as bleeding. However, Applicants have now discerned that inhibiting IL-6 restores a normal coagulation profile, which Applicants predict will prevent thrombosis. Decreased platelet counts resulting from inhibition of IL-6 is not a sign of potential danger but rather reflects the beneficial restoration of normal coagulation.

The mechanism by which normal coagulation is restored is believed to result from the interplay between IL-6 and the acute phase reaction. In response to elevated IL-6 levels, as for example in a cancer patient, the liver produces acute phase proteins. These acute phase proteins include coagulation factors, such as Factor II, Factor V, Factor VIII, Factor IX, Factor XI, Factor XII, F/fibrin degradation products, thrombin-antithrombin III complex, fibrinogen, plasminogen, prothrombin, and von Willebrand factor. This increase in coagulation factors may be measured directly, or may be inferred from functional measurements of clotting ability. Antagonists of IL-6, such as Ab1, suppresses acute phase proteins, e.g., Serum Amyloid (Example 10). Applicants now predict that this suppression of acute phase proteins will restore the normal coagulation profile, and thereby prevent thrombosis. The restoration of normal coagulation may cause a slight drop in platelet counts, but the patient will nonetheless retain normal coagulation ability and thus will not have an increased risk of bleeding. Such a treatment will represent a vast improvement over the available anticoagulation therapies whose usefulness is limited by the risk of adverse side-effects, such as major bleeding. See, e.g., WO 2011/066371.

Applicants contemplate that the same beneficial effects of inhibiting IL-6 will be obtained regardless of the method of inhibition. Suitable methods of inhibiting IL-6 include administration of anti-IL-6 antibodies, antisense therapy, soluble IL-6 receptor, either individually or in combinations.

Example 23

Ab1 Increases Plasma Albumin Concentration in Patients with Advanced Cancer

Introduction

Serum albumin concentrations are recognized as predictive indicators of survival and/or recovery success of cancer patients. Hypoalbumenia correlates strongly with poor patient performance in numerous forms of cancer. For example, in one study no patients undergoing systemic chemotherapy for metastatic pancreatic adenocarcinoma and having serum albumin levels less than 3.5 g/dL successfully responded to systemic chemotherapy. Fujishiro, et al. (2000) *Hepatogastroenterology* 47(36): 1744-46 and Senior and Maroni (1999) *Am. Soc. Nutr. Sci.* 129: 313S-314S. In at least one study, attempts to rectify hypoalbuminemia in 27 patients with metastatic cancer by daily intravenous albumin infusion of 20 g until normal serum albumin levels (>3.5 g/dL) were achieved had little success. Demirkazik, et al. (2002) *Proc. Am. Soc. Clin. Oncol.* 21:Abstr 2892. Accordingly, there remains a need in the art for methods and/or treatments that improve serum albumin concentrations in cancer patients and address hypoalbuminemic states in cancer patients, particularly those with advanced cancers.

Methods

Four patients with advanced forms of cancer [(colorectal cancer (2), NSCLC (1), cholangiocarcinoma (1)] received a single 1-hour intravenous (IV) infusion of either 80 mg or 160 mg of the Ab1 monoclonal antibody. No further dosages of the Ab1 monoclonal antibody were administered to the test population.

Patients were evaluated prior to administration of the dosage, and thereafter for at least 6 weeks post dose. At the time of each evaluation, patients were screened for plasma albumin concentration.

Results

The averaged data for both dosage concentrations (80 mg and 160 mg) of the Ab1 monoclonal antibody demonstrated an increase of about 5 g/L of plasma albumin concentration per patient over the period of 6 weeks. See, e.g., WO 2011/066371.

Example 24

Ab1 Suppresses Serum CRP in Patients with Advanced Cancer

Introduction

Serum CRP concentrations have been identified as a strong prognostic indicator in patients with certain forms of cancer. For example, Hashimoto et al. performed univariate and multivariate analysis of preoperative serum CRP concentrations in patients with hepatocellular carcinoma in order to identify factors affecting survival and disease recurrence. Hashimoto, et al. (2005) *Cancer* 103(9): 1856-1864. Patients were classified into two groups, those with serum CRP levels >1.0 mg/dL ("the CRP positive group") and those with serum CRP levels <1.0 mg/dL ("the CRP negative group"). The authors identified "a significant correlation between preoperative serum CRP level and tumor size." Id. Furthermore, the authors found that "[t]he overall survival and recurrence-free survival rates in the CRP-positive group were significantly lower compared with the rates in the CRP-negative group." Id. The authors concluded that the preoperative CRP level of patients is an independent and significant predictive indicator of poor prognosis and early recurrence in patients with hepatocellular carcinoma.

Similar correlations have been identified by other investigators. For example, Karakiewicz et al. determined that serum CRP was an independent and informative predictor of renal cell carcinoma-specific mortality. Karakiewicz, et al. (2007) *Cancer* 110(6):1241-1247. Accordingly, there remains a need in the art for methods and/or treatments that reduce serum C-Reactive Protein (CRP) concentrations in cancer patients, and particularly those with advanced cancers.

Methods

One-hundred twenty-four patients with non-small cell lung cancer (NSCLC) were divided into 4 treatment groups. Patients in one group received one 1-hour intravenous (IV) infusion of either placebo (n=31), 80 mg (n=29), 160 mg (n=32), or 320 mg (n=32) of the Ab1 monoclonal antibody every 8 weeks over a 24 week duration for a total of 3 doses. CRP concentration was quantitated by a C-reactive protein particle-enhanced immunoturbidimetric assay using latex-attached anti-CRP antibodies (i.e. Roche CRP Tinaquant®). Briefly, about 1.0 mL of patient sample serum was collected and stored in a plastic collection tube. Sample was placed into appropriate buffer, and anti-CRP antibody coupled to latex microparticles was added to the sample to start the reaction. These anti-CRP antibodies with conjugated latex microparticles react with antigen in the sample to form an antigen/antibody complex. Following agglutination, this was measured turbidimetrically using a Roche/Hitachi Modular P analizer.

Patients were evaluated prior to administration of the dosage, and thereafter at weeks 2, 4, 8, and 12. At the time of each evaluation, patients were screened for serum CRP concentration.

Results

Figure 15A:
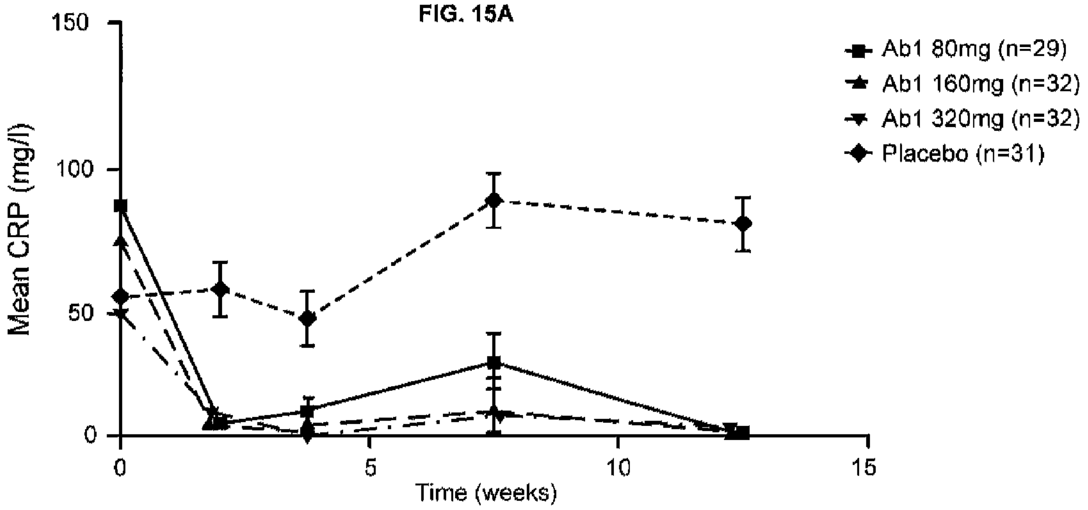
FIG. 15A depicts the mean CRP values for each dosage concentrations (placebo, 80 mg, 160 mg, and 320 mg) of the Ab1 monoclonal antibody in NSCLC patients.
Figure 15B:
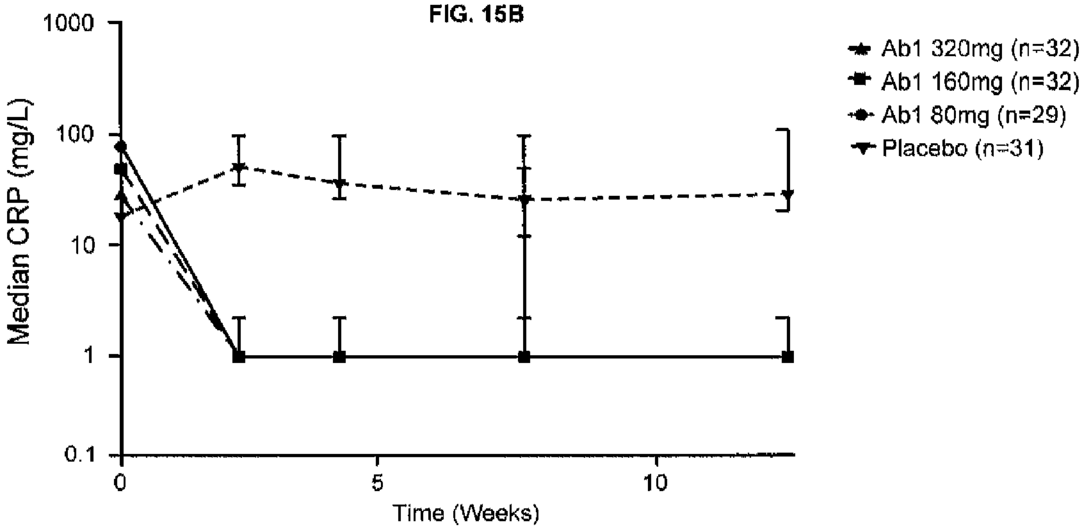
FIG. 15B depicts the change in median values of CRP from each dosage concentration group corresponding to FIG. 15A in NSCLC patients.

The averaged data for each dosage concentrations (placebo, 80 mg, 160 mg, and 320 mg) of the Ab1 monoclonal antibody are plotted in FIG. 15A. All dosage levels of Ab1 antibody demonstrated an immediate drop in CRP concentrations relative to placebo over the period of 12 weeks. CRP levels displayed breakthrough at 8 weeks post-dosing. The CRP levels fell below 5 mg/L by week 12. Median values of CRP demonstrated rapid and sustained decreases for all dosage concentrations relative to placebo (FIG. 15B). Thus, administration of Ab1 to advanced cancer patients can cause a rapid and sustained suppression of serum CRP levels.

Example 25

Ab1 Suppresses Serum CRP in Patients with Advanced Cancers

Introduction

Serum CRP concentrations have been identified as a strong prognostic indicator in patients with certain forms of cancer. For example, Hashimoto et al. performed univariate and multivariate analysis of preoperative serum CRP concentrations in patients with hepatocellular carcinoma in order to identify factors affecting survival and disease recurrence. Hashimoto, et al. (2005) *Cancer* 103(9): 1856-1864. Patients were classified into two groups, those with serum CRP levels >1.0 mg/dL ("the CRP positive group") and those with serum CRP levels <1.0 mg/dL ("the CRP negative group"). The authors identified "a significant correlation between preoperative serum CRP level and tumor size." Id. Furthermore, the authors found that "[t]he overall survival and recurrence-free survival rates in the CRP-positive group were significantly lower compared with the rates in the CRP-negative group." Id. The authors concluded that the preoperative CRP level of patients is an independent and significant predictive indicator of poor prognosis and early recurrence in patients with hepatocellular carcinoma.

Similar correlations have been identified by other investigators. For example, Karakiewicz et al. determined that serum CRP was an independent and informative predictor of renal cell carcinoma-specific mortality. Karakiewicz, et al. (2007) *Cancer* 110(6): 1241-1247. Accordingly, there remains a need in the art for methods and/or treatments that reduce serum C-Reactive Protein (CRP) concentrations in cancer patients, and particularly those with advanced cancers.

Methods

Eight patients with various forms of advanced cancer [(colorectal (3), NSCLC (1), cholangio (1), and mesothelioma (2)] received a single 1-hour intravenous infusion of either 80 mg (2 patients), 160 mg (3 patients) or 320 mg (3 patients) of the Ab1 monoclonal antibody. No further dosages of the Ab1 monoclonal antibody were administered to the test population.

Patients were evaluated prior to administration of the dosage and thereafter on a weekly basis for at least 8 weeks post dose. At the time of each evaluation, patients were screened for serum CRP concentration. CRP concentration was quantitated by a C-reactive protein particle-enhanced immunoturbidimetric assay using latex-attached anti-CRP antibodies (i.e. Roche CRP Tinaquant®). Briefly, about 1.0 mL of patient sample serum was collected and stored in a plastic collection tube. Sample was placed into appropriate buffer, and anti-CRP antibody coupled to latex microparticles was added to the sample to start the reaction. These anti-CRP antibodies with conjugated latex microparticles react with antigen in the sample to form an antigen/antibody complex. Following agglutination, this was measured turbidimetrically using a Roche/Hitachi Modular P analizer.

Results

Figure 16:
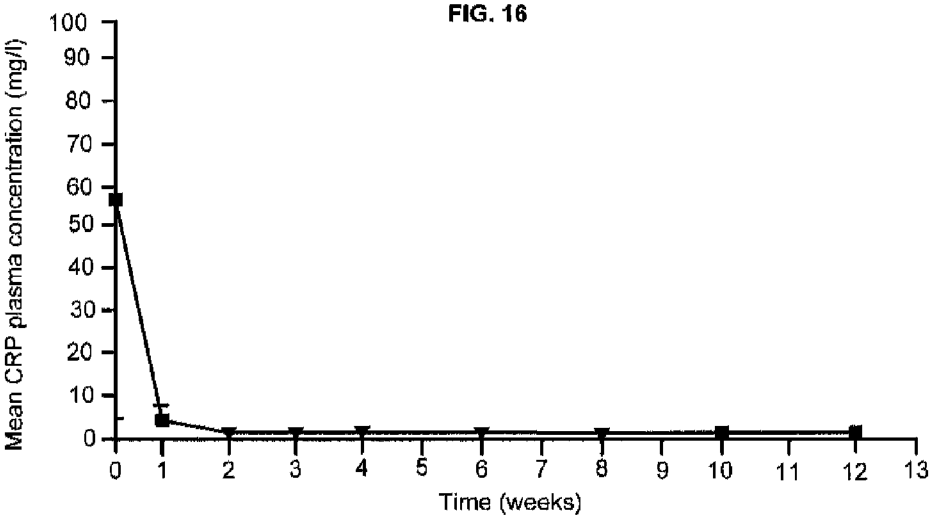
FIG. 16 depicts the mean plasma CRP concentration in patients with advanced cancer after a single I.V. infusion of 80, 160, or 320 mg of Ab1 (ALD518) (n=8).

Serum CRP levels were greatly reduced in all patients studied (FIG. 16). The reduction in serum CRP levels was rapid, with approximately 90% of the decrease occurring within one week of Ab1 administration, and prolonged diminished levels continued at least until the final measurement was taken (up to twelve weeks). In all cases except one patient with colorectal cancer, CRP levels fell to at or below the normal reference range (less than 5-6 mg/L) within one week. The colorectal cancer patient achieved similar normal levels by week 4 of the study. Thus, administration of Ab1 to advanced cancer patients can cause a rapid and sustained suppression of serum CRP levels.

Example 26

Ab1 Suppresses Serum CRP in Patients with Rheumatoid Arthritis

Introduction

Serum CRP concentrations have been identified as a strong prognostic indicator in patients with rheumatoid arthritis. Patients suffering from rheumatoid arthritis with high levels of CRP demonstrated almost universal deterioration. Amos, et al. (1977) *Br. Med. J.* 1: 195-97. Conversely, patients with low CRP levels showed no disease progression, suggesting that sustaining low levels of CRP is necessary for effectively treating rheumatoid arthritis. Id. Tracking of CRP during rheumatoid arthritis treatment regimes of gold, D-penicillamine, chloroquine, or dapsone indicated that radiological deterioration was impeded after the first 6 months of treatment when CRP levels were consistently controlled. Dawes et al., (1986) *Rheumatology* 25: 44-49. A highly significant correlation between CRP production and radiological progression was identified. van Leeuwen, et al. (1997) *Rheumatology* 32 (Supp. 3): 9-13. Another study revealed that for patients with active rheumatoid arthritis, suppression of abnormally elevated CRP led to improvement in functional testing metrics, whereas sustained CRP elevation associated with deterioration in the same metrics. Devlin, et al. (1997) *J. Rheumatol.* 24: 9-13. No further deterioration was observed without CRP re-elevation, indicating CRP suppression as a viable candidate for rheumatoid arthritis treatment. Id. Accordingly, there remains a need in the art for methods and/or treatments that reduce serum C-Reactive Protein (CRP) concentrations in rheumatoid arthritis patients.

Methods

One-hundred twenty-seven patients with active rheumatoid arthritis and CRP ≥10 mg/L were divided into 4 treatment groups. Patients in one group received one 1-hour intravenous (IV) infusion of either placebo (n=33), 80 mg (n=32), 160 mg (n=34), or 320 mg (n=28) of the Ab1 monoclonal antibody, once at the start of the 16 week trial and again at week 8. CRP concentration was quantitated by a C-reactive protein particle-enhanced immunoturbidimetric assay using latex-attached anti-CRP antibodies (i.e., Roche CRP Tinaquant®). Briefly, about 1.0 mL of patient sample serum was collected and stored in a plastic collection tube. Sample was placed into appropriate buffer, and anti-CRP antibody coupled to latex microparticles was added to the sample to start the reaction. These anti-CRP antibodies with conjugated latex microparticles react with antigen in the sample to form an antigen/antibody complex. Following agglutination, this was measured turbidimetrically using a Roche/Hitachi Modular P analizer. Data on CRP concentration was collected every week for the first 4 weeks, every two weeks between weeks 4 and 12, and at the conclusion of the test at week 16.

Results

Figure 17:
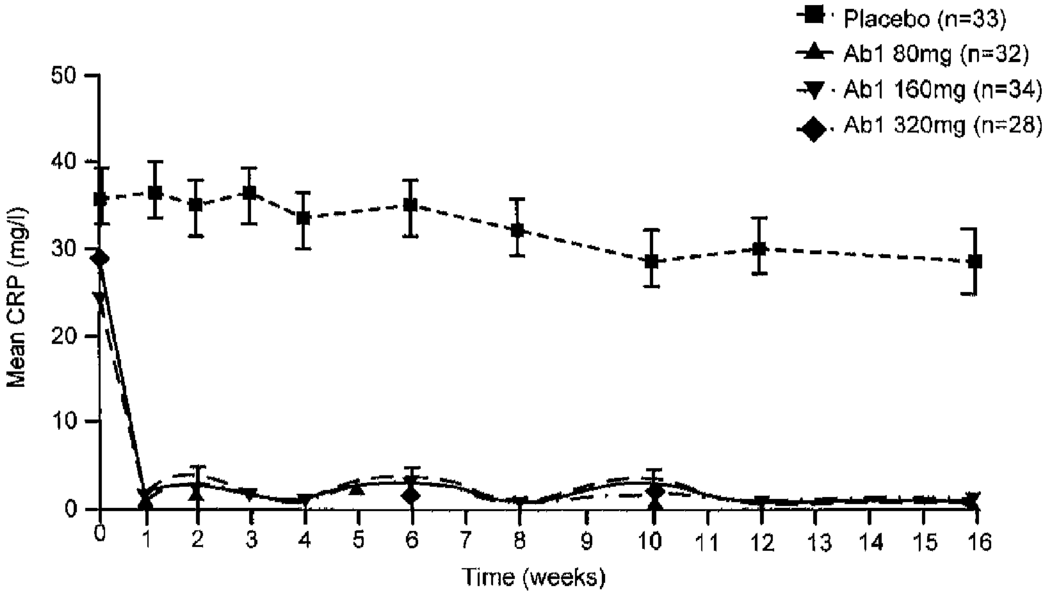
FIG. 17 depicts the mean serum CRP levels in patients with rheumatoid arthritis patients with an inadequate response to methotrexate after dosing at 80, 160, or 320 mg of Ab1 (ALD518).

Serum CRP levels were greatly reduced in all patients studied (FIG. 17). The reduction in serum CRP levels was rapid, with immediate reduction in CRP levels relative to placebo within one week of Ab1 administration, and prolonged diminished levels continued at least until the final measurement was taken (up to sixteen weeks). In all cases, CRP levels fell to at or below the normal reference range (less than 5-6 mg/L) within one week. Thus, administration of Ab1 to rheumatoid arthritis patients can cause a rapid and sustained suppression of serum CRP levels and presents an effective treatment regime.

Example 27

Ab1 Increases Hemoglobin in Patients with Advanced Cancer

Figure 18A:
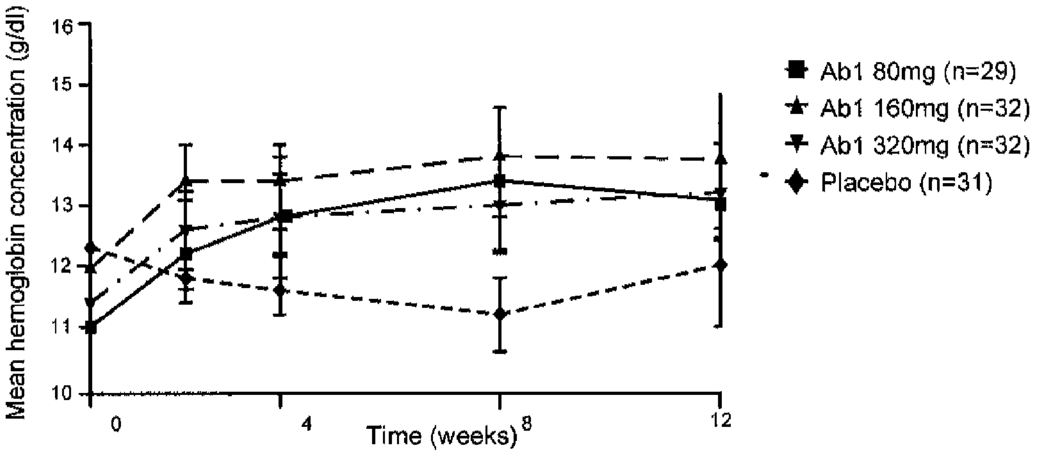
FIG. 18A depicts that Ab1 increases mean hemoglobin concentration (g/dL) at 80, 160 and 320 mg after 12 weeks of dosing in NSCLC patients versus placebo. See also WO 2011/066371.
Figure 18B:
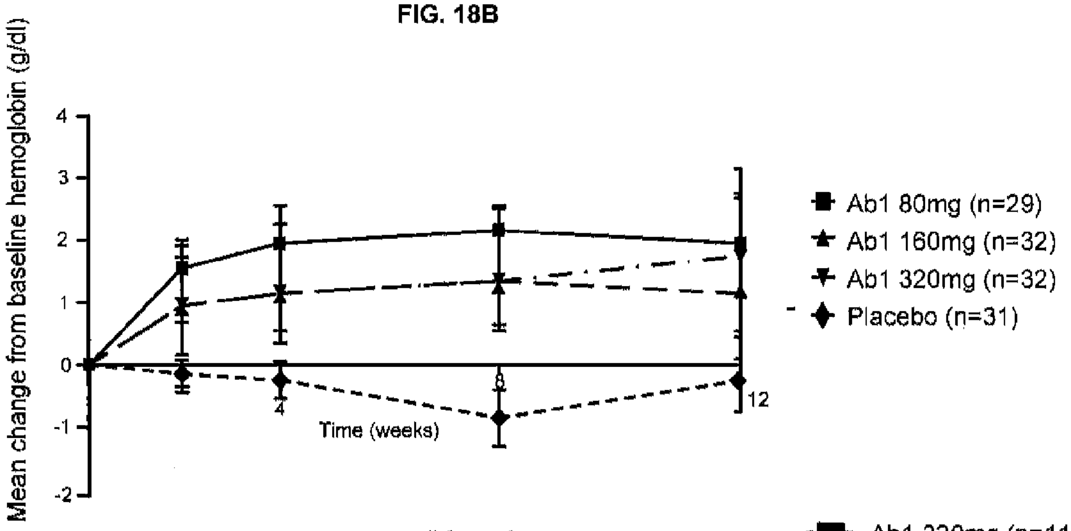
FIG. 18B depicts the mean change from baseline in hemoglobin concentration (g/dL) for NSCLC patients versus placebo. See also WO 2011/066371.

Antibody Ab1 was dosed at 80 mg, 160 mg, or 320 mg of Ab1 in phosphate buffered saline to 93 individuals with non-small cell lung carcinoma. The placebo group of 31 individuals with non-small cell lung carcinoma was dosed with phosphate buffered saline only. Blood samples were removed just prior to dosing (zero week), and at two, four, eight and twelve weeks, and the hemoglobin concentration was determined. Mean hemoglobin concentration rose for those receiving antibody Ab1, while mean hemoglobin concentration of those receiving placebo did not rise after twelve weeks when compared to the concentration just prior to dosing (zero week) (FIGS. 18A and 18B).

Figure 18C:
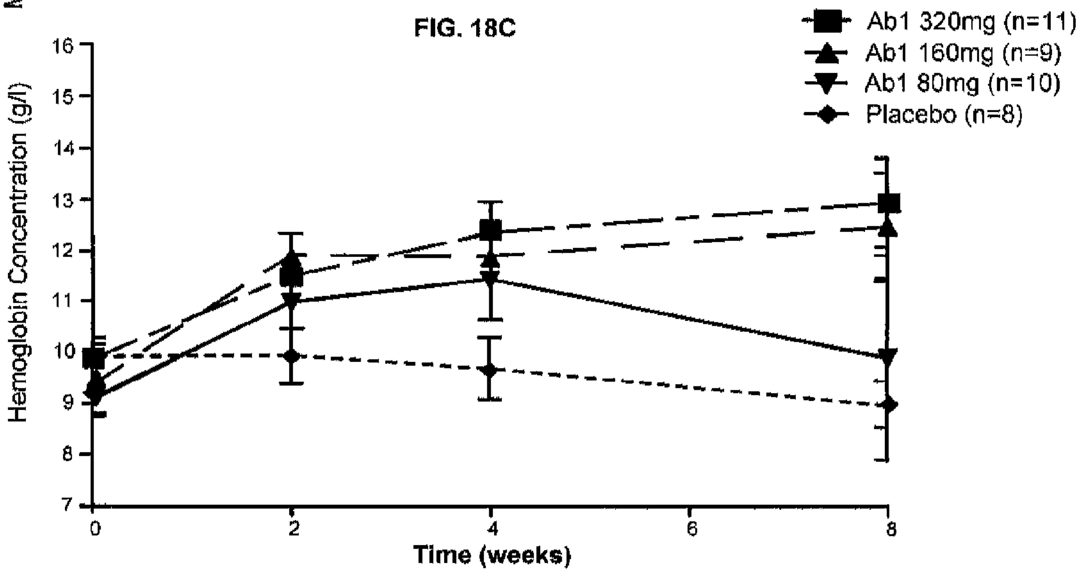
FIG. 18C depicts the mean hemoglobin concentration (g/dL) in NSCLC patients with a baseline hemoglobin below 11 g/L at baseline versus time with Ab1 compared to placebo.

A subset of the study population began the study with low levels of hemoglobin, defined as a baseline hemoglobin concentration below 11 g/l. Mean hemoglobin concentration rose above 11 g/l after eight weeks for those receiving antibody Ab1 at dosages of 160 mg and 320 mg, while mean hemoglobin concentration of those receiving antibody Ab1 at dosages of 80 mg or placebo did not rise above 11 g/l after eight weeks (FIG. 18C).

These results further demonstrate some of the beneficial effects of administration of Ab1 to chronically ill individuals. Because IL-6 is the main cytokine responsible for the anemia of chronic disease (including cancer-related anemia), neutralization of IL-6 by Ab1 increases hemoglobin concentration in these individuals.

Example 28

Ab1 Increases Hemoglobin in Patients with Rheumatoid Arthritis

Figure 19:
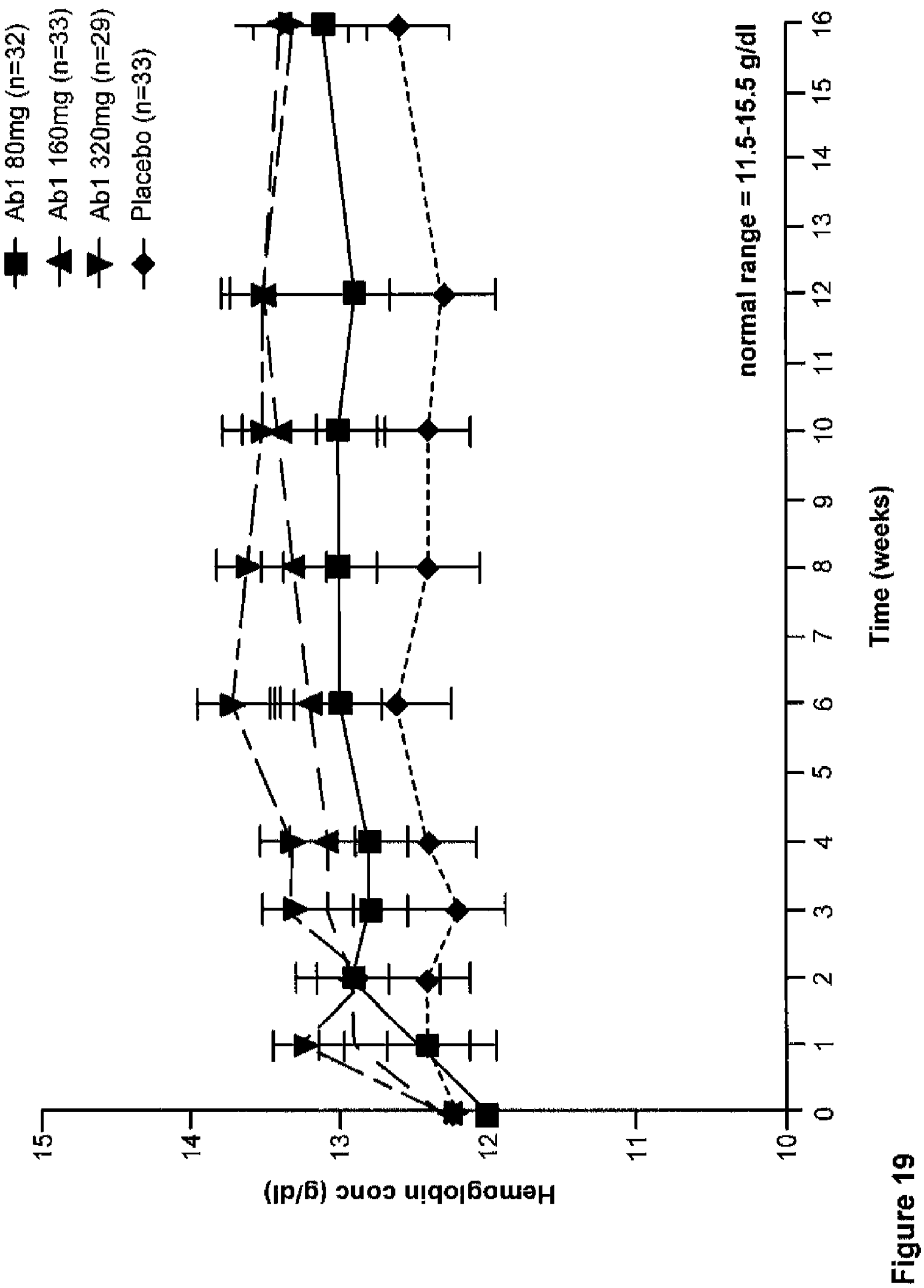
FIG. 19 depicts the mean change from baseline in hemoglobin concentration (g/dL) for rhemumatoid arthritis patients with an inadequate response to methotrexate versus placebo. The normal range of hemaglobin concentration is approximately 11.5-15.5 g/dL. See also WO 2011/066371.

Hemoglobin levels were analyzed in patients with rheumatoid arthritis during treatment with Ab1 antibody. Ab1 antibody was dosed at 80 mg, 160 mg, or 320 mg in phosphate buffered saline to 94 individuals with rheumatoid arthritis. The placebo group of 33 individuals with rheumatoid arthritis was dosed with phosphate buffered saline only. Blood samples were removed just prior to dosing (zero week), and at one, two, three, four, six, eight, ten, twelve, and sixteen weeks, and the hemoglobin concentration was determined. Mean hemoglobin concentration rose for those receiving antibody Ab1, while mean hemoglobin concentration of those receiving placebo did not appreciably rise after sixteen weeks when compared to the concentration just prior to dosing (zero week) (FIG. 19).

These results further demonstrate some of the beneficial effects of administration of Ab1 to chronically ill individuals. Because IL-6 is the main cytokine responsible for the anemia of chronic disease (including cancer-related anemia), neutralization of IL-6 by Ab1 increases hemoglobin concentration.

Example 29

Ab1 Increases Albumin in Patients with Advanced Cancer

Introduction

Serum albumin concentrations are recognized as predictive indicators of survival and/or recovery success of cancer patients. Hypoalbumenia correlates strongly with poor patient performance in numerous forms of cancer. For example, in one study no patients undergoing systemic chemotherapy for metastatic pancreatic adenocarcinoma and having serum albumin levels less than 3.5 g/dL successfully responded to systemic chemotherapy. Fujishiro, et al. (2000) *Hepatogastroenterology* 47(36): 1744-46. The authors conclude that "[p]atients with . . . hypoalbuminemia . . . might be inappropriate candidates for systemic chemotherapy and might be treated with other experimental approaches or supportive care." Id.

Similarly, Senior and Maroni state that "[t]he recent appreciation that hypoalbuminemia is the most powerful predictor of mortality in end-stage renal disease highlights the critical importance of ensuring adequate protein intake in this patient population." Senior & Maroni (1999) *Am. Soc. Nutr. Sci.* 129: 313S-314S.

In at least one study, attempts to rectify hypoalbuminemia in 27 patients with metastatic cancer by daily intravenous albumin infusion of 20 g until normal serum albumin levels (>3.5 g/dL) were achieved had little success. The authors note that "[a]ibumin infusion for the advanced stage cancer patients has limited value in clinical practice. Patients with PS 4 and hypoalbuminemia have poorer prognosis." Demirkazik, et al. (2002) *Proc. Am. Soc. Clin. Oncol.* 21: Abstr 2892.

Accordingly, there remains a need in the art for methods and/or treatments that improve serum albumin concentrations in cancer patients and address hypoalbuminemic states in cancer patients, particularly those with advanced cancers.

Methods

Antibody Ab1 was dosed at 80 mg, 160 mg, or 320 mg of Ab1 in phosphate buffered saline to 93 individuals with non-small cell lung carcinoma. Each individual received a dosage of. The placebo group of 31 individuals with non-small cell lung carcinoma was dosed with phosphate buffered saline only. Blood samples were removed just prior to dosing (zero week), and at two, four, eight and twelve weeks, and the albumin concentration was determined.

Results

Figure 20A:
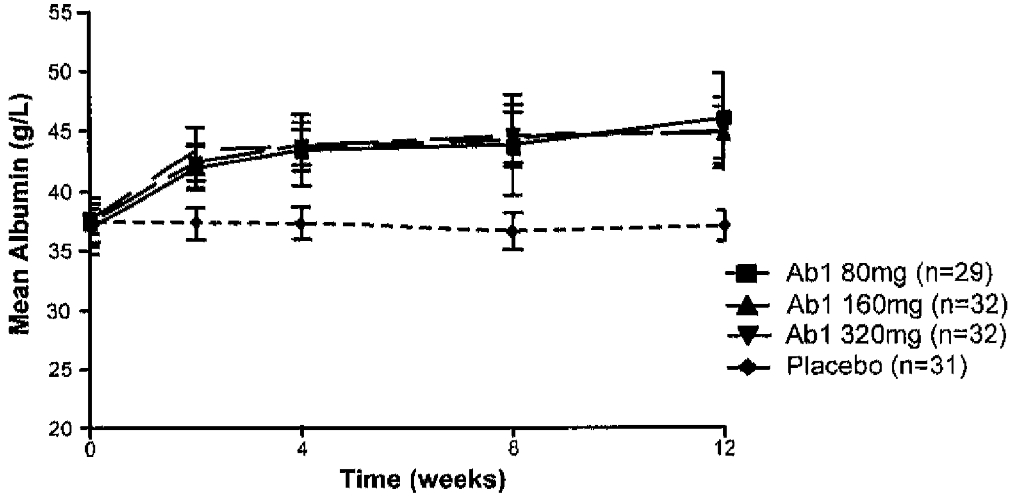
FIG. 20A depicts that Ab1 increases mean albumin concentration at 80, 160 and 320 mg in NSCLC patients. See also WO 2011/066371.
Figure 20B:
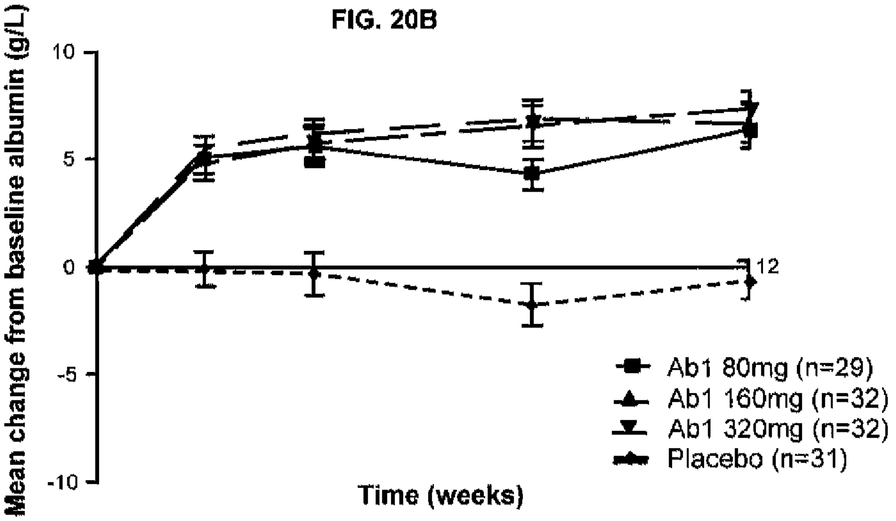
FIG. 20B depicts the change from baseline for mean albumin concentration from each dosage concentration group corresponding to FIG. 20A in NSCLC patients. See also WO 2011/066371.

Mean albumin concentration rose for those receiving antibody Ab1, while mean albumin concentration of those receiving placebo did not rise after twelve weeks when compared to the concentration just prior to dosing (zero week) (FIG. 20A). The change from baseline albumin values for all dosage concentration groups is plotted in FIG. 20B.

Figure 20C:
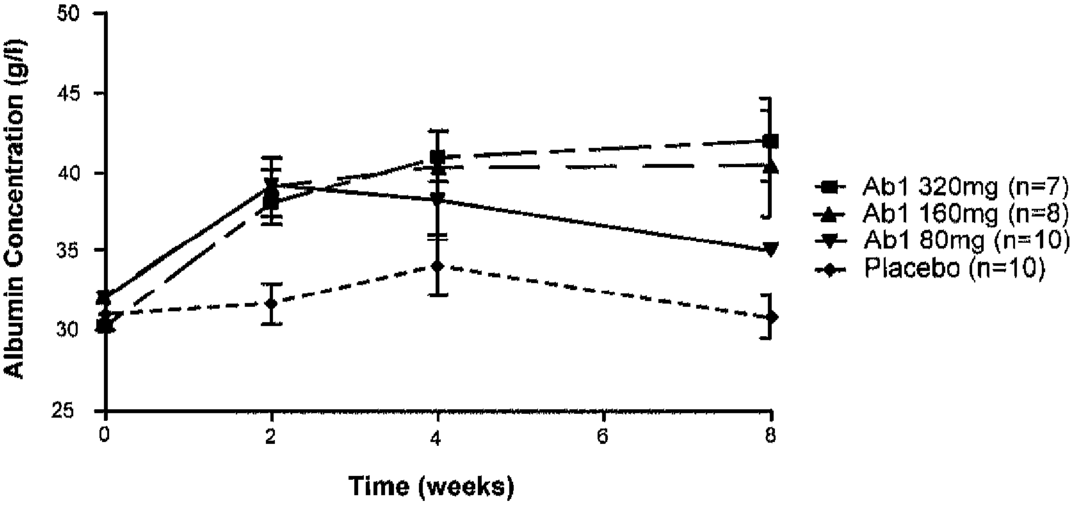
FIG. 20C depicts the mean albumin concentration in NSCLC patients with a baseline albumin ≤35 g/l at baseline versus time for Ab1 versus placebo. See also WO 2011/066371.

A subset of the study population began the study with low levels of albumin, defined as a baseline albumin concentration less than or equal to 35 g/L. Mean albumin concentration initially rose with all dosages of antibody Ab1 over placebo, but only patients receiving 160 mg or 320 mg demonstrated sustained albumin levels above 35 g/L over 8 weeks of the study (FIG. 20C). The 80 mg dosage group demonstrated an initial increase, but gradually declined after week 2 and never rose above 35 g/L during the 8 weeks where data was available. Id.

Example 30

Ab1 Improved Weight and Reduced Fatigue in Patients with Advanced Cancer

Introduction

Weight loss and fatigue are very common symptoms of patients with advanced forms of cancer, and these symptoms can worsen as the cancer continues to progress. Fatigue and weight loss can have significant negative effects on the recovery of patients with advanced forms of cancer, for example by disrupting lifestyles and relationships and affecting the willingness or ability of patients to continue cancer treatments. Known methods of addressing fatigue and weight loss include regular routines of fitness and exercise, methods of conserving the patient's energy, and treatments that address anemia-induced fatigue. Nevertheless, there remains a need in the art for methods and/or treatments that improve fatigue and weight loss in cancer patients.

Methods

One-hundred twenty-four patients with non-small cell lung cancer (NSCLC) were divided into 4 treatment groups. Patients in one group received one 1-hour intravenous (IV) infusion of either placebo (n=31), 80 mg (n=29), 160 mg (n=32), or 320 mg (n=32) of the Ab1 monoclonal antibody every 8 weeks over a 24 week duration for a total of 3 doses.

Patients were evaluated prior to administration of the dosage, and thereafter for at least 12 weeks post dose. At the time of each evaluation, patients were screened for the following: any change in weight; and fatigue as measured using the Facit-F Fatigue Subscale questionnaire a medically recognized test for evaluating fatigue. See, e.g., Cella, et al. (2002) *Cancer* 94(2): 528-538; Cella, et al. (2002) *Journal of Pain & Symptom Management* 24(6): 547-561.

Results

Weight Change

The averaged weight change data from each dosage concentration group (placebo, 80 mg, 160 mg, and 320 mg) of the Ab1 monoclonal antibody over 12 weeks. The average percent change in body weight from each dosage concentration. The averaged lean body mass data for the dosage concentration groups.

Fatigue

The averaged fatigue from each dosage concentration group (placebo, 80 mg, 160 mg, and 320 mg) of the Ab1 monoclonal antibody demonstrated increases in the mean Facit-F FS subscale score for some of the dosage concentration groups in the patient population over the period of 8 weeks.

Example 31

Ab1 Decreases D-Dimer Levels in Patients with Advanced Cancer

Introduction

D-dimer concentrations are recognized as useful diagnostic tools in predicting risks of thrombotic events in patients. Adam, et al. (2009) *Blood* 113: 2878-87. Patients that are negative for D-dimer have a low probability for thrombosis. For example, D-dimer analysis can rule out suspected lower-extremity deep-vein thrombosis in patients. Wells, et al. (2003) *N. Engl. J. Med.* 349: 1227-35. Clinical evaluation in combination with negative D-dimer test can effectively lower the instance of pulmonary embolism to 0.5%. Van Belle, et al. (2006) *JAMA* 295: 172-79; Kruip, et al. (2002) *Arch. Intern. Med.* 162: 1631-35; Wells, et al. (2001) *Ann. Intern. Med.* 135: 98-107.

D-dimer analysis may have utility in tracking the progress of treating coagulation disorders. One study indicated that anticoagulation treatment for acute venous thromboembolism resulted in a gradual decline in D-dimer concentrations. Adam, et al. (2009) *Blood* 113: 2878-87; Schutgens, et al. (2004) *J. Lab. Clin. Med.* 144: 100-107. This discovery led to the conclusion that D-dimer levels monitoring could be used to assess treatment responsiveness. Adam, at 2883.

For patients with cancer, D-dimer analysis may have additional significance, as cancer increases the prevalence of thrombosis. Adam, et al. (2009) *Blood* 113: 2878-87. One study with oncology patients indicated that D-dimer concentrations have a high negative predictive value and high sensitivity in diagnosing pulmonary embolism. King, et al. (2008) *Radiology* 247: 854-61. Deep-vein thrombosis can similarly be excluded for cancer patients with low probability of developing deep-vein thrombosis and a negative test for D-dimer, although such a combination is less likely for oncology patients. Lee, et al. (2008) *Thromb. Res.* 123: 177-83. A higher threshold for a negative D-dimer result may be necessary in cancer patients. Righini, et al. (2006) *Haemost.* 95: 715-19.

Accordingly, there remains a need in the art for methods and/or treatments of thrombosis that improve D-dimer concentrations in cancer patients and address elevated D-dimer states in cancer patients, particularly those with advanced cancers.

Methods

One-hundred twenty-four patients with non-small cell lung cancer (NSCLC) were divided into 4 treatment groups. Patients in one group received one 1-hour intravenous (IV) infusion of either placebo (n=31), 80 mg (n=29), 160 mg (n=32), or 320 mg (n=32) of the Ab1 monoclonal antibody every 8 weeks over a 24 week duration for a total of 3 doses. Data on D-dimer concentration was collected for the first 8 weeks of treatment. D-dimer data concentration was quantitated by a D-dimer immunoturbidimetric assay. Briefly, the assay is based on the change in turbidity of a microparticle suspension that is measured by photometry. About 1.5 mL of patient sample sodium citrate plasma was collected and stored in a plastic collection tube. A suspension of latex microparticles, coated by covalent bonding with monoclonal antibodies specific for D-dimer, was mixed with the test plasma whose D-dimer level was to be assayed. Antigen-antibody reactions leading to an agglutination of the latex microparticles induced an increase in turbidity of the reaction medium. This increase in turbidity was reflected by an increase in absorbance, the latter being measured photometrically using a STAGO STA analyzer. The increase in absorbance was a function of the D-dimer level present in the test sample.

Results

The averaged data for each dosage concentrations (placebo, 80 mg, 160 mg, and 320 mg) of the Ab1 monoclonal antibody. All dosage levels of Ab1 antibody demonstrated a drop in D-dimer levels over placebo over the period of 8 weeks. See WO 2011/066371.

Example 32

Ab1 Efficacy and Safety in Patients with Advanced NSCLC

The primary objective of this study was to determine the efficacy and safety of ALD518 or humanized Ab1 in patients with advanced NSCLC.

Methods 124 patients (pts) with NSCLC, ECOG 0-3, weight loss in the preceding 3 months of >5% body weight, hemoglobin (Hb) >7 g/dL, and C-reactive protein (CRP) >10 mg/L were dosed. Pts were randomized to 1 of 4 groups (n~30/group). Placebo or ALD518 80 mg, 160 mg, or 320 mg was administered intravenously every 8 weeks. Pts were followed up for 24 weeks. Data included hematology, clinical chemistry, CRP and adverse events (AEs).

Results 29 pts completed the study treatments and evaluations, 38 failed to complete every visit, 52 died of progressive disease, and 5 withdrew because of adverse events. There were no dose limiting toxicities (DLTs) or infusion reactions. 84 pts had serious AEs of which 1 was deemed to be possibly related to administration of ALD518 (rectal hemorrhage). The mean (±SD) values for Hb, hematocrit (Hct), mean corpuscular Hb (MCH), and albumin are below:

TABLE 12

Clinical Parameters measured for ALD518 (Ab1) versus Placebo

| | | n | Hb (g/dL) | Hct (%) | MCH (pg) | Albumin (g/L) |
|---|---|---|---|---|---|---|
| ALD518 | Pre-dose | 93 | 11.5 (±2.1) | 37.9 (±6.2) | 28.4 (±2.8) | 37.3 (±5.3) |
| (pooled) | Week 4 | 69 | 13.1 (±1.6)[a] | 42.5 (±5.0)[a] | 29.2 (±2.5)[a] | 43.6 (±4.7)[a] |
| | Week 12 | 39 | 13.4 (±1.6)[a] | 42.5 (±4.7)[b] | 29.8 (±2.8)[a] | 45.2 (±4.5)[a] |
| Placebo | Pre-dose | 31 | 12.2 (±1.8) | 39.0 (±5.9) | 29.0 (±2.8) | 37.5 (±5.7) |
| | Week 4 | 29 | 11.8 (±2.0) | 39.5 (±6.4) | 28.0 (±2.8)[c] | 37.3 (±6.8) |
| | Week 12 | 21 | 12.0 (±2.5) | 39.6 (±7.4) | 27.8 (±3.0)[c] | 37.0 (±7.5) |

[a] $p < 0.0001$
[b] $p = 0.0002$
[c] $p \leq 0.001$ (paired t-test compared to pre-dose)

38/93 pts treated ALD518 and 10/31 given placebo has a pre-dose Hb≤11 g/dL. 24 of these pts on ALD518 and 7 of these pts on placebo remained in the study at week 4. 14/24 pts on ALD518 and 0/7 on placebo had raised their Hb from ≤11 g/dL to ≥12 g/dL.

Conclusion

ALD518 increased Hb, Hct, MCH and albumin in NSCLC pts and raised Hb to ≥12 g/dL in 58% of pts with a Hb≤11 g/dL at baseline. This further indicates that ALD518 can be administered as a non-erythropoietic stimulating agent for treating cancer-related anemia.

Example 33

Ab1 Achieved ACR 20/50/70 in Patients with Rheumatoid Arthritis

Introduction

Rheumatoid arthritis is a chronic, systemic inflammatory disorder that principally attack synovium of joints. The disease causes painful and potentially disabling inflammation, with onset typically occurring between 40 and 50 years of age. Interpretation of drug treatment efficacy in rheumatoid arthritis is made difficult by the myriad of subjective and objective assessment tools made available over the years. The American College of Rheumatology ("ACR") released a standardized set of rheumatoid arthritis measures to facilitate evaluation of improvement of the disease in clinical trials. Felson, et al. (1993) *Arthritis & Rheumatism* 36: 729-40.

Methods

One-hundred twenty-seven patients with active rheumatoid arthritis and CRP ≥10 mg/L were divided into 4 treatment groups. Patients in one group received one 1-hour intravenous (IV) infusion of either placebo (n=33), 80 mg (n=32), 160 mg (n=34), or 320 mg (n=28) of the Ab1 monoclonal antibody, once at the start of the 16 week trial and again at week 8. Data on CRP concentration was collected every week for the first 4 weeks, every two weeks between weeks 4 and 12, and at the conclusion of the test at week 16.

Assessment under the standardized protocols from the American College of Rheumatology were employed in determining the percentage of improvement of patients during the clinical trial and conducted by a person trained in the ordinary art of evaluating rheumatoid arthritis. The evaluation was based upon activity measures, including tender joint count, swollen joint count, the patient's assessment of pain, the patient's and physician's global assessments of disease activity, and laboratory evaluation of either erythrocyte sedimentation rate or CRP level. Id. The patient's assessment of pain was based upon the Stanford Health Assessment Questionnaire Disability Index (HAQ DI). Patients that achieve a 20% increase in activity measures for rheumatoid arthritis during a clinical trial are categorized as achieving ACR 20. Similarly, patients achieving 50% and 70% improvements are categorized as ACR 50 and ACR 70, respectively.

Results

A significant portion of patients suffering from rheumatoid arthritis achieved ACR 20 or greater during the course of the study. See Table 13. Patients observed rapid improvement in systems within the first 4 weeks of the study, as well as continued, steady improvement throughout the course of the 16 week evaluation. The greatest results where exhibited by patients receiving the 320 mg dosage level, with 43% achieving ACR 70 status during the study.

TABLE 13

Percentage patients achieving ACR 20/50/70 at week 16 - MITT non responder imputation

| | Placebo (n = 33) | Ab1 80 mg (n = 32) | Ab1 160 mg (n = 34) | Ab1 320 mg (n = 28) | Ab1 Pooled (n = 94) |
|---|---|---|---|---|---|
| ACR 20 | 36% | 75% (p = 0.0026) | 65% (p = 0.0283) | 82% (p = 0.0005) | 73% (p = 0.0002) |
| ACR 50 | 15% | 41% (p = 0.0281) | 41% (p = 0.0291) | 50% (p = 0.0052) | 44% (p = 0.0032) |
| ACR 70 | 6% | 22% (p = 0.0824) | 18% (p = 0.2585) | 43% (p = 0.0015) | 27% (p = 0.0130) |

Analysis of the individual components of the ACR evaluation demonstrated gains in every component. HAQ DI scores demonstrated clinically meaningful change over placebo during the course of the evaluation. Serum CRP levels were greatly reduced in all patients studied. The reduction in serum CRP levels was rapid, with immediate reduction in CRP levels relative to placebo within one week of Ab1 administration, and prolonged diminished levels continued at least until the final measurement was taken (up to sixteen weeks). In all cases, CRP levels fell to at or below the normal reference range (less than 5-6 mg/L) within one week. Thus, administration of Ab1 can cause a rapid and sustained improvement rheumatoid arthritis patients, as evidenced by the significant improvement in ACR scores during clinical evaluation, and presents an effective treatment regime. See also WO 2011/066371.

Example 34

Ab1 Achieved Improved DAS28 and EULAR Scores in Patients with Rheumatoid Arthritis Introduction Rheumatoid arthritis is a chronic, systemic inflammatory disorder that principally attack synovium of joints. The disease causes painful and potentially disabling inflammation, with onset typically occurring between 40 and 50 years of age. Interpretation of drug treatment efficacy in rheumatoid arthritis is made difficult by the myriad of subjective and objective assessment tools made available over the years. The American College of Rheumatology ("ACR") released a standardized set of rheumatoid arthritis measures to facilitate evaluation of improvement of the disease in clinical trials. Felson, et al. (1993) *Arthritis & Rheumatism* 36: 729-40.

Inflammatory activity associated with rheumatoid arthritis is measured using numerous variables through validated response criteria such as Disease Activity Score (DAS), DAS28 and EULAR. The DAS is a clinical index of rheumatoid arthritis disease activity that combines information from swollen joints, tender joints, the acute phase response, and general health. Fransen, et al. (2005) *Clin. Exp. Rheumatol.* 23(Suppl. 39): S93-S99. The DAS 28 is an index similar to the original DAS, but utilizes a 28 tender joint count (range 0-28), a 28 swollen joint count (range 0-28), ESR (erythrocyte sedimentation rate), and an optional general health assessment on a visual analogue scale (range 0-100). Id. The European League against Rheumatism (EULAR) response criteria classify patients using the individual amount of change in the DAS and the DAS value (low, moderate, high) reached into one of the following classifications: Good; Moderate; or Non-Responders. Id.

Methods

One-hundred twenty-seven patients with active rheumatoid arthritis were divided into 4 treatment groups. Patients in one group received one 1-hour intravenous (IV) infusion of either placebo (n=33), 80 mg (n=32), 160 mg (n=34), or 320 mg (n=28) of the Ab1 monoclonal antibody, once at the start of the 16 week trial and again at week 8. Data on the DAS28 and EULAR scores was collected every week for the first 4 weeks, every two weeks between weeks 4 and 12, and at the conclusion of the test at week 16. Assessment under the standardized DAS28 and EULAR protocols were employed in determining the respective scores of patients during the clinical trial and conducted by a person trained in the ordinary art of evaluating rheumatoid arthritis.

Results

Patients receiving 80 mg, 160 mg or 320 mg of Ab1 demonstrated improved DAS28 scores relative to those patients receiving placebo over the course of 16 weeks, as presented in FIG. 62 as a mean change from the baseline DAS28 score. Furthermore, a significant percentage of patients receiving 80 mg, 160 mg or 320 mg of Ab1 achieved "Good" or "Moderate" classifications relative to those patients receiving placebo over the course of 16 weeks. Thus, administration of Ab1 can result in improved DAS28 and EULAR scores in rheumatoid arthritis when compared to those patients receiving placebo. See WO 2011/066371.

Example 35

Safety, Pharmacokinetics (PK), and Pharmacodynamics (PD) of Ab1 in Human Subjects Background A humanized antibody derived from Ab1 (humanized Ab1 or ALD518) containing the variable heavy and light sequences in SEQ ID NO: 19 and 20 was administered to rheumatoid arthritis patients. This antibody is a humanized, asialated, IgG1 monoclonal antibody against IL-6 which has been shown to have a half-life (t½) of approximately 30 days in humans. In studies in patients with RA, intravenous (IV) with this antibody (humanized Ab1) has demonstrated: efficacy over 16 weeks with rapid American College of Rheumatology (ACR) responses; Complete and durable suppression of C-reactive protein (CRP); Good tolerability, and a safety profile consistent with the biology of IL-6 blockade. This humanized antibody binds to IL-6 with high affinity, preventing interaction and signaling mediated via IL-6R. Rapid and significant treatment responses have been demonstrated with intravenous (IV) administration of humanized Ab1 in patients with RA. In this example we study the safety, pharmacokinetics and pharmacodynamics of subcutaneous (SC) administration of humanized Ab1 in healthy subjects.

The objective of this study was to assess the safety, pharmacokinetics (PK) and pharmacodynamics (PD) of a single SC injection of this humanized antibody in healthy male subjects.

Methods

In this Phase I, double-blind, placebo-controlled study, 27 subjects were randomized 2:1 to receive a single dose of humanized Ab1 or placebo in the following groups: humanized Ab150 mg SC, humanized Ab1 100 mg SC or humanized Ab1100 mg IV (n=6 active and n=3 placebo per group). The primary objective was to assess safety of SC humanized Ab1 versus placebo over 12 weeks. Plasma concentrations of humanized Ab1 and serum concentrations of C-reactive protein (CRP) were assessed as secondary objectives. Assessments were performed daily in Week 1 and then on Day 10, Weeks 2, 4, 6 and 8, and then monthly to Week 12. The study was unblinded at Week 12, and humanized Ab1 subjects were monitored to Week 24.

Study Design and Population

The study included 27 healthy male subjects (aged 18-65 years). Subjects were dosed in three treatment groups of nine subjects each, randomized 2:1 to receive a single dose of humanized Ab1 or placebo on Day 1. Humanized Ab1 treatments per group were: humanized Ab1 IV 100 mg infusion over 60 minutes; humanized Ab1 SC 50 mg injection (1 mL); or humanized Ab1 100 mg injection (1 mL). The study was unblinded at Week 12, after which placebo subjects discontinued the trial and ALD518 subjects were monitored to Week 24.

Safety and Immunogenicity Assessments

The primary objective of the study was to assess the safety of SC humanized Ab1 compared with placebo over 12 weeks. Safety was monitored over 12 weeks for all subjects. The study was unblinded at Week 12, and Humanized AB1 subjects were monitored to Week 24. Laboratory safety tests were performed pre-dose at screening and Day −1, and post dose on Days 2 and 7, Weeks 2, 4, 6, 8 and 12 for all subjects, and Weeks 16, 20 and 24 post-dose for those randomized to Humanized Ab1. Anti-Humanized AB1 antibodies were measured by enzyme-linked immunosorbent assay (ELISA). Blood samples were collected at Day 1 (pre-dose) and Week 12 post-dose for all subjects, and Week 24 post-dose for those randomized to Humanized Ab1.

Pharmacokinetic and Pharmacodynamic Assessments

Plasma Humanized AB1 and serum CRP concentrations were assessed by ELISA. For all subjects, samples were collected at screening, pre-dose on Day 1, and post-dose on Days 2 and 7 and Weeks 2, 4, 6, 8 and 12. For subjects randomized to Humanized AB1, further samples were collected at Weeks 16, 20 and 24 post-dose.

Statistical Analysis

All subjects who received a dose of Humanized AB1 or placebo were included in the safety analysis. All subjects who received a dose of Humanized AB1 or placebo were included in PD and immunogenicity analyses. All subjects who received a dose of Humanized AB1 were included in PK analyses (n=18). All PK samples for placebo subjects were confirmed as below quantification. Descriptive statistics were generated for baseline demographics, safety data, plasma Humanized AB1 parameters and serum CRP concentrations. Wilcoxon Rank Sum test was used to compare CRP concentrations for Humanized AB1 treatments versus placebo.

Results—Summary

Figure 21A:
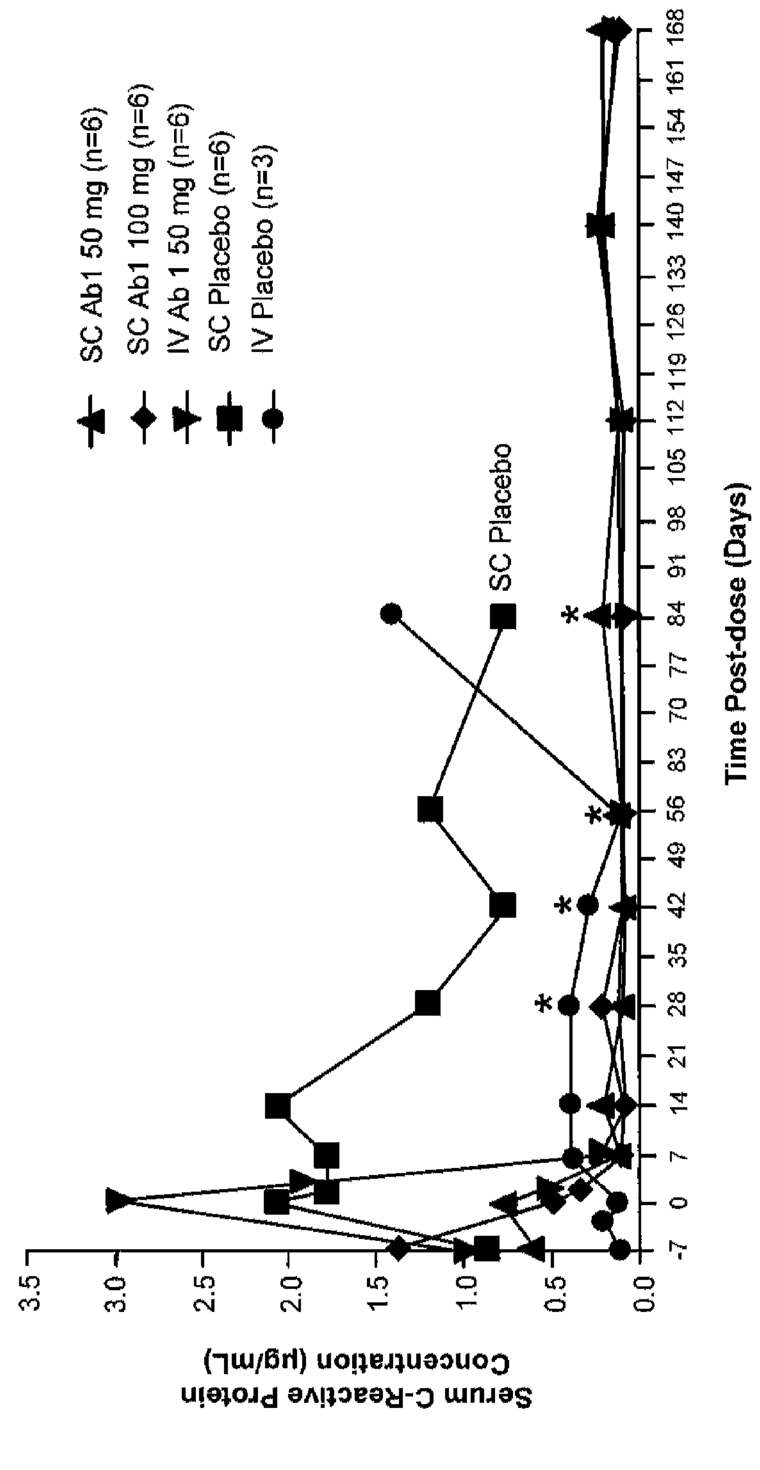
FIG. 21A depicts the mean plasma CRP levels concentration after subcutaneous or intravenous dosing of humanized Ab1.
Figure 21B:
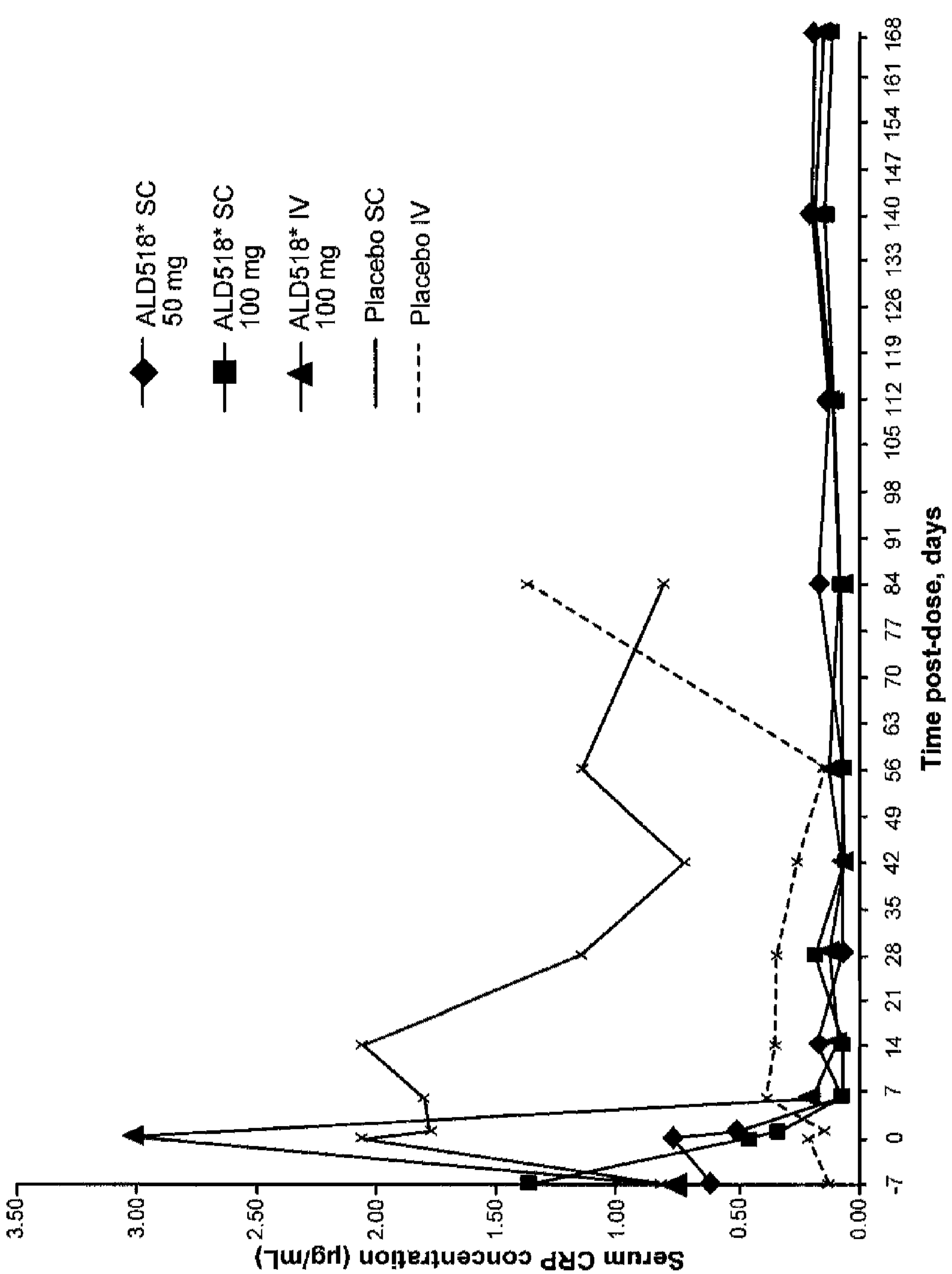
FIG. 21B depicts the mean plasma CRP levels concentration after subcutaneous or intravenous dosing of humanized Ab1 at dosing of 50 mg or 100 mg through 12 weeks.

Over 24 weeks, there were no deaths or serious AEs, and no withdrawals due to AEs. Nearly all subjects (89%) experienced AEs, which were mild or moderate except one event of severe gastroenteritis in the Humanized ab1 SC 50 mg group. Injection site reactions occurred in 5/12 Humanized Ab1 SC subjects, 1/6 placebo SC subjects and 1/3 placebo IV subjects (none were reported in Humanized Ab1 IV subjects). These were mild except one case of moderate erythema and pruritis in the Humanized Ab1100 mg SC group. Increases in direct bilirubin and neutrophil counts below the limit of normal were more common in subjects receiving Humanized Ab1 than placebo; all were CTC Grade 1 or 2. The half life of Humanized Ab1 was similar across all groups (mean range: 30.7-33.6 days). The median Tmax of Humanized Ab1 was longer after SC (~1 week) than after N administration (~end of infusion). The PK of SC Humanized Ab1 was dose-proportional in terms of AUC and Cmax at doses of 50 mg and 100 mg. Based on AUC0-∞ (day*μg/mL) of 237, 452 and 764 for the Humanized Ab150 mg SC, 100 mg SC and 100 mg N groups, respectively, the bioavailability of Humanized Ab1 was ~60% for the SC versus IV groups. Subjects receiving Humanized Ab1 experienced rapid and sustained reductions in serum CRP (FIG. 21A), similar results were seen when the antibody was administered either intravenous or subcutaneously (FIG. 21B).

Subject Disposition and Baseline Demographics

A total of 27 subjects were enrolled and completed the study (n=18 Humanized Ab1 and n=9 placebo). No subjects were withdrawn for any reason. All subjects were male; 23/27 subjects were Caucasian and 4/27 were Asian. Mean age was 29 (range 20-59) and was similar across the groups. Mean height and weight were also generally comparable across groups, although the IV placebo group were slightly lighter.

Safety and Immunogenicity to Week 12 for Humanized Ab1 and Placebo

A summary of safety is presented in TABLE 9. For the SC Humanized AB1 groups, a total of 11/12 (91%) patients experienced an adverse event (AE) compared with: 6/6 (100%) for the N Humanized AB1 group; 4/6 (66.6%) for the SC placebo group; and 3/3 (100%) for the IV placebo group.

TABLE 14

| Adverse Events | | | | | | | | |
|---|---|---|---|---|---|---|---|---|
| | Up to Week 12 | | | | | Week 12-Week 24* | | |
| MedRA Preferred Term | SC 50 mg n = 6 | SC 100 mg n = 6 | IV 100 mg n = 6 | Placebo SC n = 6 | Placebo IV n = 6 | SC 100 mg n = 6 | SC 100 mg n = 6 | IV 100 mg n = 6 |
| Subjects with an AE | 6 | 5 | 6 | 4 | 3 | 3 | 5 | 5 |
| AE severity | | | | | | | | |
| Mild | 2 | 2 | 5 | 1 | 2 | 3 | 5 | 7 |
| Moderate | 3 | 3 | 1 | 3 | 1 | 1 | 1 | 0 |
| Severe | 1 | 0 | 0 | 0 | 0 | 0 | 0 | 0 |
| Discontinuations Due to AEs | 0 | 0 | 0 | 0 | 0 | 0 | 0 | 0 |
| Deaths | 0 | 0 | 0 | 0 | 0 | 0 | 0 | 0 |
| AEs reported in ≥2 subjects in any group | | | | | | | | |
| Injection site erythema | 1 | 2 | 0 | 0 | 0 | 0 | 0 | 0 |
| Injection site pruritis | 1 | 2 | 0 | 0 | 1 | 0 | 0 | 0 |
| Gastroenteritis | 1 | 0 | 2 | 0 | 0 | 0 | 0 | 0 |
| URTI | 4 | 4 | 4 | 2 | 2 | 0 | 1 | 2 |
| Skin laceration | 2 | 1 | 2 | 0 | 0 | 0 | 0 | 0 |
| Myalgia | 0 | 0 | 0 | 2 | 0 | 0 | 0 | 0 |
| Headache | 5 | 2 | 1 | 1 | 0 | 0 | 1 | 1 |
| Nasal congestion | 0 | 0 | 2 | 0 | 0 | 0 | 0 | 0 |

*Patients randomized to placebo (IV or SC) discontinued at Week 12 and are not included in Week 24 analyses;
AE = adverse event; SC = subcutaneous; IV = intravenous; URTI = upper respiratory tract infection.

Across groups: No deaths or serious AEs were reported and there were no withdrawals due to AEs. Most AEs were mild or moderate in intensity. One case of gastroenteritis in a SC Humanized AB1 50 mg subject was considered severe, but not serious, and not related to study medication. No anti-Humanized AB1 antibodies were detected in any subject during this period.

Injection Site Reactions

Injection site reactions were reported in 26% (7/27) of subjects, and all occurred prior to Week 12 (TABLE 40). Injection site reactions occurred in 5/12 SC Humanized AB1 subjects and 1/6 SC placebo subjects. In the IV groups, 0/6 Humanized AB1 subjects and 1/3 placebo subjects experienced injection site reactions. All injection site reactions were mild except in one SC Humanized AB1 100 mg subject with moderate injection site erythema and pruritis. No injection site reactions occurred after Week 12 in any of the Humanized AB1 groups. Infusion site reactions were reported in 0/6 subjects receiving IV Humanized AB1 and 1/3 IV placebo subjects (infusion site pruritis)

TABLE 15

| Ab1 Injection Site Reactions to Week 12* | | | | | |
|---|---|---|---|---|---|
| | 50 mg n = 6 | 100 mg n = 6 | 100 mg n = 6 | Placebo SC n = 6 | Placebo IV n = 3 |
| Total subjects with injection site reaction | 2 | 3 | 0 | 1 | 1 |
| Injection site erythema | 1 | 2 | 0 | 0 | 0 |
| Injection site pain | 1 | 1 | 0 | 1 | 0 |
| Injection site pruritis | 1 | 2 | 0 | 0 | 1 |
| Injection site rash | 1 | 0 | 0 | 0 | 0 |

*All injection site reactions were reported in the first 12 weeks of the study.
SC = subcutaneous;
IV = intravenous Clinical Laboratory Evaluations TABLE 43 shows incidences of increased alanine aminotransferase (ALT) and aspartate aminotransferase (AST) and bilirubin levels across the Humanized AB1 and placebo groups. All ALT and AST levels were Grade 1 by the Common Terminology Criteria for Adverse Events (CTCAE), and no levels were ≥3 times the upper limit of normal (ULN). All increases in total and direct bilirubin were CTCAE Grade 1 or 2 and no subject met criteria for drug-induced liver damage. Only one subject (SC Humanized AB1 100 mg group) had total bilirubin out of range (26 μmol/L, range 0-24 μmol/L), at Week 24.

TABLE 16

| Clinical Laboratory Evaluations Over 24 Weeks (Ab1) | | | | |
|---|---|---|---|---|
| | SC 50 mg n = 6 | SC 100 mg n = 6 | IV 100 mg n = 6 | Placebo* n = 9 |
| Elevated ALT | 0 | 1 | 3 | 2 |
| Elevated AST | 0 | 1 | 1 | 1 |
| Elevated total bilirubin | 0 | 1 | 1 | 0 |
| Elevated direct bililrubin | 2 | 4 | 5 | 2 |
| Low neutrophil count† | 4 | 1 | 2 | 3 |
| Low platelet count† | 2 | 0 | 0 | 1 |

*SC and IV groups combined up to Week 12 only, after which placebo-treated patients discontinued;
†Below the lower limit of normal;
SC = subcutaneous;
IV = intravenous;
ALT = alanine aminotransferase;
AST = aspartate aminotransferase Sporadic decreases in neutrophil and platelet counts were also observed in the Humanized AB1 and placebo groups. Neutrophil counts below the lower limit of normal were more common in subjects receiving Humanized AB1 than placebo but all decreases were CTCAE Grade 1 or 2. Only one subject (SC Humanized AB1 50 mg group) had consistent mild neutropenia to Week 24 (1.6×109/L at Week 24). Reductions in platelet counts were all CTCAE Grade 1 (lowest level 134×109/L) and no subject had a low platelet count past Week 8.

Pharmacokinetics

Bioavailability of Humanized AB1 was 60% for SC Humanized AB1 50 and 100 mg versus IV Humanized AB1 100 mg groups based on the mean $AUC_{0-\infty}$ (TABLE 44). The half-life of Humanized AB1 was similar across all groups (mean range: 30.7-33.6 days) (Table 17). Peak plasma concentration ($C_{max}$) of SC Humanized AB1 was reduced as compared to IV (FIG. 15). Median time to maximum plasma concentration ($T_{max}$) of Humanized Ab1 was longer after SC Humanized AB1 (at approximately one week) than after N Humanized Ab1 administration (at approximately the end of infusion).

TABLE 17

Ab1 Plasma Pharmacokinetic Parameters to Week 24

| | SC 50 mg n = 6 | SC 100 mg n = 6 | IV 100 mg n = 6 |
|---|---|---|---|
| $C_{max}$ (μg/mL) (CV)* | 5.57 (24%) | 9.19 (34%) | 33.6 (30%) |
| $T_{max}$ (days) (min, max)† | 6 (6, 14) | 5.5 (2, 28) | 0.17 (0, 17, 0.34) |
| $AUC_{5-24}$ (day · μg/mL) (CV)* | 218 (34%) | 435 (19%) | 732 (22%) |
| $AUC_{8-\chi}$ (day · μg/mL) (CV)* | 224 (39%) | 444 (20%) | 746 (22%) |
| $t_{1/2}$ (days ± SD)‡ | 33.6 ± 21.7 | 31.1 ± 9.0 | 30.7 ± 5.9 |
| CL (mL/day) (CV)* | 223 (32%) | 225 (21%) | 134 (27%) |

*Data are geometric mean (coefficient of variation %, CV %).
†Data are median (minimum, maximum).
‡Data are mean (±SD).
CV = coefficient of variation;
$C_{max}$ = maximum plasma concentration;
AUC = area under curve;
SD = standard deviation;
CL = apparent total body clearance for IV and apparent total body clearance divided by bioavailability for SC;
IV = intravenous;
SC = subcutaneous;
$T_{max}$ = time to maximum plasma concentration;
$t_{1/2}$ = terminal plasma half-life Pharmacodynamics CRP levels were reduced in all subjects who received Humanized AB1 irrespective of dose or administration route. From Weeks 4 to 12, CRP levels were significantly lower in subjects who received Humanized Ab1 compared with placebo (unadjusted p-value <0.05). A high correlation between the IgG produced and antigen specificity for an exemplary IL-6 protocol was observed with 9 of 11 wells showed specific IgG correlation with antigen recognition. In Humanized AB1 subjects, CRP levels were lowered to <20% of pre-dose levels in: 72% (13/18) of subjects at Week 1; 73% (11/15) of subjects at Week 12; and 56% (10/18) of subjects at Week 24.

Conclusions

In this Phase I study, the anti-IL-6 antibody Humanized Ab1 was generally well tolerated when administered in a single SC dose in healthy male subjects. Injection site reactions were generally mild. No anti-Humanized Ab1 antibodies were detected. Changes in liver enzymes, neutrophil and platelet counts were reversible. The bioavailability of SC Humanized AB1 was approximately 60% of that observed with IV Humanized Ab1. The half-life of Humanized AB1 was approximately 30 days, irrespective of route of administration. These data concur with previous data using N Humanized Ab12. Subcutaneous Humanized AB1 led to rapid and large reductions in serum CRP. Reductions in CRP observed during the first 12 weeks of the study were sustained over 24 weeks of assessment. These preliminary data support the continued development and evaluation of subcutaneous Humanized Ab1 for the treatment of patients with mucositis.

In summary, in this Phase I study, the anti-IL-6 antibody Humanized Ab1 was well tolerated when administered in a single SC dose; injection site reactions were generally mild. The bioavailability of SC Humanized Ab1 was ~60% of N Humanized Ab1, and the half life was ~30 days. Rapid and significant reductions in CRP were observed, which were sustained over 24 weeks of assessment.

Example 36

Effect of Ab1 on DAS28-Assessed Disease Activity

ALD518* is an asialated, humanized anti-IL-6 monoclonal antibody with a half-life of ~30 days containing the humanized variable heavy and light sequences contained in SEQ ID NO:19 and 20. These humanized heavy and light sequences are derived from a parent rabbit antibody that specifically binds human IL-6 which antibody is referred to in said incorporated application as Ab1. ALD518 binds to IL-6 with high affinity, preventing interaction and signalling mediated via soluble and membrane-bound IL-6R. Rapid and significant ACR responses have been demonstrated with ALD518* in patients with RA. In this example we report the impact of ALD518 on DAS28-assessed disease activity over 16 weeks.

Methods

Patients with active RA and an inadequate response to methotrexate (MTX) were randomized 1:1:1:1 to intravenous ALD518* 80, 160 or 320 mg or placebo during this 16-week, double-blind, placebo-controlled Phase II study. Patients received two IV infusions of ALD518 (Day 1 and Week 8), while continuing on stable doses of methotrexate (MTX). The primary efficacy endpoint was the proportion of patients achieving ACR20 at Week 12; disease activity was assessed via Disease Activity Score (DAS28) based on C-reactive protein (CRP) as a secondary endpoint. The proportion of patients achieving DAS28-defined remission (score <2.6), low disease activity state (LDAS; score ≤3.2) and good EULAR responses (current DAS28≤3.2 and improvement from baseline >1.2) were assessed for the modified intent-to-treat population, and are presented for patients with available data (as observed). P-values are based on Chi-square tests.

Results

Of 127 randomized and treated patients, 116 completed the trial. At baseline, mean age was 52.3 years and RA duration was 6.8 years. At Weeks 4, 12 and 16, the proportion of patients achieving LDAS and remission was greater than placebo for all ALD518* doses; differences were significant versus placebo (p<0.05) for all assessments except ALD518* 80 mg at Week 4 (p=0.056). Similarly, EULAR responses were significantly better for all ALD518* doses versus placebo (p<0.01) at Weeks 4, 12 and 16. There was a trend toward greater responses with higher ALD518* doses.

TABLE 18

Proportion of patients achieving DAS28-defined remission, LDAS and good EULAR responses

| | ALD518* 80 mg (N = 32) | ALD518* 160 mg (N = 34) | ALD518* 320 mg (N = 28) | Placebo — (N = 33) |
|---|---|---|---|---|
| DAS28-defined remission | | | | |
| Week 4 | 10.0 | 8.8 | 17.9 | 0 |
| Week 12 | 17.2 | 21.2 | 34.6 | 3.3 |
| Week 16 | 13.8 | 28.1 | 44.0 | 0 |

TABLE 18-continued

Proportion of patients achieving DAS28-defined remission, LDAS and good EULAR responses

| | ALD518* 80 mg (N = 32) | ALD518* 160 mg (N = 34) | ALD518* 320 mg (N = 28) | Placebo — (N = 33) |
|---|---|---|---|---|
| LDAS | | | | |
| Week 4 | 10.0 | 23.5 | 28.6 | 0 |
| Week 12 | 20.6 | 33.3 | 46.1 | 6.6 |
| Week 16 | 20.7 | 50.0 | 52.0 | 3.4 |
| Good EULAR response | | | | |
| Week 4 | 10.0 | 23.5 | 28.6 | 0 |
| Week 12 | 20.7 | 33.3 | 46.2 | 6.7 |
| Week 16 | 20.7 | 50.0 | 52.0 | 3.4 |

DAS28 = Disease Activity Score 28;
LDAS = low disease activity state

SAEs were reported in two ALD518 patients (both had significant increases in liver enzymes, and discontinued treatment). Overall, elevations in liver enzymes >2×ULN occurred in 17% of ALD518*—versus 0% placebo-treated patients; the frequency was highest in the 320 mg dose group. Modest increases in total cholesterol were observed (mean increase by Week 16=1.1 mmol/L for ALD518* versus 0.2 mmol/L for placebo). Nine ALD518 patients had transient Grade II and two had transient Grade III neutropenias. There were no serious infections or infusion reactions in any treatment group, and no evident immunogenicity.

Conclusions

In this Phase II study, the novel IL-6 inhibitor ALD518 resulted in rapid and significant improvements in disease activity sustained over 16 weeks of assessment in patients with RA and an inadequate response to methotrexate (MTX). ALD518 was well tolerated, with a safety profile consistent with the biology of IL-6 blockade.

Example 37

Ab1 Administration

Methods

Patients with active RA were randomized into a 16 week, double-blind, placebo-controlled trial comparing multiple iv infusions of ALD518 (80, 160 or 320 mg). Patients received an infusion every 8 weeks and were maintained on a stable dose of MTX throughout the trial. Assessments included ACR 20/50/70 responses and DAS28. All patients were evaluated for safety. For early withdrawals, LOCF analysis was used for continuous variables and non-responder imputation for categorical variables.

Results 132 patients were randomized; 127 were dosed. Mean disease duration was 6.6 years; mean DAS28 score was 6.2 and mean HAQ-DI was 1.72. 11 patients did not complete the 16-week trial: 320 mg-3, 160 mg-1, 80 mg-3, placebo-4: 4 discontinued due to adverse events (80 mg-2, 320 mg-2), with 2 SAEs (80 mg-1, 320 mg-1). Elevations in liver enzymes (LFTs) >2×ULN were observed in 17% ALD518 versus 0% placebo. There were modest increases in total cholesterol (mean increase by week 16=1.1 mmol/L ALD518 versus 0.2 mmol/L placebo). 9 patients on ALD518 had transient grade 2 neutropenias; 2 pts transient grade 3 neutropenias. There were no serious infections reported in any treatment group. Infusions of ALD518 were well tolerated without infusion reactions or evident immunogenicity. At weeks 4 and 16, ACR responses (non responder imputation analysis) and improvements in DAS28 scores were:

TABLE 19

Week 4 DAS28 Scores for Ab1 80, 160, and 320 dosages

| Week 4 | 80 mg (n = 32) | 160 mg (n = 34) | 320 mg (n = 28) | PBO + MTX (n = 33) |
|---|---|---|---|---|
| ACR20 | 50% (16)* | 56% (19)* | 71% (20)* | 23% (8) |
| ACR50 | 9% (3) | 15% (5) | 29% (8)† | 3% (1) |
| ACR70 | 6% (2) | 0% (0) | 11% (3) | 0% (0) |
| Mean Δ DAS28 | −1.8 | −2.1 | −2 | −0.6 |

*p£0.04;
†p = 0.009

TABLE 20

Week 16 DAS28 Scores for Ab1 80, 160, and 320 dosages

| Week 16 | 80 mg (n = 32) | 160 mg (n = 34) | 320 mg (n = 28) | PBO + MTX (n = 33) |
|---|---|---|---|---|
| ACR20 | 75% (24)* | 65% (22)* | 82% (23)* | 36% (12) |
| ACR50 | 41% (13)* | 41% (14)* | 50% (140* | 15% (5) |
| ACR70 | 22% (7)† | 18% (6)‡ | 43% (12)* | 6% (2) |
| Mean Δ DAS28 | −2.7 | −2.7 | −3.2 | −1.1 |

*p£0.03
†p = 0.08
‡p = 0.26

Conclusion

ALD518 is the first mAb to IL-6, as opposed to an anti-IL-6 receptor mAb, to show a significant, rapid and sustained improvement in disease activity in RA. ALD518 in doses ranging from 80 to 320 mg given as 2 IV infusions to pts with active RA was well tolerated with increases in LFTs and total cholesterol and transient neutropenia observed in some patients. There were no infusion reactions associated with administration of ALD518 and no detectible immunogenicity.

Example 38

Treatment of Oral Mucositis with Head and Neck Cancer Receiving Concurrent Chemotherapy and Radiotherapy Subjects suffering from oral mucositis with head and neck cancer receiving concurrent chemotherapy and radiotherapy may receive a regimen of a 160 mg or 320 mg doses of a composition comprising a humanized monoclonal antibody that selectively binds IL-6.

Subjects will be assessed using tumor staging (standard TNM system) during the screening period, which may occur within 30 days prior to radiotherapy (RT) start. The RT treatment period will be approximately 7 weeks, depending on the subject's prescribed radiation plan. Post-RT treatment period visits will be at Weeks 1, 2, 3, and 4 following the treatment period. Long term follow-up visits will occur at 3, 6, 9, and 12 months following the end of RT to determine if there is an effect of ALD518 on the tumor response to CRT.

Subjects may have recently diagnosed, pathologically confirmed, non-metastatic SCC of the oral cavity, oropharynx, hypopharynx or larynx. Subjects may be scheduled to receive a continuous course of intensity-modulated radiotherapy (IMRT), with a minimum cumulative dose of 55 Gy and maximum dose of 72 Gy. Planned radiation treatment fields may include at least 2 oral sites (e.g., buccal mucosa, floor of oral cavity, tongue or soft palate) with each site receiving a total dose of ≥55 Gy. The treatment plan may include monotherapy with cisplatin administered in standard weekly (30 to 40 mg/$m^2$) or tri-weekly (80 to 100 mg/$m^2$, given on Days 0, 21 and 42) regimens or monotherapy with carboplatin administered weekly (100 mg/$m^2$).

A composition comprising a humanized monoclonal antibody that selectively binds IL-6 may be given within 2 hours prior to the subjects' radiation every 4 weeks for a total of 2 doses. A baseline visit will occur on the first day of ALD518 and RT. Safety, PK, PD, and markers of IL-6 biology (e.g., total IL-6, sIL-6r, soluble gp130, sIL-6 Complex) will be monitored during the RT treatment and Post-RT treatment period. The long term follow-up period of the treatment may include long term follow-up visits, primarily for the assessment of tumor response and survival. These assessments will take place at Months 3, 6, 9 and 12 following the last dose of RT. At Months 3, 6, 9, and 12 tumors will be assessed clinically. At the Month 6 and Month 12 follow-up visits, tumor status will be assessed using RECIST criteria and the same imaging modality (CAT, PET or MRI) that was used to evaluate tumor status prior to RT start (at the time of staging) may be used.

Following a treatment regimen comprising the administration of a humanized monoclonal antibody that selectively binds IL-6, patients may show improvement in their oral mucositis (e.g., a reduction in symptoms).

Example 39

Oral Mucositis Study 1: Single Acute Radiation Dose (40 Gy) Study

Introduction:

The efficacy of treatment with a rodent anti-IL-6 antibody (monoclonal rat IgG1 clone MP5-20F3, R&D Systems) was studied in an established mouse model of radiation-induced oral mucositis. Dorr & Kummermehr (1991) *Virchows Arch B Cell Pathol Incl Mol Pathol* 60(5): 287-94. Study endpoints included oral mucositis duration and severity, body weight, and survival in normal C3H mice.

Methods:

36 male C3H mice were exposed to a single dose of 40 Gy radiation directed to the underside of the tongue on Day 0. Animals were dosed with a rodent anti-IL-6 antibody (monoclonal rat IgG1 clone MP5-20F3, R&D Systems), control antibody (monoclonal rat IgG1 clone 43414, R&D Systems), or vehicle on Days −1, 2, 6, 9, and 13, via intravenous injection at 10 mg/kg into the tail vein. Animals were weighed daily, and food and water consumption were monitored in each treatment group.

Images of the tongue were captured daily from Days 4 to 16. An oral mucositis score was assigned to each animal based on a defined scoring scale per protocol design. The scoring scale is presented in Table 21. Following completion of the study, the tongue images were scored by blinded observers to establish the values used to determine the degree and duration of oral mucositis and any treatment effects. A score of 1-2 is considered to represent a mild stage of disease, whereas a score of 3-5 is considered to indicate moderate to severe mucositis.

TABLE 21

Rodent Model Oral Mucositis Scoring Scale

| Score | Description |
|---|---|
| 0 | Tongue completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in at least one places. Ulcers may have a yellow/gray appearance due to pseudomembrane. Cumulative size of ulcers should equal about ¼ of the tongue. Severe erythema and vasodilation. |
| 4 | Cumulative size of ulcers should equal ¼ to ½ of the tongue. Loss of pliability. Severe erythema and vasodilation. |
| 5 | Virtually all of tongue is ulcerated. |

Results:

The onset of mucositis was the same for all 3 groups with peak mucositis scores occurring on Day 10. An analysis of the number of days mice presented with scores of 3+ during the study demonstrated no statistical difference among the 3 groups (mean days of 3.3, 4 and 3.6 for vehicle, isotype control and anti-IL-6, respectively).

Figure 22:
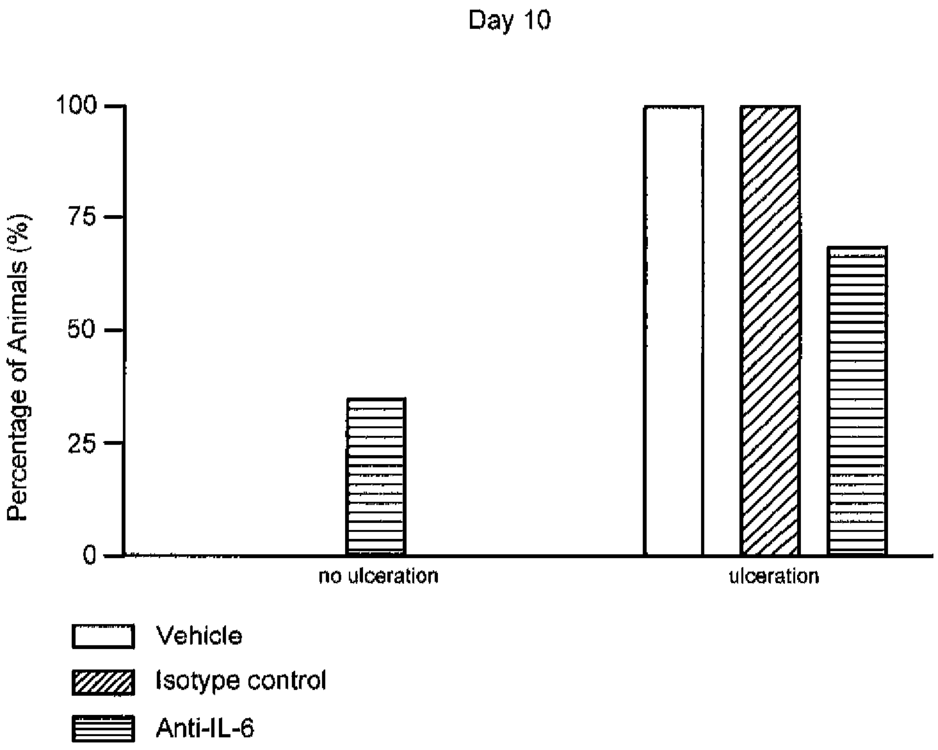
FIG. 22 depicts percentage of mice ulcerated at any timepoint after single dose radiation.

On Day 10, 100% of the mice in the vehicle and control antibody groups developed ulcers while 67% of the anti-IL-6 group developed ulcers (FIG. 22). There was no statistical difference in ulceration scores at Day 10 between the anti-IL-6 antibody and control antibody or vehicle groups. On Days 12 and 13, a numerically larger (not statistically different) number of mice in the anti-IL-6 group had ulceration compared to the mice in the vehicle or control groups.

Weight loss was seen in all 3 groups with peak weight loss occurring between Days 11 and 12. There were no statistically significant differences in weight change between the three groups. No general toxicities were noted in this study that could be attributed to treatment with the control or anti-IL-6 antibodies or the vehicle. No treatment-related deaths occurred during the study.

Example 40

Ascending Radiation Dose Levels Study in Mouse Model of Radition-Induced Oral Mucositis Introduction The efficacy of treatment with a rodent anti-IL-6 antibody (monoclonal rat IgG1 clone MP5-20F3, R&D Systems) was studied in an established mouse model of radiation-induced oral mucositis. Dorr & Kummermehr J. Proliferation kinetics of mouse tongue epithelium under normal conditions and following single dose irradiation. Virchows (1991) *Arch B Cell Pathol Incl Mol Pathol.* 60(5): 287-294. Study endpoints included oral mucositis duration and severity, body weight, and survival in normal C3H mice.

Methods 120 male C3H mice (12 per treatment group per radiation dose) were exposed to a single dose of radiation, totaling 25, 30, 35, 40, or 45 Gy directed to the underside of the tongue on Day 0. Animals were dosed with a rodent anti-IL-6 antibody (monoclonal rat IgG1 clone MP5-20F3, R&D Systems) or control antibody (monoclonal rat IgG1 clone 42414, R&D Systems) on Days −1, 2, 6, 9, and 13, via intravenous injection at 10 mg/kg into the tail vein. Animals were weighed daily; and food and water consumption was monitored in each treatment group.

Images of the tongue were captured daily from Days 4 to 16. An oral mucositis score was assigned to each animal based on a defined scoring scale per protocol design. The scoring scale is presented in Table 21. Following completion of the study, the tongue images were scored by blinded observers to establish the values used to determine the degree and duration of oral mucositis and any treatment effects. A score of 1-2 is considered to represent a mild stage of disease, whereas a score of 3-5 is considered to indicate moderate to severe mucositis.

Conclusions

Figure 23:
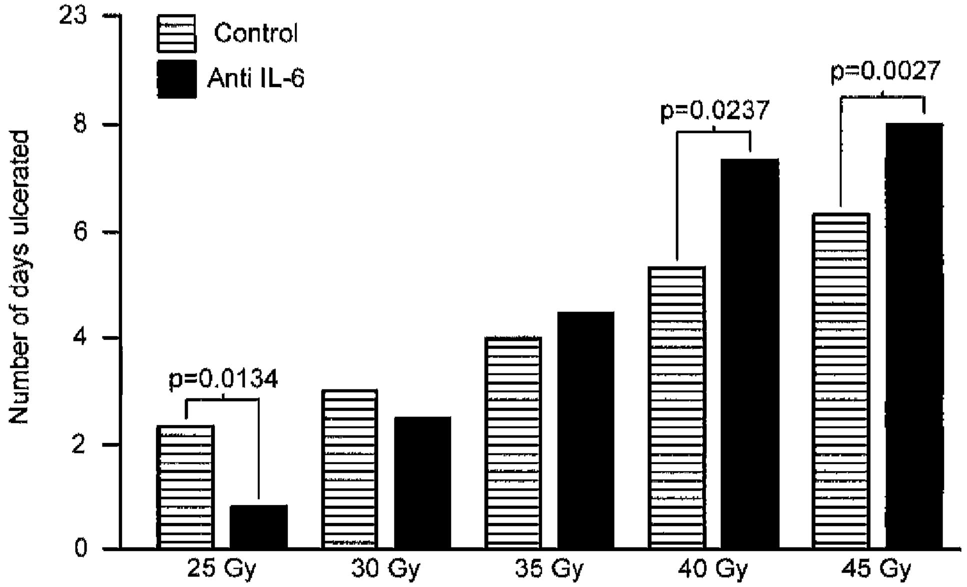
FIG. 23 depicts median tumor volume over time.

Mice treated with the anti-IL-6 antibody at 25 Gy showed a statistically significant decrease in the median number of days with ulceration compared to mice treated with the control antibody (p=0.0134). There was no difference between the treatment groups at 30 and 35 Gy. Mice treated with the anti-IL-6 antibody at 40 and 45 Gy showed a statistically significant increase in the median number of days with ulceration compared to mice treated with the control antibody (p=0.0237 and 0.0037, respectively). These data are shown in FIG. 23.

Figure 24:
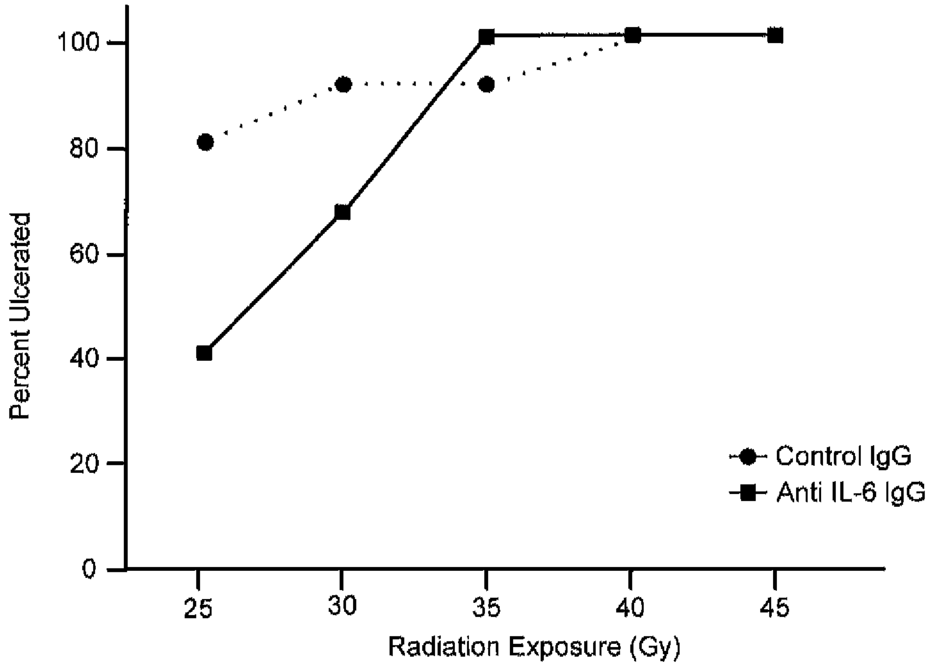
FIG. 24 depicts the percentage of mice with no ulcerations versus ulcerations on Day 10.

The anti-IL-6 treated group had a numerically lower percentage of mice that were ulcerated at any timepoint over the course of the study compared to control antibody treated group at the 25 and 30 Gy radiation levels (45% vs. 82%; 67% vs. 92%). See FIG. 24. At higher radiation dose levels the percentage of mice that were ulcerated over the course of the study in the two treatment groups were similar.

Over the course of the study, the anti-IL-6 treatment group receiving 25 Gy had statistically significant positive median percentage changes from baseline body weight compared to the control antibody group at all timepoints. Additionally, at Day 4, the anti-IL-6 group at 30 and 35 Gy radiation dose levels had statistically significant positive median percentage changes from baseline body weight compared to the control antibody group. At the 40 and 45 Gy radiation dose levels, there were no differences in median percent change from baseline between the anti-IL-6 and control antibody groups.

No general toxicities were noted in this study that could be attributed to treatment with the anti-IL-6 antibody or control antibody. No treatment-related deaths were observed during the study.

Conclusions

In conclusion, at the lowest dose (25 Gy) of radiation there was a lower incidence and duration of ulcerated oral mucositis (scores 3-5) in the anti-IL-6 treated group compared to controls. Additionally, the mice treated with the anti-IL-6 antibody did not lose body weight compared to controls. At the 30 Gy radiation dose level, there was lower incidence of ulcerated oral mucositis in the anti-IL-6 treated group compared to controls. Mice receiving higher single doses of radiation (40 Gy and 45 Gy) had a longer duration of ulcerated oral mucositis in the anti-IL-6 antibody treated group compared to controls. The radiation dose levels administered as single doses in this study are much higher than the daily doses (approximately 2 Gy) given in TMRT for the treatment of head and neck cancer. These data support with the use of a humanized monoclonal antibody (e.g., ALD518) in the prevention of CRT-induced oral mucositis in head and neck cancer patients.

Example 41

Effect of Anti-IL-6 Treatment on Tumor Growth in a Xenograft Model

Introduction

The human pharynx squamous cell carcinoma cell line (FaDu) has been utilized as a model for head and neck cancers in mouse xenograft studies. Alderson, et al (2002) *Cancer Chemother. Pharmacol.* 50: 202-212. FaDu expresses both IL-6 and the IL-6 receptor and IL-6 levels are induced in response to radiation treatment. Chen, et al. (2010) *Int. J. Radiation Oncology Biol. Phys.* 76:1214-1224 The effect of anti-IL-6 treatment on the growth of FaDu tumors in the presence or absence of radiation treatment was studied in an established mouse xenograft model. Study endpoints included tumor volume and body weights.

Methods 120, six week old, female athymic nude mice were implanted with ten million FaDu tumor cells subcutaneously. When tumors reached the weight range of 125-250 mg (Day 10), animals were divided into 3 groups of 40 mice. One group was given vehicle twice weekly via intravenous injection into the tail vein. The second group was given 10 mg/kg each of ALD518 and an anti-mouse IL-6 antibody (monoclonal rat IgG1, R&D Systems). The third treatment group was given 10 mg/kg each of isotype control antibodies (monoclonal human IgG1, R&D Systems). In each of the treatment groups, half of the animals (N=20) were irradiated with 2 Gy/day for 5 days and the other 20 animals were not irradiated. Animals were euthanized when tumor volume reached 4,000 $mm^3$ or ulceration of the tumor occurred. All animals were weighed and tumor volumes measured three times a week for the duration of the study.

Results

Figure 25:
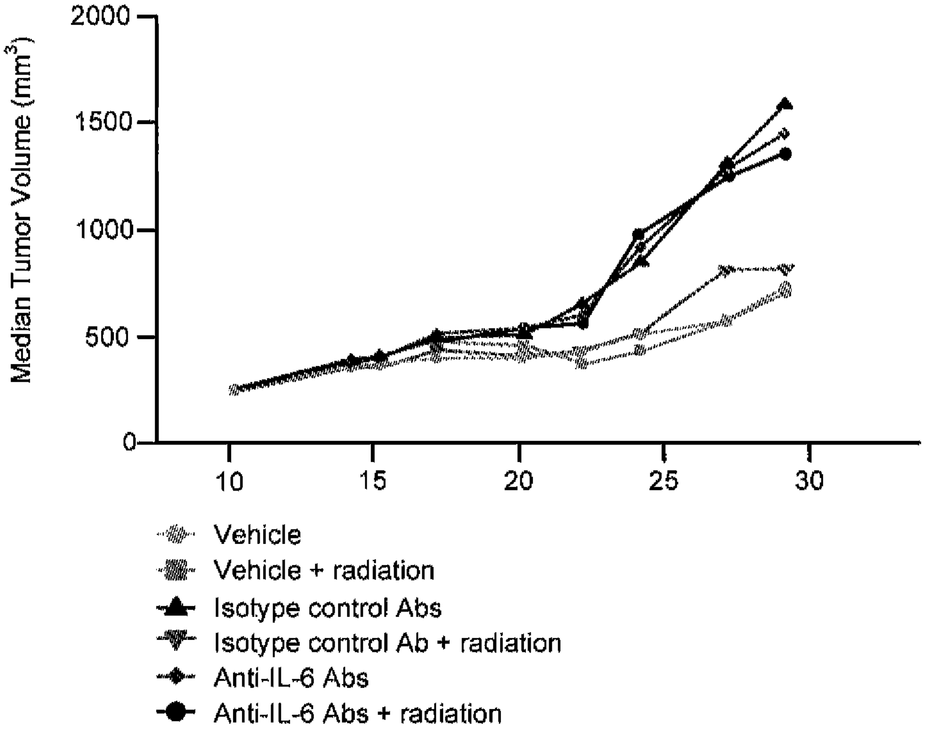
FIG. 25 depicts median number of days ulcerated after single dose of radiation.

The tumor volumes for each animal were measured three times a week starting on the first day of treatment (Day 10). The study was completed on Day 29. FaDu tumors have a high rate of ulceration; in this study, between 9 and 13 animals were sacrificed in each group by Day 29 due to tumor ulceration. No animals were euthanized due to tumor burden. The median tumor volume for each group is presented in FIG. 25. All groups had median tumor volumes between 162-167 $mm^3$ at the start of treatment (Day 10). Groups treated with vehicle, isotype control antibodies or anti-IL-6 antibodies but not irradiated displayed very similar median tumor volumes throughout the study. These groups were not statistically different. Groups treated with vehicle, isotype control antibodies or anti-IL-6 antibodies plus radiation had reduced median tumor volumes of roughly 50% compared to the non-irradiated groups post Day 22. Median tumor volumes of the irradiated groups were similar and not statistically different. Thus, treatment with anti-IL-6 antibodies had no effect on tumor growth in either the non-irradiated or irradiated groups.

Additional conclusions from the study include: no differences in weight were observed between the six groups; no general toxicities were noted that could be attributed to treatment with the vehicle, control antibodies or anti-IL-6 antibodies; and there were no treatment-related deaths.

Example 43

Clinical Trial Design

A phase 2, double-blind, placebo-controlled trial evaluating the safety, efficacy, pharmacokinetics and pharmacodynamics of ALD518, and the health and economic outcomes in subjects receiving CRT for the treatment of squamous cell carcinomas (SCCs) of the oral cavity, oropharynx, hypopharynx or larynx may be conducted. Up to 96 subjects may be enrolled into this trial. Initially 3 open-label subjects will be enrolled into a safety run-in of the 160 mg dose. Approximately 90 subjects will be randomized (1:1:1) into 1 of 2 dose levels of ALD518 (160 mg and 320 mg) or placebo during the double-blind portion of the trial. Safety, PK, PD, and markers of IL-6 biology (e.g., total IL-6, sIL-6r, soluble gp130, sIL-6 Complex) will be monitored during the RT treatment and Post-RT treatment period. Additionally, exploratory analyses of IL-6 biology including cytokine biomarkers may be performed in a subset of subjects and will require separate consent.

Subject eligibility, including tumor staging (standard TNM system), will be assessed during the screening period, which may occur within 30 days prior to radiotherapy (RT) start. The RT treatment period will be approximately 7 weeks, depending on the subject's prescribed radiation plan, Post-RT follow-up visits will be at Weeks 1, 2, 3, and 4. Long term follow-up visits will occur at 3, 6, 9, and 12 months following the end of RT to determine if there is an effect of ALD518 on the tumor response to CRT.

Eligible subjects will have recently diagnosed, pathologically confirmed, non-metastatic SCC of the oral cavity, oropharynx, hypopharynx or larynx. Subjects must be scheduled to receive a continuous course of intensity-modulated radiotherapy (IMRT), with a minimum cumulative dose of 55 Gy and maximum dose of 72 Gy. Planned radiation treatment fields must include at least 2 oral sites (e.g., buccal mucosa, floor of oral cavity, tongue or soft palate) with each site receiving a total dose of ≥55 Gy. The treatment plan must include monotherapy with cisplatin administered in standard weekly (30 to 40 mg/m$^2$) or tri-weekly (80 to 100 mg/m$^2$, given on Days 0, 21 and 42) regimens or monotherapy with carboplatin administered weekly (100 mg/m$^2$).

ALD518 or placebo will be given every 4 weeks within 2 hours prior to the subjects' radiation for a total of 2 doses. A baseline visit will occur on the first day of RT. During the RT treatment period, subjects will be assessed twice weekly for the presence and severity of OM by treatment-blinded, trained evaluators using the World Health Organization (WHO) grading scale for OM. Subjects will also complete a daily diary, containing the Oral Mucositis Daily Questionnaire (OMDQ) and a listing of analgesic use, and on a weekly basis the FACT-HN and FACIT-F subscale PRO instruments.

All subjects will return to the clinic for 4 weekly visits after RT completion for assessment of OM. During this time, subjects will also continue to complete the OMDQ and the FACT-HN and FACIT-F subscale PRO instruments. The long term follow-up period of the clinical trial will include quarterly visits, primarily for the assessment of tumor response. These assessments will take place at Months 3, 6, 9 and 12 following the last dose of RT. At Months 3, 6, 9, and 12 tumors will be assessed clinically. At the Month 6 and Month 12 follow-up visits, tumor status will be assessed using RECIST criteria and the same imaging modality (CAT, PET, or MRI) that was used to evaluate tumor status prior to RT start (at the time of staging).

Example 44

Additional Evaluation of ALD518 in RA Clinical Trials

This example describes further Phase II clinical trial results for administration of ALD518 to patients with active RA. For purposes of inclusion in this study, a patient was considered to have active RA if the patient exhibited at least 6 swollen/6 tender joints, CRP ≥10 mg/dL, and had been treated with a stable dose of methotrexate (MTX) (>10 mg/week) for at least 3 months and stable use of NSAIDs or steroids (if any).

ALD518 was administered in a double-blind, placebo-controlled study in which patients with active RA were randomized 1:1:1:1 to receive either 80 mg (n=32), 160 mg (n=34), or 320 mg (n=28) ALD518, or placebo (n=33). ALD518 or placebo were given as an intravenous infusion over 60 minutes on Day 1 and then again 8 weeks later. Patients were maintained on stable doses of methotrexate (MTX) (at least 10 mg/week). Disease-modifying antirheumatic drugs (DMARDs) other than MTX were discontinued at least 4 months prior to study entry. Efficacy endpoints were assessed at weeks 12 (primary endpoint) and week 16. HRQoL was evaluated by the Medical Outcomes Survey Short Form-36 (SF-36). Analyses were performed on the modified intent-to-treat population for patients with data available at the visit of interest (as observed).

127 active RA patients were randomized and treated, and 116 completed the trial (80 mg, 29/32; 160 mg, 33/34; 320 mg, 25/28; placebo, 29/33). Patient disposition is summarized in FIG. 26.

At baseline, mean age was 52.3 years; mean RA duration was 6.8 years; mean tender and swollen joint counts were 26.1 and 16.7, and mean Physical (PCS) and Mental component summary (MCS) scores were 31.0 and 35.0, respectively. Mean changes from baseline to week 12 in MCS were significantly greater in each ALD518 dose group vs placebo, and mean changes in both PCS and MCS scores exceeded MCID in each ALD518 group. At week 12, mean changes from baseline in one or more SF-36 domains were significantly greater in ALD518 dose groups vs placebo. Changes >MCID were observed in all domains and in SF-6D in patients receiving ALD518. Improvements at week 12 were sustained at week 16.

Results

Short Form-36 Component Summary Scores:

HRQoL was assessed by the patient-reported Short Form-36 (SF-36) questionnaire. The SF-36 includes 36 questions divided into eight domains and summarized into the physical and mental component summary scores (PCS and MCS, respectively). Scores range from 0 to 100, with higher scores indicating better health. The observed Minimum Clinically Important Differences (MCID) are 2.5-5.0 for the PCS and MCS, and 5.0-10.0 for domain scores.

Short Form-6D:

The SF-6D is a validated preference-based measure of health utilities. The SF-6D was calculated using mean changes within treatment groups across all eight SF-36 domains to yield a single utility measure. The Minimum Important Difference (MID) is 0.041.

Analysis

Analysis was performed on the modified intent-to-treat population for patients with available data at the visit of interest (as observed). Changes from baseline in SF-36 PCS, MCS and domain scores were summarized as descriptive statistics by treatment group and visit. ALD518 treatment groups were also compared with placebo at Week 12 using a two-sample t-test.

For Weeks 12 and 16, spydergrams were used to present results across all domains of the SF-36 in a single figure, and to compare with age- and gender-matched normative data from a US population. Demarcations along the domain axes of the spydergrams represent changes of 10 in domain score, and patient disposition and baseline demographics and characteristics.

As shown in FIG. 26, a total of 127 patients were randomized and received ≥1 dose of ALD518; 91.3% of patients completed the study and eleven (8.7%) patients discontinued the study.

The individual SF-36 domain scores at Baseline and Week 12 are shown in Table 22 and illustrated graphically in FIG. 27. Baseline domain scores were generally well balanced across the treatment groups At baseline, patients had impaired HRQoL. Combined mean baseline PCS and MCS scores were 31.0 and 35.0, respectively, and 1.5-2.0 standard deviations less than normative values of 50. Scores for each of the individual subscales of the SF-36 were also considerably lower than age- and gender-matched US norms.

For all ALD518 treatment groups, mean improvements from baseline to Week 12 were large across the eight domains of the SF-36 and exceeded those observed with placebo (See the Table 22 and FIG. 27). Mean improvements were significantly greater than those observed with placebo ($p<0.05$;

Table 22) at Week 12 in the following domains; Role physical (ALD518 320 mg group); bodily pain, general health, social functioning and mental health (ALP518 80 and 320 mg treatment groups); vitality (all ALD518 groups); role emotional (ALD518 80 mg group).

At all doses of ALD518, mean improvements in all eight SF-36 domains exceeded the MCID at Week 12. See Table 22. After adjustment for the change from baseline in the placebo group, improvements from baseline observed with ALD518 were greater than, and in some cases at least twice, that observed in the placebo group. There was observed dose-dependent changes (improvements) in the domains of role physical, bodily pain and mental health. Treatment with ALD518 resulted in improvements in SF-36 scores toward those observed in the 'normal' comparative population. See FIG. 29.

TABLE 22

SF-36 PCS and MCS Domains at Baseline and at Week 12

| Domain* (+age/gender norm) | Time point | ALD518 80 mg (n = 32) | ALD518 160 mg (n = 34) | ALD518 320 mg (n = 28) | Placebo (n = 33) |
|---|---|---|---|---|---|
| PCS Domains | | | | | |
| Physical functioning | Baseline | 48.3 | 42.1 | 49.3 | 42.8 |
| (79.6) | Mean at Week 12 | 61.0 | 61.6 | 70.4 | 55.0 |
| Role physical (80.1) | Baseline | 27.9 | 26.0 | 36.7 | 33.5 |
| | Mean at Week 12 | 50.0 | 53.5 | 59.7† | 47.1 |
| Bodily pain (68.3) | Baseline | 26.4 | 22.1 | 33.6 | 30.7 |
| | Mean at Week 12 | 47.8† | 50.5 | 56.9† | 39.5 |
| General health | Baseline | 36.5 | 33.4 | 38.7 | 38.9 |
| (69.5) | Mean at Week 12 | 45.1† | 45.6 | 49.5† | 39.4 |
| Vitality (58.2) | Baseline | 32.5 | 26.2 | 38.8 | 41.5 |
| | Mean at Week 12 | 50.9† | 50.8† | 60.9† | 46.3 |
| Social functioning | Baseline | 47.7 | 31.6 | 42.1 | 48.8 |
| (83.6) | Mean at Week 12 | 66.8† | 59.4 | 73.1† | 57.5 |
| Role emotional | Baseline | 44.5 | 40.8 | 37.3 | 43.1 |
| (86.8) | Mean at Week 12 | 60.3† | 63.0 | 61.7 | 51.9 |
| Mental health (74.9) | Baseline | 48.4 | 34.7 | 51.1 | 52.7 |
| | Mean at Week 12 | 61.0† | 61.6 | 70.4† | 55.0 |

*0-100 scores are presented for each domain to enable interpretation within the context of the MCIDs;
shading highlights changes ≥MCID in domain scores;
Baseline scores are mean, based on patients with available data at visit of interest;
PCS = Physical Component Score;
MCS = Mental Component Score;
MCID = Minimum Clinically Important Differences;
†represents $p < 0.05$ associated with comparison of changes from baseline between a ALD518 arm versus placebo based on an ANCOVA model, adjusted for age at baseline and sex Result Summary: 127 active RA patients were randomized and treated, and 116 completed the trial (80 mg, 29/32; 160 mg, 33/34; 320 mg, 25/28; placebo, 29/33). At baseline, mean age was 52.3 years; mean RA duration was 6.8 years; mean tender and swollen joint counts were 26.1 and 16.7, and mean Physical (PCS) and Mental component summary (MCS) scores were 31.0 and 35.0, respectively. Mean changes from baseline to week 12 in MCS were significantly greater in each ALD518 dose group vs placebo, and mean changes in both PCS and MCS scores exceeded MCID in each ALD518 group. At week 12, mean changes from baseline in one or more SF-36 domains were significantly greater in ALD518 dose groups than the placebo group (Table 23). Improvements in SF-6D were 3-4 times the MID in the ALD-518 groups compared with less than 2 times the MID in the placebo group (as noted above, the MID is 0.041). Changes exceeding the MCID were observed in all domains and in SF-6D in patients receiving ALD518. Improvements at week 12 were sustained at week 16.

TABLE 23

SF-6D Scores at Baseline and Weeks 12 and 16.

| SF-6D (+age/gender norm) | | | ALD518 80 mg (n = 32) | ALD518 160 mg (n = 34) | ALD518 320 mg (n = 28) | Placebo (n = 33) |
|---|---|---|---|---|---|---|
| SF-6D | Week 12 | n = | 32 | 33 | 29 | 32 |
| (0.831) | | Baseline | 0.582 | 0.522 | 0.612 | 0.603 |
| | | Mean at Week 12 | 0.714 | 0.715 | 0.785 | 0.664 |
| | | Mean change to Week 12 | 0.132 | 0.193 | 0.172 | 0.062 |

TABLE 23-continued

SF-6D Scores at Baseline and Weeks 12 and 16.

| SF-6D (+age/gender norm) | | ALD518 80 mg (n = 32) | ALD518 160 mg (n = 34) | ALD518 320 mg (n = 28) | Placebo (n = 33) |
|---|---|---|---|---|---|
| Week 16 | n = | 32 | 33 | 29 | 32 |
| | Baseline | 0.556 | 0.584 | 0.579 | 0.592 |
| | Mean at Week 16 | 0.692 | 0.736 | 0.751 | 0.662 |
| | Mean change to Week 16 | 0.140 | 0.150 | 0.170 | 0.070 |

Shading highlights changes that exceeded the MID (minimum important difference).

Conclusions:

Treatment with the IL-6 inhibitor ALD518 resulted in statistically significant and clinically meaningful improvements in physical and mental aspects of HRQoL. These data further support the clinical efficacy of ALD518 for treatment of patients with active RA and inadequate responses to methotrexate (MTX).

Example 45

Oral Mucositis Clinical Trial in Progress

Subjects suffering from oral mucositis with head and neck cancer receiving concurrent chemotherapy and radiotherapy are being treated with regimen of a 160 mg doses of a composition comprising a humanized monoclonal antibody that selectively binds IL-6 (ALD518, also known as Ab1 which contains the variable sequences in SEQ ID NO:19 and SEQ ID NO:20).

Subjects are being assessed using tumor staging (standard TNM system) during the screening period, which occurs within 30 days prior to radiotherapy (RT) start. The RT treatment period is approximately 7 weeks, depending on the subject's prescribed radiation plan. Post-RT treatment period visits are scheduled at weeks 1, 2, 3, and 4 following the treatment period. Long term follow-up visits are scheduled at 3, 6, 9, and 12 months following the end of RT to determine if there is an effect of ALD518 on the tumor response to CRT.

Subjects were recently diagnosed and pathologically confirmed with non-metastatic SCC of the oral cavity, oropharynx, hypopharynx or larynx. Subjects are scheduled to receive a continuous course of intensity-modulated radiotherapy (IMRT) with a minimum cumulative dose of 55 Gy and maximum dose of 72 Gy. Planned radiation treatment fields include at least 2 oral sites (e.g., buccal mucosa, floor of oral cavity, tongue or soft palate) with each site receiving a total dose of ≥55 Gy. The treatment plan include monotherapy with cisplatin administered in standard weekly (30 to 40 mg/m$^2$) or tri-weekly (80 to 100 mg/m$^2$, given on Days 0, 21 and 42) regimens or monotherapy with carboplatin administered weekly (100 mg/m$^2$).

A composition comprising a humanized monoclonal antibody that selectively binds IL-6 (ALD518 also known as Ab1) is being given within 2 hours prior to the subjects' radiation every 4 weeks for a total of 2 doses. A baseline visit occurred on the first day of ALD518 and RT. Safety, PK, PD, and markers of IL-6 biology (e.g., total IL-6, sIL-6r, soluble gp 130, sIL-6 Complex) are being monitored during the RT treatment and Post-RT treatment period. The long term follow-up period of the treatment includes scheduled long term follow-up visits, primarily for the assessment of tumor response and survival. These assessments are scheduled at months 3, 6, 9 and 12 following the last dose of RT. At months 3, 6, 9, and 12 tumors will be assessed clinically. At the Month 6 and Month 12 follow-up visits, tumor status will be assessed using RECIST criteria and the same imaging modality (CAT, PET or MRI) that was used to evaluate tumor status prior to RT start (at the time of staging) may be used.

Following a treatment regimen comprising the administration of a humanized monoclonal antibody that selectively binds IL-6 ALD-518 (Ab1) the patients show improvement in their oral mucositis (e.g., a reduction in symptoms) after only 4 weeks of treatment.

As assessed using the WHO (World Health Organization) oral mucositis scale (Table 2) 3 patients receiving 160 mg intravenous administration of ALD518 (Ab1) were assessed. The first subject (circles) has not shown any signs of developing oral mucositis, maintaining a Grade 0 for the entire 4 weeks. This is indicative of ALD518 acting to prevent the development of oral mucositis. The second patient (squares) developed Grade 2 oral mucositis, but this appears to have lessened in severity. This is indicative of ALD518 acting to prevent the development of severe oral mucositis (e.g., Grade 4) and even lessen the severity of oral mucositis. The third patient (triangles) developed Grade 2/3 oral mucosits. This is indicative of ALD518 acting to prevent the development of severe oral mucositis (e.g., Grade 4). In this patient population, it is expected that about 60% of patients to develop at least Grade 3 or Grade 4 oral mucositis with this type of IMRT+chemotherapy and over 80% of the patients to develop at least Grade 2 and above oral mucositis. Thus, this data suggests that a humanized monoclonal antibody that selectively binds IL-6 (e.g., ALD518 also known as Ab1) is effective in treating and preventing oral mucositis resulting from the combination of chemotherapy and radiotherapy.

We further conclude based on these results that other IL-6 antagonists, including those identified in this application, e.g., the exemplified anti-IL-6 antibodies and antibody fragments, as well as the identified non-antibody IL-6 antagonists, will have clinical application in treating and preventing mucositis, e.g., oral and gastrointestinal or alimentary mucositis.

Example 46

Ongoing Anemia Clinical Trial

Three cancer patients which were to be treated with cisplatin were treated with ALD-518 prior to cisplatin chemotherapy in order to prevent or lessen anemia, and in particular to prevent the onset of severe anemia which is a very common side effect of cisplatin therapy, i.e., when administered alone or in conjunction with radiotherapy.

All three patients received cisplatin every 3 weeks at a dosage of 100 mg/m$^2$. Particularly, said dosage of chemo was administered at week 0, at week 3 and in one patient another dose was administered at week 6. In these same patients, 160 mg of ALD518 (Ab1), a humanized anti-IL-6 monoclonal antibody containing the variable sequences in SEQ ID NO:19 and SEQ ID NO:20, was administered intravenously at week 0 and week 4. Radiotherapy (RT) was also administered to these patients at a dosage of 2-2.2 Gray per day from week 0 and will continue until the end of the planned RT for each patient every day 5 days a week, All 3 patients are now post-therapy (between week 8 and week 12 of the treatment regimen). The last blood count was at the end of RT about week 8. None of these patients as of week 8 after treatment shows signs of severe anemia. All three patients will be monitored at least until week 12 and are expected to show no or less severe anemia resulting from the combination of cisplatin and radiotherapy as compared to the severe anemia typically seen in patients receiving cisplatin alone or when administered in a clinical regimen also including radiation. This will be confirmed by assaying hemoglobin and/or RBC counts and other clinical indicators of anemia in these patients.

Although the invention has been described in some detail by way of illustration and example for purposes of clarity of understanding, it will be obvious that certain changes and modifications will practiced within the scope of the appended claims. Modifications of the above-described modes for carrying out the invention that are obvious to persons of skill in medicine, pharmacology, microbiology, and/or related fields are intended to be within the scope of the following claims.

All publications (e.g., Non-Patent Literature), patent application publications, and patent applications mentioned in this specification are indicative of the level of skill of those skilled in the art to which this invention pertains. All such publications (e.g., Non-Patent Literature), patent application publications, and patent applications are herein incorporated by reference to the same extent as if each individual publication, patent, patent application publication, or patent application is specifically and individually indicated to be incorporated by reference.

What we claim is:

1. A method of treating or reducing the occurrence of mucositis in a subject in need thereof, comprising administering a composition comprising an effective amount of an anti-interleukin 1 (IL-6) antibody or antibody fragment thereof that binds IL-6, wherein said antibody or antibody fragment thereof comprises the variable light ($V_L$) complementarity determining regions (CDRs) in SEQ ID NO:4, 5 and 6, and the variable heavy ($V_H$) CDRs in SEQ ID NO:7, 8 or 120, and 9, respectively.

2. The method of claim 1, wherein said mucositis is oral mucositis.

3. The method of claim 1, wherein said mucositis is alimentary track mucositis.

4. The method of claim 1, wherein said mucositis is gastrointestinal tract mucositis.

5. The method of claim 1, wherein said mucositis is mucositis associated with chemotherapy.

6. The method of claim 5, wherein said chemotherapy comprises administration of a chemotherapy agent selected from the group consisting of Alemtuzumab (Campath™), Asparaginase (Elspar™), Bleomycin (Blenoxane™), Busulfan (Myleran™, Busulfex™), Capecitabine (Xeloda™), Carboplatin (Paraplatin™), Cisplatin (PLATINOL™), Cyclophosphamide (Cytoxan™), Cytarabine (Cytosar-U™), Daunorubicin (Cerubidine™), Docetaxel (Taxotere™), Doxorubicin (Adriamycin™), Epirubicin (Ellence™), Etoposide (VePesid™), Fluorouracil (5-FU™), Gemcitabine (Gemzar™), Gemtuzumab ozogamicin (Mylotarg™), Hydroxyurea (Hydrea™), Idarubicin (Idamycin™), Interleukin 2 (Proleukin™) Irinotecan (Camptosar™), Lomustine (CeeNU™), Mechlorethamine (Mustargen™), Melphalan (Alkeran™), Methotrexate (Rheumatrex™), Mitomycin (Mutamycin™), Mitoxantrone (Novantrone™), Oxaliplatin (Eloxatin™), Paclitaxel (Taxol™), Pemetrexed (Alimta™) Pentostatin (Nipent™), Procarbazine (Matulane™), Thiotepa (Thioplex™), Topotecan (Hycamtin™), Trastuzumab (Herceptin™), Tretinoin (Vesanoid™), Vinblastine (Velban™), and Vincristine (Oncovin™).

7. The method of claim 1, wherein said mucositis is mucositis associated with radiotherapy.

8. The method of claim 1, wherein said mucositis is mucositis associated with cancer.

9. The method of claim 1, wherein said mucositis is mucositis associated with hematopoietic stem cell transplant (HSCT).

10. The method of claim 1, wherein said anti-IL-6 antibody or antibody fragment thereof comprises at least one light chain selected from the group consisting of an amino acid sequence with at least about 90% sequence identity to an amino acid sequence of SEQ ID NO: 2, 20, 647, 648, 649, 650, 651, 655, 660, 666, 667, 671, 675, 679, 683, 687, 693, 699, 702, 706, or 709.

11. The method of claim 1, wherein said anti-IL-6 antibody or antibody fragment thereof comprises at least one heavy chain selected from the group consisting of an amino acid sequence with at least about 90% sequence identity to an amino acid sequence of SEQ ID NO: 3, 18, 19, 652, 653, 654, 655, 656, 657, 658, 661, 664, 665, 668, 672, 676, 680, 684, 688, 691, 692, 704, or 708.

12. The method of claim 1, wherein said antibody or antibody fragment thereof comprises a light chain comprising the amino acid sequence of SEQ ID NO: 2, 20, 647, 648, 649, 650, 651, 660, 666, 699, 702, 706, or 709.

13. The method of claim 1, wherein said antibody or antibody fragment thereof comprises a humanized light chain comprising the amino acid sequence of SEQ ID NO: 648, 649, or 650.

14. The method of claim 1, wherein said antibody or antibody fragment thereof comprises a heavy chain comprising the amino acid sequence of SEQ ID NO: 3, 18, 19, 652, 653, 654, 655, 656, 657, 658, 661, 664, 665, 704, or 708.

15. The method of claim 1, wherein said antibody or antibody fragment thereof comprises a humanized heavy chain comprising the amino acid sequence of SEQ ID NO: 653, 654, or 655.

16. The method of claim 1, wherein anti-IL-6 antibody or antibody fragment thereof is expressed from a recombinant cell.

17. The method of claim 16, wherein the cell is mammalian, yeast, bacterial, or insect cell.

18. The method of claim 17, wherein the cell is a yeast cell.

19. The method of claim 18, wherein the cell is a diploidal yeast cell.

20. The method of claim 19, wherein the yeast cell is a *Pichia* yeast.

21. The method of claim 1, wherein said antibody or antibody fragment thereof is asialated.

22. The method of claim 1, wherein said antibody fragment is a Fab, Fab', $F(ab')_2$, Fv, scFv, IgNAR, SMIP, camelbody, or nanobody.

23. The method of claim 1, wherein said antibody or antibody fragment thereof has an in vivo half-life of at least about 30 days.

24. The method of claim 1, wherein the antibody or antibody fragment thereof is aglycosylated.

25. The method of claim 1, wherein the antibody or antibody fragment thereof contains an Fc region that has been modified to alter effector function, half-life, proteolysis, and/or glycosylation.

26. The method of claim 1, wherein the antibody or antibody fragment thereof is a human, humanized, single chain, or chimeric antibody.

27. The method of claim 1, wherein the antibody or antibody fragment thereof further comprises a human $F_c$.

28. The method of claim 1, wherein said anti-IL-6 antibody or antibody fragment thereof is administered prior to, concurrent with or after chemotherapy or radiotherapy.

29. The method of claim 1, wherein said subject is receiving concomitant chemotherapy.

30. The method claim 1, wherein said treated mucositis comprises oral or oropharyngeal mucositis induced by chemoradiation (CRT) regimens or hematopoietic stem cell transplant (HSCT) used for the treatment of cancers of the head and neck.

31. A method of treating or reducing the occurrence of emesis in a subject in need thereof, comprising administering a composition comprising an effective amount of an anti-interleukin 1 (IL-6) antibody or antibody fragment thereof that binds IL-6, wherein said antibody or antibody fragment thereof comprises the variable light ($V_L$) complementarity determining regions (CDRs) in SEQ ID NO:4, 5 and 6, and the variable heavy ($V_H$) CDRs in SEQ ID NO:7, 8 or 120, and 9, respectively.

32. The method of claim 31, wherein said emesis is emesis associated with chemotherapy.

33. The method of claim 31, wherein said emesis is emesis associated with radiotherapy.

34. The method of claim 31, wherein said emesis is emesis associated with hematopoietic stem cell transplant (HSCT).

35. A method for treating oral mucositis in a subject with head and neck cancer receiving concomitant chemotherapy, comprising administering an effective amount of a humanized monoclonal antibody that specifically binds interleukin-6 (IL-6), wherein said antibody or antibody fragment thereof comprises the variable light ($V_L$) CDRs in SEQ ID NO: 4, 5 and 6, and the variable heavy ($V_H$) CDRs in SEQ ID NO:7, 8 or 120, and 9, respectively.

* * * * *

SEQUENCE LISTING

```
<160> NUMBER OF SEQ ID NOS: 748

<210> SEQ ID NO 1
<211> LENGTH: 183
<212> TYPE: PRT
<213> ORGANISM: Homo sapiens

<400> SEQUENCE: 1

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
            100                 105                 110

Ala Val Gln Met Ser Thr Lys Val Leu Ile Gln Phe Leu Gln Lys Lys
        115                 120                 125

Ala Lys Asn Leu Asp Ala Ile Thr Thr Pro Asp Pro Thr Thr Asn Ala
    130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
            180


<210> SEQ ID NO 2
<211> LENGTH: 163
<212> TYPE: PRT
<213> ORGANISM: Oryctolagus cuniculus

<400> SEQUENCE: 2

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30
```

Val Ser Ala Ala Val Gly Gly Thr Val Thr Ile Lys Cys Gln Ala Ser
35 40 45

Gln Ser Ile Asn Asn Glu Leu Ser Trp Tyr Gln Gln Lys Pro Gly Gln
50 55 60

Arg Pro Lys Leu Leu Ile Tyr Arg Ala Ser Thr Leu Ala Ser Gly Val
65 70 75 80

Ser Ser Arg Phe Lys Gly Ser Gly Ser Gly Thr Glu Phe Thr Leu Thr
85 90 95

Ile Ser Asp Leu Glu Cys Ala Asp Ala Ala Thr Tyr Tyr Cys Gln Gln
100 105 110

Gly Tyr Ser Leu Arg Asn Ile Asp Asn Ala Phe Gly Gly Gly Thr Glu
115 120 125

Val Val Val Lys Arg Thr Val Ala Ala Pro Ser Val Phe Ile Phe Pro
130 135 140

Pro Ser Asp Glu Gln Leu Lys Ser Gly Thr Ala Ser Val Val Cys Leu
145 150 155 160

Leu Asn Asn

<210> SEQ ID NO 3
<211> LENGTH: 166
<212> TYPE: PRT
<213> ORGANISM: Oryctolagus cuniculus

<400> SEQUENCE: 3

Met Glu Thr Gly Leu Arg Trp Leu Leu Leu Val Ala Val Leu Lys Gly
1 5 10 15

Val Gln Cys Gln Ser Leu Glu Glu Ser Gly Gly Arg Leu Val Thr Pro
20 25 30

Gly Thr Pro Leu Thr Leu Thr Cys Thr Ala Ser Gly Phe Ser Leu Ser
35 40 45

Asn Tyr Tyr Val Thr Trp Val Arg Gln Ala Pro Gly Lys Gly Leu Glu
50 55 60

Trp Ile Gly Ile Ile Tyr Gly Ser Asp Glu Thr Ala Tyr Ala Thr Trp
65 70 75 80

Ala Ile Gly Arg Phe Thr Ile Ser Lys Thr Ser Thr Thr Val Asp Leu
85 90 95

Lys Met Thr Ser Leu Thr Ala Ala Asp Thr Ala Thr Tyr Phe Cys Ala
100 105 110

Arg Asp Asp Ser Ser Asp Trp Asp Ala Lys Phe Asn Leu Trp Gly Gln
115 120 125

Gly Thr Leu Val Thr Val Ser Ser Ala Ser Thr Lys Gly Pro Ser Val
130 135 140

Phe Pro Leu Ala Pro Ser Ser Lys Ser Thr Ser Gly Gly Thr Ala Ala
145 150 155 160

Leu Gly Cys Leu Val Lys
165

<210> SEQ ID NO 4
<211> LENGTH: 11
<212> TYPE: PRT
<213> ORGANISM: Oryctolagus cuniculus

<400> SEQUENCE: 4

Gln Ala Ser Gln Ser Ile Asn Asn Glu Leu Ser
1 5 10

<210> SEQ ID NO 5
<211> LENGTH: 7
<212> TYPE: PRT
<213> ORGANISM: Oryctolagus cuniculus

<400> SEQUENCE: 5

Arg Ala Ser Thr Leu Ala Ser
1 5

<210> SEQ ID NO 6
<211> LENGTH: 12
<212> TYPE: PRT
<213> ORGANISM: Oryctolagus cuniculus

<400> SEQUENCE: 6

Gln Gln Gly Tyr Ser Leu Arg Asn Ile Asp Asn Ala
1 5 10

<210> SEQ ID NO 7
<211> LENGTH: 5
<212> TYPE: PRT
<213> ORGANISM: Oryctolagus cuniculus

<400> SEQUENCE: 7

Asn Tyr Tyr Val Thr
1 5

<210> SEQ ID NO 8
<211> LENGTH: 16
<212> TYPE: PRT
<213> ORGANISM: Oryctolagus cuniculus

<400> SEQUENCE: 8

Ile Ile Tyr Gly Ser Asp Glu Thr Ala Tyr Ala Thr Trp Ala Ile Gly
1 5 10 15

<210> SEQ ID NO 9
<211> LENGTH: 12
<212> TYPE: PRT
<213> ORGANISM: Oryctolagus cuniculus

<400> SEQUENCE: 9

Asp Asp Ser Ser Asp Trp Asp Ala Lys Phe Asn Leu
1 5 10

<210> SEQ ID NO 10
<211> LENGTH: 491
<212> TYPE: DNA
<213> ORGANISM: Oryctolagus cuniculus

<400> SEQUENCE: 10
atggacacga gggcccccac tcagctgctg gggctcctgc tgctctggct cccaggtgcc 60
agatgtgcct atgatatgac ccagactcca gcctcggtgt ctgcagctgt gggaggcaca 120
gtcaccatca agtgccaggc cagtcagagc attaacaatg aattatcctg gtatcagcag 180
aaaccagggc agcgtcccaa gctcctgatc tatagggcat ccactctggc atctggggtc 240
tcatcgcggt tcaaaggcag tggatctggg acagagttca ctctcaccat cagcgacctg 300
gagtgtgccg atgctgccac ttactactgt caacagggtt atagtctgag gaatattgat 360
aatgctttcg gcggagggac cgaggtggtg gtcaaacgta cggtagcggc cccatctgtc 420
ttcatcttcc cgccatctga tgagcagttg aaatctggaa ctgcctctgt tgtgtgcctg 480
ctgaataact t 491

<210> SEQ ID NO 11
<211> LENGTH: 499
<212> TYPE: DNA
<213> ORGANISM: Oryctolagus cuniculus

<400> SEQUENCE: 11
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
acagcctctg gattctccct cagtaactac tacgtgacct gggtccgcca ggctccaggg 180
aaggggctgg aatggatcgg aatcatttat ggtagtgatg aaacggccta cgcgacctgg 240
gcgataggcc gattcaccat ctccaaaacc tcgaccacgg tggatctgaa aatgaccagt 300
ctgacagccg cggacacggc cacctatttc tgtgccagag atgatagtag tgactgggat 360
gcaaaattta acttgtgggg ccaaggcacc ctggtcaccg tctcgagcgc ctccaccaag 420
ggcccatcgg tcttcccct ggcaccctcc tccaagagca cctctggggg cacagcggcc 480
ctgggctgcc tggtcaagg 499

<210> SEQ ID NO 12
<211> LENGTH: 33
<212> TYPE: DNA
<213> ORGANISM: Oryctolagus cuniculus

<400> SEQUENCE: 12
caggccagtc agagcattaa caatgaatta tcc 33

<210> SEQ ID NO 13
<211> LENGTH: 21
<212> TYPE: DNA
<213> ORGANISM: Oryctolagus cuniculus

<400> SEQUENCE: 13
agggcatcca ctctggcatc t 21

<210> SEQ ID NO 14
<211> LENGTH: 36
<212> TYPE: DNA
<213> ORGANISM: Oryctolagus cuniculus

<400> SEQUENCE: 14
caacagggtt atagtctgag gaatattgat aatgct 36

<210> SEQ ID NO 15
<211> LENGTH: 15
<212> TYPE: DNA
<213> ORGANISM: Oryctolagus cuniculus

<400> SEQUENCE: 15
aactactacg tgacc 15

<210> SEQ ID NO 16
<211> LENGTH: 48
<212> TYPE: DNA
<213> ORGANISM: Oryctolagus cuniculus

<400> SEQUENCE: 16
atcatttatg gtagtgatga aacggcctac gcgacctggg cgataggc 48

<210> SEQ ID NO 17
<211> LENGTH: 36
<212> TYPE: DNA
<213> ORGANISM: Oryctolagus cuniculus

<400> SEQUENCE: 17
gatgatagta gtgactggga tgcaaaattt aacttg 36

<210> SEQ ID NO 18
<211> LENGTH: 109
<212> TYPE: PRT
<213> ORGANISM: Oryctolagus cuniculus

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Trp Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu
            100                 105
```

<210> SEQ ID NO 19
<211> LENGTH: 109
<212> TYPE: PRT
<213> ORGANISM: Oryctolagus cuniculus

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Ser Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu
            100                 105
```

<210> SEQ ID NO 20
<211> LENGTH: 99
<212> TYPE: PRT
<213> ORGANISM: Oryctolagus cuniculus

<400> SEQUENCE: 20

```
Ile Gln Met Thr Gln Ser Pro Ser Ser Leu Ser Ala Ser Val Gly Asp
1               5                   10                  15

Arg Val Thr Ile Thr Cys Gln Ala Ser Gln Ser Ile Asn Asn Glu Leu
```

```
            20                  25                  30

Ser Trp Tyr Gln Gln Lys Pro Gly Lys Ala Pro Lys Leu Leu Ile Tyr
        35                  40                  45

Arg Ala Ser Thr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Asp
65                  70                  75                  80

Asp Phe Ala Thr Tyr Tyr Cys Gln Gln Gly Tyr Ser Leu Arg Asn Ile
                85                  90                  95

Asp Asn Ala


<210> SEQ ID NO 21
<211> LENGTH: 170
<212> TYPE: PRT
<213> ORGANISM: Oryctolagus cuniculus

<400> SEQUENCE: 21

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Asn Cys Gln Ala Ser
        35                  40                  45

Glu Thr Ile Tyr Ser Trp Leu Ser Trp Tyr Gln Gln Lys Pro Gly Gln
    50                  55                  60

Pro Pro Lys Leu Leu Ile Tyr Gln Ala Ser Asp Leu Ala Ser Gly Val
65                  70                  75                  80

Pro Ser Arg Phe Ser Gly Ser Gly Ala Gly Thr Glu Tyr Thr Leu Thr
                85                  90                  95

Ile Ser Gly Val Gln Cys Asp Asp Ala Ala Thr Tyr Tyr Cys Gln Gln
            100                 105                 110

Gly Tyr Ser Gly Ser Asn Val Asp Asn Val Phe Gly Gly Gly Thr Glu
        115                 120                 125

Val Val Val Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys
                165                 170


<210> SEQ ID NO 22
<211> LENGTH: 167
<212> TYPE: PRT
<213> ORGANISM: Oryctolagus cuniculus

<400> SEQUENCE: 22

Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Arg Leu Val Thr
            20                  25                  30

Pro Gly Thr Pro Leu Thr Leu Thr Cys Thr Ala Ser Gly Phe Ser Leu
        35                  40                  45

Asn Asp His Ala Met Gly Trp Val Arg Gln Ala Pro Gly Lys Gly Leu
    50                  55                  60

Glu Tyr Ile Gly Phe Ile Asn Ser Gly Gly Ser Ala Arg Tyr Ala Ser
65                  70                  75                  80
```

Trp Ala Glu Gly Arg Phe Thr Ile Ser Arg Thr Ser Thr Thr Val Asp
85 90 95

Leu Lys Met Thr Ser Leu Thr Thr Glu Asp Thr Ala Thr Tyr Phe Cys
100 105 110

Val Arg Gly Gly Ala Val Trp Ser Ile His Ser Phe Asp Pro Trp Gly
115 120 125

Pro Gly Thr Leu Val Thr Val Ser Ser Ala Ser Thr Lys Gly Pro Ser
130 135 140

Val Phe Pro Leu Ala Pro Ser Ser Lys Ser Thr Ser Gly Gly Thr Ala
145 150 155 160

Ala Leu Gly Cys Leu Val Lys
165

<210> SEQ ID NO 23
<211> LENGTH: 11
<212> TYPE: PRT
<213> ORGANISM: Oryctolagus cuniculus

<400> SEQUENCE: 23

Gln Ala Ser Glu Thr Ile Tyr Ser Trp Leu Ser
1 5 10

<210> SEQ ID NO 24
<211> LENGTH: 7
<212> TYPE: PRT
<213> ORGANISM: Oryctolagus cuniculus

<400> SEQUENCE: 24

Gln Ala Ser Asp Leu Ala Ser
1 5

<210> SEQ ID NO 25
<211> LENGTH: 12
<212> TYPE: PRT
<213> ORGANISM: Oryctolagus cuniculus

<400> SEQUENCE: 25

Gln Gln Gly Tyr Ser Gly Ser Asn Val Asp Asn Val
1 5 10

<210> SEQ ID NO 26
<211> LENGTH: 5
<212> TYPE: PRT
<213> ORGANISM: Oryctolagus cuniculus

<400> SEQUENCE: 26

Asp His Ala Met Gly
1 5

<210> SEQ ID NO 27
<211> LENGTH: 16
<212> TYPE: PRT
<213> ORGANISM: Oryctolagus cuniculus

<400> SEQUENCE: 27

Phe Ile Asn Ser Gly Gly Ser Ala Arg Tyr Ala Ser Trp Ala Glu Gly
1 5 10 15

<210> SEQ ID NO 28
<211> LENGTH: 12
<212> TYPE: PRT
<213> ORGANISM: Oryctolagus cuniculus

<400> SEQUENCE: 28

Gly Gly Ala Val Trp Ser Ile His Ser Phe Asp Pro
1 5 10

<210> SEQ ID NO 29
<211> LENGTH: 511
<212> TYPE: DNA
<213> ORGANISM: Oryctolagus cuniculus

<400> SEQUENCE: 29
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca attgccaggc cagtgagacc atttacagtt ggttatcctg gtatcagcag 180
aagccagggc agcctcccaa gctcctgatc taccaggcat ccgatctggc atctggggtc 240
ccatcgcgat tcagcggcag tggggctggg acagagtaca ctctcaccat cagcggcgtg 300
cagtgtgacg atgctgccac ttactactgt caacagggtt atagtggtag taatgttgat 360
aatgttttcg gcggagggac cgaggtggtg gtcaaacgta cggtagcggc cccatctgtc 420
ttcatcttcc cgccatctga tgagcagttg aaatctggaa ctgcctctgt tgtgtgcctg 480
ctgaataact tctatcccag agaggccaaa g 511

<210> SEQ ID NO 30
<211> LENGTH: 501
<212> TYPE: DNA
<213> ORGANISM: Oryctolagus cuniculus

<400> SEQUENCE: 30
atggagactg ggctgcgctg gcttctcctg gtcgctgtgc tcaaaggtgt ccagtgtcag 60
gagcagctga aggagtccgg gggtcgcctg gtcacgcctg ggacacccct gacacttacc 120
tgcacagcct ctggattctc cctcaatgac catgcaatgg gctgggtccg ccaggctcca 180
gggaaggggc tggaatacat cggattcatt aatagtggtg gtagcgcacg ctacgcgagc 240
tgggcagaag gccgattcac catctccaga acctcgacca cggtggatct gaaaatgacc 300
agtctgacaa ccgaggacac ggccacctat ttctgtgtca gagggggtgc tgtttggagt 360
attcatagtt ttgatccctg gggcccaggg accctggtca ccgtctcgag cgcctccacc 420
aagggcccat cggtcttccc cctggcaccc tcctccaaga gcacctctgg gggcacagcg 480
gccctgggct gcctggtcaa g 501

<210> SEQ ID NO 31
<211> LENGTH: 33
<212> TYPE: DNA
<213> ORGANISM: Oryctolagus cuniculus

<400> SEQUENCE: 31
caggccagtg agaccattta cagttggtta tcc 33

<210> SEQ ID NO 32
<211> LENGTH: 21
<212> TYPE: DNA
<213> ORGANISM: Oryctolagus cuniculus

<400> SEQUENCE: 32
caggcatccg atctggcatc t 21

-continued

<210> SEQ ID NO 33
<211> LENGTH: 36
<212> TYPE: DNA
<213> ORGANISM: Oryctolagus cuniculus

<400> SEQUENCE: 33
caacagggtt atagtggtag taatgttgat aatgtt 36

<210> SEQ ID NO 34
<211> LENGTH: 15
<212> TYPE: DNA
<213> ORGANISM: Oryctolagus cuniculus

<400> SEQUENCE: 34
gaccatgcaa tgggc 15

<210> SEQ ID NO 35
<211> LENGTH: 48
<212> TYPE: DNA
<213> ORGANISM: Oryctolagus cuniculus

<400> SEQUENCE: 35
ttcattaata gtggtggtag cgcacgctac gcgagctggg cagaaggc 48

<210> SEQ ID NO 36
<211> LENGTH: 36
<212> TYPE: DNA
<213> ORGANISM: Oryctolagus cuniculus

<400> SEQUENCE: 36
gggggtgctg tttggagtat tcatagtttt gatccc 36

<210> SEQ ID NO 37
<211> LENGTH: 165
<212> TYPE: PRT
<213> ORGANISM: Oryctolagus cuniculus

<400> SEQUENCE: 37

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Ser Ile Ser Cys Gln Ala Ser
        35                  40                  45

Gln Ser Val Tyr Asp Asn Asn Tyr Leu Ser Trp Phe Gln Gln Lys Pro
    50                  55                  60

Gly Gln Pro Pro Lys Leu Leu Ile Tyr Gly Ala Ser Thr Leu Ala Ser
65                  70                  75                  80

Gly Val Pro Ser Arg Phe Val Gly Ser Gly Ser Gly Thr Gln Phe Thr
                85                  90                  95

Leu Thr Ile Thr Asp Val Gln Cys Asp Asp Ala Ala Thr Tyr Tyr Cys
            100                 105                 110

Ala Gly Val Tyr Asp Asp Asp Ser Asp Asn Ala Phe Gly Gly Gly Thr
        115                 120                 125

Glu Val Val Val Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe
                165
```

<210> SEQ ID NO 38
<211> LENGTH: 166
<212> TYPE: PRT
<213> ORGANISM: Oryctolagus cuniculus

<400> SEQUENCE: 38

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Val Tyr Tyr Met Asn Trp Val Arg Gln Ala Pro Gly Lys Gly Leu Glu
    50                  55                  60

Trp Ile Gly Phe Ile Thr Met Ser Asp Asn Ile Asn Tyr Ala Ser Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Ala
            100                 105                 110

Arg Ser Arg Gly Trp Gly Thr Met Gly Arg Leu Asp Leu Trp Gly Pro
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys
                165
```

<210> SEQ ID NO 39
<211> LENGTH: 13
<212> TYPE: PRT
<213> ORGANISM: Oryctolagus cuniculus

<400> SEQUENCE: 39

```
Gln Ala Ser Gln Ser Val Tyr Asp Asn Asn Tyr Leu Ser
1               5                   10
```

<210> SEQ ID NO 40
<211> LENGTH: 7
<212> TYPE: PRT
<213> ORGANISM: Oryctolagus cuniculus

<400> SEQUENCE: 40

```
Gly Ala Ser Thr Leu Ala Ser
1               5
```

<210> SEQ ID NO 41
<211> LENGTH: 11
<212> TYPE: PRT
<213> ORGANISM: Oryctolagus cuniculus

<400> SEQUENCE: 41

```
Ala Gly Val Tyr Asp Asp Asp Ser Asp Asn Ala
1               5                   10
```

<210> SEQ ID NO 42
<211> LENGTH: 5
<212> TYPE: PRT

<213> ORGANISM: Oryctolagus cuniculus

<400> SEQUENCE: 42

Val Tyr Tyr Met Asn
1 5

<210> SEQ ID NO 43
<211> LENGTH: 16
<212> TYPE: PRT
<213> ORGANISM: Oryctolagus cuniculus

<400> SEQUENCE: 43

Phe Ile Thr Met Ser Asp Asn Ile Asn Tyr Ala Ser Trp Ala Lys Gly
1 5 10 15

<210> SEQ ID NO 44
<211> LENGTH: 12
<212> TYPE: PRT
<213> ORGANISM: Oryctolagus cuniculus

<400> SEQUENCE: 44

Ser Arg Gly Trp Gly Thr Met Gly Arg Leu Asp Leu
1 5 10

<210> SEQ ID NO 45
<211> LENGTH: 496
<212> TYPE: DNA
<213> ORGANISM: Oryctolagus cuniculus

<400> SEQUENCE: 45
atggacacga gggcccccac tcagctgctg gggctcctgc tgctctggct cccaggtgcc 60
acatttgccg ccgtgctgac ccagactcca tctcccgtgt ctgcagctgt gggaggcaca 120
gtcagcatca gttgccaggc cagtcagagt gtttatgaca acaactactt atcctggttt 180
cagcagaaac cagggcagcc tcccaagctc ctgatctatg gtgcatccac tctggcatct 240
ggggtcccat cgcggttcgt gggcagtgga tctgggacac agttcactct caccatcaca 300
gacgtgcagt gtgacgatgc tgccacttac tattgtgcag gcgtttatga tgatgatagt 360
gataatgcct tcggcggagg gaccgaggtg gtggtcaaac gtacggtagc ggccccatct 420
gtcttcatct tcccgccatc tgatgagcag ttgaaatctg gaactgcctc tgttgtgtgc 480
ctgctgaata acttct 496

<210> SEQ ID NO 46
<211> LENGTH: 499
<212> TYPE: DNA
<213> ORGANISM: Oryctolagus cuniculus

<400> SEQUENCE: 46
atggagactg ggctgcgctg gcttctcctg gtggctgtgc tcaaaggtgt ccagtgtcag 60
tcgctggagg agtccggggg tcgcctggtc acccctggga cacccctgac actcacctgc 120
acagcctctg gattctccct cagtgtctac tacatgaact gggtccgcca ggctccaggg 180
aaggggctgg aatggatcgg attcattaca atgagtgata atataaatta cgcgagctgg 240
gcgaaaggcc gattcaccat ctccaaaacc tcgaccacgg tggatctgaa aatgaccagt 300
ccgacaaccg aggacacggc cacctatttc tgtgccagga gtcgtggctg ggggtacaatg 360 ggtcggttgg atctctgggg cccaggcacc ctcgtcaccg tctcgagcgc ctccaccaag 420
ggcccatcgg tcttccccct ggcaccctcc tccaagagca cctctggggg cacagcggcc 480

-continued ctgggctgcc tggtcaagg 499

<210> SEQ ID NO 47
<211> LENGTH: 39
<212> TYPE: DNA
<213> ORGANISM: Oryctolagus cuniculus

<400> SEQUENCE: 47
caggccagtc agagtgttta tgacaacaac tacttatcc 39

<210> SEQ ID NO 48
<211> LENGTH: 21
<212> TYPE: DNA
<213> ORGANISM: Oryctolagus cuniculus

<400> SEQUENCE: 48
ggtgcatcca ctctggcatc t 21

<210> SEQ ID NO 49
<211> LENGTH: 33
<212> TYPE: DNA
<213> ORGANISM: Oryctolagus cuniculus

<400> SEQUENCE: 49
gcaggcgttt atgatgatga tagtgataat gcc 33

<210> SEQ ID NO 50
<211> LENGTH: 15
<212> TYPE: DNA
<213> ORGANISM: Oryctolagus cuniculus

<400> SEQUENCE: 50
gtctactaca tgaac 15

<210> SEQ ID NO 51
<211> LENGTH: 48
<212> TYPE: DNA
<213> ORGANISM: Oryctolagus cuniculus

<400> SEQUENCE: 51
ttcattacaa tgagtgataa tataaattac gcgagctggg cgaaaggc 48

<210> SEQ ID NO 52
<211> LENGTH: 36
<212> TYPE: DNA
<213> ORGANISM: Oryctolagus cuniculus

<400> SEQUENCE: 52
agtcgtggct ggggtacaat gggtcggttg gatctc 36

<210> SEQ ID NO 53
<211> LENGTH: 164
<212> TYPE: PRT
<213> ORGANISM: Oryctolagus cuniculus

<400> SEQUENCE: 53

```
Met Asp Thr Arg Ala Pro Thr Gln Leu Leu Gly Leu Leu Leu Leu Trp
1               5                   10                  15

Leu Pro Gly Ala Ile Cys Asp Pro Val Leu Thr Gln Thr Pro Ser Pro
            20                  25                  30

Val Ser Ala Pro Val Gly Gly Thr Val Ser Ile Ser Cys Gln Ala Ser
        35                  40                  45
```

Gln Ser Val Tyr Glu Asn Asn Tyr Leu Ser Trp Phe Gln Gln Lys Pro
    50                  55                  60

Gly Gln Pro Pro Lys Leu Leu Ile Tyr Gly Ala Ser Thr Leu Asp Ser
65                  70                  75                  80

Gly Val Pro Ser Arg Phe Lys Gly Ser Gly Ser Gly Thr Gln Phe Thr
                85                  90                  95

Leu Thr Ile Thr Asp Val Gln Cys Asp Asp Ala Ala Thr Tyr Tyr Cys
            100                 105                 110

Ala Gly Val Tyr Asp Asp Asp Ser Asp Asp Ala Phe Gly Gly Gly Thr
        115                 120                 125

Glu Val Val Val Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn

<210> SEQ ID NO 54
<211> LENGTH: 167
<212> TYPE: PRT
<213> ORGANISM: Oryctolagus cuniculus

<400> SEQUENCE: 54

Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Gly Leu Val Thr
            20                  25                  30

Pro Gly Gly Thr Leu Thr Leu Thr Cys Thr Ala Ser Gly Phe Ser Leu
        35                  40                  45

Asn Ala Tyr Tyr Met Asn Trp Val Arg Gln Ala Pro Gly Lys Gly Leu
    50                  55                  60

Glu Trp Ile Gly Phe Ile Thr Leu Asn Asn Asn Val Ala Tyr Ala Asn
65                  70                  75                  80

Trp Ala Lys Gly Arg Phe Thr Phe Ser Lys Thr Ser Thr Thr Val Asp
                85                  90                  95

Leu Lys Met Thr Ser Pro Thr Pro Glu Asp Thr Ala Thr Tyr Phe Cys
            100                 105                 110

Ala Arg Ser Arg Gly Trp Gly Ala Met Gly Arg Leu Asp Leu Trp Gly
        115                 120                 125

His Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys
                165

<210> SEQ ID NO 55
<211> LENGTH: 13
<212> TYPE: PRT
<213> ORGANISM: Oryctolagus cuniculus

<400> SEQUENCE: 55

Gln Ala Ser Gln Ser Val Tyr Glu Asn Asn Tyr Leu Ser
1               5                   10

<210> SEQ ID NO 56
<211> LENGTH: 7
<212> TYPE: PRT

<213> ORGANISM: Oryctolagus cuniculus

<400> SEQUENCE: 56

Gly Ala Ser Thr Leu Asp Ser
1 5

<210> SEQ ID NO 57
<211> LENGTH: 11
<212> TYPE: PRT
<213> ORGANISM: Oryctolagus cuniculus

<400> SEQUENCE: 57

Ala Gly Val Tyr Asp Asp Asp Ser Asp Asp Ala
1 5 10

<210> SEQ ID NO 58
<211> LENGTH: 5
<212> TYPE: PRT
<213> ORGANISM: Oryctolagus cuniculus

<400> SEQUENCE: 58

Ala Tyr Tyr Met Asn
1 5

<210> SEQ ID NO 59
<211> LENGTH: 16
<212> TYPE: PRT
<213> ORGANISM: Oryctolagus cuniculus

<400> SEQUENCE: 59

Phe Ile Thr Leu Asn Asn Asn Val Ala Tyr Ala Asn Trp Ala Lys Gly
1 5 10 15

<210> SEQ ID NO 60
<211> LENGTH: 12
<212> TYPE: PRT
<213> ORGANISM: Oryctolagus cuniculus

<400> SEQUENCE: 60

Ser Arg Gly Trp Gly Ala Met Gly Arg Leu Asp Leu
1 5 10

<210> SEQ ID NO 61
<211> LENGTH: 494
<212> TYPE: DNA
<213> ORGANISM: Oryctolagus cuniculus

<400> SEQUENCE: 61
atggacacga gggcccccac tcagctgctg gggctcctgc tgctctggct cccaggtgcc 60
atatgtgacc ctgtgctgac ccagactcca tctcccgtat ctgcacctgt gggaggcaca 120
gtcagcatca gttgccaggc cagtcagagt gtttatgaga acaactattt atcctggttt 180
cagcagaaac cagggcagcc tcccaagctc ctgatctatg gtgcatccac tctggattct 240
ggggtcccat cgcggttcaa aggcagtgga tctgggacac agttcactct caccattaca 300
gacgtgcagt gtgacgatgc tgccacttac tattgtgcag gcgtttatga tgatgatagt 360
gatgatgcct tcggcggagg gaccgaggtg gtggtcaaac gtacggtagc ggccccatct 420
gtcttcatct tcccgccatc tgatgagcag ttgaaatctg gaactgcctc tgttgtgtgc 480
ctgctgaata actt 494

<210> SEQ ID NO 62

<211> LENGTH: 502
<212> TYPE: DNA
<213> ORGANISM: Oryctolagus cuniculus

<400> SEQUENCE: 62
atggagactg ggctgcgctg gcttctcctg gtggctgtgc tcaaaggtgt ccagtgtcag 60
gagcagctga aggagtccgg aggaggcctg gtaacgcctg gaggaaccct gacactcacc 120
tgcacagcct ctggattctc cctcaatgcc tactacatga actgggtccg ccaggctcca 180
gggaaggggc tggaatggat cggattcatt actctgaata ataatgtagc ttacgcgaac 240
tgggcgaaag gccgattcac cttctccaaa acctcgacca cggtggatct gaaaatgacc 300
agtccgacac ccgaggacac ggccacctat ttctgtgcca ggagtcgtgg ctggggtgca 360
atgggtcggt tggatctctg gggccatggc accctggtca ccgtctcgag cgcctccacc 420
aagggcccat cggtcttccc cctggcaccc tcctccaaga gcacctctgg gggcacagcg 480
gccctgggct gcctggtcaa gg 502

<210> SEQ ID NO 63
<211> LENGTH: 39
<212> TYPE: DNA
<213> ORGANISM: Oryctolagus cuniculus

<400> SEQUENCE: 63
caggccagtc agagtgttta tgagaacaac tatttatcc 39

<210> SEQ ID NO 64
<211> LENGTH: 21
<212> TYPE: DNA
<213> ORGANISM: Oryctolagus cuniculus

<400> SEQUENCE: 64
ggtgcatcca ctctggattc t 21

<210> SEQ ID NO 65
<211> LENGTH: 33
<212> TYPE: DNA
<213> ORGANISM: Oryctolagus cuniculus

<400> SEQUENCE: 65
gcaggcgttt atgatgatga tagtgatgat gcc 33

<210> SEQ ID NO 66
<211> LENGTH: 15
<212> TYPE: DNA
<213> ORGANISM: Oryctolagus cuniculus

<400> SEQUENCE: 66
gcctactaca tgaac 15

<210> SEQ ID NO 67
<211> LENGTH: 48
<212> TYPE: DNA
<213> ORGANISM: Oryctolagus cuniculus

<400> SEQUENCE: 67
ttcattactc tgaataataa tgtagcttac gcgaactggg cgaaaggc 48

<210> SEQ ID NO 68
<211> LENGTH: 36
<212> TYPE: DNA
<213> ORGANISM: Oryctolagus cuniculus -continued

<400> SEQUENCE: 68
agtcgtggct ggggtgcaat gggtcggttg gatctc 36

<210> SEQ ID NO 69
<211> LENGTH: 164
<212> TYPE: PRT
<213> ORGANISM: Oryctolagus cuniculus

<400> SEQUENCE: 69

Met Asp Thr Arg Ala Pro Thr Gln Leu Leu Gly Leu Leu Leu Leu Trp
1 5 10 15

Leu Pro Gly Ala Thr Phe Ala Gln Val Leu Thr Gln Thr Pro Ser Pro
20 25 30

Val Ser Ala Ala Val Gly Gly Thr Val Thr Ile Asn Cys Gln Ala Ser
35 40 45

Gln Ser Val Asp Asp Asn Asn Trp Leu Gly Trp Tyr Gln Gln Lys Arg
50 55 60

Gly Gln Pro Pro Lys Tyr Leu Ile Tyr Ser Ala Ser Thr Leu Ala Ser
65 70 75 80

Gly Val Pro Ser Arg Phe Lys Gly Ser Gly Ser Gly Thr Gln Phe Thr
85 90 95

Leu Thr Ile Ser Asp Leu Glu Cys Asp Asp Ala Ala Thr Tyr Tyr Cys
100 105 110

Ala Gly Gly Phe Ser Gly Asn Ile Phe Ala Phe Gly Gly Gly Thr Glu
115 120 125

Val Val Val Lys Arg Thr Val Ala Ala Pro Ser Val Phe Ile Phe Pro
130 135 140

Pro Ser Asp Glu Gln Leu Lys Ser Gly Thr Ala Ser Val Val Cys Leu
145 150 155 160

Leu Asn Asn Phe

<210> SEQ ID NO 70
<211> LENGTH: 164
<212> TYPE: PRT
<213> ORGANISM: Oryctolagus cuniculus

<400> SEQUENCE: 70

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Phe Ser Leu Ser
35 40 45

Ser Tyr Ala Met Ser Trp Val Arg Gln Ala Pro Gly Lys Gly Leu Glu
50 55 60

Trp Ile Gly Ile Ile Gly Gly Phe Gly Thr Thr Tyr Tyr Ala Thr Trp
65 70 75 80

Ala Lys Gly Arg Phe Thr Ile Ser Lys Thr Ser Thr Thr Val Asp Leu
85 90 95

Arg Ile Thr Ser Pro Thr Thr Glu Asp Thr Ala Thr Tyr Phe Cys Ala
100 105 110

Arg Gly Gly Pro Gly Asn Gly Gly Asp Ile Trp Gly Gln Gly Thr Leu
115 120 125

Val Thr Val Ser Ser Ala Ser Thr Lys Gly Pro Ser Val Phe Pro Leu
130 135 140

Ala Pro Ser Ser Lys Ser Thr Ser Gly Gly Thr Ala Ala Leu Gly Cys
145 150 155 160

Leu Val Lys Asp

<210> SEQ ID NO 71
<211> LENGTH: 13
<212> TYPE: PRT
<213> ORGANISM: Oryctolagus cuniculus

<400> SEQUENCE: 71

Gln Ala Ser Gln Ser Val Asp Asp Asn Asn Trp Leu Gly
1 5 10

<210> SEQ ID NO 72
<211> LENGTH: 7
<212> TYPE: PRT
<213> ORGANISM: Oryctolagus cuniculus

<400> SEQUENCE: 72

Ser Ala Ser Thr Leu Ala Ser
1 5

<210> SEQ ID NO 73
<211> LENGTH: 10
<212> TYPE: PRT
<213> ORGANISM: Oryctolagus cuniculus

<400> SEQUENCE: 73

Ala Gly Gly Phe Ser Gly Asn Ile Phe Ala
1 5 10

<210> SEQ ID NO 74
<211> LENGTH: 5
<212> TYPE: PRT
<213> ORGANISM: Oryctolagus cuniculus

<400> SEQUENCE: 74

Ser Tyr Ala Met Ser
1 5

<210> SEQ ID NO 75
<211> LENGTH: 16
<212> TYPE: PRT
<213> ORGANISM: Oryctolagus cuniculus

<400> SEQUENCE: 75

Ile Ile Gly Gly Phe Gly Thr Thr Tyr Tyr Ala Thr Trp Ala Lys Gly
1 5 10 15

<210> SEQ ID NO 76
<211> LENGTH: 9
<212> TYPE: PRT
<213> ORGANISM: Oryctolagus cuniculus

<400> SEQUENCE: 76

Gly Gly Pro Gly Asn Gly Gly Asp Ile
1 5

<210> SEQ ID NO 77
<211> LENGTH: 493
<212> TYPE: DNA
<213> ORGANISM: Oryctolagus cuniculus

<400> SEQUENCE: 77
atggacacga gggcccccac tcagctgctg gggctcctgc tgctctggct cccaggtgcc 60
acatttgccc aagtgctgac ccagactcca tcgcctgtgt ctgcagctgt gggaggcaca 120
gtcaccatca actgccaggc cagtcagagt gttgatgata acaactggtt aggctggtat 180
cagcagaaac gagggcagcc tcccaagtac ctgatctatt ctgcatccac tctggcatct 240
ggggtcccat cgcggttcaa aggcagtgga tctgggacac agttcactct caccatcagc 300
gacctggagt gtgacgatgc tgccacttac tactgtgcag gcggttttag tggtaatatc 360
tttgctttcg gcggagggac cgaggtggtg gtcaaacgta cggtagcggc cccatctgtc 420
ttcatcttcc cgccatctga tgagcagttg aaatctggaa ctgcctctgt tgtgtgcctg 480
ctgaataact tct 493

<210> SEQ ID NO 78
<211> LENGTH: 493
<212> TYPE: DNA
<213> ORGANISM: Oryctolagus cuniculus

<400> SEQUENCE: 78
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtctctg gcttctccct cagtagctat gcaatgagct gggtccgcca ggctccagga 180
aaggggctgg agtggatcgg aatcattggt ggttttggta ccacatacta cgcgacctgg 240
gcgaaaggcc gattcaccat ctccaaaacc tcgaccacgg tggatctgag aatcaccagt 300
ccgacaaccg aggacacggc cacctatttc tgtgccagag gtggtcctgg taatggtggt 360
gacatctggg gccaagggac cctggtcacc gtctcgagcg cctccaccaa gggcccatcg 420
gtcttccccc tggcaccctc ctccaagagc acctctgggg gcacagcggc cctgggctgc 480
ctggtcaagg act 493

<210> SEQ ID NO 79
<211> LENGTH: 39
<212> TYPE: DNA
<213> ORGANISM: Oryctolagus cuniculus

<400> SEQUENCE: 79
caggccagtc agagtgttga tgataacaac tggttaggc 39

<210> SEQ ID NO 80
<211> LENGTH: 21
<212> TYPE: DNA
<213> ORGANISM: Oryctolagus cuniculus

<400> SEQUENCE: 80
tctgcatcca ctctggcatc t 21

<210> SEQ ID NO 81
<211> LENGTH: 30
<212> TYPE: DNA
<213> ORGANISM: Oryctolagus cuniculus

<400> SEQUENCE: 81
gcaggcggtt ttagtggtaa tatctttgct 30

<210> SEQ ID NO 82
<211> LENGTH: 15
<212> TYPE: DNA

<213> ORGANISM: Oryctolagus cuniculus

<400> SEQUENCE: 82
agctatgcaa tgagc 15

<210> SEQ ID NO 83
<211> LENGTH: 48
<212> TYPE: DNA
<213> ORGANISM: Oryctolagus cuniculus

<400> SEQUENCE: 83
atcattggtg gttttggtac cacatactac gcgacctggg cgaaaggc 48

<210> SEQ ID NO 84
<211> LENGTH: 27
<212> TYPE: DNA
<213> ORGANISM: Oryctolagus cuniculus

<400> SEQUENCE: 84
ggtggtcctg gtaatggtgg tgacatc 27

<210> SEQ ID NO 85
<211> LENGTH: 164
<212> TYPE: PRT
<213> ORGANISM: Oryctolagus cuniculus

<400> SEQUENCE: 85

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Val Pro Val Gly Gly Thr Val Thr Ile Lys Cys Gln Ser Ser
        35                  40                  45

Gln Ser Val Tyr Asn Asn Phe Leu Ser Trp Tyr Gln Gln Lys Pro Gly
    50                  55                  60

Gln Pro Pro Lys Leu Leu Ile Tyr Gln Ala Ser Lys Leu Ala Ser Gly
65                  70                  75                  80

Val Pro Asp Arg Phe Ser Gly Ser Gly Ser Gly Thr Gln Phe Thr Leu
                85                  90                  95

Thr Ile Ser Gly Val Gln Cys Asp Asp Ala Ala Thr Tyr Tyr Cys Leu
            100                 105                 110

Gly Gly Tyr Asp Asp Asp Ala Asp Asn Ala Phe Gly Gly Gly Thr Glu
        115                 120                 125

Val Val Val Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe
```

<210> SEQ ID NO 86
<211> LENGTH: 170
<212> TYPE: PRT
<213> ORGANISM: Oryctolagus cuniculus

<400> SEQUENCE: 86

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30
```

```
Gly Thr Pro Leu Thr Leu Thr Cys Thr Val Ser Gly Ile Asp Leu Ser
        35                  40                  45

Asp Tyr Ala Met Ser Trp Val Arg Gln Ala Pro Gly Lys Gly Leu Glu
    50                  55                  60

Trp Ile Gly Ile Ile Tyr Ala Gly Ser Gly Ser Thr Trp Tyr Ala Ser
65                  70                  75                  80

Trp Ala Lys Gly Arg Phe Thr Ile Ser Lys Thr Ser Thr Thr Val Asp
                85                  90                  95

Leu Lys Ile Thr Ser Pro Thr Thr Glu Asp Thr Ala Thr Tyr Phe Cys
            100                 105                 110

Ala Arg Asp Gly Tyr Asp Asp Tyr Gly Asp Phe Asp Arg Leu Asp Leu
        115                 120                 125

Trp Gly Pro Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp
                165                 170


<210> SEQ ID NO 87
<211> LENGTH: 12
<212> TYPE: PRT
<213> ORGANISM: Oryctolagus cuniculus

<400> SEQUENCE: 87

Gln Ser Ser Gln Ser Val Tyr Asn Asn Phe Leu Ser
1               5                   10


<210> SEQ ID NO 88
<211> LENGTH: 7
<212> TYPE: PRT
<213> ORGANISM: Oryctolagus cuniculus

<400> SEQUENCE: 88

Gln Ala Ser Lys Leu Ala Ser
1               5


<210> SEQ ID NO 89
<211> LENGTH: 11
<212> TYPE: PRT
<213> ORGANISM: Oryctolagus cuniculus

<400> SEQUENCE: 89

Leu Gly Gly Tyr Asp Asp Asp Ala Asp Asn Ala
1               5                   10


<210> SEQ ID NO 90
<211> LENGTH: 5
<212> TYPE: PRT
<213> ORGANISM: Oryctolagus cuniculus

<400> SEQUENCE: 90

Asp Tyr Ala Met Ser
1               5


<210> SEQ ID NO 91
<211> LENGTH: 17
<212> TYPE: PRT
<213> ORGANISM: Oryctolagus cuniculus

<400> SEQUENCE: 91
```

```
Ile Ile Tyr Ala Gly Ser Gly Ser Thr Trp Tyr Ala Ser Trp Ala Lys
1               5                   10                  15

Gly


<210> SEQ ID NO 92
<211> LENGTH: 14
<212> TYPE: PRT
<213> ORGANISM: Oryctolagus cuniculus

<400> SEQUENCE: 92

Asp Gly Tyr Asp Asp Tyr Gly Asp Phe Asp Arg Leu Asp Leu
1               5                   10


<210> SEQ ID NO 93
<211> LENGTH: 492
<212> TYPE: DNA
<213> ORGANISM: Oryctolagus cuniculus

<400> SEQUENCE: 93

atggacacga gggcccccac tcagctgctg gggctcctgc tgctctggct cccaggtgcc      60

acatttgcag ccgtgctgac ccagacacca tcgcccgtgt ctgtacctgt gggaggcaca     120

gtcaccatca agtgccagtc cagtcagagt gtttataata atttcttatc gtggtatcag     180

cagaaaccag ggcagcctcc caagctcctg atctaccagg catccaaact ggcatctggg     240

gtcccagata ggttcagcgg cagtggatct gggacacagt tcactctcac catcagcggc     300

gtgcagtgtg acgatgctgc cacttactac tgtctaggcg gttatgatga tgatgctgat     360

aatgctttcg gcggagggac cgaggtggtg gtcaaacgta cggtagcggc cccatctgtc     420

ttcatcttcc cgccatctga tgagcagttg aaatctggaa ctgcctctgt tgtgtgcctg     480

ctgaataact tc                                                         492


<210> SEQ ID NO 94
<211> LENGTH: 511
<212> TYPE: DNA
<213> ORGANISM: Oryctolagus cuniculus

<400> SEQUENCE: 94

atggagactg ggctgcgctg gcttctcctg gtcgctgtgc tcaaaggtgt ccagtgtcag      60

tcggtggagg agtccggggg tcgcctggtc acgcctggga cacccctgac gctcacctgc     120

acagtctctg gaatcgacct cagtgactat gcaatgagct gggtccgcca ggctccaggg     180

aaggggctgg aatggatcgg aatcatttat gctggtagtg gtagcacatg gtacgcgagc     240

tgggcgaaag gccgattcac catctccaaa acctcgacca cggtggatct gaaaatcacc     300

agtccgacaa ccgaggacac ggccacctat ttctgtgcca gagatggata cgatgactat     360

ggtgatttcg atcgattgga tctctggggc ccaggcaccc tcgtcaccgt ctcgagcgcc     420

tccaccaagg gcccatcggt cttccccctg gcaccctcct ccaagagcac ctctgggggc     480

acagcggccc tgggctgcct ggtcaaggac t                                    511


<210> SEQ ID NO 95
<211> LENGTH: 36
<212> TYPE: DNA
<213> ORGANISM: Oryctolagus cuniculus

<400> SEQUENCE: 95

cagtccagtc agagtgttta taataatttc ttatcg                                36
```

<210> SEQ ID NO 96
<211> LENGTH: 21
<212> TYPE: DNA
<213> ORGANISM: Oryctolagus cuniculus

<400> SEQUENCE: 96
caggcatcca aactggcatc t 21

<210> SEQ ID NO 97
<211> LENGTH: 33
<212> TYPE: DNA
<213> ORGANISM: Oryctolagus cuniculus

<400> SEQUENCE: 97
ctaggcggtt atgatgatga tgctgataat gct 33

<210> SEQ ID NO 98
<211> LENGTH: 15
<212> TYPE: DNA
<213> ORGANISM: Oryctolagus cuniculus

<400> SEQUENCE: 98
gactatgcaa tgagc 15

<210> SEQ ID NO 99
<211> LENGTH: 51
<212> TYPE: DNA
<213> ORGANISM: Oryctolagus cuniculus

<400> SEQUENCE: 99
atcatttatg ctggtagtgg tagcacatgg tacgcgagct gggcgaaagg c 51

<210> SEQ ID NO 100
<211> LENGTH: 42
<212> TYPE: DNA
<213> ORGANISM: Oryctolagus cuniculus

<400> SEQUENCE: 100
gatggatacg atgactatgg tgatttcgat cgattggatc tc 42

<210> SEQ ID NO 101
<211> LENGTH: 164
<212> TYPE: PRT
<213> ORGANISM: Oryctolagus cuniculus

<400> SEQUENCE: 101

```
Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Ser Ala Ala Val Gly Gly Thr Val Thr Ile Lys Cys Gln Ala Ser
        35                  40                  45

Gln Ser Ile Asn Asn Glu Leu Ser Trp Tyr Gln Gln Lys Ser Gly Gln
    50                  55                  60

Arg Pro Lys Leu Leu Ile Tyr Arg Ala Ser Thr Leu Ala Ser Gly Val
65                  70                  75                  80

Ser Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Gln
            100                 105                 110
```

Gly Tyr Ser Leu Arg Asn Ile Asp Asn Ala Phe Gly Gly Gly Thr Glu
115 120 125

Val Val Val Lys Arg Thr Val Ala Ala Pro Ser Val Phe Ile Phe Pro
130 135 140

Pro Ser Asp Glu Gln Leu Lys Ser Gly Thr Ala Ser Val Val Cys Leu
145 150 155 160

Leu Asn Asn Phe

<210> SEQ ID NO 102
<211> LENGTH: 166
<212> TYPE: PRT
<213> ORGANISM: Oryctolagus cuniculus

<400> SEQUENCE: 102

Met Glu Thr Gly Leu Arg Trp Leu Leu Leu Val Ala Val Leu Ser Gly
1 5 10 15

Val Gln Cys Gln Ser Leu Glu Glu Ser Gly Gly Arg Leu Val Thr Pro
20 25 30

Gly Thr Pro Leu Thr Leu Thr Cys Thr Ala Ser Gly Phe Ser Leu Ser
35 40 45

Asn Tyr Tyr Met Thr Trp Val Arg Gln Ala Pro Gly Lys Gly Leu Glu
50 55 60

Trp Ile Gly Met Ile Tyr Gly Ser Asp Glu Thr Ala Tyr Ala Asn Trp
65 70 75 80

Ala Ile Gly Arg Phe Thr Ile Ser Lys Thr Ser Thr Thr Val Asp Leu
85 90 95

Lys Met Thr Ser Leu Thr Ala Ala Asp Thr Ala Thr Tyr Phe Cys Ala
100 105 110

Arg Asp Asp Ser Ser Asp Trp Asp Ala Lys Phe Asn Leu Trp Gly Gln
115 120 125

Gly Thr Leu Val Thr Val Ser Ser Ala Ser Thr Lys Gly Pro Ser Val
130 135 140

Phe Pro Leu Ala Pro Ser Ser Lys Ser Thr Ser Gly Gly Thr Ala Ala
145 150 155 160

Leu Gly Cys Leu Val Lys
165

<210> SEQ ID NO 103
<211> LENGTH: 11
<212> TYPE: PRT
<213> ORGANISM: Oryctolagus cuniculus

<400> SEQUENCE: 103

Gln Ala Ser Gln Ser Ile Asn Asn Glu Leu Ser
1 5 10

<210> SEQ ID NO 104
<211> LENGTH: 7
<212> TYPE: PRT
<213> ORGANISM: Oryctolagus cuniculus

<400> SEQUENCE: 104

Arg Ala Ser Thr Leu Ala Ser
1 5

<210> SEQ ID NO 105
<211> LENGTH: 12
<212> TYPE: PRT
<213> ORGANISM: Oryctolagus cuniculus

<400> SEQUENCE: 105

Gln Gln Gly Tyr Ser Leu Arg Asn Ile Asp Asn Ala
1 5 10

<210> SEQ ID NO 106
<211> LENGTH: 5
<212> TYPE: PRT
<213> ORGANISM: Oryctolagus cuniculus

<400> SEQUENCE: 106

Asn Tyr Tyr Met Thr
1 5

<210> SEQ ID NO 107
<211> LENGTH: 16
<212> TYPE: PRT
<213> ORGANISM: Oryctolagus cuniculus

<400> SEQUENCE: 107

Met Ile Tyr Gly Ser Asp Glu Thr Ala Tyr Ala Asn Trp Ala Ile Gly
1 5 10 15

<210> SEQ ID NO 108
<211> LENGTH: 12
<212> TYPE: PRT
<213> ORGANISM: Oryctolagus cuniculus

<400> SEQUENCE: 108

Asp Asp Ser Ser Asp Trp Asp Ala Lys Phe Asn Leu
1 5 10

<210> SEQ ID NO 109
<211> LENGTH: 492
<212> TYPE: DNA
<213> ORGANISM: Oryctolagus cuniculus

<400> SEQUENCE: 109
atggacacga gggcccccac tcagctgctg gggctcctgc tgctctggct cccaggtgcc 60
agatgtgcct atgatatgac ccagactcca gcctcggtgt ctgcagctgt gggaggcaca 120
gtcaccatca aatgccaggc cagtcagagc attaacaatg aattatcctg gtatcagcag 180
aaatcagggc agcgtcccaa gctcctgatc tatagggcat ccactctggc atctggggtc 240
tcatcgcggt tcaaaggcag tggatctggg acagagttca ctctcaccat cagcgacctg 300
gagtgtgccg atgctgccac ttactactgt caacagggtt atagtctgag gaatattgat 360
aatgctttcg gcggagggac cgaggtggtg gtcaaacgta cggtagcggc cccatctgtc 420
ttcatcttcc cgccatctga tgagcagttg aaatctggaa ctgcctctgt tgtgtgcctg 480
ctgaataact tc 492

<210> SEQ ID NO 110
<211> LENGTH: 499
<212> TYPE: DNA
<213> ORGANISM: Oryctolagus cuniculus

<400> SEQUENCE: 110
atggagactg ggctgcgctg gcttctcctg gtcgctgtgc tctcaggtgt ccagtgtcag 60
tcgctggagg agtccggggg tcgcctggtc acgcctggga cacccctgac actcacctgc 120
acagcctctg gattctccct cagtaactac tacatgacct gggtccgcca ggctccaggg 180

-continued

```
aaggggctgg aatggatcgg aatgatttat ggtagtgatg aaacagccta cgcgaactgg    240

gcgataggcc gattcaccat ctccaaaacc tcgaccacgg tggatctgaa aatgaccagt    300

ctgacagccg cggacacggc cacctatttc tgtgccagag atgatagtag tgactgggat    360

gcaaaattta acttgtgggg ccaagggacc ctcgtcaccg tctcgagcgc ctccaccaag    420

ggcccatcgg tcttccccct ggcaccctcc tccaagagca cctctggggg cacagcggcc    480

ctgggctgcc tggtcaagg                                                 499

<210> SEQ ID NO 111
<211> LENGTH: 33
<212> TYPE: DNA
<213> ORGANISM: Oryctolagus cuniculus

<400> SEQUENCE: 111

caggccagtc agagcattaa caatgaatta tcc                                 33

<210> SEQ ID NO 112
<211> LENGTH: 21
<212> TYPE: DNA
<213> ORGANISM: Oryctolagus cuniculus

<400> SEQUENCE: 112

agggcatcca ctctggcatc t                                              21

<210> SEQ ID NO 113
<211> LENGTH: 36
<212> TYPE: DNA
<213> ORGANISM: Oryctolagus cuniculus

<400> SEQUENCE: 113

caacagggtt atagtctgag gaatattgat aatgct                              36

<210> SEQ ID NO 114
<211> LENGTH: 15
<212> TYPE: DNA
<213> ORGANISM: Oryctolagus cuniculus

<400> SEQUENCE: 114

aactactaca tgacc                                                     15

<210> SEQ ID NO 115
<211> LENGTH: 48
<212> TYPE: DNA
<213> ORGANISM: Oryctolagus cuniculus

<400> SEQUENCE: 115

atgatttatg gtagtgatga aacagcctac gcgaactggg cgataggc                 48

<210> SEQ ID NO 116
<211> LENGTH: 36
<212> TYPE: DNA
<213> ORGANISM: Oryctolagus cuniculus

<400> SEQUENCE: 116

gatgatagta gtgactggga tgcaaaattt aacttg                              36

<210> SEQ ID NO 117
<211> LENGTH: 109
<212> TYPE: PRT
<213> ORGANISM: Oryctolagus cuniculus

<400> SEQUENCE: 117
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Met Thr Trp Val Arg Gln Ala Pro Gly Lys Gly Leu Glu Trp Val
        35                  40                  45

Gly Met Ile Tyr Gly Ser Asp Glu Thr Ala Tyr Ala Asn Trp Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu
            100                 105


<210> SEQ ID NO 118
<211> LENGTH: 109
<212> TYPE: PRT
<213> ORGANISM: Oryctolagus cuniculus

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Met Thr Trp Val Arg Gln Ala Pro Gly Lys Gly Leu Glu Trp Val
        35                  40                  45

Gly Met Ile Tyr Gly Ser Asp Glu Thr Ala Tyr Ala Asn Ser Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu
            100                 105


<210> SEQ ID NO 119
<211> LENGTH: 100
<212> TYPE: PRT
<213> ORGANISM: Oryctolagus cuniculus

<400> SEQUENCE: 119

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Asn Glu
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Leu Arg Asn
                85                  90                  95

Ile Asp Asn Ala
            100
```

<210> SEQ ID NO 120
<211> LENGTH: 16
<212> TYPE: PRT
<213> ORGANISM: Oryctolagus cuniculus

<400> SEQUENCE: 120

```
Ile Ile Tyr Gly Ser Asp Glu Thr Ala Tyr Ala Thr Ser Ala Ile Gly
1               5                   10                  15
```

<210> SEQ ID NO 121
<211> LENGTH: 16
<212> TYPE: PRT
<213> ORGANISM: Oryctolagus cuniculus

<400> SEQUENCE: 121

```
Met Ile Tyr Gly Ser Asp Glu Thr Ala Tyr Ala Asn Ser Ala Ile Gly
1               5                   10                  15
```

<210> SEQ ID NO 122
<211> LENGTH: 123
<212> TYPE: PRT
<213> ORGANISM: Oryctolagus cuniculus

<400> SEQUENCE: 122

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Thr Ile Ser Cys Gln Ser Ser
        35                  40                  45

Gln Ser Val Gly Asn Asn Gln Asp Leu Ser Trp Phe Gln Gln Arg Pro
    50                  55                  60

Gly Gln Pro Pro Lys Leu Leu Ile Tyr Glu Ile Ser Lys Leu Glu Ser
65                  70                  75                  80

Gly Val Pro Ser Arg Phe Ser Gly Ser Gly Ser Gly Thr His Phe Thr
            85                  90                  95

Leu Thr Ile Ser Gly Val Gln Cys Asp Asp Ala Ala Thr Tyr Tyr Cys
            100                 105                 110

Leu Gly Gly Tyr Asp Asp Asp Ala Asp Asn Ala
        115                 120
```

<210> SEQ ID NO 123
<211> LENGTH: 128
<212> TYPE: PRT
<213> ORGANISM: Oryctolagus cuniculus

<400> SEQUENCE: 123

```
Met Glu Thr Gly Leu Arg Trp Leu Leu Leu Val Ala Val Leu Lys Gly
1               5                   10                  15

Val Gln Cys His Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Arg Thr Met Ser Trp Val Arg Gln Ala Pro Gly Lys Gly Leu Glu
    50                  55                  60

Trp Ile Gly Tyr Ile Trp Ser Gly Gly Ser Thr Tyr Tyr Ala Thr Trp
65                  70                  75                  80

Ala Lys Gly Arg Phe Thr Ile Ser Lys Thr Ser Thr Thr Val Asp Leu
```

85 90 95

Lys Ile Thr Ser Pro Thr Thr Glu Asp Thr Ala Thr Tyr Phe Cys Ala
100 105 110

Arg Leu Gly Asp Thr Gly Gly His Ala Tyr Ala Thr Arg Leu Asn Leu
115 120 125

<210> SEQ ID NO 124
<211> LENGTH: 13
<212> TYPE: PRT
<213> ORGANISM: Oryctolagus cuniculus

<400> SEQUENCE: 124

Gln Ser Ser Gln Ser Val Gly Asn Asn Gln Asp Leu Ser
1 5 10

<210> SEQ ID NO 125
<211> LENGTH: 7
<212> TYPE: PRT
<213> ORGANISM: Oryctolagus cuniculus

<400> SEQUENCE: 125

Glu Ile Ser Lys Leu Glu Ser
1 5

<210> SEQ ID NO 126
<211> LENGTH: 11
<212> TYPE: PRT
<213> ORGANISM: Oryctolagus cuniculus

<400> SEQUENCE: 126

Leu Gly Gly Tyr Asp Asp Asp Ala Asp Asn Ala
1 5 10

<210> SEQ ID NO 127
<211> LENGTH: 5
<212> TYPE: PRT
<213> ORGANISM: Oryctolagus cuniculus

<400> SEQUENCE: 127

Ser Arg Thr Met Ser
1 5

<210> SEQ ID NO 128
<211> LENGTH: 16
<212> TYPE: PRT
<213> ORGANISM: Oryctolagus cuniculus

<400> SEQUENCE: 128

Tyr Ile Trp Ser Gly Gly Ser Thr Tyr Tyr Ala Thr Trp Ala Lys Gly
1 5 10 15

<210> SEQ ID NO 129
<211> LENGTH: 15
<212> TYPE: PRT
<213> ORGANISM: Oryctolagus cuniculus

<400> SEQUENCE: 129

Leu Gly Asp Thr Gly Gly His Ala Tyr Ala Thr Arg Leu Asn Leu
1 5 10 15

<210> SEQ ID NO 130
<211> LENGTH: 369
<212> TYPE: DNA
<213> ORGANISM: Oryctolagus cuniculus

<400> SEQUENCE: 130
atggacacga gggcccccac tcagctgctg gggctcctgc tgctctggct cccaggtgcc 60
acatttgcag ccgtgctgac ccagacacca tcacccgtgt ctgcagctgt gggaggcaca 120
gtcaccatca gttgccagtc cagtcagagt gttggtaata accaggactt atcctggttt 180
cagcagagac cagggcagcc tcccaagctc ctgatctacg aaatatccaa actggaatct 240
ggggtcccat cgcggttcag cggcagtgga tctgggacac acttcactct caccatcagc 300
ggcgtacagt gtgacgatgc tgccacttac tactgtctag gcggttatga tgatgatgct 360
gataatgct 369

<210> SEQ ID NO 131
<211> LENGTH: 384
<212> TYPE: DNA
<213> ORGANISM: Oryctolagus cuniculus

<400> SEQUENCE: 131
atggagactg ggctgcgctg gcttctcctg gtcgctgtgc tcaaaggtgt ccagtgtcac 60
tcggtggagg agtccggggg tcgcctggtc acgcctggga cacccctgac actcacctgc 120
acagtctctg gattctccct cagtagtcgt acaatgtcct gggtccgcca ggctccaggg 180
aaggggctgg agtggatcgg atacatttgg agtggtggta gcacatacta cgcgacctgg 240
gcgaaaggcc gattcaccat ctccaaaacc tcgaccacgg tggatctgaa aatcaccagt 300
ccgacaaccg aggacacggc cacctatttc tgtgccagat tgggcgatac tggtggtcac 360
gcttatgcta ctcgcttaaa tctc 384

<210> SEQ ID NO 132
<211> LENGTH: 39
<212> TYPE: DNA
<213> ORGANISM: Oryctolagus cuniculus

<400> SEQUENCE: 132
cagtccagtc agagtgttgg taataaccag gacttatcc 39

<210> SEQ ID NO 133
<211> LENGTH: 21
<212> TYPE: DNA
<213> ORGANISM: Oryctolagus cuniculus

<400> SEQUENCE: 133
gaaatatcca aactggaatc t 21

<210> SEQ ID NO 134
<211> LENGTH: 33
<212> TYPE: DNA
<213> ORGANISM: Oryctolagus cuniculus

<400> SEQUENCE: 134
ctaggcggtt atgatgatga tgctgataat gct 33

<210> SEQ ID NO 135
<211> LENGTH: 15
<212> TYPE: DNA
<213> ORGANISM: Oryctolagus cuniculus

<400> SEQUENCE: 135
agtcgtacaa tgtcc 15

-continued

<210> SEQ ID NO 136
<211> LENGTH: 48
<212> TYPE: DNA
<213> ORGANISM: Oryctolagus cuniculus

<400> SEQUENCE: 136
tacatttgga gtggtggtag cacatactac gcgacctggg cgaaaggc 48

<210> SEQ ID NO 137
<211> LENGTH: 45
<212> TYPE: DNA
<213> ORGANISM: Oryctolagus cuniculus

<400> SEQUENCE: 137
ttgggcgata ctggtggtca cgcttatgct actcgcttaa atctc 45

<210> SEQ ID NO 138
<211> LENGTH: 123
<212> TYPE: PRT
<213> ORGANISM: Oryctolagus cuniculus

<400> SEQUENCE: 138

Met Asp Thr Arg Ala Pro Thr Gln Leu Leu Gly Leu Leu Leu Leu Trp
1 5 10 15

Leu Pro Gly Ala Thr Phe Ala Ala Val Leu Thr Gln Thr Pro Ser Ser
20 25 30

Val Ser Ala Ala Val Gly Gly Thr Val Ser Ile Ser Cys Gln Ser Ser
35 40 45

Gln Ser Val Tyr Ser Asn Lys Tyr Leu Ala Trp Tyr Gln Gln Lys Pro
50 55 60

Gly Gln Pro Pro Lys Leu Leu Ile Tyr Trp Thr Ser Lys Leu Ala Ser
65 70 75 80

Gly Ala Pro Ser Arg Phe Ser Gly Ser Gly Ser Gly Thr Gln Phe Thr
85 90 95

Leu Thr Ile Ser Gly Val Gln Cys Asp Asp Ala Ala Thr Tyr Tyr Cys
100 105 110

Leu Gly Ala Tyr Asp Asp Asp Ala Asp Asn Ala
115 120

<210> SEQ ID NO 139
<211> LENGTH: 126
<212> TYPE: PRT
<213> ORGANISM: Oryctolagus cuniculus

<400> SEQUENCE: 139

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Lys Pro
20 25 30

Asp Glu Thr Leu Thr Leu Thr Cys Thr Ala Ser Gly Phe Ser Leu Glu
35 40 45

Gly Gly Tyr Met Thr Trp Val Arg Gln Ala Pro Gly Lys Gly Leu Glu
50 55 60

Trp Ile Gly Ile Ser Tyr Asp Ser Gly Ser Thr Tyr Tyr Ala Ser Trp
65 70 75 80

Ala Lys Gly Arg Phe Thr Ile Ser Lys Thr Ser Ser Thr Thr Val Asp
85 90 95

Leu Lys Met Thr Ser Leu Thr Thr Glu Asp Thr Ala Thr Tyr Phe Cys

-continued 100 105 110

Val Arg Ser Leu Lys Tyr Pro Thr Val Thr Ser Asp Asp Leu
115 120 125

<210> SEQ ID NO 140
<211> LENGTH: 13
<212> TYPE: PRT
<213> ORGANISM: Oryctolagus cuniculus

<400> SEQUENCE: 140

Gln Ser Ser Gln Ser Val Tyr Ser Asn Lys Tyr Leu Ala
1 5 10

<210> SEQ ID NO 141
<211> LENGTH: 7
<212> TYPE: PRT
<213> ORGANISM: Oryctolagus cuniculus

<400> SEQUENCE: 141

Trp Thr Ser Lys Leu Ala Ser
1 5

<210> SEQ ID NO 142
<211> LENGTH: 11
<212> TYPE: PRT
<213> ORGANISM: Oryctolagus cuniculus

<400> SEQUENCE: 142

Leu Gly Ala Tyr Asp Asp Asp Ala Asp Asn Ala
1 5 10

<210> SEQ ID NO 143
<211> LENGTH: 5
<212> TYPE: PRT
<213> ORGANISM: Oryctolagus cuniculus

<400> SEQUENCE: 143

Gly Gly Tyr Met Thr
1 5

<210> SEQ ID NO 144
<211> LENGTH: 16
<212> TYPE: PRT
<213> ORGANISM: Oryctolagus cuniculus

<400> SEQUENCE: 144

Ile Ser Tyr Asp Ser Gly Ser Thr Tyr Tyr Ala Ser Trp Ala Lys Gly
1 5 10 15

<210> SEQ ID NO 145
<211> LENGTH: 12
<212> TYPE: PRT
<213> ORGANISM: Oryctolagus cuniculus

<400> SEQUENCE: 145

Ser Leu Lys Tyr Pro Thr Val Thr Ser Asp Asp Leu
1 5 10

<210> SEQ ID NO 146
<211> LENGTH: 369
<212> TYPE: DNA
<213> ORGANISM: Oryctolagus cuniculus

<400> SEQUENCE: 146
atggacacga gggcccccac tcagctgctg gggctcctgc tgctctggct cccaggtgcc 60
acatttgcag ccgtgctgac ccagacacca tcgtccgtgt ctgcagctgt gggaggcaca 120
gtcagcatca gttgccagtc cagtcagagt gtttatagta ataagtacct agcctggtat 180
cagcagaaac cagggcagcc tcccaagctc ctgatctact ggacatccaa actggcatct 240
ggggccccat cacggttcag cggcagtgga tctgggacac aattcactct caccatcagc 300
ggcgtgcagt gtgacgatgc tgccacttac tactgtctag gcgcttatga tgatgatgct 360
gataatgct 369

<210> SEQ ID NO 147
<211> LENGTH: 378
<212> TYPE: DNA
<213> ORGANISM: Oryctolagus cuniculus

<400> SEQUENCE: 147
atggagactg ggctgcgctg gcttctcctg gtcgctgtgc tcaaaggtgt ccagtgtcag 60
tcggtggaag agtccggggg tcgcctggtc aagcctgacg aaaccctgac actcacctgc 120
acagcctctg gattctccct ggagggcggc tacatgacct gggtccgcca ggctccaggg 180
aaggggctgg aatggatcgg aatcagttat gatagtggta gcacatacta cgcgagctgg 240
gcgaaaggcc gattcaccat ctccaagacc tcgtcgacca cggtggatct gaaaatgacc 300
agtctgacaa ccgaggacac ggccacctat ttctgcgtca gatcactaaa atatcctact 360
gttacttctg atgacttg 378

<210> SEQ ID NO 148
<211> LENGTH: 39
<212> TYPE: DNA
<213> ORGANISM: Oryctolagus cuniculus

<400> SEQUENCE: 148
cagtccagtc agagtgttta tagtaataag tacctagcc 39

<210> SEQ ID NO 149
<211> LENGTH: 21
<212> TYPE: DNA
<213> ORGANISM: Oryctolagus cuniculus

<400> SEQUENCE: 149
tggacatcca aactggcatc t 21

<210> SEQ ID NO 150
<211> LENGTH: 33
<212> TYPE: DNA
<213> ORGANISM: Oryctolagus cuniculus

<400> SEQUENCE: 150
ctaggcgctt atgatgatga tgctgataat gct 33

<210> SEQ ID NO 151
<211> LENGTH: 15
<212> TYPE: DNA
<213> ORGANISM: Oryctolagus cuniculus

<400> SEQUENCE: 151
ggcggctaca tgacc 15

<210> SEQ ID NO 152
<211> LENGTH: 48

<212> TYPE: DNA
<213> ORGANISM: Oryctolagus cuniculus

<400> SEQUENCE: 152
atcagttatg atagtggtag cacatactac gcgagctggg cgaaaggc 48

<210> SEQ ID NO 153
<211> LENGTH: 36
<212> TYPE: DNA
<213> ORGANISM: Oryctolagus cuniculus

<400> SEQUENCE: 153
tcactaaaat atcctactgt tacttctgat gacttg 36

<210> SEQ ID NO 154
<211> LENGTH: 123
<212> TYPE: PRT
<213> ORGANISM: Oryctolagus cuniculus

<400> SEQUENCE: 154

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Thr Ile Ser Cys Gln Ser Ser
        35                  40                  45

Gln Ser Val Tyr Asn Asn Asn Asp Leu Ala Trp Tyr Gln Gln Lys Pro
    50                  55                  60

Gly Gln Pro Pro Lys Leu Leu Ile Tyr Tyr Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Ala Tyr Tyr Cys
            100                 105                 110

Leu Gly Gly Tyr Asp Asp Asp Ala Asp Asn Ala
        115                 120
```

<210> SEQ ID NO 155
<211> LENGTH: 129
<212> TYPE: PRT
<213> ORGANISM: Oryctolagus cuniculus

<400> SEQUENCE: 155

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Leu Ser Leu Ser
        35                  40                  45

Ser Asn Thr Ile Asn Trp Val Arg Gln Ala Pro Gly Lys Gly Leu Glu
    50                  55                  60

Trp Ile Gly Tyr Ile Trp Ser Gly Gly Ser Thr Tyr Tyr Ala Ser Trp
65                  70                  75                  80

Val Asn Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Gly Gly Tyr Ala Ser Gly Gly Tyr Pro Tyr Ala Thr Arg Leu Asp
```

115 120 125

Leu

<210> SEQ ID NO 156
<211> LENGTH: 13
<212> TYPE: PRT
<213> ORGANISM: Oryctolagus cuniculus

<400> SEQUENCE: 156

Gln Ser Ser Gln Ser Val Tyr Asn Asn Asn Asp Leu Ala
1 5 10

<210> SEQ ID NO 157
<211> LENGTH: 7
<212> TYPE: PRT
<213> ORGANISM: Oryctolagus cuniculus

<400> SEQUENCE: 157

Tyr Ala Ser Thr Leu Ala Ser
1 5

<210> SEQ ID NO 158
<211> LENGTH: 11
<212> TYPE: PRT
<213> ORGANISM: Oryctolagus cuniculus

<400> SEQUENCE: 158

Leu Gly Gly Tyr Asp Asp Asp Ala Asp Asn Ala
1 5 10

<210> SEQ ID NO 159
<211> LENGTH: 5
<212> TYPE: PRT
<213> ORGANISM: Oryctolagus cuniculus

<400> SEQUENCE: 159

Ser Asn Thr Ile Asn
1 5

<210> SEQ ID NO 160
<211> LENGTH: 16
<212> TYPE: PRT
<213> ORGANISM: Oryctolagus cuniculus

<400> SEQUENCE: 160

Tyr Ile Trp Ser Gly Gly Ser Thr Tyr Tyr Ala Ser Trp Val Asn Gly
1 5 10 15

<210> SEQ ID NO 161
<211> LENGTH: 16
<212> TYPE: PRT
<213> ORGANISM: Oryctolagus cuniculus

<400> SEQUENCE: 161

Gly Gly Tyr Ala Ser Gly Gly Tyr Pro Tyr Ala Thr Arg Leu Asp Leu
1 5 10 15

<210> SEQ ID NO 162
<211> LENGTH: 369
<212> TYPE: DNA
<213> ORGANISM: Oryctolagus cuniculus

<400> SEQUENCE: 162
atggacacga gggcccccac tcagctgctg gggctcctgc tgctctggct cccaggtgcc 60
acatttgcag ccgtgctgac ccagacacca tcacccgtgt ctgcagctgt gggaggcaca 120
gtcaccatca gttgccagtc cagtcagagt gtttataata ataacgactt agcctggtat 180
cagcagaaac cagggcagcc tcctaaactc ctgatctatt atgcatccac tctggcatct 240
ggggtcccat cgcggttcaa aggcagtgga tctgggacac agttcactct caccatcagc 300
ggcgtgcagt gtgacgatgc tgccgcttac tactgtctag gcggttatga tgatgatgct 360
gataatgct 369

<210> SEQ ID NO 163
<211> LENGTH: 387
<212> TYPE: DNA
<213> ORGANISM: Oryctolagus cuniculus

<400> SEQUENCE: 163
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtatctg gattatccct cagtagcaat acaataaact gggtccgcca ggctccaggg 180
aaggggctgg agtggatcgg atacatttgg agtggtggta gtacatacta cgcgagctgg 240
gtgaatggtc gattcaccat ctccaaaacc tcgaccacgg tggatctgaa aatcaccagt 300
ccgacaaccg aggacacggc cacctatttc tgtgccagag gggttacgc tagtggtggt 360 tatccttatg ccactcggtt ggatctc 387

<210> SEQ ID NO 164
<211> LENGTH: 39
<212> TYPE: DNA
<213> ORGANISM: Oryctolagus cuniculus

<400> SEQUENCE: 164
cagtccagtc agagtgttta taataataac gacttagcc 39

<210> SEQ ID NO 165
<211> LENGTH: 21
<212> TYPE: DNA
<213> ORGANISM: Oryctolagus cuniculus

<400> SEQUENCE: 165
tatgcatcca ctctggcatc t 21

<210> SEQ ID NO 166
<211> LENGTH: 33
<212> TYPE: DNA
<213> ORGANISM: Oryctolagus cuniculus

<400> SEQUENCE: 166
ctaggcggtt atgatgatga tgctgataat gct 33

<210> SEQ ID NO 167
<211> LENGTH: 15
<212> TYPE: DNA
<213> ORGANISM: Oryctolagus cuniculus

<400> SEQUENCE: 167
agcaatacaa taaac 15

<210> SEQ ID NO 168
<211> LENGTH: 48
<212> TYPE: DNA

<213> ORGANISM: Oryctolagus cuniculus

<400> SEQUENCE: 168
tacatttgga gtggtggtag tacatactac gcgagctggg tgaatggt 48

<210> SEQ ID NO 169
<211> LENGTH: 48
<212> TYPE: DNA
<213> ORGANISM: Oryctolagus cuniculus

<400> SEQUENCE: 169
gggggttacg ctagtggtgg ttatccttat gccactcggt tggatctc 48

<210> SEQ ID NO 170
<211> LENGTH: 123
<212> TYPE: PRT
<213> ORGANISM: Oryctolagus cuniculus

<400> SEQUENCE: 170

```
Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Ser
            20                  25                  30

Val Ser Ala Ala Val Gly Gly Thr Val Thr Ile Asn Cys Gln Ser Ser
        35                  40                  45

Gln Ser Val Tyr Asn Asn Asp Tyr Leu Ser Trp Tyr Gln Gln Arg Pro
    50                  55                  60

Gly Gln Arg Pro Lys Leu Leu Ile Tyr Gly Ala Ser Lys Leu Ala Ser
65                  70                  75                  80

Gly Val Pro Ser Arg Phe Lys Gly Ser Gly Ser Gly Lys Gln Phe Thr
                85                  90                  95

Leu Thr Ile Ser Gly Val Gln Cys Asp Asp Ala Ala Thr Tyr Tyr Cys
            100                 105                 110

Leu Gly Asp Tyr Asp Asp Asp Ala Asp Asn Thr
        115                 120
```

<210> SEQ ID NO 171
<211> LENGTH: 123
<212> TYPE: PRT
<213> ORGANISM: Oryctolagus cuniculus

<400> SEQUENCE: 171

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Thr Leu Ser
        35                  40                  45

Thr Asn Tyr Tyr Leu Ser Trp Val Arg Gln Ala Pro Gly Lys Gly Leu
    50                  55                  60

Glu Trp Ile Gly Ile Ile Tyr Pro Ser Gly Asn Thr Tyr Cys Ala Lys
65                  70                  75                  80

Trp Ala Lys Gly Arg Phe Thr Ile Ser Lys Thr Ser Ser Thr Thr Val
                85                  90                  95

Asp Leu Lys Met Thr Ser Pro Thr Thr Glu Asp Thr Ala Thr Tyr Phe
            100                 105                 110

Cys Ala Arg Asn Tyr Gly Gly Asp Glu Ser Leu
        115                 120
```

<210> SEQ ID NO 172
<211> LENGTH: 13
<212> TYPE: PRT
<213> ORGANISM: Oryctolagus cuniculus

<400> SEQUENCE: 172

Gln Ser Ser Gln Ser Val Tyr Asn Asn Asp Tyr Leu Ser
1               5                   10

<210> SEQ ID NO 173
<211> LENGTH: 7
<212> TYPE: PRT
<213> ORGANISM: Oryctolagus cuniculus

<400> SEQUENCE: 173

Gly Ala Ser Lys Leu Ala Ser
1               5

<210> SEQ ID NO 174
<211> LENGTH: 11
<212> TYPE: PRT
<213> ORGANISM: Oryctolagus cuniculus

<400> SEQUENCE: 174

Leu Gly Asp Tyr Asp Asp Asp Ala Asp Asn Thr
1               5                   10

<210> SEQ ID NO 175
<211> LENGTH: 6
<212> TYPE: PRT
<213> ORGANISM: Oryctolagus cuniculus

<400> SEQUENCE: 175

Thr Asn Tyr Tyr Leu Ser
1               5

<210> SEQ ID NO 176
<211> LENGTH: 16
<212> TYPE: PRT
<213> ORGANISM: Oryctolagus cuniculus

<400> SEQUENCE: 176

Ile Ile Tyr Pro Ser Gly Asn Thr Tyr Cys Ala Lys Trp Ala Lys Gly
1               5                   10                  15

<210> SEQ ID NO 177
<211> LENGTH: 8
<212> TYPE: PRT
<213> ORGANISM: Oryctolagus cuniculus

<400> SEQUENCE: 177

Asn Tyr Gly Gly Asp Glu Ser Leu
1               5

<210> SEQ ID NO 178
<211> LENGTH: 369
<212> TYPE: DNA
<213> ORGANISM: Oryctolagus cuniculus

<400> SEQUENCE: 178
atggacacga gggcccccac tcagctgctg gggctcctgc tgctctggct cccaggtgcc      60
acatttgcag ccgtgctgac ccagacacca tcctccgtgt ctgcagctgt gggaggcaca     120

```
gtcaccatca attgccagtc cagtcagagt gtttataata acgactactt atcctggtat    180

caacagaggc cagggcaacg tcccaagctc ctaatctatg gtgcttccaa actggcatct    240

ggggtcccgt cacggttcaa aggcagtgga tctgggaaac agtttactct caccatcagc    300

ggcgtgcagt gtgacgatgc tgccacttac tactgtctgg gcgattatga tgatgatgct    360

gataatact                                                            369


<210> SEQ ID NO 179
<211> LENGTH: 369
<212> TYPE: DNA
<213> ORGANISM: Oryctolagus cuniculus

<400> SEQUENCE: 179

atggagactg ggctgcgctg gcttctcctg gtcgctgtgc tcaaaggtgt ccagtgtcag     60

tcgctggagg agtccggggg tcgcctggtc acgcctggga cacccctgac actcacttgc    120

acagtctctg gattcaccct cagtaccaac tactacctga gctgggtccg ccaggctcca    180

gggaaggggc tagaatggat cggaatcatt tatcctagtg gtaacacata ttgcgcgaag    240

tgggcgaaag gccgattcac catctccaaa acctcgtcga ccacggtgga tctgaaaatg    300

accagtccga caaccgagga cacagccacg tatttctgtg ccagaaatta tggtggtgat    360

gaaagtttg                                                            369


<210> SEQ ID NO 180
<211> LENGTH: 39
<212> TYPE: DNA
<213> ORGANISM: Oryctolagus cuniculus

<400> SEQUENCE: 180

cagtccagtc agagtgttta taataacgac tacttatcc                            39


<210> SEQ ID NO 181
<211> LENGTH: 21
<212> TYPE: DNA
<213> ORGANISM: Oryctolagus cuniculus

<400> SEQUENCE: 181

ggtgcttcca aactggcatc t                                               21


<210> SEQ ID NO 182
<211> LENGTH: 33
<212> TYPE: DNA
<213> ORGANISM: Oryctolagus cuniculus

<400> SEQUENCE: 182

ctgggcgatt atgatgatga tgctgataat act                                  33


<210> SEQ ID NO 183
<211> LENGTH: 18
<212> TYPE: DNA
<213> ORGANISM: Oryctolagus cuniculus

<400> SEQUENCE: 183

accaactact acctgagc                                                   18


<210> SEQ ID NO 184
<211> LENGTH: 48
<212> TYPE: DNA
<213> ORGANISM: Oryctolagus cuniculus

<400> SEQUENCE: 184
```

atcatttatc ctagtggtaa cacatattgc gcgaagtggg cgaaaggc 48

<210> SEQ ID NO 185
<211> LENGTH: 24
<212> TYPE: DNA
<213> ORGANISM: Oryctolagus cuniculus

<400> SEQUENCE: 185
aattatggtg gtgatgaaag tttg 24

<210> SEQ ID NO 186
<211> LENGTH: 119
<212> TYPE: PRT
<213> ORGANISM: Oryctolagus cuniculus

<400> SEQUENCE: 186

```
Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Lys Cys Gln Ala Ser
        35                  40                  45

Glu Thr Ile Gly Asn Ala Leu Ala Trp Tyr Gln Gln Lys Ser Gly Gln
    50                  55                  60

Pro Pro Lys Leu Leu Ile Tyr Lys Ala Ser Lys Leu Ala Ser Gly Val
65                  70                  75                  80

Pro Ser Arg Phe Lys Gly Ser Gly Ser Gly Thr Glu Tyr Thr Leu Thr
                85                  90                  95

Ile Ser Asp Leu Glu Cys Ala Asp Ala Ala Thr Tyr Tyr Cys Gln Trp
            100                 105                 110

Cys Tyr Phe Gly Asp Ser Val
        115
```

<210> SEQ ID NO 187
<211> LENGTH: 128
<212> TYPE: PRT
<213> ORGANISM: Oryctolagus cuniculus

<400> SEQUENCE: 187

```
Met Glu Thr Gly Leu Arg Trp Leu Leu Leu Val Thr Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Thr Ala Ser Gly Phe Asp Phe
        35                  40                  45

Ser Ser Gly Tyr Tyr Met Cys Trp Val Arg Gln Ala Pro Gly Lys Gly
    50                  55                  60

Leu Glu Trp Ile Ala Cys Ile Phe Thr Ile Thr Thr Asn Thr Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Leu Cys Ala Arg Gly Ile Tyr Ser Asp Asn Asn Tyr Tyr Ala Leu
        115                 120                 125
```

<210> SEQ ID NO 188

<211> LENGTH: 11
<212> TYPE: PRT
<213> ORGANISM: Oryctolagus cuniculus

<400> SEQUENCE: 188

Gln Ala Ser Glu Thr Ile Gly Asn Ala Leu Ala
1 5 10

<210> SEQ ID NO 189
<211> LENGTH: 7
<212> TYPE: PRT
<213> ORGANISM: Oryctolagus cuniculus

<400> SEQUENCE: 189

Lys Ala Ser Lys Leu Ala Ser
1 5

<210> SEQ ID NO 190
<211> LENGTH: 9
<212> TYPE: PRT
<213> ORGANISM: Oryctolagus cuniculus

<400> SEQUENCE: 190

Gln Trp Cys Tyr Phe Gly Asp Ser Val
1 5

<210> SEQ ID NO 191
<211> LENGTH: 6
<212> TYPE: PRT
<213> ORGANISM: Oryctolagus cuniculus

<400> SEQUENCE: 191

Ser Gly Tyr Tyr Met Cys
1 5

<210> SEQ ID NO 192
<211> LENGTH: 17
<212> TYPE: PRT
<213> ORGANISM: Oryctolagus cuniculus

<400> SEQUENCE: 192

Cys Ile Phe Thr Ile Thr Thr Asn Thr Tyr Tyr Ala Ser Trp Ala Lys
1 5 10 15

Gly

<210> SEQ ID NO 193
<211> LENGTH: 11
<212> TYPE: PRT
<213> ORGANISM: Oryctolagus cuniculus

<400> SEQUENCE: 193

Gly Ile Tyr Ser Asp Asn Asn Tyr Tyr Ala Leu
1 5 10

<210> SEQ ID NO 194
<211> LENGTH: 357
<212> TYPE: DNA
<213> ORGANISM: Oryctolagus cuniculus

<400> SEQUENCE: 194
atggacacga gggcccccac tcagctgctg gggctcctgc tgctctggct cccaggtgcc 60
agatgtgatg ttgtgatgac ccagactcca gcctccgtgg aggcagctgt gggaggcaca 120
gtcaccatca agtgccaggc cagtgagacc attggcaatg cattagcctg gtatcagcag 180
aaatcagggc agcctcccaa gctcctgatc tacaaggcat ccaaactggc atctggggtc 240
ccatcgcggt tcaaaggcag tggatctggg acagagtaca ctctcaccat cagcgacctg 300
gagtgtgccg atgctgccac ttactactgt caatggtgtt attttggtga tagtgtt 357

<210> SEQ ID NO 195
<211> LENGTH: 384
<212> TYPE: DNA
<213> ORGANISM: Oryctolagus cuniculus

<400> SEQUENCE: 195
atggagactg ggctgcgctg gcttctcctg gtcactgtgc tcaaaggtgt ccagtgtcag 60
gagcagctgg tggagtccgg gggaggcctg gtccagcctg agggatccct gacactcacc 120
tgcacagcct ctggattcga cttcagtagc ggctactaca tgtgctgggt ccgccaggct 180
ccagggaagg ggctggagtg gatcgcgtgt attttcacta ttactactaa cacttactac 240
gcgagctggg cgaaaggccg attcaccatc tccaagacct cgtcgaccac ggtgactctg 300
caaatgacca gtctgacagc cgcggacacg gccacctatc tctgtgcgag agggatttat 360
tctgataata attattatgc cttg 384

<210> SEQ ID NO 196
<211> LENGTH: 33
<212> TYPE: DNA
<213> ORGANISM: Oryctolagus cuniculus

<400> SEQUENCE: 196
caggccagtg agaccattgg caatgcatta gcc 33

<210> SEQ ID NO 197
<211> LENGTH: 21
<212> TYPE: DNA
<213> ORGANISM: Oryctolagus cuniculus

<400> SEQUENCE: 197
aaggcatcca aactggcatc t 21

<210> SEQ ID NO 198
<211> LENGTH: 27
<212> TYPE: DNA
<213> ORGANISM: Oryctolagus cuniculus

<400> SEQUENCE: 198
caatggtgtt attttggtga tagtgtt 27

<210> SEQ ID NO 199
<211> LENGTH: 18
<212> TYPE: DNA
<213> ORGANISM: Oryctolagus cuniculus

<400> SEQUENCE: 199
agcggctact acatgtgc 18

<210> SEQ ID NO 200
<211> LENGTH: 51
<212> TYPE: DNA
<213> ORGANISM: Oryctolagus cuniculus

<400> SEQUENCE: 200
tgtattttca ctattactac taacacttac tacgcgagct gggcgaaagg c 51

<210> SEQ ID NO 201
<211> LENGTH: 33
<212> TYPE: DNA
<213> ORGANISM: Oryctolagus cuniculus

<400> SEQUENCE: 201
gggatttatt ctgataataa ttattatgcc ttg 33

<210> SEQ ID NO 202
<211> LENGTH: 119
<212> TYPE: PRT
<213> ORGANISM: Oryctolagus cuniculus

<400> SEQUENCE: 202

```
Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Lys Cys Gln Ala Ser
        35                  40                  45

Glu Ser Ile Gly Asn Ala Leu Ala Trp Tyr Gln Gln Lys Pro Gly Gln
    50                  55                  60

Pro Pro Lys Leu Leu Ile Tyr Lys Ala Ser Thr Leu Ala Ser Gly Val
65                  70                  75                  80

Pro Ser Arg Phe Ser Gly Ser Gly Ser Gly Thr Glu Phe Thr Leu Thr
                85                  90                  95

Ile Ser Gly Val Gln Cys Ala Asp Ala Ala Ala Tyr Tyr Cys Gln Trp
            100                 105                 110

Cys Tyr Phe Gly Asp Ser Val
        115
```

<210> SEQ ID NO 203
<211> LENGTH: 128
<212> TYPE: PRT
<213> ORGANISM: Oryctolagus cuniculus

<400> SEQUENCE: 203

```
Met Glu Thr Gly Leu Arg Trp Leu Leu Leu Val Ala Val Leu Lys Gly
1               5                   10                  15

Val Gln Cys Gln Gln Gln Leu Val Glu Ser Gly Gly Gly Leu Val Lys
            20                  25                  30

Pro Gly Ala Ser Leu Thr Leu Thr Cys Lys Ala Ser Gly Phe Ser Phe
        35                  40                  45

Ser Ser Gly Tyr Tyr Met Cys Trp Val Arg Gln Ala Pro Gly Lys Gly
    50                  55                  60

Leu Glu Ser Ile Ala Cys Ile Phe Thr Ile Thr Asp Asn Thr Tyr Tyr
65                  70                  75                  80

Ala Asn Trp Ala Lys Gly Arg Phe Thr Ile Ser Lys Pro Ser Ser Pro
                85                  90                  95

Thr Val Thr Leu Gln Met Thr Ser Leu Thr Ala Ala Asp Thr Ala Thr
            100                 105                 110

Tyr Phe Cys Ala Arg Gly Ile Tyr Ser Thr Asp Asn Tyr Tyr Ala Leu
        115                 120                 125
```

<210> SEQ ID NO 204
<211> LENGTH: 11
<212> TYPE: PRT
<213> ORGANISM: Oryctolagus cuniculus

<400> SEQUENCE: 204

Gln Ala Ser Glu Ser Ile Gly Asn Ala Leu Ala
1               5                   10

<210> SEQ ID NO 205
<211> LENGTH: 7
<212> TYPE: PRT
<213> ORGANISM: Oryctolagus cuniculus

<400> SEQUENCE: 205

Lys Ala Ser Thr Leu Ala Ser
1               5

<210> SEQ ID NO 206
<211> LENGTH: 9
<212> TYPE: PRT
<213> ORGANISM: Oryctolagus cuniculus

<400> SEQUENCE: 206

Gln Trp Cys Tyr Phe Gly Asp Ser Val
1               5

<210> SEQ ID NO 207
<211> LENGTH: 6
<212> TYPE: PRT
<213> ORGANISM: Oryctolagus cuniculus

<400> SEQUENCE: 207

Ser Gly Tyr Tyr Met Cys
1               5

<210> SEQ ID NO 208
<211> LENGTH: 17
<212> TYPE: PRT
<213> ORGANISM: Oryctolagus cuniculus

<400> SEQUENCE: 208

Cys Ile Phe Thr Ile Thr Asp Asn Thr Tyr Tyr Ala Asn Trp Ala Lys
1               5                   10                  15

Gly

<210> SEQ ID NO 209
<211> LENGTH: 11
<212> TYPE: PRT
<213> ORGANISM: Oryctolagus cuniculus

<400> SEQUENCE: 209

Gly Ile Tyr Ser Thr Asp Asn Tyr Tyr Ala Leu
1               5                   10

<210> SEQ ID NO 210
<211> LENGTH: 357
<212> TYPE: DNA
<213> ORGANISM: Oryctolagus cuniculus

<400> SEQUENCE: 210
atggacacga gggcccccac tcagctgctg gggctcctgc tgctctggct cccaggtgcc      60
agatgtgatg ttgtgatgac ccagactcca gcctccgtgg aggcagctgt gggaggcaca     120
gtcaccatca agtgccaggc cagtgagagc attggcaatg cattagcctg gtatcagcag     180
aaaccagggc agcctcccaa gctcctgatc tacaaggcat ccactctggc atctggggtc     240
ccatcgcggt tcagcggcag tggatctggg acagagttca ctctcaccat cagcggcgtg 300
cagtgtgccg atgctgccgc ttactactgt caatggtgtt attttggtga tagtgtt 357

<210> SEQ ID NO 211
<211> LENGTH: 384
<212> TYPE: DNA
<213> ORGANISM: Oryctolagus cuniculus

<400> SEQUENCE: 211
atggagactg ggctgcgctg gcttctcctg gtcgctgtgc tcaaaggtgt ccagtgtcag 60
cagcagctgg tggagtccgg gggaggcctg gtcaagccgg gggcatccct gacactcacc 120
tgcaaagcct ctggattctc cttcagtagc ggctactaca tgtgctgggt ccgccaggct 180
ccagggaagg ggctggagtc gatcgcatgc atttttacta ttactgataa cacttactac 240
gcgaactggg cgaaaggccg attcaccatc tccaagccct cgtcgcccac ggtgactctg 300
caaatgacca gtctgacagc cgcggacacg gccacctatt tctgtgcgag ggggatttat 360
tctactgata attattatgc cttg 384

<210> SEQ ID NO 212
<211> LENGTH: 33
<212> TYPE: DNA
<213> ORGANISM: Oryctolagus cuniculus

<400> SEQUENCE: 212
caggccagtg agagcattgg caatgcatta gcc 33

<210> SEQ ID NO 213
<211> LENGTH: 21
<212> TYPE: DNA
<213> ORGANISM: Oryctolagus cuniculus

<400> SEQUENCE: 213
aaggcatcca ctctggcatc t 21

<210> SEQ ID NO 214
<211> LENGTH: 27
<212> TYPE: DNA
<213> ORGANISM: Oryctolagus cuniculus

<400> SEQUENCE: 214
caatggtgtt attttggtga tagtgtt 27

<210> SEQ ID NO 215
<211> LENGTH: 18
<212> TYPE: DNA
<213> ORGANISM: Oryctolagus cuniculus

<400> SEQUENCE: 215
agcggctact acatgtgc 18

<210> SEQ ID NO 216
<211> LENGTH: 51
<212> TYPE: DNA
<213> ORGANISM: Oryctolagus cuniculus

<400> SEQUENCE: 216
tgcattttta ctattactga taacacttac tacgcgaact gggcgaaagg c 51

<210> SEQ ID NO 217
<211> LENGTH: 33

<212> TYPE: DNA
<213> ORGANISM: Oryctolagus cuniculus

<400> SEQUENCE: 217
gggatttatt ctactgataa ttattatgcc ttg 33

<210> SEQ ID NO 218
<211> LENGTH: 123
<212> TYPE: PRT
<213> ORGANISM: Oryctolagus cuniculus

<400> SEQUENCE: 218

```
Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Lys Cys Gln Ala Ser
        35                  40                  45

Gln Ser Val Ser Ser Tyr Leu Asn Trp Tyr Gln Gln Lys Pro Gly Gln
    50                  55                  60

Pro Pro Lys Leu Leu Ile Tyr Arg Ala Ser Thr Leu Glu Ser Gly Val
65                  70                  75                  80

Pro Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Cys
            100                 105                 110

Thr Tyr Gly Thr Ser Ser Ser Tyr Gly Ala Ala
        115                 120
```

<210> SEQ ID NO 219
<211> LENGTH: 133
<212> TYPE: PRT
<213> ORGANISM: Oryctolagus cuniculus

<400> SEQUENCE: 219

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Ser Leu Ser
        35                  40                  45

Ser Asn Ala Ile Ser Trp Val Arg Gln Ala Pro Gly Lys Gly Leu Glu
    50                  55                  60

Trp Ile Gly Ile Ile Ser Tyr Ser Gly Thr Thr Tyr Tyr Ala Ser Trp
65                  70                  75                  80

Ala Lys Gly Arg Phe Thr Ile Ser Lys Thr Ser Ser Thr Thr Val Asp
                85                  90                  95

Leu Lys Ile Thr Ser Pro Thr Thr Glu Asp Thr Ala Thr Tyr Phe Cys
            100                 105                 110

Ala Arg Asp Asp Pro Thr Thr Val Met Val Met Leu Ile Pro Phe Gly
        115                 120                 125

Ala Gly Met Asp Leu
    130
```

<210> SEQ ID NO 220
<211> LENGTH: 11
<212> TYPE: PRT
<213> ORGANISM: Oryctolagus cuniculus

<400> SEQUENCE: 220

Gln Ala Ser Gln Ser Val Ser Ser Tyr Leu Asn
1 5 10

<210> SEQ ID NO 221
<211> LENGTH: 7
<212> TYPE: PRT
<213> ORGANISM: Oryctolagus cuniculus

<400> SEQUENCE: 221

Arg Ala Ser Thr Leu Glu Ser
1 5

<210> SEQ ID NO 222
<211> LENGTH: 13
<212> TYPE: PRT
<213> ORGANISM: Oryctolagus cuniculus

<400> SEQUENCE: 222

Gln Cys Thr Tyr Gly Thr Ser Ser Ser Tyr Gly Ala Ala
1 5 10

<210> SEQ ID NO 223
<211> LENGTH: 5
<212> TYPE: PRT
<213> ORGANISM: Oryctolagus cuniculus

<400> SEQUENCE: 223

Ser Asn Ala Ile Ser
1 5

<210> SEQ ID NO 224
<211> LENGTH: 16
<212> TYPE: PRT
<213> ORGANISM: Oryctolagus cuniculus

<400> SEQUENCE: 224

Ile Ile Ser Tyr Ser Gly Thr Thr Tyr Tyr Ala Ser Trp Ala Lys Gly
1 5 10 15

<210> SEQ ID NO 225
<211> LENGTH: 19
<212> TYPE: PRT
<213> ORGANISM: Oryctolagus cuniculus

<400> SEQUENCE: 225

Asp Asp Pro Thr Thr Val Met Val Met Leu Ile Pro Phe Gly Ala Gly
1 5 10 15

Met Asp Leu

<210> SEQ ID NO 226
<211> LENGTH: 369
<212> TYPE: DNA
<213> ORGANISM: Oryctolagus cuniculus

<400> SEQUENCE: 226
atggacacga gggcccccac tcagctgctg gggctcctgc tgctctggct cccaggtgcc 60
agatgtgatg ttgtgatgac ccagactcca gcctccgtgg aggcagctgt gggaggcaca 120
gtcaccatca agtgccaggc cagtcagagc gttagtagct acttaaactg gtatcagcag 180
aaaccagggc agcctcccaa gctcctgatc tacagggcat ccactctgga atctggggtc 240

-continued

```
ccatcgcggt tcaaaggcag tggatctggg acagagttca ctctcaccat cagcgacctg    300

gagtgtgccg atgctgccac ttactactgt caatgtactt atggtactag tagtagttat    360

ggtgctgct                                                            369
```

<210> SEQ ID NO 227
<211> LENGTH: 399
<212> TYPE: DNA
<213> ORGANISM: Oryctolagus cuniculus

<400> SEQUENCE: 227

```
atggagactg ggctgcgctg gcttctcctg gtcgctgtgc tcaaaggtgt ccagtgtcag     60

tcggtggagg agtccggggg tcgcctggtc acgcctggga cacccctgac actcacctgc    120

accgtctctg gtatctccct cagtagcaat gcaataagct gggtccgcca ggctccaggg    180

aaggggctgg aatggatcgg aatcattagt tatagtggta ccacatacta cgcgagctgg    240

gcgaaaggcc gattcaccat ctccaaaacc tcgtcgacca cggtggatct gaaaatcact    300

agtccgacaa ccgaggacac ggccacctac ttctgtgcca gagatgaccc tacgacagtt    360

atggttatgt tgataccttt tggagccggc atggacctc                           399
```

<210> SEQ ID NO 228
<211> LENGTH: 33
<212> TYPE: DNA
<213> ORGANISM: Oryctolagus cuniculus

<400> SEQUENCE: 228

```
caggccagtc agagcgttag tagctactta aac                                  33
```

<210> SEQ ID NO 229
<211> LENGTH: 21
<212> TYPE: DNA
<213> ORGANISM: Oryctolagus cuniculus

<400> SEQUENCE: 229

```
agggcatcca ctctggaatc t                                               21
```

<210> SEQ ID NO 230
<211> LENGTH: 39
<212> TYPE: DNA
<213> ORGANISM: Oryctolagus cuniculus

<400> SEQUENCE: 230

```
caatgtactt atggtactag tagtagttat ggtgctgct                            39
```

<210> SEQ ID NO 231
<211> LENGTH: 15
<212> TYPE: DNA
<213> ORGANISM: Oryctolagus cuniculus

<400> SEQUENCE: 231

```
agcaatgcaa taagc                                                      15
```

<210> SEQ ID NO 232
<211> LENGTH: 48
<212> TYPE: DNA
<213> ORGANISM: Oryctolagus cuniculus

<400> SEQUENCE: 232

```
atcattagtt atagtggtac cacatactac gcgagctggg cgaaaggc                  48
```

<210> SEQ ID NO 233
<211> LENGTH: 57
<212> TYPE: DNA
<213> ORGANISM: Oryctolagus cuniculus

<400> SEQUENCE: 233
gatgacccta cgacagttat ggttatgttg atacctttg gagccggcat ggacctc 57

<210> SEQ ID NO 234
<211> LENGTH: 125
<212> TYPE: PRT
<213> ORGANISM: Oryctolagus cuniculus

<400> SEQUENCE: 234

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Ala Val Gly Gly Thr Val Thr Ile Asn Cys Gln Ala Ser
        35                  40                  45

Gln Ser Val Tyr Lys Asn Asn Tyr Leu Ser Trp Tyr Gln Gln Lys Pro
    50                  55                  60

Gly Gln Pro Pro Lys Gly Leu Ile Tyr Ser Ala Ser Thr Leu Asp Ser
65                  70                  75                  80

Gly Val Pro Leu Arg Phe Ser Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Ser Tyr Asp Cys Ser Ser Gly Asp Cys Tyr Ala
        115                 120                 125
```

<210> SEQ ID NO 235
<211> LENGTH: 119
<212> TYPE: PRT
<213> ORGANISM: Oryctolagus cuniculus

<400> SEQUENCE: 235

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Glu Gly Ser Leu Thr Leu Thr Cys Thr Ala Ser Gly Phe Ser Phe Ser
        35                  40                  45

Ser Tyr Trp Met Cys Trp Val Arg Gln Ala Pro Gly Lys Gly Leu Glu
    50                  55                  60

Trp Ile Ala Cys Ile Val Thr Gly Asn Gly Asn Thr Tyr Tyr Ala Asn
65                  70                  75                  80

Trp Ala Lys Gly Arg Phe Thr Ile Ser Lys Thr Ser Ser Thr Thr Val
                85                  90                  95

Thr Leu Gln Met Thr Ser Leu Thr Ala Ala Asp Thr Ala Thr Tyr Phe
            100                 105                 110

Cys Ala Lys Ala Tyr Asp Leu
        115
```

<210> SEQ ID NO 236
<211> LENGTH: 13
<212> TYPE: PRT
<213> ORGANISM: Oryctolagus cuniculus

<400> SEQUENCE: 236

Gln Ala Ser Gln Ser Val Tyr Lys Asn Asn Tyr Leu Ser
1 5 10

<210> SEQ ID NO 237
<211> LENGTH: 7
<212> TYPE: PRT
<213> ORGANISM: Oryctolagus cuniculus

<400> SEQUENCE: 237

Ser Ala Ser Thr Leu Asp Ser
1 5

<210> SEQ ID NO 238
<211> LENGTH: 13
<212> TYPE: PRT
<213> ORGANISM: Oryctolagus cuniculus

<400> SEQUENCE: 238

Leu Gly Ser Tyr Asp Cys Ser Ser Gly Asp Cys Tyr Ala
1 5 10

<210> SEQ ID NO 239
<211> LENGTH: 5
<212> TYPE: PRT
<213> ORGANISM: Oryctolagus cuniculus

<400> SEQUENCE: 239

Ser Tyr Trp Met Cys
1 5

<210> SEQ ID NO 240
<211> LENGTH: 17
<212> TYPE: PRT
<213> ORGANISM: Oryctolagus cuniculus

<400> SEQUENCE: 240

Cys Ile Val Thr Gly Asn Gly Asn Thr Tyr Tyr Ala Asn Trp Ala Lys
1 5 10 15

Gly

<210> SEQ ID NO 241
<211> LENGTH: 4
<212> TYPE: PRT
<213> ORGANISM: Oryctolagus cuniculus

<400> SEQUENCE: 241

Ala Tyr Asp Leu
1

<210> SEQ ID NO 242
<211> LENGTH: 375
<212> TYPE: DNA
<213> ORGANISM: Oryctolagus cuniculus

<400> SEQUENCE: 242
atggacacga gggcccccac tcagctgctg gggctcctgc tgctctggct cccaggtgcc 60
acatttgccc aagtgctgac ccagactgca tcgcccgtgt ctgcagctgt gggaggcaca 120
gtcaccatca actgccaggc cagtcagagt gtttataaga acaactactt atcctggtat 180
cagcagaaac cagggcagcc tcccaaaggc ctgatctatt ctgcatcgac tctagattct 240
ggggtcccat tgcggttcag cggcagtgga tctgggacac agttcactct caccatcagc 300
gacgtgcagt gtgacgatgc tgccacttac tactgtctag gcagttatga ttgtagtagt 360
ggtgattgtt atgct 375

<210> SEQ ID NO 243
<211> LENGTH: 357
<212> TYPE: DNA
<213> ORGANISM: Oryctolagus cuniculus

<400> SEQUENCE: 243
atggagactg ggctgcgctg gcttctcctg gtcgctgtgc tcaaaggtgt ccagtgtcag 60
tcgttggagg agtccggggg agacctggtc aagcctgagg gatccctgac actcacctgc 120
acagcctctg gattctcctt cagtagctac tggatgtgct gggtccgcca ggctccaggg 180
aaggggctgg agtggatcgc atgcattgtt actggtaatg gtaacactta ctacgcgaac 240
tgggcgaaag gccgattcac catctccaaa acctcgtcga ccacggtgac tctgcaaatg 300
accagtctga cagccgcgga cacggccacc tatttttgtg cgaaagccta tgacttg 357

<210> SEQ ID NO 244
<211> LENGTH: 39
<212> TYPE: DNA
<213> ORGANISM: Oryctolagus cuniculus

<400> SEQUENCE: 244
caggccagtc agagtgttta taagaacaac tacttatcc 39

<210> SEQ ID NO 245
<211> LENGTH: 21
<212> TYPE: DNA
<213> ORGANISM: Oryctolagus cuniculus

<400> SEQUENCE: 245
tctgcatcga ctctagattc t 21

<210> SEQ ID NO 246
<211> LENGTH: 39
<212> TYPE: DNA
<213> ORGANISM: Oryctolagus cuniculus

<400> SEQUENCE: 246
ctaggcagtt atgattgtag tagtggtgat tgttatgct 39

<210> SEQ ID NO 247
<211> LENGTH: 15
<212> TYPE: DNA
<213> ORGANISM: Oryctolagus cuniculus

<400> SEQUENCE: 247
agctactgga tgtgc 15

<210> SEQ ID NO 248
<211> LENGTH: 51
<212> TYPE: DNA
<213> ORGANISM: Oryctolagus cuniculus

<400> SEQUENCE: 248
tgcattgtta ctggtaatgg taacacttac tacgcgaact gggcgaaagg c 51

<210> SEQ ID NO 249
<211> LENGTH: 12
<212> TYPE: DNA

<213> ORGANISM: Oryctolagus cuniculus

<400> SEQUENCE: 249
gcctatgact tg 12

<210> SEQ ID NO 250
<211> LENGTH: 123
<212> TYPE: PRT
<213> ORGANISM: Oryctolagus cuniculus

<400> SEQUENCE: 250

```
Met Asp Thr Arg Ala Pro Thr Gln Leu Leu Gly Leu Leu Leu Leu Trp
1               5                   10                  15

Leu Pro Gly Ser Thr Phe Ala Ala Val Leu Thr Gln Thr Pro Ser Pro
            20                  25                  30

Val Ser Ala Ala Val Gly Gly Thr Val Ser Ile Ser Cys Gln Ala Ser
        35                  40                  45

Gln Ser Val Tyr Asp Asn Asn Tyr Leu Ser Trp Tyr Gln Gln Lys Pro
    50                  55                  60

Gly Gln Pro Pro Lys Leu Leu Ile Tyr Gly Ala Ser Thr Leu Ala Ser
65                  70                  75                  80

Gly Val Pro Ser Arg Phe Lys Gly Thr Gly Ser Gly Thr Gln Phe Thr
                85                  90                  95

Leu Thr Ile Thr Asp Val Gln Cys Asp Asp Ala Ala Thr Tyr Tyr Cys
            100                 105                 110

Ala Gly Val Phe Asn Asp Asp Ser Asp Asp Ala
        115                 120
```

<210> SEQ ID NO 251
<211> LENGTH: 125
<212> TYPE: PRT
<213> ORGANISM: Oryctolagus cuniculus

<400> SEQUENCE: 251

```
Met Glu Thr Gly Leu Arg Trp Leu Leu Leu Val Ala Val Pro Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Leu Ser Gly Phe Ser Leu Ser
        35                  40                  45

Ala Tyr Tyr Met Ser Trp Val Arg Gln Ala Pro Gly Lys Gly Leu Glu
    50                  55                  60

Trp Ile Gly Phe Ile Thr Leu Ser Asp His Ile Ser Tyr Ala Arg Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Ala
            100                 105                 110

Arg Ser Arg Gly Trp Gly Ala Met Gly Arg Leu Asp Leu
        115                 120                 125
```

<210> SEQ ID NO 252
<211> LENGTH: 13
<212> TYPE: PRT
<213> ORGANISM: Oryctolagus cuniculus

<400> SEQUENCE: 252

```
Gln Ala Ser Gln Ser Val Tyr Asp Asn Asn Tyr Leu Ser
```

1 5 10

<210> SEQ ID NO 253
<211> LENGTH: 7
<212> TYPE: PRT
<213> ORGANISM: Oryctolagus cuniculus

<400> SEQUENCE: 253

Gly Ala Ser Thr Leu Ala Ser
1 5

<210> SEQ ID NO 254
<211> LENGTH: 11
<212> TYPE: PRT
<213> ORGANISM: Oryctolagus cuniculus

<400> SEQUENCE: 254

Ala Gly Val Phe Asn Asp Asp Ser Asp Asp Ala
1 5 10

<210> SEQ ID NO 255
<211> LENGTH: 5
<212> TYPE: PRT
<213> ORGANISM: Oryctolagus cuniculus

<400> SEQUENCE: 255

Ala Tyr Tyr Met Ser
1 5

<210> SEQ ID NO 256
<211> LENGTH: 16
<212> TYPE: PRT
<213> ORGANISM: Oryctolagus cuniculus

<400> SEQUENCE: 256

Phe Ile Thr Leu Ser Asp His Ile Ser Tyr Ala Arg Trp Ala Lys Gly
1 5 10 15

<210> SEQ ID NO 257
<211> LENGTH: 12
<212> TYPE: PRT
<213> ORGANISM: Oryctolagus cuniculus

<400> SEQUENCE: 257

Ser Arg Gly Trp Gly Ala Met Gly Arg Leu Asp Leu
1 5 10

<210> SEQ ID NO 258
<211> LENGTH: 369
<212> TYPE: DNA
<213> ORGANISM: Oryctolagus cuniculus

<400> SEQUENCE: 258
atggacacga gggcccccac tcagctgctg gggctcctgc tgctctggct cccaggttcc 60
acatttgccg ccgtgctgac ccagactcca tctcccgtgt ctgcagctgt gggaggcaca 120
gtcagcatca gttgccaggc cagtcagagt gtttatgaca acaactattt atcctggtat 180
cagcagaaac caggacagcc tcccaagctc ctgatctatg gtgcatccac tctggcatct 240
ggggtcccat cgcggttcaa aggcacggga tctgggacac agttcactct caccatcaca 300
gacgtgcagt gtgacgatgc tgccacttac tattgtgcag gcgtttttaa tgatgatagt 360
gatgatgcc 369

<210> SEQ ID NO 259
<211> LENGTH: 375
<212> TYPE: DNA
<213> ORGANISM: Oryctolagus cuniculus

<400> SEQUENCE: 259
atggagactg ggctgcgctg gcttctcctg gtcgctgtgc ccaaaggtgt ccagtgtcag 60
tcgctggagg agtccggggg tcgcctggtc acgcctggga cacccctgac actcacctgc 120
acactctctg gattctccct cagtgcatac tatatgagct gggtccgcca ggctccaggg 180
aaggggctgg aatggatcgg attcattact ctgagtgatc atatatctta cgcgaggtgg 240
gcgaaaggcc gattcaccat ctccaaaacc tcgaccacgg tggatctgaa aatgaccagt 300
ccgacaaccg aggacacggc cacctatttc tgtgccagga gtcgtggctg ggtgcaatg 360 ggtcggttgg atctc 375

<210> SEQ ID NO 260
<211> LENGTH: 39
<212> TYPE: DNA
<213> ORGANISM: Oryctolagus cuniculus

<400> SEQUENCE: 260
caggccagtc agagtgttta tgacaacaac tatttatcc 39

<210> SEQ ID NO 261
<211> LENGTH: 21
<212> TYPE: DNA
<213> ORGANISM: Oryctolagus cuniculus

<400> SEQUENCE: 261
ggtgcatcca ctctggcatc t 21

<210> SEQ ID NO 262
<211> LENGTH: 33
<212> TYPE: DNA
<213> ORGANISM: Oryctolagus cuniculus

<400> SEQUENCE: 262
gcaggcgttt ttaatgatga tagtgatgat gcc 33

<210> SEQ ID NO 263
<211> LENGTH: 15
<212> TYPE: DNA
<213> ORGANISM: Oryctolagus cuniculus

<400> SEQUENCE: 263
gcatactata tgagc 15

<210> SEQ ID NO 264
<211> LENGTH: 48
<212> TYPE: DNA
<213> ORGANISM: Oryctolagus cuniculus

<400> SEQUENCE: 264
ttcattactc tgagtgatca tatatcttac gcgaggtggg cgaaaggc 48

<210> SEQ ID NO 265
<211> LENGTH: 36
<212> TYPE: DNA
<213> ORGANISM: Oryctolagus cuniculus

<400> SEQUENCE: 265
agtcgtggct ggggtgcaat gggtcggttg gatctc 36

<210> SEQ ID NO 266
<211> LENGTH: 123
<212> TYPE: PRT
<213> ORGANISM: Oryctolagus cuniculus

<400> SEQUENCE: 266

Met Asp Thr Arg Ala Pro Thr Gln Leu Leu Gly Leu Leu Leu Leu Trp
1 5 10 15

Leu Pro Gly Ala Thr Phe Ala Ala Val Leu Thr Gln Thr Pro Ser Pro
20 25 30

Val Ser Ala Ala Val Gly Gly Thr Val Thr Ile Ser Cys Gln Ala Ser
35 40 45

Gln Ser Val Tyr Asn Asn Lys Asn Leu Ala Trp Tyr Gln Gln Lys Ser
50 55 60

Gly Gln Pro Pro Lys Leu Leu Ile Tyr Trp Ala Ser Thr Leu Ala Ser
65 70 75 80

Gly Val Ser Ser Arg Phe Ser Gly Ser Gly Ser Gly Thr Gln Phe Thr
85 90 95

Leu Thr Val Ser Gly Val Gln Cys Asp Asp Ala Ala Thr Tyr Tyr Cys
100 105 110

Leu Gly Val Phe Asp Asp Asp Ala Asp Asn Ala
115 120

<210> SEQ ID NO 267
<211> LENGTH: 121
<212> TYPE: PRT
<213> ORGANISM: Oryctolagus cuniculus

<400> SEQUENCE: 267

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Ala Ser Gly Phe Ser Leu Ser
35 40 45

Ser Tyr Ser Met Thr Trp Val Arg Gln Ala Pro Gly Lys Gly Leu Glu
50 55 60

Tyr Ile Gly Val Ile Gly Thr Ser Gly Ser Thr Tyr Tyr Ala Thr Trp
65 70 75 80

Ala Lys Gly Arg Phe Thr Ile Ser Arg Thr Ser Thr Thr Val Ala Leu
85 90 95

Lys Ile Thr Ser Pro Thr Thr Glu Asp Thr Ala Thr Tyr Phe Cys Val
100 105 110

Arg Ser Leu Ser Ser Ile Thr Phe Leu
115 120

<210> SEQ ID NO 268
<211> LENGTH: 13
<212> TYPE: PRT
<213> ORGANISM: Oryctolagus cuniculus

<400> SEQUENCE: 268

Gln Ala Ser Gln Ser Val Tyr Asn Asn Lys Asn Leu Ala
1 5 10

<210> SEQ ID NO 269
<211> LENGTH: 7
<212> TYPE: PRT
<213> ORGANISM: Oryctolagus cuniculus

<400> SEQUENCE: 269

Trp Ala Ser Thr Leu Ala Ser
1 5

<210> SEQ ID NO 270
<211> LENGTH: 11
<212> TYPE: PRT
<213> ORGANISM: Oryctolagus cuniculus

<400> SEQUENCE: 270

Leu Gly Val Phe Asp Asp Asp Ala Asp Asn Ala
1 5 10

<210> SEQ ID NO 271
<211> LENGTH: 5
<212> TYPE: PRT
<213> ORGANISM: Oryctolagus cuniculus

<400> SEQUENCE: 271

Ser Tyr Ser Met Thr
1 5

<210> SEQ ID NO 272
<211> LENGTH: 16
<212> TYPE: PRT
<213> ORGANISM: Oryctolagus cuniculus

<400> SEQUENCE: 272

Val Ile Gly Thr Ser Gly Ser Thr Tyr Tyr Ala Thr Trp Ala Lys Gly
1 5 10 15

<210> SEQ ID NO 273
<211> LENGTH: 8
<212> TYPE: PRT
<213> ORGANISM: Oryctolagus cuniculus

<400> SEQUENCE: 273

Ser Leu Ser Ser Ile Thr Phe Leu
1 5

<210> SEQ ID NO 274
<211> LENGTH: 369
<212> TYPE: DNA
<213> ORGANISM: Oryctolagus cuniculus

<400> SEQUENCE: 274
atggacacga gggcccccac tcagctgctg gggctcctgc tgctctggct cccaggtgcc 60
acattcgcag ccgtgctgac ccagacacca tcgcccgtgt ctgcggctgt gggaggcaca 120
gtcaccatca gttgccaggc cagtcagagt gtttataaca acaaaaattt agcctggtat 180
cagcagaaat cagggcagcc tcccaagctc ctgatctact gggcatccac tctggcatct 240
ggggtctcat cgcggttcag cggcagtgga tctgggacac agttcactct caccgtcagc 300
ggcgtgcagt gtgacgatgc tgccacttac tactgtctag gcgtttttga tgatgatgct 360
gataatgct 369

<210> SEQ ID NO 275
<211> LENGTH: 363

<212> TYPE: DNA
<213> ORGANISM: Oryctolagus cuniculus

<400> SEQUENCE: 275
atggagactg ggctgcgctg gcttctcctg gtcgctgtgc tcaaaggtgt ccaatgtcag 60
tcggtggagg agtccggggg tcgcctggtc acgcctggga cacccctgac actcacctgc 120
acagcctctg gattctccct cagtagctac tccatgacct gggtccgcca ggctccaggg 180
aaggggctgg aatatatcgg agtcattggt actagtggta gcacatacta cgcgacctgg 240
gcgaaaggcc gattcaccat ctccagaacc tcgaccacgg tggctctgaa aatcaccagt 300
ccgacaaccg aggacacggc cacctatttc tgtgtcagga gtctttcttc tattactttc 360
ttg 363

<210> SEQ ID NO 276
<211> LENGTH: 39
<212> TYPE: DNA
<213> ORGANISM: Oryctolagus cuniculus

<400> SEQUENCE: 276
caggccagtc agagtgttta taacaacaaa aatttagcc 39

<210> SEQ ID NO 277
<211> LENGTH: 21
<212> TYPE: DNA
<213> ORGANISM: Oryctolagus cuniculus

<400> SEQUENCE: 277
tgggcatcca ctctggcatc t 21

<210> SEQ ID NO 278
<211> LENGTH: 33
<212> TYPE: DNA
<213> ORGANISM: Oryctolagus cuniculus

<400> SEQUENCE: 278
ctaggcgttt ttgatgatga tgctgataat gct 33

<210> SEQ ID NO 279
<211> LENGTH: 15
<212> TYPE: DNA
<213> ORGANISM: Oryctolagus cuniculus

<400> SEQUENCE: 279
agctactcca tgacc 15

<210> SEQ ID NO 280
<211> LENGTH: 48
<212> TYPE: DNA
<213> ORGANISM: Oryctolagus cuniculus

<400> SEQUENCE: 280
gtcattggta ctagtggtag cacatactac gcgacctggg cgaaaggc 48

<210> SEQ ID NO 281
<211> LENGTH: 24
<212> TYPE: DNA
<213> ORGANISM: Oryctolagus cuniculus

<400> SEQUENCE: 281
agtctttctt ctattacttt cttg 24

<210> SEQ ID NO 282
<211> LENGTH: 120
<212> TYPE: PRT
<213> ORGANISM: Oryctolagus cuniculus

<400> SEQUENCE: 282

Met Asp Thr Arg Ala Pro Thr Gln Leu Leu Gly Leu Leu Leu Leu Trp
1               5                   10                  15

Leu Pro Gly Ala Arg Cys Ala Phe Glu Leu Thr Gln Thr Pro Ala Ser
            20                  25                  30

Val Glu Ala Ala Val Gly Gly Thr Val Thr Ile Asn Cys Gln Ala Ser
        35                  40                  45

Gln Asn Ile Tyr Arg Tyr Leu Ala Trp Tyr Gln Gln Lys Pro Gly Gln
    50                  55                  60

Pro Pro Lys Phe Leu Ile Tyr Leu Ala Ser Thr Leu Ala Ser Gly Val
65                  70                  75                  80

Pro Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Ser
            100                 105                 110

Tyr Tyr Ser Ser Asn Ser Val Ala
        115                 120

<210> SEQ ID NO 283
<211> LENGTH: 128
<212> TYPE: PRT
<213> ORGANISM: Oryctolagus cuniculus

<400> SEQUENCE: 283

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Asp Leu Val Gln
            20                  25                  30

Pro Glu Gly Ser Leu Thr Leu Thr Cys Thr Ala Ser Glu Leu Asp Phe
        35                  40                  45

Ser Ser Gly Tyr Trp Ile Cys Trp Val Arg Gln Val Pro Gly Lys Gly
    50                  55                  60

Leu Glu Trp Ile Gly Cys Ile Tyr Thr Gly Ser Ser Gly Ser Thr Phe
65                  70                  75                  80

Tyr Ala Ser Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Gly Tyr Ser Gly Phe Gly Tyr Phe Lys Leu
        115                 120                 125

<210> SEQ ID NO 284
<211> LENGTH: 11
<212> TYPE: PRT
<213> ORGANISM: Oryctolagus cuniculus

<400> SEQUENCE: 284

Gln Ala Ser Gln Asn Ile Tyr Arg Tyr Leu Ala
1               5                   10

<210> SEQ ID NO 285
<211> LENGTH: 7
<212> TYPE: PRT

<213> ORGANISM: Oryctolagus cuniculus

<400> SEQUENCE: 285

Leu Ala Ser Thr Leu Ala Ser
1 5

<210> SEQ ID NO 286
<211> LENGTH: 10
<212> TYPE: PRT
<213> ORGANISM: Oryctolagus cuniculus

<400> SEQUENCE: 286

Gln Ser Tyr Tyr Ser Ser Asn Ser Val Ala
1 5 10

<210> SEQ ID NO 287
<211> LENGTH: 6
<212> TYPE: PRT
<213> ORGANISM: Oryctolagus cuniculus

<400> SEQUENCE: 287

Ser Gly Tyr Trp Ile Cys
1 5

<210> SEQ ID NO 288
<211> LENGTH: 18
<212> TYPE: PRT
<213> ORGANISM: Oryctolagus cuniculus

<400> SEQUENCE: 288

Cys Ile Tyr Thr Gly Ser Ser Gly Ser Thr Phe Tyr Ala Ser Trp Ala
1 5 10 15

Lys Gly

<210> SEQ ID NO 289
<211> LENGTH: 10
<212> TYPE: PRT
<213> ORGANISM: Oryctolagus cuniculus

<400> SEQUENCE: 289

Gly Tyr Ser Gly Phe Gly Tyr Phe Lys Leu
1 5 10

<210> SEQ ID NO 290
<211> LENGTH: 360
<212> TYPE: DNA
<213> ORGANISM: Oryctolagus cuniculus

<400> SEQUENCE: 290
atggacacga gggcccccac tcagctgctg gggctcctgc tgctctggct cccaggtgcc 60
agatgtgcat tcgaattgac ccagactcca gcctccgtgg aggcagctgt gggaggcaca 120
gtcaccatca attgccaggc cagtcagaac atttatagat acttagcctg gtatcagcag 180
aaaccagggc agcctcccaa gttcctgatc tatctggcat ctactctggc atctggggtc 240
ccatcgcggt ttaaaggcag tggatctggg acagagttca ctctcaccat cagcgacctg 300
gagtgtgccg atgctgccac ttactactgt caaagttatt atagtagtaa tagtgtcgct 360

<210> SEQ ID NO 291
<211> LENGTH: 384
<212> TYPE: DNA
<213> ORGANISM: Oryctolagus cuniculus

<400> SEQUENCE: 291
atggagactg ggctgcgctg gcttctcctg gtcgctgtgc tcaaaggtgt ccagtgtcag 60
gagcagctgg tggagtccgg gggagacctg gtccagcctg agggatccct gacactcacc 120
tgcacagctt ctgagttaga cttcagtagc ggctactgga tatgctgggt ccgccaggtt 180
ccagggaagg ggctggagtg gatcggatgc atttatactg gtagtagtgg tagcactttt 240
tacgcgagtt gggcgaaagg ccgattcacc atctccaaaa cctcgtcgac cacggtgact 300
ctgcaaatga ccagtctgac agccgcggac acggccacct atttctgtgc gagaggttat 360
agtggctttg gttactttaa gttg 384

<210> SEQ ID NO 292
<211> LENGTH: 33
<212> TYPE: DNA
<213> ORGANISM: Oryctolagus cuniculus

<400> SEQUENCE: 292
caggccagtc agaacattta tagatactta gcc 33

<210> SEQ ID NO 293
<211> LENGTH: 21
<212> TYPE: DNA
<213> ORGANISM: Oryctolagus cuniculus

<400> SEQUENCE: 293
ctggcatcta ctctggcatc t 21

<210> SEQ ID NO 294
<211> LENGTH: 30
<212> TYPE: DNA
<213> ORGANISM: Oryctolagus cuniculus

<400> SEQUENCE: 294
caaagttatt atagtagtaa tagtgtcgct 30

<210> SEQ ID NO 295
<211> LENGTH: 18
<212> TYPE: DNA
<213> ORGANISM: Oryctolagus cuniculus

<400> SEQUENCE: 295
agcggctact ggatatgc 18

<210> SEQ ID NO 296
<211> LENGTH: 54
<212> TYPE: DNA
<213> ORGANISM: Oryctolagus cuniculus

<400> SEQUENCE: 296
tgcatttata ctggtagtag tggtagcact ttttacgcga gttgggcgaa aggc 54

<210> SEQ ID NO 297
<211> LENGTH: 30
<212> TYPE: DNA
<213> ORGANISM: Oryctolagus cuniculus

<400> SEQUENCE: 297
ggttatagtg gctttggtta ctttaagttg 30

<210> SEQ ID NO 298
<211> LENGTH: 122

<212> TYPE: PRT
<213> ORGANISM: Oryctolagus cuniculus

<400> SEQUENCE: 298

Met Asp Thr Arg Ala Pro Thr Gln Leu Leu Gly Leu Leu Leu Leu Trp
1 5 10 15

Leu Pro Gly Ala Arg Cys Ala Tyr Asp Met Thr Gln Thr Pro Ala Ser
20 25 30

Val Glu Val Ala Val Gly Gly Thr Val Thr Ile Lys Cys Gln Ala Ser
35 40 45

Glu Asp Ile Tyr Arg Leu Leu Ala Trp Tyr Gln Gln Lys Pro Gly Gln
50 55 60

Pro Pro Lys Leu Leu Ile Tyr Asp Ser Ser Asp Leu Ala Ser Gly Val
65 70 75 80

Pro Ser Arg Phe Lys Gly Ser Gly Ser Gly Thr Glu Phe Thr Leu Ala
85 90 95

Ile Ser Gly Val Gln Cys Asp Asp Ala Ala Thr Tyr Tyr Cys Gln Gln
100 105 110

Ala Trp Ser Tyr Ser Asp Ile Asp Asn Ala
115 120

<210> SEQ ID NO 299
<211> LENGTH: 123
<212> TYPE: PRT
<213> ORGANISM: Oryctolagus cuniculus

<400> SEQUENCE: 299

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Ala Ser Gly Phe Ser Leu Ser
35 40 45

Ser Tyr Tyr Met Ser Trp Val Arg Gln Ala Pro Gly Lys Gly Leu Glu
50 55 60

Trp Ile Gly Ile Ile Thr Thr Ser Gly Asn Thr Phe Tyr Ala Ser Trp
65 70 75 80

Ala Lys Gly Arg Leu Thr Ile Ser Arg Thr Ser Thr Thr Val Asp Leu
85 90 95

Lys Ile Thr Ser Pro Thr Thr Glu Asp Thr Ala Thr Tyr Phe Cys Ala
100 105 110

Arg Thr Ser Asp Ile Phe Tyr Tyr Arg Asn Leu
115 120

<210> SEQ ID NO 300
<211> LENGTH: 11
<212> TYPE: PRT
<213> ORGANISM: Oryctolagus cuniculus

<400> SEQUENCE: 300

Gln Ala Ser Glu Asp Ile Tyr Arg Leu Leu Ala
1 5 10

<210> SEQ ID NO 301
<211> LENGTH: 7
<212> TYPE: PRT
<213> ORGANISM: Oryctolagus cuniculus

<400> SEQUENCE: 301

Asp Ser Ser Asp Leu Ala Ser
1 5

<210> SEQ ID NO 302
<211> LENGTH: 12
<212> TYPE: PRT
<213> ORGANISM: Oryctolagus cuniculus

<400> SEQUENCE: 302

Gln Gln Ala Trp Ser Tyr Ser Asp Ile Asp Asn Ala
1 5 10

<210> SEQ ID NO 303
<211> LENGTH: 5
<212> TYPE: PRT
<213> ORGANISM: Oryctolagus cuniculus

<400> SEQUENCE: 303

Ser Tyr Tyr Met Ser
1 5

<210> SEQ ID NO 304
<211> LENGTH: 16
<212> TYPE: PRT
<213> ORGANISM: Oryctolagus cuniculus

<400> SEQUENCE: 304

Ile Ile Thr Thr Ser Gly Asn Thr Phe Tyr Ala Ser Trp Ala Lys Gly
1 5 10 15

<210> SEQ ID NO 305
<211> LENGTH: 10
<212> TYPE: PRT
<213> ORGANISM: Oryctolagus cuniculus

<400> SEQUENCE: 305

Thr Ser Asp Ile Phe Tyr Tyr Arg Asn Leu
1 5 10

<210> SEQ ID NO 306
<211> LENGTH: 366
<212> TYPE: DNA
<213> ORGANISM: Oryctolagus cuniculus

<400> SEQUENCE: 306
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca agtgccaggc cagtgaggac atttataggt tattggcctg gtatcaacag 180
aaaccagggc agcctcccaa gctcctgatc tatgattcat ccgatctggc atctggggtc 240
ccatcgcggt tcaaaggcag tggatctggg acagagttca ctctcgccat cagcggtgtg 300
cagtgtgacg atgctgccac ttactactgt caacaggctt ggagttatag tgatattgat 360
aatgct 366

<210> SEQ ID NO 307
<211> LENGTH: 369
<212> TYPE: DNA
<213> ORGANISM: Oryctolagus cuniculus

<400> SEQUENCE: 307
atggagactg ggctgcgctg gcttctcctg gtcgctgtgc tcaaaggtgt ccagtgtcag 60
tcggtggagg agtccggggg tcgcctggtc acgccgggga cacccctgac actcacctgc 120
acagcctctg gattctccct cagtagctac tacatgagct gggtccgcca ggctccaggg 180
aaggggctgg aatggatcgg aatcattact actagtggta atacatttta cgcgagctgg 240
gcgaaaggcc ggctcaccat ctccagaacc tcgaccacgg tggatctgaa aatcaccagt 300
ccgacaaccg aggacacggc cacctatttc tgtgccagaa cttctgatat tttttattat 360
cgtaacttg 369

<210> SEQ ID NO 308
<211> LENGTH: 33
<212> TYPE: DNA
<213> ORGANISM: Oryctolagus cuniculus

<400> SEQUENCE: 308
caggccagtg aggacattta taggttattg gcc 33

<210> SEQ ID NO 309
<211> LENGTH: 21
<212> TYPE: DNA
<213> ORGANISM: Oryctolagus cuniculus

<400> SEQUENCE: 309
gattcatccg atctggcatc t 21

<210> SEQ ID NO 310
<211> LENGTH: 36
<212> TYPE: DNA
<213> ORGANISM: Oryctolagus cuniculus

<400> SEQUENCE: 310
caacaggctt ggagttatag tgatattgat aatgct 36

<210> SEQ ID NO 311
<211> LENGTH: 15
<212> TYPE: DNA
<213> ORGANISM: Oryctolagus cuniculus

<400> SEQUENCE: 311
agctactaca tgagc 15

<210> SEQ ID NO 312
<211> LENGTH: 48
<212> TYPE: DNA
<213> ORGANISM: Oryctolagus cuniculus

<400> SEQUENCE: 312
atcattacta ctagtggtaa tacattttac gcgagctggg cgaaaggc 48

<210> SEQ ID NO 313
<211> LENGTH: 30
<212> TYPE: DNA
<213> ORGANISM: Oryctolagus cuniculus

<400> SEQUENCE: 313
acttctgata tttttattta tcgtaacttg 30

<210> SEQ ID NO 314
<211> LENGTH: 123
<212> TYPE: PRT
<213> ORGANISM: Oryctolagus cuniculus

<400> SEQUENCE: 314

Met Asp Thr Arg Ala Pro Thr Gln Leu Leu Gly Leu Leu Leu Leu Trp
1 5 10 15

Leu Pro Gly Ala Thr Phe Ala Ala Val Leu Thr Gln Thr Ala Ser Pro
20 25 30

Val Ser Ala Ala Val Gly Ala Thr Val Thr Ile Asn Cys Gln Ser Ser
35 40 45

Gln Ser Val Tyr Asn Asp Met Asp Leu Ala Trp Phe Gln Gln Lys Pro
50 55 60

Gly Gln Pro Pro Lys Leu Leu Ile Tyr Ser Ala Ser Thr Leu Ala Ser
65 70 75 80

Gly Val Pro Ser Arg Phe Ser Gly Ser Gly Ser Gly Thr Glu Phe Thr
85 90 95

Leu Thr Ile Ser Gly Val Gln Cys Asp Asp Ala Ala Thr Tyr Tyr Cys
100 105 110

Leu Gly Ala Phe Asp Asp Asp Ala Asp Asn Thr
115 120

<210> SEQ ID NO 315
<211> LENGTH: 129
<212> TYPE: PRT
<213> ORGANISM: Oryctolagus cuniculus

<400> SEQUENCE: 315

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Phe Ser Leu Thr
35 40 45

Arg His Ala Ile Thr Trp Val Arg Gln Ala Pro Gly Lys Gly Leu Glu
50 55 60

Trp Ile Gly Cys Ile Trp Ser Gly Gly Ser Thr Tyr Tyr Ala Thr Trp
65 70 75 80

Ala Lys Gly Arg Phe Thr Ile Ser Lys Thr Ser Thr Thr Val Asp Leu
85 90 95

Arg Ile Thr Ser Pro Thr Thr Glu Asp Thr Ala Thr Tyr Phe Cys Ala
100 105 110

Arg Val Ile Gly Asp Thr Ala Gly Tyr Ala Tyr Phe Thr Gly Leu Asp
115 120 125

Leu

<210> SEQ ID NO 316
<211> LENGTH: 13
<212> TYPE: PRT
<213> ORGANISM: Oryctolagus cuniculus

<400> SEQUENCE: 316

Gln Ser Ser Gln Ser Val Tyr Asn Asp Met Asp Leu Ala
1 5 10

<210> SEQ ID NO 317
<211> LENGTH: 7
<212> TYPE: PRT
<213> ORGANISM: Oryctolagus cuniculus

<400> SEQUENCE: 317

Ser Ala Ser Thr Leu Ala Ser
1 5

<210> SEQ ID NO 318
<211> LENGTH: 11
<212> TYPE: PRT
<213> ORGANISM: Oryctolagus cuniculus

<400> SEQUENCE: 318

Leu Gly Ala Phe Asp Asp Asp Ala Asp Asn Thr
1 5 10

<210> SEQ ID NO 319
<211> LENGTH: 5
<212> TYPE: PRT
<213> ORGANISM: Oryctolagus cuniculus

<400> SEQUENCE: 319

Arg His Ala Ile Thr
1 5

<210> SEQ ID NO 320
<211> LENGTH: 16
<212> TYPE: PRT
<213> ORGANISM: Oryctolagus cuniculus

<400> SEQUENCE: 320

Cys Ile Trp Ser Gly Gly Ser Thr Tyr Tyr Ala Thr Trp Ala Lys Gly
1 5 10 15

<210> SEQ ID NO 321
<211> LENGTH: 16
<212> TYPE: PRT
<213> ORGANISM: Oryctolagus cuniculus

<400> SEQUENCE: 321

Val Ile Gly Asp Thr Ala Gly Tyr Ala Tyr Phe Thr Gly Leu Asp Leu
1 5 10 15

<210> SEQ ID NO 322
<211> LENGTH: 369
<212> TYPE: DNA
<213> ORGANISM: Oryctolagus cuniculus

<400> SEQUENCE: 322
atggacacga gggcccccac tcagctgctg gggctcctgc tgctctggct cccaggtgcc 60
acgtttgcag ccgtgctgac ccagactgca tcacccgtgt ctgccgctgt gggagccaca 120
gtcaccatca actgccagtc cagtcagagt gtttataatg acatggactt agcctggttt 180
cagcagaaac cagggcagcc tcccaagctc ctgatctatt ctgcatccac tctggcatct 240
ggggtcccat cgcggttcag cggcagtgga tctgggacag agttcactct caccatcagc 300
ggcgtgcagt gtgacgatgc tgccacttac tactgtctag gcgcttttga tgatgatgct 360
gataatact 369

<210> SEQ ID NO 323
<211> LENGTH: 387
<212> TYPE: DNA
<213> ORGANISM: Oryctolagus cuniculus

<400> SEQUENCE: 323
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtctctg gattctccct cactaggcat gcaataacct gggtccgcca ggctccaggg 180
aaggggctgg aatggatcgg atgcatttgg agtggtggta gcacatacta cgcgacctgg 240
gcgaaaggcc gattcaccat ctccaaaacc tcgaccacgg tggatctcag aatcaccagt 300
ccgacaaccg aggacacggc cacctacttc tgtgccagag tcattggcga tactgctggt 360
tatgcttatt ttacggggct tgacttg 387

<210> SEQ ID NO 324
<211> LENGTH: 39
<212> TYPE: DNA
<213> ORGANISM: Oryctolagus cuniculus

<400> SEQUENCE: 324
cagtccagtc agagtgttta taatgacatg gacttagcc 39

<210> SEQ ID NO 325
<211> LENGTH: 21
<212> TYPE: DNA
<213> ORGANISM: Oryctolagus cuniculus

<400> SEQUENCE: 325
tctgcatcca ctctggcatc t 21

<210> SEQ ID NO 326
<211> LENGTH: 33
<212> TYPE: DNA
<213> ORGANISM: Oryctolagus cuniculus

<400> SEQUENCE: 326
ctaggcgctt ttgatgatga tgctgataat act 33

<210> SEQ ID NO 327
<211> LENGTH: 15
<212> TYPE: DNA
<213> ORGANISM: Oryctolagus cuniculus

<400> SEQUENCE: 327
aggcatgcaa taacc 15

<210> SEQ ID NO 328
<211> LENGTH: 48
<212> TYPE: DNA
<213> ORGANISM: Oryctolagus cuniculus

<400> SEQUENCE: 328
tgcatttgga gtggtggtag cacatactac gcgacctggg cgaaaggc 48

<210> SEQ ID NO 329
<211> LENGTH: 48
<212> TYPE: DNA
<213> ORGANISM: Oryctolagus cuniculus

<400> SEQUENCE: 329
gtcattggcg atactgctgg ttatgcttat tttacggggc ttgacttg 48

<210> SEQ ID NO 330
<211> LENGTH: 121
<212> TYPE: PRT
<213> ORGANISM: Oryctolagus cuniculus

<400> SEQUENCE: 330

```
Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Gln Ser Val Tyr Asn Trp Leu Ser Trp Tyr Gln Gln Lys Pro Gly Gln
    50                  55                  60

Pro Pro Lys Leu Leu Ile Tyr Thr Ala Ser Ser Leu Ala Ser Gly Val
65                  70                  75                  80

Pro Ser Arg Phe Ser Gly Ser Gly Ser Gly Thr Glu Phe Thr Leu Thr
                85                  90                  95

Ile Ser Gly Val Glu Cys Ala Asp Ala Ala Thr Tyr Tyr Cys Gln Gln
            100                 105                 110

Gly Tyr Thr Ser Asp Val Asp Asn Val
        115                 120


<210> SEQ ID NO 331
<211> LENGTH: 130
<212> TYPE: PRT
<213> ORGANISM: Oryctolagus cuniculus

<400> SEQUENCE: 331

Met Glu Thr Gly Leu Arg Trp Leu Leu Leu Val Ala Val Leu Lys Gly
1               5                   10                  15

Val Gln Cys Gln Ser Leu Glu Glu Ala Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Tyr Ala Met Gly Trp Val Arg Gln Ala Pro Gly Lys Gly Leu Glu
    50                  55                  60

Tyr Ile Gly Ile Ile Ser Ser Ser Gly Ser Thr Tyr Tyr Ala Thr Trp
65                  70                  75                  80

Ala Lys Gly Arg Phe Thr Ile Ser Gln Ala Ser Ser Thr Thr Val Asp
                85                  90                  95

Leu Lys Ile Thr Ser Pro Thr Thr Glu Asp Ser Ala Thr Tyr Phe Cys
            100                 105                 110

Ala Arg Gly Gly Ala Gly Ser Gly Gly Val Trp Leu Leu Asp Gly Phe
        115                 120                 125

Asp Pro
    130


<210> SEQ ID NO 332
<211> LENGTH: 11
<212> TYPE: PRT
<213> ORGANISM: Oryctolagus cuniculus

<400> SEQUENCE: 332

Gln Ala Ser Gln Ser Val Tyr Asn Trp Leu Ser
1               5                   10


<210> SEQ ID NO 333
<211> LENGTH: 7
<212> TYPE: PRT
<213> ORGANISM: Oryctolagus cuniculus

<400> SEQUENCE: 333
```

Thr Ala Ser Ser Leu Ala Ser
1 5

<210> SEQ ID NO 334
<211> LENGTH: 11
<212> TYPE: PRT
<213> ORGANISM: Oryctolagus cuniculus

<400> SEQUENCE: 334

Gln Gln Gly Tyr Thr Ser Asp Val Asp Asn Val
1 5 10

<210> SEQ ID NO 335
<211> LENGTH: 5
<212> TYPE: PRT
<213> ORGANISM: Oryctolagus cuniculus

<400> SEQUENCE: 335

Ser Tyr Ala Met Gly
1 5

<210> SEQ ID NO 336
<211> LENGTH: 16
<212> TYPE: PRT
<213> ORGANISM: Oryctolagus cuniculus

<400> SEQUENCE: 336

Ile Ile Ser Ser Ser Gly Ser Thr Tyr Tyr Ala Thr Trp Ala Lys Gly
1 5 10 15

<210> SEQ ID NO 337
<211> LENGTH: 16
<212> TYPE: PRT
<213> ORGANISM: Oryctolagus cuniculus

<400> SEQUENCE: 337

Gly Gly Ala Gly Ser Gly Gly Val Trp Leu Leu Asp Gly Phe Asp Pro
1 5 10 15

<210> SEQ ID NO 338
<211> LENGTH: 363
<212> TYPE: DNA
<213> ORGANISM: Oryctolagus cuniculus

<400> SEQUENCE: 338
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca agtgccaggc cagtcagagt gtttataatt ggttatcctg gtatcagcag 180
aaaccagggc agcctcccaa gctcctgatc tatactgcat ccagtctggc atctggggtc 240
ccatcgcggt tcagtggcag tggatctggg acagagttca ctctcaccat cagcggcgtg 300
gagtgtgccg atgctgccac ttactactgt caacagggtt atactagtga tgttgataat 360
gtt 363

<210> SEQ ID NO 339
<211> LENGTH: 390
<212> TYPE: DNA
<213> ORGANISM: Oryctolagus cuniculus

<400> SEQUENCE: 339
atggagactg ggctgcgctg gcttctcctg gtcgctgtgc tcaaaggtgt ccagtgtcag 60

-continued tcgctggagg aggccggggg tcgcctggtc acgcctggga cacccctgac actcacctgc 120
acagtctctg gaatcgacct cagtagctat gcaatgggct gggtccgcca ggctccaggg 180
aaggggctgg aatacatcgg aatcattagt agtagtggta gcacatacta cgcgacctgg 240
gcgaaaggcc gattcaccat ctcacaagcc tcgtcgacca cggtggatct gaaaattacc 300
agtccgacaa ccgaggactc ggccacatat ttctgtgcca gagggggtgc tggtagtggt 360
ggtgtttggc tgcttgatgg ttttgatccc 390

<210> SEQ ID NO 340
<211> LENGTH: 33
<212> TYPE: DNA
<213> ORGANISM: Oryctolagus cuniculus

<400> SEQUENCE: 340
caggccagtc agagtgttta taattggtta tcc 33

<210> SEQ ID NO 341
<211> LENGTH: 21
<212> TYPE: DNA
<213> ORGANISM: Oryctolagus cuniculus

<400> SEQUENCE: 341
actgcatcca gtctggcatc t 21

<210> SEQ ID NO 342
<211> LENGTH: 33
<212> TYPE: DNA
<213> ORGANISM: Oryctolagus cuniculus

<400> SEQUENCE: 342
caacagggtt atactagtga tgttgataat gtt 33

<210> SEQ ID NO 343
<211> LENGTH: 15
<212> TYPE: DNA
<213> ORGANISM: Oryctolagus cuniculus

<400> SEQUENCE: 343
agctatgcaa tgggc 15

<210> SEQ ID NO 344
<211> LENGTH: 48
<212> TYPE: DNA
<213> ORGANISM: Oryctolagus cuniculus

<400> SEQUENCE: 344
atcattagta gtagtggtag cacatactac gcgacctggg cgaaaggc 48

<210> SEQ ID NO 345
<211> LENGTH: 48
<212> TYPE: DNA
<213> ORGANISM: Oryctolagus cuniculus

<400> SEQUENCE: 345
gggggtgctg gtagtggtgg tgtttggctg cttgatggtt ttgatccc 48

<210> SEQ ID NO 346
<211> LENGTH: 123
<212> TYPE: PRT
<213> ORGANISM: Oryctolagus cuniculus

<400> SEQUENCE: 346

```
Met Asp Thr Arg Ala Pro Thr Gln Leu Leu Gly Leu Leu Leu Leu Trp
1               5                   10                  15

Leu Pro Gly Ala Lys Cys Ala Asp Val Val Met Thr Gln Thr Pro Ala
            20                  25                  30

Ser Val Ser Ala Ala Val Gly Gly Thr Val Thr Ile Asn Cys Gln Ala
        35                  40                  45

Ser Glu Asn Ile Tyr Asn Trp Leu Ala Trp Tyr Gln Gln Lys Pro Gly
    50                  55                  60

Gln Pro Pro Lys Leu Leu Ile Tyr Thr Val Gly Asp Leu Ala Ser Gly
65                  70                  75                  80

Val Ser Ser Arg Phe Lys Gly Ser Gly Ser Gly Thr Glu Phe Thr Leu
                85                  90                  95

Thr Ile Ser Asp Leu Glu Cys Ala Asp Ala Ala Thr Tyr Tyr Cys Gln
            100                 105                 110

Gln Gly Tyr Ser Ser Ser Tyr Val Asp Asn Val
        115                 120


<210> SEQ ID NO 347
<211> LENGTH: 130
<212> TYPE: PRT
<213> ORGANISM: Oryctolagus cuniculus

<400> SEQUENCE: 347

Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Arg Leu Val Thr
            20                  25                  30

Pro Gly Thr Pro Leu Thr Leu Thr Cys Thr Val Ser Gly Phe Ser Leu
        35                  40                  45

Asn Asp Tyr Ala Val Gly Trp Phe Arg Gln Ala Pro Gly Lys Gly Leu
    50                  55                  60

Glu Trp Ile Gly Tyr Ile Arg Ser Ser Gly Thr Thr Ala Tyr Ala Thr
65                  70                  75                  80

Trp Ala Lys Gly Arg Phe Thr Ile Ser Ala Thr Ser Thr Thr Val Asp
                85                  90                  95

Leu Lys Ile Thr Ser Pro Thr Thr Glu Asp Thr Ala Thr Tyr Phe Cys
            100                 105                 110

Ala Arg Gly Gly Ala Gly Ser Ser Gly Val Trp Ile Leu Asp Gly Phe
        115                 120                 125

Ala Pro
    130


<210> SEQ ID NO 348
<211> LENGTH: 11
<212> TYPE: PRT
<213> ORGANISM: Oryctolagus cuniculus

<400> SEQUENCE: 348

Gln Ala Ser Glu Asn Ile Tyr Asn Trp Leu Ala
1               5                   10


<210> SEQ ID NO 349
<211> LENGTH: 7
<212> TYPE: PRT
<213> ORGANISM: Oryctolagus cuniculus

<400> SEQUENCE: 349
```

Thr Val Gly Asp Leu Ala Ser
1 5

<210> SEQ ID NO 350
<211> LENGTH: 12
<212> TYPE: PRT
<213> ORGANISM: Oryctolagus cuniculus

<400> SEQUENCE: 350

Gln Gln Gly Tyr Ser Ser Ser Tyr Val Asp Asn Val
1 5 10

<210> SEQ ID NO 351
<211> LENGTH: 5
<212> TYPE: PRT
<213> ORGANISM: Oryctolagus cuniculus

<400> SEQUENCE: 351

Asp Tyr Ala Val Gly
1 5

<210> SEQ ID NO 352
<211> LENGTH: 16
<212> TYPE: PRT
<213> ORGANISM: Oryctolagus cuniculus

<400> SEQUENCE: 352

Tyr Ile Arg Ser Ser Gly Thr Thr Ala Tyr Ala Thr Trp Ala Lys Gly
1 5 10 15

<210> SEQ ID NO 353
<211> LENGTH: 16
<212> TYPE: PRT
<213> ORGANISM: Oryctolagus cuniculus

<400> SEQUENCE: 353

Gly Gly Ala Gly Ser Ser Gly Val Trp Ile Leu Asp Gly Phe Ala Pro
1 5 10 15

<210> SEQ ID NO 354
<211> LENGTH: 369
<212> TYPE: DNA
<213> ORGANISM: Oryctolagus cuniculus

<400> SEQUENCE: 354
atggacacga gggcccccac tcagctgctg gggctcctgc tgctctggct cccaggtgcc 60
aaatgtgccg atgttgtgat gacccagact ccagcctccg tgtctgcagc tgtgggaggc 120
acagtcacca tcaattgcca ggccagtgag aacatttata attggttagc ctggtatcag 180
cagaaaccag ggcagcctcc caagctcctg atctatactg taggcgatct ggcatctggg 240
gtctcatcgc ggttcaaagg cagtggatct gggacagagt tcactctcac catcagcgac 300
ctggagtgtg ccgatgctgc cacttactat tgtcaacagg gttatagtag tagttatgtt 360
gataatgtt 369

<210> SEQ ID NO 355
<211> LENGTH: 390
<212> TYPE: DNA
<213> ORGANISM: Oryctolagus cuniculus

<400> SEQUENCE: 355
atggagactg ggctgcgctg gcttctcctg gtcgctgtgc tcaaaggtgt ccagtgtcag 60
gagcagctga aggagtccgg gggtcgcctg gtcacgcctg ggacacccct gacactcacc 120
tgcacagtct ctggattctc cctcaatgac tatgcagtgg gctggttccg ccaggctcca 180
gggaaggggc tggaatggat cggatacatt cgtagtagtg gtaccacagc ctacgcgacc 240
tgggcgaaag gccgattcac catctccgct acctcgacca cggtggatct gaaaatcacc 300
agtccgacaa ccgaggacac ggccacctat ttctgtgcca gagggggtgc tggtagtagt 360
ggtgtgtgga tccttgatgg ttttgctccc 390

<210> SEQ ID NO 356
<211> LENGTH: 33
<212> TYPE: DNA
<213> ORGANISM: Oryctolagus cuniculus

<400> SEQUENCE: 356
caggccagtg agaacattta taattggtta gcc 33

<210> SEQ ID NO 357
<211> LENGTH: 21
<212> TYPE: DNA
<213> ORGANISM: Oryctolagus cuniculus

<400> SEQUENCE: 357
actgtaggcg atctggcatc t 21

<210> SEQ ID NO 358
<211> LENGTH: 36
<212> TYPE: DNA
<213> ORGANISM: Oryctolagus cuniculus

<400> SEQUENCE: 358
caacagggtt atagtagtag ttatgttgat aatgtt 36

<210> SEQ ID NO 359
<211> LENGTH: 15
<212> TYPE: DNA
<213> ORGANISM: Oryctolagus cuniculus

<400> SEQUENCE: 359
gactatgcag tgggc 15

<210> SEQ ID NO 360
<211> LENGTH: 48
<212> TYPE: DNA
<213> ORGANISM: Oryctolagus cuniculus

<400> SEQUENCE: 360
tacattcgta gtagtggtac cacagcctac gcgacctggg cgaaaggc 48

<210> SEQ ID NO 361
<211> LENGTH: 48
<212> TYPE: DNA
<213> ORGANISM: Oryctolagus cuniculus

<400> SEQUENCE: 361
gggggtgctg gtagtagtgg tgtgtggatc cttgatggtt ttgctccc 48

<210> SEQ ID NO 362
<211> LENGTH: 121
<212> TYPE: PRT
<213> ORGANISM: Oryctolagus cuniculus

<400> SEQUENCE: 362

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Ser
            20                  25                  30

Val Ser Ala Ala Val Gly Gly Thr Val Thr Ile Asn Cys Gln Ala Ser
        35                  40                  45

Gln Ser Val Tyr Gln Asn Asn Tyr Leu Ser Trp Phe Gln Gln Lys Pro
    50                  55                  60

Gly Gln Pro Pro Lys Leu Leu Ile Tyr Gly Ala Ala Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Ala Tyr Arg Asp Val Asp Ser
        115                 120

<210> SEQ ID NO 363
<211> LENGTH: 130
<212> TYPE: PRT
<213> ORGANISM: Oryctolagus cuniculus

<400> SEQUENCE: 363

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Phe Ser Phe Thr
        35                  40                  45

Ser Thr Tyr Tyr Ile Tyr Trp Val Arg Gln Ala Pro Gly Lys Gly Leu
    50                  55                  60

Glu Trp Ile Ala Cys Ile Asp Ala Gly Ser Ser Gly Ser Thr Tyr Tyr
65                  70                  75                  80

Ala Thr Trp Val Asn Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Lys Trp Asp Tyr Gly Gly Asn Val Gly Trp Gly Tyr
        115                 120                 125

Asp Leu
    130

<210> SEQ ID NO 364
<211> LENGTH: 13
<212> TYPE: PRT
<213> ORGANISM: Oryctolagus cuniculus

<400> SEQUENCE: 364

Gln Ala Ser Gln Ser Val Tyr Gln Asn Asn Tyr Leu Ser
1               5                   10

<210> SEQ ID NO 365
<211> LENGTH: 7
<212> TYPE: PRT
<213> ORGANISM: Oryctolagus cuniculus

<400> SEQUENCE: 365

Gly Ala Ala Thr Leu Ala Ser
1 5

<210> SEQ ID NO 366
<211> LENGTH: 9
<212> TYPE: PRT
<213> ORGANISM: Oryctolagus cuniculus

<400> SEQUENCE: 366

Ala Gly Ala Tyr Arg Asp Val Asp Ser
1 5

<210> SEQ ID NO 367
<211> LENGTH: 6
<212> TYPE: PRT
<213> ORGANISM: Oryctolagus cuniculus

<400> SEQUENCE: 367

Ser Thr Tyr Tyr Ile Tyr
1 5

<210> SEQ ID NO 368
<211> LENGTH: 18
<212> TYPE: PRT
<213> ORGANISM: Oryctolagus cuniculus

<400> SEQUENCE: 368

Cys Ile Asp Ala Gly Ser Ser Gly Ser Thr Tyr Tyr Ala Thr Trp Val
1 5 10 15

Asn Gly

<210> SEQ ID NO 369
<211> LENGTH: 13
<212> TYPE: PRT
<213> ORGANISM: Oryctolagus cuniculus

<400> SEQUENCE: 369

Trp Asp Tyr Gly Gly Asn Val Gly Trp Gly Tyr Asp Leu
1 5 10

<210> SEQ ID NO 370
<211> LENGTH: 363
<212> TYPE: DNA
<213> ORGANISM: Oryctolagus cuniculus

<400> SEQUENCE: 370
atggacacga gggcccccac tcagctgctg gggctcctgc tgctctggct cccaggtgcc 60
acatttgctc aagtgctgac ccagactcca tcctccgtgt ctgcagctgt gggaggcaca 120
gtcaccatca attgccaggc cagtcagagt gtttatcaga acaactactt atcctggttt 180
cagcagaaac cagggcagcc tcccaagctc ctgatctatg gtgcggccac tctggcatct 240
ggggtcccat cgcggttcaa aggcagtgga tctgggacac agttcactct caccatcagc 300
gacctggagt gtgacgatgc tgccacttac tactgtgcag gcgcttatag ggatgtggat 360
tct 363

<210> SEQ ID NO 371
<211> LENGTH: 390
<212> TYPE: DNA
<213> ORGANISM: Oryctolagus cuniculus

<400> SEQUENCE: 371

-continued atggagactg ggctgcgctg gcttctcctg gtcgctgtgc tcaaaggtgt ccagtgtcag 60
tcgttggagg agtccggggg agacctggtc aagcctgggg catccctgac actcacctgc 120
acagcctctg gattctcctt tactagtacc tactacatct actgggtccg ccaggctcca 180
gggaaggggc tggagtggat cgcatgtatt gatgctggta gtagtggtag cacttactac 240
gcgacctggg tgaatggccg attcaccatc tccaaaacct cgtcgaccac ggtgactctg 300
caaatgacca gtctgacagc cgcggacacg gccacctatt tctgtgcgaa atgggattat 360
ggtggtaatg ttggttgggg ttatgacttg 390

<210> SEQ ID NO 372
<211> LENGTH: 39
<212> TYPE: DNA
<213> ORGANISM: Oryctolagus cuniculus

<400> SEQUENCE: 372
caggccagtc agagtgttta tcagaacaac tacttatcc 39

<210> SEQ ID NO 373
<211> LENGTH: 21
<212> TYPE: DNA
<213> ORGANISM: Oryctolagus cuniculus

<400> SEQUENCE: 373
ggtgcggcca ctctggcatc t 21

<210> SEQ ID NO 374
<211> LENGTH: 27
<212> TYPE: DNA
<213> ORGANISM: Oryctolagus cuniculus

<400> SEQUENCE: 374
gcaggcgctt atagggatgt ggattct 27

<210> SEQ ID NO 375
<211> LENGTH: 18
<212> TYPE: DNA
<213> ORGANISM: Oryctolagus cuniculus

<400> SEQUENCE: 375
agtacctact acatctac 18

<210> SEQ ID NO 376
<211> LENGTH: 54
<212> TYPE: DNA
<213> ORGANISM: Oryctolagus cuniculus

<400> SEQUENCE: 376
tgtattgatg ctggtagtag tggtagcact tactacgcga cctgggtgaa tggc 54

<210> SEQ ID NO 377
<211> LENGTH: 39
<212> TYPE: DNA
<213> ORGANISM: Oryctolagus cuniculus

<400> SEQUENCE: 377
tgggattatg gtggtaatgt tggttggggt tatgacttg 39

<210> SEQ ID NO 378
<211> LENGTH: 120
<212> TYPE: PRT
<213> ORGANISM: Oryctolagus cuniculus

<400> SEQUENCE: 378

Met Asp Thr Arg Ala Pro Thr Gln Leu Leu Gly Leu Leu Leu Leu Trp
1 5 10 15

Leu Pro Gly Ala Arg Cys Ala Phe Glu Leu Thr Gln Thr Pro Ser Ser
20 25 30

Val Glu Ala Ala Val Gly Gly Thr Val Thr Ile Lys Cys Gln Ala Ser
35 40 45

Gln Ser Ile Ser Ser Tyr Leu Ala Trp Tyr Gln Gln Lys Pro Gly Gln
50 55 60

Pro Pro Lys Phe Leu Ile Tyr Arg Ala Ser Thr Leu Ala Ser Gly Val
65 70 75 80

Pro Ser Arg Phe Lys Gly Ser Gly Ser Gly Thr Glu Phe Thr Leu Thr
85 90 95

Ile Ser Asp Leu Glu Cys Ala Asp Ala Ala Thr Tyr Tyr Cys Gln Ser
100 105 110

Tyr Tyr Asp Ser Val Ser Asn Pro
115 120

<210> SEQ ID NO 379
<211> LENGTH: 127
<212> TYPE: PRT
<213> ORGANISM: Oryctolagus cuniculus

<400> SEQUENCE: 379

Met Glu Thr Gly Leu Arg Trp Leu Leu Leu Val Ala Val Leu Lys Gly
1 5 10 15

Val Gln Cys Gln Ser Leu Glu Glu Ser Gly Gly Asp Leu Val Lys Pro
20 25 30

Glu Gly Ser Leu Thr Leu Thr Cys Lys Ala Ser Gly Leu Asp Leu Gly
35 40 45

Thr Tyr Trp Phe Met Cys Trp Val Arg Gln Ala Pro Gly Lys Gly Leu
50 55 60

Glu Trp Ile Ala Cys Ile Tyr Thr Gly Ser Ser Gly Ser Thr Phe Tyr
65 70 75 80

Ala Ser Trp Val Asn Gly Arg Phe Thr Ile Ser Lys Thr Ser Ser Thr
85 90 95

Thr Val Thr Leu Gln Met Thr Ser Leu Thr Ala Ala Asp Thr Ala Thr
100 105 110

Tyr Phe Cys Ala Arg Gly Tyr Ser Gly Tyr Gly Tyr Phe Lys Leu
115 120 125

<210> SEQ ID NO 380
<211> LENGTH: 11
<212> TYPE: PRT
<213> ORGANISM: Oryctolagus cuniculus

<400> SEQUENCE: 380

Gln Ala Ser Gln Ser Ile Ser Ser Tyr Leu Ala
1 5 10

<210> SEQ ID NO 381
<211> LENGTH: 7
<212> TYPE: PRT
<213> ORGANISM: Oryctolagus cuniculus

<400> SEQUENCE: 381

Arg Ala Ser Thr Leu Ala Ser 1 5

<210> SEQ ID NO 382
<211> LENGTH: 10
<212> TYPE: PRT
<213> ORGANISM: Oryctolagus cuniculus

<400> SEQUENCE: 382

Gln Ser Tyr Tyr Asp Ser Val Ser Asn Pro
1 5 10

<210> SEQ ID NO 383
<211> LENGTH: 6
<212> TYPE: PRT
<213> ORGANISM: Oryctolagus cuniculus

<400> SEQUENCE: 383

Thr Tyr Trp Phe Met Cys
1 5

<210> SEQ ID NO 384
<211> LENGTH: 18
<212> TYPE: PRT
<213> ORGANISM: Oryctolagus cuniculus

<400> SEQUENCE: 384

Cys Ile Tyr Thr Gly Ser Ser Gly Ser Thr Phe Tyr Ala Ser Trp Val
1 5 10 15

Asn Gly

<210> SEQ ID NO 385
<211> LENGTH: 10
<212> TYPE: PRT
<213> ORGANISM: Oryctolagus cuniculus

<400> SEQUENCE: 385

Gly Tyr Ser Gly Tyr Gly Tyr Phe Lys Leu
1 5 10

<210> SEQ ID NO 386
<211> LENGTH: 360
<212> TYPE: DNA
<213> ORGANISM: Oryctolagus cuniculus

<400> SEQUENCE: 386
atggacacga gggcccccac tcagctgctg gggctcctgc tgctctggct cccaggtgcc 60
agatgtgcat tcgaattgac ccagactcca tcctccgtgg aggcagctgt gggaggcaca 120
gtcaccatca agtgccaggc cagtcagagc attagtagtt acttagcctg gtatcagcag 180
aaaccagggc agcctcccaa gttcctgatc tacagggcgt ccactctggc atctggggtc 240
ccatcgcgat tcaaaggcag tggatctggg acagagttca ctctcaccat cagcgacctg 300
gagtgtgccg atgctgccac ttactactgt caaagctatt atgatagtgt ttcaaatcct 360

<210> SEQ ID NO 387
<211> LENGTH: 381
<212> TYPE: DNA
<213> ORGANISM: Oryctolagus cuniculus

<400> SEQUENCE: 387
atggagactg ggctgcgctg gcttctcctg gtcgctgtgc tcaaaggtgt ccagtgtcag 60
tcgttggagg agtccggggg agacctggtc aagcctgagg gatccctgac actcacctgc 120
aaagcctctg gactcgacct cggtacctac tggttcatgt gctgggtccg ccaggctcca 180
gggaaggggc tggagtggat cgcttgtatt tatactggta gtagtggttc cactttctac 240
gcgagctggg tgaatggccg attcaccatc tccaaaacct cgtcgaccac ggtgactctg 300
caaatgacca gtctgacagc cgcggacacg gccacttatt tttgtgcgag aggttatagt 360
ggttatggtt attttaagtt g 381

<210> SEQ ID NO 388
<211> LENGTH: 33
<212> TYPE: DNA
<213> ORGANISM: Oryctolagus cuniculus

<400> SEQUENCE: 388
caggccagtc agagcattag tagttactta gcc 33

<210> SEQ ID NO 389
<211> LENGTH: 21
<212> TYPE: DNA
<213> ORGANISM: Oryctolagus cuniculus

<400> SEQUENCE: 389
agggcgtcca ctctggcatc t 21

<210> SEQ ID NO 390
<211> LENGTH: 30
<212> TYPE: DNA
<213> ORGANISM: Oryctolagus cuniculus

<400> SEQUENCE: 390
caaagctatt atgatagtgt ttcaaatcct 30

<210> SEQ ID NO 391
<211> LENGTH: 18
<212> TYPE: DNA
<213> ORGANISM: Oryctolagus cuniculus

<400> SEQUENCE: 391
acctactggt tcatgtgc 18

<210> SEQ ID NO 392
<211> LENGTH: 54
<212> TYPE: DNA
<213> ORGANISM: Oryctolagus cuniculus

<400> SEQUENCE: 392
tgtatttata ctggtagtag tggttccact ttctacgcga gctgggtgaa tggc 54

<210> SEQ ID NO 393
<211> LENGTH: 30
<212> TYPE: DNA
<213> ORGANISM: Oryctolagus cuniculus

<400> SEQUENCE: 393
ggttatagtg gttatggtta ttttaagttg 30

<210> SEQ ID NO 394
<211> LENGTH: 124
<212> TYPE: PRT
<213> ORGANISM: Oryctolagus cuniculus

<400> SEQUENCE: 394

Met Asp Thr Arg Ala Pro Thr Gln Leu Leu Gly Leu Leu Leu Leu Trp
1 5 10 15

Leu Pro Gly Val Thr Phe Ala Ile Glu Met Thr Gln Ser Pro Phe Ser
20 25 30

Val Ser Ala Ala Val Gly Gly Thr Val Ser Ile Ser Cys Gln Ala Ser
35 40 45

Gln Ser Val Tyr Lys Asn Asn Gln Leu Ser Trp Tyr Gln Gln Lys Ser
50 55 60

Gly Gln Pro Pro Lys Leu Leu Ile Tyr Gly Ala Ser Ala Leu Ala Ser
65 70 75 80

Gly Val Pro Ser Arg Phe Lys Gly Ser Gly Ser Gly Thr Glu Phe Thr
85 90 95

Leu Thr Ile Ser Asp Val Gln Cys Asp Asp Ala Ala Thr Tyr Tyr Cys
100 105 110

Ala Gly Ala Ile Thr Gly Ser Ile Asp Thr Asp Gly
115 120

<210> SEQ ID NO 395
<211> LENGTH: 130
<212> TYPE: PRT
<213> ORGANISM: Oryctolagus cuniculus

<400> SEQUENCE: 395

Met Glu Thr Gly Leu Arg Trp Leu Leu Leu Val Ala Val Leu Lys Gly
1 5 10 15

Val Gln Cys Gln Ser Leu Glu Glu Ser Gly Gly Asp Leu Val Lys Pro
20 25 30

Gly Ala Ser Leu Thr Leu Thr Cys Thr Thr Ser Gly Phe Ser Phe Ser
35 40 45

Ser Ser Tyr Phe Ile Cys Trp Val Arg Gln Ala Pro Gly Lys Gly Leu
50 55 60

Glu Trp Ile Ala Cys Ile Tyr Gly Gly Asp Gly Ser Thr Tyr Tyr Ala
65 70 75 80

Ser Trp Ala Lys Gly Arg Phe Thr Ile Ser Lys Thr Ser Ser Thr Thr
85 90 95

Val Thr Leu Gln Met Thr Ser Leu Thr Ala Ala Asp Thr Ala Thr Tyr
100 105 110

Phe Cys Ala Arg Glu Trp Ala Tyr Ser Gln Gly Tyr Phe Gly Ala Phe
115 120 125

Asp Leu
130

<210> SEQ ID NO 396
<211> LENGTH: 13
<212> TYPE: PRT
<213> ORGANISM: Oryctolagus cuniculus

<400> SEQUENCE: 396

Gln Ala Ser Gln Ser Val Tyr Lys Asn Asn Gln Leu Ser
1 5 10

<210> SEQ ID NO 397
<211> LENGTH: 7
<212> TYPE: PRT
<213> ORGANISM: Oryctolagus cuniculus

<400> SEQUENCE: 397

Gly Ala Ser Ala Leu Ala Ser 1 5

<210> SEQ ID NO 398
<211> LENGTH: 12
<212> TYPE: PRT
<213> ORGANISM: Oryctolagus cuniculus

<400> SEQUENCE: 398

Ala Gly Ala Ile Thr Gly Ser Ile Asp Thr Asp Gly
1 5 10

<210> SEQ ID NO 399
<211> LENGTH: 6
<212> TYPE: PRT
<213> ORGANISM: Oryctolagus cuniculus

<400> SEQUENCE: 399

Ser Ser Tyr Phe Ile Cys
1 5

<210> SEQ ID NO 400
<211> LENGTH: 17
<212> TYPE: PRT
<213> ORGANISM: Oryctolagus cuniculus

<400> SEQUENCE: 400

Cys Ile Tyr Gly Gly Asp Gly Ser Thr Tyr Tyr Ala Ser Trp Ala Lys
1 5 10 15

Gly

<210> SEQ ID NO 401
<211> LENGTH: 14
<212> TYPE: PRT
<213> ORGANISM: Oryctolagus cuniculus

<400> SEQUENCE: 401

Glu Trp Ala Tyr Ser Gln Gly Tyr Phe Gly Ala Phe Asp Leu
1 5 10

<210> SEQ ID NO 402
<211> LENGTH: 372
<212> TYPE: DNA
<213> ORGANISM: Oryctolagus cuniculus

<400> SEQUENCE: 402
atggacacga gggcccccac tcagctgctg gggctcctgc tgctctggct cccaggtgtc 60
acatttgcca tcgaaatgac ccagagtcca ttctccgtgt ctgcagctgt gggaggcaca 120
gtcagcatca gttgccaggc cagtcagagt gtttataaga acaaccaatt atcctggtat 180
cagcagaaat cagggcagcc tcccaagctc ctgatctatg gtgcatcggc tctggcatct 240
ggggtcccat cgcggttcaa aggcagtgga tctgggacag agttcactct caccatcagc 300
gacgtgcagt gtgacgatgc tgccacttac tactgtgcag gcgctattac tggtagtatt 360
gatacggatg gt 372

<210> SEQ ID NO 403
<211> LENGTH: 390
<212> TYPE: DNA
<213> ORGANISM: Oryctolagus cuniculus

<400> SEQUENCE: 403
atggagactg ggctgcgctg gcttctcctg gtcgctgtgc tcaaaggtgt ccagtgtcag 60
tcgttggagg agtccggggg agacctggtc aagcctgggg catccctgac actcacctgc 120
acaacttctg gattctcctt cagtagcagc tacttcattt gctgggtccg ccaggctcca 180
gggaaggggc tggagtggat cgcatgcatt tatggtggtg atggcagcac atactacgcg 240
agctgggcga aaggccgatt caccatctcc aaaacctcgt cgaccacggt gacgctgcaa 300
atgaccagtc tgacagccgc ggacacggcc acctatttct gtgcgagaga atgggcatat 360
agtcaaggtt attttggtgc ttttgatctc 390

<210> SEQ ID NO 404
<211> LENGTH: 39
<212> TYPE: DNA
<213> ORGANISM: Oryctolagus cuniculus

<400> SEQUENCE: 404
caggccagtc agagtgttta taagaacaac caattatcc 39

<210> SEQ ID NO 405
<211> LENGTH: 21
<212> TYPE: DNA
<213> ORGANISM: Oryctolagus cuniculus

<400> SEQUENCE: 405
ggtgcatcgg ctctggcatc t 21

<210> SEQ ID NO 406
<211> LENGTH: 36
<212> TYPE: DNA
<213> ORGANISM: Oryctolagus cuniculus

<400> SEQUENCE: 406
gcaggcgcta ttactggtag tattgatacg gatggt 36

<210> SEQ ID NO 407
<211> LENGTH: 18
<212> TYPE: DNA
<213> ORGANISM: Oryctolagus cuniculus

<400> SEQUENCE: 407
agcagctact tcatttgc 18

<210> SEQ ID NO 408
<211> LENGTH: 51
<212> TYPE: DNA
<213> ORGANISM: Oryctolagus cuniculus

<400> SEQUENCE: 408
tgcatttatg gtggtgatgg cagcacatac tacgcgagct gggcgaaagg c 51

<210> SEQ ID NO 409
<211> LENGTH: 42
<212> TYPE: DNA
<213> ORGANISM: Oryctolagus cuniculus

<400> SEQUENCE: 409
gaatgggcat atagtcaagg ttattttggt gcttttgatc tc 42

<210> SEQ ID NO 410
<211> LENGTH: 124
<212> TYPE: PRT
<213> ORGANISM: Oryctolagus cuniculus

<400> SEQUENCE: 410

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Lys Cys Gln Ala Ser
        35                  40                  45

Glu Asp Ile Ser Ser Tyr Leu Ala Trp Tyr Gln Gln Lys Pro Gly Gln
    50                  55                  60

Pro Pro Lys Leu Leu Ile Tyr Ala Ala Ser Asn Leu Glu Ser Gly Val
65                  70                  75                  80

Ser Ser Arg Phe Lys Gly Ser Gly Ser Gly Thr Glu Tyr Thr Leu Thr
                85                  90                  95

Ile Ser Asp Leu Glu Cys Ala Asp Ala Ala Thr Tyr Tyr Cys Gln Cys
            100                 105                 110

Thr Tyr Gly Thr Ile Ser Ile Ser Asp Gly Asn Ala
        115                 120

<210> SEQ ID NO 411
<211> LENGTH: 124
<212> TYPE: PRT
<213> ORGANISM: Oryctolagus cuniculus

<400> SEQUENCE: 411

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Phe Met Thr Trp Val Arg Gln Ala Pro Gly Glu Gly Leu Glu
    50                  55                  60

Tyr Ile Gly Phe Ile Asn Pro Gly Gly Ser Ala Tyr Tyr Ala Ser Trp
65                  70                  75                  80

Val Lys Gly Arg Phe Thr Ile Ser Lys Ser Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Val Leu Ile Val Ser Tyr Gly Ala Phe Thr Ile
        115                 120

<210> SEQ ID NO 412
<211> LENGTH: 11
<212> TYPE: PRT
<213> ORGANISM: Oryctolagus cuniculus

<400> SEQUENCE: 412

Gln Ala Ser Glu Asp Ile Ser Ser Tyr Leu Ala
1               5                   10

<210> SEQ ID NO 413
<211> LENGTH: 7
<212> TYPE: PRT
<213> ORGANISM: Oryctolagus cuniculus

<400> SEQUENCE: 413

Ala Ala Ser Asn Leu Glu Ser
1               5

<210> SEQ ID NO 414
<211> LENGTH: 14
<212> TYPE: PRT
<213> ORGANISM: Oryctolagus cuniculus

<400> SEQUENCE: 414

Gln Cys Thr Tyr Gly Thr Ile Ser Ile Ser Asp Gly Asn Ala
1 5 10

<210> SEQ ID NO 415
<211> LENGTH: 5
<212> TYPE: PRT
<213> ORGANISM: Oryctolagus cuniculus

<400> SEQUENCE: 415

Ser Tyr Phe Met Thr
1 5

<210> SEQ ID NO 416
<211> LENGTH: 16
<212> TYPE: PRT
<213> ORGANISM: Oryctolagus cuniculus

<400> SEQUENCE: 416

Phe Ile Asn Pro Gly Gly Ser Ala Tyr Tyr Ala Ser Trp Val Lys Gly
1 5 10 15

<210> SEQ ID NO 417
<211> LENGTH: 11
<212> TYPE: PRT
<213> ORGANISM: Oryctolagus cuniculus

<400> SEQUENCE: 417

Val Leu Ile Val Ser Tyr Gly Ala Phe Thr Ile
1 5 10

<210> SEQ ID NO 418
<211> LENGTH: 372
<212> TYPE: DNA
<213> ORGANISM: Oryctolagus cuniculus

<400> SEQUENCE: 418
atggacacga gggcccccac tcagctgctg gggctcctgc tgctctggct cccaggtgcc 60
agatgtgatg ttgtgatgac ccagactcca gcctccgtgg aggcagctgt gggaggcaca 120
gtcaccatca agtgccaggc cagtgaggat attagtagct acttagcctg gtatcagcag 180
aaaccagggc agcctcccaa gctcctgatc tatgctgcat ccaatctgga atctggggtc 240
tcatcgcgat tcaaaggcag tggatctggg acagagtaca ctctcaccat cagcgacctg 300
gagtgtgccg atgctgccac ctattactgt caatgtactt atggtactat ttctattagt 360
gatggtaatg ct 372

<210> SEQ ID NO 419
<211> LENGTH: 372
<212> TYPE: DNA
<213> ORGANISM: Oryctolagus cuniculus

<400> SEQUENCE: 419
atggagactg ggctgcgctg gcttctcctg gtcgctgtgc tcaaaggtgt ccaatgtcag 60
tcggtggagg agtccggggg tcgcctggtc acgcctggga cacccctgac actcacctgc 120
acagtctctg gattctccct cagtagctac ttcatgacct gggtccgcca ggctccaggg 180
gaggggctgg aatacatcgg attcattaat cctggtggta gcgcttacta cgcgagctgg 240
gtgaaaggcc gattcaccat ctccaagtcc tcgaccacgg tagatctgaa aatcaccagt 300
ccgacaaccg aggacacggc cacctatttc tgtgccaggg ttctgattgt ttcttatgga 360
gcctttacca tc 372

<210> SEQ ID NO 420
<211> LENGTH: 33
<212> TYPE: DNA
<213> ORGANISM: Oryctolagus cuniculus

<400> SEQUENCE: 420
caggccagtg aggatattag tagctactta gcc 33

<210> SEQ ID NO 421
<211> LENGTH: 21
<212> TYPE: DNA
<213> ORGANISM: Oryctolagus cuniculus

<400> SEQUENCE: 421
gctgcatcca atctggaatc t 21

<210> SEQ ID NO 422
<211> LENGTH: 42
<212> TYPE: DNA
<213> ORGANISM: Oryctolagus cuniculus

<400> SEQUENCE: 422
caatgtactt atggtactat ttctattagt gatggtaatg ct 42

<210> SEQ ID NO 423
<211> LENGTH: 15
<212> TYPE: DNA
<213> ORGANISM: Oryctolagus cuniculus

<400> SEQUENCE: 423
agctacttca tgacc 15

<210> SEQ ID NO 424
<211> LENGTH: 48
<212> TYPE: DNA
<213> ORGANISM: Oryctolagus cuniculus

<400> SEQUENCE: 424
ttcattaatc ctggtggtag cgcttactac gcgagctggg tgaaaggc 48

<210> SEQ ID NO 425
<211> LENGTH: 33
<212> TYPE: DNA
<213> ORGANISM: Oryctolagus cuniculus

<400> SEQUENCE: 425
gttctgattg tttcttatgg agcctttacc atc 33

<210> SEQ ID NO 426
<211> LENGTH: 124
<212> TYPE: PRT
<213> ORGANISM: Oryctolagus cuniculus

<400> SEQUENCE: 426

Met Asp Thr Arg Ala Pro Thr Gln Leu Leu Gly Leu Leu Leu Leu Trp

-continued

```
1               5                   10                  15

Leu Pro Gly Ala Arg Cys Asp Val Val Met Thr Gln Thr Pro Ala Ser
            20                  25                  30

Val Ser Ala Ala Val Gly Gly Thr Val Thr Ile Lys Cys Gln Ala Ser
        35                  40                  45

Glu Asp Ile Glu Ser Tyr Leu Ala Trp Tyr Gln Gln Lys Pro Gly Gln
    50                  55                  60

Pro Pro Lys Leu Leu Ile Tyr Gly Ala Ser Asn Leu Glu Ser Gly Val
65                  70                  75                  80

Ser Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Cys
            100                 105                 110

Thr Tyr Gly Ile Ile Ser Ile Ser Asp Gly Asn Ala
        115                 120


<210> SEQ ID NO 427
<211> LENGTH: 124
<212> TYPE: PRT
<213> ORGANISM: Oryctolagus cuniculus

<400> SEQUENCE: 427

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Phe Met Thr Trp Val Arg Gln Ala Pro Gly Glu Gly Leu Glu
    50                  55                  60

Tyr Ile Gly Phe Met Asn Thr Gly Asp Asn Ala Tyr Tyr Ala Ser Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Val Leu Val Val Ala Tyr Gly Ala Phe Asn Ile
        115                 120


<210> SEQ ID NO 428
<211> LENGTH: 11
<212> TYPE: PRT
<213> ORGANISM: Oryctolagus cuniculus

<400> SEQUENCE: 428

Gln Ala Ser Glu Asp Ile Glu Ser Tyr Leu Ala
1               5                   10


<210> SEQ ID NO 429
<211> LENGTH: 7
<212> TYPE: PRT
<213> ORGANISM: Oryctolagus cuniculus

<400> SEQUENCE: 429

Gly Ala Ser Asn Leu Glu Ser
1               5


<210> SEQ ID NO 430
```

<211> LENGTH: 14
<212> TYPE: PRT
<213> ORGANISM: Oryctolagus cuniculus

<400> SEQUENCE: 430

Gln Cys Thr Tyr Gly Ile Ile Ser Ile Ser Asp Gly Asn Ala
1 5 10

<210> SEQ ID NO 431
<211> LENGTH: 5
<212> TYPE: PRT
<213> ORGANISM: Oryctolagus cuniculus

<400> SEQUENCE: 431

Ser Tyr Phe Met Thr
1 5

<210> SEQ ID NO 432
<211> LENGTH: 16
<212> TYPE: PRT
<213> ORGANISM: Oryctolagus cuniculus

<400> SEQUENCE: 432

Phe Met Asn Thr Gly Asp Asn Ala Tyr Tyr Ala Ser Trp Ala Lys Gly
1 5 10 15

<210> SEQ ID NO 433
<211> LENGTH: 11
<212> TYPE: PRT
<213> ORGANISM: Oryctolagus cuniculus

<400> SEQUENCE: 433

Val Leu Val Val Ala Tyr Gly Ala Phe Asn Ile
1 5 10

<210> SEQ ID NO 434
<211> LENGTH: 372
<212> TYPE: DNA
<213> ORGANISM: Oryctolagus cuniculus

<400> SEQUENCE: 434
atggacacga gggcccccac tcagctgctg gggctcctgc tgctctggct cccaggtgcc 60
agatgtgatg ttgtgatgac ccagactcca gcctccgtgt ctgcagctgt gggaggcaca 120
gtcaccatca agtgccaggc cagtgaggac attgaaagct atctagcctg gtatcagcag 180
aaaccagggc agcctcccaa gctcctgatc tatggtgcat ccaatctgga atctggggtc 240
tcatcgcggt tcaaaggcag tggatctggg acagagttca ctctcaccat cagcgacctg 300
gagtgtgccg atgctgccac ttactattgt caatgcactt atggtattat tagtattagt 360
gatggtaatg ct 372

<210> SEQ ID NO 435
<211> LENGTH: 372
<212> TYPE: DNA
<213> ORGANISM: Oryctolagus cuniculus

<400> SEQUENCE: 435
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtgtctg gattctccct cagtagctac ttcatgacct gggtccgcca ggctccaggg 180
gaggggctgg aatacatcgg attcatgaat actggtgata acgcatacta cgcgagctgg 240
gcgaaaggcc gattcaccat ctccaaaacc tcgaccacgg tggatctgaa aatcaccagt 300
ccgacaaccg aggacacggc cacctatttc tgtgccaggg ttcttgttgt tgcttatgga 360
gcctttaaca tc 372

<210> SEQ ID NO 436
<211> LENGTH: 33
<212> TYPE: DNA
<213> ORGANISM: Oryctolagus cuniculus

<400> SEQUENCE: 436
caggccagtg aggacattga aagctatcta gcc 33

<210> SEQ ID NO 437
<211> LENGTH: 21
<212> TYPE: DNA
<213> ORGANISM: Oryctolagus cuniculus

<400> SEQUENCE: 437
ggtgcatcca atctggaatc t 21

<210> SEQ ID NO 438
<211> LENGTH: 42
<212> TYPE: DNA
<213> ORGANISM: Oryctolagus cuniculus

<400> SEQUENCE: 438
caatgcactt atggtattat tagtattagt gatggtaatg ct 42

<210> SEQ ID NO 439
<211> LENGTH: 15
<212> TYPE: DNA
<213> ORGANISM: Oryctolagus cuniculus

<400> SEQUENCE: 439
agctacttca tgacc 15

<210> SEQ ID NO 440
<211> LENGTH: 48
<212> TYPE: DNA
<213> ORGANISM: Oryctolagus cuniculus

<400> SEQUENCE: 440
ttcatgaata ctggtgataa cgcatactac gcgagctggg cgaaaggc 48

<210> SEQ ID NO 441
<211> LENGTH: 33
<212> TYPE: DNA
<213> ORGANISM: Oryctolagus cuniculus

<400> SEQUENCE: 441
gttcttgttg ttgcttatgg agcctttaac atc 33

<210> SEQ ID NO 442
<211> LENGTH: 124
<212> TYPE: PRT
<213> ORGANISM: Oryctolagus cuniculus

<400> SEQUENCE: 442

Met Asp Thr Arg Ala Pro Thr Gln Leu Leu Gly Leu Leu Leu Leu Trp
1 5 10 15

Leu Pro Gly Ala Thr Phe Ala Ala Val Leu Thr Gln Thr Pro Ser Pro

```
            20                  25                  30

Val Ser Glu Pro Val Gly Gly Thr Val Ser Ile Ser Cys Gln Ser Ser
        35                  40                  45

Lys Ser Val Met Asn Asn Asn Tyr Leu Ala Trp Tyr Gln Gln Lys Pro
    50                  55                  60

Gly Gln Pro Pro Lys Leu Leu Ile Tyr Gly Ala Ser Asn Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Gln Gly Gly Tyr Thr Gly Tyr Ser Asp His Gly Thr
        115                 120


<210> SEQ ID NO 443
<211> LENGTH: 127
<212> TYPE: PRT
<213> ORGANISM: Oryctolagus cuniculus

<400> SEQUENCE: 443

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Lys Pro
            20                  25                  30

Asp Glu Thr Leu Thr Leu Thr Cys Thr Val Ser Gly Ile Asp Leu Ser
        35                  40                  45

Ser Tyr Pro Met Asn Trp Val Arg Gln Ala Pro Gly Lys Gly Leu Glu
    50                  55                  60

Trp Ile Gly Phe Ile Asn Thr Gly Gly Thr Ile Val Tyr Ala Ser Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Ala
            100                 105                 110

Arg Gly Ser Tyr Val Ser Ser Gly Tyr Ala Tyr Tyr Phe Asn Val
        115                 120                 125


<210> SEQ ID NO 444
<211> LENGTH: 13
<212> TYPE: PRT
<213> ORGANISM: Oryctolagus cuniculus

<400> SEQUENCE: 444

Gln Ser Ser Lys Ser Val Met Asn Asn Asn Tyr Leu Ala
1               5                   10


<210> SEQ ID NO 445
<211> LENGTH: 7
<212> TYPE: PRT
<213> ORGANISM: Oryctolagus cuniculus

<400> SEQUENCE: 445

Gly Ala Ser Asn Leu Ala Ser
1               5


<210> SEQ ID NO 446
<211> LENGTH: 12
<212> TYPE: PRT
<213> ORGANISM: Oryctolagus cuniculus
```

<400> SEQUENCE: 446

Gln Gly Gly Tyr Thr Gly Tyr Ser Asp His Gly Thr
1 5 10

<210> SEQ ID NO 447
<211> LENGTH: 5
<212> TYPE: PRT
<213> ORGANISM: Oryctolagus cuniculus

<400> SEQUENCE: 447

Ser Tyr Pro Met Asn
1 5

<210> SEQ ID NO 448
<211> LENGTH: 16
<212> TYPE: PRT
<213> ORGANISM: Oryctolagus cuniculus

<400> SEQUENCE: 448

Phe Ile Asn Thr Gly Gly Thr Ile Val Tyr Ala Ser Trp Ala Lys Gly
1 5 10 15

<210> SEQ ID NO 449
<211> LENGTH: 14
<212> TYPE: PRT
<213> ORGANISM: Oryctolagus cuniculus

<400> SEQUENCE: 449

Gly Ser Tyr Val Ser Ser Gly Tyr Ala Tyr Tyr Phe Asn Val
1 5 10

<210> SEQ ID NO 450
<211> LENGTH: 372
<212> TYPE: DNA
<213> ORGANISM: Oryctolagus cuniculus

<400> SEQUENCE: 450
atggacacga gggcccccac tcagctgctg gggctcctgc tgctctggct cccaggtgcc 60
acatttgccg ccgtgctgac ccagactcca tctcccgtgt ctgaacctgt gggaggcaca 120
gtcagcatca gttgccagtc cagtaagagt gttatgaata acaactactt agcctggtat 180
cagcagaaac cagggcagcc tcccaagctc ctgatctatg gtgcatccaa tctggcatct 240
ggggtcccat cacggttcag cggcagtgga tctgggacac agttcactct caccatcagc 300
gacgtgcagt gtgacgatgc tgccacttac tactgtcaag gcggttatac tggttatagt 360
gatcatggga ct 372

<210> SEQ ID NO 451
<211> LENGTH: 381
<212> TYPE: DNA
<213> ORGANISM: Oryctolagus cuniculus

<400> SEQUENCE: 451
atggagactg ggctgcgctg gcttctcctg gtcgctgtgc tcaaaggtgt ccagtgtcag 60
tcggtggagg agtccggggg tcgcctggtc aagcctgacg aaaccctgac actcacctgc 120
acagtctctg gaatcgacct cagtagctat ccaatgaact gggtccgcca ggctccaggg 180
aaggggctgg aatggatcgg attcattaat actggtggta ccatagtcta cgcgagctgg 240
gcaaaaggcc gattcaccat ctccaaaacc tcgaccacgg tggatctgaa aatgaccagt 300
ccgacaaccg aggacacggc cacctatttc tgtgccagag gcagttatgt ttcatctggt 360
tatgcctact attttaatgt c 381

<210> SEQ ID NO 452
<211> LENGTH: 39
<212> TYPE: DNA
<213> ORGANISM: Oryctolagus cuniculus

<400> SEQUENCE: 452
cagtccagta agagtgttat gaataacaac tacttagcc 39

<210> SEQ ID NO 453
<211> LENGTH: 21
<212> TYPE: DNA
<213> ORGANISM: Oryctolagus cuniculus

<400> SEQUENCE: 453
ggtgcatcca atctggcatc t 21

<210> SEQ ID NO 454
<211> LENGTH: 36
<212> TYPE: DNA
<213> ORGANISM: Oryctolagus cuniculus

<400> SEQUENCE: 454
caaggcggtt atactggtta tagtgatcat gggact 36

<210> SEQ ID NO 455
<211> LENGTH: 15
<212> TYPE: DNA
<213> ORGANISM: Oryctolagus cuniculus

<400> SEQUENCE: 455
agctatccaa tgaac 15

<210> SEQ ID NO 456
<211> LENGTH: 48
<212> TYPE: DNA
<213> ORGANISM: Oryctolagus cuniculus

<400> SEQUENCE: 456
ttcattaata ctggtggtac catagtctac gcgagctggg caaaaggc 48

<210> SEQ ID NO 457
<211> LENGTH: 42
<212> TYPE: DNA
<213> ORGANISM: Oryctolagus cuniculus

<400> SEQUENCE: 457
ggcagttatg tttcatctgg ttatgcctac tattttaatg tc 42

<210> SEQ ID NO 458
<211> LENGTH: 121
<212> TYPE: PRT
<213> ORGANISM: Oryctolagus cuniculus

<400> SEQUENCE: 458

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Ser Ile Ser Cys Gln Ser Ser

```
        35                  40                  45

Gln Ser Val Tyr Asn Asn Asn Trp Leu Ser Trp Phe Gln Gln Lys Pro
    50                  55                  60

Gly Gln Pro Pro Lys Leu Leu Ile Tyr Lys Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Gln Cys Asp Asp Val Ala Thr Tyr Tyr Cys
            100                 105                 110

Ala Gly Gly Tyr Leu Asp Ser Val Ile
        115                 120


<210> SEQ ID NO 459
<211> LENGTH: 126
<212> TYPE: PRT
<213> ORGANISM: Oryctolagus cuniculus

<400> SEQUENCE: 459

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Thr Tyr Ser Ile Asn Trp Val Arg Gln Ala Pro Gly Lys Gly Leu Glu
    50                  55                  60

Trp Ile Gly Ile Ile Ala Asn Ser Gly Thr Thr Phe Tyr Ala Asn Trp
65                  70                  75                  80

Ala Lys Gly Arg Phe Thr Val Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Glu Ser Gly Met Tyr Asn Glu Tyr Gly Lys Phe Asn Ile
        115                 120                 125


<210> SEQ ID NO 460
<211> LENGTH: 13
<212> TYPE: PRT
<213> ORGANISM: Oryctolagus cuniculus

<400> SEQUENCE: 460

Gln Ser Ser Gln Ser Val Tyr Asn Asn Asn Trp Leu Ser
1               5                   10


<210> SEQ ID NO 461
<211> LENGTH: 7
<212> TYPE: PRT
<213> ORGANISM: Oryctolagus cuniculus

<400> SEQUENCE: 461

Lys Ala Ser Thr Leu Ala Ser
1               5


<210> SEQ ID NO 462
<211> LENGTH: 9
<212> TYPE: PRT
<213> ORGANISM: Oryctolagus cuniculus

<400> SEQUENCE: 462
```

-continued

Ala Gly Gly Tyr Leu Asp Ser Val Ile
1 5

<210> SEQ ID NO 463
<211> LENGTH: 5
<212> TYPE: PRT
<213> ORGANISM: Oryctolagus cuniculus

<400> SEQUENCE: 463

Thr Tyr Ser Ile Asn
1 5

<210> SEQ ID NO 464
<211> LENGTH: 16
<212> TYPE: PRT
<213> ORGANISM: Oryctolagus cuniculus

<400> SEQUENCE: 464

Ile Ile Ala Asn Ser Gly Thr Thr Phe Tyr Ala Asn Trp Ala Lys Gly
1 5 10 15

<210> SEQ ID NO 465
<211> LENGTH: 13
<212> TYPE: PRT
<213> ORGANISM: Oryctolagus cuniculus

<400> SEQUENCE: 465

Glu Ser Gly Met Tyr Asn Glu Tyr Gly Lys Phe Asn Ile
1 5 10

<210> SEQ ID NO 466
<211> LENGTH: 363
<212> TYPE: DNA
<213> ORGANISM: Oryctolagus cuniculus

<400> SEQUENCE: 466
atggacacga gggcccccac tcagctgctg gggctcctgc tgctctggct cccaggtgcc 60
acatttgccg ccgtgctgac ccagactcca tctcccgtgt ctgcagctgt gggaggcaca 120
gtcagcatca gttgccagtc cagtcagagt gtttataata acaactggtt atcctggttt 180
cagcagaaac cagggcagcc tcccaagctc ctgatctaca aggcatccac tctggcatct 240
ggggtcccat cgcggttcaa aggcagtgga tctgggacac agttcactct caccatcagc 300
gacgtgcagt gtgacgatgt tgccacttac tactgtgcgg gcggttatct tgatagtgtt 360
att 363

<210> SEQ ID NO 467
<211> LENGTH: 378
<212> TYPE: DNA
<213> ORGANISM: Oryctolagus cuniculus

<400> SEQUENCE: 467
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtctctg gattctccct cagtacctat tcaataaact gggtccgcca ggctccaggg 180
aagggcctgg aatggatcgg aatcattgct aatagtggta ccacattcta cgcgaactgg 240
gcgaaaggcc gattcaccgt ctccaaaacc tcgaccacgg tggatctgaa aatcaccagt 300
ccgacaaccg aggacacggc cacctatttc tgtgccagag agagtggaat gtacaatgaa 360
tatggtaaat ttaacatc 378

<210> SEQ ID NO 468
<211> LENGTH: 39
<212> TYPE: DNA
<213> ORGANISM: Oryctolagus cuniculus

<400> SEQUENCE: 468
cagtccagtc agagtgttta taataacaac tggttatcc 39

<210> SEQ ID NO 469
<211> LENGTH: 21
<212> TYPE: DNA
<213> ORGANISM: Oryctolagus cuniculus

<400> SEQUENCE: 469
aaggcatcca ctctggcatc t 21

<210> SEQ ID NO 470
<211> LENGTH: 27
<212> TYPE: DNA
<213> ORGANISM: Oryctolagus cuniculus

<400> SEQUENCE: 470
gcgggcggtt atcttgatag tgttatt 27

<210> SEQ ID NO 471
<211> LENGTH: 15
<212> TYPE: DNA
<213> ORGANISM: Oryctolagus cuniculus

<400> SEQUENCE: 471
acctattcaa taaac 15

<210> SEQ ID NO 472
<211> LENGTH: 48
<212> TYPE: DNA
<213> ORGANISM: Oryctolagus cuniculus

<400> SEQUENCE: 472
atcattgcta atagtggtac cacattctac gcgaactggg cgaaaggc 48

<210> SEQ ID NO 473
<211> LENGTH: 39
<212> TYPE: DNA
<213> ORGANISM: Oryctolagus cuniculus

<400> SEQUENCE: 473
gagagtggaa tgtacaatga atatggtaaa tttaacatc 39

<210> SEQ ID NO 474
<211> LENGTH: 122
<212> TYPE: PRT
<213> ORGANISM: Oryctolagus cuniculus

<400> SEQUENCE: 474

Met Asp Thr Arg Ala Pro Thr Gln Leu Leu Gly Leu Leu Leu Leu Trp
1 5 10 15

Leu Pro Gly Ala Arg Cys Ala Ser Asp Met Thr Gln Thr Pro Ser Ser
20 25 30

Val Ser Ala Ala Val Gly Gly Thr Val Thr Ile Asn Cys Gln Ala Ser
35 40 45

Glu Asn Ile Tyr Ser Phe Leu Ala Trp Tyr Gln Gln Lys Pro Gly Gln 50 55 60

Pro Pro Lys Leu Leu Ile Phe Lys Ala Ser Thr Leu Ala Ser Gly Val
65 70 75 80

Ser Ser Arg Phe Lys Gly Ser Gly Ser Gly Thr Gln Phe Thr Leu Thr
85 90 95

Ile Ser Asp Leu Glu Cys Asp Asp Ala Ala Thr Tyr Tyr Cys Gln Gln
100 105 110

Gly Ala Thr Val Tyr Asp Ile Asp Asn Asn
115 120

<210> SEQ ID NO 475
<211> LENGTH: 128
<212> TYPE: PRT
<213> ORGANISM: Oryctolagus cuniculus

<400> SEQUENCE: 475

Met Glu Thr Gly Leu Arg Trp Leu Leu Leu Val Ala Val Leu Lys Gly
1 5 10 15

Val Gln Cys Gln Ser Leu Glu Glu Ser Gly Gly Arg Leu Val Thr Pro
20 25 30

Gly Thr Pro Leu Thr Leu Thr Cys Thr Val Ser Gly Ile Asp Leu Ser
35 40 45

Ala Tyr Ala Met Ile Trp Val Arg Gln Ala Pro Gly Glu Gly Leu Glu
50 55 60

Trp Ile Thr Ile Ile Tyr Pro Asn Gly Ile Thr Tyr Tyr Ala Asn Trp
65 70 75 80

Ala Lys Gly Arg Phe Thr Val Ser Lys Thr Ser Thr Ala Met Asp Leu
85 90 95

Lys Ile Thr Ser Pro Thr Thr Glu Asp Thr Ala Thr Tyr Phe Cys Ala
100 105 110

Arg Asp Ala Glu Ser Ser Lys Asn Ala Tyr Trp Gly Tyr Phe Asn Val
115 120 125

<210> SEQ ID NO 476
<211> LENGTH: 11
<212> TYPE: PRT
<213> ORGANISM: Oryctolagus cuniculus

<400> SEQUENCE: 476

Gln Ala Ser Glu Asn Ile Tyr Ser Phe Leu Ala
1 5 10

<210> SEQ ID NO 477
<211> LENGTH: 7
<212> TYPE: PRT
<213> ORGANISM: Oryctolagus cuniculus

<400> SEQUENCE: 477

Lys Ala Ser Thr Leu Ala Ser
1 5

<210> SEQ ID NO 478
<211> LENGTH: 12
<212> TYPE: PRT
<213> ORGANISM: Oryctolagus cuniculus

<400> SEQUENCE: 478

Gln Gln Gly Ala Thr Val Tyr Asp Ile Asp Asn Asn
1 5 10

<210> SEQ ID NO 479
<211> LENGTH: 5
<212> TYPE: PRT
<213> ORGANISM: Oryctolagus cuniculus

<400> SEQUENCE: 479

Ala Tyr Ala Met Ile
1 5

<210> SEQ ID NO 480
<211> LENGTH: 16
<212> TYPE: PRT
<213> ORGANISM: Oryctolagus cuniculus

<400> SEQUENCE: 480

Ile Ile Tyr Pro Asn Gly Ile Thr Tyr Tyr Ala Asn Trp Ala Lys Gly
1 5 10 15

<210> SEQ ID NO 481
<211> LENGTH: 15
<212> TYPE: PRT
<213> ORGANISM: Oryctolagus cuniculus

<400> SEQUENCE: 481

Asp Ala Glu Ser Ser Lys Asn Ala Tyr Trp Gly Tyr Phe Asn Val
1 5 10 15

<210> SEQ ID NO 482
<211> LENGTH: 366
<212> TYPE: DNA
<213> ORGANISM: Oryctolagus cuniculus

<400> SEQUENCE: 482
atggacacga gggcccccac tcagctgctg gggctcctgc tgctctggct cccaggtgcc 60
agatgtgcct ctgatatgac ccagactcca tcctccgtgt ctgcagctgt gggaggcaca 120
gtcaccatca attgccaggc cagtgagaac atttatagct tttggcctg gtatcagcag 180 aaaccagggc agcctcccaa gctcctgatc ttcaaggctt ccactctggc atctggggtc 240
tcatcgcggt tcaaaggcag tggatctggg acacagttca ctctcaccat cagcgacctg 300
gagtgtgacg atgctgccac ttactactgt caacagggtg ctactgtgta tgatattgat 360
aataat 366

<210> SEQ ID NO 483
<211> LENGTH: 384
<212> TYPE: DNA
<213> ORGANISM: Oryctolagus cuniculus

<400> SEQUENCE: 483
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
acagtttctg gaatcgacct cagtgcctat gcaatgatct gggtccgcca ggctccaggg 180
gaggggctgg aatggatcac aatcatttat cctaatggta tcacatacta cgcgaactgg 240
gcgaaaggcc gattcaccgt ctccaaaacc tcgaccgcga tggatctgaa aatcaccagt 300
ccgacaaccg aggacacggc cacctatttc tgtgccagag atgcagaaag tagtaagaat 360
gcttattggg gctactttaa cgtc 384

<210> SEQ ID NO 484

-continued

<211> LENGTH: 33
<212> TYPE: DNA
<213> ORGANISM: Oryctolagus cuniculus

<400> SEQUENCE: 484
caggccagtg agaacattta tagctttttg gcc 33

<210> SEQ ID NO 485
<211> LENGTH: 21
<212> TYPE: DNA
<213> ORGANISM: Oryctolagus cuniculus

<400> SEQUENCE: 485
aaggcttcca ctctggcatc t 21

<210> SEQ ID NO 486
<211> LENGTH: 36
<212> TYPE: DNA
<213> ORGANISM: Oryctolagus cuniculus

<400> SEQUENCE: 486
caacagggtg ctactgtgta tgatattgat aataat 36

<210> SEQ ID NO 487
<211> LENGTH: 15
<212> TYPE: DNA
<213> ORGANISM: Oryctolagus cuniculus

<400> SEQUENCE: 487
gcctatgcaa tgatc 15

<210> SEQ ID NO 488
<211> LENGTH: 48
<212> TYPE: DNA
<213> ORGANISM: Oryctolagus cuniculus

<400> SEQUENCE: 488
atcatttatc ctaatggtat cacatactac gcgaactggg cgaaaggc 48

<210> SEQ ID NO 489
<211> LENGTH: 45
<212> TYPE: DNA
<213> ORGANISM: Oryctolagus cuniculus

<400> SEQUENCE: 489
gatgcagaaa gtagtaagaa tgcttattgg ggctacttta acgtc 45

<210> SEQ ID NO 490
<211> LENGTH: 122
<212> TYPE: PRT
<213> ORGANISM: Oryctolagus cuniculus

<400> SEQUENCE: 490

```
Met Asp Thr Arg Ala Pro Thr Gln Leu Leu Gly Leu Leu Leu Leu Trp
1               5                   10                  15

Leu Pro Gly Ala Arg Cys Ala Ser Asp Met Thr Gln Thr Pro Ser Ser
            20                  25                  30

Val Ser Ala Ala Val Gly Gly Thr Val Thr Ile Asn Cys Gln Ala Ser
        35                  40                  45

Glu Asn Ile Tyr Ser Phe Leu Ala Trp Tyr Gln Gln Lys Pro Gly Gln
    50                  55                  60

Pro Pro Lys Leu Leu Ile Phe Arg Ala Ser Thr Leu Ala Ser Gly Val
```

```
65                  70                  75                  80

Ser Ser Arg Phe Lys Gly Ser Gly Ser Gly Thr Gln Phe Thr Leu Thr
                85                  90                  95

Ile Ser Asp Leu Glu Cys Asp Asp Ala Ala Thr Tyr Tyr Cys Gln Gln
            100                 105                 110

Gly Ala Thr Val Tyr Asp Ile Asp Asn Asn
        115                 120


<210> SEQ ID NO 491
<211> LENGTH: 128
<212> TYPE: PRT
<213> ORGANISM: Oryctolagus cuniculus

<400> SEQUENCE: 491

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ala Tyr Ala Met Ile Trp Val Arg Gln Ala Pro Gly Glu Gly Leu Glu
    50                  55                  60

Trp Ile Thr Ile Ile Tyr Pro Asn Gly Ile Thr Tyr Tyr Ala Asn Trp
65                  70                  75                  80

Ala Lys Gly Arg Phe Thr Val Ser Lys Thr Ser Thr Ala Met Asp Leu
                85                  90                  95

Lys Ile Thr Ser Pro Thr Thr Glu Asp Thr Ala Thr Tyr Phe Cys Ala
            100                 105                 110

Arg Asp Ala Glu Ser Ser Lys Asn Ala Tyr Trp Gly Tyr Phe Asn Val
        115                 120                 125


<210> SEQ ID NO 492
<211> LENGTH: 11
<212> TYPE: PRT
<213> ORGANISM: Oryctolagus cuniculus

<400> SEQUENCE: 492

Gln Ala Ser Glu Asn Ile Tyr Ser Phe Leu Ala
1               5                   10


<210> SEQ ID NO 493
<211> LENGTH: 7
<212> TYPE: PRT
<213> ORGANISM: Oryctolagus cuniculus

<400> SEQUENCE: 493

Arg Ala Ser Thr Leu Ala Ser
1               5


<210> SEQ ID NO 494
<211> LENGTH: 12
<212> TYPE: PRT
<213> ORGANISM: Oryctolagus cuniculus

<400> SEQUENCE: 494

Gln Gln Gly Ala Thr Val Tyr Asp Ile Asp Asn Asn
1               5                   10


<210> SEQ ID NO 495
<211> LENGTH: 5
```

<212> TYPE: PRT
<213> ORGANISM: Oryctolagus cuniculus

<400> SEQUENCE: 495

Ala Tyr Ala Met Ile
1               5

<210> SEQ ID NO 496
<211> LENGTH: 16
<212> TYPE: PRT
<213> ORGANISM: Oryctolagus cuniculus

<400> SEQUENCE: 496

Ile Ile Tyr Pro Asn Gly Ile Thr Tyr Tyr Ala Asn Trp Ala Lys Gly
1               5                   10                  15

<210> SEQ ID NO 497
<211> LENGTH: 15
<212> TYPE: PRT
<213> ORGANISM: Oryctolagus cuniculus

<400> SEQUENCE: 497

Asp Ala Glu Ser Ser Lys Asn Ala Tyr Trp Gly Tyr Phe Asn Val
1               5                   10                  15

<210> SEQ ID NO 498
<211> LENGTH: 366
<212> TYPE: DNA
<213> ORGANISM: Oryctolagus cuniculus

<400> SEQUENCE: 498
atggacacga gggcccccac tcagctgctg gggctcctgc tgctctggct cccaggtgcc     60
agatgtgcct ctgatatgac ccagactcca tcctccgtgt ctgcagctgt gggaggcaca    120
gtcaccatca attgccaggc cagtgagaac atttatagct ttttggcctg gtatcagcag    180
aaaccagggc agcctcccaa gctcctgatc ttcagggctt ccactctggc atctggggtc    240
tcatcgcggt tcaaaggcag tggatctggg acacagttca ctctcaccat cagcgacctg    300
gagtgtgacg atgctgccac ttactactgt caacagggtg ctactgtgta tgatattgat    360
aataat                                                               366

<210> SEQ ID NO 499
<211> LENGTH: 384
<212> TYPE: DNA
<213> ORGANISM: Oryctolagus cuniculus

<400> SEQUENCE: 499
atggagactg ggctgcgctg gcttctcctg gtcgctgtgc tcaaaggtgt ccagtgtcag     60
tcgctggagg agtccggggg tcgcctggtc acgcctggga cacccctgac actcacctgc    120
acagtttctg gaatcgacct cagtgcctat gcaatgatct gggtccgcca ggctccaggg    180
gaggggctgg aatggatcac aatcatttat cctaatggta tcacatacta cgcgaactgg    240
gcgaaaggcc gattcaccgt ctccaaaacc tcgaccgcga tggatctgaa aatcaccagt    300
ccgacaaccg aggacacggc cacctatttc tgtgccagag atgcagaaag tagtaagaat    360
gcttattggg gctactttaa cgtc                                           384

<210> SEQ ID NO 500
<211> LENGTH: 33
<212> TYPE: DNA
<213> ORGANISM: Oryctolagus cuniculus

<400> SEQUENCE: 500
caggccagtg agaacattta tagctttttg gcc 33

<210> SEQ ID NO 501
<211> LENGTH: 21
<212> TYPE: DNA
<213> ORGANISM: Oryctolagus cuniculus

<400> SEQUENCE: 501
agggcttcca ctctggcatc t 21

<210> SEQ ID NO 502
<211> LENGTH: 36
<212> TYPE: DNA
<213> ORGANISM: Oryctolagus cuniculus

<400> SEQUENCE: 502
caacagggtg ctactgtgta tgatattgat aataat 36

<210> SEQ ID NO 503
<211> LENGTH: 15
<212> TYPE: DNA
<213> ORGANISM: Oryctolagus cuniculus

<400> SEQUENCE: 503
gcctatgcaa tgatc 15

<210> SEQ ID NO 504
<211> LENGTH: 48
<212> TYPE: DNA
<213> ORGANISM: Oryctolagus cuniculus

<400> SEQUENCE: 504
atcatttatc ctaatggtat cacatactac gcgaactggg cgaaaggc 48

<210> SEQ ID NO 505
<211> LENGTH: 45
<212> TYPE: DNA
<213> ORGANISM: Oryctolagus cuniculus

<400> SEQUENCE: 505
gatgcagaaa gtagtaagaa tgcttattgg ggctacttta acgtc 45

<210> SEQ ID NO 506
<211> LENGTH: 124
<212> TYPE: PRT
<213> ORGANISM: Oryctolagus cuniculus

<400> SEQUENCE: 506

```
Met Asp Thr Arg Ala Pro Thr Gln Leu Leu Gly Leu Leu Leu Leu Trp
1               5                   10                  15

Leu Pro Gly Ala Thr Phe Ala Ile Glu Met Thr Gln Thr Pro Ser Pro
            20                  25                  30

Val Ser Ala Ala Val Gly Gly Thr Val Thr Ile Asn Cys Gln Ala Ser
        35                  40                  45

Glu Ser Val Phe Asn Asn Met Leu Ser Trp Tyr Gln Gln Lys Pro Gly
    50                  55                  60

His Ser Pro Lys Leu Leu Ile Tyr Asp Ala Ser Asp Leu Ala Ser Gly
65                  70                  75                  80

Val Pro Ser Arg Phe Lys Gly Ser Gly Ser Gly Thr Gln Phe Thr Leu
```

```
                85                  90                  95

Thr Ile Ser Gly Val Glu Cys Asp Asp Ala Ala Thr Tyr Tyr Cys Ala
            100                 105                 110

Gly Tyr Lys Ser Asp Ser Asn Asp Gly Asp Asn Val
        115                 120


<210> SEQ ID NO 507
<211> LENGTH: 123
<212> TYPE: PRT
<213> ORGANISM: Oryctolagus cuniculus

<400> SEQUENCE: 507

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Asn
        35                  40                  45

Arg Asn Ser Ile Thr Trp Val Arg Gln Ala Pro Gly Glu Gly Leu Glu
    50                  55                  60

Trp Ile Gly Ile Ile Thr Gly Ser Gly Arg Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Ala
            100                 105                 110

Arg Gly His Pro Gly Leu Gly Ser Gly Asn Ile
        115                 120


<210> SEQ ID NO 508
<211> LENGTH: 12
<212> TYPE: PRT
<213> ORGANISM: Oryctolagus cuniculus

<400> SEQUENCE: 508

Gln Ala Ser Glu Ser Val Phe Asn Asn Met Leu Ser
1               5                   10


<210> SEQ ID NO 509
<211> LENGTH: 7
<212> TYPE: PRT
<213> ORGANISM: Oryctolagus cuniculus

<400> SEQUENCE: 509

Asp Ala Ser Asp Leu Ala Ser
1               5


<210> SEQ ID NO 510
<211> LENGTH: 13
<212> TYPE: PRT
<213> ORGANISM: Oryctolagus cuniculus

<400> SEQUENCE: 510

Ala Gly Tyr Lys Ser Asp Ser Asn Asp Gly Asp Asn Val
1               5                   10


<210> SEQ ID NO 511
<211> LENGTH: 5
<212> TYPE: PRT
<213> ORGANISM: Oryctolagus cuniculus
```

<400> SEQUENCE: 511

Arg Asn Ser Ile Thr
1 5

<210> SEQ ID NO 512
<211> LENGTH: 16
<212> TYPE: PRT
<213> ORGANISM: Oryctolagus cuniculus

<400> SEQUENCE: 512

Ile Ile Thr Gly Ser Gly Arg Thr Tyr Tyr Ala Asn Trp Ala Lys Gly
1 5 10 15

<210> SEQ ID NO 513
<211> LENGTH: 10
<212> TYPE: PRT
<213> ORGANISM: Oryctolagus cuniculus

<400> SEQUENCE: 513

Gly His Pro Gly Leu Gly Ser Gly Asn Ile
1 5 10

<210> SEQ ID NO 514
<211> LENGTH: 372
<212> TYPE: DNA
<213> ORGANISM: Oryctolagus cuniculus

<400> SEQUENCE: 514
atggacacga gggcccccac tcagctgctg gggctcctgc tgctctggct cccaggtgcc 60
acatttgcca ttgaaatgac ccagactcca tcccccgtgt ctgccgctgt gggaggcaca 120
gtcaccatca attgccaggc cagtgagagt gtttttaata atatgttatc ctggtatcag 180
cagaaaccag ggcactctcc taagctcctg atctatgatg catccgatct ggcatctggg 240
gtcccatcgc ggttcaaagg cagtggatct gggacacagt tcactctcac catcagtggc 300
gtggagtgtg acgatgctgc cacttactat tgtgcagggt ataaaagtga tagtaatgat 360
ggcgataatg tt 372

<210> SEQ ID NO 515
<211> LENGTH: 369
<212> TYPE: DNA
<213> ORGANISM: Oryctolagus cuniculus

<400> SEQUENCE: 515
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
acagtctctg gattctccct caacaggaat tcaataacct gggtccgcca ggctccaggg 180
gaggggctgg aatggatcgg aatcattact ggtagtggta gaacgtacta cgcgaactgg 240
gcaaaaggcc gattcaccat ctccaaaacc tcgaccacgg tggatctgaa aatgaccagt 300
ccgacaaccg aggacacggc cacctatttc tgtgccagag gccatcctgg tcttggtagt 360
ggtaacatc 369

<210> SEQ ID NO 516
<211> LENGTH: 36
<212> TYPE: DNA
<213> ORGANISM: Oryctolagus cuniculus

<400> SEQUENCE: 516
caggccagtg agagtgtttt taataatatg ttatcc 36

<210> SEQ ID NO 517
<211> LENGTH: 21
<212> TYPE: DNA
<213> ORGANISM: Oryctolagus cuniculus

<400> SEQUENCE: 517
gatgcatccg atctggcatc t 21

<210> SEQ ID NO 518
<211> LENGTH: 39
<212> TYPE: DNA
<213> ORGANISM: Oryctolagus cuniculus

<400> SEQUENCE: 518
gcagggtata aaagtgatag taatgatggc gataatgtt 39

<210> SEQ ID NO 519
<211> LENGTH: 15
<212> TYPE: DNA
<213> ORGANISM: Oryctolagus cuniculus

<400> SEQUENCE: 519
aggaattcaa taacc 15

<210> SEQ ID NO 520
<211> LENGTH: 48
<212> TYPE: DNA
<213> ORGANISM: Oryctolagus cuniculus

<400> SEQUENCE: 520
atcattactg gtagtggtag aacgtactac gcgaactggg caaaaggc 48

<210> SEQ ID NO 521
<211> LENGTH: 30
<212> TYPE: DNA
<213> ORGANISM: Oryctolagus cuniculus

<400> SEQUENCE: 521
ggccatcctg gtcttggtag tggtaacatc 30

<210> SEQ ID NO 522
<211> LENGTH: 121
<212> TYPE: PRT
<213> ORGANISM: Oryctolagus cuniculus

<400> SEQUENCE: 522

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
            20                  25                  30

Val Ser Ala Ala Val Gly Gly Thr Val Thr Ile Asn Cys Gln Ser Ser
        35                  40                  45

Gln Ser Val Tyr Asn Asn Tyr Leu Ser Trp Tyr Gln Gln Lys Pro Gly
    50                  55                  60

Gln Pro Pro Lys Leu Leu Ile Tyr Thr Ala Ser Ser Leu Ala Ser Gly
65                  70                  75                  80

Val Pro Ser Arg Phe Lys Gly Ser Gly Ser Gly Thr Gln Phe Thr Leu
                85                  90                  95

Thr Ile Ser Glu Val Gln Cys Asp Asp Ala Ala Thr Tyr Tyr Cys Gln
```

100 105 110

Gly Tyr Tyr Ser Gly Pro Ile Ile Thr
115 120

<210> SEQ ID NO 523
<211> LENGTH: 122
<212> TYPE: PRT
<213> ORGANISM: Oryctolagus cuniculus

<400> SEQUENCE: 523

Met Glu Thr Gly Leu Arg Trp Leu Leu Leu Val Ala Val Leu Lys Gly
1 5 10 15

Val Gln Cys Gln Ser Leu Glu Glu Ser Gly Gly Arg Leu Val Thr Pro
20 25 30

Gly Thr Pro Leu Thr Leu Thr Cys Thr Ala Ser Gly Phe Ser Leu Asn
35 40 45

Asn Tyr Tyr Ile Gln Trp Val Arg Gln Ala Pro Gly Glu Gly Leu Glu
50 55 60

Trp Ile Gly Ile Ile Tyr Ala Gly Gly Ser Ala Tyr Tyr Ala Thr Trp
65 70 75 80

Ala Asn Gly Arg Phe Thr Ile Ala Lys Thr Ser Ser Thr Thr Val Asp
85 90 95

Leu Lys Met Thr Ser Leu Thr Thr Glu Asp Thr Ala Thr Tyr Phe Cys
100 105 110

Ala Arg Gly Thr Phe Asp Gly Tyr Glu Leu
115 120

<210> SEQ ID NO 524
<211> LENGTH: 12
<212> TYPE: PRT
<213> ORGANISM: Oryctolagus cuniculus

<400> SEQUENCE: 524

Gln Ser Ser Gln Ser Val Tyr Asn Asn Tyr Leu Ser
1 5 10

<210> SEQ ID NO 525
<211> LENGTH: 7
<212> TYPE: PRT
<213> ORGANISM: Oryctolagus cuniculus

<400> SEQUENCE: 525

Thr Ala Ser Ser Leu Ala Ser
1 5

<210> SEQ ID NO 526
<211> LENGTH: 10
<212> TYPE: PRT
<213> ORGANISM: Oryctolagus cuniculus

<400> SEQUENCE: 526

Gln Gly Tyr Tyr Ser Gly Pro Ile Ile Thr
1 5 10

<210> SEQ ID NO 527
<211> LENGTH: 5
<212> TYPE: PRT
<213> ORGANISM: Oryctolagus cuniculus

<400> SEQUENCE: 527

Asn Tyr Tyr Ile Gln 1 5

<210> SEQ ID NO 528
<211> LENGTH: 16
<212> TYPE: PRT
<213> ORGANISM: Oryctolagus cuniculus

<400> SEQUENCE: 528

Ile Ile Tyr Ala Gly Gly Ser Ala Tyr Tyr Ala Thr Trp Ala Asn Gly
1 5 10 15

<210> SEQ ID NO 529
<211> LENGTH: 8
<212> TYPE: PRT
<213> ORGANISM: Oryctolagus cuniculus

<400> SEQUENCE: 529

Gly Thr Phe Asp Gly Tyr Glu Leu
1 5

<210> SEQ ID NO 530
<211> LENGTH: 363
<212> TYPE: DNA
<213> ORGANISM: Oryctolagus cuniculus

<400> SEQUENCE: 530
atggacacga gggcccccac tcagctgctg gggctcctgc tgctctggct cccaggtgcc 60
acatttgcgc aagtgctgac ccagactgca tcgtccgtgt ctgcagctgt gggaggcaca 120
gtcaccatca attgccagtc cagtcagagt gtttataata actacttatc ctggtatcag 180
cagaaaccag ggcagcctcc caagctcctg atctatactg catccagcct ggcatctggg 240
gtcccatcgc ggttcaaagg cagtggatct gggacacagt tcactctcac catcagcgaa 300
gtgcagtgtg acgatgctgc cacttactac tgtcaaggct attatagtgg tcctataatt 360
act 363

<210> SEQ ID NO 531
<211> LENGTH: 366
<212> TYPE: DNA
<213> ORGANISM: Oryctolagus cuniculus

<400> SEQUENCE: 531
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
acagcctctg gattctccct caataactac tacatacaat gggtccgcca ggctccaggg 180
gaggggctgg aatggatcgg gatcatttat gctggtggta gcgcatacta cgcgacctgg 240
gcaaacggcc gattcaccat cgccaaaacc tcgtcgacca cggtggatct gaagatgacc 300
agtctgacaa ccgaggacac ggccacctat ttctgtgcca gagggacatt tgatggttat 360
gagttg 366

<210> SEQ ID NO 532
<211> LENGTH: 36
<212> TYPE: DNA
<213> ORGANISM: Oryctolagus cuniculus

<400> SEQUENCE: 532
cagtccagtc agagtgttta taataactac ttatcc 36

<210> SEQ ID NO 533
<211> LENGTH: 21
<212> TYPE: DNA
<213> ORGANISM: Oryctolagus cuniculus

<400> SEQUENCE: 533
actgcatcca gcctggcatc t 21

<210> SEQ ID NO 534
<211> LENGTH: 30
<212> TYPE: DNA
<213> ORGANISM: Oryctolagus cuniculus

<400> SEQUENCE: 534
caaggctatt atagtggtcc tataattact 30

<210> SEQ ID NO 535
<211> LENGTH: 15
<212> TYPE: DNA
<213> ORGANISM: Oryctolagus cuniculus

<400> SEQUENCE: 535
aactactaca tacaa 15

<210> SEQ ID NO 536
<211> LENGTH: 48
<212> TYPE: DNA
<213> ORGANISM: Oryctolagus cuniculus

<400> SEQUENCE: 536
atcatttatg ctggtggtag cgcatactac gcgacctggg caaacggc 48

<210> SEQ ID NO 537
<211> LENGTH: 24
<212> TYPE: DNA
<213> ORGANISM: Oryctolagus cuniculus

<400> SEQUENCE: 537
gggacatttg atggttatga gttg 24

<210> SEQ ID NO 538
<211> LENGTH: 122
<212> TYPE: PRT
<213> ORGANISM: Oryctolagus cuniculus

<400> SEQUENCE: 538

Met Asp Thr Arg Ala Pro Thr Gln Leu Leu Gly Leu Leu Leu Leu Trp
1 5 10 15

Leu Pro Gly Ala Thr Phe Ala Gln Val Leu Thr Gln Thr Pro Ser Pro
20 25 30

Val Ser Val Pro Val Gly Asp Thr Val Thr Ile Ser Cys Gln Ser Ser
35 40 45

Glu Ser Val Tyr Ser Asn Asn Leu Leu Ser Trp Tyr Gln Gln Lys Pro
50 55 60

Gly Gln Pro Pro Lys Leu Leu Ile Tyr Arg Ala Ser Asn Leu Ala Ser
65 70 75 80

Gly Val Pro Ser Arg Phe Lys Gly Ser Gly Ser Gly Thr Gln Phe Thr
85 90 95

Leu Thr Ile Ser Gly Ala Gln Cys Asp Asp Ala Ala Thr Tyr Tyr Cys
100 105 110

Gln Gly Tyr Tyr Ser Gly Val Ile Asn Ser

```
        115                 120


<210> SEQ ID NO 539
<211> LENGTH: 124
<212> TYPE: PRT
<213> ORGANISM: Oryctolagus cuniculus

<400> SEQUENCE: 539

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Phe Met Ser Trp Val Arg Gln Ala Pro Gly Glu Gly Leu Glu
    50                  55                  60

Tyr Ile Gly Phe Ile Asn Pro Gly Gly Ser Ala Tyr Tyr Ala Ser Trp
65                  70                  75                  80

Ala Ser Gly Arg Leu Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Ile Leu Ile Val Ser Tyr Gly Ala Phe Thr Ile
        115                 120


<210> SEQ ID NO 540
<211> LENGTH: 13
<212> TYPE: PRT
<213> ORGANISM: Oryctolagus cuniculus

<400> SEQUENCE: 540

Gln Ser Ser Glu Ser Val Tyr Ser Asn Asn Leu Leu Ser
1               5                   10


<210> SEQ ID NO 541
<211> LENGTH: 7
<212> TYPE: PRT
<213> ORGANISM: Oryctolagus cuniculus

<400> SEQUENCE: 541

Arg Ala Ser Asn Leu Ala Ser
1               5


<210> SEQ ID NO 542
<211> LENGTH: 10
<212> TYPE: PRT
<213> ORGANISM: Oryctolagus cuniculus

<400> SEQUENCE: 542

Gln Gly Tyr Tyr Ser Gly Val Ile Asn Ser
1               5                   10


<210> SEQ ID NO 543
<211> LENGTH: 5
<212> TYPE: PRT
<213> ORGANISM: Oryctolagus cuniculus

<400> SEQUENCE: 543

Ser Tyr Phe Met Ser
1               5
```

<210> SEQ ID NO 544
<211> LENGTH: 16
<212> TYPE: PRT
<213> ORGANISM: Oryctolagus cuniculus

<400> SEQUENCE: 544

Phe Ile Asn Pro Gly Gly Ser Ala Tyr Tyr Ala Ser Trp Ala Ser Gly
1               5                   10                  15

<210> SEQ ID NO 545
<211> LENGTH: 11
<212> TYPE: PRT
<213> ORGANISM: Oryctolagus cuniculus

<400> SEQUENCE: 545

Ile Leu Ile Val Ser Tyr Gly Ala Phe Thr Ile
1               5                   10

<210> SEQ ID NO 546
<211> LENGTH: 366
<212> TYPE: DNA
<213> ORGANISM: Oryctolagus cuniculus

<400> SEQUENCE: 546
atggacacga gggcccccac tcagctgctg gggctcctgc tgctctggct cccaggtgcc 60
acatttgccc aagtgctgac ccagactcca tcccctgtgt ctgtccctgt gggagacaca 120
gtcaccatca gttgccagtc cagtgagagc gtttatagta ataacctctt atcctggtat 180
cagcagaaac cagggcagcc tcccaagctc ctgatctaca gggcatccaa tctggcatct 240
ggtgtcccat cgcggttcaa aggcagtgga tctgggacac agttcactct caccatcagc 300
ggcgcacagt gtgacgatgc tgccacttac tactgtcaag gctattatag tggtgtcatt 360
aatagt 366

<210> SEQ ID NO 547
<211> LENGTH: 372
<212> TYPE: DNA
<213> ORGANISM: Oryctolagus cuniculus

<400> SEQUENCE: 547
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtgtctg gattctccct cagtagctac ttcatgagct gggtccgcca ggctccaggg 180
gaggggctgg aatacatcgg attcattaat cctggtggta gcgcatacta cgcgagctgg 240
gcgagtggcc gactcaccat ctccaaaacc tcgaccacgg tagatctgaa aatcaccagt 300
ccgacaaccg aggacacggc cacctatttc tgtgccagga ttcttattgt ttcttatgga 360
gcctttacca tc 372

<210> SEQ ID NO 548
<211> LENGTH: 39
<212> TYPE: DNA
<213> ORGANISM: Oryctolagus cuniculus

<400> SEQUENCE: 548
cagtccagtg agagcgttta tagtaataac ctcttatcc 39

<210> SEQ ID NO 549
<211> LENGTH: 21
<212> TYPE: DNA

<213> ORGANISM: Oryctolagus cuniculus

<400> SEQUENCE: 549
agggcatcca atctggcatc t 21

<210> SEQ ID NO 550
<211> LENGTH: 30
<212> TYPE: DNA
<213> ORGANISM: Oryctolagus cuniculus

<400> SEQUENCE: 550
caaggctatt atagtggtgt cattaatagt 30

<210> SEQ ID NO 551
<211> LENGTH: 15
<212> TYPE: DNA
<213> ORGANISM: Oryctolagus cuniculus

<400> SEQUENCE: 551
agctacttca tgagc 15

<210> SEQ ID NO 552
<211> LENGTH: 48
<212> TYPE: DNA
<213> ORGANISM: Oryctolagus cuniculus

<400> SEQUENCE: 552
ttcattaatc ctggtggtag cgcatactac gcgagctggg cgagtggc 48

<210> SEQ ID NO 553
<211> LENGTH: 33
<212> TYPE: DNA
<213> ORGANISM: Oryctolagus cuniculus

<400> SEQUENCE: 553
attcttattg tttcttatgg agcctttacc atc 33

<210> SEQ ID NO 554
<211> LENGTH: 122
<212> TYPE: PRT
<213> ORGANISM: Oryctolagus cuniculus

<400> SEQUENCE: 554

```
Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Thr
        35                  40                  45

Glu Ser Ile Gly Asn Glu Leu Ser Trp Tyr Gln Gln Lys Pro Gly Gln
    50                  55                  60

Ala Pro Lys Leu Leu Ile Tyr Ser Ala Ser Thr Leu Ala Ser Gly Val
65                  70                  75                  80

Pro Ser Arg Phe Lys Gly Ser Gly Ser Gly Thr Gln Phe Thr Leu Thr
                85                  90                  95

Ile Thr Gly Val Glu Cys Asp Asp Ala Ala Thr Tyr Tyr Cys Gln Gln
            100                 105                 110

Gly Tyr Ser Ser Ala Asn Ile Asp Asn Ala
        115                 120
```

<210> SEQ ID NO 555
<211> LENGTH: 128
<212> TYPE: PRT
<213> ORGANISM: Oryctolagus cuniculus

<400> SEQUENCE: 555

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Lys Tyr Tyr Met Ser Trp Val Arg Gln Ala Pro Glu Lys Gly Leu Lys
    50                  55                  60

Tyr Ile Gly Tyr Ile Asp Ser Thr Thr Val Asn Thr Tyr Tyr Ala Thr
65                  70                  75                  80

Trp Ala Arg Gly Arg Phe Thr Ile Ser Lys Thr Ser Thr Thr Val Asp
                85                  90                  95

Leu Lys Ile Thr Ser Pro Thr Ser Glu Asp Thr Ala Thr Tyr Phe Cys
            100                 105                 110

Ala Arg Gly Ser Thr Tyr Phe Thr Asp Gly Gly His Arg Leu Asp Leu
        115                 120                 125
```

<210> SEQ ID NO 556
<211> LENGTH: 11
<212> TYPE: PRT
<213> ORGANISM: Oryctolagus cuniculus

<400> SEQUENCE: 556

```
Gln Ala Thr Glu Ser Ile Gly Asn Glu Leu Ser
1               5                   10
```

<210> SEQ ID NO 557
<211> LENGTH: 7
<212> TYPE: PRT
<213> ORGANISM: Oryctolagus cuniculus

<400> SEQUENCE: 557

```
Ser Ala Ser Thr Leu Ala Ser
1               5
```

<210> SEQ ID NO 558
<211> LENGTH: 12
<212> TYPE: PRT
<213> ORGANISM: Oryctolagus cuniculus

<400> SEQUENCE: 558

```
Gln Gln Gly Tyr Ser Ser Ala Asn Ile Asp Asn Ala
1               5                   10
```

<210> SEQ ID NO 559
<211> LENGTH: 5
<212> TYPE: PRT
<213> ORGANISM: Oryctolagus cuniculus

<400> SEQUENCE: 559

```
Lys Tyr Tyr Met Ser
1               5
```

<210> SEQ ID NO 560
<211> LENGTH: 17
<212> TYPE: PRT

<213> ORGANISM: Oryctolagus cuniculus

<400> SEQUENCE: 560

Tyr Ile Asp Ser Thr Thr Val Asn Thr Tyr Tyr Ala Thr Trp Ala Arg
1 5 10 15

Gly

<210> SEQ ID NO 561
<211> LENGTH: 14
<212> TYPE: PRT
<213> ORGANISM: Oryctolagus cuniculus

<400> SEQUENCE: 561

Gly Ser Thr Tyr Phe Thr Asp Gly Gly His Arg Leu Asp Leu
1 5 10

<210> SEQ ID NO 562
<211> LENGTH: 366
<212> TYPE: DNA
<213> ORGANISM: Oryctolagus cuniculus

<400> SEQUENCE: 562
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca agtgccaggc cactgagagc attggcaatg agttatcctg gtatcagcag 180
aaaccagggc aggctcccaa gctcctgatc tattctgcat ccactctggc atctggggtc 240
ccatcgcggt tcaaaggcag tggatctggg acacagttca ctctcaccat caccggcgtg 300
gagtgtgatg atgctgccac ttactactgt caacagggtt atagtagtgc taatattgat 360
aatgct 366

<210> SEQ ID NO 563
<211> LENGTH: 384
<212> TYPE: DNA
<213> ORGANISM: Oryctolagus cuniculus

<400> SEQUENCE: 563
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
accgtctctg gattctccct cagtaagtac tacatgagct gggtccgcca ggctccagag 180
aaggggctga aatacatcgg atacattgat agtactactg ttaatacata ctacgcgacc 240
tgggcgagag gccgattcac catctccaaa acctcgacca cggtggatct gaagatcacc 300
agtccgacaa gtgaggacac ggccacctat ttctgtgcca gaggaagtac ttattttact 360
gatggaggcc atcggttgga tctc 384

<210> SEQ ID NO 564
<211> LENGTH: 33
<212> TYPE: DNA
<213> ORGANISM: Oryctolagus cuniculus

<400> SEQUENCE: 564
caggccactg agagcattgg caatgagtta tcc 33

<210> SEQ ID NO 565
<211> LENGTH: 21
<212> TYPE: DNA
<213> ORGANISM: Oryctolagus cuniculus

<400> SEQUENCE: 565
tctgcatcca ctctggcatc t 21

<210> SEQ ID NO 566
<211> LENGTH: 36
<212> TYPE: DNA
<213> ORGANISM: Oryctolagus cuniculus

<400> SEQUENCE: 566
caacagggtt atagtagtgc taatattgat aatgct 36

<210> SEQ ID NO 567
<211> LENGTH: 15
<212> TYPE: DNA
<213> ORGANISM: Oryctolagus cuniculus

<400> SEQUENCE: 567
aagtactaca tgagc 15

<210> SEQ ID NO 568
<211> LENGTH: 51
<212> TYPE: DNA
<213> ORGANISM: Oryctolagus cuniculus

<400> SEQUENCE: 568
tacattgata gtactactgt taatacatac tacgcgacct gggcgagagg c 51

<210> SEQ ID NO 569
<211> LENGTH: 42
<212> TYPE: DNA
<213> ORGANISM: Oryctolagus cuniculus

<400> SEQUENCE: 569
ggaagtactt attttactga tggaggccat cggttggatc tc 42

<210> SEQ ID NO 570
<211> LENGTH: 122
<212> TYPE: PRT
<213> ORGANISM: Oryctolagus cuniculus

<400> SEQUENCE: 570

```
Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Thr
        35                  40                  45

Glu Ser Ile Gly Asn Glu Leu Ser Trp Tyr Gln Gln Lys Pro Gly Gln
    50                  55                  60

Ala Pro Lys Leu Leu Ile Tyr Ser Ala Ser Thr Leu Ala Ser Gly Val
65                  70                  75                  80

Pro Ser Arg Phe Lys Gly Ser Gly Ser Gly Thr Gln Phe Thr Leu Thr
                85                  90                  95

Ile Thr Gly Val Glu Cys Asp Asp Ala Ala Thr Tyr Tyr Cys Gln Gln
            100                 105                 110

Gly Tyr Ser Ser Ala Asn Ile Asp Asn Ala
        115                 120
```

<210> SEQ ID NO 571

<211> LENGTH: 124
<212> TYPE: PRT
<213> ORGANISM: Oryctolagus cuniculus

<400> SEQUENCE: 571

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Thr Tyr Asn Met Gly Trp Val Arg Gln Ala Pro Gly Lys Gly Leu Glu
    50                  55                  60

Trp Ile Gly Ser Ile Thr Ile Asp Gly Arg Thr Tyr Tyr Ala Ser Trp
65                  70                  75                  80

Ala Lys Gly Arg Phe Thr Val Ser Lys Ser Ser Thr Thr Val Asp Leu
                85                  90                  95

Lys Met Thr Ser Leu Thr Thr Gly Asp Thr Ala Thr Tyr Phe Cys Ala
            100                 105                 110

Arg Ile Leu Ile Val Ser Tyr Gly Ala Phe Thr Ile
        115                 120

<210> SEQ ID NO 572
<211> LENGTH: 11
<212> TYPE: PRT
<213> ORGANISM: Oryctolagus cuniculus

<400> SEQUENCE: 572

Gln Ala Thr Glu Ser Ile Gly Asn Glu Leu Ser
1               5                   10

<210> SEQ ID NO 573
<211> LENGTH: 7
<212> TYPE: PRT
<213> ORGANISM: Oryctolagus cuniculus

<400> SEQUENCE: 573

Ser Ala Ser Thr Leu Ala Ser
1               5

<210> SEQ ID NO 574
<211> LENGTH: 12
<212> TYPE: PRT
<213> ORGANISM: Oryctolagus cuniculus

<400> SEQUENCE: 574

Gln Gln Gly Tyr Ser Ser Ala Asn Ile Asp Asn Ala
1               5                   10

<210> SEQ ID NO 575
<211> LENGTH: 5
<212> TYPE: PRT
<213> ORGANISM: Oryctolagus cuniculus

<400> SEQUENCE: 575

Thr Tyr Asn Met Gly
1               5

<210> SEQ ID NO 576
<211> LENGTH: 16
<212> TYPE: PRT
<213> ORGANISM: Oryctolagus cuniculus

<400> SEQUENCE: 576

Ser Ile Thr Ile Asp Gly Arg Thr Tyr Tyr Ala Ser Trp Ala Lys Gly
1 5 10 15

<210> SEQ ID NO 577
<211> LENGTH: 11
<212> TYPE: PRT
<213> ORGANISM: Oryctolagus cuniculus

<400> SEQUENCE: 577

Ile Leu Ile Val Ser Tyr Gly Ala Phe Thr Ile
1 5 10

<210> SEQ ID NO 578
<211> LENGTH: 366
<212> TYPE: DNA
<213> ORGANISM: Oryctolagus cuniculus

<400> SEQUENCE: 578
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca agtgccaggc cactgagagc attggcaatg agttatcctg gtatcagcag 180
aaaccagggc aggctcccaa gctcctgatc tattctgcat ccactctggc atctggggtc 240
ccatcgcggt tcaaaggcag tggatctggg acacagttca ctctcaccat caccggcgtg 300
gagtgtgatg atgctgccac ttactactgt caacagggtt atagtagtgc taatattgat 360
aatgct 366

<210> SEQ ID NO 579
<211> LENGTH: 372
<212> TYPE: DNA
<213> ORGANISM: Oryctolagus cuniculus

<400> SEQUENCE: 579
atggagactg ggctgcgctg gcttctcctg gtcgctgtgc tcaaaggtgt ccagtgtcag 60
tcgctggagg agtccggggg tcgcctggta acgcctggga cacccctgac actcacctgc 120
acagtctctg gattctccct cagtacctac aacatgggct gggtccgcca ggctccaggg 180
aaggggctgg aatggatcgg aagtattact attgatggtc gcacatacta cgcgagctgg 240
gcgaaaggcc gattcaccgt ctccaaaagc tcgaccacgg tggatctgaa aatgaccagt 300
ctgacaaccg gggacacggc cacctatttc tgtgccagga ttcttattgt ttcttatggg 360
gcctttacca tc 372

<210> SEQ ID NO 580
<211> LENGTH: 33
<212> TYPE: DNA
<213> ORGANISM: Oryctolagus cuniculus

<400> SEQUENCE: 580
caggccactg agagcattgg caatgagtta tcc 33

<210> SEQ ID NO 581
<211> LENGTH: 21
<212> TYPE: DNA
<213> ORGANISM: Oryctolagus cuniculus

<400> SEQUENCE: 581
tctgcatcca ctctggcatc t 21

<210> SEQ ID NO 582
<211> LENGTH: 36
<212> TYPE: DNA
<213> ORGANISM: Oryctolagus cuniculus

<400> SEQUENCE: 582
caacagggtt atagtagtgc taatattgat aatgct 36

<210> SEQ ID NO 583
<211> LENGTH: 15
<212> TYPE: DNA
<213> ORGANISM: Oryctolagus cuniculus

<400> SEQUENCE: 583
acctacaaca tgggc 15

<210> SEQ ID NO 584
<211> LENGTH: 48
<212> TYPE: DNA
<213> ORGANISM: Oryctolagus cuniculus

<400> SEQUENCE: 584
agtattacta ttgatggtcg cacatactac gcgagctggg cgaaaggc 48

<210> SEQ ID NO 585
<211> LENGTH: 33
<212> TYPE: DNA
<213> ORGANISM: Oryctolagus cuniculus

<400> SEQUENCE: 585
attcttattg tttcttatgg ggcctttacc atc 33

<210> SEQ ID NO 586
<211> LENGTH: 105
<212> TYPE: PRT
<213> ORGANISM: Artificial Sequence
<220> FEATURE:
<223> OTHER INFORMATION: Kappa constant domain

<400> SEQUENCE: 586

```
Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105
```

<210> SEQ ID NO 587
<211> LENGTH: 315
<212> TYPE: DNA
<213> ORGANISM: Artificial Sequence
<220> FEATURE:

<223> OTHER INFORMATION: Kappa constant domain

<400> SEQUENCE: 587
gtggctgcac catctgtctt catcttcccg ccatctgatg agcagttgaa atctggaact 60
gcctctgttg tgtgcctgct gaataacttc tatcccagag aggccaaagt acagtggaag 120
gtggataacg ccctccaatc gggtaactcc caggagagtg tcacagagca ggacagcaag 180
gacagcacct acagcctcag cagcaccctg acgctgagca aagcagacta cgagaaacac 240
aaagtctacg cctgcgaagt cacccatcag ggcctgagct cgcccgtcac aaagagcttc 300
aacaggggag agtgt 315

<210> SEQ ID NO 588
<211> LENGTH: 330
<212> TYPE: PRT
<213> ORGANISM: Artificial Sequence
<220> FEATURE:
<223> OTHER INFORMATION: Gamma-1 constant domain

<400> SEQUENCE: 588

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 589
<211> LENGTH: 990
<212> TYPE: DNA
<213> ORGANISM: Artificial Sequence
<220> FEATURE:
<223> OTHER INFORMATION: Gamma-1 constant domain

<400> SEQUENCE: 589
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 590
<211> LENGTH: 15
<212> TYPE: PRT
<213> ORGANISM: Homo sapiens

<400> SEQUENCE: 590

Val Pro Pro Gly Glu Asp Ser Lys Asp Val Ala Ala Pro His Arg
1 5 10 15

<210> SEQ ID NO 591
<211> LENGTH: 15
<212> TYPE: PRT
<213> ORGANISM: Homo sapiens

<400> SEQUENCE: 591

Gly Glu Asp Ser Lys Asp Val Ala Ala Pro His Arg Gln Pro Leu
1 5 10 15

<210> SEQ ID NO 592
<211> LENGTH: 15

<212> TYPE: PRT
<213> ORGANISM: Homo sapiens

<400> SEQUENCE: 592

Ser Lys Asp Val Ala Ala Pro His Arg Gln Pro Leu Thr Ser Ser
1 5 10 15

<210> SEQ ID NO 593
<211> LENGTH: 15
<212> TYPE: PRT
<213> ORGANISM: Homo sapiens

<400> SEQUENCE: 593

Val Ala Ala Pro His Arg Gln Pro Leu Thr Ser Ser Glu Arg Ile
1 5 10 15

<210> SEQ ID NO 594
<211> LENGTH: 15
<212> TYPE: PRT
<213> ORGANISM: Homo sapiens

<400> SEQUENCE: 594

Pro His Arg Gln Pro Leu Thr Ser Ser Glu Arg Ile Asp Lys Gln
1 5 10 15

<210> SEQ ID NO 595
<211> LENGTH: 15
<212> TYPE: PRT
<213> ORGANISM: Homo sapiens

<400> SEQUENCE: 595

Gln Pro Leu Thr Ser Ser Glu Arg Ile Asp Lys Gln Ile Arg Tyr
1 5 10 15

<210> SEQ ID NO 596
<211> LENGTH: 15
<212> TYPE: PRT
<213> ORGANISM: Homo sapiens

<400> SEQUENCE: 596

Thr Ser Ser Glu Arg Ile Asp Lys Gln Ile Arg Tyr Ile Leu Asp
1 5 10 15

<210> SEQ ID NO 597
<211> LENGTH: 15
<212> TYPE: PRT
<213> ORGANISM: Homo sapiens

<400> SEQUENCE: 597

Glu Arg Ile Asp Lys Gln Ile Arg Tyr Ile Leu Asp Gly Ile Ser
1 5 10 15

<210> SEQ ID NO 598
<211> LENGTH: 15
<212> TYPE: PRT
<213> ORGANISM: Homo sapiens

<400> SEQUENCE: 598

Asp Lys Gln Ile Arg Tyr Ile Leu Asp Gly Ile Ser Ala Leu Arg
1 5 10 15

<210> SEQ ID NO 599
<211> LENGTH: 15
<212> TYPE: PRT
<213> ORGANISM: Homo sapiens

<400> SEQUENCE: 599

Ile Arg Tyr Ile Leu Asp Gly Ile Ser Ala Leu Arg Lys Glu Thr
1 5 10 15

<210> SEQ ID NO 600
<211> LENGTH: 15
<212> TYPE: PRT
<213> ORGANISM: Homo sapiens

<400> SEQUENCE: 600

Ile Leu Asp Gly Ile Ser Ala Leu Arg Lys Glu Thr Cys Asn Lys
1 5 10 15

<210> SEQ ID NO 601
<211> LENGTH: 15
<212> TYPE: PRT
<213> ORGANISM: Homo sapiens

<400> SEQUENCE: 601

Gly Ile Ser Ala Leu Arg Lys Glu Thr Cys Asn Lys Ser Asn Met
1 5 10 15

<210> SEQ ID NO 602
<211> LENGTH: 15
<212> TYPE: PRT
<213> ORGANISM: Homo sapiens

<400> SEQUENCE: 602

Ala Leu Arg Lys Glu Thr Cys Asn Lys Ser Asn Met Cys Glu Ser
1 5 10 15

<210> SEQ ID NO 603
<211> LENGTH: 15
<212> TYPE: PRT
<213> ORGANISM: Homo sapiens

<400> SEQUENCE: 603

Lys Glu Thr Cys Asn Lys Ser Asn Met Cys Glu Ser Ser Lys Glu
1 5 10 15

<210> SEQ ID NO 604
<211> LENGTH: 15
<212> TYPE: PRT
<213> ORGANISM: Homo sapiens

<400> SEQUENCE: 604

Cys Asn Lys Ser Asn Met Cys Glu Ser Ser Lys Glu Ala Leu Ala
1 5 10 15

<210> SEQ ID NO 605
<211> LENGTH: 15
<212> TYPE: PRT
<213> ORGANISM: Homo sapiens

<400> SEQUENCE: 605

Ser Asn Met Cys Glu Ser Ser Lys Glu Ala Leu Ala Glu Asn Asn
1 5 10 15

<210> SEQ ID NO 606
<211> LENGTH: 15
<212> TYPE: PRT
<213> ORGANISM: Homo sapiens

<400> SEQUENCE: 606

Cys Glu Ser Ser Lys Glu Ala Leu Ala Glu Asn Asn Leu Asn Leu
1 5 10 15

<210> SEQ ID NO 607
<211> LENGTH: 15
<212> TYPE: PRT
<213> ORGANISM: Homo sapiens

<400> SEQUENCE: 607

Ser Lys Glu Ala Leu Ala Glu Asn Asn Leu Asn Leu Pro Lys Met
1 5 10 15

<210> SEQ ID NO 608
<211> LENGTH: 15
<212> TYPE: PRT
<213> ORGANISM: Homo sapiens

<400> SEQUENCE: 608

Ala Leu Ala Glu Asn Asn Leu Asn Leu Pro Lys Met Ala Glu Lys
1 5 10 15

<210> SEQ ID NO 609
<211> LENGTH: 15
<212> TYPE: PRT
<213> ORGANISM: Homo sapiens

<400> SEQUENCE: 609

Glu Asn Asn Leu Asn Leu Pro Lys Met Ala Glu Lys Asp Gly Cys
1 5 10 15

<210> SEQ ID NO 610
<211> LENGTH: 15
<212> TYPE: PRT
<213> ORGANISM: Homo sapiens

<400> SEQUENCE: 610

Leu Asn Leu Pro Lys Met Ala Glu Lys Asp Gly Cys Phe Gln Ser
1 5 10 15

<210> SEQ ID NO 611
<211> LENGTH: 15
<212> TYPE: PRT
<213> ORGANISM: Homo sapiens

<400> SEQUENCE: 611

Pro Lys Met Ala Glu Lys Asp Gly Cys Phe Gln Ser Gly Phe Asn
1 5 10 15

<210> SEQ ID NO 612
<211> LENGTH: 15
<212> TYPE: PRT
<213> ORGANISM: Homo sapiens

<400> SEQUENCE: 612

Ala Glu Lys Asp Gly Cys Phe Gln Ser Gly Phe Asn Glu Glu Thr
1 5 10 15

<210> SEQ ID NO 613
<211> LENGTH: 15
<212> TYPE: PRT
<213> ORGANISM: Homo sapiens

<400> SEQUENCE: 613

Asp Gly Cys Phe Gln Ser Gly Phe Asn Glu Glu Thr Cys Leu Val 1 5 10 15

<210> SEQ ID NO 614
<211> LENGTH: 15
<212> TYPE: PRT
<213> ORGANISM: Homo sapiens

<400> SEQUENCE: 614

Phe Gln Ser Gly Phe Asn Glu Glu Thr Cys Leu Val Lys Ile Ile
1 5 10 15

<210> SEQ ID NO 615
<211> LENGTH: 15
<212> TYPE: PRT
<213> ORGANISM: Homo sapiens

<400> SEQUENCE: 615

Gly Phe Asn Glu Glu Thr Cys Leu Val Lys Ile Ile Thr Gly Leu
1 5 10 15

<210> SEQ ID NO 616
<211> LENGTH: 15
<212> TYPE: PRT
<213> ORGANISM: Homo sapiens

<400> SEQUENCE: 616

Glu Glu Thr Cys Leu Val Lys Ile Ile Thr Gly Leu Leu Glu Phe
1 5 10 15

<210> SEQ ID NO 617
<211> LENGTH: 15
<212> TYPE: PRT
<213> ORGANISM: Homo sapiens

<400> SEQUENCE: 617

Cys Leu Val Lys Ile Ile Thr Gly Leu Leu Glu Phe Glu Val Tyr
1 5 10 15

<210> SEQ ID NO 618
<211> LENGTH: 15
<212> TYPE: PRT
<213> ORGANISM: Homo sapiens

<400> SEQUENCE: 618

Lys Ile Ile Thr Gly Leu Leu Glu Phe Glu Val Tyr Leu Glu Tyr
1 5 10 15

<210> SEQ ID NO 619
<211> LENGTH: 15
<212> TYPE: PRT
<213> ORGANISM: Homo sapiens

<400> SEQUENCE: 619

Thr Gly Leu Leu Glu Phe Glu Val Tyr Leu Glu Tyr Leu Gln Asn
1 5 10 15

<210> SEQ ID NO 620
<211> LENGTH: 15
<212> TYPE: PRT
<213> ORGANISM: Homo sapiens

<400> SEQUENCE: 620

Leu Glu Phe Glu Val Tyr Leu Glu Tyr Leu Gln Asn Arg Phe Glu
1 5 10 15

<210> SEQ ID NO 621
<211> LENGTH: 15
<212> TYPE: PRT
<213> ORGANISM: Homo sapiens

<400> SEQUENCE: 621

Glu Val Tyr Leu Glu Tyr Leu Gln Asn Arg Phe Glu Ser Ser Glu
1 5 10 15

<210> SEQ ID NO 622
<211> LENGTH: 15
<212> TYPE: PRT
<213> ORGANISM: Homo sapiens

<400> SEQUENCE: 622

Leu Glu Tyr Leu Gln Asn Arg Phe Glu Ser Ser Glu Glu Gln Ala
1 5 10 15

<210> SEQ ID NO 623
<211> LENGTH: 15
<212> TYPE: PRT
<213> ORGANISM: Homo sapiens

<400> SEQUENCE: 623

Leu Gln Asn Arg Phe Glu Ser Ser Glu Glu Gln Ala Arg Ala Val
1 5 10 15

<210> SEQ ID NO 624
<211> LENGTH: 15
<212> TYPE: PRT
<213> ORGANISM: Homo sapiens

<400> SEQUENCE: 624

Arg Phe Glu Ser Ser Glu Glu Gln Ala Arg Ala Val Gln Met Ser
1 5 10 15

<210> SEQ ID NO 625
<211> LENGTH: 15
<212> TYPE: PRT
<213> ORGANISM: Homo sapiens

<400> SEQUENCE: 625

Ser Ser Glu Glu Gln Ala Arg Ala Val Gln Met Ser Thr Lys Val
1 5 10 15

<210> SEQ ID NO 626
<211> LENGTH: 15
<212> TYPE: PRT
<213> ORGANISM: Homo sapiens

<400> SEQUENCE: 626

Glu Gln Ala Arg Ala Val Gln Met Ser Thr Lys Val Leu Ile Gln
1 5 10 15

<210> SEQ ID NO 627
<211> LENGTH: 15
<212> TYPE: PRT
<213> ORGANISM: Homo sapiens

<400> SEQUENCE: 627

Arg Ala Val Gln Met Ser Thr Lys Val Leu Ile Gln Phe Leu Gln
1 5 10 15

<210> SEQ ID NO 628

-continued

<211> LENGTH: 15
<212> TYPE: PRT
<213> ORGANISM: Homo sapiens

<400> SEQUENCE: 628

Gln Met Ser Thr Lys Val Leu Ile Gln Phe Leu Gln Lys Lys Ala
1 5 10 15

<210> SEQ ID NO 629
<211> LENGTH: 15
<212> TYPE: PRT
<213> ORGANISM: Homo sapiens

<400> SEQUENCE: 629

Thr Lys Val Leu Ile Gln Phe Leu Gln Lys Lys Ala Lys Asn Leu
1 5 10 15

<210> SEQ ID NO 630
<211> LENGTH: 15
<212> TYPE: PRT
<213> ORGANISM: Homo sapiens

<400> SEQUENCE: 630

Leu Ile Gln Phe Leu Gln Lys Lys Ala Lys Asn Leu Asp Ala Ile
1 5 10 15

<210> SEQ ID NO 631
<211> LENGTH: 15
<212> TYPE: PRT
<213> ORGANISM: Homo sapiens

<400> SEQUENCE: 631

Phe Leu Gln Lys Lys Ala Lys Asn Leu Asp Ala Ile Thr Thr Pro
1 5 10 15

<210> SEQ ID NO 632
<211> LENGTH: 15
<212> TYPE: PRT
<213> ORGANISM: Homo sapiens

<400> SEQUENCE: 632

Lys Lys Ala Lys Asn Leu Asp Ala Ile Thr Thr Pro Asp Pro Thr
1 5 10 15

<210> SEQ ID NO 633
<211> LENGTH: 15
<212> TYPE: PRT
<213> ORGANISM: Homo sapiens

<400> SEQUENCE: 633

Lys Asn Leu Asp Ala Ile Thr Thr Pro Asp Pro Thr Thr Asn Ala
1 5 10 15

<210> SEQ ID NO 634
<211> LENGTH: 15
<212> TYPE: PRT
<213> ORGANISM: Homo sapiens

<400> SEQUENCE: 634

Asp Ala Ile Thr Thr Pro Asp Pro Thr Thr Asn Ala Ser Leu Leu
1 5 10 15

<210> SEQ ID NO 635
<211> LENGTH: 15
<212> TYPE: PRT

<213> ORGANISM: Homo sapiens

<400> SEQUENCE: 635

Thr Thr Pro Asp Pro Thr Thr Asn Ala Ser Leu Leu Thr Lys Leu
1 5 10 15

<210> SEQ ID NO 636
<211> LENGTH: 15
<212> TYPE: PRT
<213> ORGANISM: Homo sapiens

<400> SEQUENCE: 636

Asp Pro Thr Thr Asn Ala Ser Leu Leu Thr Lys Leu Gln Ala Gln
1 5 10 15

<210> SEQ ID NO 637
<211> LENGTH: 15
<212> TYPE: PRT
<213> ORGANISM: Homo sapiens

<400> SEQUENCE: 637

Thr Asn Ala Ser Leu Leu Thr Lys Leu Gln Ala Gln Asn Gln Trp
1 5 10 15

<210> SEQ ID NO 638
<211> LENGTH: 15
<212> TYPE: PRT
<213> ORGANISM: Homo sapiens

<400> SEQUENCE: 638

Ser Leu Leu Thr Lys Leu Gln Ala Gln Asn Gln Trp Leu Gln Asp
1 5 10 15

<210> SEQ ID NO 639
<211> LENGTH: 15
<212> TYPE: PRT
<213> ORGANISM: Homo sapiens

<400> SEQUENCE: 639

Thr Lys Leu Gln Ala Gln Asn Gln Trp Leu Gln Asp Met Thr Thr
1 5 10 15

<210> SEQ ID NO 640
<211> LENGTH: 15
<212> TYPE: PRT
<213> ORGANISM: Homo sapiens

<400> SEQUENCE: 640

Gln Ala Gln Asn Gln Trp Leu Gln Asp Met Thr Thr His Leu Ile
1 5 10 15

<210> SEQ ID NO 641
<211> LENGTH: 15
<212> TYPE: PRT
<213> ORGANISM: Homo sapiens

<400> SEQUENCE: 641

Asn Gln Trp Leu Gln Asp Met Thr Thr His Leu Ile Leu Arg Ser
1 5 10 15

<210> SEQ ID NO 642
<211> LENGTH: 15
<212> TYPE: PRT
<213> ORGANISM: Homo sapiens

<400> SEQUENCE: 642

Leu Gln Asp Met Thr Thr His Leu Ile Leu Arg Ser Phe Lys Glu
1 5 10 15

<210> SEQ ID NO 643
<211> LENGTH: 15
<212> TYPE: PRT
<213> ORGANISM: Homo sapiens

<400> SEQUENCE: 643

Met Thr Thr His Leu Ile Leu Arg Ser Phe Lys Glu Phe Leu Gln
1 5 10 15

<210> SEQ ID NO 644
<211> LENGTH: 15
<212> TYPE: PRT
<213> ORGANISM: Homo sapiens

<400> SEQUENCE: 644

His Leu Ile Leu Arg Ser Phe Lys Glu Phe Leu Gln Ser Ser Leu
1 5 10 15

<210> SEQ ID NO 645
<211> LENGTH: 15
<212> TYPE: PRT
<213> ORGANISM: Homo sapiens

<400> SEQUENCE: 645

Leu Arg Ser Phe Lys Glu Phe Leu Gln Ser Ser Leu Arg Ala Leu
1 5 10 15

<210> SEQ ID NO 646
<211> LENGTH: 15
<212> TYPE: PRT
<213> ORGANISM: Homo sapiens

<400> SEQUENCE: 646

Phe Lys Glu Phe Leu Gln Ser Ser Leu Arg Ala Leu Arg Gln Met
1 5 10 15

<210> SEQ ID NO 647
<211> LENGTH: 111
<212> TYPE: PRT
<213> ORGANISM: Oryctolagus cuniculus

<400> SEQUENCE: 647

Ala Tyr Asp Met Thr Gln Thr Pro Ala Ser Val Ser Ala Ala Val Gly
1 5 10 15

Gly Thr Val Thr Ile Lys Cys Gln Ala Ser Gln Ser Ile Asn Asn Glu
20 25 30

Leu Ser Trp Tyr Gln Gln Lys Pro Gly Gln Arg Pro Lys Leu Leu Ile
35 40 45

Tyr Arg Ala Ser Thr Leu Ala Ser Gly Val Ser Ser Arg Phe Lys Gly
50 55 60

Ser Gly Ser Gly Thr Glu Phe Thr Leu Thr Ile Ser Asp Leu Glu Cys
65 70 75 80

Ala Asp Ala Ala Thr Tyr Tyr Cys Gln Gln Gly Tyr Ser Leu Arg Asn
85 90 95

Ile Asp Asn Ala Phe Gly Gly Gly Thr Glu Val Val Val Lys Arg
100 105 110

<210> SEQ ID NO 648
<211> LENGTH: 88
<212> TYPE: PRT
<213> ORGANISM: Homo sapiens

<400> SEQUENCE: 648

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85
```

<210> SEQ ID NO 649
<211> LENGTH: 88
<212> TYPE: PRT
<213> ORGANISM: Homo sapiens

<400> SEQUENCE: 649

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys
                85
```

<210> SEQ ID NO 650
<211> LENGTH: 88
<212> TYPE: PRT
<213> ORGANISM: Homo sapiens

<400> SEQUENCE: 650

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys
                85
```

<210> SEQ ID NO 651

<211> LENGTH: 111
<212> TYPE: PRT
<213> ORGANISM: Artificial Sequence
<220> FEATURE:
<223> OTHER INFORMATION: Humanized antibody

<400> SEQUENCE: 651

Ala Ile Gln Met Thr Gln Ser Pro Ser Ser Leu Ser Ala Ser Val Gly
1 5 10 15

Asp Arg Val Thr Ile Thr Cys Gln Ala Ser Gln Ser Ile Asn Asn Glu
20 25 30

Leu Ser Trp Tyr Gln Gln Lys Pro Gly Lys Ala Pro Lys Leu Leu Ile
35 40 45

Tyr Arg Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Tyr Ser Leu Arg Asn
85 90 95

Ile Asp Asn Ala Phe Gly Gly Gly Thr Lys Val Glu Ile Lys Arg
100 105 110

<210> SEQ ID NO 652
<211> LENGTH: 117
<212> TYPE: PRT
<213> ORGANISM: Oryctolagus cuniculus

<400> SEQUENCE: 652

Gln Ser Leu Glu Glu Ser Gly Gly Arg Leu Val Thr Pro Gly Thr Pro
1 5 10 15

Leu Thr Leu Thr Cys Thr Ala Ser Gly Phe Ser Leu Ser Asn Tyr Tyr
20 25 30

Val Thr Trp Val Arg Gln Ala Pro Gly Lys Gly Leu Glu Trp Ile Gly
35 40 45

Ile Ile Tyr Gly Ser Asp Glu Thr Ala Tyr Ala Thr Trp Ala Ile Gly
50 55 60

Arg Phe Thr Ile Ser Lys Thr Ser Thr Thr Val Asp Leu Lys Met Thr
65 70 75 80

Ser Leu Thr Ala Ala Asp Thr Ala Thr Tyr Phe Cys Ala Arg Asp Asp
85 90 95

Ser Ser Asp Trp Asp Ala Lys Phe Asn Leu Trp Gly Gln Gly Thr Leu
100 105 110

Val Thr Val Ser Ser
115

<210> SEQ ID NO 653
<211> LENGTH: 97
<212> TYPE: PRT
<213> ORGANISM: Homo sapiens

<400> SEQUENCE: 653

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Val Ser Ser Asn
20 25 30

Tyr Met Ser Trp Val Arg Gln Ala Pro Gly Lys Gly Leu Glu Trp Val
35 40 45

Ser Val Ile Tyr Ser Gly Gly Ser Thr Tyr Tyr Ala Asp Ser Val Lys

```
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg


<210> SEQ ID NO 654
<211> LENGTH: 97
<212> TYPE: PRT
<213> ORGANISM: Homo sapiens

<400> SEQUENCE: 654

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg


<210> SEQ ID NO 655
<211> LENGTH: 98
<212> TYPE: PRT
<213> ORGANISM: Homo sapiens

<400> SEQUENCE: 655

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys


<210> SEQ ID NO 656
<211> LENGTH: 120
<212> TYPE: PRT
<213> ORGANISM: Artificial sequence
<220> FEATURE:
<223> OTHER INFORMATION: Humanized antibody

<400> SEQUENCE: 656

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Trp Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
            100                 105                 110

Gly Thr Leu Val Thr Val Ser Ser
        115                 120

<210> SEQ ID NO 657
<211> LENGTH: 120
<212> TYPE: PRT
<213> ORGANISM: Artificial sequence
<220> FEATURE:
<223> OTHER INFORMATION: Humanized antibody

<400> SEQUENCE: 657

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Ser Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
            100                 105                 110

Gly Thr Leu Val Thr Val Ser Ser
        115                 120

<210> SEQ ID NO 658
<211> LENGTH: 166
<212> TYPE: PRT
<213> ORGANISM: Oryctolagus cuniculus

<400> SEQUENCE: 658

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Tyr Val Thr Trp Val Arg Gln Ala Pro Gly Lys Gly Leu Glu
    50                  55                  60

Trp Ile Gly Ile Ile Tyr Gly Ser Asp Glu Thr Ala Tyr Ala Thr Ser
65                  70                  75                  80

Ala Ile Gly Arg Phe Thr Ile Ser Lys Thr Ser Thr Thr Val Asp Leu

```
                85                  90                  95

Lys Met Thr Ser Leu Thr Ala Ala Asp Thr Ala Thr Tyr Phe Cys Ala
            100                 105                 110

Arg Asp Asp Ser Ser Asp Trp Asp Ala Lys Phe Asn Leu Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys
                165


<210> SEQ ID NO 659
<211> LENGTH: 16
<212> TYPE: PRT
<213> ORGANISM: Oryctolagus cuniculus

<400> SEQUENCE: 659

Ile Ile Tyr Gly Ser Asp Glu Thr Ala Tyr Ala Thr Ser Ala Ile Gly
1               5                   10                  15


<210> SEQ ID NO 660
<211> LENGTH: 122
<212> TYPE: PRT
<213> ORGANISM: Oryctolagus cuniculus

<400> SEQUENCE: 660

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Ser Ala Ala Val Gly Gly Thr Val Thr Ile Lys Cys Gln Ala Ser
        35                  40                  45

Gln Ser Ile Asn Asn Glu Leu Ser Trp Tyr Gln Gln Lys Pro Gly Gln
    50                  55                  60

Arg Pro Lys Leu Leu Ile Tyr Arg Ala Ser Thr Leu Ala Ser Gly Val
65                  70                  75                  80

Ser Ser Arg Phe Lys Gly Ser Gly Ser Gly Thr Glu Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Ser Leu Arg Asn Ile Asp Asn Ala
        115                 120


<210> SEQ ID NO 661
<211> LENGTH: 125
<212> TYPE: PRT
<213> ORGANISM: Oryctolagus cuniculus

<400> SEQUENCE: 661

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Tyr Val Thr Trp Val Arg Gln Ala Pro Gly Lys Gly Leu Glu
    50                  55                  60
```

Trp Ile Gly Ile Ile Tyr Gly Ser Asp Glu Thr Ala Tyr Ala Thr Trp
65 70 75 80

Ala Ile Gly Arg Phe Thr Ile Ser Lys Thr Ser Thr Thr Val Asp Leu
85 90 95

Lys Met Thr Ser Leu Thr Ala Ala Asp Thr Ala Thr Tyr Phe Cys Ala
100 105 110

Arg Asp Asp Ser Ser Asp Trp Asp Ala Lys Phe Asn Leu
115 120 125

<210> SEQ ID NO 662
<211> LENGTH: 366
<212> TYPE: DNA
<213> ORGANISM: Oryctolagus cuniculus

<400> SEQUENCE: 662
atggacacga gggcccccac tcagctgctg gggctcctgc tgctctggct cccaggtgcc 60
agatgtgcct atgatatgac ccagactcca gcctcggtgt ctgcagctgt gggaggcaca 120
gtcaccatca agtgccaggc cagtcagagc attaacaatg aattatcctg gtatcagcag 180
aaaccagggc agcgtcccaa gctcctgatc tatagggcat ccactctggc atctggggtc 240
tcatcgcggt tcaaaggcag tggatctggg acagagttca ctctcaccat cagcgacctg 300
gagtgtgccg atgctgccac ttactactgt caacagggtt atagtctgag gaatattgat 360
aatgct 366

<210> SEQ ID NO 663
<211> LENGTH: 375
<212> TYPE: DNA
<213> ORGANISM: Oryctolagus cuniculus

<400> SEQUENCE: 663
atggagactg ggctgcgctg gcttctcctg gtcgctgtgc tcaaaggtgt ccagtgtcag 60
tcgctggagg agtccggggg tcgcctggtc acgcctggga cacccctgac actcacctgc 120
acagcctctg gattctccct cagtaactac tacgtgacct gggtccgcca ggctccaggg 180
aaggggctgg aatggatcgg aatcatttat ggtagtgatg aaacggccta cgcgacctgg 240
gcgataggcc gattcaccat ctccaaaacc tcgaccacgg tggatctgaa aatgaccagt 300
ctgacagccg cggacacggc cacctatttc tgtgccagag atgatagtag tgactgggat 360
gcaaaattta acttg 375

<210> SEQ ID NO 664
<211> LENGTH: 450
<212> TYPE: PRT
<213> ORGANISM: Oryctolagus cuniculus

<400> SEQUENCE: 664

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Asn Tyr
20 25 30

Tyr Val Thr Trp Val Arg Gln Ala Pro Gly Lys Gly Leu Glu Trp Val
35 40 45

Gly Ile Ile Tyr Gly Ser Asp Glu Thr Ala Tyr Ala Thr Trp Ala Ile
50 55 60

Gly Arg Phe Thr Ile Ser Arg Asp Asn Ser Lys Asn Thr Leu Tyr Leu
65 70 75 80

```
Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 665
<211> LENGTH: 450
<212> TYPE: PRT
<213> ORGANISM: Oryctolagus cuniculus

<400> SEQUENCE: 665

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Ser Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 666
<211> LENGTH: 216
<212> TYPE: PRT
<213> ORGANISM: Oryctolagus cuniculus

<400> SEQUENCE: 666

Ile Gln Met Thr Gln Ser Pro Ser Ser Leu Ser Ala Ser Val Gly Asp
1               5                   10                  15

Arg Val Thr Ile Thr Cys Gln Ala Ser Gln Ser Ile Asn Asn Glu Leu
            20                  25                  30

Ser Trp Tyr Gln Gln Lys Pro Gly Lys Ala Pro Lys Leu Leu Ile Tyr
        35                  40                  45

Arg Ala Ser Thr Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Asp
65                  70                  75                  80

Asp Phe Ala Thr Tyr Tyr Cys Gln Gln Gly Tyr Ser Leu Arg Asn Ile
                85                  90                  95

Asp Asn Ala Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 667
<211> LENGTH: 122
<212> TYPE: PRT
<213> ORGANISM: Oryctolagus cuniculus

<400> SEQUENCE: 667

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Asn Cys Gln Ala Ser
        35                  40                  45

Glu Thr Ile Tyr Ser Trp Leu Ser Trp Tyr Gln Gln Lys Pro Gly Gln
    50                  55                  60
```

Pro Pro Lys Leu Leu Ile Tyr Gln Ala Ser Asp Leu Ala Ser Gly Val
65 70 75 80

Pro Ser Arg Phe Ser Gly Ser Gly Ala Gly Thr Glu Tyr Thr Leu Thr
85 90 95

Ile Ser Gly Val Gln Cys Asp Asp Ala Ala Thr Tyr Tyr Cys Gln Gln
100 105 110

Gly Tyr Ser Gly Ser Asn Val Asp Asn Val
115 120

<210> SEQ ID NO 668
<211> LENGTH: 126
<212> TYPE: PRT
<213> ORGANISM: Oryctolagus cuniculus

<400> SEQUENCE: 668

Met Glu Thr Gly Leu Arg Trp Leu Leu Leu Val Ala Val Leu Lys Gly
1 5 10 15

Val Gln Cys Gln Glu Gln Leu Lys Glu Ser Gly Gly Arg Leu Val Thr
20 25 30

Pro Gly Thr Pro Leu Thr Leu Thr Cys Thr Ala Ser Gly Phe Ser Leu
35 40 45

Asn Asp His Ala Met Gly Trp Val Arg Gln Ala Pro Gly Lys Gly Leu
50 55 60

Glu Tyr Ile Gly Phe Ile Asn Ser Gly Gly Ser Ala Arg Tyr Ala Ser
65 70 75 80

Trp Ala Glu Gly Arg Phe Thr Ile Ser Arg Thr Ser Thr Thr Val Asp
85 90 95

Leu Lys Met Thr Ser Leu Thr Thr Glu Asp Thr Ala Thr Tyr Phe Cys
100 105 110

Val Arg Gly Gly Ala Val Trp Ser Ile His Ser Phe Asp Pro
115 120 125

<210> SEQ ID NO 669
<211> LENGTH: 366
<212> TYPE: DNA
<213> ORGANISM: Oryctolagus cuniculus

<400> SEQUENCE: 669
atggacacga gggcccccac tcagctgctg gggctcctgc tgctctggct cccaggtgcc 60
agatgtgcct atgatatgac ccagactcca gcctctgtgg aggtagctgt gggaggcaca 120
gtcaccatca attgccaggc cagtgagacc atttacagtt ggttatcctg gtatcagcag 180
aagccagggc agcctcccaa gctcctgatc taccaggcat ccgatctggc atctggggtc 240
ccatcgcgat tcagcggcag tggggctggg acagagtaca ctctcaccat cagcggcgtg 300
cagtgtgacg atgctgccac ttactactgt caacagggtt atagtggtag taatgttgat 360
aatgtt 366

<210> SEQ ID NO 670
<211> LENGTH: 378
<212> TYPE: DNA
<213> ORGANISM: Oryctolagus cuniculus

<400> SEQUENCE: 670
atggagactg ggctgcgctg gcttctcctg gtcgctgtgc tcaaaggtgt ccagtgtcag 60
gagcagctga aggagtccgg gggtcgcctg gtcacgcctg ggacacccct gacacttacc 120

-continued

```
tgcacagcct ctggattctc cctcaatgac catgcaatgg gctgggtccg ccaggctcca    180

gggaaggggc tggaatacat cggattcatt aatagtggtg gtagcgcacg ctacgcgagc    240

tgggcagaag gccgattcac catctccaga acctcgacca cggtggatct gaaaatgacc    300

agtctgacaa ccgaggacac ggccacctat ttctgtgtca gagggggtgc tgtttggagt    360

attcatagtt ttgatccc                                                  378
```

```
<210> SEQ ID NO 671
<211> LENGTH: 123
<212> TYPE: PRT
<213> ORGANISM: Oryctolagus cuniculus

<400> SEQUENCE: 671

Met Asp Thr Arg Ala Pro Thr Gln Leu Leu Gly Leu Leu Leu Leu Trp
1               5                   10                  15

Leu Pro Gly Ala Thr Phe Ala Ala Val Leu Thr Gln Thr Pro Ser Pro
            20                  25                  30

Val Ser Ala Ala Val Gly Gly Thr Val Ser Ile Ser Cys Gln Ala Ser
        35                  40                  45

Gln Ser Val Tyr Asp Asn Asn Tyr Leu Ser Trp Phe Gln Gln Lys Pro
    50                  55                  60

Gly Gln Pro Pro Lys Leu Leu Ile Tyr Gly Ala Ser Thr Leu Ala Ser
65                  70                  75                  80

Gly Val Pro Ser Arg Phe Val Gly Ser Gly Ser Gly Thr Gln Phe Thr
                85                  90                  95

Leu Thr Ile Thr Asp Val Gln Cys Asp Asp Ala Ala Thr Tyr Tyr Cys
            100                 105                 110

Ala Gly Val Tyr Asp Asp Asp Ser Asp Asn Ala
        115                 120


<210> SEQ ID NO 672
<211> LENGTH: 125
<212> TYPE: PRT
<213> ORGANISM: Oryctolagus cuniculus

<400> SEQUENCE: 672

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Val Tyr Tyr Met Asn Trp Val Arg Gln Ala Pro Gly Lys Gly Leu Glu
    50                  55                  60

Trp Ile Gly Phe Ile Thr Met Ser Asp Asn Ile Asn Tyr Ala Ser Trp
65                  70                  75                  80

Ala Lys Gly Arg Phe Thr Ile Ser Lys Thr Ser Thr Thr Val Asp Leu
                85                  90                  95

Lys Met Thr Ser Pro Thr Thr Glu Asp Thr Ala Thr Tyr Phe Cys Ala
            100                 105                 110

Arg Ser Arg Gly Trp Gly Thr Met Gly Arg Leu Asp Leu
        115                 120                 125


<210> SEQ ID NO 673
<211> LENGTH: 369
<212> TYPE: DNA
<213> ORGANISM: Oryctolagus cuniculus
```

<400> SEQUENCE: 673
atggacacga gggcccccac tcagctgctg gggctcctgc tgctctggct cccaggtgcc 60
acatttgccg ccgtgctgac ccagactcca tctcccgtgt ctgcagctgt gggaggcaca 120
gtcagcatca gttgccaggc cagtcagagt gtttatgaca acaactactt atcctggttt 180
cagcagaaac cagggcagcc tcccaagctc ctgatctatg gtgcatccac tctggcatct 240
ggggtcccat cgcggttcgt gggcagtgga tctgggacac agttcactct caccatcaca 300
gacgtgcagt gtgacgatgc tgccacttac tattgtgcag gcgtttatga tgatgatagt 360
gataatgcc 369

<210> SEQ ID NO 674
<211> LENGTH: 375
<212> TYPE: DNA
<213> ORGANISM: Oryctolagus cuniculus

<400> SEQUENCE: 674
atggagactg ggctgcgctg gcttctcctg gtggctgtgc tcaaaggtgt ccagtgtcag 60
tcgctggagg agtccggggg tcgcctggtc acccctggga cacccctgac actcacctgc 120
acagcctctg gattctccct cagtgtctac tacatgaact gggtccgcca ggctccaggg 180
aaggggctgg aatggatcgg attcattaca atgagtgata atataaatta cgcgagctgg 240
gcgaaaggcc gattcaccat ctccaaaacc tcgaccacgg tggatctgaa aatgaccagt 300
ccgacaaccg aggacacggc cacctatttc tgtgccagga gtcgtggctg ggtacaatg 360 ggtcggttgg atctc 375

<210> SEQ ID NO 675
<211> LENGTH: 123
<212> TYPE: PRT
<213> ORGANISM: Oryctolagus cuniculus

<400> SEQUENCE: 675

Met Asp Thr Arg Ala Pro Thr Gln Leu Leu Gly Leu Leu Leu Leu Trp
1 5 10 15

Leu Pro Gly Ala Ile Cys Asp Pro Val Leu Thr Gln Thr Pro Ser Pro
20 25 30

Val Ser Ala Pro Val Gly Gly Thr Val Ser Ile Ser Cys Gln Ala Ser
35 40 45

Gln Ser Val Tyr Glu Asn Asn Tyr Leu Ser Trp Phe Gln Gln Lys Pro
50 55 60

Gly Gln Pro Pro Lys Leu Leu Ile Tyr Gly Ala Ser Thr Leu Asp Ser
65 70 75 80

Gly Val Pro Ser Arg Phe Lys Gly Ser Gly Ser Gly Thr Gln Phe Thr
85 90 95

Leu Thr Ile Thr Asp Val Gln Cys Asp Asp Ala Ala Thr Tyr Tyr Cys
100 105 110

Ala Gly Val Tyr Asp Asp Asp Ser Asp Asp Ala
115 120

<210> SEQ ID NO 676
<211> LENGTH: 126
<212> TYPE: PRT
<213> ORGANISM: Oryctolagus cuniculus

<400> SEQUENCE: 676

```
Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Gly Leu Val Thr
            20                  25                  30

Pro Gly Gly Thr Leu Thr Leu Thr Cys Thr Ala Ser Gly Phe Ser Leu
        35                  40                  45

Asn Ala Tyr Tyr Met Asn Trp Val Arg Gln Ala Pro Gly Lys Gly Leu
    50                  55                  60

Glu Trp Ile Gly Phe Ile Thr Leu Asn Asn Asn Val Ala Tyr Ala Asn
65                  70                  75                  80

Trp Ala Lys Gly Arg Phe Thr Phe Ser Lys Thr Ser Thr Thr Val Asp
                85                  90                  95

Leu Lys Met Thr Ser Pro Thr Pro Glu Asp Thr Ala Thr Tyr Phe Cys
            100                 105                 110

Ala Arg Ser Arg Gly Trp Gly Ala Met Gly Arg Leu Asp Leu
        115                 120                 125


<210> SEQ ID NO 677
<211> LENGTH: 369
<212> TYPE: DNA
<213> ORGANISM: Oryctolagus cuniculus

<400> SEQUENCE: 677

atggacacga gggcccccac tcagctgctg gggctcctgc tgctctggct cccaggtgcc      60

atatgtgacc ctgtgctgac ccagactcca tctcccgtat ctgcacctgt gggaggcaca     120

gtcagcatca gttgccaggc cagtcagagt gtttatgaga acaactattt atcctggttt     180

cagcagaaac cagggcagcc tcccaagctc ctgatctatg gtgcatccac tctggattct     240

ggggtcccat cgcggttcaa aggcagtgga tctgggacac agttcactct caccattaca     300

gacgtgcagt gtgacgatgc tgccacttac tattgtgcag gcgtttatga tgatgatagt     360

gatgatgcc                                                             369


<210> SEQ ID NO 678
<211> LENGTH: 378
<212> TYPE: DNA
<213> ORGANISM: Oryctolagus cuniculus

<400> SEQUENCE: 678

atggagactg ggctgcgctg gcttctcctg gtggctgtgc tcaaaggtgt ccagtgtcag      60

gagcagctga aggagtccgg aggaggcctg gtaacgcctg gaggaaccct gacactcacc     120

tgcacagcct ctggattctc cctcaatgcc tactacatga actgggtccg ccaggctcca     180

gggaaggggc tggaatggat cggattcatt actctgaata ataatgtagc ttacgcgaac     240

tgggcgaaag gccgattcac cttctccaaa acctcgacca cggtggatct gaaaatgacc     300

agtccgacac ccgaggacac ggccacctat ttctgtgcca ggagtcgtgg ctggggtgca     360

atgggtcggt tggatctc                                                   378


<210> SEQ ID NO 679
<211> LENGTH: 122
<212> TYPE: PRT
<213> ORGANISM: Oryctolagus cuniculus

<400> SEQUENCE: 679

Met Asp Thr Arg Ala Pro Thr Gln Leu Leu Gly Leu Leu Leu Leu Trp
1               5                   10                  15
```

```
Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ala Ser
        35                  40                  45

Gln Ser Val Asp Asp Asn Asn Trp Leu Gly Trp Tyr Gln Gln Lys Arg
    50                  55                  60

Gly Gln Pro Pro Lys Tyr Leu Ile Tyr Ser Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Gly Phe Ser Gly Asn Ile Phe Ala
        115                 120
```

<210> SEQ ID NO 680
<211> LENGTH: 122
<212> TYPE: PRT
<213> ORGANISM: Oryctolagus cuniculus

<400> SEQUENCE: 680

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Ser Trp Val Arg Gln Ala Pro Gly Lys Gly Leu Glu
    50                  55                  60

Trp Ile Gly Ile Ile Gly Gly Phe Gly Thr Thr Tyr Tyr Ala Thr Trp
65                  70                  75                  80

Ala Lys Gly Arg Phe Thr Ile Ser Lys Thr Ser Thr Thr Val Asp Leu
                85                  90                  95

Arg Ile Thr Ser Pro Thr Thr Glu Asp Thr Ala Thr Tyr Phe Cys Ala
            100                 105                 110

Arg Gly Gly Pro Gly Asn Gly Gly Asp Ile
        115                 120
```

<210> SEQ ID NO 681
<211> LENGTH: 366
<212> TYPE: DNA
<213> ORGANISM: Oryctolagus cuniculus

<400> SEQUENCE: 681

```
atggacacga gggcccccac tcagctgctg gggctcctgc tgctctggct cccaggtgcc      60

acatttgccc aagtgctgac ccagactcca tcgcctgtgt ctgcagctgt gggaggcaca     120

gtcaccatca actgccaggc cagtcagagt gttgatgata acaactggtt aggctggtat     180

cagcagaaac gagggcagcc tcccaagtac ctgatctatt ctgcatccac tctggcatct     240

ggggtcccat cgcggttcaa aggcagtgga tctgggacac agttcactct caccatcagc     300

gacctggagt gtgacgatgc tgccacttac tactgtgcag gcggttttag tggtaatatc     360

tttgct                                                                366
```

<210> SEQ ID NO 682
<211> LENGTH: 366
<212> TYPE: DNA

<213> ORGANISM: Oryctolagus cuniculus

<400> SEQUENCE: 682
atggagactg ggctgcgctg gcttctcctg gtcgctgtgc tcaaaggtgt ccagtgtcag 60
tcggtggagg agtccggggg tcgcctggtc acgcctggga cacccctgac actcacctgc 120
acagtctctg gcttctccct cagtagctat gcaatgagct gggtccgcca ggctccagga 180
aaggggctgg agtggatcgg aatcattggt ggttttggta ccacatacta cgcgacctgg 240
gcgaaaggcc gattcaccat ctccaaaacc tcgaccacgg tggatctgag aatcaccagt 300
ccgacaaccg aggacacggc cacctatttc tgtgccagag gtggtcctgg taatggtggt 360
gacatc 366

<210> SEQ ID NO 683
<211> LENGTH: 122
<212> TYPE: PRT
<213> ORGANISM: Oryctolagus cuniculus

<400> SEQUENCE: 683

Met Asp Thr Arg Ala Pro Thr Gln Leu Leu Gly Leu Leu Leu Leu Trp
1 5 10 15

Leu Pro Gly Ala Thr Phe Ala Ala Val Leu Thr Gln Thr Pro Ser Pro
20 25 30

Val Ser Val Pro Val Gly Gly Thr Val Thr Ile Lys Cys Gln Ser Ser
35 40 45

Gln Ser Val Tyr Asn Asn Phe Leu Ser Trp Tyr Gln Gln Lys Pro Gly
50 55 60

Gln Pro Pro Lys Leu Leu Ile Tyr Gln Ala Ser Lys Leu Ala Ser Gly
65 70 75 80

Val Pro Asp Arg Phe Ser Gly Ser Gly Ser Gly Thr Gln Phe Thr Leu
85 90 95

Thr Ile Ser Gly Val Gln Cys Asp Asp Ala Ala Thr Tyr Tyr Cys Leu
100 105 110

Gly Gly Tyr Asp Asp Asp Ala Asp Asn Ala
115 120

<210> SEQ ID NO 684
<211> LENGTH: 128
<212> TYPE: PRT
<213> ORGANISM: Oryctolagus cuniculus

<400> SEQUENCE: 684

Met Glu Thr Gly Leu Arg Trp Leu Leu Leu Val Ala Val Leu Lys Gly
1 5 10 15

Val Gln Cys Gln Ser Val Glu Glu Ser Gly Gly Arg Leu Val Thr Pro
20 25 30

Gly Thr Pro Leu Thr Leu Thr Cys Thr Val Ser Gly Ile Asp Leu Ser
35 40 45

Asp Tyr Ala Met Ser Trp Val Arg Gln Ala Pro Gly Lys Gly Leu Glu
50 55 60

Trp Ile Gly Ile Ile Tyr Ala Gly Ser Gly Ser Thr Trp Tyr Ala Ser
65 70 75 80

Trp Ala Lys Gly Arg Phe Thr Ile Ser Lys Thr Ser Thr Thr Val Asp
85 90 95

Leu Lys Ile Thr Ser Pro Thr Thr Glu Asp Thr Ala Thr Tyr Phe Cys
100 105 110

Ala Arg Asp Gly Tyr Asp Asp Tyr Gly Asp Phe Asp Arg Leu Asp Leu
115 120 125

<210> SEQ ID NO 685
<211> LENGTH: 366
<212> TYPE: DNA
<213> ORGANISM: Oryctolagus cuniculus

<400> SEQUENCE: 685
atggacacga gggcccccac tcagctgctg gggctcctgc tgctctggct cccaggtgcc 60
acatttgcag ccgtgctgac ccagacacca tcgcccgtgt ctgtacctgt gggaggcaca 120
gtcaccatca agtgccagtc cagtcagagt gtttataata atttcttatc gtggtatcag 180
cagaaaccag ggcagcctcc caagctcctg atctaccagg catccaaact ggcatctggg 240
gtcccagata ggttcagcgg cagtggatct gggacacagt tcactctcac catcagcggc 300
gtgcagtgtg acgatgctgc cacttactac tgtctaggcg gttatgatga tgatgctgat 360
aatgct 366

<210> SEQ ID NO 686
<211> LENGTH: 384
<212> TYPE: DNA
<213> ORGANISM: Oryctolagus cuniculus

<400> SEQUENCE: 686
atggagactg ggctgcgctg gcttctcctg gtcgctgtgc tcaaaggtgt ccagtgtcag 60
tcggtggagg agtccggggg tcgcctggtc acgcctggga cacccctgac gctcacctgc 120
acagtctctg gaatcgacct cagtgactat gcaatgagct gggtccgcca ggctccaggg 180
aaggggctgg aatggatcgg aatcatttat gctggtagtg gtagcacatg gtacgcgagc 240
tgggcgaaag gccgattcac catctccaaa acctcgacca cggtggatct gaaaatcacc 300
agtccgacaa ccgaggacac ggccacctat ttctgtgcca gagatggata cgatgactat 360
ggtgatttcg atcgattgga tctc 384

<210> SEQ ID NO 687
<211> LENGTH: 122
<212> TYPE: PRT
<213> ORGANISM: Oryctolagus cuniculus

<400> SEQUENCE: 687

Met Asp Thr Arg Ala Pro Thr Gln Leu Leu Gly Leu Leu Leu Leu Trp
1 5 10 15

Leu Pro Gly Ala Arg Cys Ala Tyr Asp Met Thr Gln Thr Pro Ala Ser
20 25 30

Val Ser Ala Ala Val Gly Gly Thr Val Thr Ile Lys Cys Gln Ala Ser
35 40 45

Gln Ser Ile Asn Asn Glu Leu Ser Trp Tyr Gln Gln Lys Ser Gly Gln
50 55 60

Arg Pro Lys Leu Leu Ile Tyr Arg Ala Ser Thr Leu Ala Ser Gly Val
65 70 75 80

Ser Ser Arg Phe Lys Gly Ser Gly Ser Gly Thr Glu Phe Thr Leu Thr
85 90 95

Ile Ser Asp Leu Glu Cys Ala Asp Ala Ala Thr Tyr Tyr Cys Gln Gln
100 105 110

Gly Tyr Ser Leu Arg Asn Ile Asp Asn Ala
115 120

<210> SEQ ID NO 688
<211> LENGTH: 125
<212> TYPE: PRT
<213> ORGANISM: Oryctolagus cuniculus

<400> SEQUENCE: 688

```
Met Glu Thr Gly Leu Arg Trp Leu Leu Leu Val Ala Val Leu Ser Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Tyr Met Thr Trp Val Arg Gln Ala Pro Gly Lys Gly Leu Glu
    50                  55                  60

Trp Ile Gly Met Ile Tyr Gly Ser Asp Glu Thr Ala Tyr Ala Asn Trp
65                  70                  75                  80

Ala Ile Gly Arg Phe Thr Ile Ser Lys Thr Ser Thr Thr Val Asp Leu
                85                  90                  95

Lys Met Thr Ser Leu Thr Ala Ala Asp Thr Ala Thr Tyr Phe Cys Ala
            100                 105                 110

Arg Asp Asp Ser Ser Asp Trp Asp Ala Lys Phe Asn Leu
        115                 120                 125
```

<210> SEQ ID NO 689
<211> LENGTH: 366
<212> TYPE: DNA
<213> ORGANISM: Oryctolagus cuniculus

<400> SEQUENCE: 689

```
atggacacga gggcccccac tcagctgctg gggctcctgc tgctctggct cccaggtgcc      60

agatgtgcct atgatatgac ccagactcca gcctcggtgt ctgcagctgt gggaggcaca     120

gtcaccatca aatgccaggc cagtcagagc attaacaatg aattatcctg gtatcagcag     180

aaatcagggc agcgtcccaa gctcctgatc tatagggcat ccactctggc atctggggtc     240

tcatcgcggt tcaaaggcag tggatctggg acagagttca ctctcaccat cagcgacctg     300

gagtgtgccg atgctgccac ttactactgt caacagggtt atagtctgag gaatattgat     360

aatgct                                                                366
```

<210> SEQ ID NO 690
<211> LENGTH: 375
<212> TYPE: DNA
<213> ORGANISM: Oryctolagus cuniculus

<400> SEQUENCE: 690

```
atggagactg ggctgcgctg gcttctcctg gtcgctgtgc tctcaggtgt ccagtgtcag      60

tcgctggagg agtccggggg tcgcctggtc acgcctggga cacccctgac actcacctgc     120

acagcctctg gattctccct cagtaactac tacatgacct gggtccgcca ggctccaggg     180

aaggggctgg aatggatcgg aatgatttat ggtagtgatg aaacagccta cgcgaactgg     240

gcgataggcc gattcaccat ctccaaaacc tcgaccacgg tggatctgaa aatgaccagt     300

ctgacagccg cggacacggc cacctatttc tgtgccagag atgatagtag tgactgggat     360

gcaaaattta acttg                                                      375
```

<210> SEQ ID NO 691
<211> LENGTH: 450

<212> TYPE: PRT
<213> ORGANISM: Oryctolagus cuniculus

<400> SEQUENCE: 691

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Met Thr Trp Val Arg Gln Ala Pro Gly Lys Gly Leu Glu Trp Val
        35                  40                  45

Gly Met Ile Tyr Gly Ser Asp Glu Thr Ala Tyr Ala Asn Trp Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 692
<211> LENGTH: 450
<212> TYPE: PRT
<213> ORGANISM: Oryctolagus cuniculus

<400> SEQUENCE: 692

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Asn Tyr
20 25 30

Tyr Met Thr Trp Val Arg Gln Ala Pro Gly Lys Gly Leu Glu Trp Val
35 40 45

Gly Met Ile Tyr Gly Ser Asp Glu Thr Ala Tyr Ala Asn Ser Ala Ile
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Asp Ser Ser Asp Trp Asp Ala Lys Phe Asn Leu Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Ala Ser Thr Tyr Arg
290 295 300

Val Val Ser Val Leu Thr Val Leu His Gln Asp Trp Leu Asn Gly Lys

```
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 693
<211> LENGTH: 217
<212> TYPE: PRT
<213> ORGANISM: Oryctolagus cuniculus

<400> SEQUENCE: 693

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Asn Glu
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Leu Arg Asn
                85                  90                  95

Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 694
<211> LENGTH: 33
<212> TYPE: DNA
<213> ORGANISM: Oryctolagus cuniculus

<400> SEQUENCE: 694
caggccagtc agagcattaa caatgagtta tcc 33

<210> SEQ ID NO 695
<211> LENGTH: 36
<212> TYPE: DNA
<213> ORGANISM: Oryctolagus cuniculus

<400> SEQUENCE: 695
caacagggtt atagtctgag gaacattgat aatgct 36

<210> SEQ ID NO 696
<211> LENGTH: 48
<212> TYPE: DNA
<213> ORGANISM: Oryctolagus cuniculus

<400> SEQUENCE: 696
atcatctatg gtagtgatga aaccgcctac gctacctccg ctataggc 48

<210> SEQ ID NO 697
<211> LENGTH: 36
<212> TYPE: DNA
<213> ORGANISM: Oryctolagus cuniculus

<400> SEQUENCE: 697
gatgatagta gtgactggga tgcaaagttc aacttg 36

<210> SEQ ID NO 698
<211> LENGTH: 336
<212> TYPE: DNA
<213> ORGANISM: Oryctolagus cuniculus

<400> SEQUENCE: 698
gctatccaga tgacccagtc tccttcctcc ctgtctgcat ctgtaggaga cagagtcacc 60
atcacttgcc aggccagtca gagcattaac aatgagttat cctggtatca gcagaaacca 120
gggaaagccc ctaagctcct gatctatagg gcatccactc tggcatctgg ggtcccatca 180
aggttcagcg gcagtggatc tgggacagac ttcactctca ccatcagcag cctgcagcct 240
gatgattttg caacttatta ctgccaacag ggttatagtc tgaggaacat tgataatgct 300
ttcggcggag ggaccaaggt ggaaatcaaa cgtacg 336

<210> SEQ ID NO 699
<211> LENGTH: 112
<212> TYPE: PRT
<213> ORGANISM: Oryctolagus cuniculus

<400> SEQUENCE: 699

Ala Ile Gln Met Thr Gln Ser Pro Ser Ser Leu Ser Ala Ser Val Gly
1 5 10 15

Asp Arg Val Thr Ile Thr Cys Gln Ala Ser Gln Ser Ile Asn Asn Glu
20 25 30

Leu Ser Trp Tyr Gln Gln Lys Pro Gly Lys Ala Pro Lys Leu Leu Ile
35 40 45

Tyr Arg Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Asp Asp Phe Ala Thr Tyr Tyr Cys Gln Gln Gly Tyr Ser Leu Arg Asn
85 90 95

Ile Asp Asn Ala Phe Gly Gly Gly Thr Lys Val Glu Ile Lys Arg Thr
100 105 110

<210> SEQ ID NO 700
<211> LENGTH: 360
<212> TYPE: DNA
<213> ORGANISM: Oryctolagus cuniculus

<400> SEQUENCE: 700
gaggtgcagc tggtggagtc tgggggaggc ttggtccagc ctggggggtc cctgagactc 60
tcctgtgcag cctctggatt ctccctcagt aactactacg tgacctgggt ccgtcaggct 120
ccagggaagg ggctggagtg ggtcggcatc atctatggta gtgatgaaac cgcctacgct 180
acctccgcta taggccgatt caccatctcc agagacaatt ccaagaacac cctgtatctt 240
caaatgaaca gcctgagagc tgaggacact gctgtgtatt actgtgctag agatgatagt 300
agtgactggg atgcaaagtt caacttgtgg ggccaaggga ccctcgtcac cgtctcgagc 360

<210> SEQ ID NO 701
<211> LENGTH: 651
<212> TYPE: DNA
<213> ORGANISM: Oryctolagus cuniculus

<400> SEQUENCE: 701
gctatccaga tgacccagtc tccttcctcc ctgtctgcat ctgtaggaga cagagtcacc 60
atcacttgcc aggccagtca gagcattaac aatgagttat cctggtatca gcagaaacca 120
gggaaagccc ctaagctcct gatctatagg gcatccactc tggcatctgg ggtcccatca 180
aggttcagcg gcagtggatc tgggacagac ttcactctca ccatcagcag cctgcagcct 240
gatgattttg caacttatta ctgccaacag ggttatagtc tgaggaacat tgataatgct 300
ttcggcggag ggaccaaggt ggaaatcaaa cgtacggtgg ctgcaccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 702
<211> LENGTH: 217
<212> TYPE: PRT
<213> ORGANISM: Oryctolagus cuniculus

<400> SEQUENCE: 702

Ala Ile Gln Met Thr Gln Ser Pro Ser Ser Leu Ser Ala Ser Val Gly
1 5 10 15

Asp Arg Val Thr Ile Thr Cys Gln Ala Ser Gln Ser Ile Asn Asn Glu
20 25 30

Leu Ser Trp Tyr Gln Gln Lys Pro Gly Lys Ala Pro Lys Leu Leu Ile
35 40 45

Tyr Arg Ala Ser Thr Leu Ala Ser Gly Val Pro Ser Arg Phe Ser Gly
50 55 60

-continued

```
Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Gly Tyr Ser Leu Arg Asn
                85                  90                  95

Ile Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 703
<211> LENGTH: 1350
<212> TYPE: DNA
<213> ORGANISM: Oryctolagus cuniculus

<400> SEQUENCE: 703

```
gaggtgcagc tggtggagtc tgggggaggc ttggtccagc ctgggggggtc cctgagactc     60

tcctgtgcag cctctggatt ctccctcagt aactactacg tgacctgggt ccgtcaggct    120

ccagggaagg ggctggagtg ggtcggcatc atctatggta gtgatgaaac cgcctacgct    180

acctccgcta taggccgatt caccatctcc agagacaatt ccaagaacac cctgtatctt    240

caaatgaaca gcctgagagc tgaggacact gctgtgtatt actgtgctag agatgatagt    300

agtgactggg atgcaaagtt caacttgtgg ggccaaggga ccctcgtcac cgtctcgagc    360

gcctccacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagag agttgagccc    660

aaatcttgtg acaaaactca cacatgccca ccgtgcccag cacctgaact cctgggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacgcc    900

agcacgtacc gtgtggtcag cgtcctcacc gtcctgcacc aggactggct gaatggcaag    960

gagtacaagt gcaaggtctc caacaaagcc ctcccagccc ccatcgagaa aaccatctcc   1020

aaagccaaag ggcagccccg agaaccacag gtgtacaccc tgcccccatc ccgggaggag   1080

atgaccaaga accaggtcag cctgacctgc ctggtcaaag gcttctatcc cagcgacatc   1140

gccgtggagt gggagagcaa tgggcagccg gagaacaact acaagaccac gcctcccgtg   1200
```

```
ctggactccg acggctcctt cttcctctac agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                    1350


<210> SEQ ID NO 704
<211> LENGTH: 450
<212> TYPE: PRT
<213> ORGANISM: Oryctolagus cuniculus

<400> SEQUENCE: 704

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Tyr Val Thr Trp Val Arg Gln Ala Pro Gly Lys Gly Leu Glu Trp Val
        35                  40                  45

Gly Ile Ile Tyr Gly Ser Asp Glu Thr Ala Tyr Ala Thr Ser Ala Ile
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Asp Ser Ser Asp Trp Asp Ala Lys Phe Asn Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 705
<211> LENGTH: 705
<212> TYPE: DNA
<213> ORGANISM: Oryctolagus cuniculus

<400> SEQUENCE: 705

atgaagtggg taacctttat ttcccttctg tttctcttta gcagcgctta ttccgctatc     60

cagatgaccc agtctccttc ctccctgtct gcatctgtag gagacagagt caccatcact    120

tgccaggcca gtcagagcat taacaatgag ttatcctggt atcagcagaa accagggaaa    180

gcccctaagc tcctgatcta tagggcatcc actctggcat ctggggtccc atcaaggttc    240

agcggcagtg gatctgggac agacttcact ctcaccatca gcagcctgca gcctgatgat    300

tttgcaactt attactgcca acagggttat agtctgagga acattgataa tgctttcggc    360

ggagggacca aggtggaaat caaacgtacg gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgt                    705


<210> SEQ ID NO 706
<211> LENGTH: 235
<212> TYPE: PRT
<213> ORGANISM: Oryctolagus cuniculus

<400> SEQUENCE: 706

Met Lys Trp Val Thr Phe Ile Ser Leu Leu Phe Leu Phe Ser Ser Ala
1               5                   10                  15

Tyr Ser Ala Ile Gln Met Thr Gln Ser Pro Ser Ser Leu Ser Ala Ser
            20                  25                  30

Val Gly Asp Arg Val Thr Ile Thr Cys Gln Ala Ser Gln Ser Ile Asn
        35                  40                  45

Asn Glu Leu Ser Trp Tyr Gln Gln Lys Pro Gly Lys Ala Pro Lys Leu
    50                  55                  60

Leu Ile Tyr Arg Ala Ser Thr Leu Ala Ser Gly Val Pro Ser Arg Phe
65                  70                  75                  80

Ser Gly Ser Gly Ser Gly Thr Asp Phe Thr Leu Thr Ile Ser Ser Leu
                85                  90                  95
```

Gln Pro Asp Asp Phe Ala Thr Tyr Tyr Cys Gln Gln Gly Tyr Ser Leu
100 105 110

Arg Asn Ile Asp Asn Ala Phe Gly Gly Gly Thr Lys Val Glu Ile Lys
115 120 125

Arg Thr Val Ala Ala Pro Ser Val Phe Ile Phe Pro Pro Ser Asp Glu
130 135 140

Gln Leu Lys Ser Gly Thr Ala Ser Val Val Cys Leu Leu Asn Asn Phe
145 150 155 160

Tyr Pro Arg Glu Ala Lys Val Gln Trp Lys Val Asp Asn Ala Leu Gln
165 170 175

Ser Gly Asn Ser Gln Glu Ser Val Thr Glu Gln Asp Ser Lys Asp Ser
180 185 190

Thr Tyr Ser Leu Ser Ser Thr Leu Thr Leu Ser Lys Ala Asp Tyr Glu
195 200 205

Lys His Lys Val Tyr Ala Cys Glu Val Thr His Gln Gly Leu Ser Ser
210 215 220

Pro Val Thr Lys Ser Phe Asn Arg Gly Glu Cys
225 230 235

<210> SEQ ID NO 707
<211> LENGTH: 1404
<212> TYPE: DNA
<213> ORGANISM: Oryctolagus cuniculus

<400> SEQUENCE: 707
atgaagtggg taacctttat ttcccttctg tttctcttta gcagcgctta ttccgaggtg 60
cagctggtgg agtctggggg aggcttggtc cagcctgggg ggtccctgag actctcctgt 120
gcagcctctg gattctccct cagtaactac tacgtgacct gggtccgtca ggctccaggg 180
aaggggctgg agtgggtcgg catcatctat ggtagtgatg aaaccgccta cgctacctcc 240
gctataggcc gattcaccat ctccagagac aattccaaga acaccctgta tcttcaaatg 300
aacagcctga gagctgagga cactgctgtg tattactgtg ctagagatga tagtagtgac 360
tgggatgcaa agttcaactt gtggggccaa gggaccctcg tcaccgtctc gagcgcctcc 420
accaagggcc catcggtctt ccccctggca ccctcctcca agagcacctc tgggggcaca 480
gcggccctgg gctgcctggt caaggactac ttccccgaac cggtgacggt gtcgtggaac 540
tcaggcgccc tgaccagcgg cgtgcacacc ttcccggctg tcctacagtc ctcaggactc 600
tactccctca gcagcgtggt gaccgtgccc tccagcagct tgggcaccca gacctacatc 660
tgcaacgtga atcacaagcc cagcaacacc aaggtggaca agagagttga gcccaaatct 720
tgtgacaaaa ctcacacatg cccaccgtgc ccagcacctg aactcctggg gggaccgtca 780
gtcttcctct tccccccaaa acccaaggac accctcatga tctcccggac ccctgaggtc 840
acatgcgtgg tggtggacgt gagccacgaa gaccctgagg tcaagttcaa ctggtacgtg 900
gacggcgtgg aggtgcataa tgccaagaca aagccgcggg aggagcagta cgccagcacg 960
taccgtgtgg tcagcgtcct caccgtcctg caccaggact ggctgaatgg caaggagtac 1020
aagtgcaagg tctccaacaa agccctccca gcccccatcg agaaaaccat ctccaaagcc 1080
aaagggcagc cccgagaacc acaggtgtac accctgcccc catcccggga ggagatgacc 1140
aagaaccagg tcagcctgac ctgcctggtc aaaggcttct atcccagcga catcgccgtg 1200
gagtgggaga gcaatgggca gccggagaac aactacaaga ccacgcctcc cgtgctggac 1260
tccgacggct ccttcttcct ctacagcaag ctcaccgtgg acaagagcag gtggcagcag 1320
gggaacgtct tctcatgctc cgtgatgcat gaggctctgc acaaccacta cacgcagaag 1380
agcctctccc tgtctccggg taaa 1404

<210> SEQ ID NO 708
<211> LENGTH: 468
<212> TYPE: PRT
<213> ORGANISM: Oryctolagus cuniculus

<400> SEQUENCE: 708

Met Lys Trp Val Thr Phe Ile Ser Leu Leu Phe Leu Phe Ser Ser Ala
1 5 10 15

Tyr Ser Glu Val Gln Leu Val Glu Ser Gly Gly Gly Leu Val Gln Pro
20 25 30

Gly Gly Ser Leu Arg Leu Ser Cys Ala Ala Ser Gly Phe Ser Leu Ser
35 40 45

Asn Tyr Tyr Val Thr Trp Val Arg Gln Ala Pro Gly Lys Gly Leu Glu
50 55 60

Trp Val Gly Ile Ile Tyr Gly Ser Asp Glu Thr Ala Tyr Ala Thr Ser
65 70 75 80

Ala Ile Gly Arg Phe Thr Ile Ser Arg Asp Asn Ser Lys Asn Thr Leu
85 90 95

Tyr Leu Gln Met Asn Ser Leu Arg Ala Glu Asp Thr Ala Val Tyr Tyr
100 105 110

Cys Ala Arg Asp Asp Ser Ser Asp Trp Asp Ala Lys Phe Asn Leu Trp
115 120 125

Gly Gln Gly Thr Leu Val Thr Val Ser Ser Ala Ser Thr Lys Gly Pro
130 135 140

Ser Val Phe Pro Leu Ala Pro Ser Ser Lys Ser Thr Ser Gly Gly Thr
145 150 155 160

Ala Ala Leu Gly Cys Leu Val Lys Asp Tyr Phe Pro Glu Pro Val Thr
165 170 175

Val Ser Trp Asn Ser Gly Ala Leu Thr Ser Gly Val His Thr Phe Pro
180 185 190

Ala Val Leu Gln Ser Ser Gly Leu Tyr Ser Leu Ser Ser Val Val Thr
195 200 205

Val Pro Ser Ser Ser Leu Gly Thr Gln Thr Tyr Ile Cys Asn Val Asn
210 215 220

His Lys Pro Ser Asn Thr Lys Val Asp Lys Arg Val Glu Pro Lys Ser
225 230 235 240

Cys Asp Lys Thr His Thr Cys Pro Pro Cys Pro Ala Pro Glu Leu Leu
245 250 255

Gly Gly Pro Ser Val Phe Leu Phe Pro Pro Lys Pro Lys Asp Thr Leu
260 265 270

Met Ile Ser Arg Thr Pro Glu Val Thr Cys Val Val Val Asp Val Ser
275 280 285

His Glu Asp Pro Glu Val Lys Phe Asn Trp Tyr Val Asp Gly Val Glu
290 295 300

Val His Asn Ala Lys Thr Lys Pro Arg Glu Glu Gln Tyr Ala Ser Thr
305 310 315 320

Tyr Arg Val Val Ser Val Leu Thr Val Leu His Gln Asp Trp Leu Asn
325 330 335

Gly Lys Glu Tyr Lys Cys Lys Val Ser Asn Lys Ala Leu Pro Ala Pro
340 345 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 709
<211> LENGTH: 111
<212> TYPE: PRT
<213> ORGANISM: Oryctolagus cuniculus

<400> SEQUENCE: 709

Ala Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Glu
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Gly Tyr Ser Leu Arg Asn
                85                  90                  95

Ile Asp Asn Ala Phe Gly Gly Gly Thr Lys Val Glu Ile Lys Arg
            100                 105                 110

<210> SEQ ID NO 710
<211> LENGTH: 11
<212> TYPE: PRT
<213> ORGANISM: Homo sapiens

<400> SEQUENCE: 710

Arg Ala Ser Gln Gly Ile Arg Asn Asp Leu Gly
1               5                   10

<210> SEQ ID NO 711
<211> LENGTH: 11
<212> TYPE: PRT
<213> ORGANISM: Homo sapiens

<400> SEQUENCE: 711

Arg Ala Ser Gln Gly Ile Ser Asn Tyr Leu Ala
1               5                   10

<210> SEQ ID NO 712
<211> LENGTH: 11
<212> TYPE: PRT

<213> ORGANISM: Homo sapiens

<400> SEQUENCE: 712

Arg Ala Ser Gln Ser Ile Ser Ser Trp Leu Ala
1 5 10

<210> SEQ ID NO 713
<211> LENGTH: 7
<212> TYPE: PRT
<213> ORGANISM: Homo sapiens

<400> SEQUENCE: 713

Ala Ala Ser Ser Leu Gln Ser
1 5

<210> SEQ ID NO 714
<211> LENGTH: 7
<212> TYPE: PRT
<213> ORGANISM: Homo sapiens

<400> SEQUENCE: 714

Ala Ala Ser Thr Leu Gln Ser
1 5

<210> SEQ ID NO 715
<211> LENGTH: 7
<212> TYPE: PRT
<213> ORGANISM: Homo sapiens

<400> SEQUENCE: 715

Lys Ala Ser Ser Leu Glu Ser
1 5

<210> SEQ ID NO 716
<211> LENGTH: 5
<212> TYPE: PRT
<213> ORGANISM: Homo sapiens

<400> SEQUENCE: 716

Ser Asn Tyr Met Ser
1 5

<210> SEQ ID NO 717
<211> LENGTH: 16
<212> TYPE: PRT
<213> ORGANISM: Homo sapiens

<400> SEQUENCE: 717

Val Ile Tyr Ser Gly Gly Ser Thr Tyr Tyr Ala Asp Ser Val Lys Gly
1 5 10 15

<210> SEQ ID NO 718
<211> LENGTH: 17
<212> TYPE: PRT
<213> ORGANISM: Homo sapiens

<400> SEQUENCE: 718

Val Ile Tyr Ser Gly Gly Ser Ser Thr Tyr Tyr Ala Asp Ser Val Lys
1 5 10 15

Gly

<210> SEQ ID NO 719
<211> LENGTH: 330
<212> TYPE: PRT

<213> ORGANISM: Artificial Sequence
<220> FEATURE:
<223> OTHER INFORMATION: Gamma-1 constant domain

<400> SEQUENCE: 719

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 720
<211> LENGTH: 297
<212> TYPE: DNA
<213> ORGANISM: Oryctolagus cuniculus

<400> SEQUENCE: 720

```
atccagatga cccagtctcc ttcctccctg tctgcatctg taggagacag agtcaccatc     60
```

-continued

```
acttgccagg ccagtcagag cattaacaat gagttatcct ggtatcagca gaaaccaggg    120

aaagccccta agctcctgat ctatagggca tccactctgg catctggggt cccatcaagg    180

ttcagcggca gtggatctgg gacagacttc actctcacca tcagcagcct gcagcctgat    240

gattttgcaa cttattactg ccaacagggt tatagtctga ggaacattga taatgct       297
```

```
<210> SEQ ID NO 721
<211> LENGTH: 333
<212> TYPE: DNA
<213> ORGANISM: Oryctolagus cuniculus

<400> SEQUENCE: 721

gcctatgata tgacccagac tccagcctcg gtgtctgcag ctgtgggagg cacagtcacc     60

atcaagtgcc aggccagtca gagcattaac aatgaattat cctggtatca gcagaaacca    120

gggcagcgtc ccaagctcct gatctatagg gcatccactc tggcatctgg ggtctcatcg    180

cggttcaaag gcagtggatc tgggacagag ttcactctca ccatcagcga cctggagtgt    240

gccgatgctg ccacttacta ctgtcaacag ggttatagtc tgaggaatat tgataatgct    300

ttcggcggag ggaccgaggt ggtggtcaaa cgt                                 333
```

```
<210> SEQ ID NO 722
<211> LENGTH: 648
<212> TYPE: DNA
<213> ORGANISM: Oryctolagus cuniculus

<400> SEQUENCE: 722

atccagatga cccagtctcc ttcctccctg tctgcatctg taggagacag agtcaccatc     60

acttgccagg ccagtcagag cattaacaat gagttatcct ggtatcagca gaaaccaggg    120

aaagccccta agctcctgat ctatagggca tccactctgg catctggggt cccatcaagg    180

ttcagcggca gtggatctgg gacagacttc actctcacca tcagcagcct gcagcctgat    240

gattttgcaa cttattactg ccaacagggt tatagtctga ggaacattga taatgctttc    300

ggcggaggga ccaaggtgga aatcaaacgt acggtggctg caccatctgt cttcatcttc    360

ccgccatctg atgagcagtt gaaatctgga actgcctctg ttgtgtgcct gctgaataac    420

ttctatccca gagaggccaa agtacagtgg aaggtggata acgccctcca atcgggtaac    480

tcccaggaga gtgtcacaga gcaggacagc aaggacagca cctacagcct cagcagcacc    540

ctgacgctga gcaaagcaga ctacgagaaa cacaaagtct acgcctgcga agtcacccat    600

cagggcctga gctcgcccgt cacaaagagc ttcaacaggg gagagtgt                 648
```

```
<210> SEQ ID NO 723
<211> LENGTH: 333
<212> TYPE: DNA
<213> ORGANISM: Oryctolagus cuniculus

<400> SEQUENCE: 723

gctatccaga tgacccagtc tccttcctcc ctgtctgcat ctgtaggaga cagagtcacc     60

atcacttgcc aggccagtca gagcattaac aatgagttat cctggtatca gcagaaacca    120

gggaaagccc ctaagctcct gatctatagg gcatccactc tggcatctgg ggtcccatca    180

aggttcagcg gcagtggatc tgggacagac ttcactctca ccatcagcag cctgcagcct    240

gatgattttg caacttatta ctgccaacag ggttatagtc tgaggaacat tgataatgct    300

ttcggcggag ggaccaaggt ggaaatcaaa cgt                                 333
```

<210> SEQ ID NO 724
<211> LENGTH: 327
<212> TYPE: DNA
<213> ORGANISM: Oryctolagus cuniculus

<400> SEQUENCE: 724
gaggtgcagc tggtggagtc tgggggaggc ttggtccagc ctgggggtc cctgagactc 60 tcctgtgcag cctctggatt ctccctcagt aactactacg tgacctgggt ccgtcaggct 120
ccagggaagg ggctggagtg ggtcggcatc atctatggta gtgatgaaac cgcctacgct 180
acctccgcta taggccgatt caccatctcc agagacaatt ccaagaacac cctgtatctt 240
caaatgaaca gcctgagagc tgaggacact gctgtgtatt actgtgctag agatgatagt 300
agtgactggg atgcaaagtt caacttg 327

<210> SEQ ID NO 725
<211> LENGTH: 351
<212> TYPE: DNA
<213> ORGANISM: Oryctolagus cuniculus

<400> SEQUENCE: 725
cagtcgctgg aggagtccgg gggtcgcctg gtcacgcctg ggacacccct gacactcacc 60
tgcacagcct ctggattctc cctcagtaac tactacgtga cctgggtccg ccaggctcca 120
gggaaggggc tggaatggat cggaatcatt tatggtagtg atgaaacggc ctacgcgacc 180
tgggcgatag gccgattcac catctccaaa acctcgacca cggtggatct gaaaatgacc 240
agtctgacag ccgcggacac ggccacctat ttctgtgcca gagatgatag tagtgactgg 300
gatgcaaaat ttaacttgtg gggccaaggc accctggtca ccgtctcgag c 351

<210> SEQ ID NO 726
<211> LENGTH: 224
<212> TYPE: PRT
<213> ORGANISM: Homo sapiens

<400> SEQUENCE: 726

Met Glu Lys Leu Leu Cys Phe Leu Val Leu Thr Ser Leu Ser His Ala
1 5 10 15

Phe Gly Gln Thr Asp Met Ser Arg Lys Ala Phe Val Phe Pro Lys Glu
20 25 30

Ser Asp Thr Ser Tyr Val Ser Leu Lys Ala Pro Leu Thr Lys Pro Leu
35 40 45

Lys Ala Phe Thr Val Cys Leu His Phe Tyr Thr Glu Leu Ser Ser Thr
50 55 60

Arg Gly Tyr Ser Ile Phe Ser Tyr Ala Thr Lys Arg Gln Asp Asn Glu
65 70 75 80

Ile Leu Ile Phe Trp Ser Lys Asp Ile Gly Tyr Ser Phe Thr Val Gly
85 90 95

Gly Ser Glu Ile Leu Phe Glu Val Pro Glu Val Thr Val Ala Pro Val
100 105 110

His Ile Cys Thr Ser Trp Glu Ser Ala Ser Gly Ile Val Glu Phe Trp
115 120 125

Val Asp Gly Lys Pro Arg Val Arg Lys Ser Leu Lys Lys Gly Tyr Thr
130 135 140

Val Gly Ala Glu Ala Ser Ile Ile Leu Gly Gln Glu Gln Asp Ser Phe
145 150 155 160

Gly Gly Asn Phe Glu Gly Ser Gln Ser Leu Val Gly Asp Ile Gly Asn
165 170 175

Val Asn Met Trp Asp Phe Val Leu Ser Pro Asp Glu Ile Asn Thr Ile
180 185 190

Tyr Leu Gly Gly Pro Phe Ser Pro Asn Val Leu Asn Trp Arg Ala Leu
195 200 205

Lys Tyr Glu Val Gln Gly Glu Val Phe Thr Lys Pro Gln Leu Trp Pro
210 215 220

<210> SEQ ID NO 727
<211> LENGTH: 468
<212> TYPE: PRT
<213> ORGANISM: Homo sapiens

<400> SEQUENCE: 727

Met Leu Ala Val Gly Cys Ala Leu Leu Ala Ala Leu Leu Ala Ala Pro
1 5 10 15

Gly Ala Ala Leu Ala Pro Arg Arg Cys Pro Ala Gln Glu Val Ala Arg
20 25 30

Gly Val Leu Thr Ser Leu Pro Gly Asp Ser Val Thr Leu Thr Cys Pro
35 40 45

Gly Val Glu Pro Glu Asp Asn Ala Thr Val His Trp Val Leu Arg Lys
50 55 60

Pro Ala Ala Gly Ser His Pro Ser Arg Trp Ala Gly Met Gly Arg Arg
65 70 75 80

Leu Leu Leu Arg Ser Val Gln Leu His Asp Ser Gly Asn Tyr Ser Cys
85 90 95

Tyr Arg Ala Gly Arg Pro Ala Gly Thr Val His Leu Leu Val Asp Val
100 105 110

Pro Pro Glu Glu Pro Gln Leu Ser Cys Phe Arg Lys Ser Pro Leu Ser
115 120 125

Asn Val Val Cys Glu Trp Gly Pro Arg Ser Thr Pro Ser Leu Thr Thr
130 135 140

Lys Ala Val Leu Leu Val Arg Lys Phe Gln Asn Ser Pro Ala Glu Asp
145 150 155 160

Phe Gln Glu Pro Cys Gln Tyr Ser Gln Glu Ser Gln Lys Phe Ser Cys
165 170 175

Gln Leu Ala Val Pro Glu Gly Asp Ser Ser Phe Tyr Ile Val Ser Met
180 185 190

Cys Val Ala Ser Ser Val Gly Ser Lys Phe Ser Lys Thr Gln Thr Phe
195 200 205

Gln Gly Cys Gly Ile Leu Gln Pro Asp Pro Pro Ala Asn Ile Thr Val
210 215 220

Thr Ala Val Ala Arg Asn Pro Arg Trp Leu Ser Val Thr Trp Gln Asp
225 230 235 240

Pro His Ser Trp Asn Ser Ser Phe Tyr Arg Leu Arg Phe Glu Leu Arg
245 250 255

Tyr Arg Ala Glu Arg Ser Lys Thr Phe Thr Thr Trp Met Val Lys Asp
260 265 270

Leu Gln His His Cys Val Ile His Asp Ala Trp Ser Gly Leu Arg His
275 280 285

Val Val Gln Leu Arg Ala Gln Glu Glu Phe Gly Gln Gly Glu Trp Ser
290 295 300

Glu Trp Ser Pro Glu Ala Met Gly Thr Pro Trp Thr Glu Ser Arg Ser
305 310 315 320

Pro Pro Ala Glu Asn Glu Val Ser Thr Pro Met Gln Ala Leu Thr Thr

```
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Ser Val Pro Leu Pro Thr Phe Leu
        355                 360                 365

Val Ala Gly Gly Ser Leu Ala Phe Gly Thr Leu Leu Cys Ile Ala Ile
    370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
    450                 455                 460

Phe Phe Pro Arg
465


<210> SEQ ID NO 728
<211> LENGTH: 918
<212> TYPE: PRT
<213> ORGANISM: Homo sapiens

<400> SEQUENCE: 728

Met Leu Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220
```

```
Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
```

```
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915


<210> SEQ ID NO 729
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 729

agcgcttatt ccgctatcca gatgacccag tc                                32


<210> SEQ ID NO 730
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 730

cgtacgtttg atttccacct tg                                           22


<210> SEQ ID NO 731
```

<211> LENGTH: 32
<212> TYPE: DNA
<213> ORGANISM: Artificial Sequence
<220> FEATURE:
<223> OTHER INFORMATION: Chemically Synthesized

<400> SEQUENCE: 731
agcgcttatt ccgaggtgca gctggtggag tc 32

<210> SEQ ID NO 732
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 732
ctcgagacgg tgacgagggt 20

<210> SEQ ID NO 733
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 733

Ala Tyr Asp Met Thr Gln Thr Pro Ala Ser Val Glu Val Ala Val Gly
1 5 10 15

Gly Thr Val Thr Ile Asn Cys Gln Ala Ser Glu Thr Ile Tyr Ser Trp
20 25 30

Leu Ser Trp Tyr Gln Gln Lys Pro Gly Gln Pro Pro Lys Leu Leu Ile
35 40 45

Tyr Gln Ala Ser Asp Leu Ala Ser Gly Val Pro Ser Arg Phe Ser Gly
50 55 60

Ser Gly Ala Gly Thr Glu Tyr Thr Leu Thr Ile Ser Gly Val Gln Cys
65 70 75 80

Asp Asp Ala Ala Thr Tyr Tyr Cys Gln Gln Gly Tyr Ser Gly Ser Asn
85 90 95

Val Asp Asn Val Phe Gly Gly Gly Thr Glu Val Val Val Lys Arg
100 105 110

<210> SEQ ID NO 734
<211> LENGTH: 99
<212> TYPE: PRT
<213> ORGANISM: Artificial Sequence
<220> FEATURE:
<223> OTHER INFORMATION: Chemically Synthesized

<400> SEQUENCE: 734

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Phe Gly Gly Gly Thr Lys Val Glu

```
                85                  90                  95

Ile Lys Arg


<210> SEQ ID NO 735
<211> LENGTH: 88
<212> TYPE: PRT
<213> ORGANISM: Artificial Sequence
<220> FEATURE:
<223> OTHER INFORMATION: Chemically Synthesized

<400> SEQUENCE: 735

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys
                85


<210> SEQ ID NO 736
<211> LENGTH: 88
<212> TYPE: PRT
<213> ORGANISM: Artificial Sequence
<220> FEATURE:
<223> OTHER INFORMATION: Chemically Synthesized

<400> SEQUENCE: 736

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85


<210> SEQ ID NO 737
<211> LENGTH: 111
<212> TYPE: PRT
<213> ORGANISM: Artificial Sequence
<220> FEATURE:
<223> OTHER INFORMATION: Chemically Synthesized

<400> SEQUENCE: 737

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Thr Ile Tyr Ser Trp
            20                  25                  30

Leu Ser Trp Tyr Gln Gln Lys Pro Gly Lys Ala Pro Lys Leu Leu Ile
        35                  40                  45
```

```
Tyr Gln Ala Ser Asp Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Gly Ser Asn
                85                  90                  95

Val Asp Asn Val Phe Gly Gly Gly Thr Lys Val Glu Ile Lys Arg
            100                 105                 110


<210> SEQ ID NO 738
<211> LENGTH: 118
<212> TYPE: PRT
<213> ORGANISM: Artificial Sequence
<220> FEATURE:
<223> OTHER INFORMATION: Chemically Synthesized

<400> SEQUENCE: 738

Gln Glu Gln Leu Lys Glu Ser Gly Gly Arg Leu Val Thr Pro Gly Thr
1               5                   10                  15

Pro Leu Thr Leu Thr Cys Thr Ala Ser Gly Phe Ser Leu Asn Asp His
            20                  25                  30

Ala Met Gly Trp Val Arg Gln Ala Pro Gly Lys Gly Leu Glu Tyr Ile
        35                  40                  45

Gly Phe Ile Asn Ser Gly Gly Ser Ala Arg Tyr Ala Ser Trp Ala Glu
    50                  55                  60

Gly Arg Phe Thr Ile Ser Arg Thr Ser Thr Thr Val Asp Leu Lys Met
65                  70                  75                  80

Thr Ser Leu Thr Thr Glu Asp Thr Ala Thr Tyr Phe Cys Val Arg Gly
                85                  90                  95

Gly Ala Val Trp Ser Ile His Ser Phe Asp Pro Trp Gly Pro Gly Thr
            100                 105                 110

Leu Val Thr Val Ser Ser
        115


<210> SEQ ID NO 739
<211> LENGTH: 109
<212> TYPE: PRT
<213> ORGANISM: Artificial Sequence
<220> FEATURE:
<223> OTHER INFORMATION: Chemically Synthesized

<400> SEQUENCE: 739

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105


<210> SEQ ID NO 740
```

<211> LENGTH: 97
<212> TYPE: PRT
<213> ORGANISM: Artificial Sequence
<220> FEATURE:
<223> OTHER INFORMATION: Chemically Synthesized

<400> SEQUENCE: 740

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg
```

<210> SEQ ID NO 741
<211> LENGTH: 97
<212> TYPE: PRT
<213> ORGANISM: Artificial Sequence
<220> FEATURE:
<223> OTHER INFORMATION: Chemically Synthesized

<400> SEQUENCE: 741

```
Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg
```

<210> SEQ ID NO 742
<211> LENGTH: 120
<212> TYPE: PRT
<213> ORGANISM: Artificial Sequence
<220> FEATURE:
<223> OTHER INFORMATION: Chemically Synthesized

<400> SEQUENCE: 742

```
Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Leu Asn Asp His
            20                  25                  30

Ala Met Gly Trp Val Arg Gln Ala Pro Gly Lys Gly Leu Glu Tyr Val
        35                  40                  45

Gly Phe Ile Asn Ser Gly Gly Ser Ala Arg Tyr Ala Ser Ser Ala Glu
    50                  55                  60
```

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Gly Ala Val Trp Ser Ile His Ser Phe Asp Pro Trp Gly Gln
100 105 110

Gly Thr Leu Val Thr Val Ser Ser
115 120

<210> SEQ ID NO 743
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 743

Phe Gly Gly Gly
1

<210> SEQ ID NO 744
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 744

Val Val Lys Arg
1

<210> SEQ ID NO 745
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 745

Phe Gly Gly Gly Thr Lys Val Glu Ile Lys Arg
1 5 10

<210> SEQ ID NO 746
<211> LENGTH: 4
<212> TYPE: PRT
<213> ORGANISM: Artificial Sequence
<220> FEATURE:
<223> OTHER INFORMATION: Chemically Synthesized
<220> FEATURE:
<221> NAME/KEY: VARIANT
<222> LOCATION: (3)..(3)
<223> OTHER INFORMATION: Xaa may be Q or P

<400> SEQUENCE: 746

Trp Gly Xaa Gly
1

<210> SEQ ID NO 747
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 747

-continued

```
Thr Val Ser Ser
1


<210> SEQ ID NO 748
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 748

Trp Gly Gln Gly Thr Leu Val Thr Val Ser Ser
1               5                   10
```